US012747291B2

(12) United States Patent
Loomis et al.

(10) Patent No.: US 12,747,291 B2
(45) Date of Patent: *Sep. 29, 2026

(54) NUCLEIC ACIDS ENCODING HUMANIZED ANTI-PACAP ANTIBODIES

(71) Applicant: H. LUNDBECK A/S, Valby (DK)

(72) Inventors: Maria-Cristina Loomis, Bothell, WA (US); Leon F. Garcia-Martinez, Woodinville, WA (US); Benjamin H. Dutzar, Seattle, WA (US); Daniel S. Allison, Lake Forest Park, WA (US); Katherine Lee Hendrix, Renton, WA (US); Ethan W. Ojala, Snohomish, WA (US); Pei Fan, Bothell, WA (US); Jeffrey T.L. Smith, Dublin (IE); John A. Latham, Seattle, WA (US); Charlie Karasek, Seattle, WA (US); Jenny Mulligan, Lake Forest Park, WA (US); Michelle Scalley-Kim, Seattle, WA (US); Erica Stewart, Seattle, WA (US); Vanessa Lisbeth Rubin, Seattle, WA (US); Jens J. Billgren, Seattle, WA (US)

(73) Assignee: H. LUNDBECK A/S, Valby (DK)

(*) Notice: Subject to any disclaimer, the term of this patent is extended or adjusted under 35 U.S.C. 154(b) by 0 days.

This patent is subject to a terminal disclaimer.

(21) Appl. No.: 18/581,446

(22) Filed: Feb. 20, 2024

(65) Prior Publication Data

US 2025/0009876 A1 Jan. 9, 2025

Related U.S. Application Data

(62) Division of application No. 17/122,243, filed on Dec. 15, 2020, now Pat. No. 11,938,185, which is a (Continued)

(51) Int. Cl.

| | |
|---|---|
| ***C07K 16/26*** | (2006.01) |
| ***C07K 14/72*** | (2006.01) |
| ***C12N 5/06*** | (2006.01) |
| ***C12N 5/07*** | (2010.01) |
| ***C12N 15/09*** | (2006.01) |

(Continued)

(52) U.S. Cl.

CPC .............. *C07K 16/26* (2013.01); *C07K 14/72* (2013.01); *C12N 5/06* (2013.01); *C12N 15/09* (2013.01); *C12N 15/63* (2013.01); *A61K 38/22* (2013.01); *A61K 39/3955* (2013.01); *A61K 2039/505* (2013.01); *A61P 9/08* (2018.01); *A61P 25/06* (2018.01); *C07K 14/575* (2013.01); *C07K 14/70503* (2013.01); *C07K 2317/24* (2013.01); *C07K 2317/34* (2013.01); *C07K 2317/56* (2013.01); *C07K 2317/565* (2013.01); *C07K 2317/76* (2013.01); *C07K 2317/92* (2013.01);

(Continued)

(58) Field of Classification Search

CPC . C07K 16/26; C07K 2317/24; A61K 39/3955

See application file for complete search history.

(56) References Cited

U.S. PATENT DOCUMENTS

| | | | |
|---|---|---|---|
| 5,198,542 | A | 3/1993 | Onda et al. |
| 5,486,472 | A | 1/1996 | Suzuki et al. |

(Continued)

FOREIGN PATENT DOCUMENTS

| | | |
|---|---|---|
| EP | 0 522 159 | 12/2001 |
| EP | 1731168 | 12/2006 |

(Continued)

OTHER PUBLICATIONS

Grider, J R et al. "Regulation of the descending relaxation phase of intestinal peristalsis by PACAP." Journal of the autonomic nervous system vol. 50,2 (1994): 151-9. doi:10.1016/0165-1838(94)90005-1.

(Continued)

*Primary Examiner* — Zachary C Howard

(74) *Attorney, Agent, or Firm* — Robin L. Teskin; Baker, Donelson, Bearman, Caldwell & Berkowitz PC

(57) ABSTRACT

The present invention is directed to antibodies and antigen binding fragments thereof having binding specificity for PACAP. The antibodies and antigen binding fragments thereof comprise the sequences of the $V_H$, $V_L$, and CDR polypeptides described herein, and the polynucleotides encoding them. Antibodies and antigen binding fragments described herein bind to and/or compete for binding to the same linear or conformational epitope(s) on human PACAP as an anti-PACAP antibody. The invention contemplates conjugates of anti-PACAP antibodies and binding fragments thereof conjugated to one or more functional or detectable moieties. Methods of making said anti-PACAP antibodies and antigen binding fragments thereof are also contemplated. Other embodiments of the invention contemplate using anti-PACAP antibodies, and binding fragments thereof, for the diagnosis, assessment, and treatment of diseases and disorders associated with PACAP and conditions where antagonism of PACAP-related activities, such as vasodilation, photophobia, mast cell degranulation, and/or neuronal activation, would be therapeutically beneficial.

18 Claims, 58 Drawing Sheets

Specification includes a Sequence Listing.

Related U.S. Application Data division of application No. 16/787,260, filed on Feb. 11, 2020, now Pat. No. 10,975,135, which is a division of application No. 15/487,642, filed on Apr. 14, 2017, now Pat. No. 10,913,783.

(60) Provisional application No. 62/408,347, filed on Oct. 14, 2016, provisional application No. 62/366,902, filed on Jul. 26, 2016, provisional application No. 62/322,957, filed on Apr. 15, 2016, provisional application No. 62/322,939, filed on Apr. 15, 2016, provisional application No. 62/323,495, filed on Apr. 15, 2016, provisional application No. 62/323,573, filed on Apr. 15, 2016.

(51) Int. Cl.

| | |
|---|---|
| ***C12N 15/63*** | (2006.01) |
| *A61K 38/22* | (2006.01) |
| *A61K 39/00* | (2006.01) |
| *A61K 39/395* | (2006.01) |
| *A61P 9/08* | (2006.01) |
| *A61P 25/06* | (2006.01) |
| *C07K 14/575* | (2006.01) |
| *C07K 14/705* | (2006.01) |

(52) U.S. Cl.

CPC ........ *G01N 2333/575* (2013.01); *Y02A 50/30* (2018.01)

(56) References Cited

U.S. PATENT DOCUMENTS

| | | | |
|---|---|---|---|
| 5,858,787 | A | 1/1999 | Onda et al. |
| 5,892,004 | A | 4/1999 | Ohtaki et al. |
| 5,973,117 | A | 10/1999 | Onda et al. |
| 6,399,316 | B1 | 6/2002 | Onda et al. |
| 7,615,219 | B2 | 11/2009 | Freson et al. |
| 8,466,118 | B2 | 6/2013 | Banks et al. |
| 8,728,473 | B2 | 5/2014 | Garcia-Martinez et al. |
| 9,255,154 | B2 | 2/2016 | Feldhaus et al. |
| 9,290,567 | B2 | 3/2016 | Bohrmann et al. |
| 9,365,653 | B2 | 6/2016 | Xu et al. |
| 9,939,449 | B2 | 4/2018 | May et al. |
| 9,989,541 | B2 | 6/2018 | Shi et al. |
| 10,202,435 | B2 | 2/2019 | Loomis et al. |
| 10,228,378 | B2 | 3/2019 | May et al. |
| 10,247,738 | B2 | 4/2019 | Shi et al. |
| 10,519,225 | B2 | 12/2019 | Patel et al. |
| 10,913,783 | B2 * | 2/2021 | Loomis .................. A61P 15/00 |
| 2002/0155533 | A1 | 10/2002 | Onda et al. |
| 2002/0182729 | A1 | 12/2002 | Dicicco-Bloom et al. |
| 2004/0014095 | A1 | 1/2004 | Gerber et al. |
| 2004/0038888 | A1 | 2/2004 | Mercer et al. |
| 2005/0129687 | A1 | 6/2005 | Vizzard et al. |
| 2006/0062785 | A1 | 3/2006 | Freson et al. |
| 2007/0054843 | A1 | 3/2007 | Yeomans et al. |
| 2007/0149439 | A1 | 6/2007 | Dicicco-Bloom et al. |
| 2007/0202099 | A1 | 8/2007 | Inooka et al. |
| 2008/0070239 | A1 | 3/2008 | Wood |
| 2010/0068208 | A1 | 3/2010 | Ogi et al. |
| 2010/0104530 | A1 | 4/2010 | Freson et al. |
| 2010/0112601 | A1 | 5/2010 | Shirakawa et al. |
| 2010/0129372 | A1 | 5/2010 | Freson et al. |
| 2010/0196393 | A1 | 8/2010 | Banks et al. |
| 2011/0212464 | A1 | 9/2011 | Hagmann |
| 2011/0229423 | A1 | 9/2011 | Vogel et al. |
| 2012/0014958 | A1 | 1/2012 | Borrasm et al. |
| 2012/0058950 | A1 | 3/2012 | Wood et al. |
| 2012/0294797 | A1 | 11/2012 | Kovacevich et al. |
| 2012/0294802 | A1 | 11/2012 | Russo et al. |
| 2012/0309696 | A1 | 12/2012 | Dores |
| 2013/0177568 | A1 | 7/2013 | Bhatt et al. |
| 2013/0267689 | A1 | 10/2013 | Latham et al. |
| 2013/0302399 | A1 | 11/2013 | Feldhaus et al. |
| 2013/0310541 | A1 | 11/2013 | Bohrmann et al. |
| 2014/0370019 | A1 | 12/2014 | Bruenker et al. |
| 2015/0010560 | A1 | 1/2015 | Xu et al. |
| 2015/0309050 | A1 | 10/2015 | May |
| 2016/0304604 | A1 | 10/2016 | Loomis et al. |
| 2016/0305962 | A1 | 10/2016 | Shi et al. |
| 2016/0361441 | A1 | 12/2016 | Kuburas et al. |
| 2016/0362488 | A1 | 12/2016 | Loomis et al. |
| 2016/0376363 | A1 | 12/2016 | Kuburas et al. |
| 2017/0298115 | A1 | 10/2017 | Loomis et al. |
| 2017/0298127 | A1 | 10/2017 | Loomis et al. |
| 2017/0343561 | A1 | 11/2017 | May et al. |
| 2018/0246126 | A1 | 8/2018 | Shi et al. |
| 2018/0362643 | A1 | 12/2018 | Hamburger et al. |
| 2019/0100579 | A1 | 4/2019 | Patel et al. |
| 2019/0178898 | A1 | 6/2019 | Shi et al. |
| 2019/0233498 | A1 | 8/2019 | Loomis et al. |
| 2019/0270807 | A1 | 9/2019 | Loomis et al. |
| 2020/0155533 | A9 | 5/2020 | Villarreal |

FOREIGN PATENT DOCUMENTS

| | | |
|---|---|---|
| EP | 2 009 026 | 12/2008 |
| JP | H06-500001 A | 1/1994 |
| JP | 2002-510500 A | 4/2002 |
| WO | 199114786 | 10/1991 |
| WO | WO 91/14786 | 10/1991 |
| WO | WO 1996/039439 | 12/1996 |
| WO | WO 1998/024900 | 6/1998 |
| WO | 199951762 | 10/1999 |
| WO | WO 1999/051762 | 10/1999 |
| WO | WO 2001/023420 | 4/2001 |
| WO | WO 2003/092716 | 11/2003 |
| WO | WO 2004/006839 | 1/2004 |
| WO | WO 2004/062684 | 7/2004 |
| WO | WO 2005/041757 | 5/2005 |
| WO | WO 2005/072385 | 8/2005 |
| WO | WO 2006/052468 | 5/2006 |
| WO | 2006118328 | 11/2006 |
| WO | WO 2009/000894 | 12/2008 |
| WO | WO 2009/033489 | 3/2009 |
| WO | 2010/005068 | 1/2010 |
| WO | WO 2010/007175 | 1/2010 |
| WO | WO 2012/010647 | 1/2012 |
| WO | WO 2012/106407 | 8/2012 |
| WO | WO 2015/058861 | 4/2015 |
| WO | WO 2015/127288 | 8/2015 |
| WO | WO 2016/168757 | 10/2016 |
| WO | WO 2016/168760 | 10/2016 |
| WO | WO 2016/168762 | 10/2016 |
| WO | WO 2016/168768 | 10/2016 |
| WO | WO 2017/106578 | 6/2017 |

OTHER PUBLICATIONS

Atsuro Miyata, Structure and function of PACAP as a brain gut peptide, Journal of Clinical and Experimental Medicine, vol. 2007, vol. 223, No. 7, pp. 569 to 572.

Seeliger, Stephan et al. “Pituitary adenylate cyclase activating polypeptide: an important vascular regulator in human skin in vivo.” The American journal of pathology vol. 177,5 (2010): 2563-75. doi:10.2353/ajpath.2010.090941.

Ahmadzadeh V, et al. “Antibody humanization methods for development of therapeutic applications,” Monoclon Antib mmunodiagn Immunother. Apr. 2014;33(2):67-73.

Alaoui-Ismaili et al. “Design of Second Generation Therapeutic Recombinant Bone Morphogenetic Proteins,” Cytokine Growth Factor Rev. 2009; 20:501-507.

Almagro J, et al. “Antibody engineering: Humanization, affinity maturation, and selection techniques” Therapeutic Monoclonal Antibodies: From Bench to Clinic, Oct. 2009, Wiley, pp. 311-334.

Amin FM, et al. “Headache and prolonged dilatation of the middle meningeal artery by PACAP38 in healthy volunteers,” Cephalalgia. Jan. 2012;32(2):140-9.

(56) References Cited

OTHER PUBLICATIONS

Amin FM, et al. "Investigation of the pathophysiological mechanisms of migraine attacks induced by pituitary adenylate cyclase-activating polypeptide-38," Brain, Mar. 2014;137(Pt 3):779-94.
Baun, M. et al., "Pharmacological characterization and expression of VIP and PACAP receptors in isolated cranial arteries of the rat", European Journal of Pharmacology, 2011; 670: 186-194.
Bhatt, D.K. et al., "PACAP-38 infusion causes sustained vasodilation of the middle meningeal artery in the rat: Possible involvement of mast cells", Cephalalgia, 2014; 0(0): 1-10.
Boni LJ, et al. "The in vivo effect of VIP, PACAP-38 and PACAP-27 and mRNA expression of their receptors in rat middle meningeal artery." Cephalalgia. Aug. 2009;29(8):837-47.
Botz, B. et al., "Role of pituitary Adenylate-Cyclase Activating Polypeptide and Tacl gene derived tachykinins in sensory, motor and vascular functions under normal and neuropathic conditions", Peptides, 2013; 43: 105-112.
Bowie et al. "Deciphering the Message in Protein Sequences: Tolerance to Amino Acid Substitutions," Science. Mar. 16, 1990;247(4948):1306-10.
Brown M, et al. "Tolerance of single, but not multiple, amino acid replacements in antibody VH CDR 2: a means of minimizing B cell wastage from somatic hypermutation?" J Immunol. May 1, 1996;156(9):3285-91.
Burgess et al. "Possible Dissociation of the Heparin-Binding and Mitogenic Activities of Heparin-Binding (Acidic Fibroblast) Growth factor-1 From Its Receptor-Binding Activities by Site-Directed Mutagenesis of a Single Lysine Residue," J Cell Biol. Nov. 1990:111(5 Pt 1):2129-38.
Casset et al., "A Peptide Mimetic of an anti-CD4 Monoclonal Antibody by Rational Design," Biochem Biophys Res Commun . Jul. 18, 2003;307(1):198-205.
Chan, K.Y. et al., "Pharmacological characterization of VIP and PACAP receptors in the human meningeal and coronary artery", Cephalalgia, 2011; 31(2): 181-189.
Chen et al., "Selection and Analysis of an Optimized anti-VEGF Antibody: Crystal Structure of an Affinity-Matured Fab in Complex With Antigen," J Mol Biol. Nov. 5, 1999;293(4):865-81.
Chen, D. et al., "Pituitary adenylyl cyclase-activating peptide: A pivotal modulator of glutamatergio regulationofthe surachiasmatic circadian clock", PNAS, 1999; 96(23): 13468-13473.
Cochaud S, et al. "Neuropeptides of the VIP family inhibit glioblastoma cell invasion," J Neurooncol. Mar. 2015;122(1):63-73.
Csaba Z., et al. "Local effect of PACAP and VIP on testicular function in immature and adult rats," Peptides, 1997; 18 (10): 1561-7.
Dickson, L. and Finlayson, K. "VPAC and PAC receptors: From ligands to function", Pharmacology & Therapeutics, 2009; 121: 294-316.
Dodick, "Migraine," Lancet. Mar. 31, 2018;391(10127):1315-1330.
Edvinsson, L., "PACAP and its receptors in migraine pathophysiology: Commentary on Walker et al., Br J Pharmacol 171: 1521-1533", British Journal of Pharmacology, 2015; 172: 4782-4784.
Farnham, M.M.J. and Pilowsky, P.M., "The role of PACAP in central cardiorespiratory regulation", Respiratory Physiology and Neurobiology, 2010; 174: 65-75.
Fleischer N, et al. "Studies of ACTH antibodies and their reactions with inactive analogues of ACTH," Endocrinology. May 1966;78(5):1067-75.
Freson K, et al. "The pituitary adenylate cyclase-activating polypeptide is a physiological inhibitor of platelet activation," J Clin Invest. Mar. 2004;113(6):905-12.
Freson, K. et al., "PACAP and its receptor VPACI regulate megakaryocyte maturation: therapeutic implications", Blood, Feb. 15, 2008; 111(4): 1885-1893.
Grande, G. et al., "Comparison of responses to vasoactive drugs in human and rat cerebral arteries using myography and pressurized cerebral artery method", Cephalalgia, 2012; 33(3): 152-159.
Guo et al., "Protein Tolerance to Random Amino Acid Change," Proc Natl Acad Sci USA. Jun. 22, 2004;101(25):9205-10.
Harmar, A.J. et al., "Pharmacology and functions of receptors forvasoactive intestinal peptide and pituitary adenylate cyclase-activating polypeptide: IUPHAR Review 1", British Journal of Pharmacology, 2012; 166: 4-17.
Holm et al., "Functional Mapping and Single Chain Construction of the Anti-Cytokeratin 8 Monoclonal Antibody TS1," Mol Immunol. Feb. 2007;44(6):1075-84.
Kaiser EA, et al. "CGRP and migraine: could PACAP play a role too?" Neuropeptides. Dec. 2013;47(6):451-61.
Khan, S. et al., "Sphenopalatine ganglion neuromodulation in migraine: What is the rationale?", Cephalalgia, 2014; 34(5): 382-391.
Kumar, S. et al., "Crystal Structure of the PACIR Extracellular Domain Unifies a Consensus Fold for Hormone Recognition by Class B G-Protein Coupled Receptors", PLOS One, 2011; 6(5): 1-11.
Maccallum et al. "Antibody-antigen Interactions: Contact Analysis and Binding Site Topography," J Mol Biol . Oct. 11, 1996;262(5):732-45.
Markovics, A. et al., "Pituitary adenylate cyclase-activating polypeptide plays a key role in nitroglycerol-induced trigeminovascular activation in mice", Neurobiology of Disease, 2012; 45: 633-644.
Moody, T.W. et al., "VIP and PACAP. Recent insights into their functions/roles in physiology and disease from molecular and genetic studies", Curr Opin Endocrinol Diabetes Obes., Feb. 2011; 18(1): 61-67.
Nair DT, et al. "Epitope recognition by diverse antibodies suggests conformational convergence in an antibody response," J Immunol. Mar. 1, 2002:168(5):2371-82.
Nassini, R. et al., "The 'headache tree' via umbellulone and TRPAI activates the trigeminovascular system", Brain, 2012; 135: 376-390.
Ng, S.Y.L. et al., "Agnathan VIP, PACAP and Their Receptors: Ancestral Origins of Today's Highly Diversified Forms", PLOS ONE, Sep. 2012; 7(9): 1-15.
Noseda et al., "Current Understanding of Photophobia, Visual Networks and Headaches," Cephalalgia Nov. 2019;39(13):1623-1634.
Noseda, R. et al., "A neural mechanism for exacerbation of headache by light", Nature Neuroscience, Feb. 2010; 13(2): 239-246.
Pascalis et al. "Grafting of 'Abbreviated' Complementarity-Determining Regions Containing Specificity-Determining Residues Essential for Ligand Contact to Engineer a Less Immunogenic Humanized Monoclonal Antibody," J Immunol Sep. 15, 2002;169(6):3076-84.
Pawson et al. "Assembly of Cell Regulatory Systems Through Protein Interaction Domains," Science. Apr. 18, 2003;300(5618):445-52.
Reglodi, et al. "Protective effects of PACAP in ischemia." The journal of headache and pain vol. 19,1 19. Mar. 2, 2018, doi:10.1186/s10194-018-0845-3).
Rubio-Beltran E, et al. "PACAP38 and PAC1 receptor blockade: a new target for headache?" J Headache Pain. Aug. 7, 2018;19(1):64.
Rudikoff, S. et al., "Single amino acid substitution altering antigen-binding specificity", PNAS, 1982; 79: 1979-1983.
Schmidt-choudhury, A. et al., "Mast cells contribute to PACAP-induced dermal oedema in mice", Regulatory Peptides, 1999; 82: 65-69.
Schwarzhoff, R. et al., "Specific monoclonal antibodies neutralize the action of PACAP 1-27 or PACAP 1-38 on intestinal muscle strips in vitro", Regulatory Peptides, 1995; 55: 57-66.
Schytz, H.W. et al., "Cutaneous nociception and neurogenic inflammation evoked by PACAP38 and VIP", J Headache Pain, 2010; 11: 309-316.
Schytz, H.W. et al., "PACAP38 induces migraine-like attacks in patients with migraine without aura", Brain, 2009; 132: 16-25.
Schytz, H.W. et al., "The PACAP Receptor: A Novel Target for Migraine Treatment", Neurotherapeutics, 2010; 7(2): 191-196.
Schytz, H.W. et al., "What have we learnt from triggering migraine?", Curr Opin Nemol, 2010; 23: 259-265.
Shimazaki Y, et al. "Epitope analysis using membrane-immobilized avidin and protein A," Protein Expr Purif. Jun. 2012;83(2):177-81.

(56) References Cited

OTHER PUBLICATIONS

Sun, C. et al., "Solution structure and mutational analysis of pituitary adenylate cyclase-activating polypeptide binding to the extracellular domain of PACI-Rs", PNAS, 2007; 104(19): 7875-7880.
Sundrum et al., "Pituitary Adenylate Cyclase-Activating Polypeptide Receptors in the Trigeminovascular System: Implications for Migraine," Br J Pharmacol. Nov. 2018;175(21):4109-4120.
Suzuki, N. et al., "Production of Immunoreactive Pituitary Adenylate Cyclase Activating Polypeptide (PACAP) by Human Neuroblastoma Cells, IMR-32: Detection and Characterization with Monoclonal and Polyclonal Antibodies against Different Epitopes of PACAP", J. Biochem., 1993; 113: 549-556.
Syed AU, et al. "Pituitary adenylate cyclase-activating polypeptide (PACAP) potently dilates middle meningeal arteries: implications for migraine," J Mol Neurosci. Nov. 2012;48(3):574-83.
Tuka, B. et al., "Alterations in PACAP-38-like immunoreactivity in the plasma during ictal and interictal periods of migraine patients", Cephalalgia, 2013; 0(0): 1-11.
Tuka, B. et al., "Peripheral and central alterations of pituitary adenylate cyclase activating polypeptide-like immunoreactivity in the rat in response to activation of the trigeminovascular system", Peptides, 2012; 33: 307-316.
Vajdos et al., "Comprehensive Functional Maps of the Antigen-Binding Site of an anti-ErbB2 Antibody Obtained With Shotgun Scanning Mutagenesis," J Mol Biol . Jul. 5, 2002;320(2):415-28.
Vecsei, L. et al., "Role of PACAP in migraine headaches", Brain (Scientific Commentaries) 2014; 137: 650-651.
Walter S, et al. "TEV-48125: a review of a monoclonal CGRP antibody in development for the preventive treatment of migraine," Curr Pain Headache Rep. Mar. 2015;19(3):6.
Wang, Z.-Y. et al., ""Distribution and effects of pituitary adenylate cyclase-activating peptide in the rabbit eye"", Neuroscience, 1995; 69(1): 297-308.
Warren, J.B. et al., "Pituitary Adenylate Cyclase Activating Polypeptide is a Potent Vasodilator in Humans", Journal of Cardiovascular Pharmacology, 1992; 20(1): 83-87.
Waschek JA, et al. "PACAP and migraine headache: immunomodulation of neural circuits in autonomic ganglia and brain parenchyma," J Headache Pain. Mar. 13, 2018;19(1):23.
White A, et al. "Characterisation of monoclonal antibodies to adrenocorticotrophin," J Immunol Methods. May 23, 1985;79(2):185-94.
Wu et al., "Humanization of a Murine Monoclonal Antibody by Simultaneous Optimization of Framework and CDR Residues," J Mol Biol. Nov. 19, 1999;294(1):151-62.
Wu et al., "Photophobia in Neurologic Disorders," Transl Neurodegener, Sep. 20, 2017;6:26.
Yada, T. et al., "Pituitary adenylate cyclase-activating polypeptide (PACAP) is an islet substance serving as an intra-islet amplifier of glucose-induced insulin secretion in rats", Journal of Physiology, 1997; 505.2: 319-328.
Zagami AS, et al. "Pituitary adenylate cyclase activating polypeptide and migraine." Ann Clin Transl Neurol. Dec. 2014;1(12):1036-40.
Zhang, Y. et al., "Capsaicin-evoked release of pituitary adenylate cyclase activating peptide (PACAP) and calcitonin gene-related peptide (CGRP) from rat spinal cord in vivo", Regulatory Peptides, 1997; 69: 83-87.

* cited by examiner

Figure 1A

Antibody Heavy chain Protein features

| Sequence Name | FR1 | CDR1 | FR2 | CDR2 |
|---|---|---|---|---|
| Ab10 | QSVEESGGRLVTPGTPLTLTCTVSGIDLN | SYYMT | WVRQAPGKGLEWIG | FIDAGGDAYYASWAKG |
| Ab20 | QSVEESGGRLVTPGTPLTLTCTVSGIDLS | SYYMS | WVRQAPGKGLEWIG | FIDTDGSAYYATWAKG |
| Ab21 | QSVEESGGRLVTPGTPLTLTCTVSGIDLS | SYYMT | WVRQAPGKGLEWVG | FIDAGGSAYYATWAKG |
| Ab22 | QEQLVESGGGLVQPEGSLTLTCTASGFDFS | SNAMC | WVRQAPGKGLEWIG | SIYNADGKNYYAIWAKG |
| Ab23 | QSVEESGGRLVTPGTPLTLTCTVSGFSLN | NYAMS | WVRQAPGKGLEWIG | IMGVNDITYYASWAKG |
| Ab10.H | EVQLVESGGGLVQPGGSLRLSCAASGIDLN | SYYMT | WVRQAPGKGLEWIG | FIDAGGDAYYASWAKG |
| Ab21.H | EVQLVESGGGLVQPGGSLRLSCAASGIDLS | SYYMT | WVRQAPGKGLEWIG | FIDAGGSAYYATWAKG |
| Ab10.H2 | EVQLVESGGGLVQPGGSLRLSCAASGIDLN | SYYMT | WVRQAPGKGLEWIG | FIDAGGDAYYASWAKG |
| Ab10.H3 | EVQLVESGGGLVQPGGSLRLSCAASGIDLN | SYYMT | WVRQAPGKGLEWIG | FIDAGGDAYYASWAKG |
| Ab10.H4 | EVQLVESGGGLVQPGGSLRLSCAASGIDLN | SYYMT | WVRQAPGKGLEWIG | FIDAGGDAYYASWAKG |
| Ab10.H5 | EVQLVESGGGLVQPGGSLRLSCAASGIDLN | SYYMT | WVRQAPGKGLEWIG | FIDAGGDAYYASWAKG |
| Ab10.H6 | EVQLVESGGGLVQPGGSLRLSCAASGIDLN | SYYMT | WVRQAPGKGLEWIG | FIDAGGDAYYASWAKG |
| Ab21.H2 | EVQLVESGGGLVQPGGSLRLSCAASGIDLS | SYYMT | WVRQAPGKGLEWIG | FIDAGGSAYYATWAKG |
| Ab21.H3 | EVQLVESGGGLVQPGGSLRLSCAASGIDLS | SYYMT | WVRQAPGKGLEWIG | FIDAGGSAYYATWAKG |
| Ab21.H4 | EVQLVESGGGLVQPGGSLRLSCAASGIDLS | SYYMT | WVRQAPGKGLEWIG | FIDAGGSAYYATWAKG |

Figure 1B

Antibody Heavy chain Protein features

| Sequence Name | FR3 | CDR3 | FR4 |
|---|---|---|---|
| Ab10 | RFTISKTSTTVDLKITSPTTEDTATYFCAR | DLDL | WGQGTLVTVSS |
| Ab20 | RFTISKTSTTVDLKITSPTTEDTATYFCAR | DLDL | WGPGTLVTVSS |
| Ab21 | RFTISKASTTVDLKITSPTTEDTATYFCAR | DLDL | WGPGTLVTVSS |
| Ab22 | RFTISRTSSTTVTLQMTSLTAADTATYFCAR | DFDL | WGQGTLVTVSS |
| Ab23 | RFTISKTSTTVDLKMTSLTTEDTATYFCTR | EIRDDGDSSDKL | WGPGTLVTVSS |
| Ab10.H | RFTISRDNSKNTVYLQMNSLRAEDTAVYFCAR | DLDL | WGQGTLVTVSS |
| Ab21.H | RFTISRDNSKNTVYLQMNSLRAEDTAVYFCAR | DLDL | WGQGTLVTVSS |
| Ab10.H2 | RFTISRDNSKNTVYLQMNSLRAEDTAVYFCAR | DLDL | WGQGTLVTVSS |
| Ab10.H3 | RFTISRDNSKNTVYLQMNSLRAEDTAVYFCAR | DLDL | WGQGTLVTVSS |
| Ab10.H4 | RFTISRDNSKNTVYLQMNSLRAEDTAVYFCAR | DLDL | WGQGTLVTVSS |
| Ab10.H5 | RFTISRDNSKNTVYLQMNSLRAEDTAVYFCAR | DLDL | WGQGTLVTVSS |
| Ab10.H6 | RFTISRDNSKNTVYLQMNSLRAEDTAVYFCAR | DLDL | WGQGTLVTVSS |
| Ab21.H2 | RFTISRDNSKNTVYLQMNSLRAEDTAVYFCAR | DLDL | WGQGTLVTVSS |
| Ab21.H3 | RFTISRDNSKNTVYLQMNSLRAEDTAVYFCAR | DLDL | WGQGTLVTVSS |
| Ab21.H4 | RFTISRDNSKNTVYLQMNSLRAEDTAVYFCAR | DLDL | WGQGTLVTVSS |

Figure 1C

Antibody Heavy chain Protein features

| Sequence Name | Constant region |
|---|---|
| Ab10 | ASTKGPSVFPLAPSSKSTSGGTAALGCLVKDYFPEPVTVSWNSGALTSGVHTFPAVLQSSGLYSLSSVVTVPSSSL |
| Ab20 | ASTKGPSVFPLAPSSKSTSGGTAALGCLVKDYFPEPVTVSWNSGALTSGVHTFPAVLQSSGLYSLSSVVTVPSSSL |
| Ab21 | ASTKGPSVFPLAPSSKSTSGGTAALGCLVKDYFPEPVTVSWNSGALTSGVHTFPAVLQSSGLYSLSSVVTVPSSSL |
| Ab22 | ASTKGPSVFPLAPSSKSTSGGTAALGCLVKDYFPEPVTVSWNSGALTSGVHTFPAVLQSSGLYSLSSVVTVPSSSL |
| Ab23 | ASTKGPSVFPLAPSSKSTSGGTAALGCLVKDYFPEPVTVSWNSGALTSGVHTFPAVLQSSGLYSLSSVVTVPSSSL |
| Ab10.H | ASTKGPSVFPLAPSSKSTSGGTAALGCLVKDYFPEPVTVSWNSGALTSGVHTFPAVLQSSGLYSLSSVVTVPSSSL |
| Ab21.H | ASTKGPSVFPLAPSSKSTSGGTAALGCLVKDYFPEPVTVSWNSGALTSGVHTFPAVLQSSGLYSLSSVVTVPSSSL |
| Ab10.H2 | ASTKGPSVFPLAPSSKSTSGGTAALGCLVKDYFPEPVTVSWNSGALTSGVHTFPAVLQSSGLYSLSSVVTVPSSSL |
| Ab10.H3 | ASTKGPSVFPLAPSSKSTSGGTAALGCLVKDYFPEPVTVSWNSGALTSGVHTFPAVLQSSGLYSLSSVVTVPSSSL |
| Ab10.H4 | ASTKGPSVFPLAPSSKSTSGGTAALGCLVKDYFPEPVTVSWNSGALTSGVHTFPAVLQSSGLYSLSSVVTVPSSSL |
| Ab10.H5 | ASTKGPSVFPLAPSSKSTSGGTAALGCLVKDYFPEPVTVSWNSGALTSGVHTFPAVLQSSGLYSLSSVVTVPSSSL |
| Ab10.H6 | ASTKGPSVFPLAPSSKSTSGGTAALGCLVKDYFPEPVTVSWNSGALTSGVHTFPAVLQSSGLYSLSSVVTVPSSSL |
| Ab21.H2 | ASTKGPSVFPLAPSSKSTSGGTAALGCLVKDYFPEPVTVSWNSGALTSGVHTFPAVLQSSGLYSLSSVVTVPSSSL |
| Ab21.H3 | ASTKGPSVFPLAPSSKSTSGGTAALGCLVKDYFPEPVTVSWNSGALTSGVHTFPAVLQSSGLYSLSSVVTVPSSSL |
| Ab21.H4 | ASTKGPSVFPLAPSSKSTSGGTAALGCLVKDYFPEPVTVSWNSGALTSGVHTFPAVLQSSGLYSLSSVVTVPSSSL |

Figure 1D

Antibody Heavy chain Protein features

| Sequence Name | Constant region |
|---|---|
| Ab10 | GTQTYICNVNHKPSNTKVDARVEPKSCDKTHTCPPCPAPELLGGPSVFLFPPKPKDTLMISRTPEVTCVVVDVSH |
| Ab20 | GTQTYICNVNHKPSNTKVDKKVEPKSCDKTHTCPPCPAPELLGGPSVFLFPPKPKDTLMISRTPEVTCVVVDVSH |
| Ab21 | GTQTYICNVNHKPSNTKVDKKVEPKSCDKTHTCPPCPAPELLGGPSVFLFPPKPKDTLMISRTPEVTCVVVDVSH |
| Ab22 | GTQTYICNVNHKPSNTKVDARVEPKSCDKTHTCPPCPAPELLGGPSVFLFPPKPKDTLMISRTPEVTCVVVDVSH |
| Ab23 | GTQTYICNVNHKPSNTKVDARVEPKSCDKTHTCPPCPAPELLGGPSVFLFPPKPKDTLMISRTPEVTCVVVDVSH |
| Ab10.H | GTQTYICNVNHKPSNTKVDKKVEPKSCDKTHTCPPCPAPELLGGPSVFLFPPKPKDTLMISRTPEVTCVVVDVSH |
| Ab21.H | GTQTYICNVNHKPSNTKVDKKVEPKSCDKTHTCPPCPAPELLGGPSVFLFPPKPKDTLMISRTPEVTCVVVDVSH |
| Ab10.H2 | GTQTYICNVNHKPSNTKVDKKVEPKSCDKTHTCPPCPAPELLGGPSVFLFPPKPKDTLMISRTPEVTCVVVDVSH |
| Ab10.H3 | GTQTYICNVNHKPSNTKVDKKVEPKSCDKTHTCPPCPAPELLGGPSVFLFPPKPKDTLMISRTPEVTCVVVDVSH |
| Ab10.H4 | GTQTYICNVNHKPSNTKVDKKVEPKSCDKTHTCPPCPAPELLGGPSVFLFPPKPKDTLMISRTPEVTCVVVDVSH |
| Ab10.H5 | GTQTYICNVNHKPSNTKVDKKVEPKSCDKTHTCPPCPAPELLGGPSVFLFPPKPKDTLMISRTPEVTCVVVDVSH |
| Ab10.H6 | GTQTYICNVNHKPSNTKVDKKVEPKSCDKTHTCPPCPAPELLGGPSVFLFPPKPKDTLMISRTPEVTCVVVDVSH |
| Ab21.H2 | GTQTYICNVNHKPSNTKVDKKVEPKSCDKTHTCPPCPAPELLGGPSVFLFPPKPKDTLMISRTPEVTCVVVDVSH |
| Ab21.H3 | GTQTYICNVNHKPSNTKVDKKVEPKSCDKTHTCPPCPAPELLGGPSVFLFPPKPKDTLMISRTPEVTCVVVDVSH |
| Ab21.H4 | GTQTYICNVNHKPSNTKVDKKVEPKSCDKTHTCPPCPAPELLGGPSVFLFPPKPKDTLMISRTPEVTCVVVDVSH |

Figure 1E

Antibody Heavy chain Protein features

| Sequence Name | Constant region |
|---|---|
| Ab10 | EDPEVKFNWYVDGVEVHNAKTKPREEQYASTYRVVSVLTVLHQDWLNGKEYKCKVSNKALPAPIEKTISKAKGQP |
| Ab20 | EDPEVKFNWYVDGVEVHNAKTKPREEQYASTYRVVSVLTVLHQDWLNGKEYKCKVSNKALPAPIEKTISKAKGQP |
| Ab21 | EDPEVKFNWYVDGVEVHNAKTKPREEQYASTYRVVSVLTVLHQDWLNGKEYKCKVSNKALPAPIEKTISKAKGQP |
| Ab22 | EDPEVKFNWYVDGVEVHNAKTKPREEQYASTYRVVSVLTVLHQDWLNGKEYKCKVSNKALPAPIEKTISKAKGQP |
| Ab23 | EDPEVKFNWYVDGVEVHNAKTKPREEQYASTYRVVSVLTVLHQDWLNGKEYKCKVSNKALPAPIEKTISKAKGQP |
| Ab10.H | EDPEVKFNWYVDGVEVHNAKTKPREEQYASTYRVVSVLTVLHQDWLNGKEYKCKVSNKALPAPIEKTISKAKGQP |
| Ab21.H | EDPEVKFNWYVDGVEVHNAKTKPREEQYASTYRVVSVLTVLHQDWLNGKEYKCKVSNKALPAPIEKTISKAKGQP |
| Ab10.H2 | EDPEVKFNWYVDGVEVHNAKTKPREEQYASTYRVVSVLTVLHQDWLNGKEYKCKVSNKALPAPIEKTISKAKGQP |
| Ab10.H3 | EDPEVKFNWYVDGVEVHNAKTKPREEQYASTYRVVSVLTVLHQDWLNGKEYKCKVSNKALPAPIEKTISKAKGQP |
| Ab10.H4 | EDPEVKFNWYVDGVEVHNAKTKPREEQYASTYRVVSVLTVLHQDWLNGKEYKCKVSNKALPAPIEKTISKAKGQP |
| Ab10.H5 | EDPEVKFNWYVDGVEVHNAKTKPREEQYASTYRVVSVLTVLHQDWLNGKEYKCKVSNKALPAPIEKTISKAKGQP |
| Ab10.H6 | EDPEVKFNWYVDGVEVHNAKTKPREEQYASTYRVVSVLTVLHQDWLNGKEYKCKVSNKALPAPIEKTISKAKGQP |
| Ab21.H2 | EDPEVKFNWYVDGVEVHNAKTKPREEQYASTYRVVSVLTVLHQDWLNGKEYKCKVSNKALPAPIEKTISKAKGQP |
| Ab21.H3 | EDPEVKFNWYVDGVEVHNAKTKPREEQYASTYRVVSVLTVLHQDWLNGKEYKCKVSNKALPAPIEKTISKAKGQP |
| Ab21.H4 | EDPEVKFNWYVDGVEVHNAKTKPREEQYASTYRVVSVLTVLHQDWLNGKEYKCKVSNKALPAPIEKTISKAKGQP |

Figure 1F

Antibody Heavy chain Protein features

| Sequence Name | Constant region |
|---|---|
| Ab10 | REPQVYTLPPSREEMTKNQVSLTCLVKGFYPSDIAVEWESNGQPENNYKTTPPVLDSDGSFFLYSKLTVDKSRWQ |
| Ab20 | REPQVYTLPPSREEMTKNQVSLTCLVKGFYPSDIAVEWESNGQPENNYKTTPPVLDSDGSFFLYSKLTVDKSRWQ |
| Ab21 | REPQVYTLPPSREEMTKNQVSLTCLVKGFYPSDIAVEWESNGQPENNYKTTPPVLDSDGSFFLYSKLTVDKSRWQ |
| Ab22 | REPQVYTLPPSREEMTKNQVSLTCLVKGFYPSDIAVEWESNGQPENNYKTTPPVLDSDGSFFLYSKLTVDKSRWQ |
| Ab23 | REPQVYTLPPSREEMTKNQVSLTCLVKGFYPSDIAVEWESNGQPENNYKTTPPVLDSDGSFFLYSKLTVDKSRWQ |
| Ab10.H | REPQVYTLPPSREEMTKNQVSLTCLVKGFYPSDIAVEWESNGQPENNYKTTPPVLDSDGSFFLYSKLTVDKSRWQ |
| Ab21.H | REPQVYTLPPSREEMTKNQVSLTCLVKGFYPSDIAVEWESNGQPENNYKTTPPVLDSDGSFFLYSKLTVDKSRWQ |
| Ab10.H2 | REPQVYTLPPSREEMTKNQVSLTCLVKGFYPSDIAVEWESNGQPENNYKTTPPVLDSDGSFFLYSKLTVDKSRWQ |
| Ab10.H3 | REPQVYTLPPSREEMTKNQVSLTCLVKGFYPSDIAVEWESNGQPENNYKTTPPVLDSDGSFFLYSKLTVDKSRWQ |
| Ab10.H4 | REPQVYTLPPSREEMTKNQVSLTCLVKGFYPSDIAVEWESNGQPENNYKTTPPVLDSDGSFFLYSKLTVDKSRWQ |
| Ab10.H5 | REPQVYTLPPSREEMTKNQVSLTCLVKGFYPSDIAVEWESNGQPENNYKTTPPVLDSDGSFFLYSKLTVDKSRWQ |
| Ab10.H6 | REPQVYTLPPSREEMTKNQVSLTCLVKGFYPSDIAVEWESNGQPENNYKTTPPVLDSDGSFFLYSKLTVDKSRWQ |
| Ab21.H2 | REPQVYTLPPSREEMTKNQVSLTCLVKGFYPSDIAVEWESNGQPENNYKTTPPVLDSDGSFFLYSKLTVDKSRWQ |
| Ab21.H3 | REPQVYTLPPSREEMTKNQVSLTCLVKGFYPSDIAVEWESNGQPENNYKTTPPVLDSDGSFFLYSKLTVDKSRWQ |
| Ab21.H4 | REPQVYTLPPSREEMTKNQVSLTCLVKGFYPSDIAVEWESNGQPENNYKTTPPVLDSDGSFFLYSKLTVDKSRWQ |

Figure 1G

Antibody Heavy chain Protein features

| Sequence Name | Constant region |
|---|---|
| Ab10 | QGNVFSCSVMHEALHNHYTQKSLSLSPGK (SEQ ID NO: 401) |
| Ab20 | QGNVFSCSVMHEALHNHYTQKSLSLSPGK (SEQ ID NO: 441) |
| Ab21 | QGNVFSCSVMHEALHNHYTQKSLSLSPGK (SEQ ID NO: 841) |
| Ab22 | QGNVFSCSVMHEALHNHYTQKSLSLSPGK (SEQ ID NO: 881) |
| Ab23 | QGNVFSCSVMHEALHNHYTQKSLSLSPGK (SEQ ID NO: 921) |
| Ab10.H | QGNVFSCSVMHEALHNHYTQKSLSLSPGK (SEQ ID NO: 961) |
| Ab21.H | QGNVFSCSVMHEALHNHYTQKSLSLSPGK (SEQ ID NO: 1201) |
| Ab10.H2 | QGNVFSCSVMHEALHNHYTQKSLSLSPGK (SEQ ID NO: 1281) |
| Ab10.H3 | QGNVFSCSVMHEALHNHYTQKSLSLSPGK (SEQ ID NO: 1321) |
| Ab10.H4 | QGNVFSCSVMHEALHNHYTQKSLSLSPGK (SEQ ID NO: 1361) |
| Ab10.H5 | QGNVFSCSVMHEALHNHYTQKSLSLSPGK (SEQ ID NO: 1401) |
| Ab10.H6 | QGNVFSCSVMHEALHNHYTQKSLSLSPGK (SEQ ID NO: 1441) |
| Ab21.H2 | QGNVFSCSVMHEALHNHYTQKSLSLSPGK (SEQ ID NO: 1481) |
| Ab21.H3 | QGNVFSCSVMHEALHNHYTQKSLSLSPGK (SEQ ID NO: 1521) |
| Ab21.H4 | QGNVFSCSVMHEALHNHYTQKSLSLSPGK (SEQ ID NO: 1561) |

Figure 2A

Antibody Light chain Protein features

| Sequence Name | FR1 | CDR1 | FR2 | CDR2 |
|---|---|---|---|---|
| Ab10 | AAVLTQTPSPVSAAVGGTVTINC | QSSESVYGNYLA | WFQQKPGQPPKLLIY | EASKLES |
| Ab20 | AAVLTQTPSPVSAAVGGTVSISC | QSSESVYSNYLA | WFQQKPGQPPKFLIY | EASKLAS |
| Ab21 | AAVLTQTPSPVSAAVGGTVSISC | KSSESVYGDYLA | WFQQKPGQPPKQLIY | DASTLAS |
| Ab22 | AAVLTQTPSPVSAAVGGTVTINC | QSSQSVYDNDWLA | WFQQKPGQPPKLLIY | LTSTLAS |
| Ab23 | AIKMTQTPSSVSAAVGGTVTINC | QASEDIYTNLA | WYQQKPGQPPNLLIY | DASDLAS |
| Ab10.H | DAQLTQSPSTLSASVGDRVTITC | QSSESVYGNYLA | WFQQKPGKAPKFLIY | EASKLES |
| Ab21.H | DAQLTQSPSTLSASVGDRVTITC | KSSESVYGDYLA | WFQQKPGKAPKQLIY | DASTLAS |
| Ab10.H2 | AVLTQSPSTLSASVGDRVTITC | QSSESVYGNYLA | WFQQKPGKAPKFLIY | EASKLES |
| Ab10.H3 | DIQLTQSPSTLSASVGDRVTITC | QSSESVYGNYLA | WFQQKPGKAPKFLIY | EASKLES |
| Ab10.H4 | DIVLTQSPSTLSASVGDRVTITC | QSSESVYGNYLA | WFQQKPGKAPKFLIY | EASKLES |
| Ab10.H5 | QLTQSPSTLSASVGDRVTITC | QSSESVYGNYLA | WFQQKPGKAPKFLIY | EASKLES |
| Ab10.H6 | QVLTQSPSTLSASVGDRVTITC | QSSESVYGNYLA | WFQQKPGKAPKFLIY | EASKLES |
| Ab21.H2 | AVLTQSPSTLSASVGDRVTITC | KSSESVYGDYLA | WFQQKPGKAPKQLIY | DASTLAS |
| Ab21.H3 | DIQLTQSPSTLSASVGDRVTITC | KSSESVYGDYLA | WFQQKPGKAPKQLIY | DASTLAS |
| Ab21.H4 | DIVLTQSPSTLSASVGDRVTITC | KSSESVYGDYLA | WFQQKPGKAPKQLIY | DASTLAS |

Figure 2B
Antibody Light chain Protein features

| Sequence Name | FR3 | CDR3 | FR4 |
|---|---|---|---|
| Ab10 | GVPSRFSGSGSGTQFTLTISDLQCDDAATYYC | AGGDISEGVA | FGGGTEVVVKR |
| Ab20 | GVPSRFKGSGSGTQFTLTISDVQCDDAGTYYC | AGGYSSEGVA | FGGGTEVVVKR |
| Ab21 | GVPSRFKGSGSGTQFTLTISGVQCDDAATYYC | AGGYVSAGVA | FGGGTEVVVKR |
| Ab22 | GVPSRFSGSGSGTQFTLTISGVQCDDAATYYC | LGGYDEDGDTHV | FGGGTEVVVKR |
| Ab23 | GVPSRFSGSGDGTQFTLTISAVQCEDAATYYC | QGVAWSSNTGYGSA | FGGGTEVVVKR |
| Ab10.H | GVPSRFSGSGSGTEFTLTISSLQPDDFATYYC | AGGDISEGVA | FGGGTKVEIKR |
| Ab21.H | GVPSRFSGSGSGTEFTLTISSLQPDDFATYYC | AGGYVSAGVA | FGGGTKVEIKR |
| Ab10.H2 | GVPSRFSGSGSGTEFTLTISSLQPDDFATYYC | AGGDISEGVA | FGGGTKVEIKR |
| Ab10.H3 | GVPSRFSGSGSGTEFTLTISSLQPDDFATYYC | AGGDISEGVA | FGGGTKVEIKR |
| Ab10.H4 | GVPSRFSGSGSGTEFTLTISSLQPDDFATYYC | AGGDISEGVA | FGGGTKVEIKR |
| Ab10.H5 | GVPSRFSGSGSGTEFTLTISSLQPDDFATYYC | AGGDISEGVA | FGGGTKVEIKR |
| Ab10.H6 | GVPSRFSGSGSGTEFTLTISSLQPDDFATYYC | AGGDISEGVA | FGGGTKVEIKR |
| Ab21.H2 | GVPSRFSGSGSGTEFTLTISSLQPDDFATYYC | AGGYVSAGVA | FGGGTKVEIKR |
| Ab21.H3 | GVPSRFSGSGSGTEFTLTISSLQPDDFATYYC | AGGYVSAGVA | FGGGTKVEIKR |
| Ab21.H4 | GVPSRFSGSGSGTEFTLTISSLQPDDFATYYC | AGGYVSAGVA | FGGGTKVEIKR |

Figure 2C
Antibody Light chain Protein features

| Sequence Name | Constant region |
|---|---|
| Ab10 | TVAAPSVFIFPPSDEQLKSGTASVVCLLNNFYPREAKVQWKVDNALQSGNSQESVTEQDSKDSTYSLSSTLTLSKA |
| Ab20 | TVAAPSVFIFPPSDEQLKSGTASVVCLLNNFYPREAKVQWKVDNALQSGNSQESVTEQDSKDSTYSLSSTLTLSKA |
| Ab21 | TVAAPSVFIFPPSDEQLKSGTASVVCLLNNFYPREAKVQWKVDNALQSGNSQESVTEQDSKDSTYSLSSTLTLSKA |
| Ab22 | TVAAPSVFIFPPSDEQLKSGTASVVCLLNNFYPREAKVQWKVDNALQSGNSQESVTEQDSKDSTYSLSSTLTLSKA |
| Ab23 | TVAAPSVFIFPPSDEQLKSGTASVVCLLNNFYPREAKVQWKVDNALQSGNSQESVTEQDSKDSTYSLSSTLTLSKA |
| Ab10.H | TVAAPSVFIFPPSDEQLKSGTASVVCLLNNFYPREAKVQWKVDNALQSGNSQESVTEQDSKDSTYSLSSTLTLSKA |
| Ab21.H | TVAAPSVFIFPPSDEQLKSGTASVVCLLNNFYPREAKVQWKVDNALQSGNSQESVTEQDSKDSTYSLSSTLTLSKA |
| Ab10.H2 | TVAAPSVFIFPPSDEQLKSGTASVVCLLNNFYPREAKVQWKVDNALQSGNSQESVTEQDSKDSTYSLSSTLTLSKA |
| Ab10.H3 | TVAAPSVFIFPPSDEQLKSGTASVVCLLNNFYPREAKVQWKVDNALQSGNSQESVTEQDSKDSTYSLSSTLTLSKA |
| Ab10.H4 | TVAAPSVFIFPPSDEQLKSGTASVVCLLNNFYPREAKVQWKVDNALQSGNSQESVTEQDSKDSTYSLSSTLTLSKA |
| Ab10.H5 | TVAAPSVFIFPPSDEQLKSGTASVVCLLNNFYPREAKVQWKVDNALQSGNSQESVTEQDSKDSTYSLSSTLTLSKA |
| Ab10.H6 | TVAAPSVFIFPPSDEQLKSGTASVVCLLNNFYPREAKVQWKVDNALQSGNSQESVTEQDSKDSTYSLSSTLTLSKA |
| Ab21.H2 | TVAAPSVFIFPPSDEQLKSGTASVVCLLNNFYPREAKVQWKVDNALQSGNSQESVTEQDSKDSTYSLSSTLTLSKA |
| Ab21.H3 | TVAAPSVFIFPPSDEQLKSGTASVVCLLNNFYPREAKVQWKVDNALQSGNSQESVTEQDSKDSTYSLSSTLTLSKA |
| Ab21.H4 | TVAAPSVFIFPPSDEQLKSGTASVVCLLNNFYPREAKVQWKVDNALQSGNSQESVTEQDSKDSTYSLSSTLTLSKA |

Figure 2D

Antibody Light chain Protein features

| Sequence Name | Constant region |
| --- | --- |
| Ab10 | DYEKHKVYACEVTHQGLSSPVTKSFNRGEC (SEQ ID NO: 421) |
| Ab20 | DYEKHKVYACEVTHQGLSSPVTKSFNRGEC (SEQ ID NO: 461) |
| Ab21 | DYEKHKVYACEVTHQGLSSPVTKSFNRGEC (SEQ ID NO: 861) |
| Ab22 | DYEKHKVYACEVTHQGLSSPVTKSFNRGEC (SEQ ID NO: 901) |
| Ab23 | DYEKHKVYACEVTHQGLSSPVTKSFNRGEC (SEQ ID NO: 941) |
| Ab10.H | DYEKHKVYACEVTHQGLSSPVTKSFNRGEC (SEQ ID NO: 981) |
| Ab21.H | DYEKHKVYACEVTHQGLSSPVTKSFNRGEC (SEQ ID NO: 1221) |
| Ab10.H2 | DYEKHKVYACEVTHQGLSSPVTKSFNRGEC (SEQ ID NO: 1301) |
| Ab10.H3 | DYEKHKVYACEVTHQGLSSPVTKSFNRGEC (SEQ ID NO: 1341) |
| Ab10.H4 | DYEKHKVYACEVTHQGLSSPVTKSFNRGEC (SEQ ID NO: 1381) |
| Ab10.H5 | DYEKHKVYACEVTHQGLSSPVTKSFNRGEC (SEQ ID NO: 1421) |
| Ab10.H6 | DYEKHKVYACEVTHQGLSSPVTKSFNRGEC (SEQ ID NO: 1461) |
| Ab21.H2 | DYEKHKVYACEVTHQGLSSPVTKSFNRGEC (SEQ ID NO: 1501) |
| Ab21.H3 | DYEKHKVYACEVTHQGLSSPVTKSFNRGEC (SEQ ID NO: 1541) |
| Ab21.H4 | DYEKHKVYACEVTHQGLSSPVTKSFNRGEC (SEQ ID NO: 1581) |

Figure 3A

Antibody Heavy chain DNA features

| Sequence Name | FR1 |
| --- | --- |
| Ab10 | cagtcggtggaggagtccgggggtcgcctggtcacgcctgggacacccctgacactcacctgcacagtctctggaa |
| Ab20 | cagtcggtggaggagtccgggggtcgcctggtcacgcctgggacacccctgacactcacctgcacagtctctggaa |
| Ab21 | cagtcggtggaggagtccgggggtcgcctggtcacgcctgggacacccctgacactcacctgcacagtctctggaa |
| Ab22 | caggagcagctggtggagtccgggggaggcctggtccagcctgagggatccctgacactcacctgcacagcctctg |
| Ab23 | cagtcggtggaggagtccgggggtcgcctggtcacgcctgggacacccctgacactcacctgcaccgtctctggat |
| Ab10.H | gaggtgcagcttgtggagtctgggggaggcttggtccagcctggggggtccctgagactctcctgtgcagcctctg |
| Ab21.H | gaggtgcagcttgtggagtctgggggaggcttggtccagcctggggggtccctgagactctcctgtgcagcctctg |
| Ab10.H2 | gaggtgcagcttgtggagtctgggggaggcttggtccagcctggggggtccctgagactctcctgtgcagcctctg |
| Ab10.H3 | gaggtgcagcttgtggagtctgggggaggcttggtccagcctggggggtccctgagactctcctgtgcagcctctg |
| Ab10.H4 | gaggtgcagcttgtggagtctgggggaggcttggtccagcctggggggtccctgagactctcctgtgcagcctctg |
| Ab10.H5 | gaggtgcagcttgtggagtctgggggaggcttggtccagcctggggggtccctgagactctcctgtgcagcctctg |
| Ab10.H6 | gaggtgcagcttgtggagtctgggggaggcttggtccagcctggggggtccctgagactctcctgtgcagcctctg |
| Ab21.H2 | gaggtgcagcttgtggagtctgggggaggcttggtccagcctggggggtccctgagactctcctgtgcagcctctg |
| Ab21.H3 | gaggtgcagcttgtggagtctgggggaggcttggtccagcctggggggtccctgagactctcctgtgcagcctctg |
| Ab21.H4 | gaggtgcagcttgtggagtctgggggaggcttggtccagcctggggggtccctgagactctcctgtgcagcctctg |

Figure 3B

Antibody Heavy chain DNA features

| Sequence Name | FR1 | CDR1 | FR2 |
|---|---|---|---|
| Ab10 | tcgacctcaat | agctactacatgacc | tgggtccgccaggctccagggaaggggctggaatggatcgga |
| Ab20 | tcgacctcagt | agctactacatgagc | tgggtccgccaggctccagggaaggggctggaatggatcgga |
| Ab21 | tcgacctcagt | agctactacatgacc | tgggtccgccaggctccagggaaggggctggaatgggtcgga |
| Ab22 | gattcgacttcagt | agcaatgcaatgtgc | tgggtccgccaggctccagggaagggcctggagtggatcgga |
| Ab23 | tctccctcaat | aactatgcaatgagc | tgggtccgccaggctccagggaaggggctggaatggatcgga |
| Ab10.H | gaatcgacctcaat | agctactacatgacc | tgggtccgtcaggctccagggaaggggctggagtggatcgga |
| Ab21.H | gaatcgacctcagt | agctactacatgacc | tgggtccgtcaggctccagggaaggggctggagtggatcgga |
| Ab10.H2 | gaatcgacctcaat | agctactacatgacc | tgggtccgtcaggctccagggaaggggctggagtggatcgga |
| Ab10.H3 | gaatcgacctcaat | agctactacatgacc | tgggtccgtcaggctccagggaaggggctggagtggatcgga |
| Ab10.H4 | gaatcgacctcaat | agctactacatgacc | tgggtccgtcaggctccagggaaggggctggagtggatcgga |
| Ab10.H5 | gaatcgacctcaat | agctactacatgacc | tgggtccgtcaggctccagggaaggggctggagtggatcgga |
| Ab10.H6 | gaatcgacctcaat | agctactacatgacc | tgggtccgtcaggctccagggaaggggctggagtggatcgga |
| Ab21.H2 | gaatcgacctcagt | agctactacatgacc | tgggtccgtcaggctccagggaaggggctggagtggatcgga |
| Ab21.H3 | gaatcgacctcagt | agctactacatgacc | tgggtccgtcaggctccagggaaggggctggagtggatcgga |
| Ab21.H4 | gaatcgacctcagt | agctactacatgacc | tgggtccgtcaggctccagggaaggggctggagtggatcgga |

Figure 3C

Antibody Heavy chain DNA features

| Sequence Name | CDR2 | FR3 |
|---|---|---|
| Ab10 | ttcattgatgctggtggtgacgcatactacgcgagctgggcgaaaggc | cgattcaccatctccaaaacctcga |
| Ab20 | ttcattgatactgatggtagcgcatactacgcgacctgggcgaaaggc | cgattcaccatctccaaaacctcga |
| Ab21 | ttcattgatgctggtggtagcgcatactacgcgacctgggcaaaaggc | cgattcaccatctccaaagcctcga |
| Ab22 | tccatttataatgctgatggtaagaattattacgcgatttgggcgaaaggc | cgattcaccatctccagaacctcgt |
| Ab23 | atcatgggtgttaatgatatcacatactacgcgagctgggcgaaaggc | cgattcaccatctccaaaacctcga |
| Ab10.H | ttcattgatgctggtggtgacgcatactacgcgagctgggcgaaaggc | cgattcaccatctccagagacaatt |
| Ab21.H | ttcattgatgctggtggtagcgcatactacgcgacctgggcaaaaggc | cgattcaccatctccagagacaatt |
| Ab10.H2 | ttcattgatgctggtggtgacgcatactacgcgagctgggcgaaaggc | cgattcaccatctccagagacaatt |
| Ab10.H3 | ttcattgatgctggtggtgacgcatactacgcgagctgggcgaaaggc | cgattcaccatctccagagacaatt |
| Ab10.H4 | ttcattgatgctggtggtgacgcatactacgcgagctgggcgaaaggc | cgattcaccatctccagagacaatt |
| Ab10.H5 | ttcattgatgctggtggtgacgcatactacgcgagctgggcgaaaggc | cgattcaccatctccagagacaatt |
| Ab10.H6 | ttcattgatgctggtggtgacgcatactacgcgagctgggcgaaaggc | cgattcaccatctccagagacaatt |
| Ab21.H2 | ttcattgatgctggtggtagcgcatactacgcgacctgggcaaaaggc | cgattcaccatctccagagacaatt |
| Ab21.H3 | ttcattgatgctggtggtagcgcatactacgcgacctgggcaaaaggc | cgattcaccatctccagagacaatt |
| Ab21.H4 | ttcattgatgctggtggtagcgcatactacgcgacctgggcaaaaggc | cgattcaccatctccagagacaatt |

Figure 3D

Antibody Heavy chain DNA features

| Sequence Name | FR3 |
|---|---|
| Ab10 | ccacggtggatctgaaaatcaccagtccgacaaccgaggacacggccacctatttctgtgccaga |
| Ab20 | ccacggtggatctgaaaatcaccagtccgacaaccgaggacacggccacctatttctgtgccaga |
| Ab21 | ccacggtggatctgaaaatcaccagtccgacaaccgaggacacggccacctatttctgtgccaga |
| Ab22 | cgaccacggtgactctgcaaatgaccagtctgacagccgcggacacggccacctatttctgtgcgaga |
| Ab23 | ccacggtggatctgaaaatgaccagtctgacaaccgaggacacggccacctatttctgtactaga |
| Ab10.H | ccaagaacaccgtgtatcttcaaatgaacagcctgagagctgaggacactgctgtgtatttctgtgctaga |
| Ab21.H | ccaagaacaccgtgtatcttcaaatgaacagcctgagagctgaggacactgctgtgtatttctgtgctaga |
| Ab10.H2 | ccaagaacaccgtgtatcttcaaatgaacagcctgagagctgaggacactgctgtgtatttctgtgctaga |
| Ab10.H3 | ccaagaacaccgtgtatcttcaaatgaacagcctgagagctgaggacactgctgtgtatttctgtgctaga |
| Ab10.H4 | ccaagaacaccgtgtatcttcaaatgaacagcctgagagctgaggacactgctgtgtatttctgtgctaga |
| Ab10.H5 | ccaagaacaccgtgtatcttcaaatgaacagcctgagagctgaggacactgctgtgtatttctgtgctaga |
| Ab10.H6 | ccaagaacaccgtgtatcttcaaatgaacagcctgagagctgaggacactgctgtgtatttctgtgctaga |
| Ab21.H2 | ccaagaacaccgtgtatcttcaaatgaacagcctgagagctgaggacactgctgtgtatttctgtgctaga |
| Ab21.H3 | ccaagaacaccgtgtatcttcaaatgaacagcctgagagctgaggacactgctgtgtatttctgtgctaga |
| Ab21.H4 | ccaagaacaccgtgtatcttcaaatgaacagcctgagagctgaggacactgctgtgtatttctgtgctaga |

Figure 3E

Antibody Heavy chain DNA features

| Sequence Name | CDR3 | FR4 |
|---|---|---|
| Ab10 | gatcttgacttg | tggggccagggcaccctggtcaccgtctcgagc |
| Ab20 | gatcttgacttg | tggggcccgggcaccctcgtcaccgtctcgagc |
| Ab21 | gatcttgacttg | tggggcccgggcaccctggtcaccgtctcgagc |
| Ab22 | gactttgacttg | tggggccagggcaccctcgtcaccgtctcgagc |
| Ab23 | gagatccgtgatgatggtgatagttctgataagttg | tggggcccgggcaccctcgtcaccgtctcgagc |
| Ab10.H | gatcttgacttg | tggggccaagggaccctcgtcaccgtctcgagc |
| Ab21.H | gatcttgacttg | tggggccaagggaccctcgtcaccgtctcgagc |
| Ab10.H2 | gatcttgacttg | tggggccaagggaccctcgtcaccgtctcgagc |
| Ab10.H3 | gatcttgacttg | tggggccaagggaccctcgtcaccgtctcgagc |
| Ab10.H4 | gatcttgacttg | tggggccaagggaccctcgtcaccgtctcgagc |
| Ab10.H5 | gatcttgacttg | tggggccaagggaccctcgtcaccgtctcgagc |
| Ab10.H6 | gatcttgacttg | tggggccaagggaccctcgtcaccgtctcgagc |
| Ab21.H2 | gatcttgacttg | tggggccaagggaccctcgtcaccgtctcgagc |
| Ab21.H3 | gatcttgacttg | tggggccaagggaccctcgtcaccgtctcgagc |
| Ab21.H4 | gatcttgacttg | tggggccaagggaccctcgtcaccgtctcgagc |

Figure 3F

Antibody Heavy chain DNA features

| Sequence Name | Constant region |
|---|---|
| Ab10 | gcctccaccaagggcccatcggtcttcccctggcaccctcctccaagagcacctctgggggcacagcggccctgg |
| Ab20 | gcctccaccaagggcccatcggtcttcccctggcaccctcctccaagagcacctctgggggcacagcggccctgg |
| Ab21 | gcctccaccaagggcccatcggtcttcccctggcaccctcctccaagagcacctctgggggcacagcggccctgg |
| Ab22 | gcctccaccaagggcccatcggtcttcccctggcaccctcctccaagagcacctctgggggcacagcggccctgg |
| Ab23 | gcctccaccaagggcccatcggtcttcccctggcaccctcctccaagagcacctctgggggcacagcggccctgg |
| Ab10.H | gcctccaccaagggcccatcggtcttcccctggcaccctcctccaagagcacctctgggggcacagcggccctgg |
| Ab21.H | gcctccaccaagggcccatcggtcttcccctggcaccctcctccaagagcacctctgggggcacagcggccctgg |
| Ab10.H2 | gcctccaccaagggcccatcggtcttcccctggcaccctcctccaagagcacctctgggggcacagcggccctgg |
| Ab10.H3 | gcctccaccaagggcccatcggtcttcccctggcaccctcctccaagagcacctctgggggcacagcggccctgg |
| Ab10.H4 | gcctccaccaagggcccatcggtcttcccctggcaccctcctccaagagcacctctgggggcacagcggccctgg |
| Ab10.H5 | gcctccaccaagggcccatcggtcttcccctggcaccctcctccaagagcacctctgggggcacagcggccctgg |
| Ab10.H6 | gcctccaccaagggcccatcggtcttcccctggcaccctcctccaagagcacctctgggggcacagcggccctgg |
| Ab21.H2 | gcctccaccaagggcccatcggtcttcccctggcaccctcctccaagagcacctctgggggcacagcggccctgg |
| Ab21.H3 | gcctccaccaagggcccatcggtcttcccctggcaccctcctccaagagcacctctgggggcacagcggccctgg |
| Ab21.H4 | gcctccaccaagggcccatcggtcttcccctggcaccctcctccaagagcacctctgggggcacagcggccctgg |

Figure 3G

Antibody Heavy chain DNA features

| Sequence Name | Constant region |
|---|---|
| Ab10 | gctgcctggtcaaggactacttccccgaaccggtgacggtgtcgtggaactcaggcgccctgaccagcggcgtgc |
| Ab20 | gctgcctggtcaaggactacttccccgaaccggtgacggtgtcgtggaactcaggcgccctgaccagcggcgtgc |
| Ab21 | gctgcctggtcaaggactacttccccgaaccggtgacggtgtcgtggaactcaggcgccctgaccagcggcgtgc |
| Ab22 | gctgcctggtcaaggactacttccccgaaccggtgacggtgtcgtggaactcaggcgccctgaccagcggcgtgc |
| Ab23 | gctgcctggtcaaggactacttccccgaaccggtgacggtgtcgtggaactcaggcgccctgaccagcggcgtgc |
| Ab10.H | gctgcctggtcaaggactacttccccgaaccggtgacggtgtcgtggaactcaggcgccctgaccagcggcgtgc |
| Ab21.H | gctgcctggtcaaggactacttccccgaaccggtgacggtgtcgtggaactcaggcgccctgaccagcggcgtgc |
| Ab10.H2 | gctgcctggtcaaggactacttccccgaaccggtgacggtgtcgtggaactcaggcgccctgaccagcggcgtgc |
| Ab10.H3 | gctgcctggtcaaggactacttccccgaaccggtgacggtgtcgtggaactcaggcgccctgaccagcggcgtgc |
| Ab10.H4 | gctgcctggtcaaggactacttccccgaaccggtgacggtgtcgtggaactcaggcgccctgaccagcggcgtgc |
| Ab10.H5 | gctgcctggtcaaggactacttccccgaaccggtgacggtgtcgtggaactcaggcgccctgaccagcggcgtgc |
| Ab10.H6 | gctgcctggtcaaggactacttccccgaaccggtgacggtgtcgtggaactcaggcgccctgaccagcggcgtgc |
| Ab21.H2 | gctgcctggtcaaggactacttccccgaaccggtgacggtgtcgtggaactcaggcgccctgaccagcggcgtgc |
| Ab21.H3 | gctgcctggtcaaggactacttccccgaaccggtgacggtgtcgtggaactcaggcgccctgaccagcggcgtgc |
| Ab21.H4 | gctgcctggtcaaggactacttccccgaaccggtgacggtgtcgtggaactcaggcgccctgaccagcggcgtgc |

Figure 3H

Antibody Heavy chain DNA features

| Sequence Name | Constant region |
|---|---|
| Ab10 | acaccttcccggctgtcctacagtcctcaggactctactccctcagcagcgtggtgaccgtgccctccagcagct |
| Ab20 | acaccttcccggctgtcctacagtcctcaggactctactccctcagcagcgtggtgaccgtgccctccagcagct |
| Ab21 | acaccttcccggctgtcctacagtcctcaggactctactccctcagcagcgtggtgaccgtgccctccagcagct |
| Ab22 | acaccttcccggctgtcctacagtcctcaggactctactccctcagcagcgtggtgaccgtgccctccagcagct |
| Ab23 | acaccttcccggctgtcctacagtcctcaggactctactccctcagcagcgtggtgaccgtgccctccagcagct |
| Ab10.H | acaccttcccggctgtcctacagtcctcaggactctactccctcagcagcgtggtgaccgtgccctccagcagct |
| Ab21.H | acaccttcccggctgtcctacagtcctcaggactctactccctcagcagcgtggtgaccgtgccctccagcagct |
| Ab10.H2 | acaccttcccggctgtcctacagtcctcaggactctactccctcagcagcgtggtgaccgtgccctccagcagct |
| Ab10.H3 | acaccttcccggctgtcctacagtcctcaggactctactccctcagcagcgtggtgaccgtgccctccagcagct |
| Ab10.H4 | acaccttcccggctgtcctacagtcctcaggactctactccctcagcagcgtggtgaccgtgccctccagcagct |
| Ab10.H5 | acaccttcccggctgtcctacagtcctcaggactctactccctcagcagcgtggtgaccgtgccctccagcagct |
| Ab10.H6 | acaccttcccggctgtcctacagtcctcaggactctactccctcagcagcgtggtgaccgtgccctccagcagct |
| Ab21.H2 | acaccttcccggctgtcctacagtcctcaggactctactccctcagcagcgtggtgaccgtgccctccagcagct |
| Ab21.H3 | acaccttcccggctgtcctacagtcctcaggactctactccctcagcagcgtggtgaccgtgccctccagcagct |
| Ab21.H4 | acaccttcccggctgtcctacagtcctcaggactctactccctcagcagcgtggtgaccgtgccctccagcagct |

Figure 3I

Antibody Heavy chain DNA features

| Sequence Name | Constant region |
|---|---|
| Ab10 | tgggcacccagacctacatctgcaacgtgaatcacaagcccagcaacaccaaggtggacgcgagagttgagccca |
| Ab20 | tgggcacccagacctacatctgcaacgtgaatcacaagcccagcaacaccaaggtggacaagaaagttgagccca |
| Ab21 | tgggcacccagacctacatctgcaacgtgaatcacaagcccagcaacaccaaggtggacaagaaagttgagccca |
| Ab22 | tgggcacccagacctacatctgcaacgtgaatcacaagcccagcaacaccaaggtggacgcgagagttgagccca |
| Ab23 | tgggcacccagacctacatctgcaacgtgaatcacaagcccagcaacaccaaggtggacgcgagagttgagccca |
| Ab10.H | tgggcacccagacctacatctgcaacgtgaatcacaagcccagcaacaccaaggtggacaagaaagttgagccca |
| Ab21.H | tgggcacccagacctacatctgcaacgtgaatcacaagcccagcaacaccaaggtggacaagaaagttgagccca |
| Ab10.H2 | tgggcacccagacctacatctgcaacgtgaatcacaagcccagcaacaccaaggtggacaagaaagttgagccca |
| Ab10.H3 | tgggcacccagacctacatctgcaacgtgaatcacaagcccagcaacaccaaggtggacaagaaagttgagccca |
| Ab10.H4 | tgggcacccagacctacatctgcaacgtgaatcacaagcccagcaacaccaaggtggacaagaaagttgagccca |
| Ab10.H5 | tgggcacccagacctacatctgcaacgtgaatcacaagcccagcaacaccaaggtggacaagaaagttgagccca |
| Ab10.H6 | tgggcacccagacctacatctgcaacgtgaatcacaagcccagcaacaccaaggtggacaagaaagttgagccca |
| Ab21.H2 | tgggcacccagacctacatctgcaacgtgaatcacaagcccagcaacaccaaggtggacaagaaagttgagccca |
| Ab21.H3 | tgggcacccagacctacatctgcaacgtgaatcacaagcccagcaacaccaaggtggacaagaaagttgagccca |
| Ab21.H4 | tgggcacccagacctacatctgcaacgtgaatcacaagcccagcaacaccaaggtggacaagaaagttgagccca |

Figure 3J

Antibody Heavy chain DNA features

| Sequence Name | Constant region |
|---|---|
| Ab10 | aatcttgtgacaaaactcacacatgcccaccgtgcccagcacctgaactcctggggggaccgtcagtcttcctct |
| Ab20 | aatcttgtgacaaaactcacacatgcccaccgtgcccagcacctgaactcctggggggaccgtcagtcttcctct |
| Ab21 | aatcttgtgacaaaactcacacatgcccaccgtgcccagcacctgaactcctggggggaccgtcagtcttcctct |
| Ab22 | aatcttgtgacaaaactcacacatgcccaccgtgcccagcacctgaactcctggggggaccgtcagtcttcctct |
| Ab23 | aatcttgtgacaaaactcacacatgcccaccgtgcccagcacctgaactcctggggggaccgtcagtcttcctct |
| Ab10.H | aatcttgtgacaaaactcacacatgcccaccgtgcccagcacctgaactcctggggggaccgtcagtcttcctct |
| Ab21.H | aatcttgtgacaaaactcacacatgcccaccgtgcccagcacctgaactcctggggggaccgtcagtcttcctct |
| Ab10.H2 | aatcttgtgacaaaactcacacatgcccaccgtgcccagcacctgaactcctggggggaccgtcagtcttcctct |
| Ab10.H3 | aatcttgtgacaaaactcacacatgcccaccgtgcccagcacctgaactcctggggggaccgtcagtcttcctct |
| Ab10.H4 | aatcttgtgacaaaactcacacatgcccaccgtgcccagcacctgaactcctggggggaccgtcagtcttcctct |
| Ab10.H5 | aatcttgtgacaaaactcacacatgcccaccgtgcccagcacctgaactcctggggggaccgtcagtcttcctct |
| Ab10.H6 | aatcttgtgacaaaactcacacatgcccaccgtgcccagcacctgaactcctggggggaccgtcagtcttcctct |
| Ab21.H2 | aatcttgtgacaaaactcacacatgcccaccgtgcccagcacctgaactcctggggggaccgtcagtcttcctct |
| Ab21.H3 | aatcttgtgacaaaactcacacatgcccaccgtgcccagcacctgaactcctggggggaccgtcagtcttcctct |
| Ab21.H4 | aatcttgtgacaaaactcacacatgcccaccgtgcccagcacctgaactcctggggggaccgtcagtcttcctct |

Figure 3K

Antibody Heavy chain DNA features

| Sequence Name | Constant region |
|---|---|
| Ab10 | tcccccccaaaacccaaggacaccctcatgatctcccggacccctgaggtcacatgcgtggtggtggacgtgagcc |
| Ab20 | tcccccccaaaacccaaggacaccctcatgatctcccggacccctgaggtcacatgcgtggtggtggacgtgagcc |
| Ab21 | tcccccccaaaacccaaggacaccctcatgatctcccggacccctgaggtcacatgcgtggtggtggacgtgagcc |
| Ab22 | tcccccccaaaacccaaggacaccctcatgatctcccggacccctgaggtcacatgcgtggtggtggacgtgagcc |
| Ab23 | tcccccccaaaacccaaggacaccctcatgatctcccggacccctgaggtcacatgcgtggtggtggacgtgagcc |
| Ab10.H | tcccccccaaaacccaaggacaccctcatgatctcccggacccctgaggtcacatgcgtggtggtggacgtgagcc |
| Ab21.H | tcccccccaaaacccaaggacaccctcatgatctcccggacccctgaggtcacatgcgtggtggtggacgtgagcc |
| Ab10.H2 | tcccccccaaaacccaaggacaccctcatgatctcccggacccctgaggtcacatgcgtggtggtggacgtgagcc |
| Ab10.H3 | tcccccccaaaacccaaggacaccctcatgatctcccggacccctgaggtcacatgcgtggtggtggacgtgagcc |
| Ab10.H4 | tcccccccaaaacccaaggacaccctcatgatctcccggacccctgaggtcacatgcgtggtggtggacgtgagcc |
| Ab10.H5 | tcccccccaaaacccaaggacaccctcatgatctcccggacccctgaggtcacatgcgtggtggtggacgtgagcc |
| Ab10.H6 | tcccccccaaaacccaaggacaccctcatgatctcccggacccctgaggtcacatgcgtggtggtggacgtgagcc |
| Ab21.H2 | tcccccccaaaacccaaggacaccctcatgatctcccggacccctgaggtcacatgcgtggtggtggacgtgagcc |
| Ab21.H3 | tcccccccaaaacccaaggacaccctcatgatctcccggacccctgaggtcacatgcgtggtggtggacgtgagcc |
| Ab21.H4 | tcccccccaaaacccaaggacaccctcatgatctcccggacccctgaggtcacatgcgtggtggtggacgtgagcc |

Figure 3L

Antibody Heavy chain DNA features

| Sequence Name | Constant region |
|---|---|
| Ab10 | acgaagaccctgaggtcaagttcaactggtacgtggacggcgtggaggtgcataatgccaagacaaagccgcggg |
| Ab20 | acgaagaccctgaggtcaagttcaactggtacgtggacggcgtggaggtgcataatgccaagacaaagccgcggg |
| Ab21 | acgaagaccctgaggtcaagttcaactggtacgtggacggcgtggaggtgcataatgccaagacaaagccgcggg |
| Ab22 | acgaagaccctgaggtcaagttcaactggtacgtggacggcgtggaggtgcataatgccaagacaaagccgcggg |
| Ab23 | acgaagaccctgaggtcaagttcaactggtacgtggacggcgtggaggtgcataatgccaagacaaagccgcggg |
| Ab10.H | acgaagaccctgaggtcaagttcaactggtacgtggacggcgtggaggtgcataatgccaagacaaagccgcggg |
| Ab21.H | acgaagaccctgaggtcaagttcaactggtacgtggacggcgtggaggtgcataatgccaagacaaagccgcggg |
| Ab10.H2 | acgaagaccctgaggtcaagttcaactggtacgtggacggcgtggaggtgcataatgccaagacaaagccgcggg |
| Ab10.H3 | acgaagaccctgaggtcaagttcaactggtacgtggacggcgtggaggtgcataatgccaagacaaagccgcggg |
| Ab10.H4 | acgaagaccctgaggtcaagttcaactggtacgtggacggcgtggaggtgcataatgccaagacaaagccgcggg |
| Ab10.H5 | acgaagaccctgaggtcaagttcaactggtacgtggacggcgtggaggtgcataatgccaagacaaagccgcggg |
| Ab10.H6 | acgaagaccctgaggtcaagttcaactggtacgtggacggcgtggaggtgcataatgccaagacaaagccgcggg |
| Ab21.H2 | acgaagaccctgaggtcaagttcaactggtacgtggacggcgtggaggtgcataatgccaagacaaagccgcggg |
| Ab21.H3 | acgaagaccctgaggtcaagttcaactggtacgtggacggcgtggaggtgcataatgccaagacaaagccgcggg |
| Ab21.H4 | acgaagaccctgaggtcaagttcaactggtacgtggacggcgtggaggtgcataatgccaagacaaagccgcggg |

Figure 3M

Antibody Heavy chain DNA features

| Sequence Name | Constant region |
|---|---|
| Ab10 | aggagcagtacgccagcacgtaccgtgtggtcagcgtcctcaccgtcctgcaccaggactggctgaatggcaagg |
| Ab20 | aggagcagtacgccagcacgtaccgtgtggtcagcgtcctcaccgtcctgcaccaggactggctgaatggcaagg |
| Ab21 | aggagcagtacgccagcacgtaccgtgtggtcagcgtcctcaccgtcctgcaccaggactggctgaatggcaagg |
| Ab22 | aggagcagtacgccagcacgtaccgtgtggtcagcgtcctcaccgtcctgcaccaggactggctgaatggcaagg |
| Ab23 | aggagcagtacgccagcacgtaccgtgtggtcagcgtcctcaccgtcctgcaccaggactggctgaatggcaagg |
| Ab10.H | aggagcagtacgccagcacgtaccgtgtggtcagcgtcctcaccgtcctgcaccaggactggctgaatggcaagg |
| Ab21.H | aggagcagtacgccagcacgtaccgtgtggtcagcgtcctcaccgtcctgcaccaggactggctgaatggcaagg |
| Ab10.H2 | aggagcagtacgccagcacgtaccgtgtggtcagcgtcctcaccgtcctgcaccaggactggctgaatggcaagg |
| Ab10.H3 | aggagcagtacgccagcacgtaccgtgtggtcagcgtcctcaccgtcctgcaccaggactggctgaatggcaagg |
| Ab10.H4 | aggagcagtacgccagcacgtaccgtgtggtcagcgtcctcaccgtcctgcaccaggactggctgaatggcaagg |
| Ab10.H5 | aggagcagtacgccagcacgtaccgtgtggtcagcgtcctcaccgtcctgcaccaggactggctgaatggcaagg |
| Ab10.H6 | aggagcagtacgccagcacgtaccgtgtggtcagcgtcctcaccgtcctgcaccaggactggctgaatggcaagg |
| Ab21.H2 | aggagcagtacgccagcacgtaccgtgtggtcagcgtcctcaccgtcctgcaccaggactggctgaatggcaagg |
| Ab21.H3 | aggagcagtacgccagcacgtaccgtgtggtcagcgtcctcaccgtcctgcaccaggactggctgaatggcaagg |
| Ab21.H4 | aggagcagtacgccagcacgtaccgtgtggtcagcgtcctcaccgtcctgcaccaggactggctgaatggcaagg |

Figure 3N
Antibody Heavy chain DNA features

| Sequence Name | Constant region |
| --- | --- |
| Ab10 | agtacaagtgcaaggtctccaacaaagccctcccagcccccatcgagaaaaccatctccaaagccaaagggcagc |
| Ab20 | agtacaagtgcaaggtctccaacaaagccctcccagcccccatcgagaaaaccatctccaaagccaaagggcagc |
| Ab21 | agtacaagtgcaaggtctccaacaaagccctcccagcccccatcgagaaaaccatctccaaagccaaagggcagc |
| Ab22 | agtacaagtgcaaggtctccaacaaagccctcccagcccccatcgagaaaaccatctccaaagccaaagggcagc |
| Ab23 | agtacaagtgcaaggtctccaacaaagccctcccagcccccatcgagaaaaccatctccaaagccaaagggcagc |
| Ab10.H | agtacaagtgcaaggtctccaacaaagccctcccagcccccatcgagaaaaccatctccaaagccaaagggcagc |
| Ab21.H | agtacaagtgcaaggtctccaacaaagccctcccagcccccatcgagaaaaccatctccaaagccaaagggcagc |
| Ab10.H2 | agtacaagtgcaaggtctccaacaaagccctcccagcccccatcgagaaaaccatctccaaagccaaagggcagc |
| Ab10.H3 | agtacaagtgcaaggtctccaacaaagccctcccagcccccatcgagaaaaccatctccaaagccaaagggcagc |
| Ab10.H4 | agtacaagtgcaaggtctccaacaaagccctcccagcccccatcgagaaaaccatctccaaagccaaagggcagc |
| Ab10.H5 | agtacaagtgcaaggtctccaacaaagccctcccagcccccatcgagaaaaccatctccaaagccaaagggcagc |
| Ab10.H6 | agtacaagtgcaaggtctccaacaaagccctcccagcccccatcgagaaaaccatctccaaagccaaagggcagc |
| Ab21.H2 | agtacaagtgcaaggtctccaacaaagccctcccagcccccatcgagaaaaccatctccaaagccaaagggcagc |
| Ab21.H3 | agtacaagtgcaaggtctccaacaaagccctcccagcccccatcgagaaaaccatctccaaagccaaagggcagc |
| Ab21.H4 | agtacaagtgcaaggtctccaacaaagccctcccagcccccatcgagaaaaccatctccaaagccaaagggcagc |

Figure 3O
Antibody Heavy chain DNA features

| Sequence Name | Constant region |
| --- | --- |
| Ab10 | cccgagaaccacaggtgtacaccctgcccccatcccgggaggagatgaccaagaaccaggtcagcctgacctgcc |
| Ab20 | cccgagaaccacaggtgtacaccctgcccccatcccgggaggagatgaccaagaaccaggtcagcctgacctgcc |
| Ab21 | cccgagaaccacaggtgtacaccctgcccccatcccgggaggagatgaccaagaaccaggtcagcctgacctgcc |
| Ab22 | cccgagaaccacaggtgtacaccctgcccccatcccgggaggagatgaccaagaaccaggtcagcctgacctgcc |
| Ab23 | cccgagaaccacaggtgtacaccctgcccccatcccgggaggagatgaccaagaaccaggtcagcctgacctgcc |
| Ab10.H | cccgagaaccacaggtgtacaccctgcccccatcccgggaggagatgaccaagaaccaggtcagcctgacctgcc |
| Ab21.H | cccgagaaccacaggtgtacaccctgcccccatcccgggaggagatgaccaagaaccaggtcagcctgacctgcc |
| Ab10.H2 | cccgagaaccacaggtgtacaccctgcccccatcccgggaggagatgaccaagaaccaggtcagcctgacctgcc |
| Ab10.H3 | cccgagaaccacaggtgtacaccctgcccccatcccgggaggagatgaccaagaaccaggtcagcctgacctgcc |
| Ab10.H4 | cccgagaaccacaggtgtacaccctgcccccatcccgggaggagatgaccaagaaccaggtcagcctgacctgcc |
| Ab10.H5 | cccgagaaccacaggtgtacaccctgcccccatcccgggaggagatgaccaagaaccaggtcagcctgacctgcc |
| Ab10.H6 | cccgagaaccacaggtgtacaccctgcccccatcccgggaggagatgaccaagaaccaggtcagcctgacctgcc |
| Ab21.H2 | cccgagaaccacaggtgtacaccctgcccccatcccgggaggagatgaccaagaaccaggtcagcctgacctgcc |
| Ab21.H3 | cccgagaaccacaggtgtacaccctgcccccatcccgggaggagatgaccaagaaccaggtcagcctgacctgcc |
| Ab21.H4 | cccgagaaccacaggtgtacaccctgcccccatcccgggaggagatgaccaagaaccaggtcagcctgacctgcc |

Figure 3P
Antibody Heavy chain DNA features

| Sequence Name | Constant region |
|---|---|
| Ab10 | tggtcaaaggcttctatcccagcgacatcgccgtggagtgggagagcaatgggcagccggagaacaactacaaga |
| Ab20 | tggtcaaaggcttctatcccagcgacatcgccgtggagtgggagagcaatgggcagccggagaacaactacaaga |
| Ab21 | tggtcaaaggcttctatcccagcgacatcgccgtggagtgggagagcaatgggcagccggagaacaactacaaga |
| Ab22 | tggtcaaaggcttctatcccagcgacatcgccgtggagtgggagagcaatgggcagccggagaacaactacaaga |
| Ab23 | tggtcaaaggcttctatcccagcgacatcgccgtggagtgggagagcaatgggcagccggagaacaactacaaga |
| Ab10.H | tggtcaaaggcttctatcccagcgacatcgccgtggagtgggagagcaatgggcagccggagaacaactacaaga |
| Ab21.H | tggtcaaaggcttctatcccagcgacatcgccgtggagtgggagagcaatgggcagccggagaacaactacaaga |
| Ab10.H2 | tggtcaaaggcttctatcccagcgacatcgccgtggagtgggagagcaatgggcagccggagaacaactacaaga |
| Ab10.H3 | tggtcaaaggcttctatcccagcgacatcgccgtggagtgggagagcaatgggcagccggagaacaactacaaga |
| Ab10.H4 | tggtcaaaggcttctatcccagcgacatcgccgtggagtgggagagcaatgggcagccggagaacaactacaaga |
| Ab10.H5 | tggtcaaaggcttctatcccagcgacatcgccgtggagtgggagagcaatgggcagccggagaacaactacaaga |
| Ab10.H6 | tggtcaaaggcttctatcccagcgacatcgccgtggagtgggagagcaatgggcagccggagaacaactacaaga |
| Ab21.H2 | tggtcaaaggcttctatcccagcgacatcgccgtggagtgggagagcaatgggcagccggagaacaactacaaga |
| Ab21.H3 | tggtcaaaggcttctatcccagcgacatcgccgtggagtgggagagcaatgggcagccggagaacaactacaaga |
| Ab21.H4 | tggtcaaaggcttctatcccagcgacatcgccgtggagtgggagagcaatgggcagccggagaacaactacaaga |

Figure 3Q
Antibody Heavy chain DNA features

| Sequence Name | Constant region |
|---|---|
| Ab10 | ccacgcctcccgtgctggactccgacggctccttcttcctctacagcaagctcaccgtggacaagagcaggtggc |
| Ab20 | ccacgcctcccgtgctggactccgacggctccttcttcctctacagcaagctcaccgtggacaagagcaggtggc |
| Ab21 | ccacgcctcccgtgctggactccgacggctccttcttcctctacagcaagctcaccgtggacaagagcaggtggc |
| Ab22 | ccacgcctcccgtgctggactccgacggctccttcttcctctacagcaagctcaccgtggacaagagcaggtggc |
| Ab23 | ccacgcctcccgtgctggactccgacggctccttcttcctctacagcaagctcaccgtggacaagagcaggtggc |
| Ab10.H | ccacgcctcccgtgctggactccgacggctccttcttcctctacagcaagctcaccgtggacaagagcaggtggc |
| Ab21.H | ccacgcctcccgtgctggactccgacggctccttcttcctctacagcaagctcaccgtggacaagagcaggtggc |
| Ab10.H2 | ccacgcctcccgtgctggactccgacggctccttcttcctctacagcaagctcaccgtggacaagagcaggtggc |
| Ab10.H3 | ccacgcctcccgtgctggactccgacggctccttcttcctctacagcaagctcaccgtggacaagagcaggtggc |
| Ab10.H4 | ccacgcctcccgtgctggactccgacggctccttcttcctctacagcaagctcaccgtggacaagagcaggtggc |
| Ab10.H5 | ccacgcctcccgtgctggactccgacggctccttcttcctctacagcaagctcaccgtggacaagagcaggtggc |
| Ab10.H6 | ccacgcctcccgtgctggactccgacggctccttcttcctctacagcaagctcaccgtggacaagagcaggtggc |
| Ab21.H2 | ccacgcctcccgtgctggactccgacggctccttcttcctctacagcaagctcaccgtggacaagagcaggtggc |
| Ab21.H3 | ccacgcctcccgtgctggactccgacggctccttcttcctctacagcaagctcaccgtggacaagagcaggtggc |
| Ab21.H4 | ccacgcctcccgtgctggactccgacggctccttcttcctctacagcaagctcaccgtggacaagagcaggtggc |

Figure 3R

Antibody Heavy chain DNA features

| Sequence Name | Constant region |
|---|---|
| Ab10 | agcaggggaacgtcttctcatgctccgtgatgcatgaggctctgcacaaccactacacgcagaagagcctctccc |
| Ab20 | agcaggggaacgtcttctcatgctccgtgatgcatgaggctctgcacaaccactacacgcagaagagcctctccc |
| Ab21 | agcaggggaacgtcttctcatgctccgtgatgcatgaggctctgcacaaccactacacgcagaagagcctctccc |
| Ab22 | agcaggggaacgtcttctcatgctccgtgatgcatgaggctctgcacaaccactacacgcagaagagcctctccc |
| Ab23 | agcaggggaacgtcttctcatgctccgtgatgcatgaggctctgcacaaccactacacgcagaagagcctctccc |
| Ab10.H | agcaggggaacgtcttctcatgctccgtgatgcatgaggctctgcacaaccactacacgcagaagagcctctccc |
| Ab21.H | agcaggggaacgtcttctcatgctccgtgatgcatgaggctctgcacaaccactacacgcagaagagcctctccc |
| Ab10.H2 | agcaggggaacgtcttctcatgctccgtgatgcatgaggctctgcacaaccactacacgcagaagagcctctccc |
| Ab10.H3 | agcaggggaacgtcttctcatgctccgtgatgcatgaggctctgcacaaccactacacgcagaagagcctctccc |
| Ab10.H4 | agcaggggaacgtcttctcatgctccgtgatgcatgaggctctgcacaaccactacacgcagaagagcctctccc |
| Ab10.H5 | agcaggggaacgtcttctcatgctccgtgatgcatgaggctctgcacaaccactacacgcagaagagcctctccc |
| Ab10.H6 | agcaggggaacgtcttctcatgctccgtgatgcatgaggctctgcacaaccactacacgcagaagagcctctccc |
| Ab21.H2 | agcaggggaacgtcttctcatgctccgtgatgcatgaggctctgcacaaccactacacgcagaagagcctctccc |
| Ab21.H3 | agcaggggaacgtcttctcatgctccgtgatgcatgaggctctgcacaaccactacacgcagaagagcctctccc |
| Ab21.H4 | agcaggggaacgtcttctcatgctccgtgatgcatgaggctctgcacaaccactacacgcagaagagcctctccc |

Figure 3S

Antibody Heavy chain DNA features

| Sequence Name | Constant region |
|---|---|
| Ab10 | tgtctccgggtaaa (SEQ ID_NO: 411) |
| Ab20 | tgtctccgggtaaa (SEQ ID_NO: 451) |
| Ab21 | tgtctccgggtaaa (SEQ ID_NO: 851) |
| Ab22 | tgtctccgggtaaa (SEQ ID_NO: 891) |
| Ab23 | tgtctccgggtaaa (SEQ ID_NO: 931) |
| Ab10.H | tgtctccgggtaaa (SEQ ID_NO: 971) |
| Ab21.H | tgtctccgggtaaa (SEQ ID_NO: 1211) |
| Ab10.H2 | tgtctccgggtaaa (SEQ ID_NO: 1291) |
| Ab10.H3 | tgtctccgggtaaa (SEQ ID_NO: 1331) |
| Ab10.H4 | tgtctccgggtaaa (SEQ ID_NO: 1371) |
| Ab10.H5 | tgtctccgggtaaa (SEQ ID_NO: 1411) |
| Ab10.H6 | tgtctccgggtaaa (SEQ ID_NO: 1451) |
| Ab21.H2 | tgtctccgggtaaa (SEQ ID_NO: 1491) |
| Ab21.H3 | tgtctccgggtaaa (SEQ ID_NO: 1531) |
| Ab21.H4 | tgtctccgggtaaa (SEQ ID_NO: 1571) |

Figure 4A

Antibody Light chain DNA features

| Sequence Name | FR1 |
|---|---|
| Ab10 | gccgccgtgctgacccagactccatctcccgtgtctgcagctgtgggaggcacagtcaccatcaattgc |
| Ab20 | gccgccgtgctgacccagactccatctcccgtgtctgcagctgtgggaggcacagtcagcatcagttgc |
| Ab21 | gccgccgtgctgacccagactccatctcccgtgtctgcagctgtgggaggcacagtcagcatcagttgc |
| Ab22 | gcagccgtgctgacccagacaccatcgcccgtgtctgcagctgtgggaggcacagtcaccatcaattgc |
| Ab23 | gccatcaaaatgacccagactccatcctccgtgtctgcagctgtgggaggcacagtcaccatcaattgc |
| Ab10.H | gacgcccagctgacccagtctccttccaccctgtctgcatctgtaggagacagagtcaccatcacttgt |
| Ab21.H | gacgcccagctgacccagtctccttccaccctgtctgcatctgtaggagacagagtcaccatcacttgt |
| Ab10.H2 | gccgtgctgacccagtctccttccaccctgtctgcatctgtaggagacagagtcaccatcacttgt |
| Ab10.H3 | gacatccagctgacccagtctccttccaccctgtctgcatctgtaggagacagagtcaccatcacttgt |
| Ab10.H4 | gacatcgtgctgacccagtctccttccaccctgtctgcatctgtaggagacagagtcaccatcacttgt |
| Ab10.H5 | cagctgacccagtctccttccaccctgtctgcatctgtaggagacagagtcaccatcacttgt |
| Ab10.H6 | caggtgctgacccagtctccttccaccctgtctgcatctgtaggagacagagtcaccatcacttgt |
| Ab21.H2 | gccgtgctgacccagtctccttccaccctgtctgcatctgtaggagacagagtcaccatcacttgt |
| Ab21.H3 | gacatccagctgacccagtctccttccaccctgtctgcatctgtaggagacagagtcaccatcacttgt |
| Ab21.H4 | gacatcgtgctgacccagtctccttccaccctgtctgcatctgtaggagacagagtcaccatcacttgt |

Figure 4B

Antibody Light chain DNA features

| Sequence Name | CDR1 | FR2 |
|---|---|---|
| Ab10 | cagtccagtgagagtgtttacggtaactacttagcc | tggtttcagcagaaaccagggcagcctcccaagctcc |
| Ab20 | cagtccagtgagagtgtttatagtaactacttagcc | tggtttcagcagaaaccagggcagcctcctaagttct |
| Ab21 | aagtccagtgagagcgtttatggtgactacttagcc | tggtttcagcagaaaccagggcagcctcccaagcaac |
| Ab22 | cagtccagtcagagtgtttatgataacgactggttagcc | tggttccagcagaaaccagggcagcctcccaagctcc |
| Ab23 | caggccagtgaggacatttacaccaatttagcc | tggtatcagcagaaaccagggcagcctcccaacctcc |
| Ab10.H | cagtccagtgagagtgtttacggtaactacttagcc | tggtttcagcagaaaccaggaaaagcccctaagttcc |
| Ab21.H | aagtccagtgagagcgtttatggtgactacttagcc | tggtttcagcagaaaccaggaaaagcccctaagcaac |
| Ab10.H2 | cagtccagtgagagtgtttacggtaactacttagcc | tggtttcagcagaaaccaggaaaagcccctaagttcc |
| Ab10.H3 | cagtccagtgagagtgtttacggtaactacttagcc | tggtttcagcagaaaccaggaaaagcccctaagttcc |
| Ab10.H4 | cagtccagtgagagtgtttacggtaactacttagcc | tggtttcagcagaaaccaggaaaagcccctaagttcc |
| Ab10.H5 | cagtccagtgagagtgtttacggtaactacttagcc | tggtttcagcagaaaccaggaaaagcccctaagttcc |
| Ab10.H6 | cagtccagtgagagtgtttacggtaactacttagcc | tggtttcagcagaaaccaggaaaagcccctaagttcc |
| Ab21.H2 | aagtccagtgagagcgtttatggtgactacttagcc | tggtttcagcagaaaccaggaaaagcccctaagcaac |
| Ab21.H3 | aagtccagtgagagcgtttatggtgactacttagcc | tggtttcagcagaaaccaggaaaagcccctaagcaac |
| Ab21.H4 | aagtccagtgagagcgtttatggtgactacttagcc | tggtttcagcagaaaccaggaaaagcccctaagcaac |

Figure 4C
Antibody Light chain DNA features

| Sequence Name | FR2 | CDR2 | FR3 |
|---|---|---|---|
| Ab10 | tgatctac | gaagcatccaaactggaatct | ggggtcccatcgcggttcagcggcagtggatctgggacacagttca |
| Ab20 | tgatctac | gaagcatccaaactggcatct | ggggtcccatcgcggttcaaaggcagtggatctgggacacagttca |
| Ab21 | tgatctat | gatgcatccactctggcatct | ggggtcccatcgcggttcaaaggcagtggatctgggacacagttca |
| Ab22 | tgatctat | ctgacatccactctggcatct | ggagtcccatcgcggttcagcggcagtggatctgggacacagttca |
| Ab23 | tgatctat | gatgcatccgatctggcatct | ggggtcccgtcgcggttcagcggcagtggagatgggacacagttca |
| Ab10.H | tgatctat | gaagcatccaaactggaatct | ggagtcccatcaaggttcagcggcagtggatctggaacagaattca |
| Ab21.H | tgatctat | gatgcatccactctggcatct | ggagtcccatcaaggttcagcggcagtggatctggaacagaattca |
| Ab10.H2 | tgatctat | gaagcatccaaactggaatct | ggagtcccatcaaggttcagcggcagtggatctggaacagaattca |
| Ab10.H3 | tgatctat | gaagcatccaaactggaatct | ggagtcccatcaaggttcagcggcagtggatctggaacagaattca |
| Ab10.H4 | tgatctat | gaagcatccaaactggaatct | ggagtcccatcaaggttcagcggcagtggatctggaacagaattca |
| Ab10.H5 | tgatctat | gaagcatccaaactggaatct | ggagtcccatcaaggttcagcggcagtggatctggaacagaattca |
| Ab10.H6 | tgatctat | gaagcatccaaactggaatct | ggagtcccatcaaggttcagcggcagtggatctggaacagaattca |
| Ab21.H2 | tgatctat | gatgcatccactctggcatct | ggagtcccatcaaggttcagcggcagtggatctggaacagaattca |
| Ab21.H3 | tgatctat | gatgcatccactctggcatct | ggagtcccatcaaggttcagcggcagtggatctggaacagaattca |
| Ab21.H4 | tgatctat | gatgcatccactctggcatct | ggagtcccatcaaggttcagcggcagtggatctggaacagaattca |

Figure 4D
Antibody Light chain DNA features

| Sequence Name | FR3 | CDR3 |
|---|---|---|
| Ab10 | ctctcaccatcagcgacttgcagtgtgacgatgctgccacttactactgt | gcaggcggtgatattagtgaaggtg |
| Ab20 | ctctcaccatcagcgacgtgcagtgtgacgatgctggcacttactactgt | gcaggcggctatagtagtgaaggtg |
| Ab21 | ctctcaccatcagcggcgtgcagtgtgacgatgctgccacttactactgt | gcaggcggttatgttagtgcaggtg |
| Ab22 | ctctcaccatcagtggtgtgcagtgtgacgatgctgccacttactactgt | ctaggcggctatgatgaagatggtg |
| Ab23 | ctctcaccatcagcgccgtgcagtgtgaagatgctgccacttactactgt | caaggtgttgcttggagtagtaata |
| Ab10.H | ctctcaccatcagcagcctgcagcctgatgattttgcaacttactactgt | gcaggcggtgatattagtgaaggtg |
| Ab21.H | ctctcaccatcagcagcctgcagcctgatgattttgcaacttactactgt | gcaggcggttatgttagtgcaggtg |
| Ab10.H2 | ctctcaccatcagcagcctgcagcctgatgattttgcaacttactactgt | gcaggcggtgatattagtgaaggtg |
| Ab10.H3 | ctctcaccatcagcagcctgcagcctgatgattttgcaacttactactgt | gcaggcggtgatattagtgaaggtg |
| Ab10.H4 | ctctcaccatcagcagcctgcagcctgatgattttgcaacttactactgt | gcaggcggtgatattagtgaaggtg |
| Ab10.H5 | ctctcaccatcagcagcctgcagcctgatgattttgcaacttactactgt | gcaggcggtgatattagtgaaggtg |
| Ab10.H6 | ctctcaccatcagcagcctgcagcctgatgattttgcaacttactactgt | gcaggcggtgatattagtgaaggtg |
| Ab21.H2 | ctctcaccatcagcagcctgcagcctgatgattttgcaacttactactgt | gcaggcggttatgttagtgcaggtg |
| Ab21.H3 | ctctcaccatcagcagcctgcagcctgatgattttgcaacttactactgt | gcaggcggttatgttagtgcaggtg |
| Ab21.H4 | ctctcaccatcagcagcctgcagcctgatgattttgcaacttactactgt | gcaggcggttatgttagtgcaggtg |

Figure 4E

Antibody Light chain DNA features

| Sequence Name | CDR3 | FR4 | Constant region |
|---|---|---|---|
| Ab10 | ttgct | ttcggcggagggaccgaggtggtggtcaaacgt | acggtagcggccccatctgtcttca |
| Ab20 | ttgct | ttcggcggagggaccgaggtggtggtcaaacgt | acggtagcggccccatctgtcttca |
| Ab21 | ttgct | ttcggcggagggaccgaggtggtggtcaaacgt | acggtagcggccccatctgtcttca |
| Ab22 | atacgcatgtt | ttcggcggagggaccgaggtggtggtcaaacgt | acggtagcggccccatctgtcttca |
| Ab23 | ctggttatggttccgct | ttcggcggagggaccgaggtggtggtcaaacgt | acggtagcggccccatctgtcttca |
| Ab10.H | ttgct | ttcggcggaggaaccaaggtggaaatcaaacgt | acggtagcggccccatctgtcttca |
| Ab21.H | ttgct | ttcggcggaggaaccaaggtggaaatcaaacgt | acggtagcggccccatctgtcttca |
| Ab10.H2 | ttgct | ttcggcggaggaaccaaggtggaaatcaaacgt | acggtagcggccccatctgtcttca |
| Ab10.H3 | ttgct | ttcggcggaggaaccaaggtggaaatcaaacgt | acggtagcggccccatctgtcttca |
| Ab10.H4 | ttgct | ttcggcggaggaaccaaggtggaaatcaaacgt | acggtagcggccccatctgtcttca |
| Ab10.H5 | ttgct | ttcggcggaggaaccaaggtggaaatcaaacgt | acggtagcggccccatctgtcttca |
| Ab10.H6 | ttgct | ttcggcggaggaaccaaggtggaaatcaaacgt | acggtagcggccccatctgtcttca |
| Ab21.H2 | ttgct | ttcggcggaggaaccaaggtggaaatcaaacgt | acggtagcggccccatctgtcttca |
| Ab21.H3 | ttgct | ttcggcggaggaaccaaggtggaaatcaaacgt | acggtagcggccccatctgtcttca |
| Ab21.H4 | ttgct | ttcggcggaggaaccaaggtggaaatcaaacgt | acggtagcggccccatctgtcttca |

Figure 4F

Antibody Light chain DNA features

| Sequence Name | Constant region |
|---|---|
| Ab10 | tcttcccgccatctgatgagcagttgaaatctggaactgcctctgttgtgtgcctgctgaataacttctatccca |
| Ab20 | tcttcccgccatctgatgagcagttgaaatctggaactgcctctgttgtgtgcctgctgaataacttctatccca |
| Ab21 | tcttcccgccatctgatgagcagttgaaatctggaactgcctctgttgtgtgcctgctgaataacttctatccca |
| Ab22 | tcttcccgccatctgatgagcagttgaaatctggaactgcctctgttgtgtgcctgctgaataacttctatccca |
| Ab23 | tcttcccgccatctgatgagcagttgaaatctggaactgcctctgttgtgtgcctgctgaataacttctatccca |
| Ab10.H | tcttcccgccatctgatgagcagttgaaatctggaactgcctctgttgtgtgcctgctgaataacttctatccca |
| Ab21.H | tcttcccgccatctgatgagcagttgaaatctggaactgcctctgttgtgtgcctgctgaataacttctatccca |
| Ab10.H2 | tcttcccgccatctgatgagcagttgaaatctggaactgcctctgttgtgtgcctgctgaataacttctatccca |
| Ab10.H3 | tcttcccgccatctgatgagcagttgaaatctggaactgcctctgttgtgtgcctgctgaataacttctatccca |
| Ab10.H4 | tcttcccgccatctgatgagcagttgaaatctggaactgcctctgttgtgtgcctgctgaataacttctatccca |
| Ab10.H5 | tcttcccgccatctgatgagcagttgaaatctggaactgcctctgttgtgtgcctgctgaataacttctatccca |
| Ab10.H6 | tcttcccgccatctgatgagcagttgaaatctggaactgcctctgttgtgtgcctgctgaataacttctatccca |
| Ab21.H2 | tcttcccgccatctgatgagcagttgaaatctggaactgcctctgttgtgtgcctgctgaataacttctatccca |
| Ab21.H3 | tcttcccgccatctgatgagcagttgaaatctggaactgcctctgttgtgtgcctgctgaataacttctatccca |
| Ab21.H4 | tcttcccgccatctgatgagcagttgaaatctggaactgcctctgttgtgtgcctgctgaataacttctatccca |

Figure 4G

Antibody Light chain DNA features

| Sequence Name | Constant region |
|---|---|
| Ab10 | gagaggccaaagtacagtggaaggtggataacgccctccaatcgggtaactcccaggagagtgtcacagagcagg |
| Ab20 | gagaggccaaagtacagtggaaggtggataacgccctccaatcgggtaactcccaggagagtgtcacagagcagg |
| Ab21 | gagaggccaaagtacagtggaaggtggataacgccctccaatcgggtaactcccaggagagtgtcacagagcagg |
| Ab22 | gagaggccaaagtacagtggaaggtggataacgccctccaatcgggtaactcccaggagagtgtcacagagcagg |
| Ab23 | gagaggccaaagtacagtggaaggtggataacgccctccaatcgggtaactcccaggagagtgtcacagagcagg |
| Ab10.H | gagaggccaaagtacagtggaaggtggataacgccctccaatcgggtaactcccaggagagtgtcacagagcagg |
| Ab21.H | gagaggccaaagtacagtggaaggtggataacgccctccaatcgggtaactcccaggagagtgtcacagagcagg |
| Ab10.H2 | gagaggccaaagtacagtggaaggtggataacgccctccaatcgggtaactcccaggagagtgtcacagagcagg |
| Ab10.H3 | gagaggccaaagtacagtggaaggtggataacgccctccaatcgggtaactcccaggagagtgtcacagagcagg |
| Ab10.H4 | gagaggccaaagtacagtggaaggtggataacgccctccaatcgggtaactcccaggagagtgtcacagagcagg |
| Ab10.H5 | gagaggccaaagtacagtggaaggtggataacgccctccaatcgggtaactcccaggagagtgtcacagagcagg |
| Ab10.H6 | gagaggccaaagtacagtggaaggtggataacgccctccaatcgggtaactcccaggagagtgtcacagagcagg |
| Ab21.H2 | gagaggccaaagtacagtggaaggtggataacgccctccaatcgggtaactcccaggagagtgtcacagagcagg |
| Ab21.H3 | gagaggccaaagtacagtggaaggtggataacgccctccaatcgggtaactcccaggagagtgtcacagagcagg |
| Ab21.H4 | gagaggccaaagtacagtggaaggtggataacgccctccaatcgggtaactcccaggagagtgtcacagagcagg |

Figure 4H

Antibody Light chain DNA features

| Sequence Name | Constant region |
|---|---|
| Ab10 | acagcaaggacagcacctacagcctcagcagcaccctgacgctgagcaaagcagactacgagaaacacaaagtct |
| Ab20 | acagcaaggacagcacctacagcctcagcagcaccctgacgctgagcaaagcagactacgagaaacacaaagtct |
| Ab21 | acagcaaggacagcacctacagcctcagcagcaccctgacgctgagcaaagcagactacgagaaacacaaagtct |
| Ab22 | acagcaaggacagcacctacagcctcagcagcaccctgacgctgagcaaagcagactacgagaaacacaaagtct |
| Ab23 | acagcaaggacagcacctacagcctcagcagcaccctgacgctgagcaaagcagactacgagaaacacaaagtct |
| Ab10.H | acagcaaggacagcacctacagcctcagcagcaccctgacgctgagcaaagcagactacgagaaacacaaagtct |
| Ab21.H | acagcaaggacagcacctacagcctcagcagcaccctgacgctgagcaaagcagactacgagaaacacaaagtct |
| Ab10.H2 | acagcaaggacagcacctacagcctcagcagcaccctgacgctgagcaaagcagactacgagaaacacaaagtct |
| Ab10.H3 | acagcaaggacagcacctacagcctcagcagcaccctgacgctgagcaaagcagactacgagaaacacaaagtct |
| Ab10.H4 | acagcaaggacagcacctacagcctcagcagcaccctgacgctgagcaaagcagactacgagaaacacaaagtct |
| Ab10.H5 | acagcaaggacagcacctacagcctcagcagcaccctgacgctgagcaaagcagactacgagaaacacaaagtct |
| Ab10.H6 | acagcaaggacagcacctacagcctcagcagcaccctgacgctgagcaaagcagactacgagaaacacaaagtct |
| Ab21.H2 | acagcaaggacagcacctacagcctcagcagcaccctgacgctgagcaaagcagactacgagaaacacaaagtct |
| Ab21.H3 | acagcaaggacagcacctacagcctcagcagcaccctgacgctgagcaaagcagactacgagaaacacaaagtct |
| Ab21.H4 | acagcaaggacagcacctacagcctcagcagcaccctgacgctgagcaaagcagactacgagaaacacaaagtct |

Figure 4I

Antibody Light chain DNA features

| Sequence Name | Constant region |
|---|---|
| Ab10 | acgcctgcgaagtcacccatcagggcctgagctcgcccgtcacaaagagcttcaacaggggagagtgt |
| Ab20 | acgcctgcgaagtcacccatcagggcctgagctcgcccgtcacaaagagcttcaacaggggagagtgt |
| Ab21 | acgcctgcgaagtcacccatcagggcctgagctcgcccgtcacaaagagcttcaacaggggagagtgt |
| Ab22 | acgcctgcgaagtcacccatcagggcctgagctcgcccgtcacaaagagcttcaacaggggagagtgt |
| Ab23 | acgcctgcgaagtcacccatcagggcctgagctcgcccgtcacaaagagcttcaacaggggagagtgt |
| Ab10.H | acgcctgcgaagtcacccatcagggcctgagctcgcccgtcacaaagagcttcaacaggggagagtgt |
| Ab21.H | acgcctgcgaagtcacccatcagggcctgagctcgcccgtcacaaagagcttcaacaggggagagtgt |
| Ab10.H2 | acgcctgcgaagtcacccatcagggcctgagctcgcccgtcacaaagagcttcaacaggggagagtgt |
| Ab10.H3 | acgcctgcgaagtcacccatcagggcctgagctcgcccgtcacaaagagcttcaacaggggagagtgt |
| Ab10.H4 | acgcctgcgaagtcacccatcagggcctgagctcgcccgtcacaaagagcttcaacaggggagagtgt |
| Ab10.H5 | acgcctgcgaagtcacccatcagggcctgagctcgcccgtcacaaagagcttcaacaggggagagtgt |
| Ab10.H6 | acgcctgcgaagtcacccatcagggcctgagctcgcccgtcacaaagagcttcaacaggggagagtgt |
| Ab21.H2 | acgcctgcgaagtcacccatcagggcctgagctcgcccgtcacaaagagcttcaacaggggagagtgt |
| Ab21.H3 | acgcctgcgaagtcacccatcagggcctgagctcgcccgtcacaaagagcttcaacaggggagagtgt |
| Ab21.H4 | acgcctgcgaagtcacccatcagggcctgagctcgcccgtcacaaagagcttcaacaggggagagtgt |

Figure 4J

Antibody Light chain DNA features

| Sequence Name | Constant region |
|---|---|
| Ab10 | (SEQ ID NO: 431) |
| Ab20 | (SEQ ID NO: 471) |
| Ab21 | (SEQ ID NO: 871) |
| Ab22 | (SEQ ID NO: 911) |
| Ab23 | (SEQ ID NO: 951) |
| Ab10.H | (SEQ ID NO: 991) |
| Ab21.H | (SEQ ID NO: 1231) |
| Ab10.H2 | (SEQ ID NO: 1311) |
| Ab10.H3 | (SEQ ID NO: 1351) |
| Ab10.H4 | (SEQ ID NO: 1391) |
| Ab10.H5 | (SEQ ID NO: 1431) |
| Ab10.H6 | (SEQ ID NO: 1471) |
| Ab21.H2 | (SEQ ID NO: 1511) |
| Ab21.H3 | (SEQ ID NO: 1551) |
| Ab21.H4 | (SEQ ID NO: 1591) |

Figure 5

Antibody Heavy chain Protein features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab10 | 1-109 | 402 | 30-34 | 404 | 49-64 | 406 | 95-98 | 408 |
| Ab20 | 1-109 | 442 | 30-34 | 444 | 49-64 | 446 | 95-98 | 448 |
| Ab21 | 1-109 | 842 | 30-34 | 844 | 49-64 | 846 | 95-98 | 848 |
| Ab22 | 1-112 | 882 | 31-35 | 884 | 50-66 | 886 | 98-101 | 888 |
| Ab23 | 1-117 | 922 | 30-34 | 924 | 49-64 | 926 | 95-106 | 928 |
| Ab10.H | 1-112 | 962 | 31-35 | 964 | 50-65 | 966 | 98-101 | 968 |
| Ab21.H | 1-112 | 1202 | 31-35 | 1204 | 50-65 | 1206 | 98-101 | 1208 |
| Ab10.H2 | 1-112 | 1282 | 31-35 | 1284 | 50-65 | 1286 | 98-101 | 1288 |
| Ab10.H3 | 1-112 | 1322 | 31-35 | 1324 | 50-65 | 1326 | 98-101 | 1328 |
| Ab10.H4 | 1-112 | 1362 | 31-35 | 1364 | 50-65 | 1366 | 98-101 | 1368 |
| Ab10.H5 | 1-112 | 1402 | 31-35 | 1404 | 50-65 | 1406 | 98-101 | 1408 |
| Ab10.H6 | 1-112 | 1442 | 31-35 | 1444 | 50-65 | 1446 | 98-101 | 1448 |
| Ab21.H2 | 1-112 | 1482 | 31-35 | 1484 | 50-65 | 1486 | 98-101 | 1488 |
| Ab21.H3 | 1-112 | 1522 | 31-35 | 1524 | 50-65 | 1526 | 98-101 | 1528 |
| Ab21.H4 | 1-112 | 1562 | 31-35 | 1564 | 50-65 | 1566 | 98-101 | 1568 |

Figure 6
Antibody Heavy chain Protein features

| Sequence Name | FR1 coordinates | SEQ ID NC: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab10 | 1-29 | 403 | 35-48 | 405 | 65-94 | 407 | 99-109 | 409 | 110-439 | 410 |
| Ab20 | 1-29 | 443 | 35-48 | 445 | 65-94 | 447 | 99-109 | 449 | 110-439 | 450 |
| Ab21 | 1-29 | 843 | 35-48 | 845 | 65-94 | 847 | 99-109 | 849 | 110-439 | 850 |
| Ab22 | 1-30 | 883 | 36-49 | 885 | 67-97 | 887 | 102-112 | 889 | 113-442 | 890 |
| Ab23 | 1-29 | 923 | 35-48 | 925 | 65-94 | 927 | 107-117 | 929 | 118-447 | 930 |
| Ab10.H | 1-30 | 963 | 36-49 | 965 | 66-97 | 967 | 102-112 | 969 | 113-442 | 970 |
| Ab21.H | 1-30 | 1203 | 36-49 | 1205 | 66-97 | 1207 | 102-112 | 1209 | 113-442 | 1210 |
| Ab10.H2 | 1-30 | 1283 | 36-49 | 1285 | 66-97 | 1287 | 102-112 | 1289 | 113-442 | 1290 |
| Ab10.H3 | 1-30 | 1323 | 36-49 | 1325 | 66-97 | 1327 | 102-112 | 1329 | 113-442 | 1330 |
| Ab10.H4 | 1-30 | 1363 | 36-49 | 1365 | 66-97 | 1367 | 102-112 | 1369 | 113-442 | 1370 |
| Ab10.H5 | 1-30 | 1403 | 36-49 | 1405 | 66-97 | 1407 | 102-112 | 1409 | 113-442 | 1410 |
| Ab10.H6 | 1-30 | 1443 | 36-49 | 1445 | 66-97 | 1447 | 102-112 | 1449 | 113-442 | 1450 |
| Ab21.H2 | 1-30 | 1483 | 36-49 | 1485 | 66-97 | 1487 | 102-112 | 1489 | 113-442 | 1490 |
| Ab21.H3 | 1-30 | 1523 | 36-49 | 1525 | 66-97 | 1527 | 102-112 | 1529 | 113-442 | 1530 |
| Ab21.H4 | 1-30 | 1563 | 36-49 | 1565 | 66-97 | 1567 | 102-112 | 1569 | 113-442 | 1570 |

Figure 7

Antibody Light chain Protein features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab10 | 1-110 | 422 | 24-35 | 424 | 51-57 | 426 | 90-99 | 428 |
| Ab20 | 1-110 | 462 | 24-35 | 464 | 51-57 | 466 | 90-99 | 468 |
| Ab21 | 1-110 | 862 | 24-35 | 864 | 51-57 | 866 | 90-99 | 868 |
| Ab22 | 1-113 | 902 | 24-36 | 904 | 52-58 | 906 | 91-102 | 908 |
| Ab23 | 1-113 | 942 | 24-34 | 944 | 50-56 | 946 | 89-102 | 948 |
| Ab10.H | 1-110 | 982 | 24-35 | 984 | 51-57 | 986 | 90-99 | 988 |
| Ab21.H | 1-110 | 1222 | 24-35 | 1224 | 51-57 | 1226 | 90-99 | 1228 |
| Ab10.H2 | 1-109 | 1302 | 23-34 | 1304 | 50-56 | 1306 | 89-98 | 1308 |
| Ab10.H3 | 1-110 | 1342 | 24-35 | 1344 | 51-57 | 1346 | 90-99 | 1348 |
| Ab10.H4 | 1-110 | 1382 | 24-35 | 1384 | 51-57 | 1386 | 90-99 | 1388 |
| Ab10.H5 | 1-108 | 1422 | 22-33 | 1424 | 49-55 | 1426 | 88-97 | 1428 |
| Ab10.H6 | 1-109 | 1462 | 23-34 | 1464 | 50-56 | 1466 | 89-98 | 1468 |
| Ab21.H2 | 1-109 | 1502 | 23-34 | 1504 | 50-56 | 1506 | 89-98 | 1508 |
| Ab21.H3 | 1-110 | 1542 | 24-35 | 1544 | 51-57 | 1546 | 90-99 | 1548 |
| Ab21.H4 | 1-110 | 1582 | 24-35 | 1584 | 51-57 | 1586 | 90-99 | 1588 |

Figure 8

Antibody Light chain Protein features

| Sequence Name | FR1 coordinates | SEQ ID NC: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab10 | 1-23 | 423 | 36-50 | 425 | 58-89 | 427 | 100-110 | 429 | 111-216 | 430 |
| Ab20 | 1-23 | 463 | 36-50 | 465 | 58-89 | 467 | 100-110 | 469 | 111-216 | 470 |
| Ab21 | 1-23 | 863 | 36-50 | 865 | 58-89 | 867 | 100-110 | 869 | 111-216 | 870 |
| Ab22 | 1-23 | 903 | 37-51 | 905 | 59-90 | 907 | 103-113 | 909 | 114-219 | 910 |
| Ab23 | 1-23 | 943 | 35-49 | 945 | 57-88 | 947 | 103-113 | 949 | 114-219 | 950 |
| Ab10.H | 1-23 | 983 | 36-50 | 985 | 58-89 | 987 | 100-110 | 989 | 111-216 | 990 |
| Ab21.H | 1-23 | 1223 | 36-50 | 1225 | 58-89 | 1227 | 100-110 | 1229 | 111-216 | 1230 |
| Ab10.H2 | 1-22 | 1303 | 35-49 | 1305 | 57-88 | 1307 | 99-109 | 1309 | 110-215 | 1310 |
| Ab10.H3 | 1-23 | 1343 | 36-50 | 1345 | 58-89 | 1347 | 100-110 | 1349 | 111-216 | 1350 |
| Ab10.H4 | 1-23 | 1383 | 36-50 | 1385 | 58-89 | 1387 | 100-110 | 1389 | 111-216 | 1390 |
| Ab10.H5 | 1-21 | 1423 | 34-48 | 1425 | 56-87 | 1427 | 98-108 | 1429 | 109-214 | 1430 |
| Ab10.H6 | 1-22 | 1463 | 35-49 | 1465 | 57-88 | 1467 | 99-109 | 1469 | 110-215 | 1470 |
| Ab21.H2 | 1-22 | 1503 | 35-49 | 1505 | 57-88 | 1507 | 99-109 | 1509 | 110-215 | 1510 |
| Ab21.H3 | 1-23 | 1543 | 36-50 | 1545 | 58-89 | 1547 | 100-110 | 1549 | 111-216 | 1550 |
| Ab21.H4 | 1-23 | 1583 | 36-50 | 1585 | 58-89 | 1587 | 100-110 | 1589 | 111-216 | 1590 |

Figure 9
Antibody Heavy chain DNA features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab10 | 1-327 | 412 | 88-102 | 414 | 145-192 | 416 | 283-294 | 418 |
| Ab20 | 1-327 | 452 | 88-102 | 454 | 145-192 | 456 | 283-294 | 458 |
| Ab21 | 1-327 | 852 | 88-102 | 854 | 145-192 | 856 | 283-294 | 858 |
| Ab22 | 1-336 | 892 | 91-105 | 894 | 148-198 | 896 | 292-303 | 898 |
| Ab23 | 1-351 | 932 | 88-102 | 934 | 145-192 | 936 | 283-318 | 938 |
| Ab10.H | 1-336 | 972 | 91-105 | 974 | 148-195 | 976 | 292-303 | 978 |
| Ab21.H | 1-336 | 1212 | 91-105 | 1214 | 148-195 | 1216 | 292-303 | 1218 |
| Ab10.H2 | 1-336 | 1292 | 91-105 | 1294 | 148-195 | 1296 | 292-303 | 1298 |
| Ab10.H3 | 1-336 | 1332 | 91-105 | 1334 | 148-195 | 1336 | 292-303 | 1338 |
| Ab10.H4 | 1-336 | 1372 | 91-105 | 1374 | 148-195 | 1376 | 292-303 | 1378 |
| Ab10.H5 | 1-336 | 1412 | 91-105 | 1414 | 148-195 | 1416 | 292-303 | 1418 |
| Ab10.H6 | 1-336 | 1452 | 91-105 | 1454 | 148-195 | 1456 | 292-303 | 1458 |
| Ab21.H2 | 1-336 | 1492 | 91-105 | 1494 | 148-195 | 1496 | 292-303 | 1498 |
| Ab21.H3 | 1-336 | 1532 | 91-105 | 1534 | 148-195 | 1536 | 292-303 | 1538 |
| Ab21.H4 | 1-336 | 1572 | 91-105 | 1574 | 148-195 | 1576 | 292-303 | 1578 |

Figure 10

Antibody Heavy chain DNA features

| Sequence Name | FR1 coordinates | SEQ ID NC: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab10 | 1-87 | 413 | 103-144 | 415 | 193-282 | 417 | 295-327 | 419 | 328-1317 | 420 |
| Ab20 | 1-87 | 453 | 103-144 | 455 | 193-282 | 457 | 295-327 | 459 | 328-1317 | 460 |
| Ab21 | 1-87 | 853 | 103-144 | 855 | 193-282 | 857 | 295-327 | 859 | 328-1317 | 860 |
| Ab22 | 1-90 | 893 | 106-147 | 895 | 199-291 | 897 | 304-336 | 899 | 337-1326 | 900 |
| Ab23 | 1-87 | 933 | 103-144 | 935 | 193-282 | 937 | 319-351 | 939 | 352-1341 | 940 |
| Ab10.H | 1-90 | 973 | 106-147 | 975 | 196-291 | 977 | 304-336 | 979 | 337-1326 | 980 |
| Ab21.H | 1-90 | 1213 | 106-147 | 1215 | 196-291 | 1217 | 304-336 | 1219 | 337-1326 | 1220 |
| Ab10.H2 | 1-90 | 1293 | 106-147 | 1295 | 196-291 | 1297 | 304-336 | 1299 | 337-1326 | 1300 |
| Ab10.H3 | 1-90 | 1333 | 106-147 | 1335 | 196-291 | 1337 | 304-336 | 1339 | 337-1326 | 1340 |
| Ab10.H4 | 1-90 | 1373 | 106-147 | 1375 | 196-291 | 1377 | 304-336 | 1379 | 337-1326 | 1380 |
| Ab10.H5 | 1-90 | 1413 | 106-147 | 1415 | 196-291 | 1417 | 304-336 | 1419 | 337-1326 | 1420 |
| Ab10.H6 | 1-90 | 1453 | 106-147 | 1455 | 196-291 | 1457 | 304-336 | 1459 | 337-1326 | 1460 |
| Ab21.H2 | 1-90 | 1493 | 106-147 | 1495 | 196-291 | 1497 | 304-336 | 1499 | 337-1326 | 1500 |
| Ab21.H3 | 1-90 | 1533 | 106-147 | 1535 | 196-291 | 1537 | 304-336 | 1539 | 337-1326 | 1540 |
| Ab21.H4 | 1-90 | 1573 | 106-147 | 1575 | 196-291 | 1577 | 304-336 | 1579 | 337-1326 | 1580 |

Figure 11

Antibody Light chain DNA features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab10 | 1-330 | 432 | 70-105 | 434 | 151-171 | 436 | 268-297 | 438 |
| Ab20 | 1-330 | 472 | 70-105 | 474 | 151-171 | 476 | 268-297 | 478 |
| Ab21 | 1-330 | 872 | 70-105 | 874 | 151-171 | 876 | 268-297 | 878 |
| Ab22 | 1-339 | 912 | 70-108 | 914 | 154-174 | 916 | 271-306 | 918 |
| Ab23 | 1-339 | 952 | 70-102 | 954 | 148-168 | 956 | 265-306 | 958 |
| Ab10.H | 1-330 | 992 | 70-105 | 994 | 151-171 | 996 | 268-297 | 998 |
| Ab21.H | 1-330 | 1232 | 70-105 | 1234 | 151-171 | 1236 | 268-297 | 1238 |
| Ab10.H2 | 1-327 | 1312 | 67-102 | 1314 | 148-168 | 1316 | 265-294 | 1318 |
| Ab10.H3 | 1-330 | 1352 | 70-105 | 1354 | 151-171 | 1356 | 268-297 | 1358 |
| Ab10.H4 | 1-330 | 1392 | 70-105 | 1394 | 151-171 | 1396 | 268-297 | 1398 |
| Ab10.H5 | 1-324 | 1432 | 64-99 | 1434 | 145-165 | 1436 | 262-291 | 1438 |
| Ab10.H6 | 1-327 | 1472 | 67-102 | 1474 | 148-168 | 1476 | 265-294 | 1478 |
| Ab21.H2 | 1-327 | 1512 | 67-102 | 1514 | 148-168 | 1516 | 265-294 | 1518 |
| Ab21.H3 | 1-330 | 1552 | 70-105 | 1554 | 151-171 | 1556 | 268-297 | 1558 |
| Ab21.H4 | 1-330 | 1592 | 70-105 | 1594 | 151-171 | 1596 | 268-297 | 1598 |

Figure 12
Antibody Light chain DNA features

| Sequence Name | FR1 coordinates | SEQ ID NC: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab10 | 1-69 | 433 | 106-150 | 435 | 172-267 | 437 | 298-330 | 439 | 331-648 | 440 |
| Ab20 | 1-69 | 473 | 106-150 | 475 | 172-267 | 477 | 298-330 | 479 | 331-648 | 480 |
| Ab21 | 1-69 | 873 | 106-150 | 875 | 172-267 | 877 | 298-330 | 879 | 331-648 | 880 |
| Ab22 | 1-69 | 913 | 109-153 | 915 | 175-270 | 917 | 307-339 | 919 | 340-657 | 920 |
| Ab23 | 1-69 | 953 | 103-147 | 955 | 169-264 | 957 | 307-339 | 959 | 340-657 | 960 |
| Ab10.H | 1-69 | 993 | 106-150 | 995 | 172-267 | 997 | 298-330 | 999 | 331-648 | 1000 |
| Ab21.H | 1-69 | 1233 | 106-150 | 1235 | 172-267 | 1237 | 298-330 | 1239 | 331-648 | 1240 |
| Ab10.H2 | 1-66 | 1313 | 103-147 | 1315 | 169-264 | 1317 | 295-327 | 1319 | 328-645 | 1320 |
| Ab10.H3 | 1-69 | 1353 | 106-150 | 1355 | 172-267 | 1357 | 298-330 | 1359 | 331-648 | 1360 |
| Ab10.H4 | 1-69 | 1393 | 106-150 | 1395 | 172-267 | 1397 | 298-330 | 1399 | 331-648 | 1400 |
| Ab10.H5 | 1-63 | 1433 | 100-144 | 1435 | 166-261 | 1437 | 292-324 | 1439 | 325-642 | 1440 |
| Ab10.H6 | 1-66 | 1473 | 103-147 | 1475 | 169-264 | 1477 | 295-327 | 1479 | 328-645 | 1480 |
| Ab21.H2 | 1-66 | 1513 | 103-147 | 1515 | 169-264 | 1517 | 295-327 | 1519 | 328-645 | 1520 |
| Ab21.H3 | 1-69 | 1553 | 106-150 | 1555 | 172-267 | 1557 | 298-330 | 1559 | 331-648 | 1560 |
| Ab21.H4 | 1-69 | 1593 | 106-150 | 1595 | 172-267 | 1597 | 298-330 | 1599 | 331-648 | 1600 |

FIG. 31A. Summary of effects of PACAP alanine scanning mutants on antibody binding

| VIP | PACAP | | Ab10 | Ab20 | Ab21 | Ab22 | Ab23 |
|---|---|---|---|---|---|---|---|
| H | H | 1 | | | | | |
| S | S | 2 | | | | | |
| D | D | 3 | | | | | |
| A | G | 4 | | | | | |
| V | I | 5 | | | | | |
| F | F | 6 | | | | | |
| T | T | 7 | | | | | |
| D | D | 8 | | | | | |
| N | S | 9 | | | | | |
| Y | Y | 10 | | | | | |
| T | S | 11 | | | | | |
| R | R | 12 | | | | | 12A |
| L | Y | 13 | | | | | |
| R | R | 14 | | | | | |
| K | K | 15 | | | | | |
| Q | Q | 16 | | | | | |
| M | M | 17 | | | | | |
| A | A | 18 | | | | | |
| V | V | 19 | 19A | 19A | 19A | | |
| K | K | 20 | | | | | 20A |
| K | K | 21 | | | | | |
| Y | Y | 22 | 22A | 22A | 22A | 22A | |
| L | L | 23 | 23A | 23A | 23A | 23A | 23A |
| N | A | 24 | | 24V | | | 24V |
| S | A | 25 | | | | | |
| I | V | 26 | | | | | 26A |
| L | L | 27 | 27A | 27A | 27A | 27A | 27A |

FIG. 31B. Summary of effects of PACAP alanine scanning mutants on antibody binding

| VIP | PACAP | | Ab10 | Ab20 | Ab21 | Ab22 | Ab23 |
|---|---|---|---|---|---|---|---|
| N | G | 28 | | | | 28A | 28A |
| | K | 29 | | | | | |
| | R | 30 | | | | | |
| | Y | 31 | | | | 31A | |
| | K | 32 | | | | | |
| | Q | 33 | | | | | |
| | R | 34 | | | | | |
| | V | 35 | | | | | |
| | K | 36 | | | | | |
| | N | 37 | | | | | |
| | K | 38 | | | | | |

NUCLEIC ACIDS ENCODING HUMANIZED ANTI-PACAP ANTIBODIES

CROSS-REFERENCE TO RELATED APPLICATIONS

This application is a divisional of U.S. application Ser. No. 17/122,243, filed Dec. 15, 2020, which is a divisional of U.S. application Ser. No. 16/787,260, filed Feb. 11, 2020, now U.S. Pat. No. 10,975,135, which is a divisional of U.S. application Ser. No. 15/487,642, filed Apr. 14, 2017, now U.S. Pat. No. 10,913,783, which claims the benefit of U.S. Provisional Appl. No. 62/322,939, filed Apr. 15, 2016, U.S. Provisional Appl. No. 62/322,957, filed Apr. 15, 2016, U.S. Provisional Appl. No. 62/323,495, filed Apr. 15, 2016, U.S. Provisional Appl. No. 62/323,573, filed Apr. 15, 2016, U.S. Provisional Appl. No. 62/366,902, filed Jul. 26, 2016, and U.S. Provisional Appl. No. 62/408,347, filed Oct. 14, 2016, each of which is hereby incorporated by reference in its entirety.

SEQUENCE LISTING DISCLOSURE

The contents of the electronic sequence listing (11432570006305.xml; Size: 955,612 bytes; and Date of Creation: Jan. 31, 2024) is herein incorporated by reference in its entirety.

FIELD OF THE INVENTION

This invention generally pertains to antibodies and antigen binding fragments thereof, preferably humanized, chimerized, and human antibodies and antigen binding fragments thereof, and compositions containing such antibodies and antigen binding fragments thereof, wherein such antibodies and antigen binding fragments thereof specifically bind to Pituitary Adenylate Cyclase-Activating Polypeptide ("PACAP") and therapeutic and diagnostic uses for the antibodies, antigen binding fragments and compositions thereof.

BACKGROUND

Pituitary Adenylate Cyclase-Activating Polypeptide ("PACAP") is a member of the secretin/vasoactive intestinal peptide ("VIP")/growth hormone-releasing hormone ("GHRH") family. PACAP is a multifunctional vasodilatory peptide that exists in two α-amidated active forms, one with 38 amino acids (PACAP38; SEQ ID NO: 1241) and the other with 27 amino acids (PACAP27; SEQ ID NO: 1242). Both peptides have the same N-terminal 27 amino acids and are synthesized from the same precursor protein, prepro-PACAP (See, Moody et al., *Curr. Opin. Endocrinol. Diabetes Obes.*, 18 (1): 61-67, 2011). PACAP38 is the more prevalent active form, representing up to 90% of PACAP forms in mammalian tissues (See, Kaiser and Russo, *Neuropeptides*, 47:451-461, 2013). The sequence of PACAP38 is identical in all mammals and differs from the avian and amphibian orthologs by only one amino acid (See, Vaudry et al., *Pharmacol. Rev.*, 52:269-324, 2000). The secretin/VIP/GHRH family includes mammalian peptide histidine methioneamide ("PHM"), secretin, glucagon, glucagon-like peptide-1 ("GLP1"), glucagon-like peptide-2 ("GLP2"), glucose-dependent-insulinotrophic-polypeptide ("GIP"), and growth-hormone-releasing-factor ("GRF"). PACAP27 has 68% sequence identity to VIP at the amino acid level (See, Vaudry et al., 2000).

PACAP is widely distributed in the brain and peripheral organs, e.g., the endocrine system, gonads, sympathetic neurons, respiratory system, gastrointestinal tract, cardiovascular system, and urogenital tracts (See, Schytz et al., *Neurotherapeutics*, 7:191-196, 2010). In particular, PACAP is expressed throughout the nervous system, including a presence in the trigeminovascular system, trigeminal ganglia, spinal cord, hypothalamus, and pituitary. PACAP has roles in neurodevelopment, neuroprotection, neuromodulation, neurogenic inflammation, and nociception with multiple actions (See, Kaiser and Russo, 2013).

Consistent with its widespread distribution, PACAP exerts pleiotropic effects including modulation of neurotransmitter release, vasodilation, bronchodilation, and activation of intestinal motility, increase of insulin and histamine secretion, as well as stimulation of cell proliferation and/or differentiation. PACAP has been shown to act as a hormone, a neurohormone, a neurotransmitter, and a trophic factor in a number of tissues (Vaudry et al., *Pharmacological Rev.*, 52 (2): 269-324, 2000).

The biological effects of PACAP are mediated via three different G-protein coupled receptors: PAC1-R, vasoactive intestinal peptide receptor type 1 ("VPAC1-R"), and vasoactive intestinal peptide receptor type 2 ("VPAC2-R"). These receptors are expressed in diverse tissues. PAC1-R is particularly abundant in the nervous system (e.g., olfactory bulb, thalamus, hypothalamus, cerebellum, and spinal dorsal horn), pituitary, and adrenal glands. By contrast, VPAC1-R and VPAC2-R are expressed mainly in the lung, liver, and testis, although they have been detected in other tissues as well. VPAC1-R expression has been detected in the nervous system (e.g., cerebral cortex and hippocampus), smooth muscle cells of lung, liver, intestine, megakaryocytes, and platelets. VPAC1-R associates with receptor-associated membrane protein ("RAMP", specifically, RAMP2) (See, Christopoulos et al., *J. Biol. Chem.*, 278:3293-3297, 2002). VPAC2-R expression profile includes the nervous (e.g., thalamus, hippocampus, brain stem, and dorsal root ganglia ("DRG")), cardiovascular system, gastrointestinal system, pancreas, and reproductive systems (See, Usdin et al., *Endocrin.*, 135:2662-2680, 1994; Sheward et al., *Neurosci.*, 67:409-418, 1995).

PAC1-R is selective for PACAP38 and PACAP27. In particular, PAC1-R binds to PACAP with 100-1000-fold greater affinity than VIP, i.e., $K_D$~0.5 nM for PACAP27/PACAP38 vs. $K_D$~500 nM for VIP. Conversely, VPAC1-R and VPAC2-R have equal affinities for PACAP and VIP ($K_D$~1 nM) (See, Schytz et al., 2010). An antibody has been developed that binds to PAC1-R (see United States Patent Application Publication No. 20160251432).

Upon activation, these receptors are all capable of causing downstream production of cyclic adenosine monophosphate ("cAMP"), and/or activation of phospholipase C ("PLC"), and/or modulation of phospholipase D ("PLD"). In particular, PAC1-R is coupled to dual signal transduction pathways acting through cAMP and $Ca^{2+}$, whereas VPAC1-R and VPAC2-R are coupled principally to adenylyl cyclase. PAC1-R is coupled to $G_s$ protein, which activates adenylyl cyclase to form cAMP that in turn activates protein kinase A. PAC1-R also couples to Gq and thereby activates PLC, which produces inositol phosphate, which increases cytosolic calcium release from intra-cellular calcium stores. There is some evidence for a role of PAC1-R in PLD activation (See, McCulloch et al., *Ann. N. Y. Acad. Sci.*, 921:175-185, 2000). Another PACAP signaling pathway results in the elevation of intra-cellular sodium levels via activation of nonselective cation channels (See, Roy et al., *American*

*Journal of Physiology: Regulatory, Integrative and Comparative Physiology,* 304 (12): R1070-R1084, 2013).

PACAP is hypothesized to play a role in a multitude of diseases and disorders, including but not limited to migraine, headache, and pain, though such a role for PACAP has not been clinically demonstrated. Migraines are believed to have a neurovascular component. Migraines affect approximately 10% of the adult population in the U.S. and are typically accompanied by intense headaches. Approximately 20-30% of migraine sufferers experience aura, comprising focal neurological phenomena that precede and/or accompany the event. A role for PACAP in migraine has been suggested by several observations: (1) plasma levels of PACAP are elevated during migraine attacks (ictal), as compared to interictal levels, in humans (see Tuka et al., *Cephalalgia,* 33 (13): 1085-1095, 2013); (2) an infusion of PACAP38 triggered headaches in healthy subjects, and headaches followed by migraine-like attacks in migraincurs (see Schytz et al., *Brain,* 132:16-25, 2009; and Amin et al., *Brain,* 137: 779-794, 2014, respectively); (3) PACAP-induced vasodilation may play a role in neurogenic inflammation (see Kaiser and Russo, *Neuropeptides,* 47:451-461, 2013); and (4) PACAP-induced migraines are associated with photophobia, phonophobia, nausea, and respond to triptans (see Amin et al., *Brain,* 32:140-149, 2012). PACAP has also been shown to induce vasodilation, photophobia, as well as mast cell degranulation and neuronal activation (See, Markovics et al., *Neurobiology of Disease,* 45:633-644, 2012; Baun et al., *Cephalalgia,* 32 (4): 337-345, 2012; Chan et al., *Pharmacology & Therapeutics,* 129:332-351, 2011).

One effective treatment for migraines is the administration of triptans, which are a family of tryptamine-based drugs, including sumatriptan and rizatriptan. Members of this family have an affinity for multiple serotonin receptors, including 5-$HT_{1B}$, 5-$HT_{1D}$, and 5-$HT_{1F}$. Members of this family of drugs selectively constrict cerebral vessels, but also cause vasoconstrictive effects on coronary vessels (See, Durham, *New Eng. J. Med.,* 350 (11): 1073-75, 2004). There is a theoretical risk of coronary spasm in patients with established heart disease following administration, and cardiac events after taking triptans in rare instances may occur. Accordingly, they are contraindicated for some patients with coronary vascular disease.

Similarly, pain may often be addressed through the administration of certain narcotics or non-steroidal anti-inflammatory drugs ("NSAIDs"). However, the administration of these treatments often has negative consequences. NSAIDs have the potential to cause kidney failure, intestinal bleeding, and liver dysfunction. Narcotics have the potential to cause nausea, vomiting, impaired mental functioning, and addiction. Therefore, it is desirable to identify alternative treatments for pain in order to avoid certain of these negative consequences.

PACAP may also be involved in diseases and disorders other than migraine, headache, and pain. For example, PACAP may correlate to or even play a causal role in anxiety disorders (WO 2012/106407); thrombocytopenia (WO 2004/062684); and inflammatory skin diseases (WO 2010/007175). PACAP and PAC1-R polymorphisms are associated with post-traumatic stress syndrome ("PTSD") in females, major depressive disorder, and generalized anxiety disorder, suggesting a role for PACAP in these conditions. Further, supporting a role for PACAP in thrombocytopenia, trisomy 18 patients have excess PACAP and exhibit defective megakaryocyte maturation (See, Schytz et al., 2010; and Moody et al., *Curr. Opin. Endocrinol. Diabetes Obes.,* 18 (1): 61-67, 2011).

Also, PACAP and other neuropeptides, such as Calcitonin Gene-Related Peptide ("CGRP"), substance P, neurokinin A, bradykinin, and endothelin-1, are expressed in the lower urinary tract ("LUT") (see Arms and Vizzard, *Handbook Exp. Pharmacol.,* 202:395-423, 2011) and reportedly may play a role in LUT dysfunction and urinary tract disorders such as urinary tract infection ("UTI"), abnormal voiding, urinary urgency, nocturia, urinary incontinence, overactive bladder, and the pain associated with such conditions.

PACAP and PACAP receptors have also been suggested to modulate inflammatory and neuropathic pain and have been implicated in both pronociception and antinociception (See, Davis-Taber et al., *J. Pain,* 9 (5): 449-56, 2008). PACAP has also been reported to be required for spinal desensitization and the induction of neuropathic pain (See, Mabuchi et al., *J. Neurosci.,* 24 (33): 7283-91, 2004). Additionally, morphine withdrawal behavior is reportedly modified in PACAP-receptor deficient mice further suggesting the role of PACAP in morphine withdrawal anxiolytic response (See, Martin et al., *Mol. Brain Res.,* 110 (1): 109-18, 2003).

BRIEF SUMMARY OF THE INVENTION

In one aspect, the present invention in general relates to anti-PACAP antibodies and antigen binding fragments thereof, preferably human, humanized, or chimerized anti-PACAP antibodies and antigen binding fragments thereof, that antagonize, inhibit, neutralize, or block at least one biological effect associated with human PACAP. In certain embodiments, the anti-PACAP antibodies and antigen binding fragments thereof inhibit or neutralize at least one biological effect elicited by PACAP, which includes PACAP27 and/or PACAP38, as discussed infra. In other embodiments, the anti-PACAP antibodies and antigen binding fragments thereof neutralize or inhibit PACAP activation of at least one of PAC1-R, VPAC1-R, and/or VPAC2-R; neutralize or inhibit PACAP activation of each of PAC1-R, VPAC1-R, and VPAC2-R; and/or neutralize or inhibit PACAP activation of PAC1-R; and/or inhibits PACAP binding to the cell surface, e.g., via a glycosaminoglycan ("GAG"). In yet other embodiments, the anti-PACAP antibodies and antigen binding fragments thereof are capable of inhibiting PACAP binding to at least one of PAC1-R, VPAC1-R, and/or VPAC2-R; are capable of inhibiting PACAP binding to each of PAC1-R, VPAC1-R, and/or VPAC2-R; or are capable of inhibiting PACAP binding to PAC1-R. In other embodiments, the anti-PACAP antibodies and antigen binding fragments thereof inhibit PACAP-induced cAMP production. In yet other embodiments, the anti-PACAP antibodies and antigen binding fragments thereof, alone or in combination, when administered to a subject, e.g., a human, reduce PACAP-induced vasodilation, photophobia, mast cell degranulation, and/or neuronal activation. In related embodiments, the human or humanized anti-PACAP antibodies and antigen binding fragments thereof are suitable for treating a human subject having an acute, episodic or chronic condition associated with increased vasodilation, photophobia, mast cell degranulation, and/or neuronal activation.

In another embodiment, the method provides a eukaryotic host cell that is mammalian selected from the group consisting of baby hamster kidney ("BHK") cells; chinese hamster ovary ("CHO") cells; mouse sertoli cells ("TM4" cells); African green monkey kidney cells ("VERO-76" cells); human cervical carcinoma ("HELA") cells; canine kidney cells ("MDCK"); buffalo rat liver ("BRL") cells; human lung cells; human liver ("Hep G2") cells; mouse mammary tumor ("MMT") cells; TRI cells; MRC 5 cells; and FS4 cells. Preferably, the mammalian host cell is a CHO cell. More preferably, the mammalian host cell is a CHO K1 cell.

In a preferred embodiment, the anti-PACAP antibodies and antigen binding fragments thereof do not substantially interact with (bind) to VIP. The present invention also encompasses the therapeutic use (as a monotherapy or combination therapy) and diagnostic use of such anti-PACAP antibodies and antigen binding fragments thereof.

More particularly, anti-PACAP antibodies and antigen binding fragments thereof according to the invention can include human, humanized, and chimerized antibodies and fragments thereof, as well as scFvs, camelbodies, shark antibodies, nanobodies, Immunoglobulin New Antigen Receptor ("IgNAR"), fragment antigen binding ("Fab") fragments, Fab' fragments, MetMab like antibodies, bispecific antibodies, monovalent antibody fragments, and F(ab') 2 fragments. Additionally, anti-PACAP antibodies and antigen binding fragments thereof according to the invention can substantially or entirely lack N-glycosylation and/or O-glycosylation. In one embodiment, the anti-PACAP antibodies and antigen binding fragments thereof comprise a human constant domain, e.g., that of IgG1, IgG2, IgG3, or IgG4 antibody or a fragment thereof. In another embodiment, the anti-PACAP antibodies and antigen binding fragments thereof may comprise an Fc region that has been modified to alter (enhance or impair) at least one of effector function, half-life, proteolysis, or glycosylation. For example, the Fc region may contain one or more mutations that alters or eliminates N- and/or O-glycosylation.

In some embodiments, anti-PACAP antibodies and antigen binding fragments thereof bind to PACAP with a $K_D$ of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M, e.g., as determined by ELISA, bio-layer interferometry ("BLI"), Kinetic Exclusion Assay (KINEXA®, Sapidyne Instruments, Boise, ID), or SPR, e.g., at 25° or 37° C. Preferably, the human, humanized, or chimerized anti-PACAP antibodies and antigen binding fragments thereof bind to PACAP with a $K_D$ of less than or equal to $5\times10^{-10}$ M, $10^{-10}$ M, $5\times10^{-11}$ M, $10^{-11}$ M, $5\times10^{-12}$ M, or $10^{-12}$ M. Preferably, the human, humanized, or chimerized anti-PACAP antibodies and antigen binding fragments thereof bind to PACAP with a $K_D$ that is less than about 100 nM, less than about 40 nM, less than about 1 nM, less than about 100 pM, less than about 50 pM, or less than about 25 pM. Alternatively, the anti-PACAP antibodies and antigen binding fragments thereof bind to PACAP with a $K_D$ that is between about 10 pM and about 100 pM. In another embodiment, the human, humanized, or chimerized anti-PACAP antibodies and antigen binding fragments thereof bind to PACAP with an off-rate ($k_{off}$) of less than or equal to $5\times10^{-4}$ $s^{-1}$, $10^{-4}$ $s^{-1}$, $5\times10^{-5}$ $s^{-1}$, or $10^{-5}$ $s^{-1}$.

In yet another embodiment, the anti-PACAP antibodies and antigen binding fragments thereof will specifically bind to the linear or conformational epitope(s) and/or compete for binding to the same linear or conformational epitope(s) on human PACAP as an anti-PACAP antibody selected from the group consisting of Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4 (the specific amino acid sequences of the variable and constant regions of these anti-PACAP antibodies, and the nucleic acids that encode for such variable and constant regions, and the epitopes bound thereby as determined using alanine scanning methods are disclosed infra). In particular, the invention embraces anti-PACAP antibodies and antigen binding fragments thereof that specifically bind to the same linear or conformational epitope(s) on human PACAP as an anti-PACAP antibody selected from the group consisting of Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4. As disclosed infra, in exemplary embodiments, the epitope(s) are determined using alanine scanning mutation strategy.

In some embodiments, the present invention provides an anti-PACAP antibodies and antigen binding fragments thereof, are preferably human, humanized, or chimerized anti-PACAP antibodies and antigen binding fragments thereof, comprising at least 2 complementarity determining regions ("CDRs"), or at least 3 CDRs, or at least 4 CDRs, or at least 5 CDRs, or all six CDRs of an anti-PACAP antibody selected from the group consisting of Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4. In instances where all 6 CDRs are not present, preferably at least the $V_H$ CDR3 and $V_L$ CDR3 are present. In exemplary embodiments, the antibodies and antigen binding fragments thereof comprise the variable heavy ("VH") chain and/or the variable light ("VL") chain of one of Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4.

In a specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 964; a CDR2 sequence consisting of SEQ ID NO: 966; and a CDR3 sequence consisting of SEQ ID NO: 968; and/or (b) a variable light chain comprising a CDR1 sequence consisting of SEQ ID NO: 984; a CDR2 sequence consisting of SEQ ID NO: 986; and a CDR3 sequence consisting of SEQ ID NO: 988. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 962, and/or (b) a variable light chain comprising an amino acid sequence with at least 80, 85, 90, 95, 96, 97, 98, or 99% sequence identity to SEQ ID NO: 982. In another embodiment, the anti-PACAP antibodies and antigen binding fragments thereof may comprise (a) a variable heavy chain having the amino acid sequence of SEQ ID NO: 962, and/or (b) a variable light chain having the amino acid sequence of SEQ ID NO: 982. More specifically, the anti-PACAP antibodies and antigen binding fragments thereof may comprise (a) a heavy chain having the amino acid sequence of SEQ ID NO: 961, and/or (b) a light chain having the amino acid sequence of SEQ ID NO: 981.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1204; a CDR2 sequence consisting of SEQ ID NO: 1206; and a CDR3 sequence consisting of SEQ ID NO: 1208; and/or (b) a variable light chain comprising a CDR1 sequence consisting of SEQ ID NO: 1224; a CDR2 sequence consisting of SEQ ID NO: 1226; and a CDR3 sequence consisting of SEQ ID NO: 1228. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1202, and/or (b) a variable light chain comprising an amino acid sequence with at least 80, 85, 90, 95, 96, 97, 98, or 99% sequence identity to SEQ ID NO: 1222. In another embodiment, the anti-PACAP antibodies and antigen binding fragments thereof may comprise (a) a variable heavy chain having the amino acid sequence of SEQ ID NO: 1202, and/or (b) a variable light chain having the amino acid sequence of SEQ ID NO: 1222. More specifically, the anti-PACAP antibodies and antigen binding fragments thereof can comprise (a) a heavy chain having the amino acid sequence of SEQ ID NO: 1201, and/or (b) a light chain having the amino acid sequence of SEQ ID NO: 1221.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1284; a CDR2 sequence consisting of SEQ ID NO: 1286; and a CDR3 sequence consisting of SEQ ID NO: 1288; and/or (b) a variable light chain comprising a CDR1 sequence consisting of SEQ ID NO: 1304; a CDR2 sequence consisting of SEQ ID NO: 1306; and a CDR3 sequence consisting of SEQ ID NO: 1308. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1282, and/or (b) a variable light chain comprising an amino acid sequence with at least 80, 85, 90, 95, 96, 97, 98, or 99% sequence identity to SEQ ID NO: 1302. In another embodiment, the anti-PACAP antibodies and antigen binding fragments thereof may comprise (a) a variable heavy chain having the amino acid sequence of SEQ ID NO: 1282, and/or (b) a variable light chain having the amino acid sequence of SEQ ID NO: 1302. More specifically, the anti-PACAP antibodies and antigen binding fragments thereof can comprise (a) a heavy chain having the amino acid sequence of SEQ ID NO: 1281, and/or (b) a light chain having the amino acid sequence of SEQ ID NO: 1301.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1324; a CDR2 sequence consisting of SEQ ID NO: 1326; and a CDR3 sequence consisting of SEQ ID NO: 1328; and/or (b) a variable light chain comprising a CDR1 sequence consisting of SEQ ID NO: 1344; a CDR2 sequence consisting of SEQ ID NO: 1346; and a CDR3 sequence consisting of SEQ ID NO: 1348. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1322, and/or (b) a variable light chain comprising an amino acid sequence with at least 80, 85, 90, 95, 96, 97, 98, or 99% sequence identity to SEQ ID NO: 1342. In another embodiment, the anti-PACAP antibodies and antigen binding fragments thereof may comprise (a) a variable heavy chain having the amino acid sequence of SEQ ID NO: 1322, and/or (b) a variable light chain having the amino acid sequence of SEQ ID NO: 1342. More specifically, the anti-PACAP antibodies and antigen binding fragments thereof can comprise (a) a heavy chain having the amino acid sequence of SEQ ID NO: 1321, and/or (b) a light chain having the amino acid sequence of SEQ ID NO: 1341.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1364; a CDR2 sequence consisting of SEQ ID NO: 1366; and a CDR3 sequence consisting of SEQ ID NO: 1368; and/or (b) a variable light chain comprising a CDR1 sequence consisting of SEQ ID NO: 1384; a CDR2 sequence consisting of SEQ ID NO: 1386; and a CDR3 sequence consisting of SEQ ID NO: 1388. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1362, and/or (b) a variable light chain comprising an amino acid sequence with at least 80, 85, 90, 95, 96, 97, 98, or 99% sequence identity to SEQ ID NO: 1382. In another embodiment, the anti-PACAP antibodies and antigen binding fragments thereof may comprise (a) a variable heavy chain having the amino acid sequence of SEQ ID NO: 1362, and/or (b) a variable light chain having the amino acid sequence of SEQ ID NO: 1382. More specifically, the anti-PACAP antibodies and antigen binding fragments thereof can comprise (a) a heavy chain having the amino acid sequence of SEQ ID NO: 1361, and/or (b) a light chain having the amino acid sequence of SEQ ID NO: 1381.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1404; a CDR2 sequence consisting of SEQ ID NO: 1406; and a CDR3 sequence consisting of SEQ ID NO: 1408; and/or (b) a variable light chain comprising a CDR1 sequence consisting of SEQ ID NO: 1424; a CDR2 sequence consisting of SEQ ID NO: 1426; and a CDR3 sequence consisting of SEQ ID NO: 1428. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1402, and/or (b) a variable light chain comprising an amino acid sequence with at least 80, 85, 90, 95, 96, 97, 98, or 99% sequence identity to SEQ ID NO: 1422. In another embodiment, the anti-PACAP antibodies and antigen binding fragments thereof may comprise (a) a variable heavy chain having the amino acid sequence of SEQ ID NO: 1402, and/or (b) a variable light chain having the amino acid sequence of SEQ ID NO: 1422. More specifically, the anti-PACAP antibodies and antigen binding fragments thereof can comprise (a) a heavy chain having the amino acid sequence of SEQ ID NO: 1401, and/or (b) a light chain having the amino acid sequence of SEQ ID NO: 1421.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1444; a CDR2 sequence consisting of SEQ ID NO: 1446; and a CDR3 sequence consisting of SEQ ID NO: 1448; and/or (b) a variable light chain comprising a CDR1 sequence consisting of SEQ ID NO: 1464; a CDR2 sequence consisting of SEQ ID NO: 1466; and a CDR3 sequence consisting of SEQ ID NO: 1468. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1442, and/or (b) a variable light chain comprising an amino acid sequence with at least 80, 85, 90, 95, 96, 97, 98, or 99% sequence identity to SEQ ID NO: 1462. In another embodiment, the anti-PACAP antibodies and antigen binding fragments thereof may comprise (a) a variable heavy chain having the amino acid sequence of SEQ ID NO: 1442, and/or (b) a variable light chain having the amino acid sequence of SEQ ID NO: 1462. More specifically, the anti-PACAP antibodies and antigen binding fragments thereof can comprise (a) a heavy chain having the amino acid sequence of SEQ ID NO: 1441, and/or (b) a light chain having the amino acid sequence of SEQ ID NO: 1461.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1484; a CDR2 sequence consisting of SEQ ID NO: 1486; and a CDR3 sequence consisting of SEQ ID NO: 1488; and/or (b) a variable light chain comprising a CDR1 sequence consisting of SEQ ID NO: 1504; a CDR2 sequence consisting of SEQ ID NO: 1506; and a CDR3 sequence consisting of SEQ ID NO: 1508. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1482, and/or (b) a variable light chain comprising an amino acid sequence with at least 80, 85, 90, 95, 96, 97, 98, or 99% sequence identity to SEQ ID NO: 1502. In another embodiment, the anti-PACAP antibodies and antigen binding fragments thereof may comprise (a) a variable heavy chain having the amino acid sequence of SEQ ID NO: 1482, and/or (b) a variable light chain having the amino acid sequence of SEQ ID NO: 1502. More specifically, the anti-PACAP antibodies and antigen binding fragments thereof can comprise (a) a heavy chain having the amino acid sequence of SEQ ID NO: 1481, and/or (b) a light chain having the amino acid sequence of SEQ ID NO: 1501.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1524; a CDR2 sequence consisting of SEQ ID NO: 1526; and a CDR3 sequence consisting of SEQ ID NO: 1528; and/or (b) a variable light chain comprising a CDR1 sequence consisting of SEQ ID NO: 1544; a CDR2 sequence consisting of SEQ ID NO: 1546; and a CDR3 sequence consisting of SEQ ID NO: 1548. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1522, and/or (b) a variable light chain comprising an amino acid sequence with at least 80, 85, 90, 95, 96, 97, 98, or 99% sequence identity to SEQ ID NO: 1542. In another embodiment, the anti-PACAP antibodies and antigen binding fragments thereof may comprise (a) a variable heavy chain having the amino acid sequence of SEQ ID NO: 1522, and/or (b) a variable light chain having the amino acid sequence of SEQ ID NO: 1542. More specifically, the anti-PACAP antibodies and antigen binding fragments thereof can comprise (a) a heavy chain having the amino acid sequence of SEQ ID NO: 1521, and/or (b) a light chain having the amino acid sequence of SEQ ID NO: 1541.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1564; a CDR2 sequence consisting of SEQ ID NO: 1566; and a CDR3 sequence consisting of SEQ ID NO: 1568; and/or (b) a variable light chain comprising a CDR1 sequence consisting of SEQ ID NO: 1584; a CDR2 sequence consisting of SEQ ID NO: 1586; and a CDR3 sequence consisting of SEQ ID NO: 1588. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1562, and/or (b) a variable light chain comprising an amino acid sequence with at least 80, 85, 90, 95, 96, 97, 98, or 99% sequence identity to SEQ ID NO: 1582. In another embodiment, the anti-PACAP antibodies and antigen binding fragments thereof may comprise (a) a variable heavy chain having the amino acid sequence of SEQ ID NO: 1562, and/or (b) a variable light chain having the amino acid sequence of SEQ ID NO: 1582. More specifically, the anti-PACAP antibodies and antigen binding fragments thereof can comprise (a) a heavy chain having the amino acid sequence of SEQ ID NO: 1561, and/or (b) a light chain having the amino acid sequence of SEQ ID NO: 1581.

Also, in some embodiments the anti-PACAP antibodies and antigen binding fragments may comprise sequence variants of any of the disclosed antibodies which are modified by mutagenesis, e.g., affinity maturation to alter one or more properties such as binding affinity or immunogenicity.

In another embodiment, the anti-PACAP antibodies and antigen binding fragments thereof are directly or indirectly attached to another moiety, such as a detectable label or therapeutic agent.

In another embodiment, the anti-PACAP antibodies and antigen binding fragments thereof inhibit or neutralize at least one biological effect elicited by PACAP; neutralize or inhibit PACAP activation of at least one of PAC1-R, VPAC1-R, and/or VPAC2-R; neutralize or inhibit PACAP activation of each of PAC1-R, VPAC1-R, and VPAC2-R; neutralize or inhibit PACAP activation of PAC1-R; are capable of inhibiting PACAP binding to at least one of PAC1-R, VPAC1-R, and/or VPAC2-R; are capable of inhibiting PACAP binding to each of PAC1-R, VPAC1-R, and/or VPAC2-R; are capable of inhibiting PACAP binding to PAC1-R; and/or inhibits PACAP binding to the cell surface, e.g., via a GAG; inhibit PACAP-induced cAMP production; and/or when administered to a subject reduce PACAP-induced vasodilation, photophobia, mast cell degranulation, and/or neuronal activation.

In another embodiment, the human, or humanized, anti-PACAP antibodies and antigen binding fragments thereof are suitable for treating a human subject having an acute, episodic, or chronic condition associated with increased vasodilation, photophobia, mast cell degranulation, and/or neuronal activation.

In another embodiment, the anti-PACAP antibodies and antigen binding fragments thereof do not substantially interact with (i.e., bind to) VIP. Preferably, the anti-PACAP antibodies and antigen binding fragments thereof have stronger affinity for PACAP as compared to VIP, i.e., although there is some cross-reactivity, the antibodies preferentially bind to PACAP as compared to VIP. For example, the affinity of said antibodies and antigen binding fragments thereof to PACAP is at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold, or stronger than the affinity of said antibodies and antigen binding fragments thereof to VIP (e.g., the $K_D$ of said antibody or fragment for binding to human PACAP is 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, or 30000000-fold lower than the $K_D$ for binding to VIP).

In one embodiment, the anti-PACAP antibodies and antigen binding fragments thereof are attached to at least one effector moiety, e.g., which comprises a chemical linker. In another embodiment, the anti-PACAP antibodies and antigen binding fragments thereof are attached to one or more detectable moieties, e.g., which comprise a fluorescent dye, enzyme, substrate, bioluminescent material, radioactive material, chemiluminescent moiety, or mixtures thereof.

In one embodiment, the anti-PACAP antibodies and antigen binding fragments thereof are attached to one or more functional moieties.

The invention also contemplates antibodies, e.g., anti-idiotypic antibodies, produced against an anti-PACAP antibodies and antigen binding fragments thereof as described above. Furthermore, the invention provides a method of using the anti-idiotypic antibody to monitor the in vivo levels of said anti-PACAP antibodies and antigen binding fragments thereof in a subject or to neutralize said anti-PACAP antibody in a subject being administered said anti-PACAP antibody or antigen binding fragment thereof.

Moreover, the present invention encompasses a composition suitable for therapeutic, prophylactic, or a diagnostic use comprising a therapeutically, prophylactically, or diagnostically effective amount of at least one anti-PACAP antibody or antigen binding fragment as described herein. In particular, compositions and dosage forms containing the subject anti-PACAP antibodies or binding fragments thereof for use in treating or preventing migraine or other headache indications are provided herein. Also provided herein are dosage forms containing the subject anti-PACAP antibodies or binding fragments thereof for use in treating or preventing photophobia. The composition may be suitable for subcutaneous administration, intra-muscular administration, and/or intravenous administration. The composition may be lyophilized. In some embodiments, the composition further comprises a pharmaceutically acceptable diluent, carrier, solubilizer, emulsifier, preservative, or mixture thereof.

Additionally, in some embodiments, the composition further comprises another active agent, e.g., a chemotherapeutic, an analgesic, an anti-inflammatory, an immunosuppressant, a cytokine, an antiproliferative, and an antiemetic. Preferably, the other therapeutic agent is an analgesic, e.g., an NSAID, an opioid analgesic, an antibody (e.g., an anti-human Nerve Growth Factor ("NGF") antibody or antibody fragment; or an anti-human CGRP or anti-human CGRP-receptor antibody or antibody fragment); or a non-antibody biologic, such as an NGF or CGRP polypeptide fragment or conjugate; or BOTOX® (Botulinum toxin). Suitable NSAIDs for use in combination with the subject anti-PACAP antibodies include, but are not limited to, a cyclooxygenase 1 and/or cyclooxygenase 2 inhibitor; propionic acid derivatives including ibuprofen, naproxen, naprosyn, diclofenac, and ketoprofen; acetic acid derivatives including tolmetin and sulindac; fenamic acid derivatives including mefenamic acid and meclofenamic acid; biphenylcarboxylic acid derivatives including diflunisal and flufenisal; and oxicams including piroxim, sudoxicam, and isoxicam. Suitable opioid analgesics for use in combination with the subject anti-PACAP antibodies include, e.g., codeine, dihydrocodeine, morphine or a morphine derivative or pharmaceutically acceptable salt thereof, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, and pentazocine, or pharmaceutically acceptable salts thereof. The combined administration of the opioid analgesic and the anti-PACAP antibody or antigen binding fragment thereof may increase the analgesic effect elicited thereby.

The present invention further contemplates an isolated nucleic acid sequence or nucleic acid sequences encoding an anti-PACAP antibody or antigen binding fragment described herein, as well as a vector or vectors containing these isolated nucleic acid sequence or sequences.

Additionally, the invention provides a host cell comprising these isolated nucleic acid sequence or sequences or the vector or set forth above. The host cell may be a eukaryotic host cell that is mammalian, selected from the group consisting of baby hamster kidney ("BHK") cells; chinese hamster ovary ("CHO") cells; mouse sertoli cells ("TM4" cells); African green monkey kidney cells ("VERO-76" cells); human cervical carcinoma ("HELA") cells; canine kidney cells ("MDCK"); buffalo rat liver ("BRL") cells; human lung cells; human liver ("Hep G2") cells; mouse mammary tumor ("MMT") cells; TRI cells; MRC 5 cells; and FS4 cells. Preferably, the mammalian host cell is a CHO cell. More preferably, the mammalian host cell is a CHO K1 cell. The host cell may be a prokaryotic cell, i.e., bacterial cell, or a eukaryotic cell, including a mammalian, fungal, yeast, avian, or insect cell. In one embodiment, the host cell is a filamentous fungus or is a yeast cell. Preferably, the yeast species is of the genus *Pichia*. Most preferably, the species of *Pichia* is selected from *Pichia pastoris, Pichia methanolica*, and *Hansenula polymorpha* (*Pichia angusta*).

The invention further provides a method of expressing anti-PACAP antibodies and antigen binding fragments thereof, typically human, humanized, or chimeric antibodies and antigen binding fragments thereof, the method comprising culturing the host cell described herein under conditions that provide for expression of said antibody or antigen binding fragment thereof. The host cell may be a cell culture, such as a Chinese hamster ovary ("CHO") cell or a polyploid yeast culture that stably expresses and secretes into the culture medium at least 10-25 mg/liter of said antibody or antigen binding fragment thereof. The polyploid yeast may be made by a method that comprises: (i) introducing at least one expression vector containing one or more heterologous polynucleotides encoding said antibody operably linked to a promoter and a signal sequence into a haploid yeast cell; (ii) producing by mating or spheroplast fusion a polyploid yeast from said first and/or second haploid yeast cell; (iii) selecting polyploid yeast cells that stably express said antibody; and (iv) producing stable polyploid yeast cultures from said polyploid yeast cells that stably express said antibody into the culture medium. Preferably, the yeast species is of the genus *Pichia*.

In other embodiments, the mammalian cell culture may be made by a method that comprises: (i) introducing at least one expression vector containing one or more heterologous polynucleotides encoding said antibody operably linked to a promoter and a signal sequence into a mammalian cell; (ii) producing single cells for culturing to express one or more heterologous polynucleotides encoding said antibody; (iii) selecting a mammalian cell that stably expresses said antibody; and (iv) producing cell cultures from said mammalian cell that stably expresses said antibody into the culture medium. Preferably, the mammalian species are CHO cells.

The invention further relates to the therapeutic and diagnostic uses of anti-PACAP antibodies and antigen binding fragments thereof, preferably a human antibody, humanized antibody, or chimeric antibody, or a fragment thereof.

In one embodiment, the invention provides a method for blocking, inhibiting, or neutralizing one or more biological effects associated with PACAP in a subject comprising administering to a subject an effective amount of a human or humanized or chimerized anti-PACAP antibody or antigen binding fragment thereof that antagonizes, inhibits, neutralizes, or blocks at least one biological effect associated with human PACAP. In a specific embodiment, the method employs an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4.

In another embodiment, the invention provides a method for blocking, inhibiting, or neutralizing one or more biological effects associated with PACAP in a subject comprising administering to a subject an effective amount of a human, humanized, or chimerized anti-PACAP antibody or antigen binding fragment thereof that antagonizes, inhibits, neutralizes, or blocks at least one biological effect associated with human PACAP and that does not substantially interact with (bind) VIP, e.g., the anti-PACAP antibody or antigen binding fragment thereof has stronger affinity for PACAP as compared to VIP, i.e., although there is some cross-reactivity, the antibodies preferentially bind to PACAP as compared to VIP. For example, the affinity of said antibody or antigen binding fragment thereof to PACAP is at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold, or higher than the affinity of said antibody or antigen binding fragment thereof to VIP (e.g., the $K_D$ of said antibody or fragment for binding to human PACAP is 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold, or lower than the $K_D$ for binding to VIP). In a specific embodiment, the method employs an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4.

In yet another embodiment, the invention provides a method for blocking, inhibiting, or neutralizing one or more biological effects associated with PACAP in a subject comprising administering to a subject an effective amount of a human, humanized, or chimerized anti-PACAP antibody or antigen binding fragment thereof that inhibits or neutralizes at least one biological effect elicited by PACAP; neutralizes or inhibits PACAP activation of at least one of PAC1-R, VPAC1-R, and/or VPAC2-R; neutralizes or inhibits PACAP activation of each of PAC1-R, VPAC1-R, and VPAC2-R; neutralizes or inhibits PACAP activation of PAC1-R; is capable of inhibiting PACAP binding to at least one of PAC1-R, VPAC1-R, and/or VPAC2-R; is capable of inhibiting PACAP binding to each of PAC1-R, VPAC1-R, and/or VPAC2-R; is capable of inhibiting PACAP binding to PAC1-R; and/or is capable of inhibiting PACAP binding to the cell surface, e.g., via GAG; inhibits PACAP-induced cAMP production; and/or when administered to a subject reduces PACAP-induced vasodilation, photophobia, mast cell degranulation, and/or neuronal activation. In a specific embodiment, the method employs an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4.

In another embodiment, the invention provides a method for treating or preventing the onset, frequency, severity, or duration of headache or migraine in a subject comprising administering to a subject an effective amount of a human, humanized, or chimerized anti-PACAP antibody or antigen binding fragment thereof that inhibits or neutralizes at least one biological effect elicited by PACAP; neutralizes or inhibits PACAP activation of at least one of PAC1-R, VPAC1-R, and/or VPAC2-R; neutralizes or inhibits PACAP activation of each of PAC1-R, VPAC1-R, and VPAC2-R; neutralizes or inhibits PACAP activation of PAC1-R; is capable of inhibiting PACAP binding to at least one of PAC1-R, VPAC1-R, and/or VPAC2-R; is capable of inhibiting PACAP binding to each of PAC1-R, VPAC1-R, and/or VPAC2-R; is capable of inhibiting PACAP binding to PAC1-R; and/or is capable of inhibiting PACAP binding to the cell surface, e.g., via GAG; inhibits PACAP-induced cAMP production; and/or when administered to a subject reduces PACAP-induced vasodilation, photophobia, mast cell degranulation, and/or neuronal activation. In another embodiment, the invention provides a method for treating or preventing in a human subject an acute, episodic, or chronic condition associated with increased vasodilation, photophobia, mast cell degranulation, and/or neuronal activation.

In a specific embodiment, the method employs an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4. The epitope can be identified using an alanine scanning mutation strategy, for example.

In a specific embodiment, the headache or migraine treated and/or prevented by administration of the subject anti-PACAP antibodies and antigen binding fragments thereof is selected from migraine with or without aura, hemiplegic migraine, cluster headache, migrainous neuralgia, chronic headache, and tension headache.

In another specific embodiment, the subject has a ocular disorder associated with photophobia selected from the group consisting of achromatopsia, aniridia, photophobia caused by an anticholinergic drug, aphakia (absence of the lens of the eye), buphthalmos (abnormally narrow angle between the cornea and iris), cataracts, cone dystrophy, congenital abnormalities of the eye, viral conjunctivitis ("pink eye"), corneal abrasion, corneal dystrophy, corneal ulcer, disruption of the corneal epithelium, ectopia lentis, endophthalmitis, eye trauma caused by disease, injury, or infection such as chalazion, episcleritis, glaucoma, keratoconus, or optic nerve hypoplasia, hydrophthalmos, or congenital glaucoma iritis, optic neuritis, pigment dispersion syndrome, pupillary dilation (naturally or chemically induced), retinal detachment, scarring of the cornea or sclera, and uveitis.

In another specific embodiment, the subject has a nervous system-related or neurological condition associated with photophobia selected from the group consisting of autism spectrum disorders, chiari malformation, dyslexia, encephalitis including myalgic encephalomyelitis (also known as "chronic fatigue syndrome"), meningitis, subarachnoid hemorrhage, tumor of the posterior cranial fossa, ankylosing spondylitis, albinism, ariboflavinosis, benzodiazepines (long term use of or withdrawal from benzodiazepines), chemotherapy, chikungunya, cystinosis, Ehlers-Danlos syndrome, hangover, influenza, infectious mononucleosis, magnesium deficiency, mercury poisoning, migraine, rabies, and tyrosinemia type II (also known as "Richner-Hanhart syndrome").

In another specific embodiment, the subject has a photophobia-associated disorder selected from the group consisting of migraine (with or without aura), iritis, uveitis, meningitis, depression, bipolar disorder, cluster headache or anther trigeminal autonomic cephalalgia ("TAC") or blepharospasm, depression, agoraphobia, Post-Traumatic Stress Disorder ("PTSD"), traumatic brain injury, and bipolar disorder.

In another embodiment, the invention provides a method for neutralizing PACAP-induced PAC1-R, VPAC1-R, and/or VPAC2-R signaling, comprising administering to a subject in need thereof an effective amount of an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4.

In another embodiment, the invention provides a method for inhibiting PACAP-induced cAMP production, comprising administering to a subject in need thereof an effective amount of an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4.

In yet another embodiment, the invention provides a method for inhibiting PACAP-induced vasodilation, photophobia, mast cell degranulation, and/or neuronal activation, comprising administering to a subject in need thereof an effective amount of an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4.

In yet another embodiment, the invention provides a method for treating or preventing a condition associated with elevated PACAP levels in a subject, comprising administering to a subject in need thereof an effective amount of an anti-PACAP antibody or antigen binding fragment thereof that specifically binds to the same or overlapping linear or conformational epitope(s) and/or competes for binding to the same or overlapping linear or conformational epitope(s) on human PACAP as an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab21, Ab22, and Ab23, preferably Ab10.H, Ab10.H2, Ab10.H3, Ab10.H4, Ab10.H5, Ab10.H6, Ab21.H, Ab21.H2, Ab21.H3, or Ab21.H4. The epitope can be identified using an alanine scanning mutation strategy, for example.

Exemplary anti-PACAP antibodies and antigen binding fragments thereof suitable for use in this invention comprise a $V_H$ chain having an amino acid sequence with at least 80, 85, 90, 95, 96, 97, 98, 99 or 100% sequence identity to a $V_H$ chain selected from SEQ ID NOs: 962, 1282, 1322, 1362, 1402, 1442, 1202, 1482, 1522, and 1562, and/or a $V_L$ chain having an amino acid sequence with at least 80, 85, 90, 95, 96, 97, 98, 99, or 100% sequence identity to a $V_L$ chain selected from selected from SEQ ID NOs: 982, 1302, 1342, 1382, 1422, 1462, 1222, 1502, 1542, and 1582, and/or at least 2, 3, 4, 5, or all 6 CDRs comprised therein.

In one embodiment, the anti-PACAP antibody or antigen binding fragment thereof employed in the methods binds to PACAP27 and/or PACAP38 and blocks PACAP27 and/or PACAP38 binding to PAC1-R, VPAC1-R, and/or VPAC2-R. In another embodiment, the anti-PACAP antibody or antigen binding fragment thereof employed in the methods binds to PACAP27 and/or PACAP38 and blocks PACAP27 and/or PACAP38 binding to each of PAC1-R, VPAC1-R, and VPAC2-R. Preferably, the anti-PACAP antibody or antigen binding fragment thereof binds to PACAP27 and/or PACAP38 and blocks PACAP27 and/or PACAP38 binding to PAC1-R.

More particularly, anti-PACAP antibodies and antigen binding fragments thereof employed in the methods according to the invention may include human, humanized, and chimerized antibodies and fragments thereof, as well as scFvs, camelbodies, shark antibodies, nanobodies, IgNAR, Fab fragments, Fab' fragments, MetMab like antibodies, bispecific antibodies, monovalent antibody fragments, and F(ab') 2 fragments. Additionally, the anti-PACAP antibody or antigen binding fragment thereof employed by the methods according to the invention may substantially or entirely lack N-glycosylation and/or O-glycosylation. In one embodiment, the anti-PACAP antibody or antigen binding fragment thereof used in the encompassed methods comprises a human constant domain, e.g., an IgG1, IgG2, IgG3, or IgG4 antibody. In another embodiment, the anti-PACAP antibody or antigen binding fragment thereof comprises an Fc region that has been modified to alter (enhance or impair) at least one of effector function, half-life, proteolysis, or glycosylation. For example, the Fc region may contain one or more mutations that alters or eliminates N- and/or O-glycosylation.

In one embodiment, the subject methods employ an anti-PACAP antibody or antigen binding fragment thereof that binds to PACAP with a $K_D$ of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M. Preferably, the human, humanized, or chimerized anti-PACAP antibody or antigen binding fragment thereof binds to PACAP with a $K_D$ of less than or equal to $5\times10^{-10}$ M, $10^{-10}$ M, $5\times10^{-11}$ M, $10^{-11}$ M, $5\times10^{-12}$ M, or $10^{-12}$ M. More preferably, the methods employ a human, humanized, or chimerized anti-PACAP antibody or antigen binding fragment thereof that binds to PACAP with a $K_D$ that is less than about 100 nM, less than about 40 nM, less than about 1 nM, less than about 100 pM, less than about 50 pM, or less than about 25 pM. Alternatively, the anti-PACAP antibody or antigen binding fragment thereof binds to PACAP with a $K_D$ that is between about 10 PM and about 100 pM. In another embodiment, the human, humanized or chimerized anti-PACAP antibody or antigen binding fragment thereof binds to PACAP with an off-rate ($k_{off}$) of less than or equal to $5\times10^{-4}$ $s^{-1}$, $10^{-4}$ $s^{-1}$, $5\times10^{-5}$ $s^{-1}$, or $10^{-5}$ $s^{-1}$.

In another embodiment, the anti-PACAP antibody or antigen binding fragment thereof used in the subject methods is directly or indirectly attached to another moiety, such as a detectable label or therapeutic agent; is attached to at least one effector moiety, e.g., which comprises a chemical linker; and/or is attached to one or more detectable moieties, e.g., which comprises a fluorescent dye, enzyme, substrate, bioluminescent material, radioactive material, chemiluminescent moiety, or mixtures thereof; and/or is attached to one or more functional moieties.

In another embodiment, the method further comprises administering separately or co-administering another agent, e.g., selected from a chemotherapeutic, an analgesic, an anti-inflammatory, an immunosuppressant, a cytokine, an antiproliferative, and an antiemetic. Preferably, the other therapeutic agent is an analgesic, e.g., an NSAID (such as a cyclooxygenase 1 and/or cyclooxygenase 2 inhibitor; propionic acid derivatives including ibuprofen, naproxen, naprosyn, diclofenac, and ketoprofen; acetic acid derivatives including tolmetin and sulindac; fenamic acid derivatives including mefenamic acid and meclofenamic acid; biphenylcarboxylic acid derivatives including diflunisal and flufenisal; and oxicams including piroxim, sudoxicam, and isoxicam), an opioid analgesic (such as morphine or a morphine derivative or pharmaceutically acceptable salt thereof; codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene and pentazocine or pharmaceutically acceptable salts thereof), another antibody (such as an anti-NGF antibody or antibody fragment or an anti-CGRP or anti-CGRP receptor ("anti-CGRP-R") antibody or antibody fragment), or a non-antibody biologic, e.g., BOTOX®.

In one embodiment, the combined administration of the opioid analgesic and the anti-PACAP antibody or antigen binding fragment thereof increase the analgesic effect as compared to either the opioid analgesic or the anti-PACAP antibody or antigen binding fragment thereof administered alone.

In another embodiment, the subject has previously been treated ("a treated subject") and received an anti-CGRP or anti-CGRP-R antibody or antibody fragment thereof. The treated subject may be a migraineur who did not adequately respond to anti-CGRP or anti-CGRP-R antibody treatment ("poor responder"). Alternatively, the treated subject may have previously received at least one anti-CGRP antibody or anti-CGRP-R or antibody fragment thereof administration, and has elicited an immune response to said antibody or antibody fragment thereof. Exemplary anti-CGRP and anti-CGRP-R antibodies and antibody fragments thereof are disclosed in U.S. Pat. Nos. 9,102,731; 9,115,194; 8,734,802; 8,623,366; 8,597,649; and 8,586,045; and U.S. Patent Application Publication Nos. 20120294822, 20120294802, and 20120294797, the contents of each which are incorporated by reference in their entireties herein.

An aspect of the invention generally relates to a humanized anti-PACAP antibody or antigen binding fragment that may specifically bind to the same or overlapping linear or conformational epitope(s) on human PACAP as Ab10.H, Ab10.H2, Ab10.H3, Ab10.H4, Ab10.H5, Ab10.H6, Ab21, Ab21.H, Ab21.H2, Ab21.H3, or Ab21.H4. In another embodiment of the invention, an anti-PACAP antibody or antigen binding fragment may specifically bind to the same or overlapping linear or conformational epitope(s) on human PACAP as Ab22 or Ab23. Said antibody or antigen binding fragment may not substantially interact with (bind) Vasoactive Intestinal Peptide ("VIP").

In another embodiment, an anti-PACAP antibody or antigen binding fragment of the invention may comprise or may elicit one of the following effects: (a) inhibit or neutralize at least one biological effect elicited by PACAP; (b) neutralize or inhibit PACAP activation of at least one of PAC1 receptor ("PAC1-R"), vasoactive intestinal peptide receptor type 1 ("VPAC1-R"), and/or vasoactive intestinal peptide receptor type 2 ("VPAC2-R"); (c) neutralize or inhibit PACAP activation of each of PAC1-R, VPAC1-R, and VPAC2-R; (d) neutralize or inhibit PACAP activation of PAC1-R; (c) inhibit PACAP binding to at least one of PAC1-R, VPAC1-R, and/or VPAC2-R; (f) inhibit PACAP binding to each of PAC1-R, VPAC1-R, and/or VPAC2-R; (g) inhibit PACAP binding to PAC1-R-expressing cells; (h) inhibit PACAP binding to the cell surface, e.g., via a glycosaminoglycan ("GAG"); (i) does not inhibit PACAP-mediated binding of such antibody to the cell surface, e.g., via a GAG; (j) inhibit PACAP-mediated binding of such antibody to the cell surface, e.g., via a GAG (k) inhibit PACAP-induced cAMP production; and/or (1) when administered to a subject reduce PACAP-induced vasodilation, photophobia, mast cell degranulation and/or neuronal activation. In some embodiments, said anti-PACAP antibody or antigen binding fragment may not bind to the cell surface in the presence of PACAP38, e.g., via a GAG. In some embodiments, said anti-PACAP antibody or antigen binding fragment may bind to the cell surface in the presence of PACAP38, e.g., via a GAG. In some embodiments, said anti-PACAP antibody or antigen binding fragment may bind in a limited manner to the cell surface in the presence of PACAP38, e.g., via a GAG.

In yet another embodiment, an anti-PACAP antibody or antigen binding fragment of the invention may be suitable for treating a human subject having an acute, episodic or chronic condition associated with increased vasodilation, photophobia, mast cell degranulation and/or neuronal activation. Additionally, the invention pertains to a humanized anti-PACAP antibody or antigen binding fragment that may specifically bind to the same or overlapping linear or conformational epitope(s) on human PACAP as Ab21.H, Ab21.H2, Ab21.H3, or Ab21.H4. also, the invention encompasses an anti-PACAP antibody or antigen binding fragment that may comprise at least 2; at least 3; at least 4; at least 5; or all 6 complementarity determining regions ("CDRs") of an anti-PACAP antibody that may comprise Ab21.H, Ab21.H2, Ab21.H3, or Ab21.H4.

In yet another embodiment, an anti-PACAP antibody or antigen binding fragment of the invention may be suitable for treating a human subject having an acute, episodic or chronic condition associated with increased vasodilation, photophobia, mast cell degranulation and/or neuronal activation. Additionally, the invention pertains to a humanized anti-PACAP antibody or antigen binding fragment that may specifically bind to the same or overlapping linear or conformational epitope(s) on human PACAP as Ab10.H, Ab10.H2, Ab10.H3, Ab10.H4, Ab10.H5, or Ab10.H6. Also, the invention encompasses an anti-PACAP antibody or antigen binding fragment that may comprise at least 2; at least 3; at least 4; at least 5; or all 6 complementarity determining regions ("CDRs") of an anti-PACAP antibody that may comprise Ab10.H, Ab10.H2, Ab10.H3, Ab10.H4, Ab10.H5, or Ab10.H6.

In an additional embodiment of the invention, an anti-PACAP antibody or antigen binding fragment may comprise at least 2, at least 3, at least 4, at least 5, or all 6 complementarity determining regions ("CDRs") of an anti-PACAP antibody selected from Ab22 or Ab23.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 964; a CDR2 sequence consisting of SEQ ID NO: 966; and a CDR3 sequence consisting of SEQ ID NO: 968; and/or (b) a variable light chain comprising a CDR1 sequence consisting of SEQ ID NO: 984; a CDR2 sequence consisting of SEQ ID NO: 986; and a CDR3 sequence consisting of SEQ ID NO: 988. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 962, and/or (b) a variable light chain comprising an amino acid sequence with at least 80, 85, 90, 95, 96, 97, 98, or 99% sequence identity to SEQ ID NO: 982. In another embodiment, the anti-PACAP antibodies and antigen binding fragments thereof may comprise (a) a variable heavy chain having the amino acid sequence of SEQ ID NO: 962, and/or (b) a variable light chain having the amino acid sequence of SEQ ID NO: 982. More specifically, the anti-PACAP antibodies and antigen binding fragments thereof may comprise (a) a heavy chain having the amino acid sequence of SEQ ID NO: 961, and/or (b) a light chain having the amino acid sequence of SEQ ID NO: 981.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1204; a CDR2 sequence consisting of SEQ ID NO: 1206; and a CDR3 sequence consisting of SEQ ID NO: 1208; and/or (b) a variable light chain comprising a CDR1 sequence consisting of SEQ ID NO: 1224; a CDR2 sequence consisting of SEQ ID NO: 1226; and a CDR3 sequence consisting of SEQ ID NO: 1228. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 1202, and/or (b) a variable light chain comprising an amino acid sequence with at least 80, 85, 90, 95, 96, 97, 98, or 99% sequence identity to SEQ ID NO: 1222. In another embodiment, the anti-PACAP antibodies and antigen binding fragments thereof may comprise (a) a variable heavy chain having the amino acid sequence of SEQ ID NO: 1202, and/or (b) a variable light chain having the amino acid sequence of SEQ ID NO: 1222. More specifically, the anti-PACAP antibodies and antigen binding fragments thereof may comprise (a) a heavy chain having the amino acid sequence of SEQ ID NO: 1201, and/or (b) a light chain having the amino acid sequence of SEQ ID NO: 1221.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 844; a CDR2 sequence consisting of SEQ ID NO: 846; and a CDR3 sequence consisting of SEQ ID NO: 848; and/or (b) a variable light chain comprising a CDR1 sequence consisting of SEQ ID NO: 864; a CDR2 sequence consisting of SEQ ID NO: 866; and a CDR3 sequence consisting of SEQ ID NO: 868. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 842, and/or (b) a variable light chain comprising an amino acid sequence with at least 80, 85, 90, 95, 96, 97, 98, or 99% sequence identity to SEQ ID NO: 862. In another embodiment, the anti-PACAP antibodies and antigen binding fragments thereof may comprise (a) a variable heavy chain having the amino acid sequence of SEQ ID NO: 842, and/or (b) a variable light chain having the amino acid sequence of SEQ ID NO: 862. More specifically, the anti-PACAP antibodies and antigen binding fragments thereof may comprise (a) a heavy chain having the amino acid sequence of SEQ ID NO: 841, and/or (b) a light chain having the amino acid sequence of SEQ ID NO: 861.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 884; a CDR2 sequence consisting of SEQ ID NO: 886; and a CDR3 sequence consisting of SEQ ID NO: 888; and/or (b) a variable light chain comprising a CDR1 sequence consisting of SEQ ID NO: 904; a CDR2 sequence consisting of SEQ ID NO: 906; and a CDR3 sequence consisting of SEQ ID NO: 908. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 882, and/or (b) a variable light chain comprising an amino acid sequence with at least 80, 85, 90, 95, 96, 97, 98, or 99% sequence identity to SEQ ID NO: 902. In another embodiment, the anti-PACAP antibodies and antigen binding fragments thereof may comprise (a) a variable heavy chain having the amino acid sequence of SEQ ID NO: 882, and/or (b) a variable light chain having the amino acid sequence of SEQ ID NO: 902. More specifically, the anti-PACAP antibodies and antigen binding fragments thereof may comprise (a) a heavy chain having the amino acid sequence of SEQ ID NO: 881, and/or (b) a light chain having the amino acid sequence of SEQ ID NO: 901.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 924; a CDR2 sequence consisting of SEQ ID NO: 926; and a CDR3 sequence consisting of SEQ ID NO: 928; and/or (b) a variable light chain comprising a CDR1 sequence consisting of SEQ ID NO: 944; a CDR2 sequence consisting of SEQ ID NO: 946; and a CDR3 sequence consisting of SEQ ID NO: 948. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 922, and/or (b) a variable light chain comprising an amino acid sequence with at least 80, 85, 90, 95, 96, 97, 98, or 99% sequence identity to SEQ ID NO: 942. In another embodiment, the anti-PACAP antibodies and antigen binding fragments thereof may comprise (a) a variable heavy chain having the amino acid sequence of SEQ ID NO: 922, and/or (b) a variable light chain having the amino acid sequence of SEQ ID NO: 942. More specifically, the anti-PACAP antibodies and antigen binding fragments thereof may comprise (a) a heavy chain having the amino acid sequence of SEQ ID NO: 921, and/or (b) a light chain having the amino acid sequence of SEQ ID NO: 941.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1284; a CDR2 sequence consisting of SEQ ID NO: 1286; and a CDR3 sequence consisting of SEQ ID NO: 1288; and/or (b) a variable light chain comprising a CDR1 sequence consisting of SEQ ID NO: 1304; a CDR2 sequence consisting of SEQ ID NO: 1306; and a CDR3 sequence consisting of SEQ ID NO: 1308. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1282, and/or (b) a variable light chain comprising an amino acid sequence with at least 80, 85, 90, 95, 96, 97, 98, or 99% sequence identity to SEQ ID NO: 1302. In another embodiment, the anti-PACAP antibodies and antigen binding fragments thereof may comprise (a) a variable heavy chain having the amino acid sequence of SEQ ID NO: 1282, and/or (b) a variable light chain having the amino acid sequence of SEQ ID NO: 1302. More specifically, the anti-PACAP antibodies and antigen binding fragments thereof can comprise (a) a heavy chain having the amino acid sequence of SEQ ID NO: 1281, and/or (b) a light chain having the amino acid sequence of SEQ ID NO: 1301.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1324; a CDR2 sequence consisting of SEQ ID NO: 1326; and a CDR3 sequence consisting of SEQ ID NO: 1328; and/or (b) a variable light chain comprising a CDR1 sequence consisting of SEQ ID NO: 1344; a CDR2 sequence consisting of SEQ ID NO: 1346; and a CDR3 sequence consisting of SEQ ID NO: 1348. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1322, and/or (b) a variable light chain comprising an amino acid sequence with at least 80, 85, 90, 95, 96, 97, 98, or 99% sequence identity to SEQ ID NO: 1342. In another embodiment, the anti-PACAP antibodies and antigen binding fragments thereof may comprise (a) a variable heavy chain having the amino acid sequence of SEQ ID NO: 1322, and/or (b) a variable light chain having the amino acid sequence of SEQ ID NO: 1342. More specifically, the anti-PACAP antibodies and antigen binding fragments thereof can comprise (a) a heavy chain having the amino acid sequence of SEQ ID NO: 1321, and/or (b) a light chain having the amino acid sequence of SEQ ID NO: 1341.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1364; a CDR2 sequence consisting of SEQ ID NO: 1366; and a CDR3 sequence consisting of SEQ ID NO: 1368; and/or (b) a variable light chain comprising a CDR1 sequence consisting of SEQ ID NO: 1384; a CDR2 sequence consisting of SEQ ID NO: 1386; and a CDR3 sequence consisting of SEQ ID NO: 1388. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1362, and/or (b) a variable light chain comprising an amino acid sequence with at least 80, 85, 90, 95, 96, 97, 98, or 99% sequence identity to SEQ ID NO: 1382. In another embodiment, the anti-PACAP antibodies and antigen binding fragments thereof may comprise (a) a variable heavy chain having the amino acid sequence of SEQ ID NO: 1362, and/or (b) a variable light chain having the amino acid sequence of SEQ ID NO: 1382. More specifically, the anti-PACAP antibodies and antigen binding fragments thereof can comprise (a) a heavy chain having the amino acid sequence of SEQ ID NO: 1361, and/or (b) a light chain having the amino acid sequence of SEQ ID NO: 1381.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1404; a CDR2 sequence consisting of SEQ ID NO: 1406; and a CDR3 sequence consisting of SEQ ID NO: 1408; and/or (b) a variable light chain comprising a CDR1 sequence consisting of SEQ ID NO: 1424; a CDR2 sequence consisting of SEQ ID NO: 1426; and a CDR3 sequence consisting of SEQ ID NO: 1428. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1402, and/or (b) a variable light chain comprising an amino acid sequence with at least 80, 85, 90, 95, 96, 97, 98, or 99% sequence identity to SEQ ID NO: 1422. In another embodiment, the anti-PACAP antibodies and antigen binding fragments thereof may comprise (a) a variable heavy chain having the amino acid sequence of SEQ ID NO: 1402, and/or (b) a variable light chain having the amino acid sequence of SEQ ID NO: 1422. More specifically, the anti-PACAP antibodies and antigen binding fragments thereof can comprise (a) a heavy chain having the amino acid sequence of SEQ ID NO: 1401, and/or (b) a light chain having the amino acid sequence of SEQ ID NO: 1421.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1444; a CDR2 sequence consisting of SEQ ID NO: 1446; and a CDR3 sequence consisting of SEQ ID NO: 1448; and/or (b) a variable light chain comprising a CDR1 sequence consisting of SEQ ID NO: 1464; a CDR2 sequence consisting of SEQ ID NO: 1466; and a CDR3 sequence consisting of SEQ ID NO: 1468. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1442, and/or (b) a variable light chain comprising an amino acid sequence with at least 80, 85, 90, 95, 96, 97, 98, or 99% sequence identity to SEQ ID NO: 1462. In another embodiment, the anti-PACAP antibodies and antigen binding fragments thereof may comprise (a) a variable heavy chain having the amino acid sequence of SEQ ID NO: 1442, and/or (b) a variable light chain having the amino acid sequence of SEQ ID NO: 1462. More specifically, the anti-PACAP antibodies and antigen binding fragments thereof can comprise (a) a heavy chain having the amino acid sequence of SEQ ID NO: 1441, and/or (b) a light chain having the amino acid sequence of SEQ ID NO: 1461.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1484; a CDR2 sequence consisting of SEQ ID NO: 1486; and a CDR3 sequence consisting of SEQ ID NO: 1488; and/or (b) a variable light chain comprising a CDR1 sequence consisting of SEQ ID NO: 1504; a CDR2 sequence consisting of SEQ ID NO: 1506; and a CDR3 sequence consisting of SEQ ID NO: 1508. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1482, and/or (b) a variable light chain comprising an amino acid sequence with at least 80, 85, 90, 95, 96, 97, 98, or 99% sequence identity to SEQ ID NO: 1502. In another embodiment, the anti-PACAP antibodies and antigen binding fragments thereof may comprise (a) a variable heavy chain having the amino acid sequence of SEQ ID NO: 1482, and/or (b) a variable light chain having the amino acid sequence of SEQ ID NO: 1502. More specifically, the anti-PACAP antibodies and antigen binding fragments thereof can comprise (a) a heavy chain having the amino acid sequence of SEQ ID NO: 1481, and/or (b) a light chain having the amino acid sequence of SEQ ID NO: 1501.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1524; a CDR2 sequence consisting of SEQ ID NO: 1526; and a CDR3 sequence consisting of SEQ ID NO: 1528; and/or (b) a variable light chain comprising a CDR1 sequence consisting of SEQ ID NO: 1544; a CDR2 sequence consisting of SEQ ID NO: 1546; and a CDR3 sequence consisting of SEQ ID NO: 1548. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1522, and/or (b) a variable light chain comprising an amino acid sequence with at least 80, 85, 90, 95, 96, 97, 98, or 99% sequence identity to SEQ ID NO: 1542. In another embodiment, the anti-PACAP antibodies and antigen binding fragments thereof may comprise (a) a variable heavy chain having the amino acid sequence of SEQ ID NO: 1522, and/or (b) a variable light chain having the amino acid sequence of SEQ ID NO: 1542. More specifically, the anti-PACAP antibodies and antigen binding fragments thereof can comprise (a) a heavy chain having the amino acid sequence of SEQ ID NO: 1521, and/or (b) a light chain having the amino acid sequence of SEQ ID NO: 1541.

In a specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1564; a CDR2 sequence consisting of SEQ ID NO: 1566; and a CDR3 sequence consisting of SEQ ID NO: 1568; and/or (b) a variable light chain comprising a CDR1 sequence consisting of SEQ ID NO: 1584; a CDR2 sequence consisting of SEQ ID NO: 1586; and a CDR3 sequence consisting of SEQ ID NO: 1588. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1562, and/or (b) a variable light chain comprising an amino acid sequence with at least 80, 85, 90, 95, 96, 97, 98, or 99% sequence identity to SEQ ID NO: 1582. In another embodiment, the anti-PACAP antibodies and antigen binding fragments thereof may comprise (a) a variable heavy chain having the amino acid sequence of SEQ ID NO: 1562, and/or (b) a variable light chain having the amino acid sequence of SEQ ID NO: 1582. More specifically, the anti-PACAP antibodies and antigen binding fragments thereof can comprise (a) a heavy chain having the amino acid sequence of SEQ ID NO: 1561, and/or (b) a light chain having the amino acid sequence of SEQ ID NO: 1581.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 962 and comprising a CDR1 sequence consisting of SEQ ID NO: 964; a CDR2 sequence consisting of SEQ ID NO: 966; and a CDR3 sequence consisting of SEQ ID NO: 968; and/or (b) a variable light chain comprising an amino acid sequence with at least 80, 85, 90, 95, 96, 97, 98, or 99% sequence identity to SEQ ID NO: 982 and comprising a CDR1 sequence consisting of SEQ ID NO: 984; a CDR2 sequence consisting of SEQ ID NO: 986; and a CDR3 sequence consisting of SEQ ID NO: 988. Alternatively, the anti-PACAP antibodies and antigen binding fragments thereof can comprise (a) a variable heavy chain having the amino acid sequence of SEQ ID NO: 962, and/or (b) a variable light chain having the amino acid sequence of SEQ ID NO: 982. Alternatively, the anti-PACAP antibodies and antigen binding fragments thereof can comprise (a) a variable heavy chain having the amino acid sequence of SEQ ID NO: 962, and (b) a variable light chain having the amino acid sequence of SEQ ID NO: 982. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 961 and comprising a CDR1 sequence consisting of SEQ ID NO: 964; a CDR2 sequence consisting of SEQ ID NO: 966; and a CDR3 sequence consisting of SEQ ID NO: 968; and/or (b) a light chain comprising an amino acid sequence with at least 80, 85, 90, 95, 96, 97, 98, or 99% sequence identity to SEQ ID NO: 981 and comprising a CDR1 sequence consisting of SEQ ID NO: 984; a CDR2 sequence consisting of SEQ ID NO: 986; and a CDR3 sequence consisting of SEQ ID NO: 988. Alternatively, the anti-PACAP antibodies and antigen binding fragments thereof can comprise (a) a heavy chain having the amino acid sequence of SEQ ID NO: 961, and/or (b) a light chain having the amino acid sequence of SEQ ID NO: 981. Alternatively, the anti-PACAP antibodies and antigen binding fragments thereof can comprise (a) a heavy chain having the amino acid sequence of SEQ ID NO: 961, and (b) a light chain having the amino acid sequence of SEQ ID NO: 981.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1202 and comprising a CDR1 sequence consisting of SEQ ID NO: 1204; a CDR2 sequence consisting of SEQ ID NO: 1206; and a CDR3 sequence consisting of SEQ ID NO: 1208; and/or (b) a variable light chain comprising an amino acid sequence with at least 80, 85, 90, 95, 96, 97, 98, or 99% sequence identity to SEQ ID NO: 1222 and comprising a CDR1 sequence consisting of SEQ ID NO: 1224; a CDR2 sequence consisting of SEQ ID NO: 1226; and a CDR3 sequence consisting of SEQ ID NO: 1228. Alternatively, the anti-PACAP antibodies and antigen binding fragments thereof can comprise (a) a variable heavy chain having the amino acid sequence of SEQ ID NO: 1202, and/or (b) a variable light chain having the amino acid sequence of SEQ ID NO: 1222. Alternatively, the anti-PACAP antibodies and antigen binding fragments thereof can comprise (a) a variable heavy chain having the amino acid sequence of SEQ ID NO: 1202, and (b) a variable light chain having the amino acid sequence of SEQ ID NO: 1222. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1201 and comprising a CDR1 sequence consisting of SEQ ID NO: 1204; a CDR2 sequence consisting of SEQ ID NO: 1206; and a CDR3 sequence consisting of SEQ ID NO: 1208; and/or (b) a light chain comprising an amino acid sequence with at least 80, 85, 90, 95, 96, 97, 98, or 99% sequence identity to SEQ ID NO: 1221 and comprising a CDR1 sequence consisting of SEQ ID NO: 1224; a CDR2 sequence consisting of SEQ ID NO: 1226; and a CDR3 sequence consisting of SEQ ID NO: 1228. Alternatively, the anti-PACAP antibodies and antigen binding fragments thereof can comprise (a) a heavy chain having the amino acid sequence of SEQ ID NO: 1201, and/or (b) a light chain having the amino acid sequence of SEQ ID NO: 1221. Alternatively, the anti-PACAP antibodies and antigen binding fragments thereof can comprise (a) a heavy chain having the amino acid sequence of SEQ ID NO: 1201, and (b) a light chain having the amino acid sequence of SEQ ID NO: 1221.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1282 and comprising a CDR1 sequence consisting of SEQ ID NO: 1284; a CDR2 sequence consisting of SEQ ID NO: 1286; and a CDR3 sequence consisting of SEQ ID NO: 1288; and/or (b) a variable light chain comprising an amino acid sequence with at least 80, 85, 90, 95, 96, 97, 98, or 99% sequence identity to SEQ ID NO: 1302 and comprising a CDR1 sequence consisting of SEQ ID NO: 1304; a CDR2 sequence consisting of SEQ ID NO: 1306; and a CDR3 sequence consisting of SEQ ID NO: 1308. Alternatively, the anti-PACAP antibodies and antigen binding fragments thereof can comprise (a) a variable heavy chain having the amino acid sequence of SEQ ID NO: 1282, and/or (b) a variable light chain having the amino acid sequence of SEQ ID NO: 1302. Alternatively, the anti-PACAP antibodies and antigen binding fragments thereof can comprise (a) a variable heavy chain having the amino acid sequence of SEQ ID NO: 1282, and (b) a variable light chain having the amino acid sequence of SEQ ID NO: 1302. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1281 and comprising a CDR1 sequence consisting of SEQ ID NO: 1284; a CDR2 sequence consisting of SEQ ID NO: 1286; and a CDR3 sequence consisting of SEQ ID NO: 1288; and/or (b) a light chain comprising an amino acid sequence with at least 80, 85, 90, 95, 96, 97, 98, or 99% sequence identity to SEQ ID NO: 1301 and comprising a CDR1 sequence consisting of SEQ ID NO: 1304; a CDR2 sequence consisting of SEQ ID NO: 1306; and a CDR3 sequence consisting of SEQ ID NO: 1308. Alternatively, the anti-PACAP antibodies and antigen binding fragments thereof can comprise (a) a heavy chain having the amino acid sequence of SEQ ID NO: 1281, and/or (b) a light chain having the amino acid sequence of SEQ ID NO: 1301. Alternatively, the anti-PACAP antibodies and antigen binding fragments thereof can comprise (a) a heavy chain having the amino acid sequence of SEQ ID NO: 1281, and (b) a light chain having the amino acid sequence of SEQ ID NO: 1301.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1322 and comprising a CDR1 sequence consisting of SEQ ID NO: 1324; a CDR2 sequence consisting of SEQ ID NO: 1326; and a CDR3 sequence consisting of SEQ ID NO: 1328; and/or (b) a variable light chain comprising an amino acid sequence with at least 80, 85, 90, 95, 96, 97, 98, or 99% sequence identity to SEQ ID NO: 1342 and comprising a CDR1 sequence consisting of SEQ ID NO: 1344; a CDR2 sequence consisting of SEQ ID NO: 1346; and a CDR3 sequence consisting of SEQ ID NO: 1348. Alternatively, the anti-PACAP antibodies and antigen binding fragments thereof can comprise (a) a variable heavy chain having the amino acid sequence of SEQ ID NO: 1322, and/or (b) a variable light chain having the amino acid sequence of SEQ ID NO: 1342. Alternatively, the anti-PACAP antibodies and antigen binding fragments thereof can comprise (a) a variable heavy chain having the amino acid sequence of SEQ ID NO: 1322, and (b) a variable light chain having the amino acid sequence of SEQ ID NO: 1342. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1321 and comprising a CDR1 sequence consisting of SEQ ID NO: 1324; a CDR2 sequence consisting of SEQ ID NO: 1326; and a CDR3 sequence consisting of SEQ ID NO: 1328; and/or (b) a light chain comprising an amino acid sequence with at least 80, 85, 90, 95, 96, 97, 98, or 99% sequence identity to SEQ ID NO: 1341 and comprising a CDR1 sequence consisting of SEQ ID NO: 1344; a CDR2 sequence consisting of SEQ ID NO: 1346; and a CDR3 sequence consisting of SEQ ID NO: 1348. Alternatively, the anti-PACAP antibodies and antigen binding fragments thereof can comprise (a) a heavy chain having the amino acid sequence of SEQ ID NO: 1321, and/or (b) a light chain having the amino acid sequence of SEQ ID NO: 1341. Alternatively, the anti-PACAP antibodies and antigen binding fragments thereof can comprise (a) a heavy chain having the amino acid sequence of SEQ ID NO: 1321, and (b) a light chain having the amino acid sequence of SEQ ID NO: 1341.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1362 and comprising a CDR1 sequence consisting of SEQ ID NO: 1364; a CDR2 sequence consisting of SEQ ID NO: 1366; and a CDR3 sequence consisting of SEQ ID NO: 1368; and/or (b) a variable light chain comprising an amino acid sequence with at least 80, 85, 90, 95, 96, 97, 98, or 99% sequence identity to SEQ ID NO: 1382 and comprising a CDR1 sequence consisting of SEQ ID NO: 1384; a CDR2 sequence consisting of SEQ ID NO: 1386; and a CDR3 sequence consisting of SEQ ID NO: 1388. Alternatively, the anti-PACAP antibodies and antigen binding fragments thereof can comprise (a) a variable heavy chain having the amino acid sequence of SEQ ID NO: 1362, and/or (b) a variable light chain having the amino acid sequence of SEQ ID NO: 1382. Alternatively, the anti-PACAP antibodies and antigen binding fragments thereof can comprise (a) a variable heavy chain having the amino acid sequence of SEQ ID NO: 1362, and (b) a variable light chain having the amino acid sequence of SEQ ID NO: 1382. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1361 and comprising a CDR1 sequence consisting of SEQ ID NO: 1364; a CDR2 sequence consisting of SEQ ID NO: 1366; and a CDR3 sequence consisting of SEQ ID NO: 1368; and/or (b) a light chain comprising an amino acid sequence with at least 80, 85, 90, 95, 96, 97, 98, or 99% sequence identity to SEQ ID NO: 1381 and comprising a CDR1 sequence consisting of SEQ ID NO: 1384; a CDR2 sequence consisting of SEQ ID NO: 1386; and a CDR3 sequence consisting of SEQ ID NO: 1388. Alternatively, the anti-PACAP antibodies and antigen binding fragments thereof can comprise (a) a heavy chain having the amino acid sequence of SEQ ID NO: 1361, and/or (b) a light chain having the amino acid sequence of SEQ ID NO: 1381. Alternatively, the anti-PACAP antibodies and antigen binding fragments thereof can comprise (a) a heavy chain having the amino acid sequence of SEQ ID NO: 1361, and (b) a light chain having the amino acid sequence of SEQ ID NO: 1381.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1402 and comprising a CDR1 sequence consisting of SEQ ID NO: 1404; a CDR2 sequence consisting of SEQ ID NO: 1406; and a CDR3 sequence consisting of SEQ ID NO: 1408; and/or (b) a variable light chain comprising an amino acid sequence with at least 80, 85, 90, 95, 96, 97, 98, or 99% sequence identity to SEQ ID NO: 1422 and comprising a CDR1 sequence consisting of SEQ ID NO: 1424; a CDR2 sequence consisting of SEQ ID NO: 1426; and a CDR3 sequence consisting of SEQ ID NO: 1428. Alternatively, the anti-PACAP antibodies and antigen binding fragments thereof can comprise (a) a variable heavy chain having the amino acid sequence of SEQ ID NO: 1402, and/or (b) a variable light chain having the amino acid sequence of SEQ ID NO: 1422. Alternatively, the anti-PACAP antibodies and antigen binding fragments thereof can comprise (a) a variable heavy chain having the amino acid sequence of SEQ ID NO: 1402, and (b) a variable light chain having the amino acid sequence of SEQ ID NO: 1422. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1401 and comprising a CDR1 sequence consisting of SEQ ID NO: 1404; a CDR2 sequence consisting of SEQ ID NO: 1406; and a CDR3 sequence consisting of SEQ ID NO: 1408; and/or (b) a light chain comprising an amino acid sequence with at least 80, 85, 90, 95, 96, 97, 98, or 99% sequence identity to SEQ ID NO: 1421 and comprising a CDR1 sequence consisting of SEQ ID NO: 1424; a CDR2 sequence consisting of SEQ ID NO: 1426; and a CDR3 sequence consisting of SEQ ID NO: 1428. Alternatively, the anti-PACAP antibodies and antigen binding fragments thereof can comprise (a) a heavy chain having the amino acid sequence of SEQ ID NO: 1401, and/or (b) a light chain having the amino acid sequence of SEQ ID NO: 1421. Alternatively, the anti-PACAP antibodies and antigen binding fragments thereof can comprise (a) a heavy chain having the amino acid sequence of SEQ ID NO: 1401, and (b) a light chain having the amino acid sequence of SEQ ID NO: 1421.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1442 and comprising a CDR1 sequence consisting of SEQ ID NO: 1444; a CDR2 sequence consisting of SEQ ID NO: 1446; and a CDR3 sequence consisting of SEQ ID NO: 1448; and/or (b) a variable light chain comprising an amino acid sequence with at least 80, 85, 90, 95, 96, 97, 98, or 99% sequence identity to SEQ ID NO: 1462 and comprising a CDR1 sequence consisting of SEQ ID NO: 1464; a CDR2 sequence consisting of SEQ ID NO: 1466; and a CDR3 sequence consisting of SEQ ID NO: 1468. Alternatively, the anti-PACAP antibodies and antigen binding fragments thereof can comprise (a) a variable heavy chain having the amino acid sequence of SEQ ID NO: 1442, and/or (b) a variable light chain having the amino acid sequence of SEQ ID NO: 1462. Alternatively, the anti-PACAP antibodies and antigen binding fragments thereof can comprise (a) a variable heavy chain having the amino acid sequence of SEQ ID NO: 1442, and (b) a variable light chain having the amino acid sequence of SEQ ID NO: 1462. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1441 and comprising a CDR1 sequence consisting of SEQ ID NO: 1444; a CDR2 sequence consisting of SEQ ID NO: 1446; and a CDR3 sequence consisting of SEQ ID NO: 1448; and/or (b) a light chain comprising an amino acid sequence with at least 80, 85, 90, 95, 96, 97, 98, or 99% sequence identity to SEQ ID NO: 1461 and comprising a CDR1 sequence consisting of SEQ ID NO: 1464; a CDR2 sequence consisting of SEQ ID NO: 1466; and a CDR3 sequence consisting of SEQ ID NO: 1468. Alternatively, the anti-PACAP antibodies and antigen binding fragments thereof can comprise (a) a heavy chain having the amino acid sequence of SEQ ID NO: 1441, and/or (b) a light chain having the amino acid sequence of SEQ ID NO: 1461. Alternatively, the anti-PACAP antibodies and antigen binding fragments thereof can comprise (a) a heavy chain having the amino acid sequence of SEQ ID NO: 1441, and (b) a light chain having the amino acid sequence of SEQ ID NO: 1461.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1482 and comprising a CDR1 sequence consisting of SEQ ID NO: 1484; a CDR2 sequence consisting of SEQ ID NO: 1486; and a CDR3 sequence consisting of SEQ ID NO: 1488; and/or (b) a variable light chain comprising an amino acid sequence with at least 80, 85, 90, 95, 96, 97, 98, or 99% sequence identity to SEQ ID NO: 1502 and comprising a CDR1 sequence consisting of SEQ ID NO: 1504; a CDR2 sequence consisting of SEQ ID NO: 1506; and a CDR3 sequence consisting of SEQ ID NO: 1508. Alternatively, the anti-PACAP antibodies and antigen binding fragments thereof can comprise (a) a variable heavy chain having the amino acid sequence of SEQ ID NO: 1482, and/or (b) a variable light chain having the amino acid sequence of SEQ ID NO: 1502. Alternatively, the anti-PACAP antibodies and antigen binding fragments thereof can comprise (a) a variable heavy chain having the amino acid sequence of SEQ ID NO: 1482, and (b) a variable light chain having the amino acid sequence of SEQ ID NO: 1502. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1481 and comprising a CDR1 sequence consisting of SEQ ID NO: 1484; a CDR2 sequence consisting of SEQ ID NO: 1486; and a CDR3 sequence consisting of SEQ ID NO: 1488; and/or (b) a light chain comprising an amino acid sequence with at least 80, 85, 90, 95, 96, 97, 98, or 99% sequence identity to SEQ ID NO: 1501 and comprising a CDR1 sequence consisting of SEQ ID NO: 1504; a CDR2 sequence consisting of SEQ ID NO: 1506; and a CDR3 sequence consisting of SEQ ID NO: 1508. Alternatively, the anti-PACAP antibodies and antigen binding fragments thereof can comprise (a) a heavy chain having the amino acid sequence of SEQ ID NO: 1481, and/or (b) a light chain having the amino acid sequence of SEQ ID NO: 1501. Alternatively, the anti-PACAP antibodies and antigen binding fragments thereof can comprise (a) a heavy chain having the amino acid sequence of SEQ ID NO: 1481, and (b) a light chain having the amino acid sequence of SEQ ID NO: 1501.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1522 and comprising a CDR1 sequence consisting of SEQ ID NO: 1524; a CDR2 sequence consisting of SEQ ID NO: 1526; and a CDR3 sequence consisting of SEQ ID NO: 1528; and/or (b) a variable light chain comprising an amino acid sequence with at least 80, 85, 90, 95, 96, 97, 98, or 99% sequence identity to SEQ ID NO: 1542 and comprising a CDR1 sequence consisting of SEQ ID NO: 1544; a CDR2 sequence consisting of SEQ ID NO: 1546; and a CDR3 sequence consisting of SEQ ID NO: 1548. Alternatively, the anti-PACAP antibodies and antigen binding fragments thereof can comprise (a) a variable heavy chain having the amino acid sequence of SEQ ID NO: 1522, and/or (b) a variable light chain having the amino acid sequence of SEQ ID NO: 1542. Alternatively, the anti-PACAP antibodies and antigen binding fragments thereof can comprise (a) a variable heavy chain having the amino acid sequence of SEQ ID NO: 1522, and (b) a variable light chain having the amino acid sequence of SEQ ID NO: 1542. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1521 and comprising a CDR1 sequence consisting of SEQ ID NO: 1524; a CDR2 sequence consisting of SEQ ID NO: 1526; and a CDR3 sequence consisting of SEQ ID NO: 1528; and/or (b) a light chain comprising an amino acid sequence with at least 80, 85, 90, 95, 96, 97, 98, or 99% sequence identity to SEQ ID NO: 1541 and comprising a CDR1 sequence consisting of SEQ ID NO: 1544; a CDR2 sequence consisting of SEQ ID NO: 1546; and a CDR3 sequence consisting of SEQ ID NO: 1548. Alternatively, the anti-PACAP antibodies and antigen binding fragments thereof can comprise (a) a heavy chain having the amino acid sequence of SEQ ID NO: 1521, and/or (b) a light chain having the amino acid sequence of SEQ ID NO: 1541. Alternatively, the anti-PACAP antibodies and antigen binding fragments thereof can comprise (a) a heavy chain having the amino acid sequence of SEQ ID NO: 1521, and (b) a light chain having the amino acid sequence of SEQ ID NO: 1541.

In another specific embodiment, the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1562 and comprising a CDR1 sequence consisting of SEQ ID NO: 1564; a CDR2 sequence consisting of SEQ ID NO: 1566; and a CDR3 sequence consisting of SEQ ID NO: 1568; and/or (b) a variable light chain comprising an amino acid sequence with at least 80, 85, 90, 95, 96, 97, 98, or 99% sequence identity to SEQ ID NO: 1582 and comprising a CDR1 sequence consisting of SEQ ID NO: 1584; a CDR2 sequence consisting of SEQ ID NO: 1586; and a CDR3 sequence consisting of SEQ ID NO: 1588. Alternatively, the anti-PACAP antibodies and antigen binding fragments thereof can comprise (a) a variable heavy chain having the amino acid sequence of SEQ ID NO: 1562, and/or (b) a variable light chain having the amino acid sequence of SEQ ID NO: 1582. Alternatively, the anti-PACAP antibodies and antigen binding fragments thereof can comprise (a) a variable heavy chain having the amino acid sequence of SEQ ID NO: 1562, and (b) a variable light chain having the amino acid sequence of SEQ ID NO: 1582. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1561 and comprising a CDR1 sequence consisting of SEQ ID NO: 1564; a CDR2 sequence consisting of SEQ ID NO: 1566; and a CDR3 sequence consisting of SEQ ID NO: 1568; and/or (b) a light chain comprising an amino acid sequence with at least 80, 85, 90, 95, 96, 97, 98, or 99% sequence identity to SEQ ID NO: 1581 and comprising a CDR1 sequence consisting of SEQ ID NO: 1584; a CDR2 sequence consisting of SEQ ID NO: 1586; and a CDR3 sequence consisting of SEQ ID NO: 1588. Alternatively, the anti-PACAP antibodies and antigen binding fragments thereof can comprise (a) a heavy chain having the amino acid sequence of SEQ ID NO: 1561, and/or (b) a light chain having the amino acid sequence of SEQ ID NO: 1581. Alternatively, the anti-PACAP antibodies and antigen binding fragments thereof can comprise (a) a heavy chain having the amino acid sequence of SEQ ID NO: 1561, and (b) a light chain having the amino acid sequence of SEQ ID NO: 1581.

Another embodiment of the invention generally pertains to a human, humanized or chimerized anti-human PACAP antibody or antibody fragment that specifically binds to an epitope on human PACAP or a fragment or variant thereof containing the corresponding amino acid residues wherein said epitope may be selected from the group consisting of:

i. at least one of residues 22, 23, 27, 28, and 31 of a human PACAP;
ii. at least one of residues 12, 20, 23, 24, 26, 27, and 28 of a human PACAP;
iii. at least one of residues 19, 22, 23, and 27 of a human PACAP;
iv. at least two of the residues of (i), (ii), or (iii);
v. at least three of the residues of (i), (ii), or (iii);
vi. at least four of the residues of (i), (ii), or (iii);
vii. at least five of the residues of (i) or (ii);
viii. at least six of the residues of (ii);
ix. at least seven of the residues of (ii); and
x. at least the residues 23, 27, and 28, of a human PACAP, and optionally, between one to six of the additional residues of (i) and/or (ii).

In yet another embodiment of the invention, a human, humanized or chimerized anti-human PACAP antibody or antibody fragment may specifically bind to an epitope on human PACAP (or a fragment or variant thereof containing the corresponding amino acid residues that is present in human wild-type PACAP38) but not human wild-type human PACAP27. Also, another embodiment of the invention relates to a human, humanized or chimerized anti-human PACAP antibody or antibody fragment that may specifically bind to an epitope on human PACAP or a fragment or variant thereof containing the corresponding amino acid residues, wherein said epitope consists of the residues of any one of (i), (ii), or (iii). Also, another embodiment of the invention pertains to a human, humanized or chimerized anti-human PACAP antibody or antibody fragment that may specifically bind to an epitope on human PACAP (or a fragment or variant thereof containing the corresponding amino acid residues) that is present in human wild-type PACAP38 and in human wild-type human PACAP27. Said epitope may be identified by alanine scanning, e.g., as disclosed in Example 12 herein, or by another art recognized method.

Another embodiment of the invention generally relates to an anti-PACAP antibody or antigen binding fragment that may be chimeric, human or humanized. In yet another embodiment, an anti-PACAP antibody or antigen binding fragment may be selected from the group consisting of scFvs, camelbodies, nanobodies, Immunoglobulin New Antigen Receptor ("IgNAR"), fragment antigen binding ("Fab") fragments, Fab' fragments, MetMab like antibodies, monovalent antigen binding fragments, and $F(ab')_2$ fragments. Additionally, yet another embodiment encompasses an anti-PACAP antibody or antigen binding fragment that may substantially or entirely lacks N-glycosylation and/or O-glycosylation.

Another embodiment of the invention encompasses an anti-PACAP antibody or antigen binding fragment that may comprise a human constant domain, e.g., an IgG1, IgG2, IgG3, or IgG4 antibody. Moreover, an embodiment of the invention relates to an anti-PACAP antibody or antigen binding fragment that may comprise an Fc region that has been modified to alter at least one of effector function, half-life, proteolysis, or glycosylation, e.g., wherein the Fc region may contain one or more mutations that alters or eliminates N- and/or O-glycosylation.

In yet another embodiment of the invention, an anti-PACAP antibody or antigen binding fragment may bind to PACAP with a binding affinity ($K_D$) of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M, e.g., as determined by ELISA, bio-layer interferometry ("BLI"), KINEXA or surface plasmon resonance at 25° or 37° C. Also, another embodiment of the invention encompasses an anti-PACAP antibody or antigen binding fragment that may bind to PACAP with a binding affinity ($K_D$) of less than or equal to $5\times10^{-10}$ M, $10^{-10}$ M, $5\times10^{-11}$ M, $10^{-11}$ M, $5\times10^{-12}$ M, or $10^{-12}$ M. Also, an additional embodiment of the invention pertains to an anti-PACAP antibody or antigen binding fragment that may bind to PACAP with an off-rate ($k_d$) of less than or equal to $5\times10^{-4}$ $s^{-1}$, $10^{-4}$ $s^{-1}$, $5\times10^{-5}$ $s^{-1}$, or $10^{-5}$ $s^{-1}$.

An additional embodiment of the invention relates to an anti-PACAP antibody or antigen binding fragment that may be directly or indirectly attached to a detectable label or therapeutic agent. Also, another embodiment of the invention pertains to an anti-PACAP antibody or antigen binding fragment that may bind to PACAP with a $K_D$ that is less than about 100 nM, 40 nM, 50 pM, 25 pM, or is between about 10 pM and about 100 pM. An additional embodiment relates to an anti-PACAP antibody or antigen binding fragment that may have stronger affinity for PACAP as compared to VIP and/or does not bind to VIP, e.g., wherein the affinity of said antibody or antigen binding fragment to PACAP may be at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold or more stronger than the affinity of said antibody or antigen binding fragment to VIP Also, another aspect of the invention generally relates to an anti-PACAP antibody or antigen binding fragment that may be attached to at least one effector or functional moiety and/or one or more detectable moieties, e.g., a fluorescent dye, enzyme, substrate, bioluminescent material, radioactive material, chemiluminescent moiety, or mixture thereof. Yet another embodiment of the invention pertains to an anti-idiotypic antibody that may be produced against an anti-PACAP antibody or antigen binding fragment that optionally may neutralize one or more biological effects of the anti-PACAP antibody to which it may bind. Also, said anti-idiotypic antibody may be used to monitor the in vivo levels of said anti-PACAP antibody or antigen binding fragment in a subject or to neutralize in vivo effects of said anti-PACAP antibody in a subject.

Another embodiment of the invention encompasses a composition that may be suitable for therapeutic, prophylactic, or a diagnostic use that may comprise a therapeutically, prophylactically or diagnostically effective amount of at least one anti-PACAP antibody or antigen binding fragment or anti-idiotypic antibody. Said composition may be suitable for subcutaneous administration; and/or may be suitable for intravenous or intramuscular administration. Additionally in an embodiment said composition may be lyophilized, stabilized, and/or formulated for administration by injection. Also, said composition may further comprise a pharmaceutically acceptable diluent, carrier, solubilizer, emulsifier, preservative, or mixture thereof and/or another active agent, e.g., wherein the other active agent may be selected from the group consisting of a chemotherapeutic, an analgesic, an anti-inflammatory, an immunosuppressant, a cytokine, an antiproliferative, an antiemetic, and a cytotoxin.

Also, another embodiment pertains to an isolated nucleic acid sequence or nucleic acid sequences that may encode an anti-PACAP antibody or antigen binding fragment or anti-idiotypic antibody. In an embodiment of the invention, a vector or vectors may contain the isolated nucleic acid sequence or sequences. Furthermore, another embodiment relates to a host cell that may comprise the isolated nucleic acid sequence or sequences and/or vector or vectors. Said host cell may be a mammalian, bacterial, fungal, yeast, avian, amphibian, plant or insect cell, or is a CHO cell. Also, said host cell may be a filamentous fungus or a yeast, e.g., selected from the following genera: *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces* preferably *Pichia* and more preferably *Pichia pastoris, Pichia methanolica* or *Hansenula polymorpha* (*Pichia angusta*); or said host cell may be a mammalian cell, e.g., selected from baby hamster kidney ("BHK") cells; chinese hamster ovary ("CHO") cells; mouse sertoli cells ("TM4" cells); African green monkey kidney cells ("VERO-76" cells); human cervical carcinoma ("HELA") cells; canine kidney cells ("MDCK"); buffalo rat liver ("BRL") cells; human lung cells; human liver ("Hep G2") cells; mouse mammary tumor ("MMT") cells; TRI cells; MRC 5 cells; and FS4 cells. Additionally, said CHO cell may be selected from one of the following subclones or sub-cell lines: DP12 (CHO K1 dhfr-) cell line, NS0 cells, CHO-DXB11 (CHO-DUKX), CHO-pro3, CHO-DG44, CHO 1-15, CHO DP-12, Lec2, M1WT3, Lec8, or pgsA-745.

Another embodiment of the invention relates to a method of expressing an anti-PACAP antibody or antigen binding fragment that may comprise culturing said host cell under conditions that provide for expression of said antibody or antigen binding fragment. Additionally, said host cell may be a polyploid yeast culture or CHO cell that stably expresses and secretes into the culture medium at least 10-25 mg/liter of said antibody or antigen binding fragment. Also, said polyploid yeast, preferably a *Pichia* yeast, may be made by a method that may comprise: (i) introducing at least one expression vector containing one or more heterologous polynucleotides encoding said antibody operably linked to a promoter and a signal sequence into a haploid yeast cell; (ii) producing by mating or spheroplast fusion a polyploid yeast from said first and/or second haploid yeast cell; (iii) selecting polyploid yeast cells that stably express said antibody; and (iv) producing stable polyploid yeast cultures from said polyploid yeast cells that stably express said antibody into the culture medium.

Another aspect of the invention generally relates to a method for blocking, inhibiting or neutralizing one or more biological effects associated with pituitary adenylate cyclase-activating peptide ("PACAP") in a subject that may comprise administering to a subject in need thereof an effective amount of an anti-PACAP antibody or antigen binding fragment as disclosed herein or a composition as disclosed herein. In another embodiment, the invention generally relates to a method for blocking, inhibiting or neutralizing one or more biological effects associated with pituitary adenylate cyclase-activating peptide ("PACAP") in a subject that may comprise administering to a subject in need thereof an effective amount of an anti-PACAP antibody or antigen binding fragment as discussed herein or a composition as discussed herein that may antagonize, inhibit, neutralize, or block at least one biological effect associated with human PACAP and that does not substantially interact with (bind) Vasoactive Intestinal Peptide ("VIP").

Also, another embodiment encompasses a method for blocking, inhibiting or neutralizing one or more biological effects associated with pituitary adenylate cyclase-activating peptide ("PACAP") in a subject that may comprise administering to a subject in need thereof an effective amount of an anti-PACAP antibody or antigen binding fragment as disclosed herein or a composition as disclosed herein that may elicit or may comprise one or more of the following: (a) inhibits or neutralizes at least one biological effect elicited by PACAP; (b) neutralizes or inhibits PACAP activation of at least one of PAC1 receptor ("PAC1-R"), vasoactive intestinal peptide receptor type 1 ("VPAC1-R"), and/or vasoactive intestinal peptide receptor type 2 ("VPAC2-R"); (c) neutralizes or inhibits PACAP activation of each of PAC1-R, VPAC1-R, and VPAC2-R; (d) neutralizes or inhibits PACAP activation of PAC1-R; (e) is capable of inhibiting PACAP binding to at least one of PAC1-R, VPAC1-R, and/or VPAC2-R; (f) is capable of inhibiting PACAP binding to each of PAC1-R, VPAC1-R, and/or VPAC2-R; (g) is capable of inhibiting PACAP binding to PAC1-R-expressing cells; (h) is capable of inhibiting PACAP binding to the cell surface, e.g., via a glycosaminoglycan ("GAG"); (i) does not inhibit PACAP-mediated binding of such antibody to the cell surface, e.g., via a GAG; (j) inhibits PACAP-mediated binding of such antibody to the cell surface, e.g., via a GAG; (k) inhibits PACAP-induced cAMP production; and/or (1) when administered to a subject reduces PACAP-induced vasodilation, photophobia, mast cell degranulation and/or neuronal activation.

Yet another embodiment of the invention pertains to a method for treating or preventing the onset, frequency, severity or duration of headache or migraine, e.g. wherein the headache or migraine may be selected from migraine with aura, migraine without aura, hemiplegic migraine, cluster headache, migrainous neuralgia, chronic headache, chronic migraine, medication overuse headache, and tension headache, in a subject that may comprise administering to a subject in need thereof an effective amount of a human, humanized, or chimerized anti-Pituitary Adenylate Cyclase-Activating Polypeptide ("PACAP") antibody or antigen binding fragment as discussed herein or a composition as discussed herein that may elicit or may comprise one or more of the following: (a) inhibits or neutralizes at least one biological effect elicited by PACAP; (b) neutralizes or inhibits PACAP activation of at least one of PAC1 receptor ("PAC1-R"), vasoactive intestinal peptide receptor type 1 ("VPAC1-R"), and/or vasoactive intestinal peptide receptor type 2 ("VPAC2-R"); (c) neutralizes or inhibits PACAP activation of each of PAC1-R, VPAC1-R, and VPAC2-R; (d) neutralizes or inhibits PACAP activation of PAC1-R; (c) is capable of inhibiting PACAP binding to at least one of PAC1-R, VPAC1-R, and/or VPAC2-R; (f) is capable of inhibiting PACAP binding to each of PAC1-R, VPAC1-R, and/or VPAC2-R; (g) is capable of inhibiting PACAP binding to PAC1-R-expressing cells; (h) is capable of inhibiting PACAP binding to the cell surface, e.g., via a glycosaminoglycan ("GAG"); (i) does not inhibit PACAP-mediated binding of such antibody to the cell surface, e.g., via a GAG; (j) inhibits PACAP-mediated binding of such antibody to the cell surface, e.g., via a GAG; (k) inhibits PACAP-induced cAMP production; and/or (1) when administered to a subject reduces PACAP-induced vasodilation, photophobia, mast cell degranulation and/or neuronal activation.

Yet another embodiment of the invention pertains to a method of treating a human subject having an acute, episodic or chronic condition associated with at least one of increased vasodilation, photophobia, mast cell degranulation and neuronal activation or a combination of any of the above that may comprise administering to a subject in need thereof an effective amount of an anti-Pituitary Adenylate Cyclase-Activating Polypeptide ("PACAP") antibody or antigen binding fragment as discussed herein or a composition as discussed herein.

An additional embodiment relates to a method for blocking, inhibiting or neutralizing one or more biological effects associated with pituitary adenylate cyclase-activating peptide ("PACAP") that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab21.H, Ab21.H2, Ab21.H3, Ab21.H4, or one disclosed herein or a composition disclosed herein.

Yet another embodiment pertains to a method for neutralizing pituitary adenylate cyclase-activating peptide ("PACAP")-induced PAC1 receptor ("PAC1-R"), vasoactive intestinal peptide receptor type 1 ("VPAC1-R"), and/or vasoactive intestinal peptide receptor type 2 ("VPAC2-R") signaling, that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab21.H, Ab21.H2, Ab21.H3, Ab21.H4, or one disclosed herein or a composition disclosed herein.

In a further embodiment the invention encompasses a method for inhibiting pituitary adenylate cyclase-activating peptide ("PACAP")-induced cyclic adenosine monophosphate ("CAMP") production, that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab21.H, Ab21.H2, Ab21.H3, Ab21.H4, or one disclosed herein or a composition disclosed herein.

Yet another embodiment relates to a method for inhibiting pituitary adenylate cyclase-activating peptide ("PACAP")-induced vasodilation, that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab21.H, Ab21.H2, Ab21.H3, Ab21.H4, or one as disclosed herein or a composition discussed herein.

A further embodiment of the invention encompasses a method for treating or preventing a condition associated with elevated anti-pituitary adenylate cyclase-activating peptide ("PACAP") levels in a subject, that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab21.H, Ab21.H2, Ab21.H3, Ab21.H4, or one discussed herein or a composition discussed herein.

An additional embodiment relates to a method for blocking, inhibiting or neutralizing one or more biological effects associated with pituitary adenylate cyclase-activating peptide ("PACAP") that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab10.H, Ab10.H2, Ab10.H3, Ab10.H4, Ab10.H5, Ab10.H6, or one disclosed herein or a composition disclosed herein.

Yet another embodiment pertains to a method for neutralizing pituitary adenylate cyclase-activating peptide ("PACAP")-induced PAC1 receptor ("PAC1-R"), vasoactive intestinal peptide receptor type 1 ("VPAC1-R"), and/or vasoactive intestinal peptide receptor type 2 ("VPAC2-R") signaling, that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab10.H, Ab10.H2, Ab10.H3, Ab10.H4, Ab10.H5, Ab10.H6, or one disclosed herein or a composition disclosed herein.

In a further embodiment the invention encompasses a method for inhibiting pituitary adenylate cyclase-activating peptide ("PACAP")-induced cyclic adenosine monophosphate ("CAMP") production, that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab10.H, Ab10.H2, Ab10.H3, Ab10.H4, Ab10.H5, Ab10.H6, or one disclosed herein or a composition disclosed herein.

Yet another embodiment relates to a method for inhibiting pituitary adenylate cyclase-activating peptide ("PACAP")-induced vasodilation, that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab10.H, Ab10.H2, Ab10.H3, Ab10.H4, Ab10.H5, Ab10.H6, or one as disclosed herein or a composition discussed herein.

A further embodiment of the invention encompasses a method for treating or preventing a condition associated with elevated anti-pituitary adenylate cyclase-activating peptide ("PACAP") levels in a subject, that may comprise administering to a subject in need thereof an effective amount of an anti-PACAP antibody or antigen binding fragment that may specifically bind to the same or overlapping linear or conformational epitope(s) and/or may compete for binding to the same or overlapping linear or conformational epitope(s) on human PACAP as an anti-PACAP antibody comprising Ab10.H, Ab10.H2, Ab10.H3, Ab10.H4, Ab10.H5, Ab10.H6, or one discussed herein or a composition discussed herein.

Another aspect of the invention generally relates to a method wherein an anti-PACAP antibody may be a human antibody or antigen binding fragment; and/or may be a humanized antibody or antigen binding fragment; and/or may be a chimeric antibody or antigen binding fragment. Another aspect of the invention generally pertains to a method wherein an anti-PACAP antibody or antigen binding fragment may bind to PACAP27 and/or PACAP38 and may block PACAP27 and/or PACAP38 binding to PAC1-R, VPAC1-R, and/or VPAC2-R. Also, another embodiment relates to a method wherein an anti-PACAP antibody or antigen binding fragment may bind to PACAP27 and/or PACAP38 and may block PACAP27 and/or PACAP38 binding to each of PAC1-R, VPAC1-R, and VPAC2-R.

Yet another embodiment of the invention pertains to a method wherein the anti-PACAP antibody or antigen binding fragment may bind to PACAP27 and/or PACAP38 and may block PACAP27 and/or PACAP38 binding to PAC1-R-expressing cells. Also, another embodiment of the invention relates to a method wherein a subject may have a condition that may be selected from the group consisting of migraine with aura, migraine without aura, hemiplegic migraines, cluster headaches, migrainous neuralgia, chronic headaches, chronic migraine, medication overuse headache, tension headaches, general headaches, hot flush, photophobia, chronic paroxysmal hemicrania, secondary headaches due to an underlying structural problem in the head, secondary headaches due to an underlying structural problem in the neck, cranial neuralgia, sinus headaches, headache associated with sinusitis, allergy-induced headaches, allergy-induced migraines, trigeminal neuralgia, post-herpetic neuralgia, phantom limb pain, fibromyalgia, reflex sympathetic dystrophy, pain, chronic pain, inflammatory pain, post-operative incision pain, post-surgical pain, trauma-related pain, lower back pain, eye pain, tooth pain, complex regional pain syndrome, cancer pain, primary or metastatic bone cancer pain, fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, menstrual pain, ovarialgia, osteoarthritis pain, rheumatoid arthritis pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder ("PTSD"), anxiety disorders, autoimmune diabetes, Sjögren's syndrome, multiple sclerosis, overactive bladder, bronchial hyperreactivity, asthma, stroke, bronchitis, bronchodilation, emphysema, chronic obstructive pulmonary disease ("COPD"), inflammatory dermatitis, acne vulgaris, atopic dermatitis, urticaria, keloids, hypertrophic scars and rosacea, endothelial dysfunction, Raynaud's syndrome, coronary heart disease ("CHD"), coronary artery disease ("CAD"), heart failure, peripheral arterial disease ("PAD"), diabetes, pulmonary hypertension ("PH"), connective tissue disorder, allergic dermatitis, psoriasis, pruritus, neurogenic cutaneous redness, erythema, sarcoidosis, shock, sepsis, opiate withdrawal syndrome, morphine tolerance, and epilepsy; and/or wherein said subject may have a condition that may be selected from the group consisting of migraine, headache and a pain associated disease or condition; and/or wherein said headache or migraine may be selected from the group consisting of migraine with aura, migraine without aura, hemiplegic migraine, cluster headache, migrainous neuralgia, chronic headache, chronic migraine, medication overuse headache, and tension headache. Also, said subject may have a ocular disorder associated with photophobia selected from the group consisting of achromatopsia, aniridia, photophobia caused by an anticholinergic drug, aphakia, buphthalmos, cataracts, cone dystrophy, congenital abnormalities of the eye, viral conjunctivitis, corneal abrasion, corneal dystrophy, corneal ulcer, disruption of the corneal epithelium, ectopia lentis, endophthalmitis, eye trauma caused by disease, eye trauma caused by injury, eye trauma caused by infection, chalazion, episcleritis, glaucoma, keratoconus, optic nerve hypoplasia, hydrophthalmos, congenital glaucoma iritis, optic neuritis, pigment dispersion syndrome, pupillary dilation, retinal detachment, scarring of the cornea, sclera and uveitis.

Moreover, said subject may have a nervous system-related or neurological condition associated with photophobia selected from the group consisting of autism spectrum disorders, Chiari malformation, dyslexia, encephalitis, meningitis, subarachnoid hemorrhage, tumor of the posterior cranial fossa, ankylosing spondylitis, albinism, ariboflavinosis, benzodiazepines, chemotherapy, chikungunya, cystinosis, Ehlers-Danlos syndrome, hangover, influenza, infectious mononucleosis, magnesium deficiency, mercury poisoning, migraine, rabies, and tyrosinemia type II; and/or said subject may have a photophobia associated disorder selected from the group consisting of migraine with aura, migraine without aura, iritis, uveitis, meningitis, depression, bipolar disorder, cluster headache or anther trigeminal autonomic cephalalgia ("TAC") or blepharospasm, depression, agoraphobia, and bipolar disorder.

Another embodiment of the invention relates to a method wherein an anti-PACAP antibody or antigen binding fragment may comprise 2, 3, 4, 5 or all 6 complementarity determining regions ("CDRs") of Ab21.H, Ab21.H2, Ab21.H3, Ab21.H4, Ab22, or Ab23 or all 6 complementarity determining regions of Ab10.H, Ab10.H2, Ab10.H3, Ab10.H4, Ab10.H5, or Ab10.H6. Also, another embodiment of the invention pertains to a method wherein an anti-PACAP antibody or antigen binding fragment may be humanized and may comprise all 6 CDRs of an anti-PACAP antibody selected from Ab10.H, Ab10.H2, Ab10.H3, Ab10.H4, Ab10.H5, Ab10.H6, Ab21.H, Ab21.H2, Ab21.H3, Ab21.H4, Ab22, or Ab23.

In a specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 964; a CDR2 sequence consisting of SEQ ID NO: 966; and a CDR3 sequence consisting of SEQ ID NO: 968; and/or (b) a variable light chain comprising a CDR1 sequence consisting of SEQ ID NO: 984; a CDR2 sequence consisting of SEQ ID NO: 986; and a CDR3 sequence consisting of SEQ ID NO: 988. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 962, and/or (b) a variable light chain comprising an amino acid sequence with at least 80, 85, 90, 95, 96, 97, 98, or 99% sequence identity to SEQ ID NO: 982. In another embodiment, the anti-PACAP antibodies and antigen binding fragments thereof may comprise (a) a variable heavy chain having the amino acid sequence of SEQ ID NO: 962, and/or (b) a variable light chain having the amino acid sequence of SEQ ID NO: 982. More specifically, the anti-PACAP antibodies and antigen binding fragments thereof may comprise (a) a heavy chain having the amino acid sequence of SEQ ID NO: 961, and/or (b) a light chain having the amino acid sequence of SEQ ID NO: 981.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1204; a CDR2 sequence consisting of SEQ ID NO: 1206; and a CDR3 sequence consisting of SEQ ID NO: 1208; and/or (b) a variable light chain comprising a CDR1 sequence consisting of SEQ ID NO: 1224; a CDR2 sequence consisting of SEQ ID NO: 1226; and a CDR3 sequence consisting of SEQ ID NO: 1228. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 1202, and/or (b) a variable light chain comprising an amino acid sequence with at least 80, 85, 90, 95, 96, 97, 98, or 99% sequence identity to SEQ ID NO: 1222. In another embodiment, the anti-PACAP antibodies and antigen binding fragments thereof may comprise (a) a variable heavy chain having the amino acid sequence of SEQ ID NO: 1202, and/or (b) a variable light chain having the amino acid sequence of SEQ ID NO: 1222. More specifically, the anti-PACAP antibodies and antigen binding fragments thereof may comprise (a) a heavy chain having the amino acid sequence of SEQ ID NO: 1201, and/or (b) a light chain having the amino acid sequence of SEQ ID NO: 1221.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 844; a CDR2 sequence consisting of SEQ ID NO: 846; and a CDR3 sequence consisting of SEQ ID NO: 848; and/or (b) a variable light chain comprising a CDR1 sequence consisting of SEQ ID NO: 864; a CDR2 sequence consisting of SEQ ID NO: 866; and a CDR3 sequence consisting of SEQ ID NO: 868. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 842, and/or (b) a variable light chain comprising an amino acid sequence with at least 80, 85, 90, 95, 96, 97, 98, or 99% sequence identity to SEQ ID NO: 862. In another embodiment, the anti-PACAP antibodies and antigen binding fragments thereof may comprise (a) a variable heavy chain having the amino acid sequence of SEQ ID NO: 842, and/or (b) a variable light chain having the amino acid sequence of SEQ ID NO: 862. More specifically, the anti-PACAP antibodies and antigen binding fragments thereof may comprise (a) a heavy chain having the amino acid sequence of SEQ ID NO: 841, and/or (b) a light chain having the amino acid sequence of SEQ ID NO: 861.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 884; a CDR2 sequence consisting of SEQ ID NO: 886; and a CDR3 sequence consisting of SEQ ID NO: 888; and/or (b) a variable light chain comprising a CDR1 sequence consisting of SEQ ID NO: 904; a CDR2 sequence consisting of SEQ ID NO: 906; and a CDR3 sequence consisting of SEQ ID NO: 908. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 882, and/or (b) a variable light chain comprising an amino acid sequence with at least 80, 85, 90, 95, 96, 97, 98, or 99% sequence identity to SEQ ID NO: 902. In another embodiment, the anti-PACAP antibodies and antigen binding fragments thereof may comprise (a) a variable heavy chain having the amino acid sequence of SEQ ID NO: 882, and/or (b) a variable light chain having the amino acid sequence of SEQ ID NO: 902. More specifically, the anti-PACAP antibodies and antigen binding fragments thereof may comprise (a) a heavy chain having the amino acid sequence of SEQ ID NO: 881, and/or (b) a light chain having the amino acid sequence of SEQ ID NO: 901.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 924; a CDR2 sequence consisting of SEQ ID NO: 926; and a CDR3 sequence consisting of SEQ ID NO: 928; and/or (b) a variable light chain comprising a CDR1 sequence consisting of SEQ ID NO: 944; a CDR2 sequence consisting of SEQ ID NO: 946; and a CDR3 sequence consisting of SEQ ID NO: 948. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 922, and/or (b) a variable light chain comprising an amino acid sequence with at least 80, 85, 90, 95, 96, 97, 98, or 99% sequence identity to SEQ ID NO: 942. In another embodiment, the anti-PACAP antibodies and antigen binding fragments thereof may comprise (a) a variable heavy chain having the amino acid sequence of SEQ ID NO: 922, and/or (b) a variable light chain having the amino acid sequence of SEQ ID NO: 942. More specifically, the anti-PACAP antibodies and antigen binding fragments thereof may comprise (a) a heavy chain having the amino acid sequence of SEQ ID NO: 921, and/or (b) a light chain having the amino acid sequence of SEQ ID NO: 941.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1284; a CDR2 sequence consisting of SEQ ID NO: 1286; and a CDR3 sequence consisting of SEQ ID NO: 1288; and/or (b) a variable light chain comprising a CDR1 sequence consisting of SEQ ID NO: 1304; a CDR2 sequence consisting of SEQ ID NO: 1306; and a CDR3 sequence consisting of SEQ ID NO: 1308. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1282, and/or (b) a variable light chain comprising an amino acid sequence with at least 80, 85, 90, 95, 96, 97, 98, or 99% sequence identity to SEQ ID NO: 1302. In another embodiment, the anti-PACAP antibodies and antigen binding fragments thereof may comprise (a) a variable heavy chain having the amino acid sequence of SEQ ID NO: 1282, and/or (b) a variable light chain having the amino acid sequence of SEQ ID NO: 1302. More specifically, the anti-PACAP antibodies and antigen binding fragments thereof can comprise (a) a heavy chain having the amino acid sequence of SEQ ID NO: 1281, and/or (b) a light chain having the amino acid sequence of SEQ ID NO: 1301.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1324; a CDR2 sequence consisting of SEQ ID NO: 1326; and a CDR3 sequence consisting of SEQ ID NO: 1328; and/or (b) a variable light chain comprising a CDR1 sequence consisting of SEQ ID NO: 1344; a CDR2 sequence consisting of SEQ ID NO: 1346; and a CDR3 sequence consisting of SEQ ID NO: 1348. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1322, and/or (b) a variable light chain comprising an amino acid sequence with at least 80, 85, 90, 95, 96, 97, 98, or 99% sequence identity to SEQ ID NO: 1342. In another embodiment, the anti-PACAP antibodies and antigen binding fragments thereof may comprise (a) a variable heavy chain having the amino acid sequence of SEQ ID NO: 1322, and/or (b) a variable light chain having the amino acid sequence of SEQ ID NO: 1342. More specifically, the anti-PACAP antibodies and antigen binding fragments thereof can comprise (a) a heavy chain having the amino acid sequence of SEQ ID NO: 1321, and/or (b) a light chain having the amino acid sequence of SEQ ID NO: 1341.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1364; a CDR2 sequence consisting of SEQ ID NO: 1366; and a CDR3 sequence consisting of SEQ ID NO: 1368; and/or (b) a variable light chain comprising a CDR1 sequence consisting of SEQ ID NO: 1384; a CDR2 sequence consisting of SEQ ID NO: 1386; and a CDR3 sequence consisting of SEQ ID NO: 1388. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1362, and/or (b) a variable light chain comprising an amino acid sequence with at least 80, 85, 90, 95, 96, 97, 98, or 99% sequence identity to SEQ ID NO: 1382. In another embodiment, the anti-PACAP antibodies and antigen binding fragments thereof may comprise (a) a variable heavy chain having the amino acid sequence of SEQ ID NO: 1362, and/or (b) a variable light chain having the amino acid sequence of SEQ ID NO: 1382. More specifically, the anti-PACAP antibodies and antigen binding fragments thereof can comprise (a) a heavy chain having the amino acid sequence of SEQ ID NO: 1361, and/or (b) a light chain having the amino acid sequence of SEQ ID NO: 1381.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1404; a CDR2 sequence consisting of SEQ ID NO: 1406; and a CDR3 sequence consisting of SEQ ID NO: 1408; and/or (b) a variable light chain comprising a CDR1 sequence consisting of SEQ ID NO: 1424; a CDR2 sequence consisting of SEQ ID NO: 1426; and a CDR3 sequence consisting of SEQ ID NO: 1428. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1402, and/or (b) a variable light chain comprising an amino acid sequence with at least 80, 85, 90, 95, 96, 97, 98, or 99% sequence identity to SEQ ID NO: 1422. In another embodiment, the anti-PACAP antibodies and antigen binding fragments thereof may comprise (a) a variable heavy chain having the amino acid sequence of SEQ ID NO: 1402, and/or (b) a variable light chain having the amino acid sequence of SEQ ID NO: 1422. More specifically, the anti-PACAP antibodies and antigen binding fragments thereof can comprise (a) a heavy chain having the amino acid sequence of SEQ ID NO: 1401, and/or (b) a light chain having the amino acid sequence of SEQ ID NO: 1421.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1444; a CDR2 sequence consisting of SEQ ID NO: 1446; and a CDR3 sequence consisting of SEQ ID NO: 1448; and/or (b) a variable light chain comprising a CDR1 sequence consisting of SEQ ID NO: 1464; a CDR2 sequence consisting of SEQ ID NO: 1466; and a CDR3 sequence consisting of SEQ ID NO: 1468. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1442, and/or (b) a variable light chain comprising an amino acid sequence with at least 80, 85, 90, 95, 96, 97, 98, or 99% sequence identity to SEQ ID NO: 1462. In another embodiment, the anti-PACAP antibodies and antigen binding fragments thereof may comprise (a) a variable heavy chain having the amino acid sequence of SEQ ID NO: 1442, and/or (b) a variable light chain having the amino acid sequence of SEQ ID NO: 1462. More specifically, the anti-PACAP antibodies and antigen binding fragments thereof can comprise (a) a heavy chain having the amino acid sequence of SEQ ID NO: 1441, and/or (b) a light chain having the amino acid sequence of SEQ ID NO: 1461.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1484; a CDR2 sequence consisting of SEQ ID NO: 1486; and a CDR3 sequence consisting of SEQ ID NO: 1488; and/or (b) a variable light chain comprising a CDR1 sequence consisting of SEQ ID NO: 1504; a CDR2 sequence consisting of SEQ ID NO: 1506; and a CDR3 sequence consisting of SEQ ID NO: 1508. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1482, and/or (b) a variable light chain comprising an amino acid sequence with at least 80, 85, 90, 95, 96, 97, 98, or 99% sequence identity to SEQ ID NO: 1502. In another embodiment, the anti-PACAP antibodies and antigen binding fragments thereof may comprise (a) a variable heavy chain having the amino acid sequence of SEQ ID NO: 1482, and/or (b) a variable light chain having the amino acid sequence of SEQ ID NO: 1502. More specifically, the anti-PACAP antibodies and antigen binding fragments thereof can comprise (a) a heavy chain having the amino acid sequence of SEQ ID NO: 1481, and/or (b) a light chain having the amino acid sequence of SEQ ID NO: 1501.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1524; a CDR2 sequence consisting of SEQ ID NO: 1526; and a CDR3 sequence consisting of SEQ ID NO: 1528; and/or (b) a variable light chain comprising a CDR1 sequence consisting of SEQ ID NO: 1544; a CDR2 sequence consisting of SEQ ID NO: 1546; and a CDR3 sequence consisting of SEQ ID NO: 1548. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1522, and/or (b) a variable light chain comprising an amino acid sequence with at least 80, 85, 90, 95, 96, 97, 98, or 99% sequence identity to SEQ ID NO: 1542. In another embodiment, the anti-PACAP antibodies and antigen binding fragments thereof may comprise (a) a variable heavy chain having the amino acid sequence of SEQ ID NO: 1522, and/or (b) a variable light chain having the amino acid sequence of SEQ ID NO: 1542. More specifically, the anti-PACAP antibodies and antigen binding fragments thereof can comprise (a) a heavy chain having the amino acid sequence of SEQ ID NO: 1521, and/or (b) a light chain having the amino acid sequence of SEQ ID NO: 1541.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1564; a CDR2 sequence consisting of SEQ ID NO: 1566; and a CDR3 sequence consisting of SEQ ID NO: 1568; and/or (b) a variable light chain comprising a CDR1 sequence consisting of SEQ ID NO: 1584; a CDR2 sequence consisting of SEQ ID NO: 1586; and a CDR3 sequence consisting of SEQ ID NO: 1588. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 1562, and/or (b) a variable light chain comprising an amino acid sequence with at least 80, 85, 90, 95, 96, 97, 98, or 99% sequence identity to SEQ ID NO: 1582. In another embodiment, the anti-PACAP antibodies and antigen binding fragments thereof may comprise (a) a variable heavy chain having the amino acid sequence of SEQ ID NO: 1562, and/or (b) a variable light chain having the amino acid sequence of SEQ ID NO: 1582. More specifically, the anti-PACAP antibodies and antigen binding fragments thereof can comprise (a) a heavy chain having the amino acid sequence of SEQ ID NO: 1561, and/or (b) a light chain having the amino acid sequence of SEQ ID NO: 1581.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 962 and comprising a CDR1 sequence consisting of SEQ ID NO: 964; a CDR2 sequence consisting of SEQ ID NO: 966; and a CDR3 sequence consisting of SEQ ID NO: 968; and/or (b) a variable light chain comprising an amino acid sequence with at least 80, 85, 90, 95, 96, 97, 98, or 99% sequence identity to SEQ ID NO: 982 and comprising a CDR1 sequence consisting of SEQ ID NO: 984; a CDR2 sequence consisting of SEQ ID NO: 986; and a CDR3 sequence consisting of SEQ ID NO: 988. Alternatively, the anti-PACAP antibodies and antigen binding fragments thereof can comprise (a) a variable heavy chain having the amino acid sequence of SEQ ID NO: 962, and/or (b) a variable light chain having the amino acid sequence of SEQ ID NO: 982. Alternatively, the anti-PACAP antibodies and antigen binding fragments thereof can comprise (a) a variable heavy chain having the amino acid sequence of SEQ ID NO: 962, and (b) a variable light chain having the amino acid sequence of SEQ ID NO: 982. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 961 and comprising a CDR1 sequence consisting of SEQ ID NO: 964; a CDR2 sequence consisting of SEQ ID NO: 966; and a CDR3 sequence consisting of SEQ ID NO: 968; and/or (b) a light chain comprising an amino acid sequence with at least 80, 85, 90, 95, 96, 97, 98, or 99% sequence identity to SEQ ID NO: 981 and comprising a CDR1 sequence consisting of SEQ ID NO: 984; a CDR2 sequence consisting of SEQ ID NO: 986; and a CDR3 sequence consisting of SEQ ID NO: 988. Alternatively, the anti-PACAP antibodies and antigen binding fragments thereof can comprise (a) a heavy chain having the amino acid sequence of SEQ ID NO: 961, and/or (b) a light chain having the amino acid sequence of SEQ ID NO: 981. Alternatively, the anti-PACAP antibodies and antigen binding fragments thereof can comprise (a) a heavy chain having the amino acid sequence of SEQ ID NO: 961, and (b) a light chain having the amino acid sequence of SEQ ID NO: 981.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1204; a CDR2 sequence consisting of SEQ ID NO: 1206; and a CDR3 sequence consisting of SEQ ID NO: 1208; and/or (b) a variable light chain comprising a CDR1 sequence consisting of SEQ ID NO: 1224; a CDR2 sequence consisting of SEQ ID NO: 1226; and a CDR3 sequence consisting of SEQ ID NO: 1228. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 1202, and/or (b) a variable light chain comprising an amino acid sequence with at least 80, 85, 90, 95, 96, 97, 98, or 99% sequence identity to SEQ ID NO: 1222. In another embodiment, the anti-PACAP antibodies and antigen binding fragments thereof may comprise (a) a variable heavy chain having the amino acid sequence of SEQ ID NO: 1202, and/or (b) a variable light chain having the amino acid sequence of SEQ ID NO: 1222. More specifically, the anti-PACAP antibodies and antigen binding fragments thereof may comprise (a) a heavy chain having the amino acid sequence of SEQ ID NO: 1201, and/or (b) a light chain having the amino acid sequence of SEQ ID NO: 1221.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1282 and comprising a CDR1 sequence consisting of SEQ ID NO: 1284; a CDR2 sequence consisting of SEQ ID NO: 1286; and a CDR3 sequence consisting of SEQ ID NO: 1288; and/or (b) a variable light chain comprising an amino acid sequence with at least 80, 85, 90, 95, 96, 97, 98, or 99% sequence identity to SEQ ID NO: 1302 and comprising a CDR1 sequence consisting of SEQ ID NO: 1304; a CDR2 sequence consisting of SEQ ID NO: 1306; and a CDR3 sequence consisting of SEQ ID NO: 1308. Alternatively, the anti-PACAP antibodies and antigen binding fragments thereof can comprise (a) a variable heavy chain having the amino acid sequence of SEQ ID NO: 1282, and/or (b) a variable light chain having the amino acid sequence of SEQ ID NO: 1302. Alternatively, the anti-PACAP antibodies and antigen binding fragments thereof can comprise (a) a variable heavy chain having the amino acid sequence of SEQ ID NO: 1282, and (b) a variable light chain having the amino acid sequence of SEQ ID NO: 1302. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1281 and comprising a CDR1 sequence consisting of SEQ ID NO: 1284; a CDR2 sequence consisting of SEQ ID NO: 1286; and a CDR3 sequence consisting of SEQ ID NO: 1288; and/or (b) a light chain comprising an amino acid sequence with at least 80, 85, 90, 95, 96, 97, 98, or 99% sequence identity to SEQ ID NO: 1301 and comprising a CDR1 sequence consisting of SEQ ID NO: 1304; a CDR2 sequence consisting of SEQ ID NO: 1306; and a CDR3 sequence consisting of SEQ ID NO: 1308. Alternatively, the anti-PACAP antibodies and antigen binding fragments thereof can comprise (a) a heavy chain having the amino acid sequence of SEQ ID NO: 1281, and/or (b) a light chain having the amino acid sequence of SEQ ID NO: 1301. Alternatively, the anti-PACAP antibodies and antigen binding fragments thereof can comprise (a) a heavy chain having the amino acid sequence of SEQ ID NO: 1281, and (b) a light chain having the amino acid sequence of SEQ ID NO: 1301.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1322 and comprising a CDR1 sequence consisting of SEQ ID NO: 1324; a CDR2 sequence consisting of SEQ ID NO: 1326; and a CDR3 sequence consisting of SEQ ID NO: 1328; and/or (b) a variable light chain comprising an amino acid sequence with at least 80, 85, 90, 95, 96, 97, 98, or 99% sequence identity to SEQ ID NO: 1342 and comprising a CDR1 sequence consisting of SEQ ID NO: 1344; a CDR2 sequence consisting of SEQ ID NO: 1346; and a CDR3 sequence consisting of SEQ ID NO: 1348. Alternatively, the anti-PACAP antibodies and antigen binding fragments thereof can comprise (a) a variable heavy chain having the amino acid sequence of SEQ ID NO: 1322, and/or (b) a variable light chain having the amino acid sequence of SEQ ID NO: 1342. Alternatively, the anti-PACAP antibodies and antigen binding fragments thereof can comprise (a) a variable heavy chain having the amino acid sequence of SEQ ID NO: 1322, and (b) a variable light chain having the amino acid sequence of SEQ ID NO: 1342. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1321 and comprising a CDR1 sequence consisting of SEQ ID NO: 1324; a CDR2 sequence consisting of SEQ ID NO: 1326; and a CDR3 sequence consisting of SEQ ID NO: 1328; and/or (b) a light chain comprising an amino acid sequence with at least 80, 85, 90, 95, 96, 97, 98, or 99% sequence identity to SEQ ID NO: 1341 and comprising a CDR1 sequence consisting of SEQ ID NO: 1344; a CDR2 sequence consisting of SEQ ID NO: 1346; and a CDR3 sequence consisting of SEQ ID NO: 1348. Alternatively, the anti-PACAP antibodies and antigen binding fragments thereof can comprise (a) a heavy chain having the amino acid sequence of SEQ ID NO: 1321, and/or (b) a light chain having the amino acid sequence of SEQ ID NO: 1341. Alternatively, the anti-PACAP antibodies and antigen binding fragments thereof can comprise (a) a heavy chain having the amino acid sequence of SEQ ID NO: 1321, and (b) a light chain having the amino acid sequence of SEQ ID NO: 1341.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1362 and comprising a CDR1 sequence consisting of SEQ ID NO: 1364; a CDR2 sequence consisting of SEQ ID NO: 1366; and a CDR3 sequence consisting of SEQ ID NO: 1368; and/or (b) a variable light chain comprising an amino acid sequence with at least 80, 85, 90, 95, 96, 97, 98, or 99% sequence identity to SEQ ID NO: 1382 and comprising a CDR1 sequence consisting of SEQ ID NO: 1384; a CDR2 sequence consisting of SEQ ID NO: 1386; and a CDR3 sequence consisting of SEQ ID NO: 1388. Alternatively, the anti-PACAP antibodies and antigen binding fragments thereof can comprise (a) a variable heavy chain having the amino acid sequence of SEQ ID NO: 1362, and/or (b) a variable light chain having the amino acid sequence of SEQ ID NO: 1382. Alternatively, the anti-PACAP antibodies and antigen binding fragments thereof can comprise (a) a variable heavy chain having the amino acid sequence of SEQ ID NO: 1362, and (b) a variable light chain having the amino acid sequence of SEQ ID NO: 1382. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1361 and comprising a CDR1 sequence consisting of SEQ ID NO: 1364; a CDR2 sequence consisting of SEQ ID NO: 1366; and a CDR3 sequence consisting of SEQ ID NO: 1368; and/or (b) a light chain comprising an amino acid sequence with at least 80, 85, 90, 95, 96, 97, 98, or 99% sequence identity to SEQ ID NO: 1381 and comprising a CDR1 sequence consisting of SEQ ID NO: 1384; a CDR2 sequence consisting of SEQ ID NO: 1386; and a CDR3 sequence consisting of SEQ ID NO: 1388. Alternatively, the anti-PACAP antibodies and antigen binding fragments thereof can comprise (a) a heavy chain having the amino acid sequence of SEQ ID NO: 1361, and/or (b) a light chain having the amino acid sequence of SEQ ID NO: 1381. Alternatively, the anti-PACAP antibodies and antigen binding fragments thereof can comprise (a) a heavy chain having the amino acid sequence of SEQ ID NO: 1361, and (b) a light chain having the amino acid sequence of SEQ ID NO: 1381.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1402 and comprising a CDR1 sequence consisting of SEQ ID NO: 1404; a CDR2 sequence consisting of SEQ ID NO: 1406; and a CDR3 sequence consisting of SEQ ID NO: 1408; and/or (b) a variable light chain comprising an amino acid sequence with at least 80, 85, 90, 95, 96, 97, 98, or 99% sequence identity to SEQ ID NO: 1422 and comprising a CDR1 sequence consisting of SEQ ID NO: 1424; a CDR2 sequence consisting of SEQ ID NO: 1426; and a CDR3 sequence consisting of SEQ ID NO: 1428. Alternatively, the anti-PACAP antibodies and antigen binding fragments thereof can comprise (a) a variable heavy chain having the amino acid sequence of SEQ ID NO: 1402, and/or (b) a variable light chain having the amino acid sequence of SEQ ID NO: 1422. Alternatively, the anti-PACAP antibodies and antigen binding fragments thereof can comprise (a) a variable heavy chain having the amino acid sequence of SEQ ID NO: 1402, and (b) a variable light chain having the amino acid sequence of SEQ ID NO: 1422. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1401 and comprising a CDR1 sequence consisting of SEQ ID NO: 1404; a CDR2 sequence consisting of SEQ ID NO: 1406; and a CDR3 sequence consisting of SEQ ID NO: 1408; and/or (b) a light chain comprising an amino acid sequence with at least 80, 85, 90, 95, 96, 97, 98, or 99% sequence identity to SEQ ID NO: 1421 and comprising a CDR1 sequence consisting of SEQ ID NO: 1424; a CDR2 sequence consisting of SEQ ID NO: 1426; and a CDR3 sequence consisting of SEQ ID NO: 1428. Alternatively, the anti-PACAP antibodies and antigen binding fragments thereof can comprise (a) a heavy chain having the amino acid sequence of SEQ ID NO: 1401, and/or (b) a light chain having the amino acid sequence of SEQ ID NO: 1421. Alternatively, the anti-PACAP antibodies and antigen binding fragments thereof can comprise (a) a heavy chain having the amino acid sequence of SEQ ID NO: 1401, and (b) a light chain having the amino acid sequence of SEQ ID NO: 1421.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising an amino acid sequence with at least 80, 85, 90, 95, 96, 97, 98, or 99% sequence identity to SEQ ID NO: 1442 and comprising a CDR1 sequence consisting of SEQ ID NO: 1444; a CDR2 sequence consisting of SEQ ID NO: 1446; and a CDR3 sequence consisting of SEQ ID NO: 1448; and/or (b) a variable light chain comprising an amino acid sequence with at least 80, 85, 90, 95, 96, 97, 98, or 99% sequence identity to SEQ ID NO: 1462 and comprising a CDR1 sequence consisting of SEQ ID NO: 1464; a CDR2 sequence consisting of SEQ ID NO: 1466; and a CDR3 sequence consisting of SEQ ID NO: 1468. Alternatively, the anti-PACAP antibodies and antigen binding fragments thereof can comprise (a) a variable heavy chain having the amino acid sequence of SEQ ID NO: 1442, and/or (b) a variable light chain having the amino acid sequence of SEQ ID NO: 1462. Alternatively, the anti-PACAP antibodies and antigen binding fragments thereof can comprise (a) a variable heavy chain having the amino acid sequence of SEQ ID NO: 1442, and (b) a variable light chain having the amino acid sequence of SEQ ID NO: 1462. In another embodiment, the anti-PACAP antibodies and antigen binding fragments thereof may comprise (a) a heavy chain comprising an amino acid sequence with at least 80, 85, 90, 95, 96, 97, 98, or 99% sequence identity to SEQ ID NO: 1441 and comprising a CDR1 sequence consisting of SEQ ID NO: 1444; a CDR2 sequence consisting of SEQ ID NO: 1446; and a CDR3 sequence consisting of SEQ ID NO: 1448; and/or (b) a light chain comprising an amino acid sequence with at least 80, 85, 90, 95, 96, 97, 98, or 99% sequence identity to SEQ ID NO: 1461 and comprising a CDR1 sequence consisting of SEQ ID NO: 1464; a CDR2 sequence consisting of SEQ ID NO: 1466; and a CDR3 sequence consisting of SEQ ID NO: 1468. Alternatively, the anti-PACAP antibodies and antigen binding fragments thereof can comprise (a) a heavy chain having the amino acid sequence of SEQ ID NO: 1441, and/or (b) a light chain having the amino acid sequence of SEQ ID NO: 1461. Alternatively, the anti-PACAP antibodies and antigen binding fragments thereof can comprise (a) a heavy chain having the amino acid sequence of SEQ ID NO: 1441, and (b) a light chain having the amino acid sequence of SEQ ID NO: 1461.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1484; a CDR2 sequence consisting of SEQ ID NO: 1486; and a CDR3 sequence consisting of SEQ ID NO: 1488; and/or (b) a variable light chain comprising a CDR1 sequence consisting of SEQ ID NO: 1504; a CDR2 sequence consisting of SEQ ID NO: 1506; and a CDR3 sequence consisting of SEQ ID NO: 1508. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 1482, and/or (b) a variable light chain comprising an amino acid sequence with at least 80, 85, 90, 95, 96, 97, 98, or 99% sequence identity to SEQ ID NO: 1502. In another embodiment, the anti-PACAP antibodies and antigen binding fragments thereof may comprise (a) a variable heavy chain having the amino acid sequence of SEQ ID NO: 1482, and/or (b) a variable light chain having the amino acid sequence of SEQ ID NO: 1502. More specifically, the anti-PACAP antibodies and antigen binding fragments thereof may comprise (a) a heavy chain having the amino acid sequence of SEQ ID NO: 1481, and/or (b) a light chain having the amino acid sequence of SEQ ID NO: 1501.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1524; a CDR2 sequence consisting of SEQ ID NO: 1526; and a CDR3 sequence consisting of SEQ ID NO: 1528; and/or (b) a variable light chain comprising a CDR1 sequence consisting of SEQ ID NO: 1544; a CDR2 sequence consisting of SEQ ID NO: 1546; and a CDR3 sequence consisting of SEQ ID NO: 1548. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 1522, and/or (b) a variable light chain comprising an amino acid sequence with at least 80, 85, 90, 95, 96, 97, 98, or 99% sequence identity to SEQ ID NO: 1542. In another embodiment, the anti-PACAP antibodies and antigen binding fragments thereof may comprise (a) a variable heavy chain having the amino acid sequence of SEQ ID NO: 1522, and/or (b) a variable light chain having the amino acid sequence of SEQ ID NO: 1542. More specifically, the anti-PACAP antibodies and antigen binding fragments thereof may comprise (a) a heavy chain having the amino acid sequence of SEQ ID NO: 1521, and/or (b) a light chain having the amino acid sequence of SEQ ID NO: 1541.

In another specific embodiment, the invention also embraces any of the methods disclosed herein wherein the anti-PACAP antibodies and antigen binding fragments thereof according to the invention, are preferably human, humanized, or chimerized anti-PACAP antibodies or antigen binding fragments thereof, and comprise (a) a variable heavy chain comprising a CDR1 sequence consisting of SEQ ID NO: 1564; a CDR2 sequence consisting of SEQ ID NO: 1566; and a CDR3 sequence consisting of SEQ ID NO: 1568; and/or (b) a variable light chain comprising a CDR1 sequence consisting of SEQ ID NO: 1584; a CDR2 sequence consisting of SEQ ID NO: 1586; and a CDR3 sequence consisting of SEQ ID NO: 1588. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 1562, and/or (b) a variable light chain comprising an amino acid sequence with at least 80, 85, 90, 95, 96, 97, 98, or 99% sequence identity to SEQ ID NO: 1582. In another embodiment, the anti-PACAP antibodies and antigen binding fragments thereof may comprise (a) a variable heavy chain having the amino acid sequence of SEQ ID NO: 1562, and/or (b) a variable light chain having the amino acid sequence of SEQ ID NO: 1582. More specifically, the anti-PACAP antibodies and antigen binding fragments thereof may comprise (a) a heavy chain having the amino acid sequence of SEQ ID NO: 1561, and/or (b) a light chain having the amino acid sequence of SEQ ID NO: 1581.

Another aspect of the invention generally relates to a method wherein the anti-PACAP antibody or antigen binding fragment may be selected from the group consisting of scFvs, camelbodies, nanobodies, Immunoglobulin New Antigen Receptor ("IgNAR"), fragment antigen binding ("Fab") fragments, Fab' fragments, MetMab like antibodies, monovalent antigen binding fragments, and F(ab') 2 fragments. Another embodiment of the invention also generally relates to a method wherein the anti-PACAP antibody or antigen binding fragment may substantially or entirely lack N-glycosylation and/or O-glycosylation. Yet another embodiment pertains to a method wherein the anti-PACAP antibody or antigen binding fragment may comprise a human constant domain, e.g., an IgG1, IgG2, IgG3, or IgG4 antibody.

Also, another embodiment of the invention generally pertains to a method wherein the anti-PACAP antibody or antigen binding fragment may comprise an Fc region that has been modified to alter at least one of effector function, half-life, proteolysis, or glycosylation, e.g., wherein the Fc region may contain one or more mutations that alters or eliminates N- and/or O-glycosylation.

Additionally, another embodiment of the invention pertains to a method wherein the anti-PACAP antibody or antigen binding fragment may bind to PACAP with a binding affinity ($K_D$)) of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M. Also, another embodiment of the invention relates to a method wherein the anti-PACAP antibody or antigen binding fragment may bind to PACAP with a binding affinity ($K_D$) of less than or equal to $5\times10^{-10}$ M, $10^{-10}$ M, $5\times10^{-11}$ M, $10^{-11}$ M, $5\times10^{-12}$ M, or $10^{-12}$ M and/or binds to PACAP with an off-rate ($k_d$) of less than or equal to $5\times10^{-4}$ $s^{-1}$, $10^{-4}$ $s^{-1}$, $5\times10^{-5}$ $s^{-1}$, or $10^{-5}$ $s^{-1}$.

Another aspect of the invention encompasses a method wherein the anti-PACAP antibody or antigen binding fragment may be directly or indirectly attached to a detectable label or therapeutic agent. Another aspect of the invention encompasses a method wherein the anti-PACAP antibody or antigen binding fragment may bind to PACAP with a $K_D$ that is less than about 100 nM, less than about 40 nM, less than about 1 nM, less than about 100 pM, less than about 50 pM, or less than about 25 pM or a $K_D$ that is between about 10 pM and about 100 pM.

Another aspect of the invention encompasses a method wherein the method further may comprise administering separately or co-administering another agent e.g., a chemotherapeutic, an analgesic, an anti-inflammatory, an immunosuppressant, a cytokine, an antiproliferative, an antiemetic, cytotoxin, an analgesic, e.g., wherein the analgesic may be a non-steroidal anti-inflammatory drug ("NSAID"), an opioid analgesic, another antibody or a non-antibody biologic, e.g., an anti-NGF antibody or antigen binding fragment or an anti-Calcitonin Gene-Related Peptide ("CGRP") antibody or antigen binding fragment. Said NSAID may be a cyclooxygenase 1 and/or cyclooxygenase 2 inhibitor or may be selected from the group consisting of (1) propionic acid derivatives including ibuprofen, naproxen, naprosyn, diclofenac, and ketoprofen; (2) acetic acid derivatives including tolmetin and sulindac; (3) fenamic acid derivatives including mefenamic acid and meclofenamic acid; (4) biphenylcarboxylic acid derivatives including diflunisal and flufenisal; and (5) oxicams including piroxim, sudoxicam, and isoxicam or is an opioid analgesic selected from the group consisting of codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, pentazocine, and pharmaceutically acceptable salts thereof, preferably morphine or a morphine derivative or pharmaceutically acceptable salt thereof.

Another aspect of the invention encompasses a method wherein the combined administration of the opioid analgesic and the PACAP antibody or antigen binding fragment may increase the analgesic effect as compared to either the opioid analgesic or the PACAP antibody or antigen binding fragment administered alone. Additionally, a further embodiment of the invention relates to a method wherein the subject may have previously received an anti-CGRP antibody or antigen binding fragment and/or is a migraineur who may not have adequately responded to anti-CGRP antibody treatment and/or may have elicited an immune response to a prior administered anti-CGRP antibody or antigen binding fragment.

BRIEF DESCRIPTION OF THE SEVERAL VIEWS OF THE DRAWINGS

FIGS. 1A-1G provide the polypeptide sequences of the full-length heavy chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4 (SEQ ID NOS: 401; 441; 841; 881; 921; 961; 1201; 1281; 1321; 1361; 1401; 1441; 1481; 1521; and 1561, respectively) aligned by their FRs, and CDRs, and constant regions.

FIGS. 2A-2D provide the polypeptide sequences of the full-length light chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4 (SEQ ID NOS: 421; 461; 861; 901; 941; 981; 1221; 1301; 1341; 1381; 1421; 1461; 1501; 1541; and 1581, respectively) aligned by their FRs, and CDRs, and constant regions.

FIGS. 3A-3S provide the polynucleotide sequences encoding the full-length heavy chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4 (SEQ ID NOS: 411; 451; 851; 891; 931; 971; 1211; 1291; 1331; 1371; 1411; 1451; 1491; 1531; and 1571, respectively) aligned by their FRs, and CDRs, and constant regions.

FIGS. 4A-4J provide the polynucleotide sequences encoding the full-length light chain Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4 (SEQ ID NOS: 431; 471; 871; 911; 951; 991; 1231; 1311; 1351; 1391; 1431; 1471; 1511; 1551; and 1591, respectively) aligned by their FRs, and CDRs, and constant regions.

FIG. 5 provides the polypeptide sequence coordinates for certain antibody heavy chain protein sequence features including the variable region and CDRs of the heavy chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4.

FIG. 6 provides the polypeptide sequence coordinates for certain antibody heavy chain protein sequence features including the constant region and framework regions FRs of the heavy chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4.

FIG. 7 provides the polypeptide sequence coordinates for certain antibody light chain protein sequence features including the variable region and CDRs of the light chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4.

FIG. 8 provides the polypeptide sequence coordinates for certain antibody light chain protein sequence features including the constant region and framework regions FRs of the light chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4.

FIG. 9 provides the polynucleotide sequence coordinates for certain antibody heavy chain DNA sequence features including the variable region and CDRs of the heavy chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4.

FIG. 10 provides the polynucleotide sequence coordinates for certain antibody heavy chain DNA sequence features including the constant region and FRs of the heavy chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4.

FIG. 11 provide the polynucleotide sequence coordinates for certain antibody light chain DNA sequence features including the variable region and CDRs of the light chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4.

FIG. 12 provide the polynucleotide sequence coordinates for certain antibody light chain DNA sequence features including the constant region and FRs of the light chain for antibodies Ab10, Ab20, Ab21, Ab22, Ab23, Ab10.H, Ab21.H, Ab10.H2, Ab10.H3, Ab10.H4, Ab10.H5, Ab10.H6, Ab21.H2, Ab21.H3, and Ab21.H4.

FIG. 31A presents a summary of the effects of PACAP alanine scanning mutants on antibody binding. In column 1 of FIG. 31A, VIP residues are listed in the order of their spatial arrangement along the VIP primary sequence from amino acid residues 1-27. In column 2 of FIG. 31A, PACAP residues are listed in the order of their spatial arrangement along the PACAP primary sequence from amino acid residues 1-27. Column 3 of FIG. 31A provides the number corresponding to each residue from 1-27 for both VIP and PACAP, as arranged spatially along their primary sequences. In columns 4-8 of FIG. 31A, each antibody tested during the alanine scanning studies (such as Ab10, Ab20, for example), and the PACAP residues determined to contribute to PACAP/antibody binding, (such as 5A, 6A, for example) are listed.

FIG. 31B presents a summary of the effects of PACAP alanine scanning mutants on antibody binding. In column 1 of FIG. 31B, VIP residue 28 is listed. In column 2 of FIG. 31B, PACAP residues are listed in the order of their spatial arrangement along the PACAP primary sequence from amino acid residues 28-38. Column 3 of FIG. 31B provides the number corresponding to residue 28 of VIP and each of residues 28-38 for PACAP, as arranged spatially along their primary sequences. In columns 4-8 of FIG. 31B, each antibody tested during the alanine scanning studies (such as Ab10, Ab20, for example), and the PACAP residues determined to contribute to PACAP/antibody binding, (such as 5A, 6A, for example) are listed.

DETAILED DESCRIPTION

Definitions

Figures 13A, 13B, 13C, 13D:
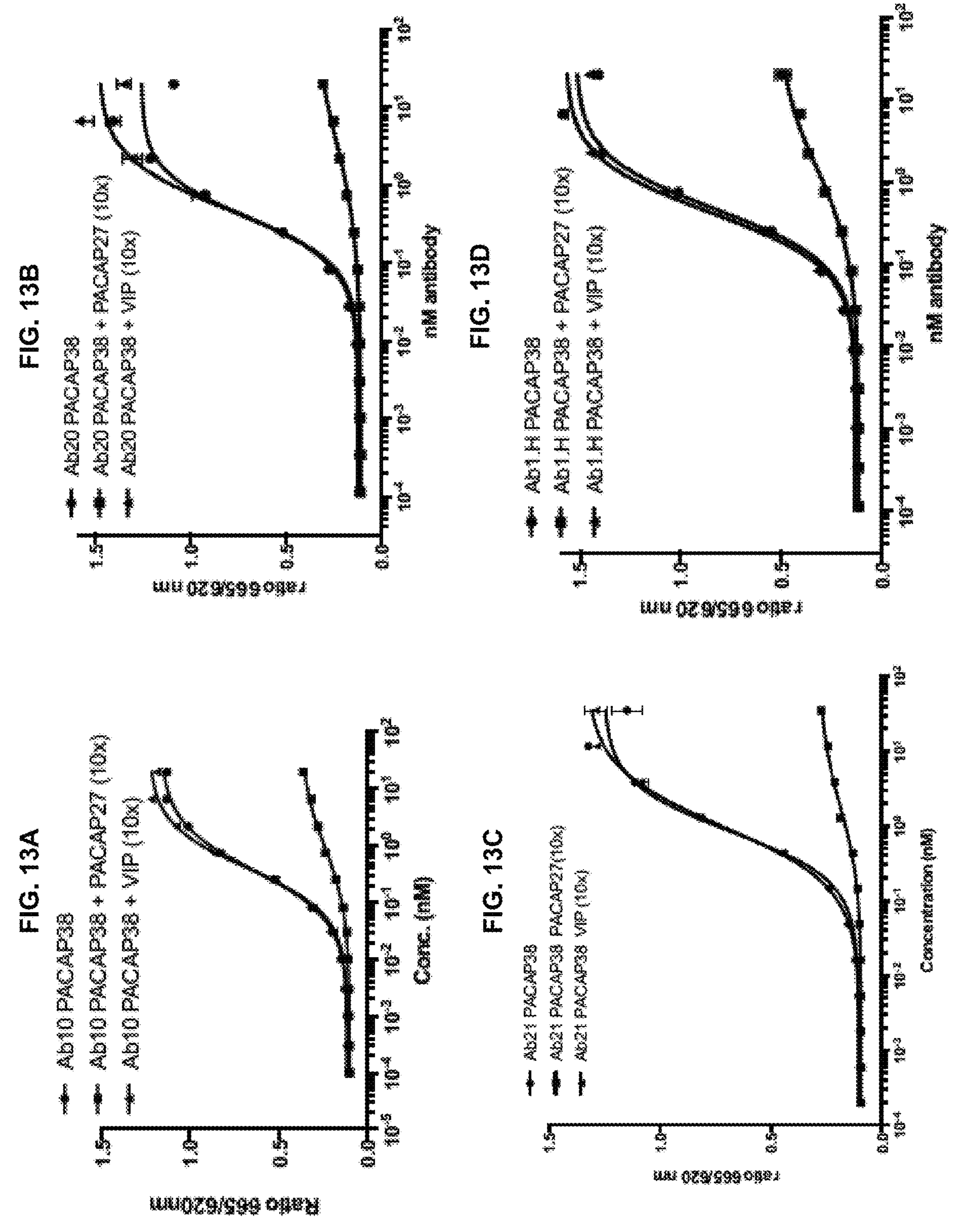
FIGS. 13A-13F provide representative competitive binding data for Ab10 (FIG. 13A), Ab20 (FIG. 13B), Ab21 (FIG. 13C), Ab1.H (FIG. 13D), Ab22 (FIG. 13E), and Ab23 (FIG. 13F) obtained following the protocol in Example 1 infra.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Pituitary Adenylate Cyclase-Activating Polypeptide (PACAP): As used herein, unless stated otherwise PACAP includes any mammalian form of PACAP, and in particular encompasses the following *Homo sapiens* PACAP27 and *Homo sapiens* PACAP38 amino acid sequences:

PACAP38:

HSDGIFTDSYSRYRKQMAVKKY-LAAVLGKRYKQRVKNK (SEQ ID NO: 1241), wherein the C-terminal lysine is amidated; but also any mutants, splice variants, isoforms, orthologs, homologs, and variants of this sequence.

PACAP27:

HSDGIFTDSYSRYRKQMAVKKYLAAVL (SEQ ID NO: 1242), wherein the C-terminal leucine is amidated; but also any mutants, splice variants, isoforms, orthologs, homologs, and variants of this sequence.

"Photophobia" herein refers to a symptom of abnormal intolerance to visual perception of light, sometimes additionally defined by abnormal or irrational fear of light, or by presence of actual physical photosensitivity of the eyes. In the present invention photophobia includes in particular light aversion associated with migraine, cluster headaches and other neurological causes of light aversive behavior that can trigger a migraine or cluster headache. Patients/subjects can develop photophobia as a result of several different medical conditions, related to the eye or the nervous system. Photophobia can be caused by an increased response to light starting at any step in the visual system such as: (i) too much light entering the eye, (ii) too much light can enter the eye if it is damaged, such as with corneal abrasion and retinal damage, or if a pupil(s) is unable to normally constrict (seen with damage to the oculomotor nerve), (iii) overstimulation of the photoreceptors in the retina, (iv) excessive electric impulses to the optic nerve, and (v) excessive response in the central nervous system.

"Effective treatment or prevention of photophobia" herein refers to inhibiting light aversive behavior or photophobia or inhibiting the onset of light aversive behavior or photophobia in a subject in need thereof, e.g., a subject having an active migraine attack or cluster headache or a subject prone to migraine or cluster headaches, or one of the other photophobia-associated disorders identified herein after administration of an effective amount of an anti-PACAP antibody or antigen binding fragment thereof according to the invention. The treatment may be effected as a monotherapy or in association with another active agent such as topiramate or dihydroergotamine by way of example.

The term "migraine" refers to a complex and disabling neurological disorder that may progress during four stages: prodrome, aura, headache, and postdrome. A migraine is defined by the International Headache Society as a headache that lasts for 4-72 hours and is characterized by at least two of the following: unilateral localization, pulsating quality, moderate to severe pain intensity; and aggravation by movement such as walking. In addition, the headache must be accompanied by at least one of the following: nausea and/or vomiting, photophobia, or phonophobia. A migraine may also be accompanied by aura, which typically precedes the deadline during the premonition or prodrome phase, and often results in visual changes, e.g., a scintillating scotoma that moves across the visual field. The prodrome may also be accompanied by other symptoms, e.g., fatigue, gastrointestinal issues, and mood changes. A migraineur is often incapacitated for extended periods of time. The postdrome is the final phase and occurs after the attack, during which time the migraineur may feel exhausted or mildly euphoric.

The term "headache" refers to pain in any region of the head. Headaches may occur on one or both sides of the head, be isolated to a certain location, radiate across the head from one point, or have a vise-like quality. A headache may be a sharp pain, throbbing sensation or dull ache. Headaches may appear gradually or suddenly, and they may last less than an hour or for several days.

The term "pain associated disease or condition" refers to any disease or condition defined, in whole or in part, by acute and/or chronic pain. Pain is generally defined as an unpleasant sensory and emotional experience associated with actual or potential tissue damage, or described in terms of such damage. Pain may be classified as neurogenic, neuropathic, inflammatory, or nociceptic.

The term "opioid analgesic" herein refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Exemplary opioid analgesics include codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, and pentazocine, or pharmaceutically acceptable salts thereof.

The term "NSAID" refers to a non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and sulindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam. Another class of NSAID has been described that selectively inhibit cyclooxygenase 2. COX-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

As used herein, "treatment" is an approach for obtaining beneficial or desired clinical results. For purposes of this invention, beneficial or desired clinical results include, but are not limited to, one or more of the following: improvement in any aspect of PACAP-related conditions such as migraine or headache. For example in the context of headache or migraine treatment this includes lessening severity, alleviation of pain intensity, and other associated symptoms, reducing frequency of recurrence, increasing the quality of life of those suffering from the headache, and decreasing dose of other medications required to treat the headache. For migraine, other associated symptoms include, but are not limited to, nausea, vomiting, and sensitivity to light, sound, and/or movement. For cluster headache, other associated symptoms include, but are not limited to swelling under or around the eyes, excessive tears, red eye, rhinorrhea or nasal congestion, and red flushed face.

"Reducing incidence" or "prophylaxis" or "prevention" means any of reducing severity for a particular disease, condition, symptom, or disorder (the terms disease, condition, and disorder are used interchangeably throughout the application). Reduction in severity includes reducing drugs and/or therapies generally used for the condition by, for example, reducing the need for, amount of, and/or exposure to drugs or therapies. Reduction in severity also includes reducing the duration, and/or frequency of the particular condition, symptom, or disorder (including, for example, delaying or increasing time to next episodic attack in an individual).

"Ameliorating" headache or one or more symptoms of headache or migraine or other PACAP-related condition means a lessening or improvement of one or more symptoms of the condition, e.g., headache or migraine as compared to not administering an anti-PACAP antagonist antibody. "Ameliorating" also includes shortening or reduction in duration of a symptom.

As used herein, "controlling headache" or "controlling migraine" or "controlling" another PACAP-related condition refers to maintaining or reducing severity or duration of one or more symptoms of the condition, e.g., headache or migraine or frequency of headache or migraine attacks in an individual (as compared to the level before treatment). For example, the duration or severity of head pain, or frequency of attacks, is reduced by at least about any of 10%, 20%, 30%, 40%, 50%, 60%, 70%, 80%, 90%, or 100%, in the individual as compared to the level before treatment. The reduction in the duration or severity of head pain, or frequency of attacks can last for any length of time, e.g., 2 weeks, 4 weeks (1 month), 8 weeks (2 months), 16 weeks (3 months), 4 months, 5 months, 6 months, 9 months, 12 months, etc.

As used therein, "delaying" the development of a PACAP-related condition such as migraine or headache means to defer, hinder, slow, retard, stabilize, and/or postpone progression of the condition or disease. This delay can be of varying lengths of time, depending on the history of the condition or disease and/or individuals being treated. As is evident to one skilled in the art, a sufficient or significant delay can, in effect, encompass prevention, in that the individual does not develop headache (e.g., migraine). A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of a PACAP-related condition such as migraine or headache means initial manifestations and/or ensuing progression of the disorder. Development of headache or migraine can be detectable and assessed using standard clinical techniques as well known in the art. However, development also refers to progression that may be undetectable. For purpose of this invention, development, or progression refers to the biological course of the symptoms. "Development" includes occurrence, recurrence, and onset. As used herein "onset" or "occurrence" of a condition such as headache or migraine includes initial onset and/or recurrence.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological, and/or behavioral symptoms of the disease, its complications and intermediate pathological phenotypes presenting during development of the disease. For therapeutic use, beneficial or desired results include clinical results such as reducing pain intensity, duration, or frequency of headache attack, and decreasing one or more symptoms resulting from headache (biochemical, histological, and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

A "suitable host cell" or "host cell" generally includes any cell wherein the subject anti-PACAP antibodies and antigen binding fragments thereof can be produced recombinantly using techniques and materials readily available. For example, the anti-PACAP antibodies and antigen binding fragments thereof of the present invention can be produced in genetically engineered host cells according to conventional techniques. Suitable host cells are those cell types that can be transformed or transfected with exogenous DNA and grown in culture, and include bacteria, fungal cells (e.g., yeast), and cultured higher eukaryotic cells (including cultured cells of multicellular organisms), particularly cultured mammalian cells, e.g., human or non-human mammalian cells. In an exemplary embodiment these antibodies may be expressed in CHO cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor, N.Y.: Cold Spring Harbor Laboratory Press (1989), and *Current Protocols in Molecular Biology*, Ausubel et al., editors, New York, NY: Green and Wiley and Sons (1993).

In some exemplary embodiments the antibodies may be expressed in mating competent yeast, e.g., any haploid, diploid, or tetraploid yeast that can be grown in culture. Yeast useful in fermentation expression methods may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or spheroplast fusion. By way of example, such yeast may include members of the Saccharomycesaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia; Rhodosporidium; Candida; Hansenula; Filobasium; Sporidiobolus; Bullera; Leucosporidium* and *Filobasidella*.

In a preferred exemplary embodiment of the invention, the mating competent yeast used for antibody expression may comprise a member of the genus *Pichia*. In a further preferred exemplary embodiment of the invention, the mating competent yeast of the genus *Pichia* is one of the following species: *Pichia pastoris, Pichia methanolica*, and *Hansenula polymorpha* (*Pichia angusta*). In a particularly preferred embodiment of the invention, the mating competent yeast of the genus *Pichia* is the species *Pichia pastoris.*

A "selectable marker" herein refers to a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two temperature sensitive ("ts") mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

An "expression vector" herein refers to DNA vectors containing elements that facilitate manipulation for the expression of a foreign protein within the target host cell, e.g., a bacterial, insect, yeast, plant, amphibian, reptile, avian, or mammalian cell, and most typically a yeast or mammalian cell, e.g., a CHO cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T., *Methods in yeast genetics: a Cold Spring Harbor Laboratory course manual*, Plainview, NY: Cold Spring Harbor Laboratory Press (2000).

Expression vectors for use in the methods of the invention may include yeast or mammalian specific sequences, including a selectable auxotrophic or drug marker for identifying transformed host strains. A drug marker may further be used to amplify copy number of the vector in a yeast host cell.

The polypeptide coding sequence of interest is operably linked to transcriptional and translational regulatory sequences that provide for expression of the polypeptide in the desired host cells, e.g., yeast or mammalian cells. These vector components may include, but are not limited to, one or more of the following: an enhancer element, a promoter, and a transcription termination sequence. Sequences for the secretion of the polypeptide may also be included, e.g. a signal sequence, and the like. An origin of replication, e.g., a yeast origin of replication, is optional, as expression vectors are often integrated into the host cell genome. In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (GATEWAY® Technology; Invitrogen, Carlsbad California). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The promoter fragment may also serve as the site for homologous recombination and integration of the expression vector into the same site in the host cell, e.g., yeast cell, genome; alternatively, a selectable marker may be used as the site for homologous recombination. *Pichia* transformation is described in Cregg et al., *Mol. Cell. Biol.,* 5:3376-3385 (1985).

Suitable promoters for use in different eukaryotic and prokaryotic cells are well known and commercially available.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell, e.g., a mammalian cell, an insect cell, or a yeast cell. Additionally, these signal peptide sequences may be engineered to provide for enhanced secretion in expression systems. Secretion signals of interest also include mammalian and yeast signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al., *Protein Eng.,* 11 (2): 75 (1998); and Kobayashi et. al., *Therapeutic Apheresis,* 2 (4): 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion, and/or sequenced.

As an alternative to restriction and ligation of fragments, recombination methods based on specific attachment ("att") sites and recombination enzymes may be used to insert DNA sequences into a vector. Such methods are described, for example, by Landy, *Ann. Rev. Biochem.,* 58:913-949 (1989); and are known to those of skill in the art. Such methods utilize intermolecular DNA recombination that is mediated by a mixture of lambda and *E. coli*-encoded recombination proteins. Recombination occurs between att sites on the interacting DNA molecules. For a description of att sites see Weisberg and Landy, *Site-Specific Recombination in Phage Lambda*, in Lambda II, p. 211-250, Cold Spring Harbor, NY: Cold Spring Harbor Press (1983). The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic protein disulfide isomerase ("PDI") is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of immunoglobulin heavy chain binding protein ("BIP"); cyclophilin; and the like. In one embodiment of the invention, each of the haploid parental strains expresses a distinct folding enzyme, e.g. one strain may express BIP, and the other strain may express PDI or combinations thereof.

Cultured mammalian cells are also preferred exemplary hosts for production of the disclosed anti-PACAP antibodies and antigen binding fragments thereof. As mentioned, CHO cells are particularly suitable for expression of antibodies. Many procedures are known in the art for manufacturing monoclonal antibodies in mammalian cells. (See, Galfre, G. and Milstein, C., *Methods Enzym.,* 73:3-46, 1981; Basalp et al., *Turk. J. Biol.,* 24:189-196, 2000; Wurm, F. M., *Nat. Biotechnol.,* 22:1393-1398, 2004; and Li et al., *mAbs,* 2 (5): 466-477, 2010). As mentioned in further detail infra, common host cell lines employed in mammalian monoclonal antibody manufacturing schemes include, but are not limited to, human embryonic retinoblast cell line PER.C6® (Crucell N.V., Leiden, The Netherlands), NS0 murine myeloma cells (Medical Research Council, London, UK), CV1 monkey kidney cell line, 293 human embryonic kidney cell line, BHK baby hamster kidney cell line, VERO African green monkey kidney cell line, human cervical carcinoma cell line HELA, MDCK canine kidney cells, BRL buffalo rat liver cells, W138 human lung cells, HepG2 human liver cells, MMT mouse mammary tumor cells, TRI cells, MRC5 cells, Fs4 cells, myeloma or lymphoma cells, or Chinese Hamster (*Cricetulus griseus*) Ovary (CHO) cells, and the like. Many different subclones or sub-cell lines of CHO cells known in the art that are useful and optimized for production of recombinant monoclonal antibodies, such as the DP12 (CHO K1 dhfr-) cell line, NS0 cells are a non-Ig secreting, non-light chain-synthesizing subclone of NS-1 cells that are resistant to azaguanine. Other Chinese Hamster and CHO cells are commercially available (from ATCC, etc.), including CHO-DXB11 (CHO-DUKX), CHO-pro3, CHO-DG44, CHO 1-15, CHO DP-12, Lec2, M1WT3, Lec8, pgsA-745, and the like, all of which are genetically altered to optimize the cell line for various parameters. Monoclonal antibodies are commonly manufactured using a batch fed method whereby the monoclonal antibody chains are expressed in a mammalian cell line and secreted into the tissue culture medium in a bioreactor. Medium (or feed) is continuously supplied to the bioreactor to maximize recombinant protein expression. Recombinant monoclonal antibody is then purified from the collected media. In some circumstances, additional steps are needed to reassemble the antibodies through reduction of disulfide bonds, etc. Such production methods can be scaled to be as large as 10,000 L in a single batch or more. It is now routine to obtain as much as 20 pg/cell/day through the use of such cell lines and methodologies, providing titers as high as 10 g/L or more, amounting to 15 to 100 kg from bioreactors of 10 kL to 25 kL. (Li et al., 2010). Various details of this production methodology, including cloning of the polynucleotides encoding the antibodies into expression vectors, transfecting cells with these expression vectors, selecting for transfected cells, and expressing and purifying the recombinant monoclonal antibodies from these cells are provided below.

For recombinant production of an anti-PACAP antibody or antigen binding fragment in mammalian cells, nucleic acids encoding the antibody or fragment thereof are generally inserted into a replicable vector for further cloning (amplification of the DNA) or for expression. DNA encoding the antibody is readily isolated or synthesized using conventional procedures (e.g., by using oligonucleotide probes that are capable of binding specifically to DNAs encoding the heavy and light chains of the antibody). The vector components generally include, but are not limited to, one or more of the following: a signal sequence, an origin of replication, one or more marker genes, an enhancer element, a promoter, and a transcription termination sequence. Selection of promoters, terminators, selectable markers, vectors, and other elements is a matter of routine design within the level of ordinary skill in the art. Many such elements are known in the art and are available through commercial suppliers.

The antibodies of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The homologous or heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

Such expression vectors and cloning vectors will generally contain a nucleic acid sequence that enables the vector to replicate in one or more selected host cells. Typically, in cloning vectors this sequence is one that enables the vector to replicate independently of the host chromosomal DNA, and includes origins of replication or autonomously replicating sequences. Such sequences are well known for a variety of bacteria, yeast, and viruses, e.g., the origin of replication from the plasmid pBR322 is suitable for most Gram-negative bacteria, the 2mu plasmid origin is suitable for yeast, and various viral origins (Simian Virus 40 ("SV40"), polyoma, adenovirus, vesicular stomatitis virus ("VSV"), or bovine papillomavirus ("BPV") are useful for cloning vectors in mammalian cells. Generally, the origin of replication component is not needed for mammalian expression vectors (the SV40 origin may typically be used only because it contains the early promoter).

These vectors will also typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." Examples of such dominant selection use the drugs neomycin, mycophenolic acid, and hygromycin. An exemplary selectable marker is a gene encoding resistance to the antibiotic neomycin. Selection is carried out in the presence of a neomycin-type drug, such as G-418 or the like. Those cells that are successfully transformed with a heterologous gene produce a protein conferring drug resistance and thus survive the selection regimen.

Selection systems can also be used to increase the expression level of the gene of interest, a process referred to as "amplification." Amplification of transfectants typically occurs by culturing the cells in the presence of a low level of the selective agent and then increasing the amount of selective agent to select for cells that produce high levels of the products of the introduced genes. Exemplary suitable selectable markers for mammalian cells are those that enable the identification of cells competent to take up the antibody nucleic acid, such as dihydrofolate reductase ("DHFR"), thymidine kinase, metallothionein-I and -II, preferably primate metallothionein genes, adenosine deaminase, ornithine decarboxylase, etc.

For example, an amplifiable selectable marker for mammalian cells is dihydrofolate reductase, which confers resistance to methotrexate. Other drug resistance genes (e.g. hygromycin resistance, multi-drug resistance, puromycin acetyltransferase) can also be used. Cells transformed with the DHFR selection gene are first identified by culturing all of the transformants in a culture medium that contains methotrexate ("MTX"), a competitive antagonist of DHFR. An appropriate host cell when wild-type DHFR is employed is the Chinese hamster ovary ("CHO") cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase ("APH") can be selected by cell growth in medium containing a selection agent for the selectable marker such as an aminoglycosidic antibiotic, e.g., kanamycin, neomycin, or G-418. See U.S. Pat. No. 4,965,199.

These vectors may comprise an enhancer sequence that facilitates transcription of a DNA encoding the antibody. Many enhancer sequences are known from mammalian genes (for example, globin, elastase, albumin, alpha-fetoprotein, and insulin). A frequently used enhancer is one derived from a eukaryotic cell virus. Examples thereof include the SV40 enhancer on the late side of the replication origin (bp 100-270), the cytomegalovirus early promoter enhancer, the polyoma enhancer on the late side of the replication origin, and adenovirus enhancers (See, also Yaniv, *Nature,* 297:17-18, 1982, on enhancing elements for activation of eukaryotic promoters). The enhancer may be spliced into the vector at a position 5' or 3' to the antibody-encoding sequence, but is preferably located at a site 5' from the promoter.

Expression and cloning vectors will also generally comprise a promoter that is recognized by the host organism and is operably linked to the antibody nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody transcription from vectors in mammalian host cells is controlled, for example, by promoters obtained from the genomes of viruses such as polyoma virus, fowlpox virus, adenovirus (such as Adenovirus 2), BPV, avian sarcoma virus, cytomegalovirus, a retrovirus, hepatitis-B virus, and most preferably SV40, from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the BPV as a vector is disclosed in U.S. Pat. No. 4,419,446. A modification of this system is described in U.S. Pat. No. 4,601,978. See also Reyes et al., *Nature,* 297:598-601 (1982) on expression of human beta-interferon cDNA in mouse cells under the control of a thymidine kinase promoter from herpes simplex virus. Alternatively, the rous sarcoma virus long terminal repeat can be used as the promoter.

Strong transcription promoters can be used, such as promoters from SV40, cytomegalovirus, or myeloproliferative sarcoma virus. Sec, e.g., U.S. Pat. No. 4,956,288 and U.S. Patent Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, VA. USA under accession numbers 98669, 98668, and PTA-5266, respectively, and derivatives of these vectors.

Expression vectors used in eukaryotic host cells (yeast, fungus, insect, plant, animal, human, or a nucleated cell from other multicellular organism) will also generally contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO 94/11026 and the expression vector disclosed therein.

Suitable host cells for cloning or expressing the subject antibodies include prokaryote, yeast, or higher eukaryote cells described above. However, interest has been greatest in vertebrate cells, and propagation of vertebrate cells in culture has become a routine procedure. Examples of useful mammalian host cell lines are monkey kidney CV1 line transformed by SV40 (COS-1 (ATCC No. CRL 1650); and COS-7, ATCC CRL 1651); human embryonic kidney line (293 or 293 cells subcloned for growth in suspension culture, (ATCC No. CRL 1573; Graham et al., *J. Gen. Virol.,* 36:59-72 (1977)); baby hamster kidney cells (BHK, ATCC CCL 10, ATCC No. CRL 1632; BHK 570, ATCC No. CRL 10314); CHO cells (CHO-K1, ATCC No. CCL 61; CHO-DG44, Urlaub et al., *Proc. Natl. Acad. Sci. USA,* 77:4216-4220 (1980)); mouse sertoli cells (TM4, *Mather, Biol. Reprod.,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2). Additional suitable cell lines are known in the art and available from public depositories such as the American Type Culture Collection, Manassas, VA.

Host cells are transformed with the above-described expression or cloning vectors for antibody production and cultured in conventional nutrient media modified as appropriate for inducing promoters, selecting transformants, or amplifying the genes encoding the desired sequences as discussed supra.

The mammalian host cells used to produce the antibody of this invention may be cultured in a variety of media. Commercially available media such as Ham's F10 (Sigma-Aldrich Corporation, St. Louis, MO), Minimal Essential Medium (("MEM" (Sigma-Aldrich Corporation, St. Louis, MO), Roswell Park Memorial Institute-1640 medium ("RPMI-1640", Sigma-Aldrich Corporation, St. Louis, MO), and Dulbecco's Modified Eagle's Medium (("DMEM" Sigma-Aldrich Corporation, St. Louis, MO) are suitable for culturing the host cells. In addition, any of the media described in Ham et al., *Meth. Enz.,* 58:44 (1979); Barnes et al., *Anal. Biochem.,* 102:255 (1980); U.S. Pat. Nos. 4,767,704; 4,657,866; 4,927,762; 4,560,655; or 5,122,469; WO 90/03430; WO 87/00195; or U.S. Patent Reexam No. 30,985, can be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. Methods of development and optimization of media and culture conditions are known in the art. (See, Gronemeyer et al., *Bioengineering,* 1 (4): 188-212, 2014).

After culture conditions are optimized and a preferred cell line clone is selected, these cells are cultured (either adherent cells or suspension cultures) most typically in a batch-fed process in a bioreactor (many models are commercially available) that involves continuously feeding the cell culture with medium and feed, optimized for the particular cell line chosen and selected for this purpose. (See, Butler, M., *Appl. Microbiol. Biotechnol.,* 68:283-291, 2005; and Kelley, B., mAb, 1 (5): 443-452, 2009). Perfusion systems are also available in which media and feed are continuously supplied to the culture while the same volume of media is being withdrawn from the bioreactor. (Wurm, 2004). Synthetic media, also commercially available, are available for growing cells in a batch-fed culture, avoiding the possibility of contamination from outside sources, such as with the use of animal components, such as bovine serum albumin, etc. However, animal-component-free hydrolysates are commercially available to help boost cell density, culture viability and productivity. (Li et al., 2010). Many studies have been performed in an effort to optimize cell culture media, including careful attention to head space available in roller bottles, redox potentials during growth and expression phases, presence of reducing agents to maintain disulfide bonds during production, etc. (See, for instance, Hutterer et al., *mAbs,* 5 (4): 608-613, 2013; and Mullan et al., *BMC Proceed.,* 5 (Suppl 8):P110, 2011). Various methodologies have been developed to address the possibility of harmful oxidation during recombinant monoclonal antibody production. (See, for example, U.S. Pat. No. 8,574,869). Cultured cells may be grown by feeding nutrients continuously or as separately administered amounts. Often various process parameters such as cell concentration, pH, temperature, $CO_2$, $dO_2$, osmolality, amount of metabolites such as glucose, lactate, glutamine and glutamate, and the like, are monitored by the use of probes during the cell growth either on-line by direct connection to calibrated analyzers or off-line by intervention of operators. The culturing step also typically involves ensuring that the cells growing in culture maintain the transfected recombinant genes by any means known in the art for cell selection.

Following fermentation, i.e., upon reaching maximum cell growth and recombinant protein expression, the culturing step is typically followed by a harvesting step, whereby the cells are separated from the medium and a harvested cell culture media is thereby obtained. (See, Liu et al., *mAbs,* 2 (5): 480-499, 2010). Typically various purification steps, involving column chromatography and the like, follow culturing to separate the recombinant monoclonal antibody from cell components and cell culture media components. The exact purification steps needed for this phase of the production of recombinant monoclonal antibodies depends on the site of expression of the proteins, i.e., in the cytosol of the cells themselves, or the more commonly preferred route of protein excreted into the cell culture medium. Various cell components may be separated using techniques known in the art such as differential centrifugation techniques, gravity-based cell settling, and/or size exclusion chromatograph/filtration techniques that can include tangential flow micro-filtration or depth filtration. (See, Pollock et al., *Biotechnol. Bioeng.,* 110:206-219, 2013, and Liu et al., 2010). Centrifugation of cell components may be achieved on a large scale by use of continuous disk stack centrifuges followed by clarification using depth and membrane filters. (See, Kelley, 2009). Most often, after clarification, the recombinant protein is further purified by Protein A chromatography due to the high affinity of Protein A for the Fc domain of antibodies, and typically occurs using a low pH/acidification elution step (typically the acidification step is combined with a precautionary virus inactivation step). Flocculation and/or precipitation steps using acidic or cationic polyelectrolytes may also be employed to separate animal cells in suspension cultures from soluble proteins. (Liu et al., 2010). Lastly, anion- and cation-exchange chromatography, hydrophobic interaction chromatograph ("HIC"), hydrophobic charge induction chromatograph (HCIC), hydroxyapatite chromatography using ceramic hydroxyapatite $(Ca_5(PO_4)_3OH)_2$, and combinations of these techniques are typically used to polish the solution of recombinant monoclonal antibody. Final formulation and concentration of the desired monoclonal antibody may be achieved by use of ultracentrifugation techniques. Purification yields are typically 70 to 80%. (Kelley, 2009).

The terms "desired protein" or "desired antibody" are used interchangeably and refer generally to a parent antibody specific to a target, i.e., PACAP or a chimeric or humanized antibody or a binding portion thereof derived therefrom as described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Examples thereof include chimeric antibodies, human antibodies and other non-human mammalian antibodies, humanized antibodies, single chain antibodies (such as scFvs), camelbodies, nanobodies, IgNAR (single-chain antibodies which may be derived from sharks, for example), small-modular immunopharmaceuticals ("SMIPs"), and antibody fragments such as Fabs, Fab', $F(ab')_2$, and the like (See, Streltsov et al., *Protein Sci.,* 14 (11): 2901-9, 2005; Greenberg et al., *Nature,* 374 (6518): 168-73, 1995; Nuttall et al., *Mol. Immunol.,* 38 (4): 313-26, 2001; Hamers-Casterman et al., *Nature,* 363 (6428): 446-8, 1993; Gill et al., *Curr. Opin. Biotechnol.*, (6): 653-8, 2006).

For example, antibodies or antigen binding fragments thereof may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones that co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid ("aa") substitutions, additions, or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc.). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the $V_L$ and $V_H$ regions, obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, and IgG4 constant regions.

Humanized antibodies are engineered to contain even more human-like immunoglobulin domains, and incorporate only the complementarity determining regions of the animal-derived antibody. This is accomplished by carefully examining the sequence of the hyper-variable loops of the variable regions of the monoclonal antibody and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', $F(ab')_2$, or other fragments) may be synthesized. "Fragment" or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, small molecule immunopharmaceuticals ("SMIPs"), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties, and the like, or specific binding moieties, such as streptavidin, avidin, or biotin, and the like may be utilized in the methods and compositions of the present invention. Examples of additional effector molecules are provided infra.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the DNA flanking the gene usually does not flank the mammalian genomic DNA in the genome of the source organism. Another example of a heterologous region is a construct where the coding sequence itself is not found in nature (e.g., a cDNA where the genomic coding sequence contains introns or synthetic sequences having codons different than the native gene). Allelic variations or naturally-occurring mutational events do not give rise to a heterologous region of DNA as defined herein.

A "coding sequence" is an in-frame sequence of codons that correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of initiating transcription of a downstream (3' direction) coding sequence, and typically contain additional sites for binding of regulatory molecules, e.g., transcription factors, that affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

The general structure of antibodies in vertebrates now is well understood. See Edelman, G. M., *Ann. N.Y. Acad. Sci.,* 190:5 (1971). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the Fab region; the stem portion of the "Y" configuration is designated the Fc region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to $\gamma$, $\mu$, $\alpha$, $\delta$, and $\varepsilon$ (gamma, mu, alpha, delta, or epsilon) heavy chain constant regions). The constant region or class determines subsequent effector function of the antibody, including activation of complement (see Kabat, E. A., *Structural Concepts in Immunology and Immunochemistry,* 2nd Ed., p. 413-436, New York, NY: Holt, Rinehart, Winston (1976)), and other cellular responses (see Andrews et al., *Clinical Immunology*, pp. 1-18, W. B. Sanders, Philadelphia, PA (1980); Kohl et al., *Immunology,* 48:187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B-cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions ("CDRs") found in the variable regions of light or heavy chains of an antibody (See Kabat et al., *Sequences of Proteins of Immunological Interest,* $4^{th}$ ed., Bethesda, MD: U.S. Dept. of Health and Human Services, Public Health Service, National Institutes of Health (1987)). These expressions include the hypervariable regions as defined by Kabat et al., (*Sequences of Proteins of Immunological Interest*, NIH Publication No. 91-3242, Bethesda, MD: U.S. Dept. of Health and Human Services, National Institutes of Health (1983)) or the hypervariable loops in 3-dimensional structures of antibodies (Chothia and Lesk, *J. Mol. Biol.,* 196: 901-917, 1987). The CDRs in each chain are held in close proximity by framework regions ("FRs") and, with the CDRs from the other chain, contribute to the formation of the antigen binding site. Within the CDRs there are select amino acids that have been described as the selectivity determining regions ("SDRs") that represent the critical contact residues used by the CDR in the antibody-antigen interaction. (See, Kashmiri et al., *Methods,* 36 (1): 25-34, 2005).

An "epitope" or "binding site" is an area or region on an antigen to which an antigen-binding peptide (such as an antibody) specifically binds. A protein epitope may comprise amino acid residues directly involved in the binding (also called immunodominant component of the epitope) and other amino acid residues, which are not directly involved in the binding, such as amino acid residues that are effectively blocked by the specifically antigen binding peptide (in other words, the amino acid residue is within the "footprint" of the specifically antigen binding peptide). The term epitope herein includes both types of amino acid binding sites in any particular region of PACAP, i.e., PACAP38 and PACAP27, that specifically binds to an anti-PACAP antibody. PACAP may comprise a number of different epitopes, which may include, without limitation, (1) linear peptide antigenic determinants, (2) conformational antigenic determinants that consist of one or more non-contiguous amino acids located near each other in a mature PACAP conformation; and (3) post-translational antigenic determinants that consist, either in whole or part, of molecular structures covalently attached to a PACAP protein such as carbohydrate groups. In particular, the term "epitope" includes the specific residues in a protein or peptide, e.g., PACAP, which are involved in the binding of an antibody to such protein or peptide as determined by known and accepted methods such as alanine scanning techniques. Such methods are exemplified herein.

The phrase that an antibody (e.g., first antibody) binds "substantially" or "at least partially" the same epitope as another antibody (e.g., second antibody) means that the epitope binding site for the first antibody comprises at least 10%, 20%, 30%, 40%, 50%, 60%, 70%, 80%, 90%, or more of the amino acid residues on the antigen that constitutes the epitope binding site of the second antibody. Also, that a first antibody binds substantially or partially the same or overlapping epitope as a second antibody means that the first and second antibodies compete in binding to the antigen, as described above. Thus, the term "binds to substantially the same epitope or determinant as" a monoclonal antibody means that an antibody "competes" with the antibody.

The phrase "binds to the same or overlapping epitope or determinant as" an antibody of interest means that an antibody "competes" with said antibody of interest for at least one, (e.g., at least 2, at least 3, at least 4, at least 5) or all residues on PACAP to which said antibody of interest specifically binds. The identification of one or more antibodies that bind(s) to substantially or essentially the same epitope as the monoclonal antibodies described herein can be readily determined using alanine scanning. Additionally, any one of variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same or overlapping epitope as the monoclonal antibody described herein.

For example, where the test antibodies to be examined are obtained from different source animals, or are even of a different Ig isotype, a simple competition assay may be employed in which the control antibody is mixed with the test antibody and then applied to a sample containing PACAP. Protocols based upon ELISAs, radioimmunoassays, Western blotting, and the use of BIACORE® (GE Healthcare Life Sciences, Marlborough, MA) analysis are suitable for use in such simple competition studies.

In certain embodiments, the control anti-PACAP antibody is pre-mixed with varying amounts of the test antibody (e.g., in ratios of about 1:1, 1:2, 1:10, or about 1:100) for a period of time prior to applying to the PACAP38 or PACAP27 antigen sample. In other embodiments, the control and varying amounts of test antibody can simply be added separately and admixed during exposure to the PACAP38 or PACAP27 antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labeling the control antibody with a detectable label) it can be determined if the test antibody reduces the binding of the control antibody to the PACAP38 or PACAP27 antigens, indicating that the test antibody recognizes substantially the same epitope as the control anti-PACAP antibody. The binding of the (labeled) control antibody in the presence of a completely irrelevant antibody (that does not bind PACAP) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of the control antibody to PACAP38 or PACAP27 by at least about 50%, such as at least about 60%, or more preferably at least about 70% (e.g., about 65-100%), at any ratio of test antibody between about 1:1 or 1:10 and about 1:100 is considered to be an antibody that binds to substantially the same or overlapping epitope or determinant as the control antibody.

Preferably, such test antibody will reduce the binding of the control antibody to PACAP38 or PACAP27 antigen preferably at least about 50%, at least about 60%, at least about 80%, or at least about 90% (e.g., about 95%) of the binding of the control antibody observed in the absence of the test antibody.

A simple competition assay in which a test antibody is applied at saturating concentration to a surface onto which PACAP38 or PACAP27 is immobilized also may be advantageously employed. The surface in the simple competition assay is preferably a BIACORE® (GE Healthcare Life Sciences, Marlborough, MA) chip (or other media suitable for surface plasmon resonance ("SPR") analysis). The binding of a control antibody that binds PACAP38 or PACAP27 to the PACAP-coated surface is measured. This binding to the PACAP38- or PACAP27-containing surface of the control antibody alone is compared with the binding of the control antibody in the presence of a test antibody. A significant reduction in binding to the PACAP38- or PACAP27-containing surface by the control antibody in the presence of a test antibody indicates that the test antibody recognizes substantially the same epitope as the control antibody such that the test antibody "competes" with the control antibody. Any test antibody that reduces the binding of control antibody by at least about 20% or more, at least about 40%, at least about 50%, at least about 70%, or more, can be considered to be an antibody that binds to substantially the same epitope or determinant as the control antibody. Preferably, such test antibody will reduce the binding of the control antibody to PACAP38 or PACAP27 by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the "sandwich-style" binding assay exemplified in Example 9 infra is used. Alternatively, the antibody having greater affinity for PACAP38 or PACAP27 antigen is bound to the PACAP38- or PACAP27-containing surface first, as it will be expected that the decrease in binding seen for the second antibody (assuming the antibodies are competing) will be of greater magnitude. Further examples of such assays are provided in e.g., Saunal and Regenmortel, *J. Immunol. Methods,* 183:33-41 (1995), the disclosure of which is incorporated herein by reference.

In addition, whether an antibody binds the same or overlapping epitope(s) on PACAP as another antibody or the epitope bound by a test antibody may in particular be determined using a Western-blot based assay. In this assay a library of peptides corresponding to the antigen bound by the antibody, the PACAP protein, is made, that comprise overlapping portions of the protein, typically 10-25, 10-20, or 10-15 amino acids long. These different overlapping amino acid peptides encompassing the PACAP sequence are synthesized and covalently bound to a PEPSPOTS™ nitrocellulose membrane (JPT Peptide Technologies, Berlin, Germany). Blots are then prepared and probed according to the manufacturer's recommendations.

Essentially, the immunoblot assay then detects by fluorometric means what peptides in the library bind to the test antibody and thereby can identify what residues on the antigen, i.e., PACAP, interact with the test antibody. (See U.S. Pat. No. 7,935,340, incorporated by reference herein).

Various epitope mapping techniques are known in the art. By way of example, X-ray co-crystallography of the antigen and antibody; NMR; SPR (e.g., at 25° or 37° C.); array-based oligo-peptide scanning (or "pepscan analysis"); site-directed mutagenesis (e.g., alanine scanning); mutagenesis mapping; hydrogen-deuterium exchange; phage display; and limited proteolysis are all epitope mapping techniques that are well known in the art. (See, e.g., *Epitope Mapping Protocols: Second Edition, Methods in Molecular Biology*, editors Mike Schutkowski and Ulrich Reineke, 2nd Ed., New York, NY: Humana Press, 2009; and *Epitope Mapping Protocols, Methods in Molecular Biology*, editor Glenn Morris, 1st Ed., New York, NY: Humana Press, 1996, both of which are herein incorporated by referenced in their entirety).

The identification of one or more antibodies that bind(s) to substantially or essentially the same epitope as the monoclonal antibodies described herein, e.g., Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23, can be readily determined using any one of variety of immunological screening assays in which antibody competition can be assessed. A number of such assays are routinely practiced and well known in the art (see, e.g., U.S. Pat. No. 5,660,827, incorporated herein by reference). It will be understood that determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control antibody (one of Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23, for example) is mixed with the test antibody and then applied to a sample containing either or both PACAP38 and PACAP27, each of which is known to be bound by Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23. Protocols based upon ELISAs, radioimmunoassays, Western blotting, and BIACORE® (GE Healthcare Life Sciences, Marlborough, MA) analysis (as described in the Examples section herein) are suitable for use in such simple competition studies.

In certain embodiments, the method comprises pre-mixing the control antibody with varying amounts of the test antibody (e.g., in ratios of about 1:1, 1:2, 1:10, or about 1:100) for a period of time prior to applying to the PACAP antigen sample. In other embodiments, the control and varying amounts of test antibody can be added separately and admixed during exposure to the PACAP antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labelling the control antibody with a detectable label), the method can be used to determine that the test antibody reduces the binding of the control antibody to the PACAP antigen, indicating that the test antibody recognizes substantially the same epitope as the control antibody (e.g., Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23). The binding of the (labeled) control antibody in the presence of a completely irrelevant antibody (that does not bind PACAP) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23 to both of PACAP38 and PACAP27 antigens by at least about 50%, such as at least about 60%, or more preferably at least about 70% (e.g., about 65-100%), at any ratio of control Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22 or Ab23: test antibody, or Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23: test antibody between about 1:1 or 1:10 and about 1:100 is considered to be an antibody that binds to substantially the same epitope or determinant as Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23, respectively. Preferably, such test antibody will reduce the binding of Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23 to at least one, preferably each, of the PACAP38 and PACAP27 antigens preferably at least about 50%, at least about 60%, at least about 80% or at least about 90% (e.g., about 95%) of the binding of Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23 observed in the absence of the test antibody. These methods can be adapted to identify and/or evaluate antibodies that compete with other control antibodies.

A simple competition assay in which a test antibody is applied at saturating concentration to a surface onto which either PACAP38 or PACAP27, or both, are immobilized also may be advantageously employed. The surface in the simple competition assay is preferably of a media suitable for OCTET® and/or PROTEON®. The binding of a control antibody (e.g., Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23) to the PACAP-coated surface is measured. This binding to the PACAP-containing surface of the control antibody alone is compared with the binding of the control antibody in the presence of a test antibody. A significant reduction in binding to the PACAP-containing surface by the control antibody in the presence of a test antibody indicates that the test antibody recognizes substantially the same epitope as the control antibody such that the test antibody "competes" with the control antibody. Any test antibody that reduces the binding of control antibody (such as Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23) to both of PACAP38 and PACAP27 antigens by at least about 20% or more, at least about 40%, at least about 50%, at least about 70%, or more, can be considered to be an antibody that binds to substantially the same epitope or determinant as the control antibody (e.g., Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23). Preferably, such test antibody will reduce the binding of the control antibody (e.g., Ab10, Ab10.H, Ab10.H2, Ab10.H3, Ab10.H4, Ab10.H5, Ab10.H6, Ab20, Ab21, Ab21.H, Ab21.H2, Ab21.H3, Ab21.H4, Ab22, or Ab23) to the PACAP antigen by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for PACAP38 and PACAP27 is bound to the PACAP-containing surface first, as it will be expected that the decrease in binding seen for the second antibody (assuming the antibodies are competing) will be of greater magnitude. Further examples of such assays are provided in, e.g., Saunal and Regenmortel, *J. Immunol. Methods,* 183: 33-41 (1989), the disclosure of which is incorporated herein by reference.

Determination of whether an antibody, antigen binding fragment thereof, or antibody derivative binds within one of the epitope regions defined above can be carried out in ways known to the person skilled in the art. In another example of such mapping/characterization methods, an epitope region for an anti-PACAP antibody may be determined by epitope "footprinting" using chemical modification of the exposed amines/carboxyls in the PACAP38 and PACAP27 protein. One specific example of such a foot-printing technique is the use of hydrogen-deuterium exchange detected by mass spectrometry ("HXMS"), wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. (See, e.g., Ehring H., *Anal. Biochem.,* 267 (2): 252-259, 1999; and Engen, J. R. & Smith, D. L., *Anal. Chem.,* 73: 256A-265A, 2001). Another example of a suitable epitope identification technique is nuclear magnetic resonance epitope mapping ("NMR"), where typically the position of the signals in two-dimensional NMR spectres of the free antigen and the antigen complexed with the antigen binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. (See, e.g., *Ernst Schering Res. Found. Workshop*, (44):

149-67, 2004; Huang et al., *J. Mol. Biol.,* 281 (1): 61-67, 1998; and Saito and Patterson, *Methods,* 9 (3): 516-24, 1996).

Epitope mapping/characterization also can be performed using mass spectrometry ("MS") methods. (See, e.g., Downard, *J. Mass Spectrom.,* 35 (4): 493-503, 2000; and Kiselar and Downard, *Anal. Chem.,* 71 (9): 1792-801, 1999).

Protease digestion techniques also can be useful in the context of epitope mapping and identification. Antigenic determinant-relevant regions/sequences can be determined by protease digestion, e.g. by using trypsin in a ratio of about 1:50 to PACAP38 or PACAP27 overnight ("o/n") digestion at 37° C. and pH 7-8, followed by mass spectrometry ("MS") analysis for peptide identification. The peptides protected from trypsin cleavage by the anti-PACAP antibody can subsequently be identified by comparison of samples subjected to trypsin digestion and samples incubated with antibody and then subjected to digestion by e.g. trypsin (thereby revealing a footprint for the antibody). Other enzymes like chymotrypsin or pepsin can be used in similar epitope characterization methods. Moreover, enzymatic digestion can provide a quick method for analyzing whether a potential antigenic determinant sequence is within a region of PACAP in the context of a PACAP-binding polypeptide. If the polypeptide is not surface exposed, it is most likely not relevant in terms of immunogenicity/antigenicity. (See, e.g., Manca, *Ann. Ist. Super. Sanità,* 27 (1): 15-9, 1991, for a discussion of similar techniques).

Site-directed mutagenesis is another technique useful for characterization of a binding epitope. For example, in "alanine-scanning" site-directed mutagenesis (also known as alanine scanning, alanine scanning mutagenesis, alanine scanning mutations, combinatorial alanine scanning, or creation of alanine point mutations, for example), each residue within a protein segment is replaced with an alanine residue (or another residue such as valine where alanine is present in the wild-type sequence) through such methodologies as direct peptide or protein synthesis, site-directed mutagenesis, the GENEART™ Mutagenesis Service (Thermo Fisher Scientific, Waltham, MA U.S.A.) or shotgun mutagenesis, for example. A series of single point mutants of the molecule is thereby generated using this technique; the number of mutants generated is equivalent to the number of residues in the molecule, each residue being replaced, one at a time, by a single alanine residue. Alanine is generally used to replace native (wild-type) residues because of its non-bulky, chemically inert, methyl functional group that can mimic the secondary structure preferences that many other amino acids may possess. Subsequently, the effects replacing a native residue with an alanine has on binding affinity of an alanine scanning mutant and its binding partner can be measured using such methods as, but not limited to, SPR binding experiments. If a mutation leads to a significant reduction in binding affinity, it is most likely that the mutated residue is involved in binding. Monoclonal antibodies specific for structural epitopes (i.e., antibodies that do not bind the unfolded protein) can be used as a positive control for binding affinity experiments to verify that the alanine-replacement does not influence the overall tertiary structure of the protein (as changes to the overall fold of the protein may indirectly affect binding and thereby produce a false positive result). (See, e.g., Clackson and Wells, *Science,* 267:383-386 (1995); Weiss et al., *Proc. Natl. Acad. Sci. USA,* 97 (16): 8950-8954 (2000); and Wells, *Proc. Natl. Acad. Sci. USA,* 93:1-6 (1996)). In Example 12 alanine scanning methods are used to identify the specific epitope or residues of PACAP which specifically interact with the anti-PACAP antibodies disclosed herein.

Electron microscopy can also be used for epitope "footprinting". For example, Wang et al., *Nature,* 355:275-278 (1992) used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include SPR (sold commercially as the BIACORE® system, GE Healthcare Life Sciences, Marlborough, MA) and reflectometric interference spectroscopy ("RifS"). (See, e.g., Fagerstam et al., *J. Mol. Recog.,* 3:208-14, 1990; Nice et al., *J. Chromatogr.,* 646:159-168, 1993; Leipert et al., *Angew. Chem. Int. Ed.,* 37:3308-3311, 1998; Kroger et al., *Biosensors and Bioelectronics,* 17:937-944, 2002).

The expressions "framework region" or "FR" refer to one or more of the framework regions within the variable regions of the light and heavy chains of an antibody. (See, Kabat et al., *Sequences of Proteins of Immunological Interest,* $4^{th}$ edition, Bethesda, MD: U.S. Dept. of Health and Human Services, Public Health Service, National Institutes of Health, 1987). These expressions include those amino acid sequence regions interposed between the CDRs within the variable regions of the light and heavy chains of an antibody.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. (See, Kabat et al., *Sequences of Proteins of Immunological Interest,* 5th edition, Bethesda, MD: U.S. Dept. of Health and Human Services, Public Health Service, National Institutes of Health, 1991). The Fc region of an immunoglobulin generally comprises two constant domains, CH2 and CH3.

The terms "Fc receptor" and "FcR" describe a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinect, *Ann. Rev. Immunol.,* 9:457-92 (1991); Capel et al., *Immunomethods,* 4:25-34 (1994); and de Haas et al., *J. Lab. Clin. Med.,* 126:330-41 (1995). "FcR" also includes the neonatal receptor, FcRn, which is responsible for the transfer of maternal IgGs to the fetus (Guyer et al., *J. Immunol.,* 117:587, 1976; and Kim et al., *J. Immunol.,* 24:249, 1994), and which primarily functions to modulate and/or extend the half-life of antibodies in circulation. To the extent that the disclosed anti-PACAP antibodies are aglycosylated, as a result of the expression system and/or sequence, the subject antibodies are expected to bind FcRn receptors, but not to bind (or to minimally bind) Fcγ receptors.

A "functional Fc region" possesses at least one effector function of a native sequence Fc region. Exemplary "effector functions" include C1q binding; complement dependent cytotoxicity ("CDC"); Fc receptor binding; antibody-dependent cell-mediated cytotoxicity ("ADCC"); phagocytosis; down-regulation of cell surface receptors (e.g. B cell receptor ("BCR")), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence that differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95%, at least about 96%, at least about 97%, at least about 98%, or at least about 99% sequence identity therewith.

Anti-PACAP Antibodies and Binding Fragments Thereof Having Binding Activity for PACAP PACAP is a multifunctional vasodilatory peptide with expression throughout the central nervous system ("CNS") and periphery. PACAP is a member of the secretin/VIP/GRH family. PACAP exists in two α-amidated active forms, PACAP38 (SEQ ID NO: 1241) and PACAP27 (SEQ ID NO: 1242). Herein, the term "PACAP" includes either or both of PACAP38 and PACAP27 unless expressly indicated otherwise. PACAP is highly conserved between species.

In humans, PACAP is derived from a 176 amino acid precursor protein (preproPACAP) and the gene is located on chromosome 18p11, with PACAP38 encoded for by exon 5. (See, Vaudry et al., *Pharmacol. Rev.,* 61:283-357, 2009). PreproPACAP contains an N-terminal 24 amino acid signal protein, a 29 amino acid PACAP-related peptide and PACAP in the C-terminal domain. The precursor is metabolized by prohormone convertase enzymes into biologically active PACAP38 and PACAP27.

VIP (SEQ ID NO: 1243) belongs to the same protein family as PACAP and shares high homology with PACAP, i.e., VIP and PACAP27 have 68% sequence homology at the amino acid level, as well as similar overall secondary structure, i.e. long alpha-helical structures at the C-terminus.

PACAP's actions are mediated via three different G-protein coupled receptors: PAC1-R, VPAC1-R, and VPAC2-R. VPAC1-R can associate with all of the receptor-associated membrane proteins ("RAMPs," see Kaiser and Russo, *Neuropeptides* 47:451-461, 2013). PAC1-R is selective for PACAP, whereas VPAC1-R and VPAC2-R bind to both VIP and PACAP with high affinity. PAC1-R binds to PACAP with 100-1000-fold higher affinity than VIP, i.e., $K_D$~0.5 nM for PACAP27/PACAP38 vs. $K_D$~500 nM for VIP. Conversely, VPAC1-R and VPAC2-R have equal affinities for PACAP and VIP ($K_D$)~1 nM). (See, Schytz et al., 2010). All three receptors are widely expressed in both peripheral tissues and in the CNS, with PAC1-R predominantly expressed in the CNS, most abundantly in the olfactory bulb, thalamus, hypothalamus, the dentate gyrus of the hippocampus and in granule cells of the cerebellum. (See, Hashimoto et al., *J. Comp. Neurol.,* 371:567-577, 1996; and Shioda et al., *Neurosci. Res.,* 28:345-354, 1997).

Activation of the PAC1-R, VPAC1-R, and/or VPAC2-R results in increased adenylate cyclase activity and, thus, increased cAMP production. However, PACAP receptors can also mediate their effects through PLC, leading to increased $Ca^{2+}$ levels, and PLD.

PACAP has a wide range of biological effects, including a role in neurodevelopment, neuroprotection, neuromodulation, neurogenic inflammation, and nociception. PACAP is also reported to interact with glycosaminoglycans ("GAGs"). GAGs are long, unbranched polysaccharides composed of repeating disaccharide units, such as heparin, chondroitin, keratin, and hyaluronic acid. It has been shown that the cellular uptake of PACAP is dependent on the expression of GAG proteins and that PACAP bound to sulfated GAGs. Particularly, it was determined that PACAP38 binding to GAGs was capable of inducing receptor-independent cellular uptake of PACAP38. This study further demonstrated that a random coil-to-α-helix transition in PACAP38 was essential for GAG-dependent uptake of PACAP38, as a mutant PACAP38 that could not undergo the structural transition was not internalized by GAG-containing cell lines as efficiently as the wild-type form of PACAP38 (Neree et al., *FEBS Lett.,* 588 (24): 4590-4596, 2014). In a follow up study, it was determined that PACAP's ability to cluster GAGs, i.e., heparin, was directly related to its ability to function as a cell penetrating peptide ("CPP"). It is hypothesized that this activity is attributable to the heparin-binding, or Cardin-Weintraub, motif found in secretin/glucagon/GHRH family members, such as PACAP (Neree et al., *Int. J. Mol. Sci.,* 16:27391-27400, 2015). Interestingly, Neree et al. (2015) presented data demonstrating that PACAP38 was able to cluster sulfated GAGs in vitro. These data suggested that the observed clustering effect is important for the GAG-mediated cellular uptake of PACAP38, as other peptides, such as glucagon, displayed higher binding affinities for sulfated GAGs (heparin) but are not internalized by cells as efficiently as PACAP38. Further, it is reported that in in vitro studies in which cells are exposed to PACAP, cartilage formation is increased, including cartilage matrix that is rich in sulphated GAG proteins, consistent with its putative protective role expressed during various cellular stress responses (Juhász et al., *PLoS ONE,* 9 (3): c91541, 2014). Using cell types that lack PACAP-specific receptors on their plasma membranes, such as CHO-K1 cells, Doan et al. presented data demonstrating the ability of such cells to engage in receptor-independent cellular uptake of various forms of fluorescently-labeled PACAP38 and PACAP27 (Doan et al., *Biochem. Biophys. Acta,* 1823:940-949, 2012).

The present invention provides exemplary antibodies or antigen binding fragments thereof that bind PACAP, including human PACAP. Other antibodies or antigen binding fragments thereof that bind PACAP, including those having different CDRs, and epitopic specificity may be obtained using the disclosure of the present specification, and using methods that are generally known in the art. Such antibodies and antigen binding fragments thereof antagonize the biological effects of PACAP in vivo and therefore are useful in treating or preventing PACAP-related conditions including, for example, headache, migraine, pain, photophobia, hot flush, PTSD, and anxiety disorders. In preferred embodiments, the antibody or antigen binding fragment thereof according to the invention comprises one or more CDRs, a $V_L$ chain and/or $V_H$ chain of the anti-PACAP antibodies and antigen binding fragments thereof described herein.

In some embodiments, an anti-PACAP antibody or antigen binding fragment thereof according to the invention will interfere with, block, reduce, or modulate the interaction between PACAP and its receptor(s) (e.g., PAC1-R, VPAC1-R, and VPAC2-R). In some instances an anti-PACAP antibody or antigen binding fragment thereof according to the invention is "neutralizing", e.g., it totally prevents the specific interaction of PACAP with PAC1-R, VPAC1-R, and/or VPAC2-R. In some embodiments, the antibody or antigen binding fragment thereof neutralizes PACAP, e.g., by remaining bound to PACAP in a location and/or manner that prevents PACAP from specifically binding to PAC1-R, VPAC1-R, and/or VPAC2-R.

In some embodiments, the antibody or antigen binding fragment thereof according to the invention is capable of inhibiting PACAP-mediated activity (including binding to PAC1R-expressing cells). In some embodiments, the antibody or antigen binding fragment thereof according to the invention are humanized, such as humanized rabbit antibodies to PACAP.

As mentioned, the anti-PACAP antibodies or antigen binding fragments thereof according to the invention have a variety of uses. For example, the subject antibodies and fragments can be useful in therapeutic applications, as well as diagnostically in binding assays. The subject anti-PACAP antibodies or antigen binding fragments thereof are useful for affinity purification of PACAP, in particular human PACAP or its ligands and in screening assays to identify other antagonists of PACAP activity. Some of the antibodies or antigen binding fragments thereof are useful for inhibiting binding of PACAP to PAC1-R, VPAC1-R, and/or VPAC2-R, or inhibiting PACAP-mediated activities and/or biological effects.

As used herein, the term "one or more biological effects associated with PACAP refers to any biological effect mediated, induced, or otherwise attributable to PACAP, e.g., binding properties, functional properties, and other properties of biological significance. Non-limiting exemplary biological effects of PACAP include PACAP binding to PAC1-R, VPAC1-R, and/or VPAC2-R; PACAP activating PAC1-R, VPAC1-R, and/or VPAC2-R-mediated signaling; PACAP-mediated increase in cAMP production; PACAP-mediated increase in PLC activity; PACAP-mediated increase in PLD activity; PACAP-mediated increase in $Ca^{2+}$ levels; and PACAP-mediated vasodilation, photophobia, mast cell degranulation, and/or neuronal activation. The subject anti-PACAP antibodies are capable of inhibiting one, a combination of, or all of these exemplary PACAP biological activities. For example, the anti-PACAP antibodies and antigen binding fragments thereof provided herein are capable of inhibiting PACAP-induced vasodilation (see Example 7 and Example 8).

The antibody or antigen binding fragment thereof according to the invention can be used in a variety of therapeutic applications. For example, in some embodiments the anti-PACAP antibody or antigen binding fragment thereof are useful for treating conditions associated with PACAP, such as, but not limited to, migraine (with or without aura), hemiplegic migraines, cluster headaches, migrainous neuralgia, chronic headaches, tension headaches, general headaches, hot flush, photophobia, chronic paroxysmal hemicrania, secondary headaches due to an underlying structural problem in the head or neck, cranial neuralgia, sinus headaches (e.g., headache associated with sinusitis), allergy-induced headaches or migraines, pain, chronic pain, neuroinflammatory or inflammatory pain, post-operative incision pain, post-surgical pain, trauma-related pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, PTSD, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, bronchial hyperreactivity, asthma, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures, acne vulgaris, atopic dermatitis, urticaria, keloids, hypertrophic scars and rosacea, allergic dermatitis, psoriasis, pruritus, neurogenic cutaneous redness, erythema, weight loss, anorexia, sarcoidosis, shock, sepsis, opiate withdrawal syndrome, morphine tolerance, epilepsy, LUT disorders such as urinary tract infection, abnormal voiding, urinary urgency, nocturia, urinary incontinence, overactive bladder, and for preventing or alleviating the pain associated with such LUT conditions.

Specific examples of visceral pain, i.e., pain associated with the viscera, or the internal organs of the body include pain that affects organs such as e.g., the heart, lungs, reproductive organs, bladder, ureters, the digestive organs, liver, pancreas, spleen, and kidneys. Conditions associated therewith include by way of example pancreatitis, labor, abdominal surgery associated with ileus, cystitis, menstrual period, or dysmenorrhea. Likewise, kidney pain, epigastric pain, pleural pain, and painful biliary colic, appendicitis pain may all be considered to be visceral pain. Substernal pain or pressure from early myocardial infarction is also visceral. Diseases of the stomach, duodenum or colon can cause visceral pain. Commonly encountered gastrointestinal ("GI") disorders that cause visceral pain include functional bowel disorder ("FBD") and inflammatory bowel disease ("IBD"). Such GI disorders may further include gastroesophageal reflux, dyspepsia, irritable bowel syndrome ("IBS") and functional abdominal pain syndrome ("FAPS"), and, with respect to IBD, Crohn's disease, ileitis, and ulcerative colitis.

The subject anti-PACAP antibodies and antigen binding fragments thereof may be used alone or in association with other active agents or drugs, including other biologics, to treat any subject in which blocking, inhibiting, or neutralizing the in vivo effect of PACAP or blocking or inhibiting the interaction of PACAP and its receptors, PAC1-R, VPAC1-R, and VPAC2-R, is therapeutically desirable.

Exemplary anti-PACAP antibodies and antigen binding fragments thereof according to the invention, and the specific CDRs thereof are identified in this section. For convenience, each exemplified antibody or antigen binding fragment thereof, and corresponding sequences are separately identified by a specific nomenclature, i.e., Ab10, Ab10.H, Ab10.H2, Ab10.H3, Ab10.H4, Ab10.H5, Ab10.H6 Ab20, Ab21, Ab21.H, Ab21.H2, Ab21.H3, Ab21.H4, Ab22, and Ab23.

The anti-PACAP antibodies and antigen binding fragments thereof comprising the invention have binding affinity for PACAP, wherein the binding affinity comprises anti-PACAP antibodies or antigen binding fragments thereof specifically binding to PACAP38 and PACAP27, but not binding VIP, and/or antibodies or antigen binding fragments thereof specifically binding to PACAP38, but not binding to PACAP27 or VIP, and/or antibodies or antigen binding fragments thereof specifically binding to a linear and/or conformational epitope within PACAP38 and/or PACAP27. More specifically, the epitopes of PACAP38 and/or PACAP27 to which antagonistic anti-PACAP antibodies or antigen binding fragments thereof according to the invention bind will include those which are identified in Example 12 or residues thereof (as determined by use of alanine scanning) and/or other epitopic identification methods.

Anti-PACAP Antibody Polypeptide Sequences

Antibody Ab10.H

In one embodiment, the invention includes antibodies and antigen-binding fragments having binding specificity to PACAP that possess a heavy chain sequence comprising the sequence of SEQ ID NO: 961 which consists of the heavy chain variable region of SEQ ID NO: 962 linked to the heavy chain constant region of SEQ ID NO: 970.

In one embodiment, the invention includes antibodies and antigen-binding fragments having binding specificity to PACAP that contain a variable heavy chain sequence comprising the sequence set forth below:

(SEQ ID NO: 962)
EVQLVESGGGLVQPGGSLRLSCAASGIDLNSYYMTWVRQAPGKGLEWIGFI

DAGGDAYYASWAKGRFTISRDNSKNTVYLQMNSLRAEDTAVYFCARDLDLW

GQGTLVTVSS.

In another embodiment, the invention includes antibodies and antigen-binding fragments having binding specificity to PACAP that bind the same epitope as Ab10.H, and that contain a constant heavy chain sequence comprising the polypeptide of SEQ ID NO: 1244, 1245, or 1246, or comprising the sequence set forth below:

(SEQ ID NO: 970)
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

-continued

CDKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNGKEYKC

KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPGK.

In another embodiment, the invention includes antibodies and antigen-binding fragments having binding specificity to PACAP that contain a light chain sequence comprising the sequence of SEQ ID NO: 981 which consists of the light chain variable region of SEQ ID NO: 982 linked to the light chain constant region of SEQ ID NO: 990.

In another embodiment, the invention includes antibodies and antigen-binding fragments having binding specificity to PACAP that contain a variable light chain sequence comprising the sequence set forth below:

(SEQ ID NO: 982)
DAQLTQSPSTLSASVGDRVTITCQSSESVYGNYLAWFQQKPGKAPKFLIYE

ASKLESGVPSRFSGSGSGTEFTLTISSLQPDDFATYYCAGGDISEGVAFGG

GTKVEIKR.

In another embodiment, the invention includes antibodies and antigen-binding fragments having binding specificity to PACAP, that bind the same epitope as Ab10.H, and that contain a constant light chain sequence comprising the sequence set forth below:

(SEQ ID NO: 990)
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFN

RGEC.

In another embodiment, the invention includes antibodies and antigen-binding fragments having binding specificity to PACAP that contain one, two, or three of the polypeptide sequences of SEQ ID NO: 964; SEQ ID NO: 966; and SEQ ID NO: 968, which correspond to the CDRs (hypervariable regions) of the heavy chain sequence of SEQ ID NO: 961, or which contain the variable heavy chain sequence of SEQ ID NO: 962, and/or which further contain one, two, or three of the polypeptide sequences of SEQ ID NO: 984; SEQ ID NO: 986; and SEQ ID NO: 988, which correspond to the CDRs (hypervariable regions) of the light chain sequence of SEQ ID NO: 981, or which contain the variable light chain sequence of SEQ ID NO: 982, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 963; SEQ ID NO: 965; SEQ ID NO: 967; and SEQ ID NO: 969, which correspond to the FRs (constant regions) of the heavy chain sequence of SEQ ID NO: 961, or the variable heavy chain sequence of SEQ ID NO: 962, and/or one, two, three, or four of the polypeptide sequences of SEQ ID NO: 983; SEQ ID NO: 985; SEQ ID NO: 987; and SEQ ID NO: 989, which correspond to the FRs (constant regions) of the light chain sequence of SEQ ID NO: 981, or the variable light chain sequence of SEQ ID NO: 982, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 961, or SEQ ID NO: 962, or polypeptides that are at least 90% or 95% identical thereto. In another embodiment of the invention, the antibodies and antigen-binding fragments of the invention comprise, or alternatively consist of, the polypeptide sequence of SEQ ID NO: 981, or SEQ ID NO: 982, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 964; SEQ ID NO: 966; and SEQ ID NO: 968, which correspond to the CDRs (hypervariable regions) of the heavy chain sequence of SEQ ID NO: 961, or the variable heavy chain sequence of SEQ ID NO: 962, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 984; SEQ ID NO: 986; and SEQ ID NO: 988, which correspond to the CDRs (hypervariable regions) of the light chain sequence of SEQ ID NO: 981, or the variable light chain sequence of SEQ ID NO: 982, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 963; SEQ ID NO: 965; SEQ ID NO: 967; and SEQ ID NO: 969, which correspond to the FRs (constant regions) of the heavy chain sequence of SEQ ID NO: 961, or the variable heavy chain sequence of SEQ ID NO: 962, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 983; SEQ ID NO: 985; SEQ ID NO: 987; and SEQ ID NO: 989, which correspond to the FRs (constant regions) of the light chain sequence of SEQ ID NO: 981, or the variable light chain sequence of SEQ ID NO: 982, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 962; the variable light chain region of SEQ ID NO: 982; the complementarity determining regions (SEQ ID NO: 964; SEQ ID NO: 966; and SEQ ID NO: 968) of the variable heavy chain region of SEQ ID NO: 962; and the complementarity determining regions (SEQ ID NO: 984; SEQ ID NO: 986; and SEQ ID NO: 988) of the variable light chain region of SEQ ID NO: 982, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 962; the variable light chain region of SEQ ID NO: 982; the framework regions (SEQ ID NO: 963; SEQ ID NO: 965; SEQ ID NO: 967; and SEQ ID NO: 969) of the variable heavy chain region of SEQ ID NO: 962; and the framework regions (SEQ ID NO: 983; SEQ ID NO: 985; SEQ ID NO: 987; and SEQ ID NO: 989) of the variable light chain region of SEQ ID NO: 982, or sequences that are at least 90% or 95% identical thereto.

In another embodiment of the invention, the anti-PACAP antibody is Ab10.H, comprising, or alternatively consisting of, SEQ ID NO: 961 and SEQ ID NO: 981, or SEQ ID NO: 962 and SEQ ID NO: 982, or an antibody or antigen-binding fragment comprising the CDRs of Ab10.H and having at least one of the biological activities set forth herein, or is an anti-PACAP antibody that competes with Ab10.H in binding PACAP, preferably one containing sequences that are at least 90%, 95%, 96%, 97%, 98%, or 99% identical to that of Ab10.H, or an antibody that binds to the same or overlapping epitope(s) on PACAP as Ab10.H.

In a further embodiment of the invention, antigen-binding fragments comprise, or alternatively consist of, Fab fragments having binding specificity for PACAP. With respect to antibody Ab10.H, the Fab fragment preferably includes the variable heavy chain sequence of SEQ ID NO: 962 and the variable light chain sequence of SEQ ID NO: 982, or sequences that are at least 90%, 95%, 96%, 97%, 98%, or 99% identical thereto. This embodiment of the invention further includes Fabs containing additions, deletions, and variants of SEQ ID NO: 962 and/or SEQ ID NO: 982 that retain the binding specificity for PACAP.

In one embodiment of the invention described herein, Fab fragments may be produced by enzymatic digestion (e.g., papain) of Ab10.H. In another embodiment of the invention, anti-PACAP antibodies such as Ab10.H and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab10.H, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab21

In one embodiment, the invention includes antibodies and antigen-binding fragments having binding specificity to PACAP that possess a heavy chain sequence comprising the sequence of SEQ ID NO: 841 which consists of the heavy chain variable region of SEQ ID NO: 842 linked to the heavy chain constant region of SEQ ID NO: 850.

In one embodiment, the invention includes antibodies and antigen-binding fragments having binding specificity to PACAP that contain a variable heavy chain sequence comprising the sequence set forth below:

(SEQ ID NO: 842)

QSVEESGGRLVTPGTPLTLTCTVSGIDLSSYYMTWVRQAPGKGLEWVGFID

AGGSAYYATWAKGRFTISKASTTVDLKITSPTTEDTATYFCARDLDLWGPG

TLVTVSS.

In another embodiment, the invention includes antibodies and antigen-binding fragments having binding specificity to PACAP that bind the same epitope as Ab21, and that contain a constant heavy chain sequence comprising the polypeptide of SEQ ID NO: 1244, 1245, or 1246, or comprising the sequence set forth below:

(SEQ ID NO: 850)

ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYASTYRVVSVLTVLHQDWLNGKEYKC

KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPGK.

In another embodiment, the invention includes antibodies and antigen-binding fragments having binding specificity to PACAP that contain a light chain sequence comprising the sequence of SEQ ID NO: 861 which consists of the light chain variable region of SEQ ID NO: 862 linked to the light chain constant region of SEQ ID NO: 870.

In another embodiment, the invention includes antibodies and antigen-binding fragments having binding specificity to PACAP that contain a variable light chain sequence comprising the sequence set forth below:

(SEQ ID NO: 862)

AAVLTQTPSPVSAAVGGTVSISCKSSESVYGDYLAWFQQKPGQPPKQLIYD

ASTLASGVPSRFKGSGSGTQFTLTISGVQCDDAATYYCAGGYVSAGVAFGG

GTEVVVKR.

In another embodiment, the invention includes antibodies and antigen-binding fragments having binding specificity to PACAP, that bind the same epitope as Ab21, and that contain a constant light chain sequence comprising the sequence set forth below:

(SEQ ID NO: 870)

TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFN

RGEC.

In another embodiment, the invention includes antibodies and antigen-binding fragments having binding specificity to PACAP that contain one, two, or three of the polypeptide sequences of SEQ ID NO: 844; SEQ ID NO: 846; and SEQ ID NO: 848, which correspond to the CDRs (hypervariable regions) of the heavy chain sequence of SEQ ID NO: 841, or which contain the variable heavy chain sequence of SEQ ID NO: 842, and/or which further contain one, two, or three of the polypeptide sequences of SEQ ID NO: 864; SEQ ID NO: 866; and SEQ ID NO: 868, which correspond to the CDRs (hypervariable regions) of the light chain sequence of SEQ ID NO: 861, or which contain the variable light chain sequence of SEQ ID NO: 862, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 843; SEQ ID NO: 845; SEQ ID NO: 847; and SEQ ID NO: 849, which correspond to the FRs (constant regions) of the heavy chain sequence of SEQ ID NO: 841, or the variable heavy chain sequence of SEQ ID NO: 842, and/or one, two, three, or four of the polypeptide sequences of SEQ ID NO: 863; SEQ ID NO: 865; SEQ ID NO: 867; and SEQ ID NO: 869, which correspond to the FRs (constant regions) of the light chain sequence of SEQ ID NO: 861, or the variable light chain sequence of SEQ ID NO: 862, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 841, or SEQ ID NO: 842, or polypeptides that are at least 90% or 95% identical thereto. In another embodiment of the invention, the antibodies and antigen-binding fragments of the invention comprise, or alternatively consist of, the polypeptide sequence of SEQ ID NO: 861, or SEQ ID NO: 862, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 844; SEQ ID NO: 846; and SEQ ID NO: 848, which correspond to the CDRs (hypervariable regions) of the heavy chain sequence of SEQ ID NO: 841, or the variable heavy chain sequence of SEQ ID NO: 842, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 864; SEQ ID NO: 866; and SEQ ID NO: 868, which correspond to the CDRs (hypervariable regions) of the light chain sequence of SEQ ID NO: 861, or the variable light chain sequence of SEQ ID NO: 862, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 843; SEQ ID NO: 845; SEQ ID NO: 847; and SEQ ID NO: 849, which correspond to the FRs (constant regions) of the heavy chain sequence of SEQ ID NO: 841, or the variable heavy chain sequence of SEQ ID NO: 842, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 863; SEQ ID NO: 865; SEQ ID NO: 867; and SEQ ID NO: 869, which correspond to the FRs (constant regions) of the light chain sequence of SEQ ID NO: 861, or the variable light chain sequence of SEQ ID NO: 862, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 842; the variable light chain region of SEQ ID NO: 862; the complementarity determining regions (SEQ ID NO: 844; SEQ ID NO: 846; and SEQ ID NO: 848) of the variable heavy chain region of SEQ ID NO: 842; and the complementarity determining regions (SEQ ID NO: 864; SEQ ID NO: 866; and SEQ ID NO: 868) of the variable light chain region of SEQ ID NO: 862, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 842; the variable light chain region of SEQ ID NO: 862; the framework regions (SEQ ID NO: 843; SEQ ID NO: 845; SEQ ID NO: 847; and SEQ ID NO: 849) of the variable heavy chain region of SEQ ID NO: 842; and the framework regions (SEQ ID NO: 863; SEQ ID NO: 865; SEQ ID NO: 867; and SEQ ID NO: 869) of the variable light chain region of SEQ ID NO: 862, or sequences that are at least 90% or 95% identical thereto.

In another embodiment of the invention, the anti-PACAP antibody is Ab21, comprising, or alternatively consisting of, SEQ ID NO: 841 and SEQ ID NO: 861, or SEQ ID NO: 842 and SEQ ID NO: 862, or an antibody or antigen-binding fragment comprising the CDRs of Ab21 and having at least one of the biological activities set forth herein, or is an anti-PACAP antibody that competes with Ab21 in binding PACAP, preferably one containing sequences that are at least 90%, 95%, 96%, 97%, 98%, or 99% identical to that of Ab21, or an antibody that binds to the same or overlapping epitope(s) on PACAP as Ab21.

In a further embodiment of the invention, antigen-binding fragments comprise, or alternatively consist of, Fab fragments having binding specificity for PACAP. With respect to antibody Ab21, the Fab fragment preferably includes the variable heavy chain sequence of SEQ ID NO: 842 and the variable light chain sequence of SEQ ID NO: 862, or sequences that are at least 90%, 95%, 96%, 97%, 98%, or 99% identical thereto. This embodiment of the invention further includes Fabs containing additions, deletions, and variants of SEQ ID NO: 842 and/or SEQ ID NO: 862 that retain the binding specificity for PACAP.

In one embodiment of the invention described herein, Fab fragments may be produced by enzymatic digestion (e.g., papain) of Ab21. In another embodiment of the invention, anti-PACAP antibodies such as Ab21 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab21, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab21.H

In one embodiment, the invention includes antibodies and antigen-binding fragments having binding specificity to PACAP that possess a heavy chain sequence comprising the sequence of SEQ ID NO: 1201 which consists of the heavy chain variable region of SEQ ID NO: 1202 linked to the heavy chain constant region of SEQ ID NO: 1210.

In one embodiment, the invention includes antibodies and antigen-binding fragments having binding specificity to PACAP that contain a variable heavy chain sequence comprising the sequence set forth below:

(SEQ ID NO: 1202)
EVQLVESGGGLVQPGGSLRLSCAASGIDLSSYYMTWVRQAPGKGLEWIGFI
DAGGSAYYATWAKGRFTISRDNSKNTVYLQMNSLRAEDTAVYFCARDLDLW
GQGTLVTVSS.

In another embodiment, the invention includes antibodies and antigen-binding fragments having binding specificity to PACAP that bind the same epitope as Ab21.H, and that contain a constant heavy chain sequence comprising the polypeptide of SEQ ID NO: 1244, 1245, or 1246, or comprising the sequence set forth below:

(SEQ ID NO: 1210)
ASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHED
PEVKFNWYVDGVEVHNAKTKPREEQYASTYRVVSVLTVLHQDWLNGKEYKC

-continued

```
KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPGK.
```

In another embodiment, the invention includes antibodies and antigen-binding fragments having binding specificity to PACAP that contain a light chain sequence comprising the sequence of SEQ ID NO: 1221 which consists of the light chain variable region of SEQ ID NO: 1222 linked to the light chain constant region of SEQ ID NO: 1230.

In another embodiment, the invention includes antibodies and antigen-binding fragments having binding specificity to PACAP that contain a variable light chain sequence comprising the sequence set forth below:

```
                                      (SEQ ID NO: 1222)
DAQLTQSPSTLSASVGDRVTITCKSSESVYGDYLAWFQQKPGKAPKQLIYD

ASTLASGVPSRFSGSGSGTEFTLTISSLQPDDFATYYCAGGYVSAGVAFGG

GTKVEIKR.
```

In another embodiment, the invention includes antibodies and antigen-binding fragments having binding specificity to PACAP, that bind the same epitope as Ab21.H, and that contain a constant light chain sequence comprising the sequence set forth below:

```
                                      (SEQ ID NO: 1230)
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFN

RGEC.
```

In another embodiment, the invention includes antibodies and antigen-binding fragments having binding specificity to PACAP that contain one, two, or three of the polypeptide sequences of SEQ ID NO: 1204; SEQ ID NO: 1206; and SEQ ID NO: 1208, which correspond to the CDRs (hypervariable regions) of the heavy chain sequence of SEQ ID NO: 1201, or which contain the variable heavy chain sequence of SEQ ID NO: 1202, and/or which further contain one, two, or three of the polypeptide sequences of SEQ ID NO: 1224; SEQ ID NO: 1226; and SEQ ID NO: 1228, which correspond to the CDRs (hypervariable regions) of the light chain sequence of SEQ ID NO: 1221, or which contain the variable light chain sequence of SEQ ID NO: 1222, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1203; SEQ ID NO: 1205; SEQ ID NO: 1207; and SEQ ID NO: 1209, which correspond to the FRs (constant regions) of the heavy chain sequence of SEQ ID NO: 1201, or the variable heavy chain sequence of SEQ ID NO: 1202, and/or one, two, three, or four of the polypeptide sequences of SEQ ID NO: 1223; SEQ ID NO: 1225; SEQ ID NO: 1227; and SEQ ID NO: 1229, which correspond to the FRs (constant regions) of the light chain sequence of SEQ ID NO: 1221, or the variable light chain sequence of SEQ ID NO: 1222, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1201, or SEQ ID NO: 1202, or polypeptides that are at least 90% or 95% identical thereto. In another embodiment of the invention, the antibodies and antigen-binding fragments of the invention comprise, or alternatively consist of, the polypeptide sequence of SEQ ID NO: 1221, or SEQ ID NO: 1222, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1204; SEQ ID NO: 1206; and SEQ ID NO: 1208, which correspond to the CDRs (hypervariable regions) of the heavy chain sequence of SEQ ID NO: 1201, or the variable heavy chain sequence of SEQ ID NO: 1202, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1224; SEQ ID NO: 1226; and SEQ ID NO: 1228, which correspond to the CDRs (hypervariable regions) of the light chain sequence of SEQ ID NO: 1221, or the variable light chain sequence of SEQ ID NO: 1222, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1203; SEQ ID NO: 1205; SEQ ID NO: 1207; and SEQ ID NO: 1209, which correspond to the FRs (constant regions) of the heavy chain sequence of SEQ ID NO: 1201, or the variable heavy chain sequence of SEQ ID NO: 1202, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1223; SEQ ID NO: 1225; SEQ ID NO: 1227; and SEQ ID NO: 1229, which correspond to the FRs (constant regions) of the light chain sequence of SEQ ID NO: 1221, or the variable light chain sequence of SEQ ID NO: 1222, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1202; the variable light chain region of SEQ ID NO: 1222; the complementarity determining regions (SEQ ID NO: 1204; SEQ ID NO: 1206; and SEQ ID NO: 1208) of the variable heavy chain region of SEQ ID NO: 1202; and the complementarity determining regions (SEQ ID NO: 1224; SEQ ID NO: 1226; and SEQ ID NO: 1228) of the variable light chain region of SEQ ID NO: 1222, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1202; the variable light chain region of SEQ ID NO: 1222; the framework regions (SEQ ID NO: 1203; SEQ ID NO: 1205; SEQ ID NO: 1207; and SEQ ID NO: 1209) of the variable heavy chain region of SEQ ID NO: 1202; and the framework regions (SEQ ID NO: 1223; SEQ ID NO: 1225; SEQ ID NO: 1227; and SEQ ID NO: 1229) of the variable light chain region of SEQ ID NO: 1222, or sequences that are at least 90% or 95% identical thereto.

In another embodiment of the invention, the anti-PACAP antibody is Ab21.H, comprising, or alternatively consisting of, SEQ ID NO: 1201 and SEQ ID NO: 1221, or SEQ ID NO: 1202 and SEQ ID NO: 1222, or an antibody or antigen-binding fragment comprising the CDRs of Ab21.H and having at least one of the biological activities set forth herein, or is an anti-PACAP antibody that competes with Ab21.H in binding PACAP, preferably one containing sequences that are at least 90%, 95%, 96%, 97%, 98%, or 99% identical to that of Ab21.H, or an antibody that binds to the same or overlapping epitope(s) on PACAP as Ab21.H.

In a further embodiment of the invention, antigen-binding fragments comprise, or alternatively consist of, Fab fragments having binding specificity for PACAP. With respect to antibody Ab21.H, the Fab fragment preferably includes the variable heavy chain sequence of SEQ ID NO: 1202 and the variable light chain sequence of SEQ ID NO: 1222, or sequences that are at least 90%, 95%, 96%, 97%, 98%, or 99% identical thereto. This embodiment of the invention further includes Fabs containing additions, deletions, and variants of SEQ ID NO: 1202 and/or SEQ ID NO: 1222 that retain the binding specificity for PACAP.

In one embodiment of the invention described herein, Fab fragments may be produced by enzymatic digestion (e.g., papain) of Ab21.H. In another embodiment of the invention, anti-PACAP antibodies such as Ab21.H and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab21.H, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab22

In one embodiment, the invention includes antibodies and antigen-binding fragments having binding specificity to PACAP that possess a heavy chain sequence comprising the sequence of SEQ ID NO: 881 which consists of the heavy chain variable region of SEQ ID NO: 882 linked to the heavy chain constant region of SEQ ID NO: 890.

In one embodiment, the invention includes antibodies and antigen-binding fragments having binding specificity to PACAP that contain a variable heavy chain sequence comprising the sequence set forth below:

```
                                        (SEQ ID NO: 882)
QEQLVESGGGLVQPEGSLTLTCTASGFDFSSNAMCWVRQAPGKGLEWIGSI

YNADGKNYYAIWAKGRFTISRTSSTTVTLQMTSLTAADTATYFCARDFDLW

GQGTLVTVSS.
```

In another embodiment, the invention includes antibodies and antigen-binding fragments having binding specificity to PACAP that bind the same epitope as Ab22, and that contain a constant heavy chain sequence comprising the polypeptide of SEQ ID NO: 1244, 1245, or 1246, or comprising the sequence set forth below:

```
                                        (SEQ ID NO: 890)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDARVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In another embodiment, the invention includes antibodies and antigen-binding fragments having binding specificity to PACAP that contain a light chain sequence comprising the sequence of SEQ ID NO: 901 which consists of the light chain variable region of SEQ ID NO: 902 linked to the light chain constant region of SEQ ID NO: 910.

In another embodiment, the invention includes antibodies and antigen-binding fragments having binding specificity to PACAP that contain a variable light chain sequence comprising the sequence set forth below:

```
                                        (SEQ ID NO: 902)
AAVLTQTPSPVSAAVGGTVTINCQSSQSVYDNDWLAWFQQKPGQPPKLLI

YLTSTLASGVPSRFSGSGSGTQFTLTISGVQCDDAATYYCLGGYDEDGDT

HVFGGGTEVVVKR.
```

In another embodiment, the invention includes antibodies and antigen-binding fragments having binding specificity to PACAP, that bind the same epitope as Ab22, and that contain a constant light chain sequence comprising the sequence set forth below:

```
                                        (SEQ ID NO: 910)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.
```

In another embodiment, the invention includes antibodies and antigen-binding fragments having binding specificity to PACAP that contain one, two, or three of the polypeptide sequences of SEQ ID NO: 884; SEQ ID NO: 886; and SEQ ID NO: 888, which correspond to the CDRs (hypervariable regions) of the heavy chain sequence of SEQ ID NO: 881, or which contain the variable heavy chain sequence of SEQ ID NO: 882, and/or which further contain one, two, or three of the polypeptide sequences of SEQ ID NO: 904; SEQ ID NO: 906; and SEQ ID NO: 908, which correspond to the CDRs (hypervariable regions) of the light chain sequence of SEQ ID NO: 901, or which contain the variable light chain sequence of SEQ ID NO: 902, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 883; SEQ ID NO: 885; SEQ ID NO: 887; and SEQ ID NO: 889, which correspond to the FRs (constant regions) of the heavy chain sequence of SEQ ID NO: 881, or the variable heavy chain sequence of SEQ ID NO: 882, and/or one, two, three, or four of the polypeptide sequences of SEQ ID NO: 903; SEQ ID NO: 905; SEQ ID NO: 907; and SEQ ID NO: 909, which correspond to the FRs (constant regions) of the light chain sequence of SEQ ID NO: 901, or the variable light chain sequence of SEQ ID NO: 902, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 881, or SEQ ID NO: 882, or polypeptides that are at least 90% or 95% identical thereto. In another embodiment of the invention, the antibodies and antigen-binding fragments of the invention comprise, or alternatively consist of, the polypeptide sequence of SEQ ID NO: 901, or SEQ ID NO: 902, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 884; SEQ ID NO: 886; and SEQ ID NO: 888, which correspond to the CDRs (hypervariable regions) of the heavy chain sequence of SEQ ID NO: 881, or the variable heavy chain sequence of SEQ ID NO: 882, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 904; SEQ ID NO: 906; and SEQ ID NO: 908, which correspond to the CDRs (hypervariable regions) of the light chain sequence of SEQ ID NO: 901, or the variable light chain sequence of SEQ ID NO: 902, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 883; SEQ ID NO: 885; SEQ ID NO: 887; and SEQ ID NO: 889, which correspond to the FRs (constant regions) of the heavy chain sequence of SEQ ID NO: 881, or the variable heavy chain sequence of SEQ ID NO: 882, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 903; SEQ ID NO: 905; SEQ ID NO: 907; and SEQ ID NO: 909, which correspond to the FRs (constant regions) of the light chain sequence of SEQ ID NO: 901, or the variable light chain sequence of SEQ ID NO: 902, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 882; the variable light chain region of SEQ ID NO: 902; the complementarity determining regions (SEQ ID NO: 884; SEQ ID NO: 886; and SEQ ID NO: 888) of the variable heavy chain region of SEQ ID NO: 882; and the complementarity determining regions (SEQ ID NO: 904; SEQ ID NO: 906; and SEQ ID NO: 908) of the variable light chain region of SEQ ID NO: 902, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 882; the variable light chain region of SEQ ID NO: 902; the framework regions (SEQ ID NO: 883; SEQ ID NO: 885; SEQ ID NO: 887; and SEQ ID NO: 889) of the variable heavy chain region of SEQ ID NO: 882; and the framework regions (SEQ ID NO: 903; SEQ ID NO: 905; SEQ ID NO: 907; and SEQ ID NO: 909) of the variable light chain region of SEQ ID NO: 902, or sequences that are at least 90% or 95% identical thereto.

In another embodiment of the invention, the anti-PACAP antibody is Ab22, comprising, or alternatively consisting of, SEQ ID NO: 881 and SEQ ID NO: 901, or SEQ ID NO: 882 and SEQ ID NO: 902, or an antibody or antigen-binding fragment comprising the CDRs of Ab22 and having at least one of the biological activities set forth herein, or is an anti-PACAP antibody that competes with Ab22 in binding PACAP, preferably one containing sequences that are at least 90%, 95%, 96%, 97%, 98%, or 99% identical to that of Ab22, or an antibody that binds to the same or overlapping epitope(s) on PACAP as Ab22.

In a further embodiment of the invention, antigen-binding fragments comprise, or alternatively consist of, Fab fragments having binding specificity for PACAP. With respect to antibody Ab22, the Fab fragment preferably includes the variable heavy chain sequence of SEQ ID NO: 882 and the variable light chain sequence of SEQ ID NO: 902, or sequences that are at least 90%, 95%, 96%, 97%, 98%, or 99% identical thereto. This embodiment of the invention further includes Fabs containing additions, deletions, and variants of SEQ ID NO: 882 and/or SEQ ID NO: 902 that retain the binding specificity for PACAP.

In one embodiment of the invention described herein, Fab fragments may be produced by enzymatic digestion (e.g., papain) of Ab22. In another embodiment of the invention, anti-PACAP antibodies such as Ab22 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab22, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab23

In one embodiment, the invention includes antibodies and antigen-binding fragments having binding specificity to PACAP that possess a heavy chain sequence comprising the sequence of SEQ ID NO: 921 which consists of the heavy chain variable region of SEQ ID NO: 922 linked to the heavy chain constant region of SEQ ID NO: 930.

In one embodiment, the invention includes antibodies and antigen-binding fragments having binding specificity to PACAP that contain a variable heavy chain sequence comprising the sequence set forth below:

```
                                    (SEQ ID NO: 922)
QSVEESGGRLVTPGTPLTLTCTVSGFSLNNYAMSWVRQAPGKGLEWIGIM

GVNDITYYASWAKGRFTISKTSTTVDLKMTSLTTEDTATYFCTREIRDDG

DSSDKLWGPGTLVTVSS.
```

In another embodiment, the invention includes antibodies and antigen-binding fragments having binding specificity to PACAP that bind the same epitope as Ab23, and that contain a constant heavy chain sequence comprising the polypeptide of SEQ ID NO: 1244, 1245, or 1246, or comprising the sequence set forth below:

```
                                    (SEQ ID NO: 930)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDARVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In another embodiment, the invention includes antibodies and antigen-binding fragments having binding specificity to PACAP that contain a light chain sequence comprising the sequence of SEQ ID NO: 941 which consists of the light chain variable region of SEQ ID NO: 942 linked to the light chain constant region of SEQ ID NO: 950.

In another embodiment, the invention includes antibodies and antigen-binding fragments having binding specificity to PACAP that contain a variable light chain sequence comprising the sequence set forth below:

```
                                    (SEQ ID NO: 942)
AIKMTQTPSSVSAAVGGTVTINCQASEDIYTNLAWYQQKPGQPPNLLIYD

ASDLASGVPSRFSGSGDGTQFTLTISAVQCEDAATYYCQGVAWSSNTGYG

SAFGGGTEVVVKR.
```

In another embodiment, the invention includes antibodies and antigen-binding fragments having binding specificity to PACAP, that bind the same epitope as Ab23, and that contain a constant light chain sequence comprising the sequence set forth below:

```
                                    (SEQ ID NO: 950)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.
```

In another embodiment, the invention includes antibodies and antigen-binding fragments having binding specificity to PACAP that contain one, two, or three of the polypeptide sequences of SEQ ID NO: 924; SEQ ID NO: 926; and SEQ ID NO: 928, which correspond to the CDRs (hypervariable regions) of the heavy chain sequence of SEQ ID NO: 921, or which contain the variable heavy chain sequence of SEQ ID NO: 922, and/or which further contain one, two, or three of the polypeptide sequences of SEQ ID NO: 944; SEQ ID NO: 946; and SEQ ID NO: 948, which correspond to the CDRs (hypervariable regions) of the light chain sequence of SEQ ID NO: 941, or which contain the variable light chain sequence of SEQ ID NO: 942, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 923; SEQ ID NO: 925; SEQ ID NO: 927; and SEQ ID NO: 929, which correspond to the FRs (constant regions) of the heavy chain sequence of SEQ ID NO: 921, or the variable heavy chain sequence of SEQ ID NO: 922, and/or one, two, three, or four of the polypeptide sequences of SEQ ID NO: 943; SEQ ID NO: 945; SEQ ID NO: 947; and SEQ ID NO: 949, which correspond to the FRs (constant regions) of the light chain sequence of SEQ ID NO: 941, or the variable light chain sequence of SEQ ID NO: 942, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 921, or SEQ ID NO: 922, or polypeptides that are at least 90% or 95% identical thereto. In another embodiment of the invention, the antibodies and antigen-binding fragments of the invention comprise, or alternatively consist of, the polypeptide sequence of SEQ ID NO: 941, or SEQ ID NO: 942, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 924; SEQ ID NO: 926; and SEQ ID NO: 928, which correspond to the CDRs (hypervariable regions) of the heavy chain sequence of SEQ ID NO: 921, or the variable heavy chain sequence of SEQ ID NO: 922, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 944; SEQ ID NO: 946; and SEQ ID NO: 948, which correspond to the CDRs (hypervariable regions) of the light chain sequence of SEQ ID NO: 941, or the variable light chain sequence of SEQ ID NO: 942, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 923; SEQ ID NO: 925; SEQ ID NO: 927; and SEQ ID NO: 929, which correspond to the FRs (constant regions) of the heavy chain sequence of SEQ ID NO: 921, or the variable heavy chain sequence of SEQ ID NO: 922, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 943; SEQ ID NO: 945; SEQ ID NO: 947; and SEQ ID NO: 949, which correspond to the FRs (constant regions) of the light chain sequence of SEQ ID NO: 941, or the variable light chain sequence of SEQ ID NO: 942, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 922; the variable light chain region of SEQ ID NO: 942; the complementarity determining regions (SEQ ID NO: 924; SEQ ID NO: 926; and SEQ ID NO: 928) of the variable heavy chain region of SEQ ID NO: 922; and the complementarity determining regions (SEQ ID NO: 944; SEQ ID NO: 946; and SEQ ID NO: 948) of the variable light chain region of SEQ ID NO: 942, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 922; the variable light chain region of SEQ ID NO: 942; the framework regions (SEQ ID NO: 923; SEQ ID NO: 925; SEQ ID NO: 927; and SEQ ID NO: 929) of the variable heavy chain region of SEQ ID NO: 922; and the framework regions (SEQ ID NO: 943; SEQ ID NO: 945; SEQ ID NO: 947; and SEQ ID NO: 949) of the variable light chain region of SEQ ID NO: 942, or sequences that are at least 90% or 95% identical thereto.

In another embodiment of the invention, the anti-PACAP antibody is Ab23, comprising, or alternatively consisting of, SEQ ID NO: 921 and SEQ ID NO: 941, or SEQ ID NO: 922 and SEQ ID NO: 942, or an antibody or antigen-binding fragment comprising the CDRs of Ab23 and having at least one of the biological activities set forth herein, or is an anti-PACAP antibody that competes with Ab23 in binding PACAP, preferably one containing sequences that are at least 90%, 95%, 96%, 97%, 98%, or 99% identical to that of Ab23, or an antibody that binds to the same or overlapping epitope(s) on PACAP as Ab23.

In a further embodiment of the invention, antigen-binding fragments comprise, or alternatively consist of, Fab fragments having binding specificity for PACAP. With respect to antibody Ab23, the Fab fragment preferably includes the variable heavy chain sequence of SEQ ID NO: 922 and the variable light chain sequence of SEQ ID NO: 942, or sequences that are at least 90%, 95%, 96%, 97%, 98%, or 99% identical thereto. This embodiment of the invention further includes Fabs containing additions, deletions, and variants of SEQ ID NO: 922 and/or SEQ ID NO: 942 that retain the binding specificity for PACAP.

In one embodiment of the invention described herein, Fab fragments may be produced by enzymatic digestion (e.g., papain) of Ab23. In another embodiment of the invention, anti-PACAP antibodies such as Ab23 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab23, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab10.H2

In one embodiment, the invention includes antibodies and antigen-binding fragments having binding specificity to PACAP that possess a heavy chain sequence comprising the sequence of SEQ ID NO: 1281 which consists of the heavy chain variable region of SEQ ID NO: 1282 linked to the heavy chain constant region of SEQ ID NO: 1290.

In one embodiment, the invention includes antibodies and antigen-binding fragments having binding specificity to PACAP that contain a variable heavy chain sequence comprising the sequence set forth below:

(SEQ ID NO: 1282)
EVQLVESGGGLVQPGGSLRLSCAASGIDLNSYYMTWVRQAPGKGLEWIGF

IDAGGDAYYASWAKGRFTISRDNSKNTVYLQMNSLRAEDTAVYFCARDLD

LWGQGTLVTVSS.

In another embodiment, the invention includes antibodies and antigen-binding fragments having binding specificity to PACAP that bind the same epitope as Ab10.H2, and that contain a constant heavy chain sequence comprising the polypeptide of SEQ ID NO: 1244, 1245, or 1246, or comprising the sequence set forth below:

(SEQ ID NO: 1290)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In another embodiment, the invention includes antibodies and antigen-binding fragments having binding specificity to PACAP that contain a light chain sequence comprising the sequence of SEQ ID NO: 1301 which consists of the light chain variable region of SEQ ID NO: 1302 linked to the light chain constant region of SEQ ID NO: 1310.

In another embodiment, the invention includes antibodies and antigen-binding fragments having binding specificity to PACAP that contain a variable light chain sequence comprising the sequence set forth below:

(SEQ ID NO: 1302)
AVLTQSPSTLSASVGDRVTITCQSSESVYGNYLAWFQQKPGKAPKFLIYE

ASKLESGVPSRFSGSGSGTEFTLTISSLQPDDFATYYCAGGDISEGVAFG

GGTKVEIKR.

In another embodiment, the invention includes antibodies and antigen-binding fragments having binding specificity to PACAP, that bind the same epitope as Ab10.H2, and that contain a constant light chain sequence comprising the sequence set forth below:

(SEQ ID NO: 1310)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another embodiment, the invention includes antibodies and antigen-binding fragments having binding specificity to PACAP that contain one, two, or three of the polypeptide sequences of SEQ ID NO: 1284; SEQ ID NO: 1286; and SEQ ID NO: 1288, which correspond to the CDRs (hypervariable regions) of the heavy chain sequence of SEQ ID NO: 1281, or which contain the variable heavy chain sequence of SEQ ID NO: 1282, and/or which further contain one, two, or three of the polypeptide sequences of SEQ ID NO: 1304; SEQ ID NO: 1306; and SEQ ID NO: 1308, which correspond to the CDRs (hypervariable regions) of the light chain sequence of SEQ ID NO: 1301, or which contain the variable light chain sequence of SEQ ID NO: 1302, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1283; SEQ ID NO: 1285; SEQ ID NO: 1287; and SEQ ID NO: 1289, which correspond to the FRs (constant regions) of the heavy chain sequence of SEQ ID NO: 1281, or the variable heavy chain sequence of SEQ ID NO: 1282, and/or one, two, three, or four of the polypeptide sequences of SEQ ID NO: 1303; SEQ ID NO: 1305; SEQ ID NO: 1307; and SEQ ID NO: 1309, which correspond to the FRs (constant regions) of the light chain sequence of SEQ ID NO: 1301, or the variable light chain sequence of SEQ ID NO: 1302, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1281, or SEQ ID NO: 1282, or polypeptides that are at least 90% or 95% identical thereto. In another embodiment of the invention, the antibodies and antigen-binding fragments of the invention comprise, or alternatively consist of, the polypeptide sequence of SEQ ID NO: 1301, or SEQ ID NO: 1302, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1284; SEQ ID NO: 1286; and SEQ ID NO: 1288, which correspond to the CDRs (hypervariable regions) of the heavy chain sequence of SEQ ID NO: 1281, or the variable heavy chain sequence of SEQ ID NO: 1282, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1304; SEQ ID NO: 1306; and SEQ ID NO: 1308, which correspond to the CDRs (hypervariable regions) of the light chain sequence of SEQ ID NO: 1301, or the variable light chain sequence of SEQ ID NO: 1302, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1283;

SEQ ID NO: 1285; SEQ ID NO: 1287; and SEQ ID NO: 1289, which correspond to the FRs (constant regions) of the heavy chain sequence of SEQ ID NO: 1281, or the variable heavy chain sequence of SEQ ID NO: 1282, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1303; SEQ ID NO: 1305; SEQ ID NO: 1307; and SEQ ID NO: 1309, which correspond to the FRs (constant regions) of the light chain sequence of SEQ ID NO: 1301, or the variable light chain sequence of SEQ ID NO: 1302, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1282; the variable light chain region of SEQ ID NO: 1302; the complementarity determining regions (SEQ ID NO: 1284; SEQ ID NO: 1286; and SEQ ID NO: 1288) of the variable heavy chain region of SEQ ID NO: 1282; and the complementarity determining regions (SEQ ID NO: 1304; SEQ ID NO: 1306; and SEQ ID NO: 1308) of the variable light chain region of SEQ ID NO: 1302, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1282; the variable light chain region of SEQ ID NO: 1302; the framework regions (SEQ ID NO: 1283; SEQ ID NO: 1285; SEQ ID NO: 1287; and SEQ ID NO: 1289) of the variable heavy chain region of SEQ ID NO: 1282; and the framework regions (SEQ ID NO: 1303; SEQ ID NO: 1305; SEQ ID NO: 1307; and SEQ ID NO: 1309) of the variable light chain region of SEQ ID NO: 1302, or sequences that are at least 90% or 95% identical thereto.

In another embodiment of the invention, the anti-PACAP antibody is Ab10.H2, comprising, or alternatively consisting of, SEQ ID NO: 1281 and SEQ ID NO: 1301, or SEQ ID NO: 1282 and SEQ ID NO: 1302, or an antibody or antigen-binding fragment comprising the CDRs of Ab10.H2 and having at least one of the biological activities set forth herein, or is an anti-PACAP antibody that competes with Ab10.H2 in binding PACAP, preferably one containing sequences that are at least 90%, 95%, 96%, 97%, 98%, or 99% identical to that of Ab10.H2, or an antibody that binds to the same or overlapping epitope(s) on PACAP as Ab10.H2.

In a further embodiment of the invention, antigen-binding fragments comprise, or alternatively consist of, Fab fragments having binding specificity for PACAP. With respect to antibody Ab10.H2, the Fab fragment preferably includes the variable heavy chain sequence of SEQ ID NO: 1282 and the variable light chain sequence of SEQ ID NO: 1302, or sequences that are at least 90%, 95%, 96%, 97%, 98%, or 99% identical thereto. This embodiment of the invention further includes Fabs containing additions, deletions, and variants of SEQ ID NO: 1282 and/or SEQ ID NO: 1302 that retain the binding specificity for PACAP.

In one embodiment of the invention described herein, Fab fragments may be produced by enzymatic digestion (e.g., papain) of Ab10.H2. In another embodiment of the invention, anti-PACAP antibodies such as Ab10.H2 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris.*

In an additional embodiment, the invention is further directed to polynucleotides encoding antibody polypeptides having binding specificity to PACAP, including the heavy and/or light chains of Ab10.H2, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab10.H3

In one embodiment, the invention includes antibodies and antigen-binding fragments having binding specificity to PACAP that possess a heavy chain sequence comprising the sequence of SEQ ID NO: 1321 which consists of the heavy chain variable region of SEQ ID NO: 1322 linked to the heavy chain constant region of SEQ ID NO: 1330.

In one embodiment, the invention includes antibodies and antigen-binding fragments having binding specificity to PACAP that contain a variable heavy chain sequence comprising the sequence set forth below:

```
                                          (SEQ ID NO: 1322)
EVQLVESGGGLVQPGGSLRLSCAASGIDLNSYYMTWVRQAPGKGLEWIGF

IDAGGDAYYASWAKGRFTISRDNSKNTVYLQMNSLRAEDTAVYFCARDLD

LWGQGTLVTVSS.
```

In another embodiment, the invention includes antibodies and antigen-binding fragments having binding specificity to PACAP that bind the same epitope as Ab10.H3, and that contain a constant heavy chain sequence comprising the polypeptide of SEQ ID NO: 1244, 1245, or 1246, or comprising the sequence set forth below:

```
                                          (SEQ ID NO: 1330)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In another embodiment, the invention includes antibodies and antigen-binding fragments having binding specificity to PACAP that contain a light chain sequence comprising the sequence of SEQ ID NO: 1341 which consists of the light chain variable region of SEQ ID NO: 1342 linked to the light chain constant region of SEQ ID NO: 1350.

In another embodiment, the invention includes antibodies and antigen-binding fragments having binding specificity to PACAP that contain a variable light chain sequence comprising the sequence set forth below:

(SEQ ID NO: 1342)
DIQLTQSPSTLSASVGDRVTITCQSSESVYGNYLAWFQQKPGKAPKFLIY

EASKLESGVPSRFSGSGSGTEFTLTISSLQPDDFATYYCAGGDISEGVAF

GGGTKVEIKR.

In another embodiment, the invention includes antibodies and antigen-binding fragments having binding specificity to PACAP, that bind the same epitope as Ab10.H3, and that contain a constant light chain sequence comprising the sequence set forth below:

(SEQ ID NO: 1350)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another embodiment, the invention includes antibodies and antigen-binding fragments having binding specificity to PACAP that contain one, two, or three of the polypeptide sequences of SEQ ID NO: 1324; SEQ ID NO: 1326; and SEQ ID NO: 1328, which correspond to the CDRs (hypervariable regions) of the heavy chain sequence of SEQ ID NO: 1321, or which contain the variable heavy chain sequence of SEQ ID NO: 1322, and/or which further contain one, two, or three of the polypeptide sequences of SEQ ID NO: 1344; SEQ ID NO: 1346; and SEQ ID NO: 1348, which correspond to the CDRs (hypervariable regions) of the light chain sequence of SEQ ID NO: 1341, or which contain the variable light chain sequence of SEQ ID NO: 1342, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1323; SEQ ID NO: 1325; SEQ ID NO: 1327; and SEQ ID NO: 1329, which correspond to the FRs (constant regions) of the heavy chain sequence of SEQ ID NO: 1321, or the variable heavy chain sequence of SEQ ID NO: 1322, and/or one, two, three, or four of the polypeptide sequences of SEQ ID NO: 1343; SEQ ID NO: 1345; SEQ ID NO: 1347; and SEQ ID NO: 1349, which correspond to the FRs (constant regions) of the light chain sequence of SEQ ID NO: 1341, or the variable light chain sequence of SEQ ID NO: 1342, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1321, or SEQ ID NO: 1322, or polypeptides that are at least 90% or 95% identical thereto. In another embodiment of the invention, the antibodies and antigen-binding fragments of the invention comprise, or alternatively consist of, the polypeptide sequence of SEQ ID NO: 1341, or SEQ ID NO: 1342, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1324; SEQ ID NO: 1326; and SEQ ID NO: 1328, which correspond to the CDRs (hypervariable regions) of the heavy chain sequence of SEQ ID NO: 1321, or the variable heavy chain sequence of SEQ ID NO: 1322, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1344; SEQ ID NO: 1346; and SEQ ID NO: 1348, which correspond to the CDRs (hypervariable regions) of the light chain sequence of SEQ ID NO: 1341, or the variable light chain sequence of SEQ ID NO: 1342, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1323; SEQ ID NO: 1325; SEQ ID NO: 1327; and SEQ ID NO: 1329, which correspond to the FRs (constant regions) of the heavy chain sequence of SEQ ID NO: 1321, or the variable heavy chain sequence of SEQ ID NO: 1322, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1343; SEQ ID NO: 1345; SEQ ID NO: 1347; and SEQ ID NO: 1349, which correspond to the FRs (constant regions) of the light chain sequence of SEQ ID NO: 1341, or the variable light chain sequence of SEQ ID NO: 1342, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1322; the variable light chain region of SEQ ID NO: 1342; the complementarity determining regions (SEQ ID NO: 1324; SEQ ID NO: 1326; and SEQ ID NO: 1328) of the variable heavy chain region of SEQ ID NO: 1322; and the complementarity determining regions (SEQ ID NO: 1344; SEQ ID NO: 1346; and SEQ ID NO: 1348) of the variable light chain region of SEQ ID NO: 1342, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1322; the variable light chain region of SEQ ID NO: 1342; the framework regions (SEQ ID NO: 1323; SEQ ID NO: 1325; SEQ ID NO: 1327; and SEQ ID NO: 1329) of the variable heavy chain region of SEQ ID NO: 1322; and the framework regions (SEQ ID NO: 1343; SEQ ID NO: 1345; SEQ ID NO: 1347; and SEQ ID NO: 1349) of the variable light chain region of SEQ ID NO: 1342, or sequences that are at least 90% or 95% identical thereto.

In another embodiment of the invention, the anti-PACAP antibody is Ab10.H3, comprising, or alternatively consisting of, SEQ ID NO: 1321 and SEQ ID NO: 1341, or SEQ ID NO: 1322 and SEQ ID NO: 1342, or an antibody or antigen-binding fragment comprising the CDRs of Ab10.H3 and having at least one of the biological activities set forth herein, or is an anti-PACAP antibody that competes with Ab10.H3 in binding PACAP, preferably one containing sequences that are at least 90%, 95%, 96%, 97%, 98%, or 99% identical to that of Ab10.H3, or an antibody that binds to the same or overlapping epitope(s) on PACAP as Ab10.H3.

In a further embodiment of the invention, antigen-binding fragments comprise, or alternatively consist of, Fab fragments having binding specificity for PACAP. With respect to antibody Ab10.H3, the Fab fragment preferably includes the variable heavy chain sequence of SEQ ID NO: 1322 and the variable light chain sequence of SEQ ID NO: 1342, or sequences that are at least 90%, 95%, 96%, 97%, 98%, or 99% identical thereto. This embodiment of the invention further includes Fabs containing additions, deletions, and variants of SEQ ID NO: 1322 and/or SEQ ID NO: 1342 that retain the binding specificity for PACAP.

In one embodiment of the invention described herein, Fab fragments may be produced by enzymatic digestion (e.g., papain) of Ab10.H3. In another embodiment of the invention, anti-PACAP antibodies such as Ab10.H3 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab10.H3, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab10.H4

In one embodiment, the invention includes antibodies and antigen-binding fragments having binding specificity to PACAP that possess a heavy chain sequence comprising the sequence of SEQ ID NO: 1361 which consists of the heavy chain variable region of SEQ ID NO: 1362 linked to the heavy chain constant region of SEQ ID NO: 1370.

In one embodiment, the invention includes antibodies and antigen-binding fragments having binding specificity to PACAP that contain a variable heavy chain sequence comprising the sequence set forth below:

(SEQ ID NO: 1362)
EVQLVESGGGLVQPGGSLRLSCAASGIDLNSYYMTWVRQAPGKGLEWIGF

IDAGGDAYYASWAKGRFTISRDNSKNTVYLQMNSLRAEDTAVYFCARDLD

LWGQGTLVTVSS.

In another embodiment, the invention includes antibodies and antigen-binding fragments having binding specificity to PACAP that bind the same epitope as Ab10.H4, and that contain a constant heavy chain sequence comprising the polypeptide of SEQ ID NO: 1244, 1245, or 1246, or comprising the sequence set forth below:

(SEQ ID NO: 1370)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In another embodiment, the invention includes antibodies and antigen-binding fragments having binding specificity to PACAP that contain a light chain sequence comprising the sequence of SEQ ID NO: 1381 which consists of the light chain variable region of SEQ ID NO: 1382 linked to the light chain constant region of SEQ ID NO: 1390.

In another embodiment, the invention includes antibodies and antigen-binding fragments having binding specificity to PACAP that contain a variable light chain sequence comprising the sequence set forth below:

(SEQ ID NO: 1382)
DIVLTQSPSTLSASVGDRVTITCQSSESVYGNYLAWFQQKPGKAPKFLIY

EASKLESGVPSRFSGSGSGTEFTLTISSLQPDDFATYYCAGGDISEGVAF

GGGTKVEIKR.

In another embodiment, the invention includes antibodies and antigen-binding fragments having binding specificity to PACAP, that bind the same epitope as Ab10.H4, and that contain a constant light chain sequence comprising the sequence set forth below:

(SEQ ID NO: 1390)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another embodiment, the invention includes antibodies and antigen-binding fragments having binding specificity to PACAP that contain one, two, or three of the polypeptide sequences of SEQ ID NO: 1364; SEQ ID NO: 1366; and SEQ ID NO: 1368, which correspond to the CDRs (hypervariable regions) of the heavy chain sequence of SEQ ID NO: 1361, or which contain the variable heavy chain sequence of SEQ ID NO: 1362, and/or which further contain one, two, or three of the polypeptide sequences of SEQ ID NO: 1384; SEQ ID NO: 1386; and SEQ ID NO: 1388, which correspond to the CDRs (hypervariable regions) of the light chain sequence of SEQ ID NO: 1381, or which contain the variable light chain sequence of SEQ ID NO: 1382, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1363; SEQ ID NO: 1365; SEQ ID NO: 1367; and SEQ ID NO: 1369, which correspond to the FRs (constant regions) of the heavy chain sequence of SEQ ID NO: 1361, or the variable heavy chain sequence of SEQ ID NO: 1362, and/or one, two, three, or four of the polypeptide sequences of SEQ ID NO: 1383; SEQ ID NO: 1385; SEQ ID NO: 1387; and SEQ ID NO: 1389, which correspond to the FRs (constant regions) of the light chain sequence of SEQ ID NO: 1381, or the variable light chain sequence of SEQ ID NO: 1382, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1361, or SEQ ID NO: 1362, or polypeptides that are at least 90% or 95% identical thereto. In another embodiment of the invention, the antibodies and antigen-binding fragments of the invention comprise, or alternatively consist of, the polypeptide sequence of SEQ ID NO: 1381, or SEQ ID NO: 1382, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1364; SEQ ID NO: 1366; and SEQ ID NO: 1368, which correspond to the CDRs (hypervariable regions) of the heavy chain sequence of SEQ ID NO: 1361, or the variable heavy chain sequence of SEQ ID NO: 1362, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1384; SEQ ID NO: 1386; and SEQ ID NO: 1388, which correspond to the CDRs (hypervariable regions) of the light chain sequence of SEQ ID NO: 1381, or the variable light chain sequence of SEQ ID NO: 1382, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1363; SEQ ID NO: 1365; SEQ ID NO: 1367; and SEQ ID NO: 1369, which correspond to the FRs (constant regions) of the heavy chain sequence of SEQ ID NO: 1361, or the variable heavy chain sequence of SEQ ID NO: 1362, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1383; SEQ ID NO: 1385; SEQ ID NO: 1387; and SEQ ID NO: 1389, which correspond to the FRs (constant regions) of the light chain sequence of SEQ ID NO: 1381, or the variable light chain sequence of SEQ ID NO: 1382, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1362; the variable light chain region of SEQ ID NO: 1382; the complementarity determining regions (SEQ ID NO: 1364; SEQ ID NO: 1366; and SEQ ID NO: 1368) of the variable heavy chain region of SEQ ID NO: 1362; and the complementarity determining regions (SEQ ID NO: 1384; SEQ ID NO: 1386; and SEQ ID NO: 1388) of the variable light chain region of SEQ ID NO: 1382, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1362; the variable light chain region of SEQ ID NO: 1382; the framework regions (SEQ ID NO: 1363; SEQ ID NO: 1365; SEQ ID NO: 1367; and SEQ ID NO: 1369) of the variable heavy chain region of SEQ ID NO: 1362; and the framework regions (SEQ ID NO: 1383; SEQ ID NO: 1385; SEQ ID NO: 1387; and SEQ ID NO: 1389) of the variable light chain region of SEQ ID NO: 1382, or sequences that are at least 90% or 95% identical thereto.

In another embodiment of the invention, the anti-PACAP antibody is Ab10.H4, comprising, or alternatively consisting of, SEQ ID NO: 1361 and SEQ ID NO: 1381, or SEQ ID NO: 1362 and SEQ ID NO: 1382, or an antibody or antigen-binding fragment comprising the CDRs of Ab10.H4 and having at least one of the biological activities set forth herein, or is an anti-PACAP antibody that competes with Ab10.H4 in binding PACAP, preferably one containing sequences that are at least 90%, 95%, 96%, 97%, 98%, or 99% identical to that of Ab10.H4, or an antibody that binds to the same or overlapping epitope(s) on PACAP as Ab10.H4.

In a further embodiment of the invention, antigen-binding fragments comprise, or alternatively consist of, Fab fragments having binding specificity for PACAP. With respect to antibody Ab10.H4, the Fab fragment preferably includes the variable heavy chain sequence of SEQ ID NO: 1362 and the variable light chain sequence of SEQ ID NO: 1382, or sequences that are at least 90%, 95%, 96%, 97%, 98%, or 99% identical thereto. This embodiment of the invention further includes Fabs containing additions, deletions, and variants of SEQ ID NO: 1362 and/or SEQ ID NO: 1382 that retain the binding specificity for PACAP.

In one embodiment of the invention described herein, Fab fragments may be produced by enzymatic digestion (e.g., papain) of Ab10.H4. In another embodiment of the invention, anti-PACAP antibodies such as Ab10.H4 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris.*

In an additional embodiment, the invention is further directed to polynucleotides encoding antibody polypeptides having binding specificity to PACAP, including the heavy and/or light chains of Ab10.H4, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab10.H5

In one embodiment, the invention includes antibodies and antigen-binding fragments having binding specificity to PACAP that possess a heavy chain sequence comprising the sequence of SEQ ID NO: 1401 which consists of the heavy chain variable region of SEQ ID NO: 1402 linked to the heavy chain constant region of SEQ ID NO: 1410.

In one embodiment, the invention includes antibodies and antigen-binding fragments having binding specificity to PACAP that contain a variable heavy chain sequence comprising the sequence set forth below:

(SEQ ID NO: 1402)
EVQLVESGGGLVQPGGSLRLSCAASGIDLNSYYMTWVRQAPGKGLEWIGF

IDAGGDAYYASWAKGRFTISRDNSKNTVYLQMNSLRAEDTAVYFCARDLD

LWGQGTLVTVSS.

In another embodiment, the invention includes antibodies and antigen-binding fragments having binding specificity to PACAP that bind the same epitope as Ab10.H5, and that contain a constant heavy chain sequence comprising the polypeptide of SEQ ID NO: 1244, 1245, or 1246, or comprising the sequence set forth below:

(SEQ ID NO: 1410)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In another embodiment, the invention includes antibodies and antigen-binding fragments having binding specificity to PACAP that contain a light chain sequence comprising the sequence of SEQ ID NO: 1421 which consists of the light chain variable region of SEQ ID NO: 1422 linked to the light chain constant region of SEQ ID NO: 1430.

In another embodiment, the invention includes antibodies and antigen-binding fragments having binding specificity to PACAP that contain a variable light chain sequence comprising the sequence set forth below:

(SEQ ID NO: 1422)
QLTQSPSTLSASVGDRVTITCQSSESVYGNYLAWFQQKPGKAPKFLIYEA

SKLESGVPSRFSGSGSGTEFTLTISSLQPDDFATYYCAGGDISEGVAFGG

GTKVEIKR.

In another embodiment, the invention includes antibodies and antigen-binding fragments having binding specificity to PACAP, that bind the same epitope as Ab10.H5, and that contain a constant light chain sequence comprising the sequence set forth below:

(SEQ ID NO: 1430)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another embodiment, the invention includes antibodies and antigen-binding fragments having binding specificity to PACAP that contain one, two, or three of the polypeptide sequences of SEQ ID NO: 1404; SEQ ID NO: 1406; and SEQ ID NO: 1408, which correspond to the CDRs (hypervariable regions) of the heavy chain sequence of SEQ ID NO: 1401, or which contain the variable heavy chain sequence of SEQ ID NO: 1402, and/or which further contain one, two, or three of the polypeptide sequences of SEQ ID NO: 1424; SEQ ID NO: 1426; and SEQ ID NO: 1428, which correspond to the CDRs (hypervariable regions) of the light chain sequence of SEQ ID NO: 1421, or which contain the variable light chain sequence of SEQ ID NO: 1422, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1403; SEQ ID NO: 1405; SEQ ID NO: 1407; and SEQ ID NO: 1409, which correspond to the FRs (constant regions) of the heavy chain sequence of SEQ ID NO: 1401, or the variable heavy chain sequence of SEQ ID NO: 1402, and/or one, two, three, or four of the polypeptide sequences of SEQ ID NO: 1423; SEQ ID NO: 1425; SEQ ID NO: 1427; and SEQ ID NO: 1429, which correspond to the FRs (constant regions) of the light chain sequence of SEQ ID NO: 1421, or the variable light chain sequence of SEQ ID NO: 1422, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1401, or SEQ ID NO: 1402, or polypeptides that are at least 90% or 95% identical thereto. In another embodiment of the invention, the antibodies and antigen-binding fragments of the invention comprise, or alternatively consist of, the polypeptide sequence of SEQ ID NO: 1421, or SEQ ID NO: 1422, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1404; SEQ ID NO: 1406; and SEQ ID NO: 1408, which correspond to the CDRs (hypervariable regions) of the heavy chain sequence of SEQ ID NO: 1401, or the variable heavy chain sequence of SEQ ID NO: 1402, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1424; SEQ ID NO: 1426; and SEQ ID NO: 1428, which correspond to the CDRs (hypervariable regions) of the light chain sequence of SEQ ID NO: 1421, or the variable light chain sequence of SEQ ID NO: 1422, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1403; SEQ ID NO: 1405; SEQ ID NO: 1407; and SEQ ID NO: 1409, which correspond to the FRs (constant regions) of the heavy chain sequence of SEQ ID NO: 1401, or the variable heavy chain sequence of SEQ ID NO: 1402, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1423; SEQ ID NO: 1425; SEQ ID NO: 1427; and SEQ ID NO: 1429, which correspond to the FRs (constant regions) of the light chain sequence of SEQ ID NO: 1421, or the variable light chain sequence of SEQ ID NO: 1422, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1402; the variable light chain region of SEQ ID NO: 1422; the complementarity determining regions (SEQ ID NO: 1404; SEQ ID NO: 1406; and SEQ ID NO: 1408) of the variable heavy chain region of SEQ ID NO: 1402; and the complementarity determining regions (SEQ ID NO: 1424; SEQ ID NO: 1426; and SEQ ID NO: 1428) of the variable light chain region of SEQ ID NO: 1422, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1402; the variable light chain region of SEQ ID NO: 1422; the framework regions (SEQ ID NO: 1403; SEQ ID NO: 1405; SEQ ID NO: 1407; and SEQ ID NO: 1409) of the variable heavy chain region of SEQ ID NO: 1402; and the framework regions (SEQ ID NO: 1423; SEQ ID NO: 1425; SEQ ID NO: 1427; and SEQ ID NO: 1429) of the variable light chain region of SEQ ID NO: 1422, or sequences that are at least 90% or 95% identical thereto.

In another embodiment of the invention, the anti-PACAP antibody is Ab10.H5, comprising, or alternatively consisting of, SEQ ID NO: 1401 and SEQ ID NO: 1421, or SEQ ID NO: 1402 and SEQ ID NO: 1422, or an antibody or antigen-binding fragment comprising the CDRs of Ab10.H5 and having at least one of the biological activities set forth herein, or is an anti-PACAP antibody that competes with Ab10.H5 in binding PACAP, preferably one containing sequences that are at least 90%, 95%, 96%, 97%, 98%, or 99% identical to that of Ab10.H5, or an antibody that binds to the same or overlapping epitope(s) on PACAP as Ab10.H5.

In a further embodiment of the invention, antigen-binding fragments comprise, or alternatively consist of, Fab fragments having binding specificity for PACAP. With respect to antibody Ab10.H5, the Fab fragment preferably includes the variable heavy chain sequence of SEQ ID NO: 1402 and the variable light chain sequence of SEQ ID NO: 1422, or sequences that are at least 90%, 95%, 96%, 97%, 98%, or 99% identical thereto. This embodiment of the invention further includes Fabs containing additions, deletions, and variants of SEQ ID NO: 1402 and/or SEQ ID NO: 1422 that retain the binding specificity for PACAP.

In one embodiment of the invention described herein, Fab fragments may be produced by enzymatic digestion (e.g., papain) of Ab10.H5. In another embodiment of the invention, anti-PACAP antibodies such as Ab10.H5 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab10.H5, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab10.H6

In one embodiment, the invention includes antibodies and antigen-binding fragments having binding specificity to PACAP that possess a heavy chain sequence comprising the sequence of SEQ ID NO: 1441 which consists of the heavy chain variable region of SEQ ID NO: 1442 linked to the heavy chain constant region of SEQ ID NO: 1450.

In one embodiment, the invention includes antibodies and antigen-binding fragments having binding specificity to PACAP that contain a variable heavy chain sequence comprising the sequence set forth below:

(SEQ ID NO: 1442)
EVQLVESGGGLVQPGGSLRLSCAASGIDLNSYYMTWVRQAPGKGLEWIGF
IDAGGDAYYASWAKGRFTISRDNSKNTVYLQMNSLRAEDTAVYFCARDLD
LWGQGTLVTVSS.

In another embodiment, the invention includes antibodies and antigen-binding fragments having binding specificity to PACAP that bind the same epitope as Ab10.H6, and that contain a constant heavy chain sequence comprising the polypeptide of SEQ ID NO: 1244, 1245, or 1246, or comprising the sequence set forth below:

(SEQ ID NO: 1450)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In another embodiment, the invention includes antibodies and antigen-binding fragments having binding specificity to PACAP that contain a light chain sequence comprising the sequence of SEQ ID NO: 1461 which consists of the light chain variable region of SEQ ID NO: 1462 linked to the light chain constant region of SEQ ID NO: 1470.

In another embodiment, the invention includes antibodies and antigen-binding fragments having binding specificity to PACAP that contain a variable light chain sequence comprising the sequence set forth below:

(SEQ ID NO: 1462)
QVLTQSPSTLSASVGDRVTITCQSSESVYGNYLAWFQQKPGKAPKFLIYE

ASKLESGVPSRFSGSGSGTEFTLTISSLQPDDFATYYCAGGDISEGVAFG

GGTKVEIKR.

In another embodiment, the invention includes antibodies and antigen-binding fragments having binding specificity to PACAP, that bind the same epitope as Ab10.H6, and that contain a constant light chain sequence comprising the sequence set forth below:

(SEQ ID NO: 1470)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another embodiment, the invention includes antibodies and antigen-binding fragments having binding specificity to PACAP that contain one, two, or three of the polypeptide sequences of SEQ ID NO: 1444; SEQ ID NO: 1446; and SEQ ID NO: 1448, which correspond to the CDRs (hypervariable regions) of the heavy chain sequence of SEQ ID NO: 1441, or which contain the variable heavy chain sequence of SEQ ID NO: 1442, and/or which further contain one, two, or three of the polypeptide sequences of SEQ ID NO: 1464; SEQ ID NO: 1466; and SEQ ID NO: 1468, which correspond to the CDRs (hypervariable regions) of the light chain sequence of SEQ ID NO: 1461, or which contain the variable light chain sequence of SEQ ID NO: 1462, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1443; SEQ ID NO: 1445; SEQ ID NO: 1447; and SEQ ID NO: 1449, which correspond to the FRs (constant regions) of the heavy chain sequence of SEQ ID NO: 1441, or the variable heavy chain sequence of SEQ ID NO: 1442, and/or one, two, three, or four of the polypeptide sequences of SEQ ID NO: 1463; SEQ ID NO: 1465; SEQ ID NO: 1467; and SEQ ID NO: 1469, which correspond to the FRs (constant regions) of the light chain sequence of SEQ ID NO: 1461, or the variable light chain sequence of SEQ ID NO: 1462, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1441, or SEQ ID NO: 1442, or polypeptides that are at least 90% or 95% identical thereto. In another embodiment of the invention, the antibodies and antigen-binding fragments of the invention comprise, or alternatively consist of, the polypeptide sequence of SEQ ID NO: 1461, or SEQ ID NO: 1462, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1444; SEQ ID NO: 1446; and SEQ ID NO: 1448, which correspond to the CDRs (hypervariable regions) of the heavy chain sequence of SEQ ID NO: 1441, or the variable heavy chain sequence of SEQ ID NO: 1442, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1464; SEQ ID NO: 1466; and SEQ ID NO: 1468, which correspond to the CDRs (hypervariable regions) of the light chain sequence of SEQ ID NO: 1461, or the variable light chain sequence of SEQ ID NO: 1462, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1443; SEQ ID NO: 1445; SEQ ID NO: 1447; and SEQ ID NO: 1449, which correspond to the FRs (constant regions) of the heavy chain sequence of SEQ ID NO: 1441, or the variable heavy chain sequence of SEQ ID NO: 1442, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1463; SEQ ID NO: 1465; SEQ ID NO: 1467; and SEQ ID NO: 1469, which correspond to the FRs (constant regions) of the light chain sequence of SEQ ID NO: 1461, or the variable light chain sequence of SEQ ID NO: 1462, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1442; the variable light chain region of SEQ ID NO: 1462; the complementarity determining regions (SEQ ID NO: 1444; SEQ ID NO: 1446; and SEQ ID NO: 1448) of the variable heavy chain region of SEQ ID NO: 1442; and the complementarity determining regions (SEQ ID NO: 1464; SEQ ID NO: 1466; and SEQ ID NO: 1468) of the variable light chain region of SEQ ID NO: 1462, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1442; the variable light chain region of SEQ ID NO: 1462; the framework regions (SEQ ID NO: 1443; SEQ ID NO: 1445; SEQ ID NO: 1447; and SEQ ID NO: 1449) of the variable heavy chain region of SEQ ID NO: 1442; and the framework regions (SEQ ID NO: 1463; SEQ ID NO: 1465; SEQ ID NO: 1467; and SEQ ID NO: 1469) of the variable light chain region of SEQ ID NO: 1462, or sequences that are at least 90% or 95% identical thereto.

In another embodiment of the invention, the anti-PACAP antibody is Ab10.H6, comprising, or alternatively consisting of, SEQ ID NO: 1441 and SEQ ID NO: 1461, or SEQ ID NO: 1442 and SEQ ID NO: 1462, or an antibody or antigen-binding fragment comprising the CDRs of Ab10.H6 and having at least one of the biological activities set forth herein, or is an anti-PACAP antibody that competes with Ab10.H6 in binding PACAP, preferably one containing sequences that are at least 90%, 95%, 96%, 97%, 98%, or 99% identical to that of Ab10.H6, or an antibody that binds to the same or overlapping epitope(s) on PACAP as Ab10.H6.

In a further embodiment of the invention, antigen-binding fragments comprise, or alternatively consist of, Fab fragments having binding specificity for PACAP. With respect to antibody Ab10.H6, the Fab fragment preferably includes the variable heavy chain sequence of SEQ ID NO: 1442 and the variable light chain sequence of SEQ ID NO: 1462, or sequences that are at least 90%, 95%, 96%, 97%, 98%, or 99% identical thereto. This embodiment of the invention further includes Fabs containing additions, deletions, and variants of SEQ ID NO: 1442 and/or SEQ ID NO: 1462 that retain the binding specificity for PACAP.

In one embodiment of the invention described herein, Fab fragments may be produced by enzymatic digestion (e.g., papain) of Ab10.H6. In another embodiment of the invention, anti-PACAP antibodies such as Ab10.H6 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris.*

In an additional embodiment, the invention is further directed to polynucleotides encoding antibody polypeptides having binding specificity to PACAP, including the heavy and/or light chains of Ab10.H6, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab21.H2

In one embodiment, the invention includes antibodies and antigen-binding fragments having binding specificity to PACAP that possess a heavy chain sequence comprising the sequence of SEQ ID NO: 1481 which consists of the heavy chain variable region of SEQ ID NO: 1482 linked to the heavy chain constant region of SEQ ID NO: 1490.

In one embodiment, the invention includes antibodies and antigen-binding fragments having binding specificity to PACAP that contain a variable heavy chain sequence comprising the sequence set forth below:

```
                                        (SEQ ID NO: 1482)
EVQLVESGGGLVQPGGSLRLSCAASGIDLSSYYMTWVRQAPGKGLEWIGF

IDAGGSAYYATWAKGRFTISRDNSKNTVYLQMNSLRAEDTAVYFCARDLD

LWGQGTLVTVSS.
```

In another embodiment, the invention includes antibodies and antigen-binding fragments having binding specificity to PACAP that bind the same epitope as Ab21.H2, and that contain a constant heavy chain sequence comprising the polypeptide of SEQ ID NO: 1244, 1245, or 1246, or comprising the sequence set forth below:

```
                                        (SEQ ID NO: 1490)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In another embodiment, the invention includes antibodies and antigen-binding fragments having binding specificity to PACAP that contain a light chain sequence comprising the sequence of SEQ ID NO: 1501 which consists of the light chain variable region of SEQ ID NO: 1502 linked to the light chain constant region of SEQ ID NO: 1510.

In another embodiment, the invention includes antibodies and antigen-binding fragments having binding specificity to PACAP that contain a variable light chain sequence comprising the sequence set forth below:

```
                                        (SEQ ID NO: 1502)
AVLTQSPSTLSASVGDRVTITCKSSESVYGDYLAWFQQKPGKAPKQLIYD

ASTLASGVPSRFSGSGSGTEFTLTISSLQPDDFATYYCAGGYVSAGVAFG

GGTKVEIKR.
```

In another embodiment, the invention includes antibodies and antigen-binding fragments having binding specificity to PACAP, that bind the same epitope as Ab21.H2, and that contain a constant light chain sequence comprising the sequence set forth below:

(SEQ ID NO: 1510)
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC.

In another embodiment, the invention includes antibodies and antigen-binding fragments having binding specificity to PACAP that contain one, two, or three of the polypeptide sequences of SEQ ID NO: 1484; SEQ ID NO: 1486; and SEQ ID NO: 1488, which correspond to the CDRs (hypervariable regions) of the heavy chain sequence of SEQ ID NO: 1481, or which contain the variable heavy chain sequence of SEQ ID NO: 1482, and/or which further contain one, two, or three of the polypeptide sequences of SEQ ID NO: 1504; SEQ ID NO: 1506; and SEQ ID NO: 1508, which correspond to the CDRs (hypervariable regions) of the light chain sequence of SEQ ID NO: 1501, or which contain the variable light chain sequence of SEQ ID NO: 1502, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1483; SEQ ID NO: 1485; SEQ ID NO: 1487; and SEQ ID NO: 1489, which correspond to the FRs (constant regions) of the heavy chain sequence of SEQ ID NO: 1481, or the variable heavy chain sequence of SEQ ID NO: 1482, and/or one, two, three, or four of the polypeptide sequences of SEQ ID NO: 1503; SEQ ID NO: 1505; SEQ ID NO: 1507; and SEQ ID NO: 1509, which correspond to the FRs (constant regions) of the light chain sequence of SEQ ID NO: 1501, or the variable light chain sequence of SEQ ID NO: 1502, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1481, or SEQ ID NO: 1482, or polypeptides that are at least 90% or 95% identical thereto. In another embodiment of the invention, the antibodies and antigen-binding fragments of the invention comprise, or alternatively consist of, the polypeptide sequence of SEQ ID NO: 1501, or SEQ ID NO: 1502, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1484; SEQ ID NO: 1486; and SEQ ID NO: 1488, which correspond to the CDRs (hypervariable regions) of the heavy chain sequence of SEQ ID NO: 1481, or the variable heavy chain sequence of SEQ ID NO: 1482, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1504; SEQ ID NO: 1506; and SEQ ID NO: 1508, which correspond to the CDRs (hypervariable regions) of the light chain sequence of SEQ ID NO: 1501, or the variable light chain sequence of SEQ ID NO: 1502, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1483; SEQ ID NO: 1485; SEQ ID NO: 1487; and SEQ ID NO: 1489, which correspond to the FRs (constant regions) of the heavy chain sequence of SEQ ID NO: 1481, or the variable heavy chain sequence of SEQ ID NO: 1482, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1503; SEQ ID NO: 1505; SEQ ID NO: 1507; and SEQ ID NO: 1509, which correspond to the FRs (constant regions) of the light chain sequence of SEQ ID NO: 1501, or the variable light chain sequence of SEQ ID NO: 1502, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1482; the variable light chain region of SEQ ID NO: 1502; the complementarity determining regions (SEQ ID NO: 1484; SEQ ID NO: 1486; and SEQ ID NO: 1488) of the variable heavy chain region of SEQ ID NO: 1482; and the complementarity determining regions (SEQ ID NO: 1504; SEQ ID NO: 1506; and SEQ ID NO: 1508) of the variable light chain region of SEQ ID NO: 1502, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1482; the variable light chain region of SEQ ID NO: 1502; the framework regions (SEQ ID NO: 1483; SEQ ID NO: 1485; SEQ ID NO: 1487; and SEQ ID NO: 1489) of the variable heavy chain region of SEQ ID NO: 1482; and the framework regions (SEQ ID NO: 1503; SEQ ID NO: 1505; SEQ ID NO: 1507; and SEQ ID NO: 1509) of the variable light chain region of SEQ ID NO: 1502, or sequences that are at least 90% or 95% identical thereto.

In another embodiment of the invention, the anti-PACAP antibody is Ab21.H2, comprising, or alternatively consisting of, SEQ ID NO: 1481 and SEQ ID NO: 1501, or SEQ ID NO: 1482 and SEQ ID NO: 1502, or an antibody or antigen-binding fragment comprising the CDRs of Ab21.H2 and having at least one of the biological activities set forth herein, or is an anti-PACAP antibody that competes with Ab21.H2 in binding PACAP, preferably one containing sequences that are at least 90%, 95%, 96%, 97%, 98%, or 99% identical to that of Ab21.H2, or an antibody that binds to the same or overlapping epitope(s) on PACAP as Ab21.H2.

In a further embodiment of the invention, antigen-binding fragments comprise, or alternatively consist of, Fab fragments having binding specificity for PACAP. With respect to antibody Ab21.H2, the Fab fragment preferably includes the variable heavy chain sequence of SEQ ID NO: 1482 and the variable light chain sequence of SEQ ID NO: 1502, or sequences that are at least 90%, 95%, 96%, 97%, 98%, or 99% identical thereto. This embodiment of the invention further includes Fabs containing additions, deletions, and variants of SEQ ID NO: 1482 and/or SEQ ID NO: 1502 that retain the binding specificity for PACAP.

In one embodiment of the invention described herein, Fab fragments may be produced by enzymatic digestion (e.g., papain) of Ab21.H2. In another embodiment of the invention, anti-PACAP antibodies such as Ab21.H2 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris.*

In an additional embodiment, the invention is further directed to polynucleotides encoding antibody polypeptides having binding specificity to PACAP, including the heavy and/or light chains of Ab21.H2, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab21.H3

In one embodiment, the invention includes antibodies and antigen-binding fragments having binding specificity to PACAP that possess a heavy chain sequence comprising the sequence of SEQ ID NO: 1521 which consists of the heavy chain variable region of SEQ ID NO: 1522 linked to the heavy chain constant region of SEQ ID NO: 1530.

In one embodiment, the invention includes antibodies and antigen-binding fragments having binding specificity to PACAP that contain a variable heavy chain sequence comprising the sequence set forth below:

(SEQ ID NO: 1522)
EVQLVESGGGLVQPGGSLRLSCAASGIDLSSYYMTWVRQAPGKGLEWIG

FIDAGGSAYYATWAKGRFTISRDNSKNTVYLQMNSLRAEDTAVYFCARD

LDLWGQGTLVTVSS.

In another embodiment, the invention includes antibodies and antigen-binding fragments having binding specificity to PACAP that bind the same epitope as Ab21.H3, and that contain a constant heavy chain sequence comprising the polypeptide of SEQ ID NO: 1244, 1245, or 1246, or comprising the sequence set forth below:

(SEQ ID NO: 1530)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

-continued

DVSHEDPEVKFNWYVDGVEVHNAKTKPREEQYASTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK.

In another embodiment, the invention includes antibodies and antigen-binding fragments having binding specificity to PACAP that contain a light chain sequence comprising the sequence of SEQ ID NO: 1541 which consists of the light chain variable region of SEQ ID NO: 1542 linked to the light chain constant region of SEQ ID NO: 1550.

In another embodiment, the invention includes antibodies and antigen-binding fragments having binding specificity to PACAP that contain a variable light chain sequence comprising the sequence set forth below:

(SEQ ID NO: 1542)
DIQLTQSPSTLSASVGDRVTITCKSSESVYGDYLAWFQQKPGKAPKQLI

YDASTLASGVPSRFSGSGSGTEFTLTISSLQPDDFATYYCAGGYVSAGV

AFGGGTKVEIKR.

In another embodiment, the invention includes antibodies and antigen-binding fragments having binding specificity to PACAP, that bind the same epitope as Ab21.H3, and that contain a constant light chain sequence comprising the sequence set forth below:

(SEQ ID NO: 1550)
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC.

In another embodiment, the invention includes antibodies and antigen-binding fragments having binding specificity to PACAP that contain one, two, or three of the polypeptide sequences of SEQ ID NO: 1524; SEQ ID NO: 1526; and SEQ ID NO: 1528, which correspond to the CDRs (hypervariable regions) of the heavy chain sequence of SEQ ID NO: 1521, or which contain the variable heavy chain sequence of SEQ ID NO: 1522, and/or which further contain one, two, or three of the polypeptide sequences of SEQ ID NO: 1544; SEQ ID NO: 1546; and SEQ ID NO: 1548, which correspond to the CDRs (hypervariable regions) of the light chain sequence of SEQ ID NO: 1541, or which contain the variable light chain sequence of SEQ ID NO: 1542, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1523; SEQ ID NO: 1525; SEQ ID NO: 1527; and SEQ ID NO: 1529, which correspond to the FRs (constant regions) of the heavy chain sequence of SEQ ID NO: 1521, or the variable heavy chain sequence of SEQ ID NO: 1522, and/or one, two, three, or four of the polypeptide sequences of SEQ ID NO: 1543; SEQ ID NO: 1545; SEQ ID NO: 1547; and SEQ ID NO: 1549, which correspond to the FRs (constant regions) of the light chain sequence of SEQ ID NO: 1541, or the variable light chain sequence of SEQ ID NO: 1542, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1521, or SEQ ID NO: 1522, or polypeptides that are at least 90% or 95% identical thereto. In another embodiment of the invention, the antibodies and antigen-binding fragments of the invention comprise, or alternatively consist of, the polypeptide sequence of SEQ ID NO: 1541, or SEQ ID NO: 1542, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1524; SEQ ID NO: 1526; and SEQ ID NO: 1528, which correspond to the CDRs (hypervariable regions) of the heavy chain sequence of SEQ ID NO: 1521, or the variable heavy chain sequence of SEQ ID NO: 1522, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1544; SEQ ID NO: 1546; and SEQ ID NO: 1548, which correspond to the CDRs (hypervariable regions) of the light chain sequence of SEQ ID NO: 1541, or the variable light chain sequence of SEQ ID NO: 1542, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1523; SEQ ID NO: 1525; SEQ ID NO: 1527; and SEQ ID NO: 1529, which correspond to the FRs (constant regions) of the heavy chain sequence of SEQ ID NO: 1521, or the variable heavy chain sequence of SEQ ID NO: 1522, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1543; SEQ ID NO: 1545; SEQ ID NO: 1547; and SEQ ID NO: 1549, which correspond to the FRs (constant regions) of the light chain sequence of SEQ ID NO: 1541, or the variable light chain sequence of SEQ ID NO: 1542, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1522; the variable light chain region of SEQ ID NO: 1542; the complementarity determining regions (SEQ ID NO: 1524; SEQ ID NO: 1526; and SEQ ID NO: 1528) of the variable heavy chain region of SEQ ID NO: 1522; and the complementarity determining regions (SEQ ID NO: 1544; SEQ ID NO: 1546; and SEQ ID NO: 1548) of the variable light chain region of SEQ ID NO: 1542, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1522; the variable light chain region of SEQ ID NO: 1542; the framework regions (SEQ ID NO: 1523; SEQ ID NO: 1525; SEQ ID NO: 1527; and SEQ ID NO: 1529) of the variable heavy chain region of SEQ ID NO: 1522; and the framework regions (SEQ ID NO: 1543; SEQ ID NO: 1545; SEQ ID NO: 1547; and SEQ ID NO: 1549) of the variable light chain region of SEQ ID NO: 1542, or sequences that are at least 90% or 95% identical thereto.

In another embodiment of the invention, the anti-PACAP antibody is Ab21.H3, comprising, or alternatively consisting of, SEQ ID NO: 1521 and SEQ ID NO: 1541, or SEQ ID NO: 1522 and SEQ ID NO: 1542, or an antibody or antigen-binding fragment comprising the CDRs of Ab21.H3 and having at least one of the biological activities set forth herein, or is an anti-PACAP antibody that competes with Ab21.H3 in binding PACAP, preferably one containing sequences that are at least 90%, 95%, 96%, 97%, 98%, or 99% identical to that of Ab21.H3, or an antibody that binds to the same or overlapping epitope(s) on PACAP as Ab21.H3.

In a further embodiment of the invention, antigen-binding fragments comprise, or alternatively consist of, Fab fragments having binding specificity for PACAP. With respect to antibody Ab21.H3, the Fab fragment preferably includes the variable heavy chain sequence of SEQ ID NO: 1522 and the variable light chain sequence of SEQ ID NO: 1542, or sequences that are at least 90%, 95%, 96%, 97%, 98%, or 99% identical thereto. This embodiment of the invention further includes Fabs containing additions, deletions, and variants of SEQ ID NO: 1522 and/or SEQ ID NO: 1542 that retain the binding specificity for PACAP.

In one embodiment of the invention described herein, Fab fragments may be produced by enzymatic digestion (e.g., papain) of Ab21.H3. In another embodiment of the invention, anti-PACAP antibodies such as Ab21.H3 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab21.H3, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

Antibody Ab21.H4

In one embodiment, the invention includes antibodies and antigen-binding fragments having binding specificity to PACAP that possess a heavy chain sequence comprising the sequence of SEQ ID NO: 1561 which consists of the heavy chain variable region of SEQ ID NO: 1562 linked to the heavy chain constant region of SEQ ID NO: 1570.

In one embodiment, the invention includes antibodies and antigen-binding fragments having binding specificity to PACAP that contain a variable heavy chain sequence comprising the sequence set forth below:

(SEQ ID NO: 1562)
EVQLVESGGGLVQPGGSLRLSCAASGIDLSSYYMTWVRQAPGKGLEWIG

FIDAGGSAYYATWAKGRFTISRDNSKNTVYLQMNSLRAEDTAVYFCARD

LDLWGQGTLVTVSS.

In another embodiment, the invention includes antibodies and antigen-binding fragments having binding specificity to PACAP that bind the same epitope as Ab21.H4, and that contain a constant heavy chain sequence comprising the polypeptide of SEQ ID NO: 1244, 1245, or 1246, or comprising the sequence set forth below:

(SEQ ID NO: 1570)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYASTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK.

In another embodiment, the invention includes antibodies and antigen-binding fragments having binding specificity to PACAP that contain a light chain sequence comprising the sequence of SEQ ID NO: 1581 which consists of the light chain variable region of SEQ ID NO: 1582 linked to the light chain constant region of SEQ ID NO: 1590.

In another embodiment, the invention includes antibodies and antigen-binding fragments having binding specificity to PACAP that contain a variable light chain sequence comprising the sequence set forth below:

(SEQ ID NO: 1582)
DIVLTQSPSTLSASVGDRVTITCKSSESVYGDYLAWFQQKPGKAPKQLI

YDASTLASGVPSRFSGSGSGTEFTLTISSLQPDDFATYYCAGGYVSAGV

AFGGGTKVEIKR.

In another embodiment, the invention includes antibodies and antigen-binding fragments having binding specificity to PACAP, that bind the same epitope as Ab21.H4, and that contain a constant light chain sequence comprising the sequence set forth below:

(SEQ ID NO: 1590)
TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC.

In another embodiment, the invention includes antibodies and antigen-binding fragments having binding specificity to PACAP that contain one, two, or three of the polypeptide sequences of SEQ ID NO: 1564; SEQ ID NO: 1566; and SEQ ID NO: 1568, which correspond to the CDRs (hypervariable regions) of the heavy chain sequence of SEQ ID NO: 1561, or which contain the variable heavy chain sequence of SEQ ID NO: 1562, and/or which further contain one, two, or three of the polypeptide sequences of SEQ ID NO: 1584; SEQ ID NO: 1586; and SEQ ID NO: 1588, which correspond to the CDRs (hypervariable regions) of the light chain sequence of SEQ ID NO: 1581, or which contain the variable light chain sequence of SEQ ID NO: 1582, or antibodies or antigen-binding fragments containing combinations of sequences that are at least 80%, 85%, 90%, 95%, 96%, 97%, 98%, or 99% identical thereto. In another embodiment of the invention, the antibodies of the invention and antigen-binding fragments comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates anti-PACAP antibodies and antigen-binding fragments comprising one, two, three, or four of the polypeptide sequences of SEQ ID NO: 1563; SEQ ID NO: 1565; SEQ ID NO: 1567; and SEQ ID NO: 1569, which correspond to the FRs (constant regions) of the heavy chain sequence of SEQ ID NO: 1561, or the variable heavy chain sequence of SEQ ID NO: 1562, and/or one, two, three, or four of the polypeptide sequences of SEQ ID NO: 1583; SEQ ID NO: 1585; SEQ ID NO: 1587; and SEQ ID NO: 1589, which correspond to the FRs (constant regions) of the light chain sequence of SEQ ID NO: 1581, or the variable light chain sequence of SEQ ID NO: 1582, or combinations of these polypeptide sequences, or sequences that are at least 80%, 90%, 95%, 96%, 97%, 98%, or 99% identical therewith.

In another embodiment of the invention, the anti-PACAP antibodies and antigen-binding fragments of the invention or fragments comprise, or alternatively consist of, combinations of one or more of the FRs, CDRs, the variable heavy chain and variable light chain sequences, and the heavy chain and light chain sequences set forth above, including all of them, or sequences that are at least 90% or 95% identical thereto.

In another embodiment of the invention, the anti-PACAP antibodies and antigen-binding fragments of the invention comprise, or alternatively consist of, the polypeptide sequence of SEQ ID NO: 1561, or SEQ ID NO: 1562, or polypeptides that are at least 90% or 95% identical thereto. In another embodiment of the invention, the antibodies and antigen-binding fragments of the invention comprise, or alternatively consist of, the polypeptide sequence of SEQ ID NO: 1581, or SEQ ID NO: 1582, or polypeptides that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1564; SEQ ID NO: 1566; and SEQ ID NO: 1568, which correspond to the CDRs (hypervariable regions) of the heavy chain sequence of SEQ ID NO: 1561, or the variable heavy chain sequence of SEQ ID NO: 1562, or sequences that are at least 90% or 95% identical thereto.

In a further embodiment of the invention, the antibodies and antigen-binding fragments having binding specificity to PACAP comprise, or alternatively consist of, one, two, or three of the polypeptide sequences of SEQ ID NO: 1584; SEQ ID NO: 1586; and SEQ ID NO: 1588, which correspond to the CDRs (hypervariable regions) of the light chain sequence of SEQ ID NO: 1581, or the variable light chain sequence of SEQ ID NO: 1582, or sequences that are at least 90% or 95% identical thereto.

In a further embodiment of the invention, the antibodies and antigen-binding fragments having binding specificity to PACAP comprise, or alternatively consist of, one, two, three, or four of the polypeptide sequences of SEQ ID NO: 1563; SEQ ID NO: 1565; SEQ ID NO: 1567; and SEQ ID NO: 1569, which correspond to the FRs (constant regions) of the heavy chain sequence of SEQ ID NO: 1561, or the variable heavy chain sequence of SEQ ID NO: 1562, or sequences that are at least 90% or 95% identical thereto.

In a further embodiment of the invention, the subject antibodies and antigen-binding fragments having binding specificity to PACAP comprise, or alternatively consist of, one, two, three, or four of the polypeptide sequences of SEQ ID NO: 1583; SEQ ID NO: 1585; SEQ ID NO: 1587; and SEQ ID NO: 1589, which correspond to the FRs (constant regions) of the light chain sequence of SEQ ID NO: 1581, or the variable light chain sequence of SEQ ID NO: 1582, or sequences that are at least 90% or 95% identical thereto.

The invention also contemplates anti-PACAP antibodies and antigen-binding fragments that include one or more of the antibody fragments described herein. In one embodiment of the invention, antibodies and antigen-binding fragments having binding specificity to PACAP comprise, or alternatively consist of, one, two, three, or more, including all of the following antibody fragments: the variable heavy chain region of SEQ ID NO: 1562; the variable light chain region of SEQ ID NO: 1582; the complementarity determining regions (SEQ ID NO: 1564; SEQ ID NO: 1566; and SEQ ID NO: 1568) of the variable heavy chain region of SEQ ID NO: 1562; and the complementarity determining regions (SEQ ID NO: 1584; SEQ ID NO: 1586; and SEQ ID NO: 1588) of the variable light chain region of SEQ ID NO: 1582, or sequences that are at least 90% or 95% identical thereto. In another embodiment of the invention, fragments of the antibodies having binding specificity to PACAP comprise, or alternatively consist of, one, two, three, or more, including all of the following antibody fragments: the variable heavy chain region of SEQ ID NO: 1562; the variable light chain region of SEQ ID NO: 1582; the framework regions (SEQ ID NO: 1563; SEQ ID NO: 1565; SEQ ID NO: 1567; and SEQ ID NO: 1569) of the variable heavy chain region of SEQ ID NO: 1562; and the framework regions (SEQ ID NO: 1583; SEQ ID NO: 1585; SEQ ID NO: 1587; and SEQ ID NO: 1589) of the variable light chain region of SEQ ID NO: 1582, or sequences that are at least 90% or 95% identical thereto.

In another embodiment of the invention, the anti-PACAP antibody is Ab21.H4, comprising, or alternatively consisting of, SEQ ID NO: 1561 and SEQ ID NO: 1581, or SEQ ID NO: 1562 and SEQ ID NO: 1582, or an antibody or antigen-binding fragment comprising the CDRs of Ab21.H4 and having at least one of the biological activities set forth herein, or is an anti-PACAP antibody that competes with Ab21.H4 in binding PACAP, preferably one containing sequences that are at least 90%, 95%, 96%, 97%, 98%, or 99% identical to that of Ab21.H4, or an antibody that binds to the same or overlapping epitope(s) on PACAP as Ab21.H4.

In a further embodiment of the invention, antigen-binding fragments comprise, or alternatively consist of, Fab fragments having binding specificity for PACAP. With respect to antibody Ab21.H4, the Fab fragment preferably includes the variable heavy chain sequence of SEQ ID NO: 1562 and the variable light chain sequence of SEQ ID NO: 1582, or sequences that are at least 90%, 95%, 96%, 97%, 98%, or 99% identical thereto. This embodiment of the invention further includes Fabs containing additions, deletions, and variants of SEQ ID NO: 1562 and/or SEQ ID NO: 1582 that retain the binding specificity for PACAP.

In one embodiment of the invention described herein, Fab fragments may be produced by enzymatic digestion (e.g., papain) of Ab21.H4. In another embodiment of the invention, anti-PACAP antibodies such as Ab21.H4 and Fab fragments may be produced via expression in mammalian cells, such as CHO, NSO, or HEK 293 cells, fungal, insect, or microbial systems, such as yeast cells (for example haploid or diploid yeast, such as haploid or diploid *Pichia*) and other yeast strains. Suitable *Pichia* species include, but are not limited to, *Pichia pastoris*.

In an additional embodiment, the invention is further directed to polynucleotides encoding antibody polypeptides having binding specificity to PACAP, including the heavy and/or light chains of Ab21.H4, as well as fragments, variants, and combinations of one or more of the FRs, CDRs, the variable heavy chain and variable light chain sequences, and the heavy chain and light chain sequences set forth above, including all of them, or sequences that are at least 90% or 95% identical thereto.

In another embodiment, the invention contemplates an isolated anti-PACAP antibody comprising a $V_H$ polypeptide sequence selected from: SEQ ID NO: 962; SEQ ID NO: 1282; SEQ ID NO: 1322; SEQ ID NO: 1362; SEQ ID NO: 1402; SEQ ID NO: 1442; SEQ ID NO: 842; SEQ ID NO: 1202; SEQ ID NO: 1482; SEQ ID NO: 1522; SEQ ID NO: 1562 SEQ ID NO: 882; SEQ ID NO: 922, or a variant thereof; and further comprising a $V_L$ polypeptide sequence selected from: SEQ ID NO: 982; SEQ ID NO: 1302; SEQ ID NO: 1342; SEQ ID NO: 1382; SEQ ID NO: 1422; SEQ ID NO: 1462; SEQ ID NO: 862; SEQ ID NO: 1222; SEQ ID NO: 1502; SEQ ID NO: 1542; SEQ ID NO: 1582; SEQ ID NO: 902; SEQ ID NO: 942, or a variant thereof, wherein one or more of the framework region residues ("FR residues") and/or CDR residues in said $V_H$ or $V_L$ polypeptide has been substituted with another amino acid residue resulting in an anti-PACAP antibody that specifically binds PACAP. The invention also includes humanized and chimeric forms of these antibodies. The chimeric and humanized antibodies may include an Fc derived from IgG1, IgG2, IgG3, or IgG4 constant regions.

In one embodiment of the invention, the chimeric or humanized antibodies or fragments or $V_H$ or $V_L$ polypeptides originate or are derived from one or more rabbit antibodies, e.g., a rabbit antibody isolated from a clonal rabbit B cell population.

In some aspects, the invention provides a vector comprising a nucleic acid molecule encoding an anti-PACAP antibody or fragment thereof as disclosed herein. In some embodiments, the invention provides a host cell comprising a nucleic acid molecule encoding an anti-PACAP antibody or fragment thereof as disclosed herein.

In some aspects, the invention provides an isolated antibody or antigen binding fragment thereof that competes for binding to PACAP with an antibody or antigen binding fragment thereof disclosed herein.

In some aspects, the invention provides a nucleic acid molecule encoding an antibody or antigen binding fragment thereof as disclosed herein.

In some aspects, the invention provides a pharmaceutical or diagnostic composition comprising at least one antibody or antigen binding fragment thereof as disclosed herein.

In some aspects, the invention provides a method for treating or preventing a condition associated with elevated PACAP levels in a subject, comprising administering to a subject in need thereof an effective amount of at least one isolated antibody or antigen binding fragment thereof as disclosed herein.

In some aspects, the invention provides a method of inhibiting binding of PACAP to PAC1-R, VPAC1-R, and/or VPAC2-R in a subject comprising administering an effective amount of at least one antibody or antigen binding fragment thereof as disclosed herein.

In some aspects, the invention provides an antibody or antigen binding fragment thereof that selectively binds to PACAP, wherein the antibody or antigen binding fragment thereof binds to PACAP with a $K_D$ of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M; preferably, with a $K_D$ of less than or equal to $5\times10^{-10}$ M, $10^{-10}$ M, $5\times10^{-11}$ M, $10^{-11}$ M, $5\times10^{-12}$ M, or $10^{-12}$ M; more preferably, with a $K_D$ that is less than about 100 pM, less than about 50 pM, less than about 40 pM, less than about 25 pM, less than about 1 pM, between about 10 pM and about 100 pM, between about 1 pM and about 100 pM, or between about 1 pM and about 10 pM. Preferably, the anti-PACAP antibody or antigen binding fragment thereof has no cross-reactivity or minimal cross-reactivity with VIP.

The inventive antibodies and antigen binding fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Antibodies and antigen binding fragments thereof may also be chemically modified to provide additional advantages such as increased solubility, stability and circulating time (in vivo half-life) of the polypeptide, or decreased immunogenicity (See U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol, and the like. The antibodies and fragments thereof may be modified at random positions within the molecule, or at predetermined positions within the molecule and may include one, two, three, or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for case in handling and manufacturing. Other sizes may be used, depending on the desired therapeutic profile (e.g., the duration of sustained release desired, the effects, if any on biological activity, the case in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. Branched polyethylene glycols are described, for example, in U.S. Pat. No. 5,643,575; Morpurgo et al., *Appl. Biochem. Biotechnol.,* 56:59-72 (1996); Vorobjev et al., *Nucleosides and Nucleotides,* 18:2745-2750 (1999); and Caliceti et al., *Bioconjug. Chem.,* 10:638-646 (1999), the disclosures of each of which are incorporated herein by reference.

There are a number of attachment methods available to those skilled in the art (See e.g., EP 0 401 384, herein incorporated by reference, disclosing a method of coupling PEG to G-CSF; and Malik et al., *Exp. Hematol.,* 20:1028-1035 (1992) (reporting pegylation of GM-CSF using tresyl chloride)). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof).

Alternatively, antibodies or antigen binding fragments thereof may have increased in vivo half-lives via fusion with albumin (including but not limited to recombinant human serum albumin or fragments or variants thereof (See, e.g., U.S. Pat. No. 5,876,969, EP 0 413 622, and U.S. Pat. No. 5,766,883, herein incorporated by reference in their entirety)), or other circulating blood proteins such as transferrin or ferritin. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP 0 322 094) which is herein incorporated by reference in its entirety. Polynucleotides encoding fusion proteins of the invention are also encompassed by the invention.

Regarding detectable moieties, further exemplary enzymes include, but are not limited to, horseradish peroxidase, acetylcholinesterase, alkaline phosphatase, beta-galactosidase, and luciferase. Further exemplary fluorescent materials include, but are not limited to, rhodamine, fluorescein, fluorescein isothiocyanate, umbelliferone, dichlorotriazinylamine, phycoerythrin, and dansyl chloride. Further exemplary chemiluminescent moieties include, but are not limited to, luminol. Further exemplary bioluminescent materials include, but are not limited to, luciferin and acquorin. Further exemplary radioactive materials include, but are not limited to, Iodine 125 ($^{125}I$), Carbon 14 ($^{14}C$), Sulfur 35 ($^{35}S$), Tritium ($^{3}H$) and Phosphorus 32 ($^{32}P$).

Methods are known in the art for conjugating an antibody or antigen binding fragment thereof to a detectable moiety and the like, such as for example those methods described by Hunter et al., *Nature,* 144:945 (1962); David et al., *Biochemistry,* 13:1014 (1974); Pain et al., *J. Immunol. Meth.,* 40:219 (1981); and Nygren, J., *Histochem. and Cytochem.,* 30:407 (1982).

Embodiments described herein further include variants and equivalents that are substantially homologous to the antibodies, antibody fragments, diabodies, SMIPs, camelbodies, nanobodies, IgNAR, polypeptides, variable regions, and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antigen binding fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antigen binding fragments, variable regions, and CDRs set forth herein.

Methods for determining homology between nucleic acid and amino acid sequences are well known to those of ordinary skill in the art.

In another embodiment, the invention further contemplates the above-recited polypeptide homologs of the antigen binding fragments, variable regions and CDRs set forth herein further having anti-PACAP activity. Non-limiting examples of anti-PACAP activity are set forth herein, e.g., ability to inhibit PACAP binding to PAC1-R, VPAC1-R, and/or VPAC2-R, thereby resulting in the reduced production of cAMP.

In another embodiment, the invention further contemplates the generation and use of antibodies that bind any of the foregoing sequences, including, but not limited to, anti-idiotypic antibodies. In an exemplary embodiment, such an anti-idiotypic antibody could be administered to a subject who has received an anti-PACAP antibody to modulate, reduce, or neutralize, the effect of the anti-PACAP antibody. Such antibodies could also be useful for treatment of an autoimmune disease characterized by the presence of anti-PACAP antibodies. A further exemplary use of such antibodies, e.g., anti-idiotypic antibodies, is for detection of the anti-PACAP antibodies of the present invention, for example to monitor the levels of the anti-PACAP antibodies present in a subject's blood or other bodily fluids. For example, in one embodiment, the invention provides a method of using the anti-idiotypic antibody to monitor the in vivo levels of said anti-PACAP antibody or antigen binding fragment thereof in a subject or to neutralize said anti-PACAP antibody in a subject being administered said anti-PACAP antibody or antigen binding fragment thereof.

The present invention also contemplates anti-PACAP antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Exemplary Polynucleotides Encoding Anti-PACAP Antibody Polypeptides

The invention is further directed to polynucleotides encoding antibody polypeptides having binding specificity to PACAP.

Antibody Ab10.H

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 971 which encodes the heavy chain sequence of SEQ ID NO: 961 and which consists of the heavy chain variable region coding sequence of SEQ ID NO: 972 and the heavy chain constant region coding sequence of SEQ ID NO: 980.

In another embodiment of the invention, the polynucleotides of the invention comprise, or alternatively consist of, the following polynucleotide sequence encoding the variable heavy chain polypeptide sequence of SEQ ID NO: 962:

```
                                          (SEQ ID NO: 972)
gaggtgcagcttgtggagtagggggaggcttggtccagcctggggggtc

cctgagactacctgtgcagcctaggaatcgacctcaatagctactacat

gacctgggtccgtcaggctccagggaaggggctggagtggatcggattc

attgatgctggtggtgacgcatactacgcgagagggcgaaaggccgatt

caccataccagagacaattccaagaacaccgtgtatcttcaaatgaaca

gcctgagagctgaggacactgctgtgtatttctgtgctagagatcttga

cttgtggggccaagggaccctcgtcaccgtctcgagc.
```

In another embodiment of the invention, polynucleotides of the invention comprise, or alternatively consist of, the following polynucleotide sequence encoding the constant heavy chain polypeptide sequence of SEQ ID NO: 970:

```
                                          (SEQ ID NO: 980)
gcctccaccaagggcccatcggtcttccccctggcaccctcctccaaga

gcacctctgggggcacagcggccctgggctgcctggtcaaggactactt

ccccgaaccggtgacggtgtcgtggaactcaggcgccctgaccagcggc

gtgcacaccttcccggctgtcctacagtcctcaggactctactccctca

gcagcgtggtgaccgtgccctccagcagcttgggcacccagacctacat

ctgcaacgtgaatcacaagcccagcaacaccaaggtggacaagaaagtt

gagcccaaatcttgtgacaaaactcacacatgcccaccgtgcccagcac

ctgaactcctggggggaccgtcagtcttcctcttccccccaaaacccaa

ggacaccctcatgatctcccggacccctgaggtcacatgcgtggtggtg
```

-continued

```
gacgtgagccacgaagaccctgaggtcaagttcaactggtacgtggacg
gcgtggaggtgcataatgccaagacaaagccgcgggaggagcagtacgc
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggaggagatgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacgcagaagagcctctccctgtc
tccgggtaaa.
```

In another embodiment of the invention, polynucleotides comprise, or alternatively consist of, the polynucleotide sequence of SEQ ID NO: 991 which encodes the light chain polypeptide sequence of SEQ ID NO: 981 and which consists of the light chain variable region coding sequence of SEQ ID NO: 992 and the light chain constant region coding sequence of SEQ ID NO: 1000.

In another embodiment of the invention, polynucleotides of the invention comprise, or alternatively consist of, the following polynucleotide sequence encoding the variable light chain polypeptide sequence of SEQ ID NO: 982:

```
                                             (SEQ ID NO: 992)
gacgcccagctgacccagtctccttccaccctgtctgcatctgtaggag
acagagtcaccatcacttgtcagtccagtgagagtgtttacggtaacta
cttagcctggtttcagcagaaaccaggaaaagcccctaagttcctgatc
tatgaagcatccaaactggaatctggagtcccatcaaggttcagcggca
gtggatctggaacagaattcactctcaccatcagcagcctgcagcctga
tgattttgcaacttactactgtgcaggcggtgatattagtgaaggtgtt
gctttcggcggaggaaccaaggtggaaatcaaacgt.
```

In another embodiment of the invention, polynucleotides of the invention comprise, or alternatively consist of, the following polynucleotide sequence encoding the constant light chain polypeptide sequence of SEQ ID NO: 990:

```
                                            (SEQ ID NO: 1000)
acggtagcggccccatctgtcttcatcttcccgccatctgatgagcagt
tgaaatctggaactgcctctgttgtgtgcctgctgaataacttctatcc
cagagaggccaaagtacagtggaaggtggataacgccctccaatcgggt
aactcccaggagagtgtcacagagcaggacagcaaggacagcacctaca
gcctcagcagcaccctgacgctgagcaaagcagactacgagaaacacaa
agtctacgcctgcgaagtcacccatcagggcctgagctcgcccgtcaca
aagagcttcaacaggggagagtgt.
```

In a further embodiment of the invention, polynucleotides encoding antigen-binding fragments having binding specificity to PACAP comprise, or alternatively consist of, one or more of the polynucleotide sequences of SEQ ID NO: 974; SEQ ID NO: 976; and SEQ ID NO: 978, which correspond to polynucleotides encoding the CDRs (hypervariable regions) of the heavy chain sequence of SEQ ID NO: 961, or the variable heavy chain sequence of SEQ ID NO: 962, and/or one or more of the polynucleotide sequences of SEQ ID NO: 994; SEQ ID NO: 996; and SEQ ID NO: 998, which correspond to the CDRs (hypervariable regions) of the light chain sequence of SEQ ID NO: 981, or the variable light chain sequence of SEQ ID NO: 982, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 973; SEQ ID NO: 975; SEQ ID NO: 977; and SEQ ID NO: 979, which correspond to polynucleotides encoding the FRs (constant regions) of the heavy chain sequence of SEQ ID NO: 961, or the variable heavy chain sequence of SEQ ID NO: 962, and/or one or more of the polynucleotide sequences of SEQ ID NO: 993; SEQ ID NO: 995; SEQ ID NO: 997; and SEQ ID NO: 999, which correspond to the FRs (constant regions) of the light chain sequence of SEQ ID NO: 981, or the variable light chain sequence of SEQ ID NO: 982, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 971 encoding the heavy chain sequence of SEQ ID NO: 961; the polynucleotide SEQ ID NO: 972 encoding the variable heavy chain sequence of SEQ ID NO: 962; the polynucleotide SEQ ID NO: 991 encoding the light chain sequence of SEQ ID NO: 981; the polynucleotide SEQ ID NO: 992 encoding the variable light chain sequence of SEQ ID NO: 982; polynucleotides encoding the CDRs (SEQ ID NO: 974; SEQ ID NO: 976; and SEQ ID NO: 978) of the heavy chain sequence of SEQ ID NO: 961, or the variable heavy chain sequence of SEQ ID NO: 962; polynucleotides encoding the CDRs (SEQ ID NO: 994; SEQ ID NO: 996; and SEQ ID NO: 998) of the light chain sequence of SEQ ID NO: 981, or the variable light chain sequence of SEQ ID NO: 982; polynucleotides encoding the FRs (SEQ ID NO: 973; SEQ ID NO: 975; SEQ ID NO: 977; and SEQ ID NO: 979) of the heavy chain sequence of SEQ ID NO: 961, or the variable heavy chain sequence of SEQ ID NO: 962; and polynucleotides encoding the FRs (SEQ ID NO: 993; SEQ ID NO: 995; SEQ ID NO: 997; and SEQ ID NO: 999) of the light chain sequence of SEQ ID NO: 981, or the variable light chain sequence of SEQ ID NO: 982.

In another embodiment of the invention, polynucleotides of the invention comprise, or alternatively consist of, polynucleotides encoding Fab fragments having binding specificity for PACAP. With respect to antibody Ab10.H, the polynucleotides encoding the full length Ab10.H antibody comprise, or alternatively consist of, the polynucleotide SEQ ID NO: 971 encoding the heavy chain sequence of SEQ ID NO: 961, and the polynucleotide SEQ ID NO: 991 encoding the light chain sequence of SEQ ID NO: 981.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab10.H following expression of the full-length polynucleotides in a suitable host. In another embodiment of the invention, anti-PACAP antibodies, such as Ab10.H or Fab fragments thereof, can be produced via expression of Ab10.H polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab21

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 851 which encodes the heavy chain sequence of SEQ ID NO: 841 and which consists of the heavy chain variable region coding sequence of SEQ ID NO: 852 and the heavy chain constant region coding sequence of SEQ ID NO: 860.

In another embodiment of the invention, the polynucleotides of the invention comprise, or alternatively consist of, the following polynucleotide sequence encoding the variable heavy chain polypeptide sequence of SEQ ID NO: 842:

(SEQ ID NO: 852)
cagtcggtggaggagtccgggggtcgcctggtcacgcctgggacacccc tgacactcacctgcacagtctctggaatcgacctcagtagctactacat gacctgggtccgccaggctccagggaaggggctggaatgggtcggattc attgatgctggtggtagcgcatactacgcgacctgggcaaaaggccgat tcaccatctccaaagcctcgaccacggtggatctgaaaatcaccagtcc gacaaccgaggacacggccacctatttctgtgccagagatcttgacttg tggggcccgggcaccctggtcaccgtctcgagc.

In another embodiment of the invention, polynucleotides of the invention comprise, or alternatively consist of, the following polynucleotide sequence encoding the constant heavy chain polypeptide sequence of SEQ ID NO: 850:

(SEQ ID NO: 860)
gcctccaccaagggcccatcggtcttccccctggcaccctcctccaaga gcacctctgggggcacagcggccctgggctgcctggtcaaggactactt ccccgaaccggtgacggtgtcgtggaactcaggcgccctgaccagcggc -continued gtgcacaccttcccggctgtcctacagtcctcaggactctactccctca gcagcgtggtgaccgtgccctccagcagcttgggcacccagacctacat ctgcaacgtgaatcacaagcccagcaacaccaaggtggacaagaaagtt gagcccaaatcttgtgacaaaactcacacatgcccaccgtgcccagcac ctgaactcctggggggaccgtcagtcttcctcttccccccaaaacccaa ggacaccctcatgatctcccggacccctgaggtcacatgcgtggtggtg gacgtgagccacgaagaccctgaggtcaagttcaactggtacgtggacg gcgtggaggtgcataatgccaagacaaagccgcgggaggagcagtacgc cagcacgtaccgtgtggtcagcgtcctcaccgtcctgcaccaggactgg ctgaatggcaaggagtacaagtgcaaggtctccaacaaagccctcccag cccccatcgagaaaaccatctccaaagccaaagggcagccccgagaacc acaggtgtacaccctgcccccatcccgggaggagatgaccaagaaccag gtcagcctgacctgcctggtcaaaggcttctatcccagcgacatcgccg tggagtgggagagcaatgggcagccggagaacaactacaagaccacgcc tcccgtgctggactccgacggctccttcttcctctacagcaagctcacc gtggacaagagcaggtggcagcaggggaacgtcttctcatgctccgtga tgcatgaggctctgcacaaccactacacgcagaagagcctctccctgtc tccgggtaaa.

In another embodiment of the invention, polynucleotides comprise, or alternatively consist of, the polynucleotide sequence of SEQ ID NO: 871 which encodes the light chain polypeptide sequence of SEQ ID NO: 861 and which consists of the light chain variable region coding sequence of SEQ ID NO: 872 and the light chain constant region coding sequence of SEQ ID NO: 880.

In another embodiment of the invention, polynucleotides of the invention comprise, or alternatively consist of, the following polynucleotide sequence encoding the variable light chain polypeptide sequence of SEQ ID NO: 862:

(SEQ ID NO: 872)
gccgccgtgctgacccagactccatctcccgtgtctgcagctgtgggag gcacagtcagcatcagttgcaagtccagtgagagcgtttatggtgacta cttagcctggtttcagcagaaaccagggcagcctcccaagcaactgatc tatgatgcatccactctggcatctggggtcccatcgcggttcaaaggca gtggatctgggacacagttcactctcaccatcagcggcgtgcagtgtga cgatgctgccacttactactgtgcaggcggttatgttagtgcaggtgtt gctttcggcggagggaccgaggtggtggtcaaacgt.

In another embodiment of the invention, polynucleotides of the invention comprise, or alternatively consist of, the following polynucleotide sequence encoding the constant light chain polypeptide sequence of SEQ ID NO: 870:

(SEQ ID NO: 880)
acggtagcggccccatctgtcttcatcttcccgccatctgatgagcagt tgaaatctggaactgcctctgttgtgtgcctgctgaataacttctatcc -continued

```
cagagaggccaaagtacagtggaaggtggataacgccctccaatcgggt

aactcccaggagagtgtcacagagcaggacagcaaggacagcacctaca

gcctcagcagcaccctgacgctgagcaaagcagactacgagaaacacaa

agtctacgcctgcgaagtcacccatcagggcctgagctcgcccgtcaca

aagagcttcaacaggggagagtgt.
```

In a further embodiment of the invention, polynucleotides encoding antigen-binding fragments having binding specificity to PACAP comprise, or alternatively consist of, one or more of the polynucleotide sequences of SEQ ID NO: 854; SEQ ID NO: 856; and SEQ ID NO: 858, which correspond to polynucleotides encoding the CDRs (hypervariable regions) of the heavy chain sequence of SEQ ID NO: 841, or the variable heavy chain sequence of SEQ ID NO: 842, and/or one or more of the polynucleotide sequences of SEQ ID NO: 874; SEQ ID NO: 876; and SEQ ID NO: 878, which correspond to the CDRs (hypervariable regions) of the light chain sequence of SEQ ID NO: 861, or the variable light chain sequence of SEQ ID NO: 862, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 853; SEQ ID NO: 855; SEQ ID NO: 857; and SEQ ID NO: 859, which correspond to polynucleotides encoding the FRs (constant regions) of the heavy chain sequence of SEQ ID NO: 841, or the variable heavy chain sequence of SEQ ID NO: 842, and/or one or more of the polynucleotide sequences of SEQ ID NO: 873; SEQ ID NO: 875; SEQ ID NO: 877; and SEQ ID NO: 879, which correspond to the FRs (constant regions) of the light chain sequence of SEQ ID NO: 861, or the variable light chain sequence of SEQ ID NO: 862, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 851 encoding the heavy chain sequence of SEQ ID NO: 841; the polynucleotide SEQ ID NO: 852 encoding the variable heavy chain sequence of SEQ ID NO: 842; the polynucleotide SEQ ID NO: 871 encoding the light chain sequence of SEQ ID NO: 861; the polynucleotide SEQ ID NO: 872 encoding the variable light chain sequence of SEQ ID NO: 862; polynucleotides encoding the CDRs (SEQ ID NO: 854; SEQ ID NO: 856; and SEQ ID NO: 858) of the heavy chain sequence of SEQ ID NO: 841, or the variable heavy chain sequence of SEQ ID NO: 842; polynucleotides encoding the CDRs (SEQ ID NO: 874; SEQ ID NO: 876; and SEQ ID NO: 878) of the light chain sequence of SEQ ID NO: 861, or the variable light chain sequence of SEQ ID NO: 862; polynucleotides encoding the FRs (SEQ ID NO: 853; SEQ ID NO: 855; SEQ ID NO: 857; and SEQ ID NO: 859) of the heavy chain sequence of SEQ ID NO: 841, or the variable heavy chain sequence of SEQ ID NO: 842; and polynucleotides encoding the FRs (SEQ ID NO: 873; SEQ ID NO: 875; SEQ ID NO: 877; and SEQ ID NO: 879) of the light chain sequence of SEQ ID NO: 861, or the variable light chain sequence of SEQ ID NO: 862.

In another embodiment of the invention, polynucleotides of the invention comprise, or alternatively consist of, polynucleotides encoding Fab fragments having binding specificity for PACAP. With respect to antibody Ab21, the polynucleotides encoding the full length Ab21 antibody comprise, or alternatively consist of, the polynucleotide SEQ ID NO: 851 encoding the heavy chain sequence of SEQ ID NO: 841, and the polynucleotide SEQ ID NO: 871 encoding the light chain sequence of SEQ ID NO: 861.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab21 following expression of the full-length polynucleotides in a suitable host. In another embodiment of the invention, anti-PACAP antibodies, such as Ab21 or Fab fragments thereof, can be produced via expression of Ab21 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab21.H

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1211 which encodes the heavy chain sequence of SEQ ID NO: 1201 and which consists of the heavy chain variable region coding sequence of SEQ ID NO: 1212 and the heavy chain constant region coding sequence of SEQ ID NO: 1220.

In another embodiment of the invention, the polynucleotides of the invention comprise, or alternatively consist of, the following polynucleotide sequence encoding the variable heavy chain polypeptide sequence of SEQ ID NO: 1202:

```
                                          (SEQ ID NO: 1212)
gaggtgcagcttgtggagtctgggggaggcttggtccagcctggggggt

ccctgagactctcctgtgcagcctctggaatcgacctcagtagctacta

catgacctgggtccgtcaggctccagggaaggggctggagtggatcgga

ttcattgatgctggtggtagcgcatactacgcgacctgggcaaaaggcc

gattcaccatctccagagacaattccaagaacaccgtgtatcttcaaat
```

-continued gaacagcctgagagctgaggacactgctgtgtatttctgtgctagagat cttgacttgtggggccaagggaccctcgtcaccgtctcgagc.

In another embodiment of the invention, polynucleotides of the invention comprise, or alternatively consist of, the following polynucleotide sequence encoding the constant heavy chain polypeptide sequence of SEQ ID NO: 1210:

(SEQ ID NO: 1220)

gcctccaccaagggcccatcggtcttccccctggcaccctcctccaaga gcacctctgggggcacagcggccctgggctgcctggtcaaggactactt ccccgaaccggtgacggtgtcgtggaactcaggcgccctgaccagcggc gtgcacaccttcccggctgtcctacagtcctcaggactctactccctca gcagcgtggtgaccgtgccctccagcagcttgggcacccagacctacat ctgcaacgtgaatcacaagcccagcaacaccaaggtggacaagaaagtt gagcccaaatcttgtgacaaaactcacacatgcccaccgtgcccagcac ctgaactcctggggggaccgtcagtcttcctcttccccccaaaacccaa ggacaccctcatgatctcccggacccctgaggtcacatgcgtggtggtg gacgtgagccacgaagaccctgaggtcaagttcaactggtacgtggacg gcgtggaggtgcataatgccaagacaaagccgcgggaggagcagtacgc cagcacgtaccgtgtggtcagcgtcctcaccgtcctgcaccaggactgg ctgaatggcaaggagtacaagtgcaaggtctccaacaaagccctcccag cccccatcgagaaaaccatctccaaagccaaagggcagccccgagaacc acaggtgtacaccctgcccccatcccgggaggagatgaccaagaaccag gtcagcctgacctgcctggtcaaaggcttctatcccagcgacatcgccg tggagtgggagagcaatgggcagccggagaacaactacaagaccacgcc tcccgtgctggactccgacggctccttcttcctctacagcaagctcacc gtggacaagagcaggtggcagcaggggaacgtcttctcatgctccgtga tgcatgaggctctgcacaaccactacacgcagaagagcctctccctgtc tccgggtaaa.

In another embodiment of the invention, polynucleotides comprise, or alternatively consist of, the polynucleotide sequence of SEQ ID NO: 1231 which encodes the light chain polypeptide sequence of SEQ ID NO: 1221 and which consists of the light chain variable region coding sequence of SEQ ID NO: 1232 and the light chain constant region coding sequence of SEQ ID NO: 1240.

In another embodiment of the invention, polynucleotides of the invention comprise, or alternatively consist of, the following polynucleotide sequence encoding the variable light chain polypeptide sequence of SEQ ID NO: 1222:

(SEQ ID NO: 1232)

gacgcccagctgacccagtctccttccaccctgtctgcatctgtaggag acagagtcaccatcacttgtaagtccagtgagagcgtttatggtgacta cttagcctggtttcagcagaaaccaggaaaagcccctaagcaactgatc tatgatgcatccactctggcatctggagtcccatcaaggttcagcggca gtggatctggaacagaattcactctcaccatcagcagcctgcagcctga -continued tgattttgcaacttactactgtgcaggcggttatgttagtgcaggtgtt gattcggcggaggaaccaaggtggaaatcaaacgt.

In another embodiment of the invention, polynucleotides of the invention comprise, or alternatively consist of, the following polynucleotide sequence encoding the constant light chain polypeptide sequence of SEQ ID NO: 1230:

(SEQ ID NO: 1240)

acggtagcggccccatctgtcttcatcttcccgccatctgatgagcagt tgaaatctggaactgcctctgttgtgtgcctgctgaataacttctatcc cagagaggccaaagtacagtggaaggtggataacgccctccaatcgggt aactcccaggagagtgtcacagagcaggacagcaaggacagcacctaca gcctcagcagcaccctgacgctgagcaaagcagactacgagaaacacaa agtctacgcctgcgaagtcacccatcagggcctgagctcgcccgtcaca aagagcttcaacaggggagagtgt.

In a further embodiment of the invention, polynucleotides encoding antigen-binding fragments having binding specificity to PACAP comprise, or alternatively consist of, one or more of the polynucleotide sequences of SEQ ID NO: 1214; SEQ ID NO: 1216; and SEQ ID NO: 1218, which correspond to polynucleotides encoding the CDRs (hypervariable regions) of the heavy chain sequence of SEQ ID NO: 1201, or the variable heavy chain sequence of SEQ ID NO: 1202, and/or one or more of the polynucleotide sequences of SEQ ID NO: 1234; SEQ ID NO: 1236; and SEQ ID NO: 1238, which correspond to the CDRs (hypervariable regions) of the light chain sequence of SEQ ID NO: 1221, or the variable light chain sequence of SEQ ID NO: 1222, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1213; SEQ ID NO: 1215; SEQ ID NO: 1217; and SEQ ID NO: 1219, which correspond to polynucleotides encoding the FRs (constant regions) of the heavy chain sequence of SEQ ID NO: 1201, or the variable heavy chain sequence of SEQ ID NO: 1202, and/or one or more of the polynucleotide sequences of SEQ ID NO: 1233; SEQ ID NO: 1235; SEQ ID NO: 1237; and SEQ ID NO: 1239, which correspond to the FRs (constant regions) of the light chain sequence of SEQ ID NO: 1221, or the variable light chain sequence of SEQ ID NO: 1222, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1211 encoding the heavy chain sequence of SEQ ID NO: 1201; the polynucleotide SEQ ID NO: 1212 encoding the variable heavy chain sequence of SEQ ID NO: 1202; the polynucleotide SEQ ID NO: 1231 encoding the light chain sequence of SEQ ID NO: 1221; the polynucleotide SEQ ID NO: 1232 encoding the variable light chain sequence of SEQ ID NO: 1222; polynucleotides encoding the CDRs (SEQ ID NO: 1214; SEQ ID NO: 1216; and SEQ ID NO: 1218) of the heavy chain sequence of SEQ ID NO: 1201, or the variable heavy chain sequence of SEQ ID NO: 1202; polynucleotides encoding the CDRs (SEQ ID NO: 1234; SEQ ID NO: 1236; and SEQ ID NO: 1238) of the light chain sequence of SEQ ID NO: 1221, or the variable light chain sequence of SEQ ID NO: 1222; polynucleotides encoding the FRs (SEQ ID NO: 1213; SEQ ID NO: 1215; SEQ ID NO: 1217; and SEQ ID NO: 1219) of the heavy chain sequence of SEQ ID NO: 1201, or the variable heavy chain sequence of SEQ ID NO: 1202; and polynucleotides encoding the FRs (SEQ ID NO: 1233; SEQ ID NO: 1235; SEQ ID NO: 1237; and SEQ ID NO: 1239) of the light chain sequence of SEQ ID NO: 1221, or the variable light chain sequence of SEQ ID NO: 1222.

In another embodiment of the invention, polynucleotides of the invention comprise, or alternatively consist of, polynucleotides encoding Fab fragments having binding specificity for PACAP. With respect to antibody Ab21.H, the polynucleotides encoding the full length Ab21.H antibody comprise, or alternatively consist of, the polynucleotide SEQ ID NO: 1211 encoding the heavy chain sequence of SEQ ID NO: 1201, and the polynucleotide SEQ ID NO: 1231 encoding the light chain sequence of SEQ ID NO: 1221.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab21.H following expression of the full-length polynucleotides in a suitable host. In another embodiment of the invention, anti-PACAP antibodies, such as Ab21.H or Fab fragments thereof, can be produced via expression of Ab21.H polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab22

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 891 which encodes the heavy chain sequence of SEQ ID NO: 881 and which consists of the heavy chain variable region coding sequence of SEQ ID NO: 892 and the heavy chain constant region coding sequence of SEQ ID NO: 900.

In another embodiment of the invention, the polynucleotides of the invention comprise, or alternatively consist of, the following polynucleotide sequence encoding the variable heavy chain polypeptide sequence of SEQ ID NO: 882:

```
                                            (SEQ ID NO: 892)
caggagcagaggtggagtccgggggaggcctggtccagcctgagggatcc
ctgacactcacctgcacagcctaggattcgacttcagtagcaatgcaatg
tgctgggtccgccaggctccagggaagggcctggagtggatcggatccat
ttataatgctgatggtaagaattattacgcgatttgggcgaaaggccgat
tcaccataccagaacctcgtcgaccacggtgactagcaaatgaccagtag
acagccgcggacacggccacctatttctgtgcgagagactttgacttgtg
gggccagggcaccctcgtcaccgtctcgagc.
```

In another embodiment of the invention, polynucleotides of the invention comprise, or alternatively consist of, the following polynucleotide sequence encoding the constant heavy chain polypeptide sequence of SEQ ID NO: 890:

```
                                            (SEQ ID NO: 900)
gcctccaccaagggcccatcggtcttccccctggcaccctcctccaaga
gcacctctgggggcacagcggccctgggctgcctggtcaaggactactt
ccccgaaccggtgacggtgtcgtggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacgcgagagtt
gagcccaaatcttgtgacaaaactcacacatgcccaccgtgcccagcac
ctgaactcctggggggaccgtcagtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacgc
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggaggagatgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacgcagaagagcctctccctgtc
tccgggtaaa.
```

In another embodiment of the invention, polynucleotides comprise, or alternatively consist of, the polynucleotide sequence of SEQ ID NO: 911 which encodes the light chain polypeptide sequence of SEQ ID NO: 901 and which consists of the light chain variable region coding sequence of SEQ ID NO: 912 and the light chain constant region coding sequence of SEQ ID NO: 920.

In another embodiment of the invention, polynucleotides of the invention comprise, or alternatively consist of, the following polynucleotide sequence encoding the variable light chain polypeptide sequence of SEQ ID NO: 902:

(SEQ ID NO: 912)

gcagccgtgctgacccagacaccatcgcccgtgtctgcagctgtgggag gcacagtcaccatcaattgccagtccagtcagagtgtttatgataacga ctggttagcctggttccagcagaaaccagggcagcctcccaagctcctg atctatctgacatccactctggcatctggagtcccatcgcggttcagcg gcagtggatctgggacacagttcactctcaccatcagtggtgtgcagtg tgacgatgctgccacttactactgtctaggcggctatgatgaagatggt gatacgcatgttttcggcggagggaccgaggtggtggtcaaacgt.

In another embodiment of the invention, polynucleotides of the invention comprise, or alternatively consist of, the following polynucleotide sequence encoding the constant light chain polypeptide sequence of SEQ ID NO: 910:

(SEQ ID NO: 920)

acggtagcggccccatctgtcttcatcttcccgccatctgatgagcagt tgaaatctggaactgcctctgttgtgtgcctgctgaataacttctatcc cagagaggccaaagtacagtggaaggtggataacgccctccaatcgggt aactcccaggagagtgtcacagagcaggacagcaaggacagcacctaca gcctcagcagcaccctgacgctgagcaaagcagactacgagaaacacaa agtctacgcctgcgaagtcacccatcagggcctgagctcgcccgtcaca aagagcttcaacaggggagagtgt.

In a further embodiment of the invention, polynucleotides encoding antigen-binding fragments having binding specificity to PACAP comprise, or alternatively consist of, one or more of the polynucleotide sequences of SEQ ID NO: 894; SEQ ID NO: 896; and SEQ ID NO: 898, which correspond to polynucleotides encoding the CDRs (hypervariable regions) of the heavy chain sequence of SEQ ID NO: 881, or the variable heavy chain sequence of SEQ ID NO: 882, and/or one or more of the polynucleotide sequences of SEQ ID NO: 914; SEQ ID NO: 916; and SEQ ID NO: 918, which correspond to the CDRs (hypervariable regions) of the light chain sequence of SEQ ID NO: 901, or the variable light chain sequence of SEQ ID NO: 902, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 893; SEQ ID NO: 895; SEQ ID NO: 897; and SEQ ID NO: 899, which correspond to polynucleotides encoding the FRs (constant regions) of the heavy chain sequence of SEQ ID NO: 881, or the variable heavy chain sequence of SEQ ID NO: 882, and/or one or more of the polynucleotide sequences of SEQ ID NO: 913; SEQ ID NO: 915; SEQ ID NO: 917; and SEQ ID NO: 919, which correspond to the FRs (constant regions) of the light chain sequence of SEQ ID NO: 901, or the variable light chain sequence of SEQ ID NO: 902, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 891 encoding the heavy chain sequence of SEQ ID NO: 881; the polynucleotide SEQ ID NO: 892 encoding the variable heavy chain sequence of SEQ ID NO: 882; the polynucleotide SEQ ID NO: 911 encoding the light chain sequence of SEQ ID NO: 901; the polynucleotide SEQ ID NO: 912 encoding the variable light chain sequence of SEQ ID NO: 902; polynucleotides encoding the CDRs (SEQ ID NO: 894; SEQ ID NO: 896; and SEQ ID NO: 898) of the heavy chain sequence of SEQ ID NO: 881, or the variable heavy chain sequence of SEQ ID NO: 882; polynucleotides encoding the CDRs (SEQ ID NO: 914; SEQ ID NO: 916; and SEQ ID NO: 918) of the light chain sequence of SEQ ID NO: 901, or the variable light chain sequence of SEQ ID NO: 902; polynucleotides encoding the FRs (SEQ ID NO: 893; SEQ ID NO: 895; SEQ ID NO: 897; and SEQ ID NO: 899) of the heavy chain sequence of SEQ ID NO: 881, or the variable heavy chain sequence of SEQ ID NO: 882; and polynucleotides encoding the FRs (SEQ ID NO: 913; SEQ ID NO: 915; SEQ ID NO: 917; and SEQ ID NO: 919) of the light chain sequence of SEQ ID NO: 901, or the variable light chain sequence of SEQ ID NO: 902.

In another embodiment of the invention, polynucleotides of the invention comprise, or alternatively consist of, polynucleotides encoding Fab fragments having binding specificity for PACAP. With respect to antibody Ab22, the polynucleotides encoding the full length Ab22 antibody comprise, or alternatively consist of, the polynucleotide SEQ ID NO: 891 encoding the heavy chain sequence of SEQ ID NO: 881, and the polynucleotide SEQ ID NO: 911 encoding the light chain sequence of SEQ ID NO: 901.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab22 following expression of the full-length polynucleotides in a suitable host. In another embodiment of the invention, anti-PACAP antibodies, such as Ab22 or Fab fragments thereof, can be produced via expression of Ab22 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab23

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 931 which encodes the heavy chain sequence of SEQ ID NO: 921 and which consists of the heavy chain variable region coding sequence of SEQ ID NO: 932 and the heavy chain constant region coding sequence of SEQ ID NO: 940.

In another embodiment of the invention, the polynucleotides of the invention comprise, or alternatively consist of, the following polynucleotide sequence encoding the variable heavy chain polypeptide sequence of SEQ ID NO: 922:

(SEQ ID NO: 932)
cagtcggtggaggagtccgggggtcgcctggtcacgcctgggacacccc tgacactcacctgcaccgtactggattaccctcaataactatgcaatga gagggtccgccaggctccagggaaggggctggaatggatcggaatcatg ggtgttaatgatatcacatactacgcgagagggcgaaaggccgattcac cataccaaaacctcgaccacggtggatctgaaaatgaccagtctgacaa ccgaggacacggccacctatttctgtactagagagatccgtgatgatgg tgatagttctgataagttgtggggcccgggcaccctcgtcaccgtctcg agc.

In another embodiment of the invention, polynucleotides of the invention comprise, or alternatively consist of, the following polynucleotide sequence encoding the constant heavy chain polypeptide sequence of SEQ ID NO: 930:

(SEQ ID NO: 940)
gcctccaccaagggcccatcggtcttccccctggcaccctcctccaaga gcacctctgggggcacagcggccctgggctgcctggtcaaggactactt ccccgaaccggtgacggtgtcgtggaactcaggcgccctgaccagcggc gtgcacaccttcccggctgtcctacagtcctcaggactctactccctca gcagcgtggtgaccgtgccctccagcagcttgggcacccagacctacat ctgcaacgtgaatcacaagcccagcaacaccaaggtggacgcgagagtt gagcccaaatcttgtgacaaaactcacacatgcccaccgtgcccagcac ctgaactcctggggggaccgtcagtcttcctcttccccccaaaacccaa ggacaccctcatgatctcccggacccctgaggtcacatgcgtggtggtg gacgtgagccacgaagaccctgaggtcaagttcaactggtacgtggacg gcgtggaggtgcataatgccaagacaaagccgcgggaggagcagtacgc cagcacgtaccgtgtggtcagcgtcctcaccgtcctgcaccaggactgg ctgaatggcaaggagtacaagtgcaaggtctccaacaaagccctcccag cccccatcgagaaaaccatctccaaagccaaagggcagccccgagaacc acaggtgtacaccctgcccccatcccgggaggagatgaccaagaaccag gtcagcctgacctgcctggtcaaaggcttctatcccagcgacatcgccg tggagtgggagagcaatgggcagccggagaacaactacaagaccacgcc tcccgtgctggactccgacggctccttcttcctctacagcaagctcacc -continued gtggacaagagcaggtggcagcaggggaacgtcttctcatgctccgtga tgcatgaggctctgcacaaccactacacgcagaagagcctctccctgtc tccgggtaaa.

In another embodiment of the invention, polynucleotides comprise, or alternatively consist of, the polynucleotide sequence of SEQ ID NO: 951 which encodes the light chain polypeptide sequence of SEQ ID NO: 941 and which consists of the light chain variable region coding sequence of SEQ ID NO: 952 and the light chain constant region coding sequence of SEQ ID NO: 960.

In another embodiment of the invention, polynucleotides of the invention comprise, or alternatively consist of, the following polynucleotide sequence encoding the variable light chain polypeptide sequence of SEQ ID NO: 942:

(SEQ ID NO: 952)
gccatcaaaatgacccagactccatcctccgtgtctgcagctgtgggag gcacagtcaccatcaattgccaggccagtgaggacatttacaccaattt agcctggtatcagcagaaaccagggcagcctcccaacctcctgatctat gatgcatccgatctggcatctggggtcccgtcgcggttcagcggcagtg gagatgggacacagttcactctcaccatcagcgccgtgcagtgtgaaga tgctgccacttactactgtcaaggtgttgcttggagtagtaatactggt tatggttccgctttcggcggagggaccgaggtggtggtcaaacgt.

In another embodiment of the invention, polynucleotides of the invention comprise, or alternatively consist of, the following polynucleotide sequence encoding the constant light chain polypeptide sequence of SEQ ID NO: 950:

(SEQ ID NO: 960)
acggtagcggccccatctgtcttcatcttcccgccatctgatgagcagt tgaaatctggaactgcctagttgtgtgcctgctgaataacttctatccc agagaggccaaagtacagtggaaggtggataacgccaccaatcgggtaa ctcccaggagagtgtcacagagcaggacagcaaggacagcacctacagc ctcagcagcaccctgacgctgagcaaagcagactacgagaaacacaaag tctacgcctgcgaagtcacccatcagggcctgagctcgcccgtcacaaa gagcttcaacaggggagagtgt.

In a further embodiment of the invention, polynucleotides encoding antigen-binding fragments having binding specificity to PACAP comprise, or alternatively consist of, one or more of the polynucleotide sequences of SEQ ID NO: 934; SEQ ID NO: 936; and SEQ ID NO: 938, which correspond to polynucleotides encoding the CDRs (hypervariable regions) of the heavy chain sequence of SEQ ID NO: 921, or the variable heavy chain sequence of SEQ ID NO: 922, and/or one or more of the polynucleotide sequences of SEQ ID NO: 954; SEQ ID NO: 956; and SEQ ID NO: 958, which correspond to the CDRs (hypervariable regions) of the light chain sequence of SEQ ID NO: 941, or the variable light chain sequence of SEQ ID NO: 942, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 933; SEQ ID NO: 935; SEQ ID NO: 937; and SEQ ID NO: 939, which correspond to polynucleotides encoding the FRs (constant regions) of the heavy chain sequence of SEQ ID NO: 921, or the variable heavy chain sequence of SEQ ID NO: 922, and/or one or more of the polynucleotide sequences of SEQ ID NO: 953; SEQ ID NO: 955; SEQ ID NO: 957; and SEQ ID NO: 959, which correspond to the FRs (constant regions) of the light chain sequence of SEQ ID NO: 941, or the variable light chain sequence of SEQ ID NO: 942, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 931 encoding the heavy chain sequence of SEQ ID NO: 921; the polynucleotide SEQ ID NO: 932 encoding the variable heavy chain sequence of SEQ ID NO: 922; the polynucleotide SEQ ID NO: 951 encoding the light chain sequence of SEQ ID NO: 941; the polynucleotide SEQ ID NO: 952 encoding the variable light chain sequence of SEQ ID NO: 942; polynucleotides encoding the CDRs (SEQ ID NO: 934; SEQ ID NO: 936; and SEQ ID NO: 938) of the heavy chain sequence of SEQ ID NO: 921, or the variable heavy chain sequence of SEQ ID NO: 922; polynucleotides encoding the CDRs (SEQ ID NO: 954; SEQ ID NO: 956; and SEQ ID NO: 958) of the light chain sequence of SEQ ID NO: 941, or the variable light chain sequence of SEQ ID NO: 942; polynucleotides encoding the FRs (SEQ ID NO: 933; SEQ ID NO: 935; SEQ ID NO: 937; and SEQ ID NO: 939) of the heavy chain sequence of SEQ ID NO: 921, or the variable heavy chain sequence of SEQ ID NO: 922; and polynucleotides encoding the FRs (SEQ ID NO: 953; SEQ ID NO: 955; SEQ ID NO: 957; and SEQ ID NO: 959) of the light chain sequence of SEQ ID NO: 941, or the variable light chain sequence of SEQ ID NO: 942.

In another embodiment of the invention, polynucleotides of the invention comprise, or alternatively consist of, polynucleotides encoding Fab fragments having binding specificity for PACAP. With respect to antibody Ab23, the polynucleotides encoding the full length Ab23 antibody comprise, or alternatively consist of, the polynucleotide SEQ ID NO: 931 encoding the heavy chain sequence of SEQ ID NO: 921, and the polynucleotide SEQ ID NO: 951 encoding the light chain sequence of SEQ ID NO: 941.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab23 following expression of the full-length polynucleotides in a suitable host. In another embodiment of the invention, anti-PACAP antibodies, such as Ab23 or Fab fragments thereof, can be produced via expression of Ab23 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris.*

Antibody Ab10.H2

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1291 which encodes the heavy chain sequence of SEQ ID NO: 1281 and which consists of the heavy chain variable region coding sequence of SEQ ID NO: 1292 and the heavy chain constant region coding sequence of SEQ ID NO: 1300.

In another embodiment of the invention, the polynucleotides of the invention comprise, or alternatively consist of, the following polynucleotide sequence encoding the variable heavy chain polypeptide sequence of SEQ ID NO: 1282:

```
                                          (SEQ ID NO: 1292)
gaggtgcagcttgtggagtagggggaggcttggtccagcctgggggtc

cctgagactacctgtgcagcctaggaatcgacctcaatagctactacat

gacctgggtccgtcaggctccagggaaggggctggagtggatcggattc

attgatgctggtggtgacgcatactacgcgagagggcgaaaggccgatt

caccataccagagacaattccaagaacaccgtgtatcttcaaatgaaca

gcctgagagctgaggacactgctgtgtatttctgtgctagagatcttga

cttgtggggccaagggaccctcgtcaccgtctcgagc.
```

In another embodiment of the invention, polynucleotides of the invention comprise, or alternatively consist of, the following polynucleotide sequence encoding the constant heavy chain polypeptide sequence of SEQ ID NO: 1290:

```
                                          (SEQ ID NO: 1300)
gcctccaccaagggcccatcggtcttccccctggcaccctcctccaaga

gcacctctgggggcacagcggccctgggctgcctggtcaaggactactt

ccccgaaccggtgacggtgtcgtggaactcaggcgccctgaccagcggc

gtgcacaccttcccggctgtcctacagtcctcaggactctactccctca

gcagcgtggtgaccgtgccctccagcagcttgggcacccagacctacat

ctgcaacgtgaatcacaagcccagcaacaccaaggtggacaagaaagtt

gagcccaaatcttgtgacaaaactcacacatgcccaccgtgcccagcac

ctgaactcctggggggaccgtcagtcttcctcttccccccaaaacccaa

ggacaccctcatgatctcccggacccctgaggtcacatgcgtggtggtg

gacgtgagccacgaagaccctgaggtcaagttcaactggtacgtggacg

gcgtggaggtgcataatgccaagacaaagccgcgggaggagcagtacgc
```

-continued cagcacgtaccgtgtggtcagcgtcctcaccgtcctgcaccaggactgg ctgaatggcaaggagtacaagtgcaaggtctccaacaaagccctcccag cccccatcgagaaaaccatctccaaagccaaagggcagccccgagaacc acaggtgtacaccctgcccccatcccgggaggagatgaccaagaaccag gtcagcctgacctgcctggtcaaaggcttctatcccagcgacatcgccg tggagtgggagagcaatgggcagccggagaacaactacaagaccacgcc tcccgtgctggactccgacggctccttcttcctctacagcaagctcacc gtggacaagagcaggtggcagcaggggaacgtcttctcatgctccgtga tgcatgaggctctgcacaaccactacacgcagaagagcctctccctgtc tccgggtaaa.

In another embodiment of the invention, polynucleotides comprise, or alternatively consist of, the polynucleotide sequence of SEQ ID NO: 1311 which encodes the light chain polypeptide sequence of SEQ ID NO: 1301 and which consists of the light chain variable region coding sequence of SEQ ID NO: 1312 and the light chain constant region coding sequence of SEQ ID NO: 1320.

In another embodiment of the invention, polynucleotides of the invention comprise, or alternatively consist of, the following polynucleotide sequence encoding the variable light chain polypeptide sequence of SEQ ID NO: 1302:

(SEQ ID NO: 1312)

gccgtgctgacccagtctccttccaccctgtctgcatctgtaggagaca gagtcaccatcacttgtcagtccagtgagagtgtttacggtaactactt agcctggtttcagcagaaaccaggaaaagcccctaagttcctgatctat gaagcatccaaactggaatctggagtcccatcaaggttcagcggcagtg gatctggaacagaattcactctcaccatcagcagcctgcagcctgatga ttttgcaacttactactgtgcaggcggtgatattagtgaaggtgttgct ttcggcggaggaaccaaggtggaaatcaaacgt.

In another embodiment of the invention, polynucleotides of the invention comprise, or alternatively consist of, the following polynucleotide sequence encoding the constant light chain polypeptide sequence of SEQ ID NO: 1310:

(SEQ ID NO: 1320)

acggtagcggccccatctgtcttcatcttcccgccatctgatgagcagt tgaaatctggaactgcctctgttgtgtgcctgctgaataacttctatcc cagagaggccaaagtacagtggaaggtggataacgccctccaatcgggt aactcccaggagagtgtcacagagcaggacagcaaggacagcacctaca gcctcagcagcaccctgacgctgagcaaagcagactacgagaaacacaa agtctacgcctgcgaagtcacccatcagggcctgagctcgcccgtcaca aagagcttcaacaggggagagtgt.

In a further embodiment of the invention, polynucleotides encoding antigen-binding fragments having binding specificity to PACAP comprise, or alternatively consist of, one or more of the polynucleotide sequences of SEQ ID NO: 1294; SEQ ID NO: 1296; and SEQ ID NO: 1298, which correspond to polynucleotides encoding the CDRs (hypervariable regions) of the heavy chain sequence of SEQ ID NO: 1281, or the variable heavy chain sequence of SEQ ID NO: 1282, and/or one or more of the polynucleotide sequences of SEQ ID NO: 1314; SEQ ID NO: 1316; and SEQ ID NO: 1318, which correspond to the CDRs (hypervariable regions) of the light chain sequence of SEQ ID NO: 1301, or the variable light chain sequence of SEQ ID NO: 1302, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1293; SEQ ID NO: 1295; SEQ ID NO: 1297; and SEQ ID NO: 1299, which correspond to polynucleotides encoding the FRs (constant regions) of the heavy chain sequence of SEQ ID NO: 1281, or the variable heavy chain sequence of SEQ ID NO: 1282, and/or one or more of the polynucleotide sequences of SEQ ID NO: 1313; SEQ ID NO: 1315; SEQ ID NO: 1317; and SEQ ID NO: 1319, which correspond to the FRs (constant regions) of the light chain sequence of SEQ ID NO: 1301, or the variable light chain sequence of SEQ ID NO: 1302, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1291 encoding the heavy chain sequence of SEQ ID NO: 1281; the polynucleotide SEQ ID NO: 1292 encoding the variable heavy chain sequence of SEQ ID NO: 1282; the polynucleotide SEQ ID NO: 1311 encoding the light chain sequence of SEQ ID NO: 1301; the polynucleotide SEQ ID NO: 1312 encoding the variable light chain sequence of SEQ ID NO: 1302; polynucleotides encoding the CDRs (SEQ ID NO: 1294; SEQ ID NO: 1296; and SEQ ID NO: 1298) of the heavy chain sequence of SEQ ID NO: 1281, or the variable heavy chain sequence of SEQ ID NO: 1282; polynucleotides encoding the CDRs (SEQ ID NO: 1314; SEQ ID NO: 1316; and SEQ ID NO: 1318) of the light chain sequence of SEQ ID NO: 1301, or the variable light chain sequence of SEQ ID NO: 1302; polynucleotides encoding the FRs (SEQ ID NO: 1293; SEQ ID NO: 1295; SEQ ID NO: 1297; and SEQ ID NO: 1299) of the heavy chain sequence of SEQ ID NO: 1281, or the variable heavy chain sequence of SEQ ID NO: 1282; and polynucleotides encoding the FRs (SEQ ID NO: 1313; SEQ ID NO: 1315; SEQ ID NO: 1317; and SEQ ID NO: 1319) of the light chain sequence of SEQ ID NO: 1301, or the variable light chain sequence of SEQ ID NO: 1302.

In another embodiment of the invention, polynucleotides of the invention comprise, or alternatively consist of, polynucleotides encoding Fab fragments having binding specificity for PACAP. With respect to antibody Ab10.H2, the polynucleotides encoding the full length Ab10.H2 antibody comprise, or alternatively consist of, the polynucleotide SEQ ID NO: 1291 encoding the heavy chain sequence of SEQ ID NO: 1281, and the polynucleotide SEQ ID NO: 1311 encoding the light chain sequence of SEQ ID NO: 1301.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab10.H2 following expression of the full-length polynucleotides in a suitable host. In another embodiment of the invention, anti-PACAP antibodies, such as Ab10.H2 or Fab fragments thereof, can be produced via expression of Ab10.H2 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab10.H3

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1331 which encodes the heavy chain sequence of SEQ ID NO: 1321 and which consists of the heavy chain variable region coding sequence of SEQ ID NO: 1332 and the heavy chain constant region coding sequence of SEQ ID NO: 1340.

In another embodiment of the invention, the polynucleotides of the invention comprise, or alternatively consist of, the following polynucleotide sequence encoding the variable heavy chain polypeptide sequence of SEQ ID NO: 1322:

(SEQ ID NO: 1332)
gaggtgcagcttgtggagtctgggggaggcttggtccagcctggggggt ccctgagactctcctgtgcagcctctggaatcgacctcaatagctacta catgacctgggtccgtcaggctccagggaaggggctggagtggatcgga ttcattgatgctggtggtgacgcatactacgcgagctgggcgaaaggcc gattcaccatctccagagacaattccaagaacaccgtgtatcttcaaat gaacagcctgagagctgaggacactgctgtgtatttctgtgctagagat cttgacttgtggggccaagggaccctcgtcaccgtctcgagc.

In another embodiment of the invention, polynucleotides of the invention comprise, or alternatively consist of, the following polynucleotide sequence encoding the constant heavy chain polypeptide sequence of SEQ ID NO: 1330:

(SEQ ID NO: 1340)
gcctccaccaagggcccatcggtcttccccctggcaccctcctccaaga gcacctctgggggcacagcggccctgggctgcctggtcaaggactactt -continued ccccgaaccggtgacggtgtcgtggaactcaggcgccctgaccagcggc gtgcacaccttcccggctgtcctacagtcctcaggactctactccctca gcagcgtggtgaccgtgccctccagcagcttgggcacccagacctacat ctgcaacgtgaatcacaagcccagcaacaccaaggtggacaagaaagtt gagcccaaatcttgtgacaaaactcacacatgcccaccgtgcccagcac ctgaactcctggggggaccgtcagtcttcctcttccccccaaaacccaa ggacaccctcatgatctcccggacccctgaggtcacatgcgtggtggtg gacgtgagccacgaagaccctgaggtcaagttcaactggtacgtggacg gcgtggaggtgcataatgccaagacaaagccgcgggaggagcagtacgc cagcacgtaccgtgtggtcagcgtcctcaccgtcctgcaccaggactgg ctgaatggcaaggagtacaagtgcaaggtctccaacaaagccctcccag cccccatcgagaaaaccatctccaaagccaaagggcagccccgagaacc acaggtgtacaccctgcccccatcccgggaggagatgaccaagaaccag gtcagcctgacctgcctggtcaaaggcttctatcccagcgacatcgccg tggagtgggagagcaatgggcagccggagaacaactacaagaccacgcc tcccgtgctggactccgacggctccttcttcctctacagcaagctcacc gtggacaagagcaggtggcagcaggggaacgtcttctcatgctccgtga tgcatgaggctctgcacaaccactacacgcagaagagcctctccctgtc tccgggtaaa.

In another embodiment of the invention, polynucleotides comprise, or alternatively consist of, the polynucleotide sequence of SEQ ID NO: 1351 which encodes the light chain polypeptide sequence of SEQ ID NO: 1341 and which consists of the light chain variable region coding sequence of SEQ ID NO: 1352 and the light chain constant region coding sequence of SEQ ID NO: 1360.

In another embodiment of the invention, polynucleotides of the invention comprise, or alternatively consist of, the following polynucleotide sequence encoding the variable light chain polypeptide sequence of SEQ ID NO: 1342:

(SEQ ID NO: 1352)
gacatccagctgacccagtctccttccaccctgtctgcatctgtaggag acagagtcaccatcacttgtcagtccagtgagagtgtttacggtaacta cttagcctggtttcagcagaaaccaggaaaagcccctaagttcctgatc tatgaagcatccaaactggaatctggagtcccatcaaggttcagcggca gtggatctggaacagaattcactctcaccatcagcagcctgcagcctga tgattttgcaacttactactgtgcaggcggtgatattagtgaaggtgtt gctttcggcggaggaaccaaggtggaaatcaaacgt.

In another embodiment of the invention, polynucleotides of the invention comprise, or alternatively consist of, the following polynucleotide sequence encoding the constant light chain polypeptide sequence of SEQ ID NO: 1350:

(SEQ ID NO: 1360)

```
acggtagcggccccatctgtcttcatcttcccgccatctgatgagcagt
tgaaatctggaactgcctctgttgtgtgcctgctgaataacttctatcc
cagagaggccaaagtacagtggaaggtggataacgccctccaatcgggt
aactcccaggagagtgtcacagagcaggacagcaaggacagcacctaca
gcctcagcagcaccctgacgctgagcaaagcagactacgagaaacacaa
agtctacgcctgcgaagtcacccatcagggcctgagctcgcccgtcaca
aagagcttcaacaggggagagtgt.
```

In a further embodiment of the invention, polynucleotides encoding antigen-binding fragments having binding specificity to PACAP comprise, or alternatively consist of, one or more of the polynucleotide sequences of SEQ ID NO: 1334; SEQ ID NO: 1336; and SEQ ID NO: 1338, which correspond to polynucleotides encoding the CDRs (hypervariable regions) of the heavy chain sequence of SEQ ID NO: 1321, or the variable heavy chain sequence of SEQ ID NO: 1322, and/or one or more of the polynucleotide sequences of SEQ ID NO: 1354; SEQ ID NO: 1356; and SEQ ID NO: 1358, which correspond to the CDRs (hypervariable regions) of the light chain sequence of SEQ ID NO: 1341, or the variable light chain sequence of SEQ ID NO: 1342, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1333; SEQ ID NO: 1335; SEQ ID NO: 1337; and SEQ ID NO: 1339, which correspond to polynucleotides encoding the FRs (constant regions) of the heavy chain sequence of SEQ ID NO: 1321, or the variable heavy chain sequence of SEQ ID NO: 1322, and/or one or more of the polynucleotide sequences of SEQ ID NO: 1353; SEQ ID NO: 1355; SEQ ID NO: 1357; and SEQ ID NO: 1359, which correspond to the FRs (constant regions) of the light chain sequence of SEQ ID NO: 1341, or the variable light chain sequence of SEQ ID NO: 1342, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1331 encoding the heavy chain sequence of SEQ ID NO: 1321; the polynucleotide SEQ ID NO: 1332 encoding the variable heavy chain sequence of SEQ ID NO: 1322; the polynucleotide SEQ ID NO: 1351 encoding the light chain sequence of SEQ ID NO: 1341; the polynucleotide SEQ ID NO: 1352 encoding the variable light chain sequence of SEQ ID NO: 1342; polynucleotides encoding the CDRs (SEQ ID NO: 1334; SEQ ID NO: 1336; and SEQ ID NO: 1338) of the heavy chain sequence of SEQ ID NO: 1321, or the variable heavy chain sequence of SEQ ID NO: 1322; polynucleotides encoding the CDRs (SEQ ID NO: 1354; SEQ ID NO: 1356; and SEQ ID NO: 1358) of the light chain sequence of SEQ ID NO: 1341, or the variable light chain sequence of SEQ ID NO: 1342; polynucleotides encoding the FRs (SEQ ID NO: 1333; SEQ ID NO: 1335; SEQ ID NO: 1337; and SEQ ID NO: 1339) of the heavy chain sequence of SEQ ID NO: 1321, or the variable heavy chain sequence of SEQ ID NO: 1322; and polynucleotides encoding the FRs (SEQ ID NO: 1353; SEQ ID NO: 1355; SEQ ID NO: 1357; and SEQ ID NO: 1359) of the light chain sequence of SEQ ID NO: 1341, or the variable light chain sequence of SEQ ID NO: 1342.

In another embodiment of the invention, polynucleotides of the invention comprise, or alternatively consist of, polynucleotides encoding Fab fragments having binding specificity for PACAP. With respect to antibody Ab10.H3, the polynucleotides encoding the full length Ab10.H3 antibody comprise, or alternatively consist of, the polynucleotide SEQ ID NO: 1331 encoding the heavy chain sequence of SEQ ID NO: 1321, and the polynucleotide SEQ ID NO: 1351 encoding the light chain sequence of SEQ ID NO: 1341.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab10.H3 following expression of the full-length polynucleotides in a suitable host. In another embodiment of the invention, anti-PACAP antibodies, such as Ab10.H3 or Fab fragments thereof, can be produced via expression of Ab10.H3 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab10.H4

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1371 which encodes the heavy chain sequence of SEQ ID NO: 1361 and which consists of the heavy chain variable region coding sequence of SEQ ID NO: 1372 and the heavy chain constant region coding sequence of SEQ ID NO: 1380.

In another embodiment of the invention, the polynucleotides of the invention comprise, or alternatively consist of, the following polynucleotide sequence encoding the variable heavy chain polypeptide sequence of SEQ ID NO: 1362:

(SEQ ID NO: 1372)
gaggtgcagcttgtggagtctgggggaggcttggtccagcctggggggt ccctgagactctcctgtgcagcctctggaatcgacctcaatagctacta catgacctgggtccgtcaggctccagggaaggggctggagtggatcgga ttcattgatgctggtggtgacgcatactacgcgagctgggcgaaaggcc gattcaccatctccagagacaattccaagaacaccgtgtatcttcaaat gaacagcctgagagctgaggacactgctgtgtatttctgtgctagagat cttgacttgtggggccaagggaccctcgtcaccgtctcgagc.

In another embodiment of the invention, polynucleotides of the invention comprise, or alternatively consist of, the following polynucleotide sequence encoding the constant heavy chain polypeptide sequence of SEQ ID NO: 1370:

(SEQ ID NO: 1380)
gcctccaccaagggcccatcggtcttccccctggcaccctcctccaaga gcacctctgggggcacagcggccctgggctgcctggtcaaggactactt ccccgaaccggtgacggtgtcgtggaactcaggcgccctgaccagcggc gtgcacaccttcccggctgtcctacagtcctcaggactctactccctca gcagcgtggtgaccgtgccctccagcagcttgggcacccagacctacat ctgcaacgtgaatcacaagcccagcaacaccaaggtggacaagaaagtt gagcccaaatcttgtgacaaaactcacacatgcccaccgtgcccagcac ctgaactcctggggggaccgtcagtcttcctcttccccccaaaacccaa ggacaccctcatgatctcccggacccctgaggtcacatgcgtggtggtg gacgtgagccacgaagaccctgaggtcaagttcaactggtacgtggacg gcgtggaggtgcataatgccaagacaaagccgcgggaggagcagtacgc cagcacgtaccgtgtggtcagcgtcctcaccgtcctgcaccaggactgg ctgaatggcaaggagtacaagtgcaaggtctccaacaaagccctcccag cccccatcgagaaaaccatctccaaagccaaagggcagccccgagaacc acaggtgtacaccctgcccccatcccgggaggagatgaccaagaaccag gtcagcctgacctgcctggtcaaaggcttctatcccagcgacatcgccg tggagtgggagagcaatgggcagccggagaacaactacaagaccacgcc tcccgtgctggactccgacggctccttcttcctctacagcaagctcacc gtggacaagagcaggtggcagcaggggaacgtcttctcatgctccgtga tgcatgaggctctgcacaaccactacacgcagaagagcctctccctgtc tccgggtaaa.

In another embodiment of the invention, polynucleotides comprise, or alternatively consist of, the polynucleotide sequence of SEQ ID NO: 1391 which encodes the light chain polypeptide sequence of SEQ ID NO: 1381 and which consists of the light chain variable region coding sequence of SEQ ID NO: 1392 and the light chain constant region coding sequence of SEQ ID NO: 1400.

In another embodiment of the invention, polynucleotides of the invention comprise, or alternatively consist of, the following polynucleotide sequence encoding the variable light chain polypeptide sequence of SEO ID NO: 1382:

(SEQ ID NO: 1392)
gacatcgtgctgacccagtctccttccaccctgtctgcatctgtaggag acagagtcaccatcacttgtcagtccagtgagagtgtttacggtaacta cttagcctggtttcagcagaaaccaggaaaagcccctaagttcctgatc tatgaagcatccaaactggaatctggagtcccatcaaggttcagcggca gtggatctggaacagaattcactctcaccatcagcagcctgcagcctga tgattttgcaacttactactgtgcaggcggtgatattagtgaaggtgtt gctttcggcggaggaaccaaggtggaaatcaaacgt.

In another embodiment of the invention, polynucleotides of the invention comprise, or alternatively consist of, the following polynucleotide sequence encoding the constant light chain polypeptide sequence of SEQ ID NO: 1390:

(SEQ ID NO: 1400)
acggtagcggccccatctgtcttcatcttcccgccatctgatgagcagt tgaaatctggaactgcctctgttgtgtgcctgctgaataacttctatcc cagagaggccaaagtacagtggaaggtggataacgccctccaatcgggt aactcccaggagagtgtcacagagcaggacagcaaggacagcacctaca gcctcagcagcaccctgacgctgagcaaagcagactacgagaaacacaa agtctacgcctgcgaagtcacccatcagggcctgagctcgcccgtcaca aagagcttcaacaggggagagtgt.

In a further embodiment of the invention, polynucleotides encoding antigen-binding fragments having binding specificity to PACAP comprise, or alternatively consist of, one or more of the polynucleotide sequences of SEQ ID NO: 1374; SEQ ID NO: 1376; and SEQ ID NO: 1378, which correspond to polynucleotides encoding the CDRs (hypervariable regions) of the heavy chain sequence of SEQ ID NO: 1361, or the variable heavy chain sequence of SEQ ID NO: 1362, and/or one or more of the polynucleotide sequences of SEQ ID NO: 1394; SEQ ID NO: 1396; and SEQ ID NO: 1398, which correspond to the CDRs (hypervariable regions) of the light chain sequence of SEQ ID NO: 1381, or the variable light chain sequence of SEQ ID NO: 1382, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1373; SEQ ID NO: 1375; SEQ ID NO: 1377; and SEQ ID NO: 1379, which correspond to polynucleotides encoding the FRs (constant regions) of the heavy chain sequence of SEQ ID NO: 1361, or the variable heavy chain sequence of SEQ ID NO: 1362, and/or one or more of the polynucleotide sequences of SEQ ID NO: 1393; SEQ ID NO: 1395; SEQ ID NO: 1397; and SEQ ID NO: 1399, which correspond to the FRs (constant regions) of the light chain sequence of SEQ ID NO: 1381, or the variable light chain sequence of SEQ ID NO: 1382, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1371 encoding the heavy chain sequence of SEQ ID NO: 1361; the polynucleotide SEQ ID NO: 1372 encoding the variable heavy chain sequence of SEQ ID NO: 1362; the polynucleotide SEQ ID NO: 1391 encoding the light chain sequence of SEQ ID NO: 1381; the polynucleotide SEQ ID NO: 1392 encoding the variable light chain sequence of SEQ ID NO: 1382; polynucleotides encoding the CDRs (SEQ ID NO: 1374; SEQ ID NO: 1376; and SEQ ID NO: 1378) of the heavy chain sequence of SEQ ID NO: 1361, or the variable heavy chain sequence of SEQ ID NO: 1362; polynucleotides encoding the CDRs (SEQ ID NO: 1394; SEQ ID NO: 1396; and SEQ ID NO: 1398) of the light chain sequence of SEQ ID NO: 1381, or the variable light chain sequence of SEQ ID NO: 1382; polynucleotides encoding the FRs (SEQ ID NO: 1373; SEQ ID NO: 1375; SEQ ID NO: 1377; and SEQ ID NO: 1379) of the heavy chain sequence of SEQ ID NO: 1361, or the variable heavy chain sequence of SEQ ID NO: 1362; and polynucleotides encoding the FRs (SEQ ID NO: 1393; SEQ ID NO: 1395; SEQ ID NO: 1397; and SEQ ID NO: 1399) of the light chain sequence of SEQ ID NO: 1381, or the variable light chain sequence of SEQ ID NO: 1382.

In another embodiment of the invention, polynucleotides of the invention comprise, or alternatively consist of, polynucleotides encoding Fab fragments having binding specificity for PACAP. With respect to antibody Ab10.H4, the polynucleotides encoding the full length Ab10.H4 antibody comprise, or alternatively consist of, the polynucleotide SEQ ID NO: 1371 encoding the heavy chain sequence of SEQ ID NO: 1361, and the polynucleotide SEQ ID NO: 1391 encoding the light chain sequence of SEQ ID NO: 1381.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab10.H4 following expression of the full-length polynucleotides in a suitable host. In another embodiment of the invention, anti-PACAP antibodies, such as Ab10.H4 or Fab fragments thereof, can be produced via expression of Ab10.H4 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab10.H5

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1411 which encodes the heavy chain sequence of SEQ ID NO: 1401 and which consists of the heavy chain variable region coding sequence of SEQ ID NO: 1412 and the heavy chain constant region coding sequence of SEQ ID NO: 1420.

In another embodiment of the invention, the polynucleotides of the invention comprise, or alternatively consist of, the following polynucleotide sequence encoding the variable heavy chain polypeptide sequence of SEQ ID NO: 1402:

```
                                        (SEQ ID NO: 1412)
gaggtgcagcttgtggagtctgggggaggcttggtccagcctggggggt
ccctgagactctcctgtgcagcctctggaatcgacctcaatagctacta
catgacctgggtccgtcaggctccagggaaggggctggagtggatcgga
ttcattgatgctggtggtgacgcatactacgcgagctgggcgaaaggcc
gattcaccatctccagagacaattccaagaacaccgtgtatcttcaaat
gaacagcctgagagctgaggacactgctgtgtatttctgtgctagagat
cttgacttgtggggccaagggaccctcgtcaccgtctcgagc.
```

In another embodiment of the invention, polynucleotides of the invention comprise, or alternatively consist of, the following polynucleotide sequence encoding the constant heavy chain polypeptide sequence of SEQ ID NO: 1410:

```
                                        (SEQ ID NO: 1420)
gcctccaccaagggcccatcggtcttccccctggcaccctcctccaaga
gcacctctgggggcacagcggccctgggctgcctggtcaaggactactt
ccccgaaccggtgacggtgtcgtggaactcaggcgccctgaccagcggc
gtgcacaccttcccggctgtcctacagtcctcaggactctactccctca
gcagcgtggtgaccgtgccctccagcagcttgggcacccagacctacat
ctgcaacgtgaatcacaagcccagcaacaccaaggtggacaagaaagtt
gagcccaaatcttgtgacaaaactcacacatgcccaccgtgcccagcac
ctgaactcctggggggaccgtcagtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacgc
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggaggagatgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacgcagaagagcctctccctgtc
tccgggtaaa.
```

In another embodiment of the invention, polynucleotides comprise, or alternatively consist of, the polynucleotide sequence of SEQ ID NO: 1431 which encodes the light chain polypeptide sequence of SEQ ID NO: 1421 and which consists of the light chain variable region coding sequence of SEQ ID NO: 1432 and the light chain constant region coding sequence of SEQ ID NO: 1440.

In another embodiment of the invention, polynucleotides of the invention comprise, or alternatively consist of, the following polynucleotide sequence encoding the variable light chain polypeptide sequence of SEQ ID NO: 1422:

```
                                        (SEQ ID NO: 1432)
cagctgacccagtctccttccaccctgtctgcatctgtaggagacagag

tcaccatcacttgtcagtccagtgagagtgtttacggtaactacttagc

ctggtttcagcagaaaccaggaaaagcccctaagttcctgatctatgaa

gcatccaaactggaatctggagtcccatcaaggttcagcggcagtggat

ctggaacagaattcactctcaccatcagcagcctgcagcctgatgattt

tgcaacttactactgtgcaggcggtgatattagtgaaggtgttgctttc

ggcggaggaaccaaggtggaaatcaaacgt.
```

In another embodiment of the invention, polynucleotides of the invention comprise, or alternatively consist of, the following polynucleotide sequence encoding the constant light chain polypeptide sequence of SEQ ID NO: 1430:

```
                                        (SEQ ID NO: 1440)
acggtagcggccccatctgtcttcatcttcccgccatctgatgagcagt

tgaaatctggaactgcctctgttgtgtgcctgctgaataacttctatcc

cagagaggccaaagtacagtggaaggtggataacgccctccaatcgggt

aactcccaggagagtgtcacagagcaggacagcaaggacagcacctaca

gcctcagcagcaccctgacgctgagcaaagcagactacgagaaacacaa

agtctacgcctgcgaagtcacccatcagggcctgagctcgcccgtcaca

aagagcttcaacaggggagagtgt.
```

In a further embodiment of the invention, polynucleotides encoding antigen-binding fragments having binding specificity to PACAP comprise, or alternatively consist of, one or more of the polynucleotide sequences of SEQ ID NO: 1414; SEQ ID NO: 1416; and SEQ ID NO: 1418, which correspond to polynucleotides encoding the CDRs (hypervariable regions) of the heavy chain sequence of SEQ ID NO: 1401, or the variable heavy chain sequence of SEQ ID NO: 1402, and/or one or more of the polynucleotide sequences of SEQ ID NO: 1434; SEQ ID NO: 1436; and SEQ ID NO: 1438, which correspond to the CDRs (hypervariable regions) of the light chain sequence of SEQ ID NO: 1421, or the variable light chain sequence of SEQ ID NO: 1422, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1413; SEQ ID NO: 1415; SEQ ID NO: 1417; and SEQ ID NO: 1419, which correspond to polynucleotides encoding the FRs (constant regions) of the heavy chain sequence of SEQ ID NO: 1401, or the variable heavy chain sequence of SEQ ID NO: 1402, and/or one or more of the polynucleotide sequences of SEQ ID NO: 1433; SEQ ID NO: 1435; SEQ ID NO: 1437; and SEQ ID NO: 1439, which correspond to the FRs (constant regions) of the light chain sequence of SEQ ID NO: 1421, or the variable light chain sequence of SEQ ID NO: 1422, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1411 encoding the heavy chain sequence of SEQ ID NO: 1401; the polynucleotide SEQ ID NO: 1412 encoding the variable heavy chain sequence of SEQ ID NO: 1402; the polynucleotide SEQ ID NO: 1431 encoding the light chain sequence of SEQ ID NO: 1421; the polynucleotide SEQ ID NO: 1432 encoding the variable light chain sequence of SEQ ID NO: 1422; polynucleotides encoding the CDRs (SEQ ID NO: 1414; SEQ ID NO: 1416; and SEQ ID NO: 1418) of the heavy chain sequence of SEQ ID NO: 1401, or the variable heavy chain sequence of SEQ ID NO: 1402; polynucleotides encoding the CDRs (SEQ ID NO: 1434; SEQ ID NO: 1436; and SEQ ID NO: 1438) of the light chain sequence of SEQ ID NO: 1421, or the variable light chain sequence of SEQ ID NO: 1422; polynucleotides encoding the FRs (SEQ ID NO: 1413; SEQ ID NO: 1415; SEQ ID NO: 1417; and SEQ ID NO: 1419) of the heavy chain sequence of SEQ ID NO: 1401, or the variable heavy chain sequence of SEQ ID NO: 1402; and polynucleotides encoding the FRs (SEQ ID NO: 1433; SEQ ID NO: 1435; SEQ ID NO: 1437; and SEQ ID NO: 1439) of the light chain sequence of SEQ ID NO: 1421, or the variable light chain sequence of SEQ ID NO: 1422.

In another embodiment of the invention, polynucleotides of the invention comprise, or alternatively consist of, polynucleotides encoding Fab fragments having binding specificity for PACAP. With respect to antibody Ab10.H5, the polynucleotides encoding the full length Ab10.H5 antibody comprise, or alternatively consist of, the polynucleotide SEQ ID NO: 1411 encoding the heavy chain sequence of SEQ ID NO: 1401, and the polynucleotide SEQ ID NO: 1431 encoding the light chain sequence of SEQ ID NO: 1421.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab10.H5 following expression of the full-length polynucleotides in a suitable host. In another embodiment of the invention, anti-PACAP antibodies, such as Ab10.H5 or Fab fragments thereof, can be produced via expression of Ab10.H5 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab10.H6

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1451 which encodes the heavy chain sequence of SEQ ID NO: 1441 and which consists of the heavy chain variable region coding sequence of SEQ ID NO: 1452 and the heavy chain constant region coding sequence of SEQ ID NO: 1460.

In another embodiment of the invention, the polynucleotides of the invention comprise, or alternatively consist of, the following polynucleotide sequence encoding the variable heavy chain polypeptide sequence of SEQ ID NO: 1442:

(SEQ ID NO: 1452)

gaggtgcagcttgtggagtctgggggaggcttggtccagcctggggggt ccctgagactctcctgtgcagcctctggaatcgacctcaatagctacta catgacctgggtccgtcaggctccagggaaggggctggagtggatcgga ttcattgatgctggtggtgacgcatactacgcgagctgggcgaaaggcc gattcaccatctccagagacaattccaagaacaccgtgtatcttcaaat gaacagcctgagagctgaggacactgctgtgtatttctgtgctagagat cttgacttgtggggccaagggaccctcgtcaccgtctcgagc.

In another embodiment of the invention, polynucleotides of the invention comprise, or alternatively consist of, the following polynucleotide sequence encoding the constant heavy chain polypeptide sequence of SEQ ID NO: 1450:

(SEQ ID NO: 1460)

gcctccaccaagggcccatcggtcttccccctggcaccctcctccaaga gcacctctgggggcacagcggccctgggctgcctggtcaaggactactt ccccgaaccggtgacggtgtcgtggaactcaggcgccctgaccagcggc gtgcacaccttcccggctgtcctacagtcctcaggactctactccctca gcagcgtggtgaccgtgccctccagcagcttgggcacccagacctacat ctgcaacgtgaatcacaagcccagcaacaccaaggtggacaagaaagtt gagcccaaatcttgtgacaaaactcacacatgcccaccgtgcccagcac ctgaactcctggggggaccgtcagtcttcctcttccccccaaaacccaa ggacaccctcatgatctcccggacccctgaggtcacatgcgtggtggtg gacgtgagccacgaagaccctgaggtcaagttcaactggtacgtggacg gcgtggaggtgcataatgccaagacaaagccgcgggaggagcagtacgc cagcacgtaccgtgtggtcagcgtcctcaccgtcctgcaccaggactgg ctgaatggcaaggagtacaagtgcaaggtctccaacaaagccctcccag -continued cccccatcgagaaaaccatctccaaagccaaagggcagccccgagaacc acaggtgtacaccctgcccccatcccgggaggagatgaccaagaaccag gtcagcctgacctgcctggtcaaaggcttctatcccagcgacatcgccg tggagtgggagagcaatgggcagccggagaacaactacaagaccacgcc tcccgtgctggactccgacggctccttcttcctctacagcaagctcacc gtggacaagagcaggtggcagcaggggaacgtcttctcatgctccgtga tgcatgaggctctgcacaaccactacacgcagaagagcctctccctgtc tccgggtaaa.

In another embodiment of the invention, polynucleotides comprise, or alternatively consist of, the polynucleotide sequence of SEQ ID NO: 1471 which encodes the light chain polypeptide sequence of SEQ ID NO: 1461 and which consists of the light chain variable region coding sequence of SEQ ID NO: 1472 and the light chain constant region coding sequence of SEQ ID NO: 1480.

In another embodiment of the invention, polynucleotides of the invention comprise, or alternatively consist of, the following polynucleotide sequence encoding the variable light chain polypeptide sequence of SEQ ID NO: 1462:

(SEQ ID NO: 1472)

caggtgctgacccagtctccttccaccctgtctgcatctgtaggagaca gagtcaccatcacttgtcagtccagtgagagtgtttacggtaactactt agcctggtttcagcagaaaccaggaaaagcccctaagttcctgatctat gaagcatccaaactggaatctggagtcccatcaaggttcagcggcagtg gatctggaacagaattcactctcaccatcagcagcctgcagcctgatga ttttgcaacttactactgtgcaggcggtgatattagtgaaggtgttgct ttcggcggaggaaccaaggtggaaatcaaacgt.

In another embodiment of the invention, polynucleotides of the invention comprise, or alternatively consist of, the following polynucleotide sequence encoding the constant light chain polypeptide sequence of SEQ ID NO: 1470:

(SEQ ID NO: 1480)

acggtagcggccccatctgtcttcatcttcccgccatctgatgagcagtt gaaatctggaactgcctctgttgtgtgcctgctgaataacttctatccca gagaggccaaagtacagtggaaggtggataacgccctccaatcgggtaac tcccaggagagtgtcacagagcaggacagcaaggacagcacctacagcct cagcagcaccctgacgctgagcaaagcagactacgagaaacacaaagtct acgcctgcgaagtcacccatcagggcctgagctcgcccgtcacaaagagc ttcaacaggggagagtgt.

In a further embodiment of the invention, polynucleotides encoding antigen-binding fragments having binding specificity to PACAP comprise, or alternatively consist of, one or more of the polynucleotide sequences of SEQ ID NO: 1454; SEQ ID NO: 1456; and SEQ ID NO: 1458, which correspond to polynucleotides encoding the CDRs (hypervariable regions) of the heavy chain sequence of SEQ ID NO: 1441, or the variable heavy chain sequence of SEQ ID NO: 1442, and/or one or more of the polynucleotide sequences of SEQ ID NO: 1474; SEQ ID NO: 1476; and SEQ ID NO: 1478, which correspond to the CDRs (hypervariable regions) of the light chain sequence of SEQ ID NO: 1461, or the variable light chain sequence of SEQ ID NO: 1462, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1453; SEQ ID NO: 1455; SEQ ID NO: 1457; and SEQ ID NO: 1459, which correspond to polynucleotides encoding the FRs (constant regions) of the heavy chain sequence of SEQ ID NO: 1441, or the variable heavy chain sequence of SEQ ID NO: 1442, and/or one or more of the polynucleotide sequences of SEQ ID NO: 1473; SEQ ID NO: 1475; SEQ ID NO: 1477; and SEQ ID NO: 1479, which correspond to the FRs (constant regions) of the light chain sequence of SEQ ID NO: 1461, or the variable light chain sequence of SEQ ID NO: 1462, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1451 encoding the heavy chain sequence of SEQ ID NO: 1441; the polynucleotide SEQ ID NO: 1452 encoding the variable heavy chain sequence of SEQ ID NO: 1442; the polynucleotide SEQ ID NO: 1471 encoding the light chain sequence of SEQ ID NO: 1461; the polynucleotide SEQ ID NO: 1472 encoding the variable light chain sequence of SEQ ID NO: 1462; polynucleotides encoding the CDRs (SEQ ID NO: 1454; SEQ ID NO: 1456; and SEQ ID NO: 1458) of the heavy chain sequence of SEQ ID NO: 1441, or the variable heavy chain sequence of SEQ ID NO: 1442; polynucleotides encoding the CDRs (SEQ ID NO: 1474; SEQ ID NO: 1476; and SEQ ID NO: 1478) of the light chain sequence of SEQ ID NO: 1461, or the variable light chain sequence of SEQ ID NO: 1462; polynucleotides encoding the FRs (SEQ ID NO: 1453; SEQ ID NO: 1455; SEQ ID NO: 1457; and SEQ ID NO: 1459) of the heavy chain sequence of SEQ ID NO: 1441, or the variable heavy chain sequence of SEQ ID NO: 1442; and polynucleotides encoding the FRs (SEQ ID NO: 1473; SEQ ID NO: 1475; SEQ ID NO: 1477; and SEQ ID NO: 1479) of the light chain sequence of SEQ ID NO: 1461, or the variable light chain sequence of SEQ ID NO: 1462.

In another embodiment of the invention, polynucleotides of the invention comprise, or alternatively consist of, polynucleotides encoding Fab fragments having binding specificity for PACAP. With respect to antibody Ab10.H6, the polynucleotides encoding the full length Ab10.H6 antibody comprise, or alternatively consist of, the polynucleotide SEQ ID NO: 1451 encoding the heavy chain sequence of SEQ ID NO: 1441, and the polynucleotide SEQ ID NO: 1471 encoding the light chain sequence of SEQ ID NO: 1461.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab10.H6 following expression of the full-length polynucleotides in a suitable host. In another embodiment of the invention, anti-PACAP antibodies, such as Ab10.H6 or Fab fragments thereof, can be produced via expression of Ab10.H6 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab21.H2

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1491 which encodes the heavy chain sequence of SEQ ID NO: 1481 and which consists of the heavy chain variable region coding sequence of SEQ ID NO: 1492 and the heavy chain constant region coding sequence of SEQ ID NO: 1500.

In another embodiment of the invention, the polynucleotides of the invention comprise, or alternatively consist of, the following polynucleotide sequence encoding the variable heavy chain polypeptide sequence of SEQ ID NO: 1482:

(SEQ ID NO: 1492)
gaggtgcagcttgtggagtctgggggaggcttggtccagcctggggggtc
cctgagactctcctgtgcagcctctggaatcgacctcagtagctactaca
tgacctgggtccgtcaggctccagggaaggggctggagtggatcggattc
attgatgctggtggtagcgcatactacgcgacctgggcaaaaggccgatt
caccatctccagagacaattccaagaacaccgtgtatcttcaaatgaaca
gcctgagagctgaggacactgctgtgtatttctgtgctagagatcttgac
ttgtggggccaagggaccctcgtcaccgtctcgagc.

In another embodiment of the invention, polynucleotides of the invention comprise, or alternatively consist of, the following polynucleotide sequence encoding the constant heavy chain polypeptide sequence of SEQ ID NO: 1490:

(SEQ ID NO: 1500)
gcctccaccaagggcccatcggtcttccccctggcaccctcctccaaga
gcacctctgggggcacagcggccctgggctgcctggtcaaggactactt
ccccgaaccggtgacggtgtcgtggaactcaggcgccctgaccagcggc
gtgcacaccttcccggctgtcctacagtcctcaggactctactccctca
gcagcgtggtgaccgtgccctccagcagcttgggcacccagacctacat -continued

```
ctgcaacgtgaatcacaagcccagcaacaccaaggtggacaagaaagtt
gagcccaaatcttgtgacaaaactcacacatgcccaccgtgcccagcac
ctgaactcctggggggaccgtcagtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacgc
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggaggagatgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctacagcaagctcacc
gtggacaagagcaggtggcagcaggggaacgtcttctcatgctccgtga
tgcatgaggctctgcacaaccactacacgcagaagagcctctccctgtc
tccgggtaaa.
```

In another embodiment of the invention, polynucleotides comprise, or alternatively consist of, the polynucleotide sequence of SEQ ID NO: 1511 which encodes the light chain polypeptide sequence of SEQ ID NO: 1501 and which consists of the light chain variable region coding sequence of SEQ ID NO: 1512 and the light chain constant region coding sequence of SEQ ID NO: 1520.

In another embodiment of the invention, polynucleotides of the invention comprise, or alternatively consist of, the following polynucleotide sequence encoding the variable light chain polypeptide sequence of SEQ ID NO: 1502:

```
                                        (SEQ ID NO: 1512)
gccgtgctgacccagtctccttccaccctgtctgcatctgtaggagaca
gagtcaccatcacttgtaagtccagtgagagcgtttatggtgactactt
agcctggtttcagcagaaaccaggaaaagcccctaagcaactgatctat
gatgcatccactctggcatctggagtcccatcaaggttcagcggcagtg
gatctggaacagaattcactctcaccatcagcagcctgcagcctgatga
ttttgcaacttactactgtgcaggcggttatgttagtgcaggtgttgct
ttcggcggaggaaccaaggtggaaatcaaacgt.
```

In another embodiment of the invention, polynucleotides of the invention comprise, or alternatively consist of, the following polynucleotide sequence encoding the constant light chain polypeptide sequence of SEQ ID NO: 1510:

```
                                        (SEQ ID NO: 1520)
acggtagcggccccatctgtcttcatcttcccgccatctgatgagcagt
tgaaatctggaactgcctctgttgtgtgcctgctgaataacttctatcc
cagagaggccaaagtacagtggaaggtggataacgccctccaatcgggt
aactcccaggagagtgtcacagagcaggacagcaaggacagcacctaca
```

-continued

```
gcctcagcagcaccctgacgctgagcaaagcagactacgagaaacacaa
agtctacgcctgcgaagtcacccatcagggcctgagctcgcccgtcaca
aagagcttcaacaggggagagtgt.
```

In a further embodiment of the invention, polynucleotides encoding antigen-binding fragments having binding specificity to PACAP comprise, or alternatively consist of, one or more of the polynucleotide sequences of SEQ ID NO: 1494; SEQ ID NO: 1496; and SEQ ID NO: 1498, which correspond to polynucleotides encoding the CDRs (hypervariable regions) of the heavy chain sequence of SEQ ID NO: 1481, or the variable heavy chain sequence of SEQ ID NO: 1482, and/or one or more of the polynucleotide sequences of SEQ ID NO: 1514; SEQ ID NO: 1516; and SEQ ID NO: 1518, which correspond to the CDRs (hypervariable regions) of the light chain sequence of SEQ ID NO: 1501, or the variable light chain sequence of SEQ ID NO: 1502, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1493; SEQ ID NO: 1495; SEQ ID NO: 1497; and SEQ ID NO: 1499, which correspond to polynucleotides encoding the FRs (constant regions) of the heavy chain sequence of SEQ ID NO: 1481, or the variable heavy chain sequence of SEQ ID NO: 1482, and/or one or more of the polynucleotide sequences of SEQ ID NO: 1513; SEQ ID NO: 1515; SEQ ID NO: 1517; and SEQ ID NO: 1519, which correspond to the FRs (constant regions) of the light chain sequence of SEQ ID NO: 1501, or the variable light chain sequence of SEQ ID NO: 1502, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1491 encoding the heavy chain sequence of SEQ ID NO: 1481; the polynucleotide SEQ ID NO: 1492 encoding the variable heavy chain sequence of SEQ ID NO: 1482; the polynucleotide SEQ ID NO: 1511 encoding the light chain sequence of SEQ ID NO: 1501; the polynucleotide SEQ ID NO: 1512 encoding the variable light chain sequence of SEQ ID NO: 1502; polynucleotides encoding the CDRs (SEQ ID NO: 1494; SEQ ID NO: 1496; and SEQ ID NO: 1498) of the heavy chain sequence of SEQ ID NO: 1481, or the variable heavy chain sequence of SEQ ID NO: 1482; polynucleotides encoding the CDRs (SEQ ID NO:

1514; SEQ ID NO: 1516; and SEQ ID NO: 1518) of the light chain sequence of SEQ ID NO: 1501, or the variable light chain sequence of SEQ ID NO: 1502; polynucleotides encoding the FRs (SEQ ID NO: 1493; SEQ ID NO: 1495; SEQ ID NO: 1497; and SEQ ID NO: 1499) of the heavy chain sequence of SEQ ID NO: 1481, or the variable heavy chain sequence of SEQ ID NO: 1482; and polynucleotides encoding the FRs (SEQ ID NO: 1513; SEQ ID NO: 1515; SEQ ID NO: 1517; and SEQ ID NO: 1519) of the light chain sequence of SEQ ID NO: 1501, or the variable light chain sequence of SEQ ID NO: 1502.

In another embodiment of the invention, polynucleotides of the invention comprise, or alternatively consist of, polynucleotides encoding Fab fragments having binding specificity for PACAP. With respect to antibody Ab21.H2, the polynucleotides encoding the full length Ab21.H2 antibody comprise, or alternatively consist of, the polynucleotide SEQ ID NO: 1491 encoding the heavy chain sequence of SEQ ID NO: 1481, and the polynucleotide SEQ ID NO: 1511 encoding the light chain sequence of SEQ ID NO: 1501.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab21.H2 following expression of the full-length polynucleotides in a suitable host. In another embodiment of the invention, anti-PACAP antibodies, such as Ab21.H2 or Fab fragments thereof, can be produced via expression of Ab21.H2 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab21.H3

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1531 which encodes the heavy chain sequence of SEQ ID NO: 1521 and which consists of the heavy chain variable region coding sequence of SEQ ID NO: 1532 and the heavy chain constant region coding sequence of SEQ ID NO: 1540.

In another embodiment of the invention, the polynucleotides of the invention comprise, or alternatively consist of, the following polynucleotide sequence encoding the variable heavy chain polypeptide sequence of SEQ ID NO: 1522:

(SEQ ID NO: 1532)
gaggtgcagcttgtggagtctgggggaggcttggtccagcctggggggt ccctgagactctcctgtgcagcctctggaatcgacctcagtagctacta catgacctgggtccgtcaggctccagggaaggggctggagtggatcgga ttcattgatgctggtggtagcgcatactacgcgacctgggcaaaaggcc gattcaccatctccagagacaattccaagaacaccgtgtatcttcaaat -continued gaacagcctgagagctgaggacactgctgtgtatttctgtgctagagat cttgacttgtggggccaagggaccctcgtcaccgtctcgagc.

In another embodiment of the invention, polynucleotides of the invention comprise, or alternatively consist of, the following polynucleotide sequence encoding the constant heavy chain polypeptide sequence of SEQ ID NO: 1530:

(SEQ ID NO: 1540)
gcctccaccaagggcccatcggtcttccccctggcaccctcctccaaga gcacctctgggggcacagcggccctgggctgcctggtcaaggactactt ccccgaaccggtgacggtgtcgtggaactcaggcgccctgaccagcggc gtgcacaccttcccggctgtcctacagtcctcaggactctactccctca gcagcgtggtgaccgtgccctccagcagcttgggcacccagacctacat ctgcaacgtgaatcacaagcccagcaacaccaaggtggacaagaaagtt gagcccaaatcttgtgacaaaactcacacatgcccaccgtgcccagcac ctgaactcctggggggaccgtcagtcttcctcttccccccaaaacccaa ggacaccctcatgatctcccggacccctgaggtcacatgcgtggtggtg gacgtgagccacgaagaccctgaggtcaagttcaactggtacgtggacg gcgtggaggtgcataatgccaagacaaagccgcgggaggagcagtacgc cagcacgtaccgtgtggtcagcgtcctcaccgtcctgcaccaggactgg ctgaatggcaaggagtacaagtgcaaggtctccaacaaagccctcccag cccccatcgagaaaaccatctccaaagccaaagggcagccccgagaacc acaggtgtacaccctgcccccatcccgggaggagatgaccaagaaccag gtcagcctgacctgcctggtcaaaggcttctatcccagcgacatcgccg tggagtgggagagcaatgggcagccggagaacaactacaagaccacgcc tcccgtgctggactccgacggctccttcttcctctacagcaagctcacc gtggacaagagcaggtggcagcaggggaacgtcttctcatgctccgtga tgcatgaggctctgcacaaccactacacgcagaagagcctctccctgtc tccgggtaaa.

In another embodiment of the invention, polynucleotides comprise, or alternatively consist of, the polynucleotide sequence of SEQ ID NO: 1551 which encodes the light chain polypeptide sequence of SEQ ID NO: 1541 and which consists of the light chain variable region coding sequence of SEQ ID NO: 1552 and the light chain constant region coding sequence of SEQ ID NO: 1560.

In another embodiment of the invention, polynucleotides of the invention comprise, or alternatively consist of, the following polynucleotide sequence encoding the variable light chain polypeptide sequence of SEQ ID NO: 1542:

(SEQ ID NO: 1552)
gacatccagctgacccagtctccttccaccctgtctgcatctgtaggag acagagtcaccatcacttgtaagtccagtgagagcgtttatggtgacta cttagcctggtttcagcagaaaccaggaaaagcccctaagcaactgatc tatgatgcatccactctggcatctggagtcccatcaaggttcagcggca gtggatctggaacagaattcactctcaccatcagcagcctgcagcctga -continued

```
tgattttgcaacttactactgtgcaggcggttatgttagtgcaggtgtt

gctttcggcggaggaaccaaggtggaaatcaaacgt.
```

In another embodiment of the invention, polynucleotides of the invention comprise, or alternatively consist of, the following polynucleotide sequence encoding the constant light chain polypeptide sequence of SEQ ID NO: 1550:

```
                                        (SEQ ID NO: 1560)
acggtagcggccccatctgtcttcatcttcccgccatctgatgagcagt

tgaaatctggaactgcctctgttgtgtgcctgctgaataacttctatcc

cagagaggccaaagtacagtggaaggtggataacgccctccaatcgggt

aactcccaggagagtgtcacagagcaggacagcaaggacagcacctaca

gcctcagcagcaccctgacgctgagcaaagcagactacgagaaacacaa

agtctacgcctgcgaagtcacccatcagggcctgagctcgcccgtcaca

aagagcttcaacaggggagagtgt.
```

In a further embodiment of the invention, polynucleotides encoding antigen-binding fragments having binding specificity to PACAP comprise, or alternatively consist of, one or more of the polynucleotide sequences of SEQ ID NO: 1534; SEQ ID NO: 1536; and SEQ ID NO: 1538, which correspond to polynucleotides encoding the CDRs (hypervariable regions) of the heavy chain sequence of SEQ ID NO: 1521, or the variable heavy chain sequence of SEQ ID NO: 1522, and/or one or more of the polynucleotide sequences of SEQ ID NO: 1554; SEQ ID NO: 1556; and SEQ ID NO: 1558, which correspond to the CDRs (hypervariable regions) of the light chain sequence of SEQ ID NO: 1541, or the variable light chain sequence of SEQ ID NO: 1542, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1533; SEQ ID NO: 1535; SEQ ID NO: 1537; and SEQ ID NO: 1539, which correspond to polynucleotides encoding the FRs (constant regions) of the heavy chain sequence of SEQ ID NO: 1521, or the variable heavy chain sequence of SEQ ID NO: 1522, and/or one or more of the polynucleotide sequences of SEQ ID NO: 1553; SEQ ID NO: 1555; SEQ ID NO: 1557; and SEQ ID NO: 1559, which correspond to the FRs (constant regions) of the light chain sequence of SEQ ID NO: 1541, or the variable light chain sequence of SEQ ID NO: 1542, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1531 encoding the heavy chain sequence of SEQ ID NO: 1521; the polynucleotide SEQ ID NO: 1532 encoding the variable heavy chain sequence of SEQ ID NO: 1522; the polynucleotide SEQ ID NO: 1551 encoding the light chain sequence of SEQ ID NO: 1541; the polynucleotide SEQ ID NO: 1552 encoding the variable light chain sequence of SEQ ID NO: 1542; polynucleotides encoding the CDRs (SEQ ID NO: 1534; SEQ ID NO: 1536; and SEQ ID NO: 1538) of the heavy chain sequence of SEQ ID NO: 1521, or the variable heavy chain sequence of SEQ ID NO: 1522; polynucleotides encoding the CDRs (SEQ ID NO: 1554; SEQ ID NO: 1556; and SEQ ID NO: 1558) of the light chain sequence of SEQ ID NO: 1541, or the variable light chain sequence of SEQ ID NO: 1542; polynucleotides encoding the FRs (SEQ ID NO: 1533; SEQ ID NO: 1535; SEQ ID NO: 1537; and SEQ ID NO: 1539) of the heavy chain sequence of SEQ ID NO: 1521, or the variable heavy chain sequence of SEQ ID NO: 1522; and polynucleotides encoding the FRs (SEQ ID NO: 1553; SEQ ID NO: 1555; SEQ ID NO: 1557; and SEQ ID NO: 1559) of the light chain sequence of SEQ ID NO: 1541, or the variable light chain sequence of SEQ ID NO: 1542.

In another embodiment of the invention, polynucleotides of the invention comprise, or alternatively consist of, polynucleotides encoding Fab fragments having binding specificity for PACAP. With respect to antibody Ab21.H3, the polynucleotides encoding the full length Ab21.H3 antibody comprise, or alternatively consist of, the polynucleotide SEQ ID NO: 1531 encoding the heavy chain sequence of SEQ ID NO: 1521, and the polynucleotide SEQ ID NO: 1551 encoding the light chain sequence of SEQ ID NO: 1541.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab21.H3 following expression of the full-length polynucleotides in a suitable host. In another embodiment of the invention, anti-PACAP antibodies, such as Ab21.H3 or Fab fragments thereof, can be produced via expression of Ab21.H3 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Antibody Ab21.H4

In one embodiment, the invention is further directed to polynucleotides encoding antibody polypeptides having binding specificity to PACAP. In one embodiment of the invention, polynucleotides of the invention comprise, or alternatively consist of, the polynucleotide sequence of SEQ ID NO: 1571 which encodes the heavy chain sequence of SEQ ID NO: 1561 and which consists of the heavy chain variable region coding sequence of SEQ ID NO: 1572 and the heavy chain constant region coding sequence of SEQ ID NO: 1580.

In another embodiment of the invention, the polynucleotides of the invention comprise, or alternatively consist of, the following polynucleotide sequence encoding the variable heavy chain polypeptide sequence of SEQ ID NO: 1562:

```
                                  (SEQ ID NO: 1572)
gaggtgcagcttgtggagtctgggggaggcttggtccagcctggggggt

ccctgagactctcctgtgcagcctctggaatcgacctcagtagctacta

catgacctgggtccgtcaggctccagggaaggggctggagtggatcgga

ttcattgatgctggtggtagcgcatactacgcgacctgggcaaaaggcc

gattcaccatctccagagacaattccaagaacaccgtgtatcttcaaat

gaacagcctgagagctgaggacactgctgtgtatttctgtgctagagat

cttgacttgtggggccaagggaccctcgtcaccgtctcgagc.
```

In another embodiment of the invention, polynucleotides of the invention comprise, or alternatively consist of, the following polynucleotide sequence encoding the constant heavy chain polypeptide sequence of SEQ ID NO: 1570:

```
                                  (SEQ ID NO: 1580)
gcctccaccaagggcccatcggtcttccccctggcaccctcctccaaga

gcacctctgggggcacagcggccctgggctgcctggtcaaggactactt

ccccgaaccggtgacggtgtcgtggaactcaggcgccctgaccagcggc

gtgcacaccttcccggctgtcctacagtcctcaggactctactccctca

gcagcgtggtgaccgtgccctccagcagcttgggcacccagacctacat

ctgcaacgtgaatcacaagcccagcaacaccaaggtggacaagaaagtt

gagcccaaatcttgtgacaaaactcacacatgcccaccgtgcccagcac

ctgaactcctggggggaccgtcagtcttcctcttccccccaaaacccaa

ggacaccctcatgatctcccggacccctgaggtcacatgcgtggtggtg

gacgtgagccacgaagaccctgaggtcaagttcaactggtacgtggacg

gcgtggaggtgcataatgccaagacaaagccgcgggaggagcagtacgc

cagcacgtaccgtgtggtcagcgtcctcaccgtcctgcaccaggactgg

ctgaatggcaaggagtacaagtgcaaggtctccaacaaagccctcccag

cccccatcgagaaaaccatctccaaagccaaagggcagccccgagaacc

acaggtgtacaccctgcccccatcccgggaggagatgaccaagaaccag

gtcagcctgacctgcctggtcaaaggcttctatcccagcgacatcgccg

tggagtgggagagcaatgggcagccggagaacaactacaagaccacgcc

tcccgtgctggactccgacggctccttcttcctctacagcaagctcacc

gtggacaagagcaggtggcagcaggggaacgtcttctcatgctccgtga

tgcatgaggctctgcacaaccactacacgcagaagagcctctccctgtc

tccgggtaaa.
```

In another embodiment of the invention, polynucleotides comprise, or alternatively consist of, the polynucleotide sequence of SEQ ID NO: 1591 which encodes the light chain polypeptide sequence of SEQ ID NO: 1581 and which consists of the light chain variable region coding sequence of SEQ ID NO: 1592 and the light chain constant region coding sequence of SEQ ID NO: 1600.

In another embodiment of the invention, polynucleotides of the invention comprise, or alternatively consist of, the following polynucleotide sequence encoding the variable light chain polypeptide sequence of SEQ ID NO: 1582:

```
                                  (SEQ ID NO: 1592)
gacatcgtgctgacccagtctccttccaccctgtctgcatctgtaggag

acagagtcaccatcacttgtaagtccagtgagagcgtttatggtgacta

cttagcctggtttcagcagaaaccaggaaaagcccctaagcaactgatc

tatgatgcatccactctggcatctggagtcccatcaaggttcagcggca

gtggatctggaacagaattcactctcaccatcagcagcctgcagcctga

tgattttgcaacttactactgtgcaggcggttatgttagtgcaggtgtt

gattcggcggaggaaccaaggtggaaatcaaacgt.
```

In another embodiment of the invention, polynucleotides of the invention comprise, or alternatively consist of, the following polynucleotide sequence encoding the constant light chain polypeptide sequence of SEQ ID NO: 1590:

```
                                  (SEQ ID NO: 1600)
acggtagcggccccatctgtcttcatcttcccgccatctgatgagcag

ttgaaatctggaactgcctctgttgtgtgcctgctgaataacttctat

cccagagaggccaaagtacagtggaaggtggataacgccctccaatcg

ggtaactcccaggagagtgtcacagagcaggacagcaaggacagcacc

tacagcctcagcagcaccctgacgctgagcaaagcagactacgagaaa

cacaaagtctacgcctgcgaagtcacccatcagggcctgagctcgccc

gtcacaaagagcttcaacaggggagagtgt.
```

In a further embodiment of the invention, polynucleotides encoding antigen-binding fragments having binding specificity to PACAP comprise, or alternatively consist of, one or more of the polynucleotide sequences of SEQ ID NO: 1574; SEQ ID NO: 1576; and SEQ ID NO: 1578, which correspond to polynucleotides encoding the CDRs (hypervariable regions) of the heavy chain sequence of SEQ ID NO: 1561, or the variable heavy chain sequence of SEQ ID NO: 1562, and/or one or more of the polynucleotide sequences of SEQ ID NO: 1594; SEQ ID NO: 1596; and SEQ ID NO: 1598, which correspond to the CDRs (hypervariable regions) of the light chain sequence of SEQ ID NO: 1581, or the variable light chain sequence of SEQ ID NO: 1582, or combinations of these polynucleotide sequences. In another embodiment of the invention, the polynucleotides encoding the antibodies of the invention or antigen-binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen-binding fragments having binding specificity to PACAP comprise, or alternatively consist of, one or more of the polynucleotide sequences of SEQ ID NO: 1573; SEQ ID NO: 1575; SEQ ID NO: 1577; and SEQ ID NO: 1579, which correspond to polynucleotides encoding the FRs (constant regions) of the heavy chain sequence of SEQ ID NO: 1561, or the variable heavy chain sequence of SEQ ID NO: 1562, and/or one or more of the polynucleotide sequences of SEQ ID NO: 1593; SEQ ID NO: 1595; SEQ ID NO: 1597; and SEQ ID NO: 1599, which correspond to the FRs (constant regions) of the light chain sequence of SEQ ID NO: 1581, or the variable light chain sequence of SEQ ID NO: 1582, or combinations of these polynucleotide sequences. In another embodiment of the invention, the polynucleotides encoding the antibodies of the invention or fragments thereof comprise, or alternatively consist of, combinations of one or more of the FRs, the variable heavy chain and variable light chain sequences, and the heavy chain and light chain sequences set forth above, including all of them.

The invention also contemplates polynucleotide sequences including one or more of the polynucleotide sequences encoding antigen-binding fragments described herein. In one embodiment of the invention, polynucleotides encoding antigen-binding fragments having binding specificity to PACAP comprise, or alternatively consist of, one, two, three or more, including all of the following polynucleotides encoding antigen-binding fragments: the polynucleotide SEQ ID NO: 1571 encoding the heavy chain sequence of SEQ ID NO: 1561; the polynucleotide SEQ ID NO: 1572 encoding the variable heavy chain sequence of SEQ ID NO: 1562; the polynucleotide SEQ ID NO: 1591 encoding the light chain sequence of SEQ ID NO: 1581; the polynucleotide SEQ ID NO: 1592 encoding the variable light chain sequence of SEQ ID NO: 1582; polynucleotides encoding the CDRs (SEQ ID NO: 1574; SEQ ID NO: 1576; and SEQ ID NO: 1578) of the heavy chain sequence of SEQ ID NO: 1561, or the variable heavy chain sequence of SEQ ID NO: 1562; polynucleotides encoding the CDRs (SEQ ID NO: 1594; SEQ ID NO: 1596; and SEQ ID NO: 1598) of the light chain sequence of SEQ ID NO: 1581, or the variable light chain sequence of SEQ ID NO: 1582; polynucleotides encoding the FRs (SEQ ID NO: 1573; SEQ ID NO: 1575; SEQ ID NO: 1577; and SEQ ID NO: 1579) of the heavy chain sequence of SEQ ID NO: 1561, or the variable heavy chain sequence of SEQ ID NO: 1562; and polynucleotides encoding the FRs (SEQ ID NO: 1593; SEQ ID NO: 1595; SEQ ID NO: 1597; and SEQ ID NO: 1599) of the light chain sequence of SEQ ID NO: 1581, or the variable light chain sequence of SEQ ID NO: 1582.

In another embodiment of the invention, polynucleotides of the invention comprise, or alternatively consist of, polynucleotides encoding Fab fragments having binding specificity for PACAP. With respect to antibody Ab21.H4, the polynucleotides encoding the full length Ab21.H4 antibody comprise, or alternatively consist of, the polynucleotide SEQ ID NO: 1571 encoding the heavy chain sequence of SEQ ID NO: 1561, and the polynucleotide SEQ ID NO: 1591 encoding the light chain sequence of SEQ ID NO: 1581.

Another embodiment of the invention contemplates these polynucleotides incorporated into an expression vector for expression in mammalian cells such as CHO, NSO, or HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab21.H4 following expression of the full-length polynucleotides in a suitable host. In another embodiment of the invention, anti-PACAP antibodies, such as Ab21.H4 or Fab fragments thereof, can be produced via expression of Ab21.H4 polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Host cells and vectors comprising said polynucleotides are also contemplated.

The invention further contemplates vectors comprising the polynucleotide sequences encoding the variable heavy and light chain polypeptide sequences, as well as the individual CDRs (hypervariable regions), as set forth herein, as well as host cells comprising said vector sequences. In embodiments of the invention, the host cells are mammalian cells, such as CHO cells. In embodiments of the invention, the host cells are yeast cells, such as yeast cells of the genus *Pichia*.

B-Cell Screening and Isolation

In one embodiment, the present invention contemplates the preparation and isolation of a clonal population of antigen-specific B-cells that may be used for isolating at least one PACAP antigen-specific cell, which can be used to produce a monoclonal antibody against PACAP, which is specific to a desired PACAP antigen, or a nucleic acid sequence corresponding to such an antibody. Methods of preparing and isolating said clonal population of antigen-specific B-cells are taught, for example, in U.S. Patent Publication No. 2007/0269868 to Carvalho-Jensen et al., the disclosure of which is herein incorporated by reference in its entirety. Methods of preparing and isolating said clonal population of antigen-specific B-cells are also taught herein in the examples. Methods of "enriching" a cell population by size or density are known in the art (See, e.g., U.S. Pat. No. 5,627,052). These steps can be used in addition to enriching the cell population by antigen-specificity.

Methods of Humanizing Antibodies

In another embodiment, the present invention contemplates methods for humanizing antibody heavy and light chains. Methods for humanizing antibody heavy and light chains that may be applied to anti-PACAP antibodies are taught, for example, in U.S. Patent Publication No. 2009/0022659 to Olson et al, and in U.S. Pat. No. 7,935,340 to Garcia-Martinez et al., the disclosures of each of which are herein incorporated by reference in their entireties.

Methods of Producing Antibodies and Fragments Thereof

In another embodiment, the present invention contemplates methods for producing anti-PACAP antibodies and fragments thereof. Methods for producing anti-PACAP antibodies and fragments thereof secreted from polyploidal, preferably diploid or tetraploid strains of mating competent yeast are taught, for example, in U.S. Patent Publication No. 2009/0022659 to Olson et al., and in U.S. Pat. No. 7,935,340 to Garcia-Martinez et al., the disclosures of each of which are herein incorporated by reference in their entireties.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., *Proc. Natl. Acad. Sci. U.S.A.,* 81:8651-55, 1984; Neuberger et al., *Nature,* 314:268-270, 1985; and Boulianne et al., *Nature,* 312:643-46, 1984; the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al., *Nature,* 321:522-525 (1986); Reichmann, L. et al., *Nature,* 332:323-327 (1988); Verhoeyen, M. et al., *Science,* 239:1534-36 (1988), the disclosures of each of which are herein incorporated by reference in their entireties).

Antibody polypeptides of the invention having PACAP binding specificity may also be produced by constructing, using conventional techniques well known to those of ordinary skill in the art, an expression vector containing a promoter (optionally as a component of a eukaryotic or prokaryotic operon) and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing a promoter (optionally as a component of a eukaryotic or prokaryotic operon) and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding a promoter (optionally as a component of a eukaryotic or prokaryotic operon) and a light chain-derived polypeptide and the second vector containing DNA encoding a promoter (optionally as a component of a eukaryotic or prokaryotic operon) and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibody polypeptides may be either a bacterial cell such as *E. coli*, or a eukaryotic cell such as *P. pastoris*. In one embodiment of the invention, a mammalian cell of a well-defined type for this purpose, such as a myeloma cell, a CHO cell line, a NSO cell line, or a HEK293 cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an *E. coli*-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography, hydrophobic interaction chromatography ("HIC"), and the like.

The antibody polypeptides described herein may also be used for the design and synthesis of either peptide or non-peptide mimetics that would be useful for the same therapeutic applications as the antibody polypeptides of the invention. (See, for example, Saragobi et al., *Science,* 253: 792-795, 1991, the contents of which are herein incorporated by reference in its entirety).

Screening Assays

The screening assays described here are designed to identify high affinity anti-PACAP Abs which may be useful in the treatment of diseases and disorders associated with PACAP in subjects exhibiting symptoms of a PACAP associated disease or disorder.

In some embodiments, the antibody is used as a diagnostic tool. The antibody can be used to assay the amount of PACAP present in a sample and/or subject. As will be appreciated by one of skill in the art, such antibodies need not be neutralizing antibodies. In some embodiments, the diagnostic antibody is not a neutralizing antibody. In some embodiments, the diagnostic antibody binds to a different epitope than the neutralizing antibody binds to. In some embodiments, the two antibodies do not compete with one another.

In some embodiments, the antibodies disclosed herein are used or provided in an assay kit and/or method for the detection of PACAP in mammalian tissues or cells in order to screen/diagnose for a disease or disorder associated with changes in levels of PACAP. The kit comprises an antibody that binds PACAP and means for indicating the binding of the antibody with PACAP, if present, and optionally PACAP protein levels. Various means for indicating the presence of an antibody can be used. For example, fluorophores, other molecular probes, or enzymes can be linked to the antibody and the presence of the antibody can be observed in a variety of ways. The method for screening for such disorders can involve the use of the kit, or simply the use of one of the disclosed antibodies and the determination of whether the antibody binds to PACAP in a sample. As will be appreciated by one of skill in the art, high or elevated levels of PACAP will result in larger amounts of the antibody binding to PACAP in the sample. Thus, degree of antibody binding can be used to determine how much PACAP is in a sample. Subjects or samples with an amount of PACAP that is greater than a predetermined amount (e.g., an amount or range that a person without a PACAP-related disorder would have) can be characterized as having a PACAP-mediated disorder, e.g., migraine, headache, pain, or other condition.

The present invention further provides for a kit for detecting binding of an anti-PACAP antibody of the invention to PACAP. In particular, the kit may be used to detect the presence of PACAP specifically reactive with an anti-PACAP antibody of the invention or an immunoreactive fragment thereof. The kit may also include an antibody bound to a substrate, a secondary antibody reactive with the antigen and a reagent for detecting a reaction of the secondary antibody with the antigen. Such a kit may be an ELISA kit and can comprise the substrate, primary and secondary antibodies when appropriate, and any other necessary reagents such as detectable moieties, enzyme substrates, and color reagents, for example as described herein. The diagnostic kit may also be in the form of an immunoblot kit. The diagnostic kit may also be in the form of a chemiluminescent kit (Meso Scale Discovery, Gaithersburg, MD). The diagnostic kit may also be a lanthanide-based detection kit (PerkinElmer, San Jose, CA).

A skilled clinician would understand that a biological sample includes, but is not limited to, sera, plasma, urine, saliva, mucous, pleural fluid, synovial fluid, and spinal fluid.

Methods of Ameliorating or Reducing Symptoms of, or Treating, or Preventing, Diseases and Disorders Associated with PACAP In another embodiment of the invention, anti-PACAP antibodies described herein, or antigen binding fragments thereof, are useful for ameliorating or reducing the symptoms of, or treating, or preventing, diseases and disorders associated with PACAP. Anti-PACAP antibodies described herein, or antigen binding fragments thereof, as well as combinations, can also be administered in a therapeutically effective amount to patients in need of treatment of diseases and disorders associated with PACAP in the form of a pharmaceutical composition as described in greater detail below.

In another embodiment of the invention, anti-PACAP antibodies described herein, or antigen binding fragments thereof, are useful (either alone or in combination with another agent) for ameliorating or reducing the symptoms of, or treating, or preventing a disease or condition associated with PACAP.

In another embodiment of the invention, anti-PACAP antibodies described herein, or antigen binding fragments thereof, with or without a second agent, are useful for ameliorating or reducing the symptoms of, or treating, or preventing, the following non-limiting listing of diseases and disorders: migraine (with or without aura), hemiplegic migraines, cluster headaches, migrainous neuralgia, chronic headaches, tension headaches, general headaches, hot flush, photophobia, chronic paroxysmal hemicrania, secondary headaches due to an underlying structural problem in the head or neck, cranial neuralgia, sinus headaches (e.g., headache associated with sinusitis), allergy-induced headaches or migraines, pain, chronic pain, neuroinflammatory or inflammatory pain, post-operative incision pain, post-surgical pain, trauma-related pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, bronchial hyperreactivity, asthma, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures, acne vulgaris, atopic dermatitis, urticaria, keloids, hypertrophic scars and rosacea, allergic dermatitis, psoriasis, pruritus, neurogenic cutaneous redness, erythema, weight loss, anorexia, sarcoidosis, shock, sepsis, opiate withdrawal syndrome, morphine tolerance, epilepsy, lower urinary tract ("LUT") disorders such as urinary tract infection, abnormal voiding, urinary urgency, nocturia, urinary incontinence, overactive bladder and for preventing or alleviating the pain associated with such LUT conditions. Preferably, the subject anti-PACAP antibodies and antigen binding fragments described herein are useful for ameliorating or reducing the symptoms of, treating, or preventing migraine, headache and a pain associated disease or condition.

In particular, the subject anti-PACAP antibodies and antigen binding fragments can also be useful for ameliorating or reducing the symptoms of, treating, or preventing photophobia, occurring with a headache and/or migraine as well as occurring independent of a headache and/or a migraine.

Migraineurs typically develop worsening pain and migraine symptoms when exposed to light, a phenomenon known as photophobia. Photophobia is also common in ocular disorders, such as iritis and uveitis, and intracranial disorders, such as meningitis. In the classic visual pathway, light activates rods and cones in the retina, which activate retinal ganglion cells that project via the optic nerve, to the lateral geniculate nucleus, superior colliculus, and then the visual cortex. This pathway includes image-forming and non-image-forming data. A new pathway (non-image-forming information) allows maintenance of normal circadian rhythms via the suprachiasmatic nucleus and is regulated by intrinsically photosensitive retinal ganglion cells (ipRGCs). These ipRGCs are independent of the rods and cones and contain melanopsin, a photopigment.

Noseda, R. et al., *Nat. Neurosci.,* 13:239-245 (2010) studied blind individuals who had migraine and correlated these findings with rat models involving tracing of ipRGC projections to areas in perception of pain from the dura. Of the blind patients with migraine, 6 had no light perception due to severe optic nerve damage or bilateral enucleation. These subjects experienced abnormal sleep patterns and poor pupillary light responses. Their migraines did not worsen with light exposure. In contrast, 14 blind subjects who were able to detect light despite minimal perception of images had normal sleep patterns and a normal pupillary light reflex. Despite widespread rod and cone degeneration, these patients had worsening migraine symptoms with light exposure during migraine attacks, suggesting that ipRGCs, and not rods and cones, are important in photophobia.

These retinal projections of non-image-forming brain areas project to the contralateral dorsocaudal region of the posterior thalamus, as demonstrated by anterograde tracing in the rat. ipRGC input to this area modulates dura-sensitive pain neurons, which also project to this region. Thalamic neurons, dually sensitive to dural pain and light input, project widely to multiple cortical regions, including the primary somatosensory cortex, the primary and secondary motor cortices, the parietal association cortex, and the primary and secondary visual cortices. These cortical projections may help explain other common migraine symptoms, in addition to photophobia, such as motor weakness or incoordination, visual disturbances, and poor concentration.

Photophobia also accompanies other less frequent but likewise disabling conditions, such as cluster headache and other trigeminal autonomic cephalalgias and blepharospasm. The mechanisms underlying photophobia involve the trigeminal system. Photophobia in blind patients suggests contributions from a nonvisual pathway. In addition, trigeminal autonomic cephalalgias, a less common group of primary headache disorders, are characterized by unilateral trigeminal-mediated pain frequently associated with ipsilateral photophobia.

Common causes of photophobia include migraine headaches, cataracts, or severe ophthalmologic diseases such as uveitis or corneal abrasion. A more extensive list of disorders associated with photophobia includes eye related causes such as achromatopsia, aniridia, anticholinergic drugs may cause photophobia by paralyzing the iris sphincter muscle, aphakia (absence of the lens of the eye), buphthalmos (abnormally narrow angle between the cornea and iris), cataracts, cone dystrophy, congenital abnormalities of the eye, viral conjunctivitis ("pink eye"), corneal abrasion, corneal dystrophy, corneal ulcer, disruption of the corneal epithelium, such as that caused by a corneal foreign body or keratitis, ectopia lentis, endophthalmitis, eye trauma caused by disease, injury, or infection such as chalazion, episcleritis, glaucoma, keratoconus, or optic nerve hypoplasia, hydrophthalmos, or congenital glaucoma iritis, optic neuritis, pigment dispersion syndrome, pupillary dilation (naturally or chemically induced), retinal detachment, scarring of the cornea or sclera and uveitis.

In addition, photophobia has nervous-system-related or neurological causes including: autism spectrum disorders, Chiari malformation, dyslexia, encephalitis including myalgic encephalomyelitis aka chronic fatigue syndrome, meningitis, subarachnoid hemorrhage, tumor of the posterior cranial fossa, as well as other causes such as ankylosing spondylitis, albinism, ariboflavinosis, benzodiazepines (long term use of or withdrawal from benzodiazepines), chemotherapy, chikungunya, cystinosis, Ehlers-Danlos syndrome, hangover, influenza, infectious mononucleosis, magnesium deficiency, mercury poisoning, migraine, rabies, and tyrosinemia type II, also known as "Richner-Hanhart syndrome".

Additionally, it is known that photophobia is elevated in depression, bipolar disorder and agoraphobia.

The subject anti-PACAP antibodies and antigen binding fragments described herein can be effective for treating or preventing photophobia in any of these conditions, preferably, in a subject with post-traumatic stress disorder ("PTSD") or in a subject with traumatic brain injury.

Headaches may be classified by cause, as discussed below.

Primary headaches. A primary headache is caused by problems with or overactivity of pain-sensitive structures in the head. A primary headache is generally not considered to be a symptom of an underlying disease. Instead, chemical activity in the brain, the nerves or blood vessels of the head outside the skull, or muscles of the head and neck, or some combination of these factors, may play a role in primary headaches. Some people may carry genes that make them more likely to develop such headaches. Exemplary common primary headaches include, but are not limited to, cluster headache; tension headache (or tension-type headache); and trigeminal autonomic cephalalgia ("TAC"), including paroxysmal hemicrania. There are other headache patterns that may be considered types of primary headache, e.g., chronic daily headaches, cough headaches, exercise headaches, and sex headaches. These headaches are less common and have distinct features, such as an unusual duration or pain associated with a certain activity. Although these headaches are generally considered primary, each of them could be a symptom of an underlying disease. Additionally, some primary headaches can be triggered by lifestyle factors, including: alcohol; certain foods (e.g., processed meats that contain nitrates); changes in sleep or lack of sleep; poor posture; skipped meals; and stress.

Secondary headaches. A secondary headache is a symptom of a disease that can activate the pain-sensitive nerves of the head. Any number of conditions, which can vary greatly in severity, may cause secondary headaches. Exemplary sources of secondary headaches include, but are not limited to, acute sinusitis; arterial tears (carotid or vertebral dissections); venous thrombosis in the brain; brain aneurysm; brain arteriovenous malformation; carbon monoxide poisoning; Chiari malformation; concussion; dehydration; dental problems; car infection (middle car); encephalitis; giant cell arteritis; glaucoma; hangovers; influenza (flu); intracranial hematoma; medications to treat other disorders; meningitis; monosodium glutamate ("MSG"); overuse of pain medication; panic attacks; post-concussion syndrome; pressure from tight-fitting headgear, e.g., helmet or goggles; pseudotumor cerebri; toxoplasmosis; and trigeminal neuralgia. Specific types of secondary headaches include, but are not limited to, external compression headaches (a result of pressure-causing headgear); ice cream headaches (commonly called "brain freeze"); rebound headaches (caused by overuse of pain medication); sinus headaches (caused by inflammation and congestion in sinus cavities); spinal headaches (caused by low levels of cerebrospinal fluid, possibly the result of trauma, spinal tap or spinal anesthesia); and thunderclap headaches (a group of disorders that involves sudden, severe headaches).

Exemplary, non-limiting pain associated diseases and disorders that can be treated and/or prevented by the administration of the anti-PACAP antibodies of the present invention include, pain resulting from any condition associated with neurogenic, neuropathic, inflammatory, or nociceptic pain. Preferably, the pain-associated disorder will be associated with increased PACAP at the pain site.

In certain embodiments, the pain associated disorder to be treated is cancer pain arising from malignancy or from cancer selected from one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of metastasis in the bone, postsurgical pain, sarcomas cancer of the connective tissue, cancer of bone tissue, cancer of blood-forming cells of the bone marrow, multiple myeloma, leukemia, primary or secondary bone cancer.

In other embodiments, the pain associated condition to be treated is associated with neuropathic pain and included, by way of example, trigeminal neuralgia, post-herpetic neuralgia, phantom limb pain, fibromyalgia, and reflex sympathetic dystrophy are preferably treated.

Further exemplary pain associated diseases or conditions, include but are not limited to, general pain, chronic pain, inflammatory pain, post-operative incision pain, post-surgical pain, trauma-related pain, lower back pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, overactive bladder, bronchial hyperreactivity, asthma, bronchitis, bronchodilation, emphysema, chronic obstructive pulmonary disease ("COPD"), inflammatory dermatitis, acne vulgaris, atopic dermatitis, urticaria, keloids, hypertrophic scars and rosacea, allergic dermatitis, psoriasis, puritus, neurogenic cutaneous redness, erythema, sarcoidosis, shock, sepsis, and opiate withdrawal syndrome.

Thus, the present invention includes methods of treating, preventing, and/or ameliorating any disease or disorder associated with PACAP activity or PACAP upregulation (including any of the above mentioned exemplary pain associated diseases, disorders and conditions) through use of the antibodies and antigen binding fragments of the invention.

Also, the subject anti-PACAP antibodies and antigen binding fragments may be used alone or in conjunction with other active agents, e.g., opioids and non-opioid analgesics such as NSAIDs to elicit analgesia or to potentiate the efficacy of another analgesic.

The subject antibodies potentially may be combined with any opioid analgesic or NSAID or other analgesic, potentially another antibody or another biologic such as, e.g., an anti-NGF or anti-CGRP or anti-CGRP-R antibody or antibody fragment or NGF, CGRP or CGRP-R polypeptide fragment or conjugate, in order to increase or enhance pain management. This may allow for such analgesic compounds to be administered for longer duration or at reduced dosages thereby potentially alleviating adverse side effects associated therewith.

Of particular interest is the co-administration of the subject anti-PACAP antibodies and antibody fragments with an anti-CGRP antibody (e.g., ALD403) or an anti-CGRP-R antibody or antibody fragment and, moreover, the use of the subject anti-PACAP antibodies and antibody fragments to treat subjects that previously received an anti-CGRP or anti-CGRP-R antibody or antibody fragment. For example, the previously treated subject (who previously received at least one anti-CGRP or anti-CGRP-R antibody or antibody fragment administration) may be a migraineur who did not adequately respond to anti-CGRP or anti-CGRP-R antibody treatment ("poor responder") and/or has elicited an immune response to the anti-CGRP or anti-CGRP-R antibody or antibody fragment.

Likewise, the co-administration of the subject anti-PACAP antibodies and antigen binding fragments with BOTOX® (Botulinum toxin) is also of particular interest, e.g., in treating a migraineur. In some instances, the migraineur may not have adequately responded to previous treatments ("poor responder") and/or has elicited an immune response to the previous treatment.

In some embodiments, aspirin and/or acetaminophen may be taken in conjunction with the subject anti-PACAP antibody or antigen binding fragment. Aspirin is another type of non-steroidal anti-inflammatory compound.

The subject to which the pharmaceutical formulation is administered can be, e.g., any human or non-human animal that is in need of such treatment, prevention and/or amelioration, or who would otherwise benefit from the inhibition or attenuation of PACAP-mediated activity. For example, the subject can be an individual that is diagnosed with, or who is deemed to be at risk of being afflicted by any of the aforementioned diseases or disorders. The present invention further includes the use of any of the pharmaceutical formulations disclosed herein in the manufacture of a medicament for the treatment, prevention and/or amelioration of any disease or disorder associated with PACAP activity (including any of the above mentioned exemplary diseases, disorders and conditions).

Administration

In one embodiment of the invention, the anti-PACAP antibodies described herein, or PACAP binding fragments thereof, as well as combinations of said antibodies or antigen binding fragments thereof, are administered to a subject at a concentration of between 0.1 mg/ml and about any one of 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190, or 200 mg/ml, +/−10% error.

In another embodiment of the invention, the anti-PACAP antibodies and fragments thereof described herein are administered to a subject at a dose of between about 0.01 and 100.0 or 200.0 mg/kg of body weight of the recipient subject. In certain embodiments, depending on the type and severity of the PACAP-related disease, about 1 μg/kg to 50 mg/kg (e.g., 0.1-20 mg/kg) of antibody is an initial candidate dosage for administration to the patient, whether, for example, by one or more separate administrations, or by continuous infusion. In another embodiment, about 1 μg/kg to 15 mg/kg (e.g., 0.1 mg/kg-10 mg/kg) of antibody is an initial candidate dosage for administration to the patient. A typical daily dosage might range from about 1 μg/kg to 100 mg/kg or more, depending on several factors, e.g., the particular mammal being treated, the clinical condition of the individual patient, the cause of the disorder, the site of delivery of the agent, the method of administration, the scheduling of administration, and other factors known to medical practitioners. However, other dosage regimens may be useful.

For example, in addition to the relative dosages (mg/kg) discussed herein, the subject anti-PACAP antibodies and antigen binding fragments thereof can be administered to a subject at an absolute dose (mg). Accordingly, in one embodiment of the invention, the anti-PACAP antibodies and antigen binding fragments thereof described herein are administered to a subject at a dose of between about 1 microgram and about 1000 milligrams regardless of the route of administration.

In a preferred embodiment of the invention, the anti-PACAP antibodies described herein, or anti-PACAP antigen binding fragments thereof, as well as combinations of said antibodies or antigen binding fragments thereof, are administered to a recipient subject with a frequency of once every twenty-six weeks or less, such as once every sixteen weeks or less, once every eight weeks or less, once every four weeks or less, once every two weeks or less, once every week or less, or once daily or less.

According to preferred embodiments, the antibody containing medicament or pharmaceutical composition is peripherally administered to a subject via a route selected from one or more of: orally, sublingually, buccally, topically, rectally, via inhalation, transdermally, subcutaneously, intravenously, intra-arterially, or intramuscularly, via intracardiac administration, intraosseously, intradermally, intraperitoneally, transmucosally, vaginally, intravitreally, epicutaneously, intra-articularly, peri-articularly, or locally.

Fab fragments may be administered every two weeks or less, every week or less, once daily or less, multiple times per day, and/or every few hours. In one embodiment of the invention, a patient receives Fab fragments of 0.1 mg/kg to 40 mg/kg per day given in divided doses of 1 to 6 times a day, or in a continuous perfusion form, effective to obtain desired results.

It is to be understood that the concentration of the antibody or Fab administered to a given patient may be greater or lower than the exemplary administration concentrations set forth above.

A person of skill in the art would be able to determine an effective dosage and frequency of administration through routine experimentation, for example guided by the disclosure herein and the teachings in, *Goodman & Gilman's The Pharmacological Basis of Therapeutics*, Brunton, L. L. et al. editors, 11$^{th}$ edition, New York, New York: McGraw-Hill (2006); Howland, R. D. et al., *Pharmacology, Volume* 864, *Lippincott's illustrated reviews*., Philadelphia, PA: Lippincott Williams & Wilkins (2006); and Golan, D. E., *Principles of pharmacology: the pathophysiologic basis of drug therapy*, Philadelphia, PA: Lippincott Williams & Wilkins (2007).

In another embodiment of the invention, the anti-PACAP antibodies described herein, or PACAP binding fragments thereof, as well as combinations of said antibodies or antigen binding fragments thereof, are administered to a subject in a pharmaceutical formulation. In a preferred embodiment, the subject is a human.

A "pharmaceutical composition" or "medicament" refers to a chemical or biological composition suitable for administration to a subject, preferably a mammal, more preferably a human. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-PACAP antibodies described herein, or PACAP binding fragments thereof, as well as combinations of said antibodies or antigen binding fragments thereof, may be optionally administered in combination with one or more active agents. Such active agents include analgesic, anti-histamine, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor ("HGF"), Hepcidin, NGF, CGRP including antibodies reactive against any of the foregoing, and antibodies reactive against any of their receptors. Active agents also include but are not limited to 2-arylpropionic acids, aceclofenac, acemetacin, acetylsalicylic acid (aspirin), alclofenac, alminoprofen, amoxiprin, ampyrone, arylalkanoic acids, azapropazone, benorylate/benorilate, benoxaprofen, bromfenac, carprofen, celecoxib, choline magnesium salicylate, clofezone, COX-2 inhibitors, dexibuprofen, dexketoprofen, diclofenac, diflunisal, droxicam, ethenzamide, etodolac, etoricoxib, faislamine, fenamic acids, fenbufen, fenoprofen, flufenamic acid, flunoxaprofen, flurbiprofen, ibuprofen, ibuproxam, indomethacin, indoprofen, kebuzone, ketoprofen, ketorolac, lornoxicam, loxoprofen, lumiracoxib, magnesium salicylate, meclofenamic acid, mefenamic acid, meloxicam, metamizole, methyl salicylate, mofebutazone, nabumetone, naproxen, N-arylanthranilic acids, NGF, oxametacin, oxaprozin, oxicams, oxyphenbutazone, oxytocin, parecoxib, phenazone, phenylbutazone, phenylbutazone, piroxicam, pirprofen, profens, proglumetacin, pyrazolidine derivatives, rofecoxib, salicyl salicylate, salicylamide, salicylates, substance P, sulfinpyrazone, sulindac, suprofen, tenoxicam, tiaprofenic acid, tolfenamic acid, tolmetin, and valdecoxib. For instance, the selected anti-PACAP antibodies, or PACAP-binding fragments thereof, as well as combinations of these antibodies or antigen binding fragments, can be optionally administered in combination with oxytocin, for instance administered in a nasal formulation, for intranasal delivery.

An anti-histamine can be any compound that opposes the action of histamine or its release from cells (e.g., mast cells). Anti-histamines include but are not limited to acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratadine, methscopolamine, mizolastine, norastemizole, phenindamine, promethazine, pyrilamine, terfenadine, and tranilast.

Antibiotics include but are not limited to amikacin, aminoglycosides, amoxicillin, ampicillin, ansamycins, arsphenamine, azithromycin, azlocillin, aztreonam, bacitracin, carbacephem, carbapenems, carbenicillin, cefaclor, cefadroxil, cefalexin, cefalothin, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalosporins, chloramphenicol, cilastatin, ciprofloxacin, clarithromycin, clindamycin, cloxacillin, colistin, co-trimoxazole, dalfopristin, demeclocycline, dicloxacillin, dirithromycin, doripenem, doxycycline, enoxacin, ertapenem, erythromycin, ethambutol, flucloxacillin, fosfomycin, furazolidone, fusidic acid, gatifloxacin, geldanamycin, gentamicin, glycopeptides, herbimycin, imipenem, isoniazid, kanamycin, levofloxacin, lincomycin, linezolid, lomefloxacin, loracarbef, macrolides, mafenide, meropenem, methicillin, metronidazole, mezlocillin, minocycline, monobactams, moxifloxacin, mupirocin, nafcillin, neomycin, netilmicin, nitrofurantoin, norfloxacin, ofloxacin, oxacillin, oxytetracycline, paromomycin, penicillin, penicillins, piperacillin, platensimycin, polymyxin B, polypeptides, prontosil, pyrazinamide, quinolones, quinupristin, rifampicin, rifampin, roxithromycin, spectinomycin, streptomycin, sulfacetamide, sulfamethizole, sulfanilamide, sulfasalazine, sulfisoxazole, sulfonamides, teicoplanin, telithromycin, tetracycline, tetracyclines, ticarcillin, tinidazole, tobramycin, trimethoprim, trimethoprim-sulfamethoxazole, troleandomycin, trovafloxacin, and vancomycin.

Active agents also include aldosterone, beclomethasone, betamethasone, corticosteroids, cortisol, cortisone acetate, deoxycorticosterone acetate, dexamethasone, fludrocortisone acetate, glucocorticoids, hydrocortisone, methylprednisolone, prednisolone, prednisone, steroids, and triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found, for example, in *Remington's Pharmaceutical Sciences*, Gennaro, A. editor, 19$^{th}$ edition, Philadelphia, PA: Williams and Wilkins (1995), which is incorporated by reference.

As used herein "pharmaceutically acceptable carrier" or "excipient" includes any and all solvents, dispersion media, coatings, antibacterial and antifungal agents, isotonic, and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the maintenance of the required particle size in the case of dispersion and by the use of surfactants.

In many cases, it will be preferable to include isotonic agents, for example, sugars, polyalcohols such as mannitol and sorbitol, or sodium chloride in the composition. Absorption of the injectable compositions can be prolonged by including an agent that delays absorption, for example, monostearate salts and gelatin. Moreover, the alkaline polypeptide can be formulated in a time-release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid, polylactic and polyglycolic copolymers ("PLG"). Many methods for the preparation of such formulations are known to those skilled in the art.

For each of the recited embodiments, the compounds can be administered by a variety of dosage forms. Any biologically acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B-cells were disclosed in U.S. Patent Publication No. 2013/0316353, the disclosure of which is herein incorporated by reference in its entirety.

Certain teachings related to humanization of rabbit-derived monoclonal antibodies and preferred sequence modifications to maintain antigen-binding affinity were disclosed in International Publication No. WO 2008/144757, entitled *Novel Rabbit Antibody Humanization Methods and Humanized Rabbit Antibodies*, filed May 21, 2008, the disclosure of which is herein incorporated by reference in its entirety.

Certain teachings related to producing antibodies or fragments thereof using mating competent yeast and corresponding methods were disclosed in U.S. Patent Publication No. US2006/0270045, the disclosure of which is herein incorporated by reference in its entirety.

Certain teachings related to producing antibodies or fragments thereof in *Pichia* and preferred methods for obtaining and purifying antibodies are also disclosed in U.S. Patent Publication Nos. 2014/0288272; 2014/0287952; 2013/0055888; and 2012/0277408, the disclosures of each of which are herein incorporated by reference in their entirety.

Certain teachings related to producing antibodies or fragments thereof in CHO cells and exemplary methods for obtaining and purifying antibodies are also disclosed in U.S. Patent and Publication Nos. 7,932,087; 2009/0285795; 9,090,672; and 2010/0221781; the disclosures of each of which are herein incorporated by reference in their entirety.

Certain anti-PACAP antibody polynucleotides and polypeptides and uses thereof are disclosed in co-owned U.S. Provisional Application Ser. No. 62/148,550, filed Apr. 16, 2015, U.S. Provisional Application Ser. No. 62/148,557, filed Apr. 16, 2015, U.S. Provisional Application Ser. No. 62/148,562, filed Apr. 16, 2015, U.S. Provisional Application Ser. No. 62/148,596, filed Apr. 16, 2015, U.S. Provisional Application Ser. No. 62/148,643, filed Apr. 16, 2015, U.S. Provisional Application Ser. No. 62/148,583, filed Apr. 16, 2015, U.S. Provisional Application Ser. No. 62/148,640, filed Apr. 16, 2015, U.S. Ser. No. 15/130,263 filed Apr. 15, 2016, and U.S. Ser. No. 15/130,848 filed Apr. 15, 2016, each of which is hereby incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.), but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1: Preparation of Antibodies that Selectively Bind PACAP

By using an antibody selection protocol substantially as described herein, a panel of antibodies specific to PACAP38 and PACAP27, and a panel of antibodies specific to PACAP38 only, were produced.

Immunization Strategy

Rabbits were immunized with PACAP38 (American Peptide, Vista, CA) (SEQ ID NO: 1241). Peptides were prepared for immunization as follows. A 0.15 ml volume of 10 mg/ml keyhole limpet hemocyanin ("KLH") dissolved in Dulbecco's phosphate buffered saline ("DPBS") supplemented to 1 M NaCl was combined with 1.0 ml of 1 mg/ml peptide (dissolved in deionized water). Then 1.0 ml of 40 mM carbodiimide was added prior to a 12-hour incubation at room temperature with gentle mixing. Excess carbodiimide and unconjugated peptide were removed by dialysis to DPBS prior to sterile filtration. Next unconjugated peptide equal to the initial mass of KLH was added prior to preparation for injection into rabbits. Alternatively, equal masses of sterile KLH and peptide were mixed without carbodiimide chemistry.

Immunizations were performed by diluting 200 μg of antigen to 0.5 ml with DPBS and mixing with an equal volume of complete Freund's adjuvant for subcutaneous 1 ml injection at Day 1.

Boost injections of 100 μg were performed with incomplete Freund's adjuvant at Days 21 and 42.

Antibody Selection Functional Titer Assessment

To identify antibodies that neutralize PACAP38 (SEQ ID NO: 1241) induced signaling via PAC1-R, polyclonal antibody solutions were first purified via Protein A and dialyzed into a neutral buffer. Briefly, antibody solutions were incubated with PACAP38 (SEQ ID NO: 1241) at 4× the final concentration (100 pM) for 1 hr. While the antibody/antigen complexes were incubated, PAC1-R expressing PC-12 cells (Japanese Collection of Research Bioresources Cell Bank) were washed and re-suspended at $2\times10^6$ cells per ml in cell culture media. Cells (10 μl) and antigen/antibody complex (40 μl) were transferred to a homogenous time resolved fluorescence ("HTRF") plate and shaken at room temperature for 30 min. Following the incubation, 20 μl of (1:20 diluted) $Eu^{3+}$ cryptate-labeled mAb anti-cAMP and 20 μl of (1:20 diluted) d2-labeled cAMP in lysis buffer were added, and the plate was incubated for 1 hr while shaking. Following incubation, plates were read (excitation 330 nm, emission 620/665 nm), and a ratio of 620:665 signal was determined.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 μm (Thermo Fisher Scientific, Waltham, MA) with a plunger of a 20 cc syringe. Cells were collected in phosphate buffered saline ("PBS"). Cells were then washed twice by centrifugation. After the last wash, cell density was determined by trypan blue. Cells were centrifuged at 1500 RPM for 10 minutes; the supernatant was then discarded. Cells were resuspended in the appropriate volume of 10% dimethyl sulfoxide ("DMSO", Sigma-Aldrich Co., St. Louis, MO) in fetal bovine serum ("FBS" HYCLONE™, GE Healthcare Life Sciences, Marlborough, MA) and dispensed at 1 ml/vial. Vials were stored at −70° C. in a slow freezing chamber for 24 hours and stored in liquid nitrogen.

Peripheral blood mononuclear cells ("PBMCs") were isolated by mixing whole blood with equal parts of PBS. 35 ml of the whole blood mixture was carefully layered onto 8 ml of LYMPHOLYTE® Rabbit (Cedarlane Laboratories, Burlington, Ontario) into a 45 ml conical tube (Corning, Corning, NY) and centrifuged for 30 minutes at 2500 RPM at room temperature without brakes. After centrifugation, the PBMC layers were carefully removed using a glass Pasteur pipette (VWR International, Radnor, PA), combined, and placed into a clean 50 ml vial. Cells were washed twice with PBS by centrifugation at 1500 RPM for 10 minutes at room temperature, and cell density was determined by trypan blue staining. After the last wash, cells were resuspended in an appropriate volume of 10% DMSO/FBS medium and frozen as described above.

B-Cell Selection, Enrichment, and Culture Conditions

On the day of setting up B-cell culture, PBMC, splenocyte, or lymph node vials were thawed for use. Vials were removed from liquid nitrogen tank and placed in a 37° C. water bath until thawed. Contents of vials were transferred into 15 ml conical centrifuge tube (Corning, Inc., Corning, NY) and 10 ml of modified RPMI was slowly added to the tube. Cells were centrifuged for 5 minutes at 2000 RPM, and the supernatant was discarded. Cells were resuspended in 10 ml of fresh media. Cell density and viability was determined by trypan blue.

For positive selection of anti-PACAP38 producing B-cells, biotinylated PACAP38 (SEQ ID NO: 1241) was pre-loaded onto the streptavidin beads as follows. 75 μl of streptavidin beads (Miltenyi Biotec, Auburn, CA) were mixed with N-terminally biotinylated PACAP38 (10 μg/ml final concentration) and 300 μl of PBS supplemented with 0.5% biotin free bovine serum albumin ("BSA") and 2 mM EDTA ("PBF"). This mixture was incubated at 4° C. for 30 minutes, and unbound biotinylated PACAP38 (AnaSpec, Fremont, CA) was removed using a MACS® separation column (Miltenyi Biotec, Auburn, CA) with a 1 ml rinse to remove unbound material. The bound material was plunged out by detachment from the magnet and used to resuspend cells from above in 100 μl per $1\times10^7$ cells. The mixture was then incubated at 4° C. for 30 minutes and washed once with 10 ml of PBF. After washing, the cells were resuspended in 500 μl of PBF and set aside. A MACS® MS column (Miltenyi Biotec, Auburn, CA) was pre-rinsed with 500 μl of PBF on a magnetic stand (Miltenyi Biotec, Auburn, CA). Cell suspension was applied to the column through a pre-filter, and unbound fraction was collected. The column was washed with 2.5 ml of PBF buffer. The column was removed from the magnet stand and placed onto a clean, sterile 1.5 ml EPPENDORF™ tube. 1 ml of PBF buffer was added to the top of the column, and positive selected cells were collected. The yield and viability of positive cell fraction was determined by trypan blue staining. Positive selection yielded an average of 1% of the starting cell concentration.

A pilot cell screen was established to provide information on seeding levels for the culture. Plates were seeded at 5, 10, 25, 50, 100, or 200 enriched B-cells/well. In addition, each well contained 25-50K cells/well of irradiated EL-4.B5 cells (5,000 Rads) and an appropriate level of activated rabbit T-cell supernatant (See U.S. Patent Application Publication No. 20070269868) (ranging from 1-5% depending on preparation) in high glucose modified RPMI medium at a final volume of 250 μl/well. Cultures were incubated for 5 to 7 days at 37° C. in 4% $CO_2$.

B-Cell Culture Screening by Antigen-Recognition (ELISA)

To identify wells producing anti-PACAP38 antibodies, B-cell supernatants were tested by antigen-recognition (ELISA). Briefly, NEUTRAVIDIN™-coated plates (Thermo Fisher Scientific, Waltham, MA), were coated with either N-term or C-term biotinylated PACAP38 (AnaSpec Inc., Fremont, CA) (50 μl per well; 1 μg/ml) diluted in ELISA buffer (0.5% fish skin gelatin in PBS pH 7.4) either for approximately 1 hour at room temperature or alternatively overnight at 4° C. The plates were then further blocked with ELISA buffer for one hour at room temperature and washed using PBS with 0.05% Tween 20 ("wash buffer"). B-cell supernatant samples (50 μl) were transferred onto the wells and incubated for one hour at room temperature. After this incubation, the plate was washed with wash buffer. For development, an anti-rabbit specific Fc-Horse Radish Peroxidase ("Fc-HRP") (1:5000 dilution in ELISA buffer) was added onto the wells and incubated for 45 minutes at room temperature. After a 3× wash step with wash solution, the plate was developed using 3,3',5,5'-Tetramethylbenzidine ("TMB") substrate for two minutes at room temperature, and the reaction was quenched using 0.5 M HCl. The well absorbance was read at 450 nm.

To identify wells producing anti-PACAP38 antibodies that do not recognize VIP (SEQ ID NO: 1243), supernatant from wells positive for PACAP38 binding by ELISA were tested by ELISA for binding to VIP. Briefly, biotinylated VIP (AnaSpec Inc., Fremont, CA) was bound onto NEUTRAVIDIN™ coated plates (50 μg per well, 1 μg/μl each peptide). B-cell supernatant samples (50 μl) were tested without prior dilution. Recognition in this assay may indicate cross reactivity with a closely related peptide, VIP.

Identification of Functional Activity in B-Cell Supernatants Using One or More Assays To identify wells producing anti-PACAP38 antibodies that block signaling of PACAP38 via PAC1-R, supernatant from positive wells for PACAP38 binding by ELISA were tested in a CAMP HTRF assay (Cisbio US, Bedford, MA). Supernatants (78 μl) were pre-incubated with 2 μl 5 nM PACAP38 (American Peptide Company, Sunnyvale, CA) for 1 hour at 37° C. During the incubation, PC-12 cells were prepared as described for titer assessment. Cells (10 μl) and antigen/antibody complex (40 μl) were transferred to an HTRF plate and shaken at room temperature for 30 minutes. Following the incubation, 20 μl of (1:20 diluted) $Eu^{3+}$ cryptate-labeled mAb anti-cAMP and 20 μl of (1:20 diluted) d2-labeled CAMP in lysis buffer were added, and the plate was incubated for 1 hour while shaking. Following incubation plates were read (excitation 330 nm, emission 620/665 nm), and a ratio of 620:665 signal was determined.

Isolation of Antigen-Specific B-Cells

Antigen-specific B-cells were isolated (for general methods see co-owned publication no. WO 2014/146074, which is hereby incorporated by reference in its entirety). Plates containing wells of interest were removed from −70° C., and the cells from each well were recovered using five washes of 200 μl of medium (10% RPMI complete, 55 UM β-mercaptoethanol ("BME")) per well. The recovered cells were pelleted by centrifugation and the supernatant was carefully removed. Cells from each well were then re-suspended in 100 μl of medium and transferred to a 96 well plate. Cells were incubated for 90 minutes at 37° C. Following incubation, cells were pelleted by centrifugation, stained with a fluorescein isothiocyanate-labeled ("FITC-labeled") anti-rabbit IgG (final concentration 6.25 μg/ml) (Creative Diagnostics, Shirley, NY), and washed with up to 2 ml fluorescence-activated cell sorting buffer ("FACS buffer") (Dulbecco's PBS w/2% FBS) and re-suspended in 250 μl of FACS buffer.

Control wells from the same culture sets that were similar in composition to pooled wells of interest were thawed and stained alongside target wells. These samples were initially run on FACS (BD INFLUX™, Becton, Dickinson and Company, Franklin Lakes, NJ), and gates were established for IgG, viability, and physical parameters (Forward scatter ("FSC")/side scatter ("SSC")) that differentiate B-cells from the murine EL4 cells. Once gates were established, the sample of interest was run, and IgG positive, viable cells that were of a consistent physical (FSC/SSC) population were sorted individually into wells of a 96 well plate pre-loaded with RT-PCR master mix. Upwards of 8 cells per well were sorted. Sorted plates were removed from the sorter and transferred directly to thermocyclers for PCR.

Amplification and Sequence Determination of Antibody Sequences from FACS-Sorted B-Cells Antibody sequences were recovered using a combined RT-PCR based method from a single cell sorted B-cell. Primers containing restriction enzymes were designed to anneal in conserved and constant regions of the target immunoglobulin genes (heavy and light), such as rabbit immunoglobulin sequences, and a two-step nested PCR recovery was used to amplify the antibody sequence. Amplicons from each well were sequenced and analyzed. Representative antibodies from the resulting sequence clusters were selected for recombinant protein expression. The original heavy and light variable regions amplified from rabbit cells were cloned into human heavy and light chain constant region expression vectors via restriction enzyme digestion and ligation, and via Gibson method. Vectors containing subcloned DNA fragments were amplified and purified. The sequences of the subcloned heavy and light chains were verified prior to expression.

Recombinant Production of Monoclonal Antibody of Desired Antigen Specificity and/or Functional Properties To determine antigen specificity and functional properties of recovered antibodies from specific B-cells, the heavy and light chain plasmids were co-transfected to generate rabbit/human chimeric antibodies for testing. Briefly, heavy and light chimeric plasmids were transiently transfected into HEK-293 cells. Transfections were allowed to incubate for 5-7 days, and upon harvest, cells were pelleted by centrifugation. Supernatants were submitted for purification via Protein A. Resulting purified chimeric antibodies were then evaluated in a variety of assays to confirm specificity and potency.

Using the above-described methods, numerous functional (antagonistic) antibodies that bind PACAP38 and PACAP27, or that bind PACAP38 only, but which do not, or do not appreciably, bind to VIP were identified. Polypeptide and exemplary coding sequences of exemplary antagonistic anti-PACAP antibodies are contained in the included biological sequence listing.

The full-length antibodies Ab10, Ab10.H, Ab10.H2, Ab10.H3, Ab10.H4, Ab10.H5, Ab20, Ab21, Ab21.H, Ab22, Ab23, Ab21.H2, Ab21.H3, and Ab21.H4 used in these examples were expressed as the heavy chain polypeptides having the sequences of SEQ ID NOS: 401; 961; 1281; 1321; 1361; 1401; 441; 841; 1201; 881; 921; 1481; 1521; and 1561, respectively, and the light chain polypeptides of SEQ ID NOS: 421; 981; 1301; 1341; 1381; 1421; 461; 861; 1221; 901; 941; 1501; 1541; and 1581, respectively. The heavy chain polypeptides of antibodies Ab10, Ab10.H, Ab10.H2, Ab10.H3, Ab10.H4, Ab10.H5, Ab20, Ab21, Ab21.H, Ab22, Ab23, Ab21.H2, Ab21.H3, and Ab21.H4 were expressed from the polynucleotides of SEQ ID NOS: 411; 971; 1291; 1331; 1371; 1411; 451; 851; 1211; 891; 931; 1491; 1531; and 1571, respectively. The light chain polypeptides of antibodies Ab10, Ab10.H, Ab10.H2, Ab10.H3, Ab10.H4, Ab10.H5, Ab20, Ab21, Ab21.H, Ab22, Ab23, Ab21.H2, Ab21.H3, and Ab21.H4 were expressed from the polynucleotides of SEQ ID NOS: 431; 991; 1311; 1351; 1391; 1431; 471; 871; 1231; 911; 951; 1511; 1551; and 1591, respectively. Additional features of said antibodies are identified by SEQ ID NOS in FIGS. 1A-12.

Antigen Binding Specificity of Antibodies by Competitive HTRF Binding Assay

The binding and functional properties of exemplary anti-PACAP38 and anti-PACAP27 antibodies produced according to the invention are further described below.

To identify antibodies that preferentially bind PACAP38 (SEQ ID NO: 1241) and PACAP27 (SEQ ID NO: 1242), but do not bind VIP (SEQ ID NO: 1243), or to identify antibodies that specifically bind PACAP38, but do not bind appreciably PACAP27, or do not appreciably bind VIP, etc., a competition HTRF binding assay was performed.

In parallel, 10 μl of an antibody dilution series (highest final concentration of 100 nM) were incubated with 10 μl of N-terminal or C-terminal biotinylated PACAP38 (35 nM final) alone, or in combination with either PACAP27 (350 nM final) or VIP (350 nM final), i.e., 10× PACAP27 or 10×VIP, respectively, in a HTRF plate. 20 μl of $Eu^{3+}$ cryptate labeled anti-hu Fc donor and 20 μl of d2-labeled streptavidin acceptor were added to each well and incubated for 1 hour at room temperature. Fluorescence was measured at 620 and 665 nm with a delay of 300 usec.

Figure 13E:
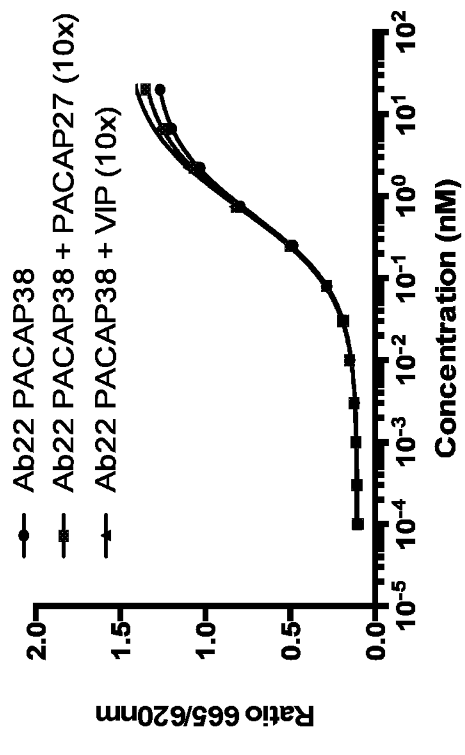
Figure 13F:
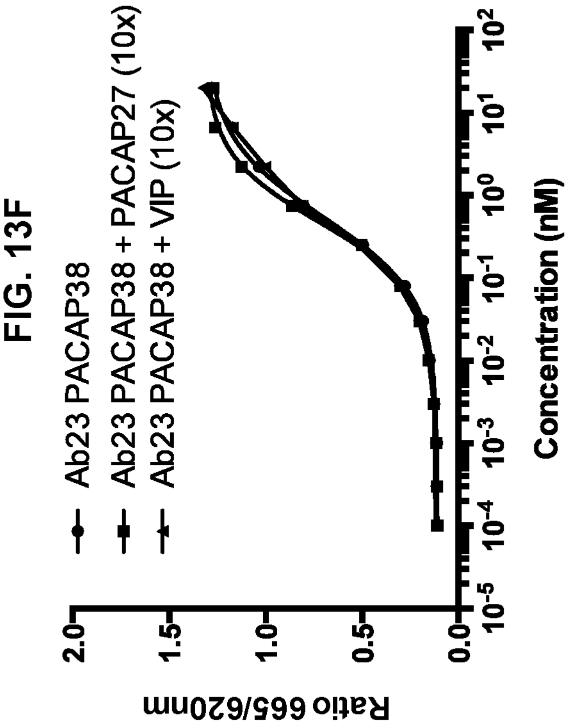
Figure 14A:
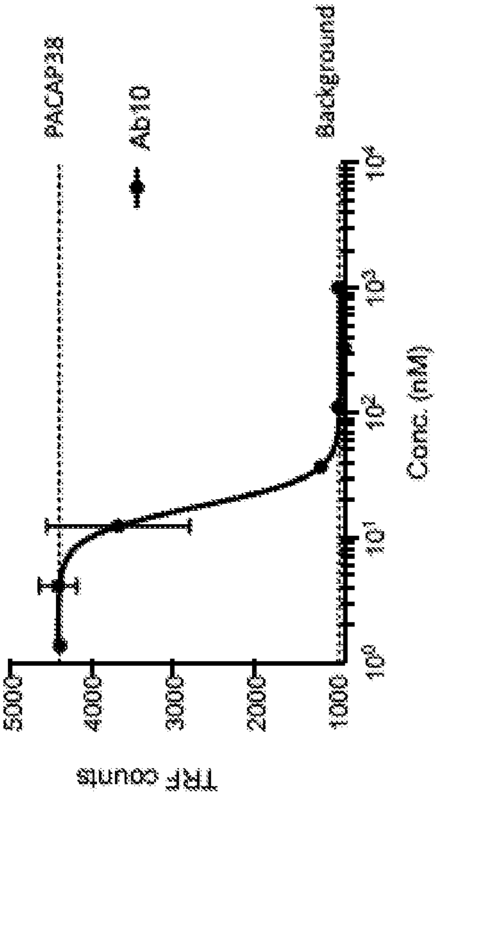
FIGS. 14A-14H provide representative data showing Ab10-mediated (FIG. 14A), Ab20-mediated (FIG. 14B), Ab21-mediated (FIG. 14C), Ab1.H-mediated (FIG. 14D), Ab10.H-mediated (FIG. 14E), Ab21.H-mediated (FIG. 14F), Ab22-mediated (FIG. 14G), and Ab23-mediated (FIG. 14H) inhibition of PACAP38 binding to PAC1-R-expressing PC-12 cells obtained following the protocol in Example 5 infra.
Figure 14B:
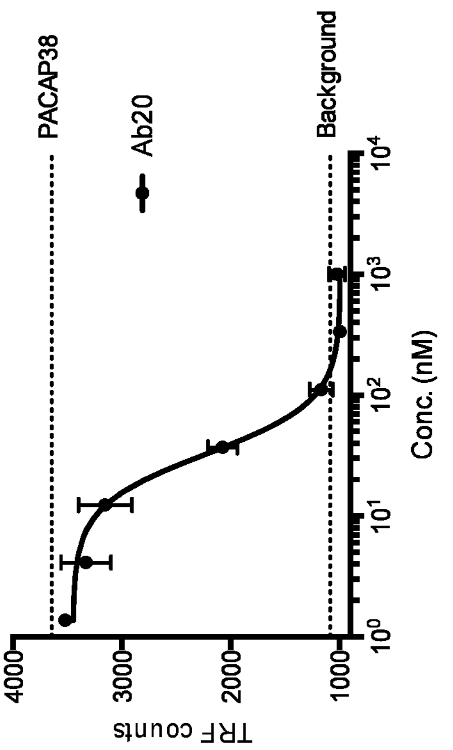
Figure 14C:
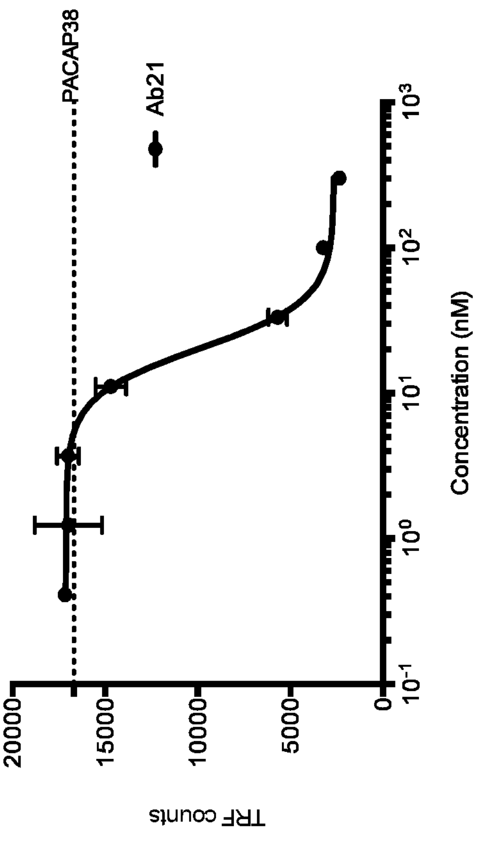
Figure 14D:
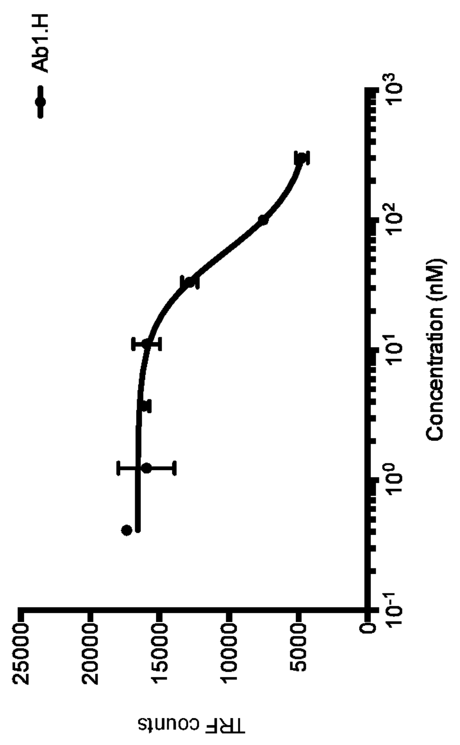
Figure 14E:
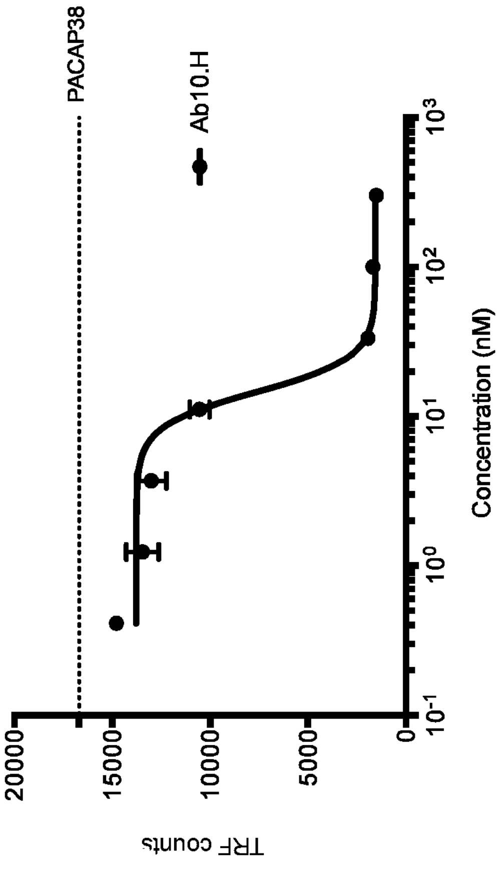
Figure 14F:
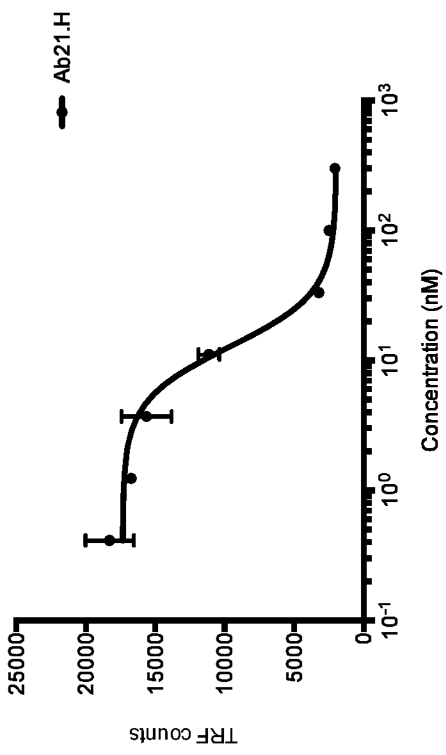
Figure 14G:
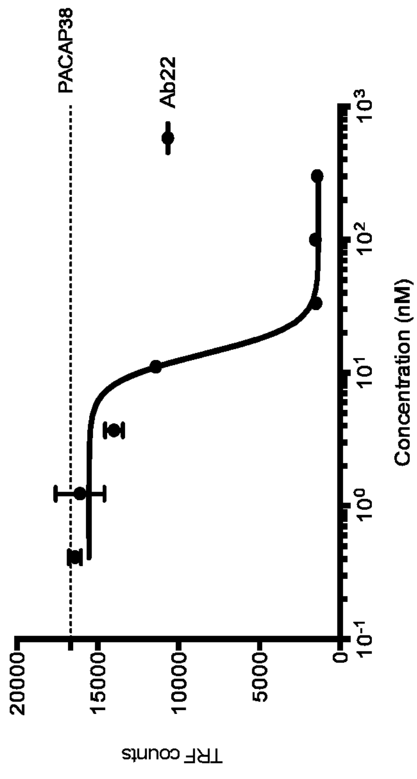
Figure 14H:
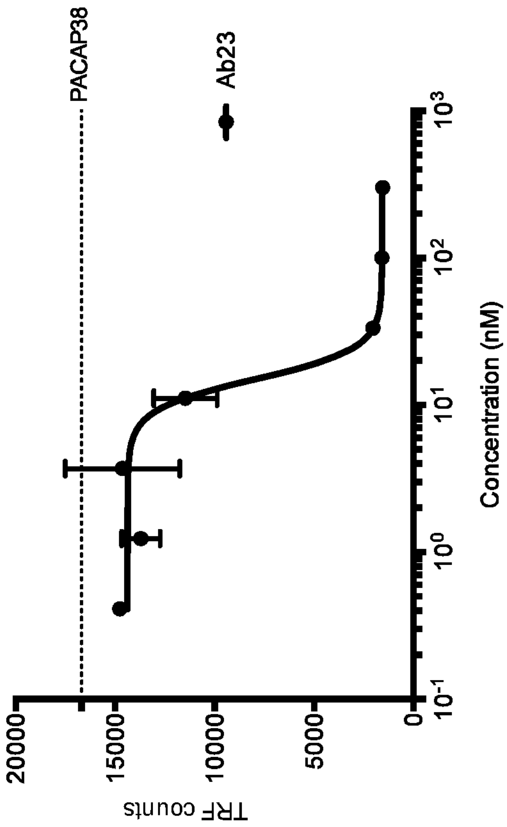

FIGS. 13A-13D provide representative binding data for Ab10, Ab20, Ab21, and Ab1.H to PACAP38 and to PACAP27, and the inability of VIP to compete with binding of PACAP38. FIG. 13E and FIG. 13F provide representative binding data for the anti-PACAP antibodies Ab22 and Ab23 to PACAP38 and the inability of PACAP27 or VIP to compete with binding of PACAP38. The lack of effect of VIP on binding to PACAP38 indicated its inability to compete with binding of PACAP38. These results demonstrated that Ab10, Ab20, Ab21, and Ab1.H bind to PACAP38 and PACAP27, but do not bind (or do not appreciably bind) VIP. These results also demonstrated that Ab22 and Ab23 bind to PACAP38, but do not bind (or do not appreciably bind) PACAP27 or VIP.

$EC_{50}$ values, i.e. the concentration of an antibody that yields a response halfway between the baseline and the maximum value within a specified time period, were computed for each antibody based upon their binding curves and are shown in Table 1 below. The results demonstrated that Ab10, Ab20, Ab21, Ab22, and Ab23 bound to and recognized human PACAP38 with high affinity. A humanized form of antibody Ab1 identified by an appended ".H", i.e., Ab1.H also bound PACAP38 with high affinity.

TABLE 1

Binding ($EC_{50}$) of PACAP38 by anti-PACAP antibodies

| ANTIBODY | PACAP38-binding $EC_{50}$ (nM) |
|---|---|
| Ab10 | 0.36 |
| Ab20 | 0.38 |
| Ab21 | 0.84 |
| Ab1.H | 0.46 |
| Ab22 | 0.57 |
| Ab23 | 0.56 |

Ability of Anti-PACAP Antibodies to Neutralize PACAP38-Induced and PACAP27-Induced CAMP Production The ability of anti-PACAP antibodies to neutralize PACAP38-induced and PACAP27-induced PAC1-R signaling was tested in a cell-based assay.

For Ab10, Ab20, Ab21, Ab1.H, Ab10.H, Ab21.H, Ab22, Ab23, Ab10.H2, Ab10.H3, Ab10.H4, Ab10.H5, Ab21.H2, Ab21.H3, and Ab21.H4 to identify antibodies that neutralized PACAP38-induced and PACAP27-induced signaling via PAC1-R, antibody solutions were incubated with either PACAP38 at 4×the final concentration (100 pM) for 1 hour, or with PACAP27 at 4×the final concentration (100 pM for Ab10, Ab20, Ab21, Ab1.H, Ab10.H, Ab21.H, Ab22, and Ab23; and 1 nM for Ab10.H2, Ab10.H3, Ab10.H4, Ab10.H5, Ab21.H2, Ab21.H3, and Ab21.H4) for 1 hour. While the antibody/antigen complexes were incubated, PAC1-R expressing PC-12 cells (Japanese Collection of Research Bioresources Cell Bank) were washed and re-suspended at $2\times10^6$ cells per ml in cell culture media. Cells (10 μl) and antigen/antibody complex (40 μl) were transferred to an HTRF plate and shaken at room temperature for 30 minutes. Following the incubation, 20 μl of (1:20 diluted) $Eu^{3+}$ cryptate-labeled mAb anti-cAMP and 20 μl of (1:20 diluted) d2-labeled CAMP in lysis buffer were added, and the plate was incubated for 1 hour while shaking. Following incubation, plates were read (excitation 330 nm, emission 620/665 nm), and a ratio of 620:665 signal was determined. The final concentration of PACAP38 in each well was 0.1 nM, and the final concentration of PACAP27 in each well was 0.1 nM for Ab10, Ab20, Ab21, Ab1.H, Ab10.H, Ab21.H, Ab22, and Ab23; and 1 nM for Ab10.H2, Ab10.H3, Ab10.H4, Ab10.H5, Ab21.H2, Ab21.H3, and Ab21.H4.

Figure 16A:
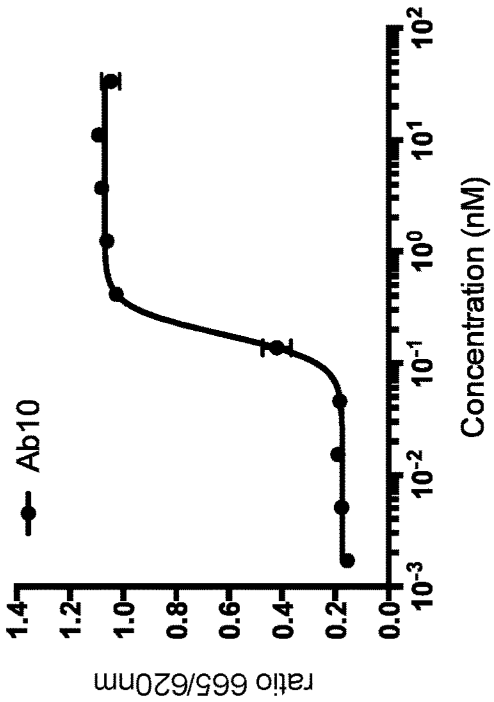
FIGS. 16A-16O provide representative data showing Ab10-mediated (FIG. 16A), Ab20-mediated (FIG. 16B), Ab21-mediated (FIG. 16C), Ab1.H-mediated (FIG. 16D), Ab10.H-mediated (FIG. 16E), Ab21.H-mediated (FIG. 16F), Ab22-mediated (FIG. 16G), Ab23-mediated (FIG. 16H), Ab10.H2-mediated (FIG. 16I), Ab10.H3-mediated (FIG. 16J), Ab10.H4-mediated (FIG. 16K), Ab10.H5-mediated (FIG. 16L), Ab21.H2-mediated (FIG. 16M), Ab21.H3-mediated (FIG. 16N), and Ab21.H4-mediated (FIG. 16O) inhibition of PACAP38-driven cAMP production via PAC1-R-expressing PC-12 cells obtained following the protocol in Example 1 infra.
Figure 16B:
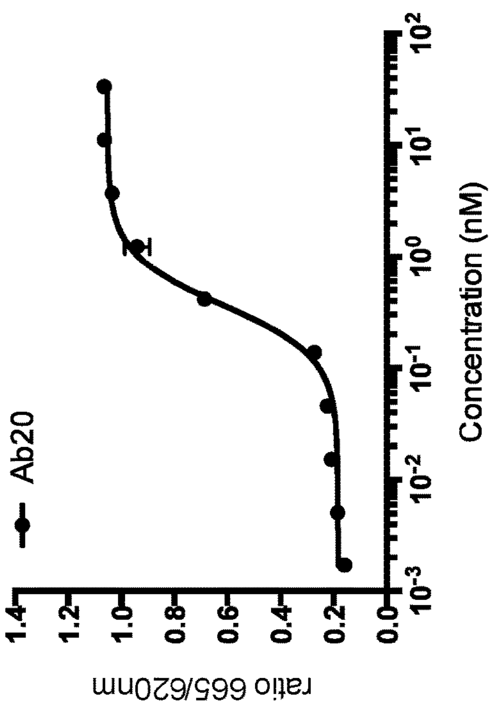
Figure 16C:
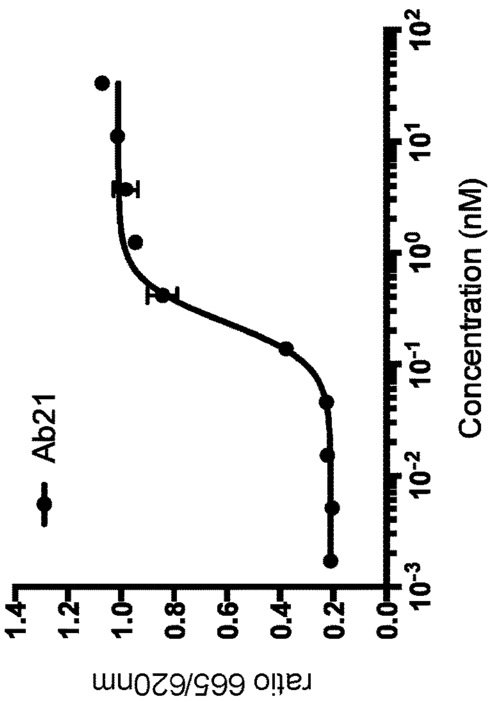
Figure 16D:
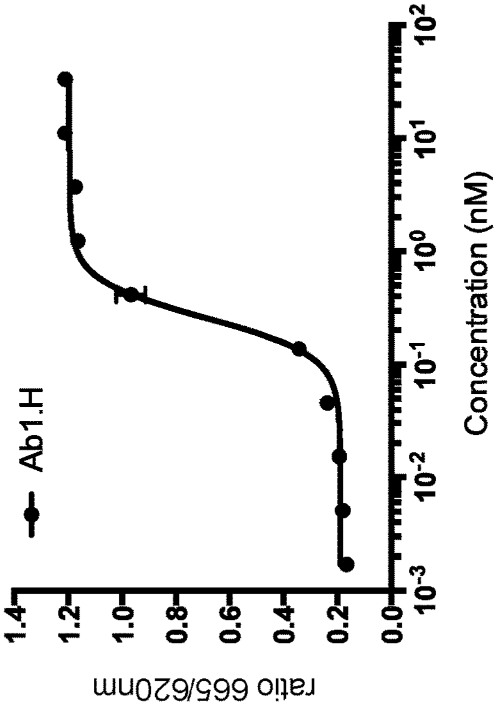
Figure 16E:
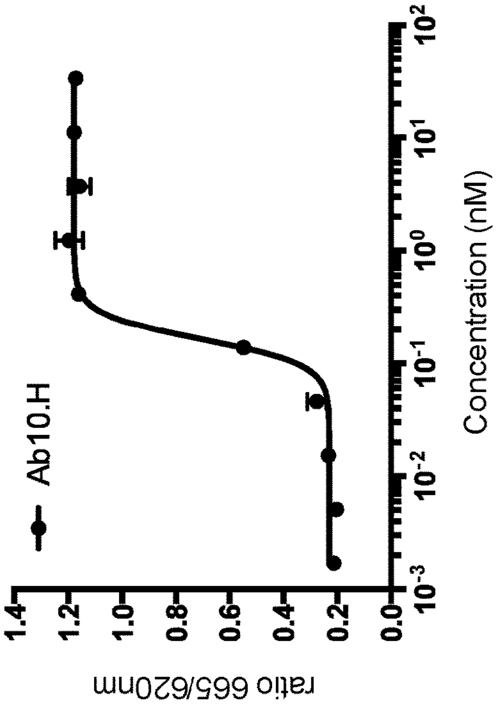
Figure 16F:
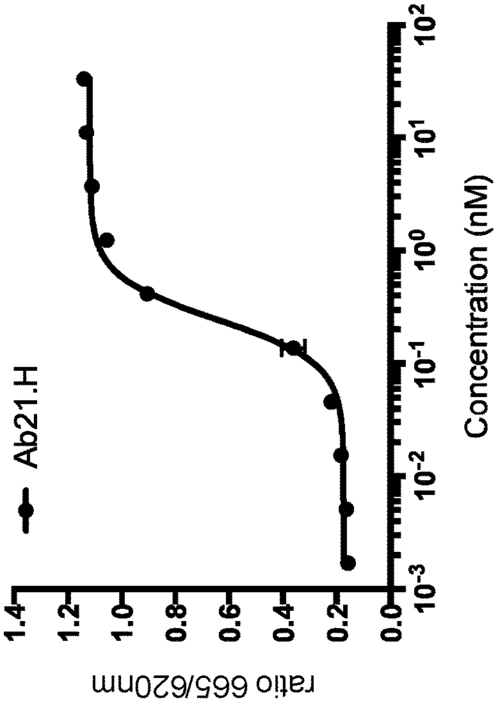
Figure 16G:
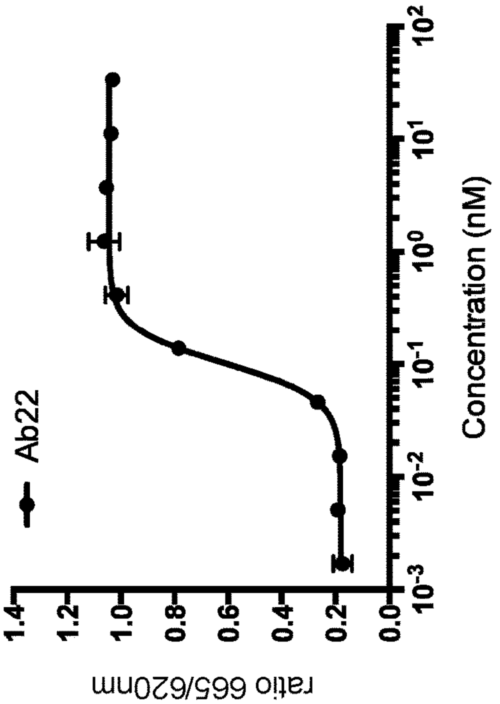
Figure 16H:
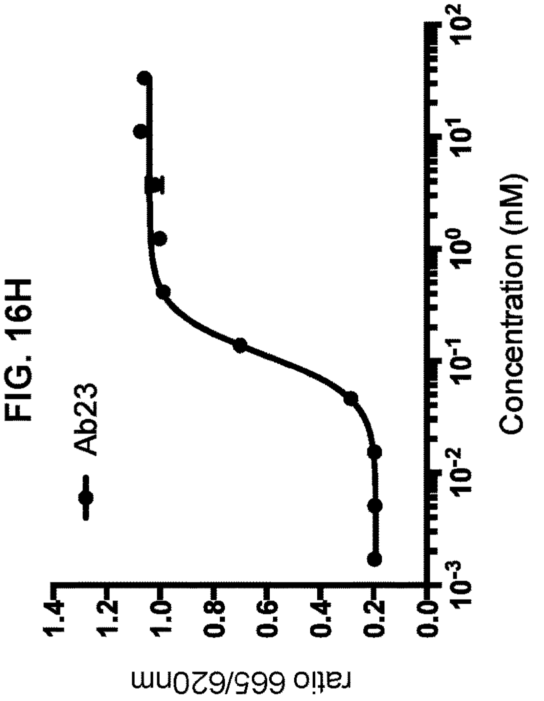
Figure 16I:
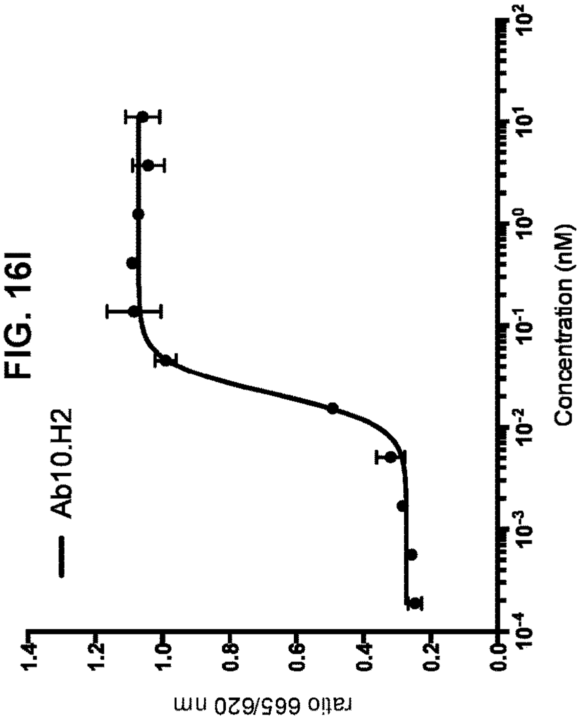
Figure 16J:
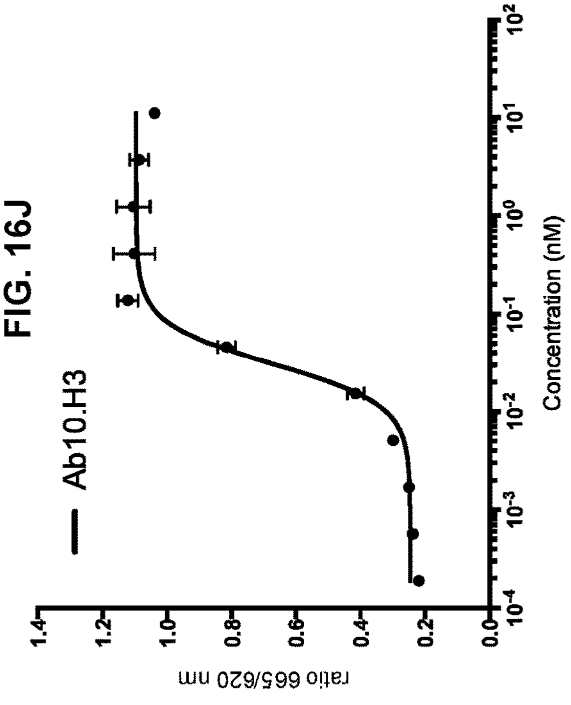
Figure 16K:
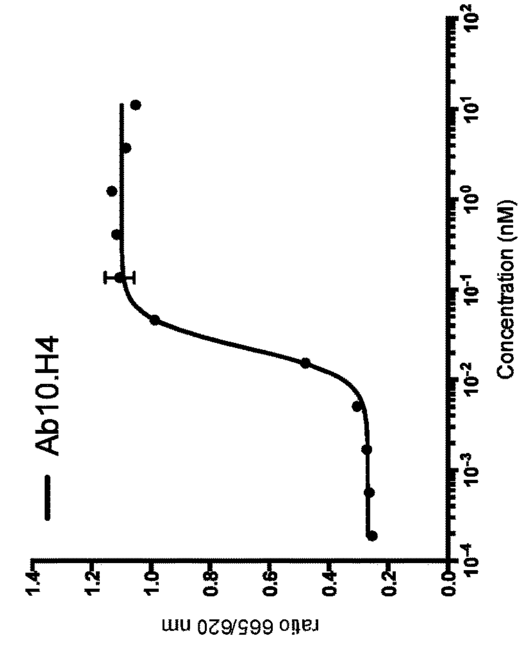
Figure 16L:
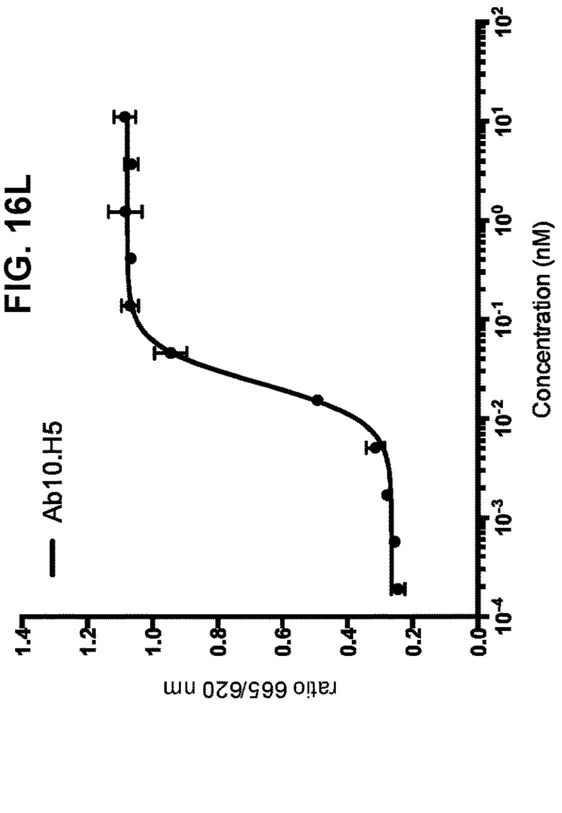
Figure 16M:
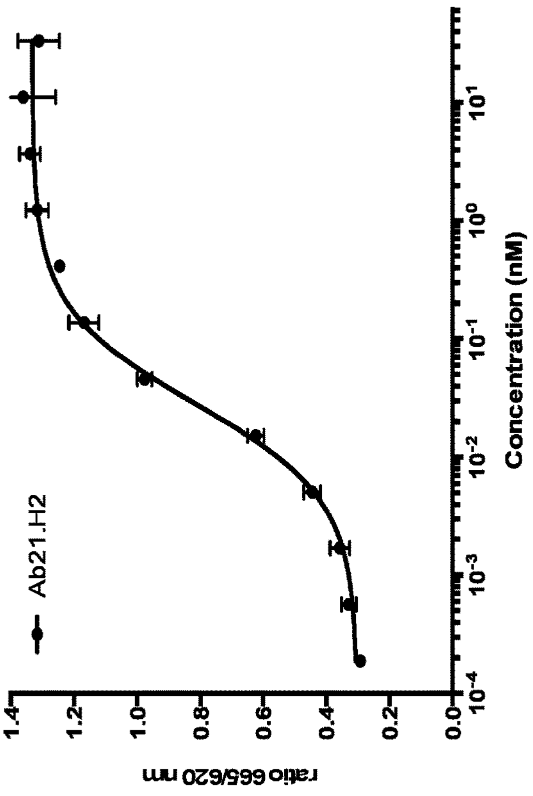
Figure 16N:
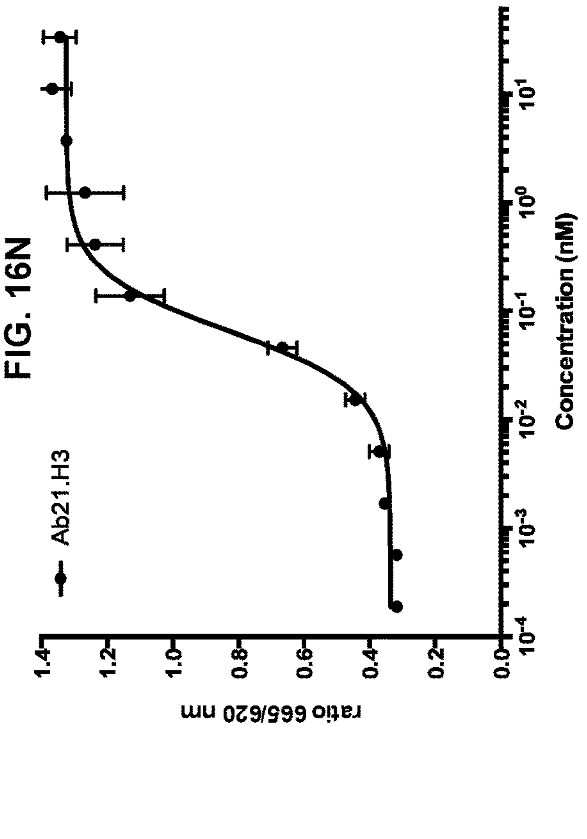
Figure 16O:
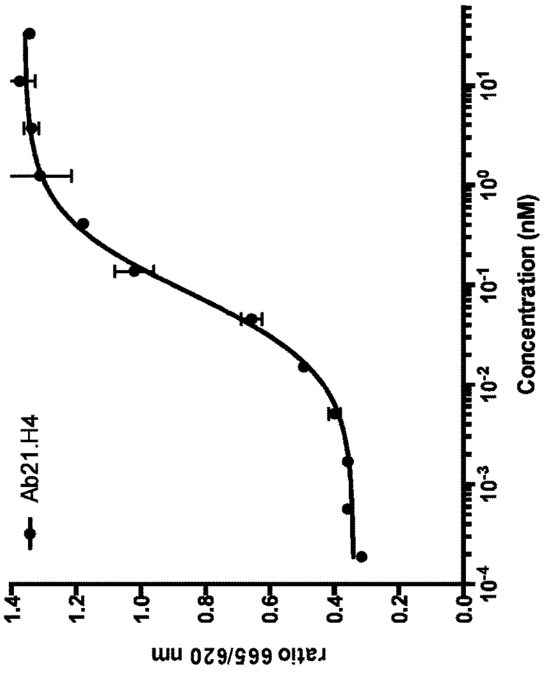
Figure 17A:
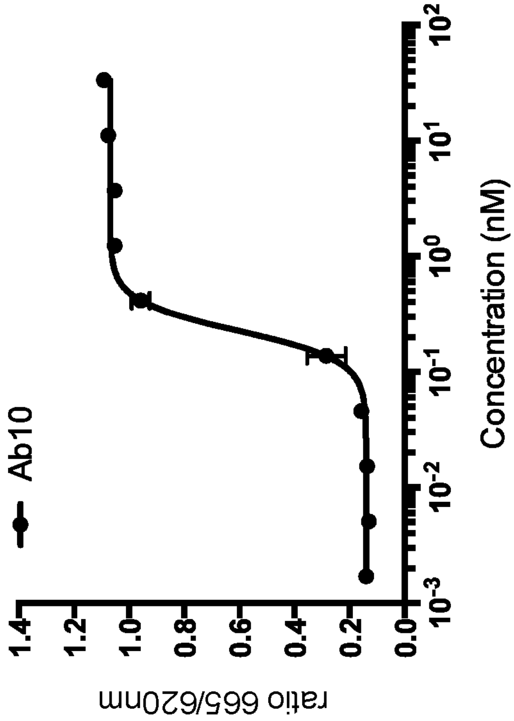
FIGS. 17A-17O provide representative data showing Ab10-mediated (FIG. 17A), Ab20-mediated (FIG. 17B), Ab21-mediated (FIG. 17C), Ab1.H-mediated (FIG. 17D), Ab10.H-mediated (FIG. 17E), Ab21.H-mediated (FIG. 17F), Ab22-mediated (FIG. 17G), Ab23-mediated (FIG. 17H), Ab10.H2-mediated (FIG. 17I), Ab10.H3-mediated (FIG. 17J), Ab10.H4-mediated (FIG. 17K), Ab10.H5-mediated (FIG. 17L), Ab21.H2-mediated (FIG. 17M), Ab21.H3-mediated (FIG. 17N), and Ab21.H4-mediated (FIG. 17O) inhibition of PACAP27-driven cAMP production via PAC1-R-expressing PC-12 cells obtained following the protocol in Example 1 infra.
Figure 17B:
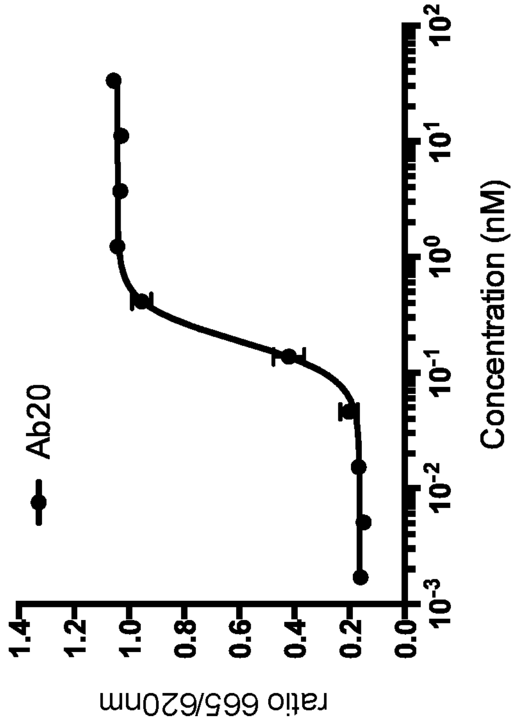
Figure 17C:
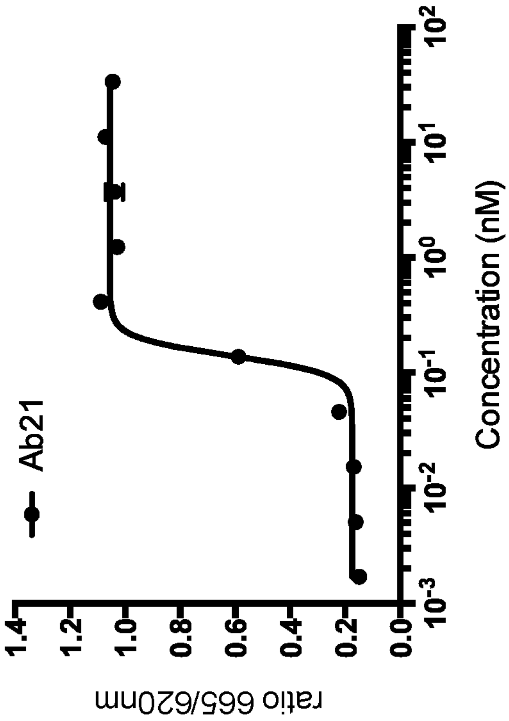
Figure 17D:
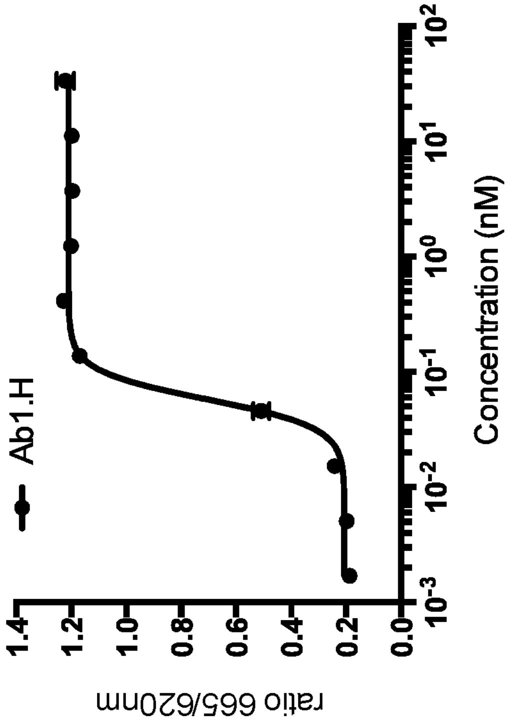
Figure 17E:
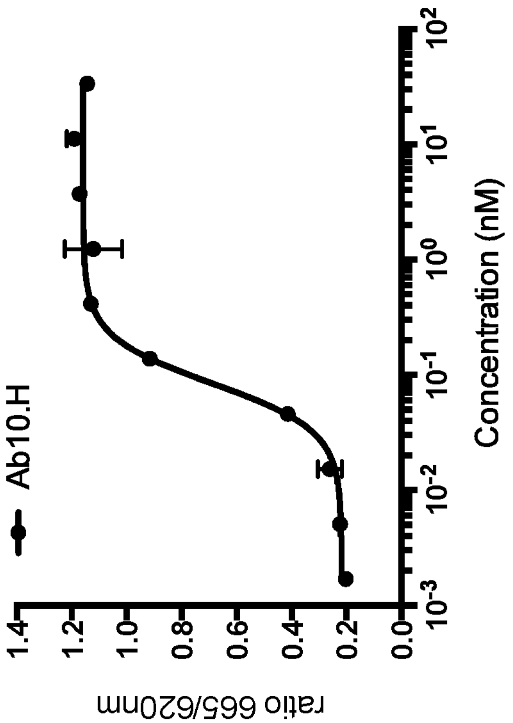
Figure 17F:
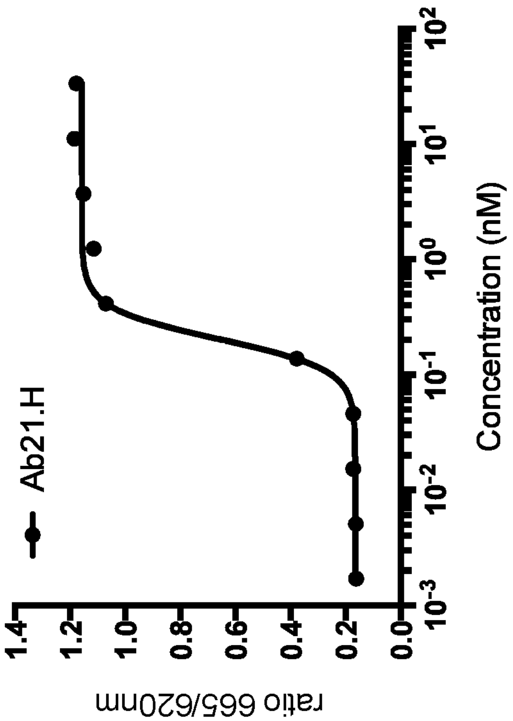
Figure 17G:
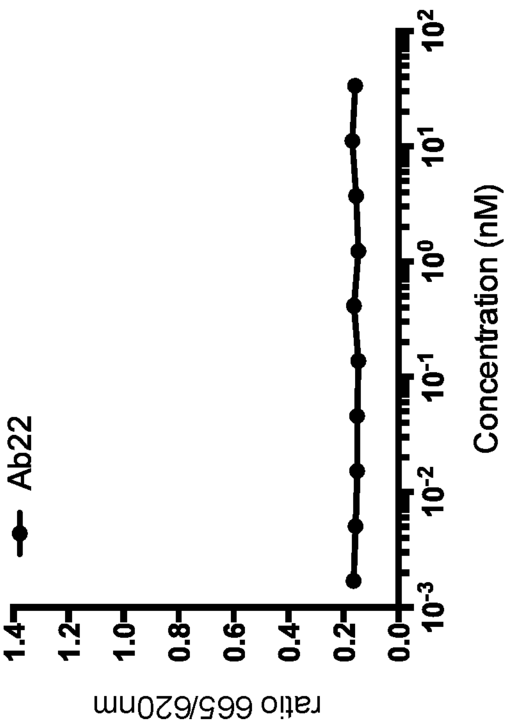
Figure 17H:
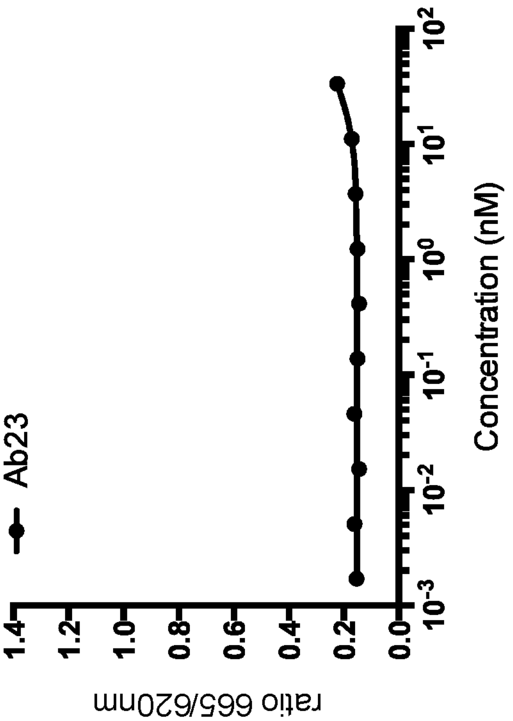
Figure 17I:
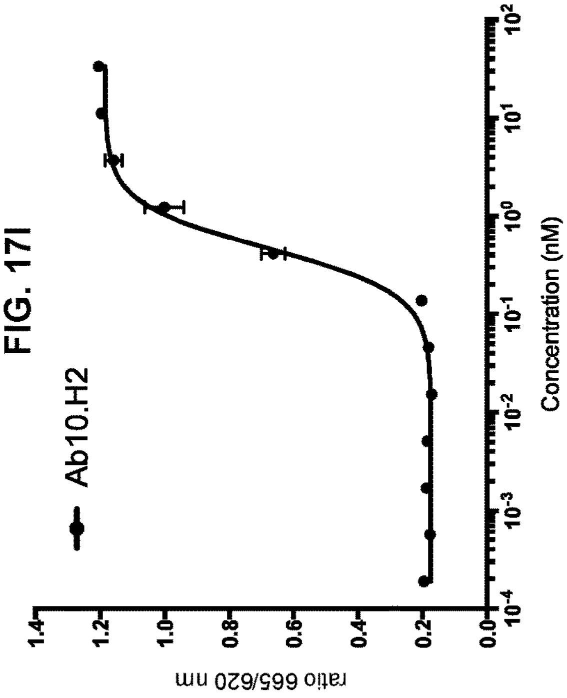
Figure 17J:
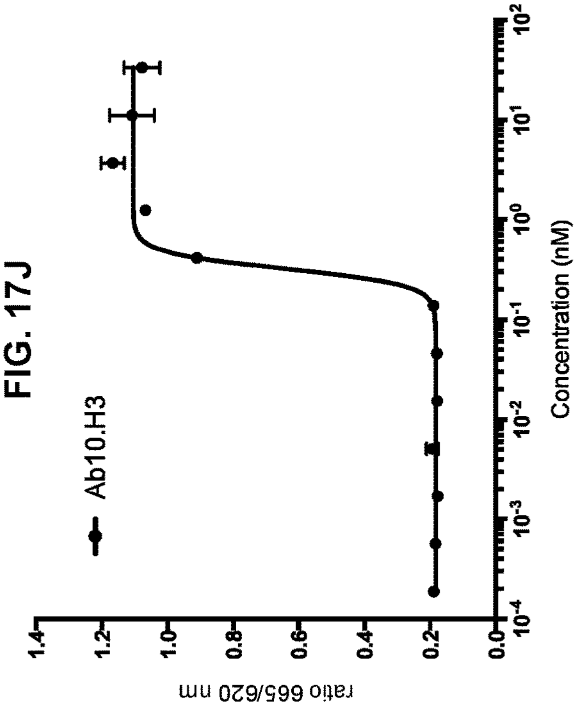
Figure 17K:
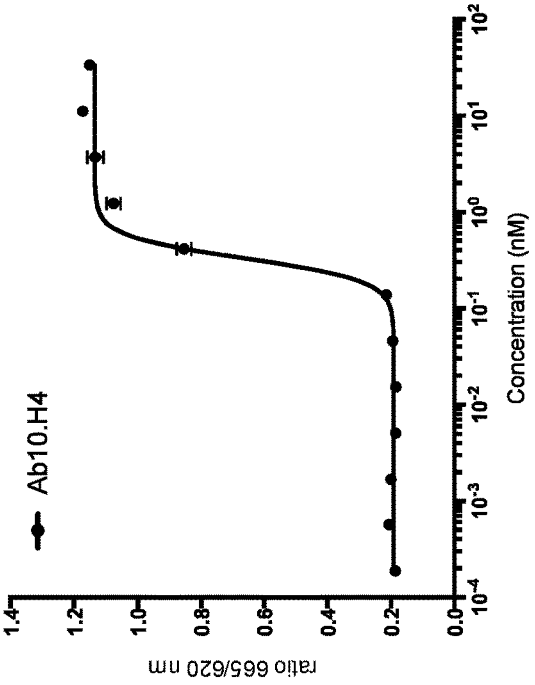
Figure 17L:
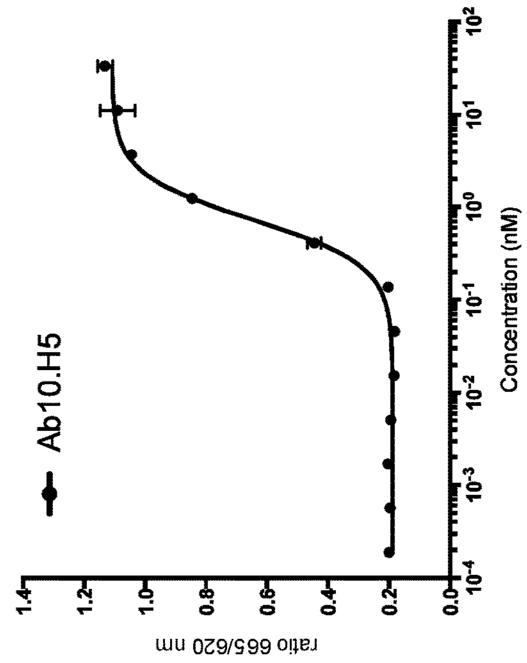
Figure 17M:
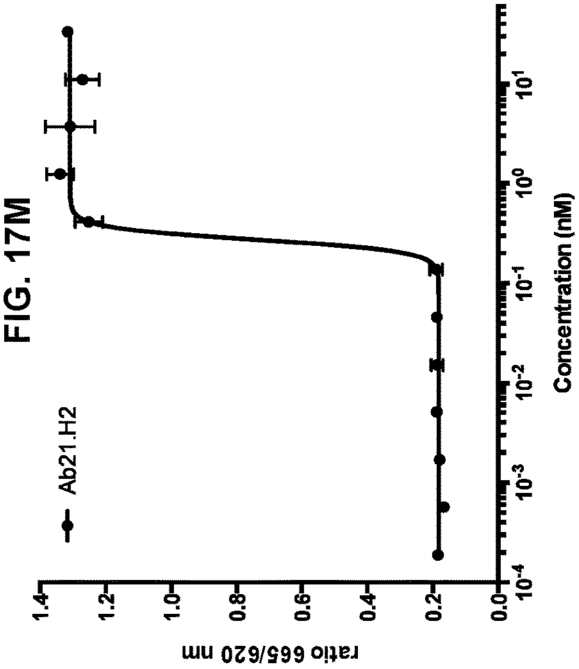
Figure 17N:
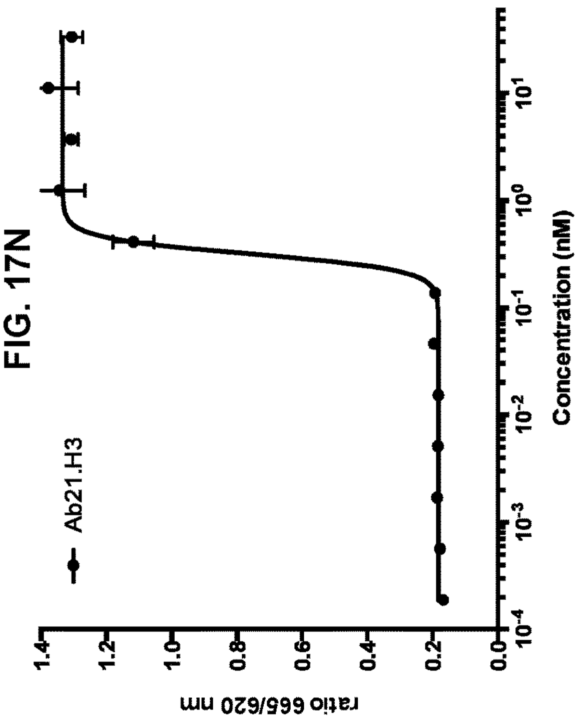
Figure 17O:
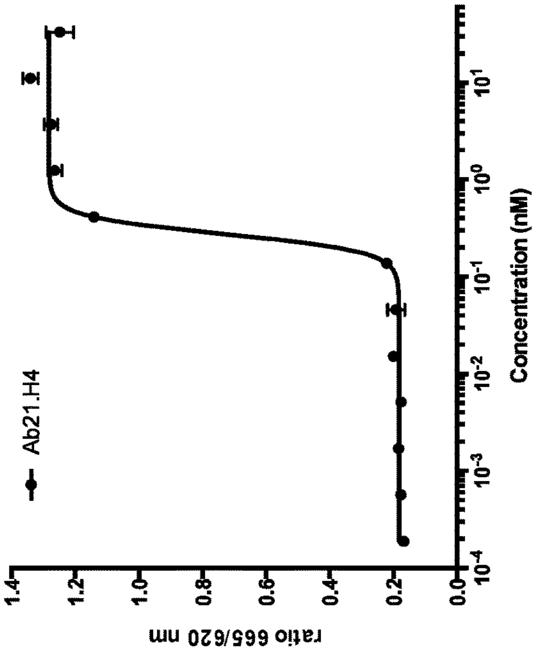
Figure 18A:
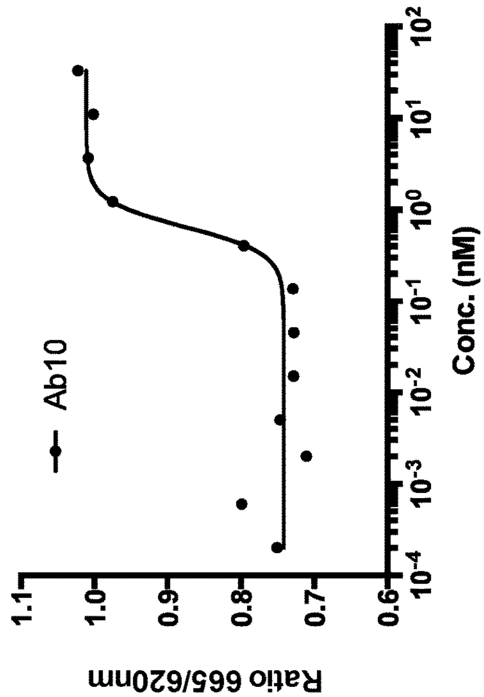
FIGS. 18A-18L provide representative data showing Ab10-mediated (FIG. 18A), Ab20-mediated (FIG. 18B), Ab21-mediated (FIG. 18C), Ab1.H-mediated (FIG. 18D), Ab10.H-mediated (FIG. 18E), Ab21.H (FIG. 18F) Ab22-mediated (FIG. 18G), Ab23-mediated (FIG. 18H), Ab10.H3-mediated (FIG. 18I), Ab21.H2-mediated (FIG. 18J), Ab21.H3-mediated (FIG. 18K), and Ab21.H4-mediated (FIG. 18L) inhibition of PACAP38-driven cAMP production via VPAC1-R-expressing CHO-K1 cells obtained following the protocol in Example 3 infra.
Figure 18B:
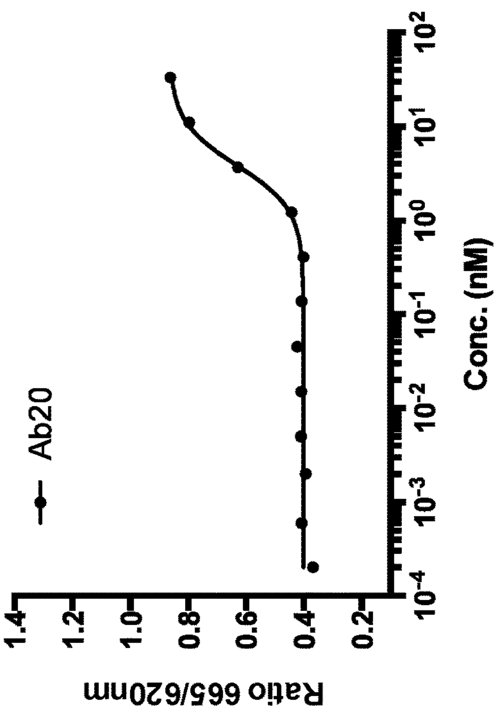
Figure 18C:
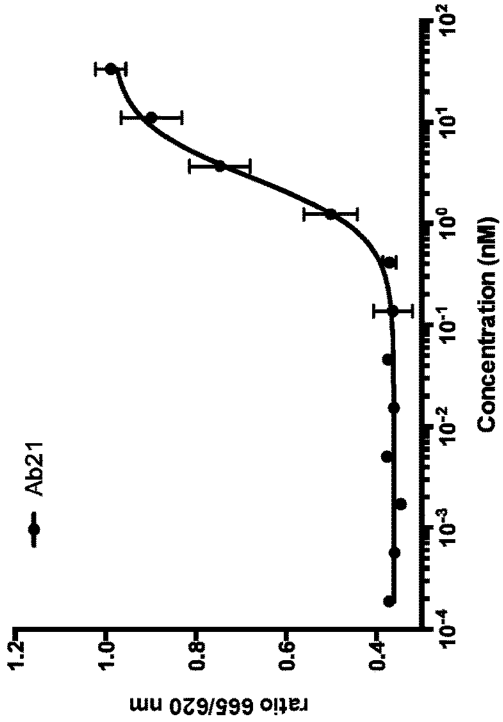
Figure 18D:
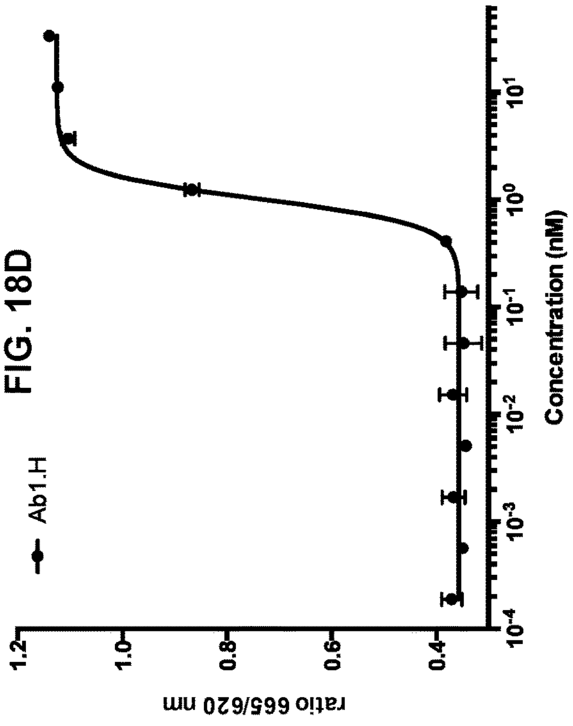
Figure 18E:
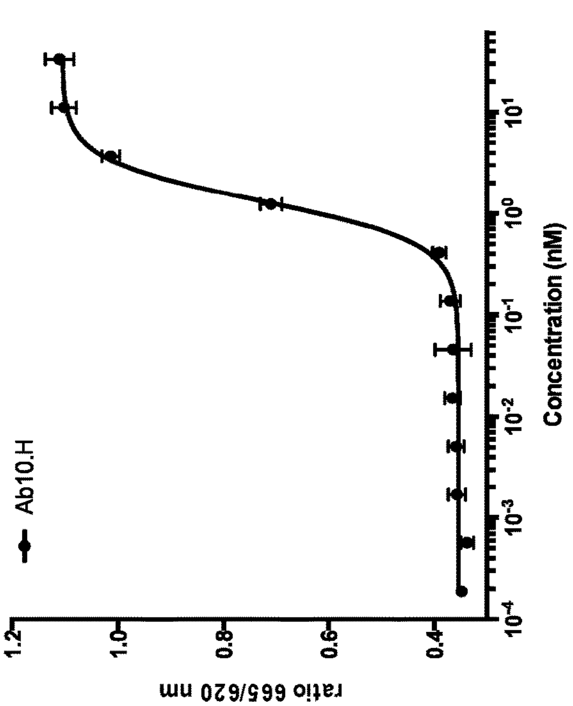
Figure 18F:
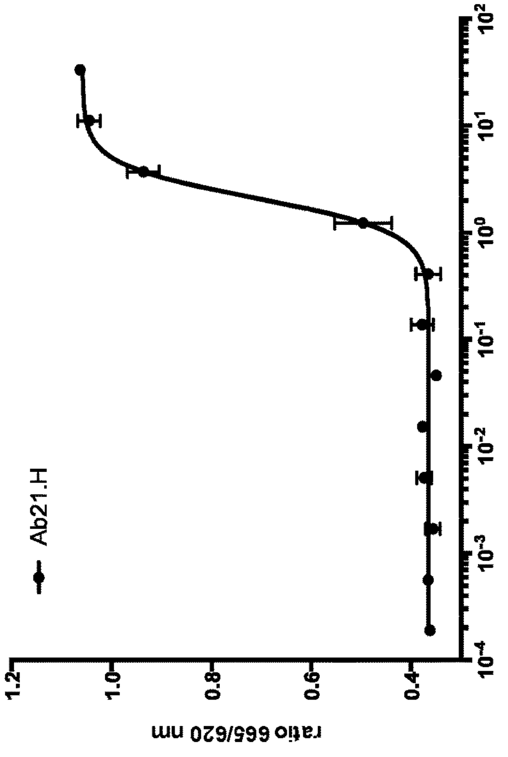
Figure 18G:
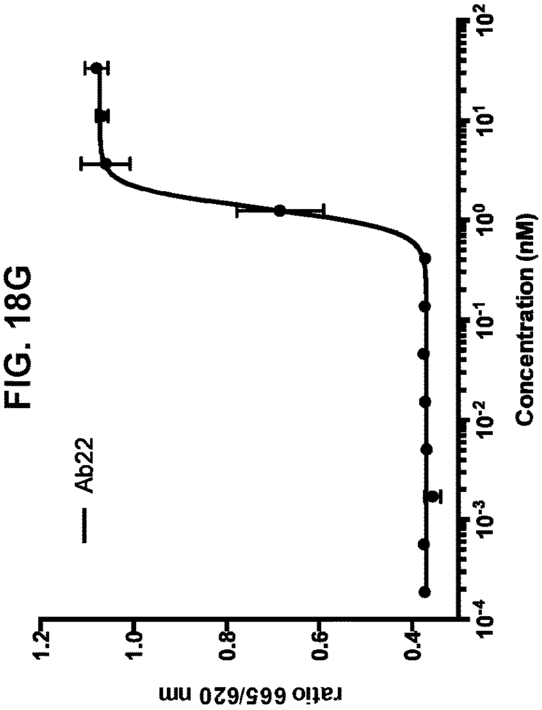
Figure 18H:
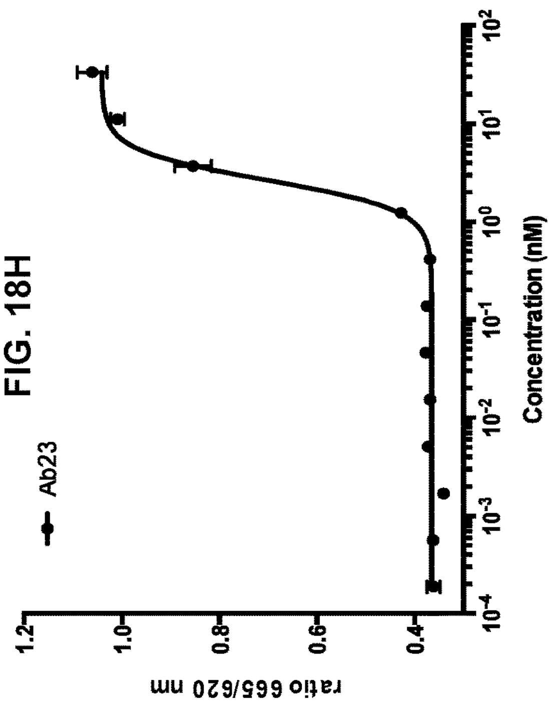
Figure 18I:
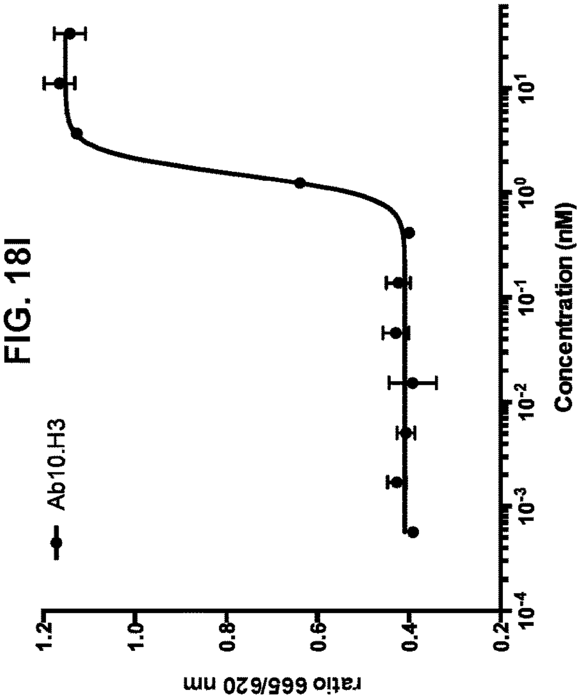
Figure 18K:
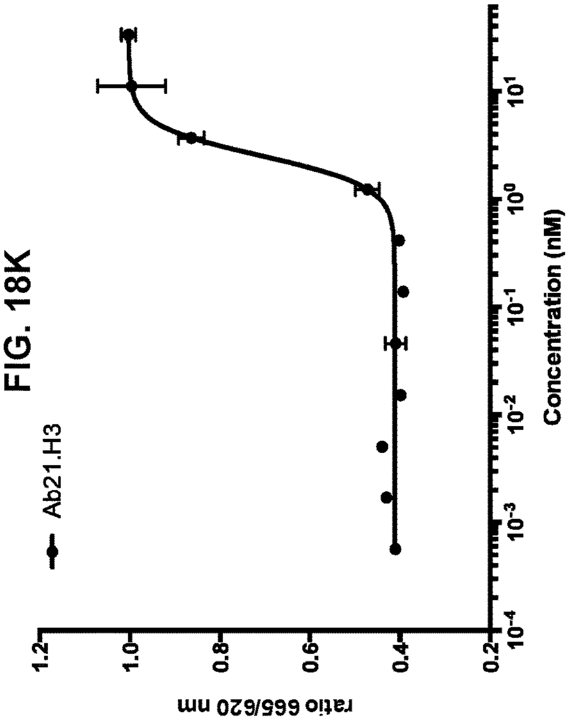
Figure 19A:
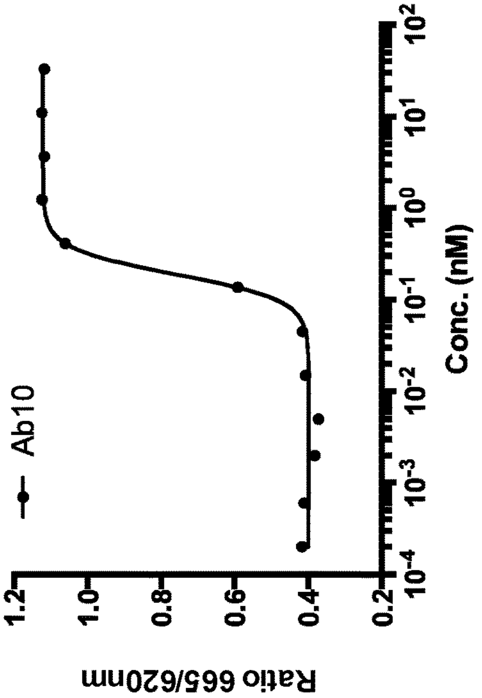
FIGS. 19A-19L provide representative data showing Ab10-mediated (FIG. 19A), Ab20-mediated (FIG. 19B), Ab21-mediated (FIG. 19B), Ab1.H-mediated (FIG. 19D), Ab10.H-mediated (FIG. 19E), Ab21.H (FIG. 19F), Ab22-mediated (FIG. 19G), Ab23-mediated (FIG. 19H), Ab10.H3-mediated (FIG. 191), Ab21.H2-mediated (FIG. 19J), Ab21.H3-mediated (FIG. 19K), and Ab21.H4-mediated (FIG. 19L) inhibition of PACAP38-driven cAMP production via VPAC2-R-expressing CHO-K1 cells obtained following the protocol in Example 4 infra.
Figure 18J:
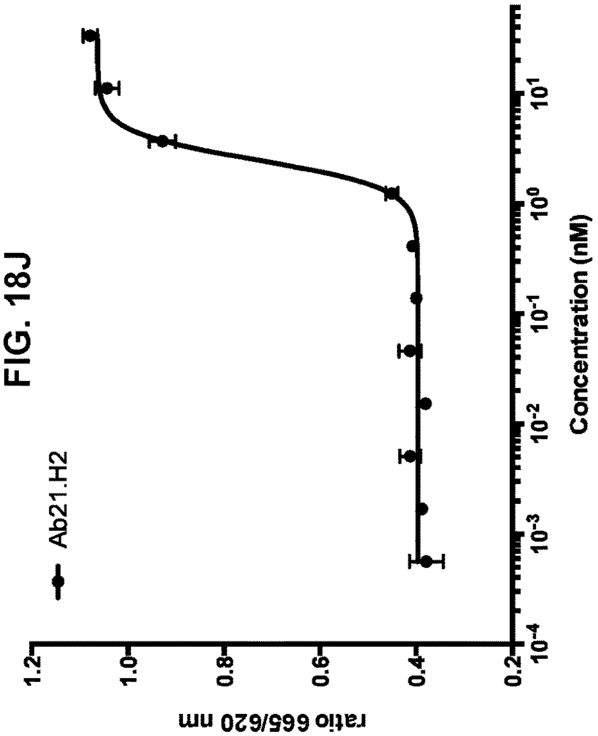
Figure 18L:
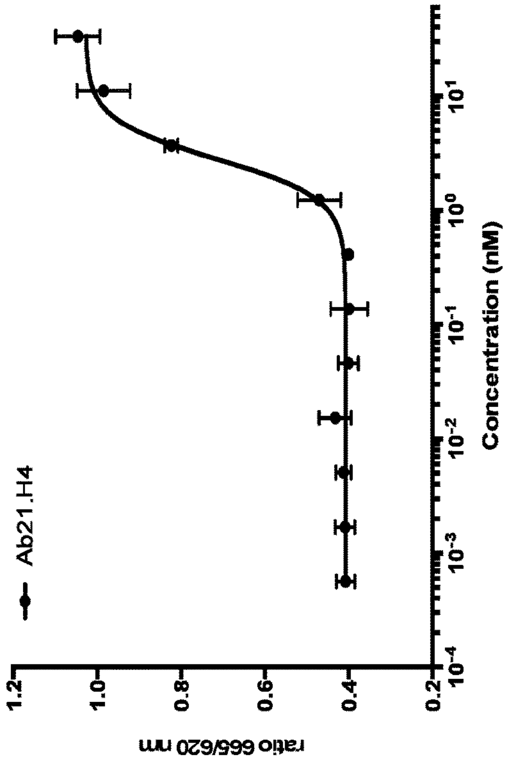
Figure 19B:
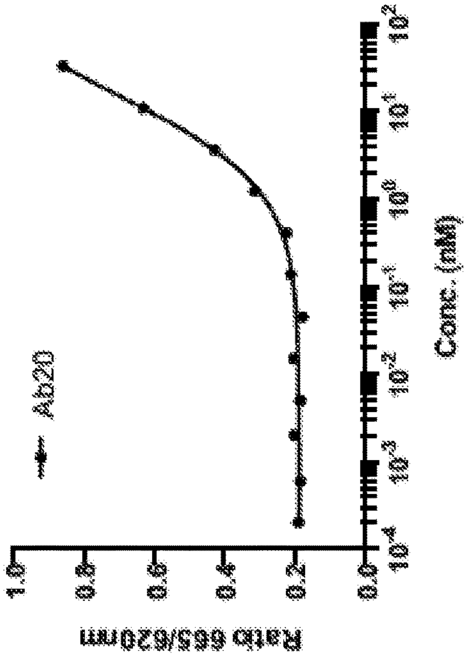
Figure 19C:
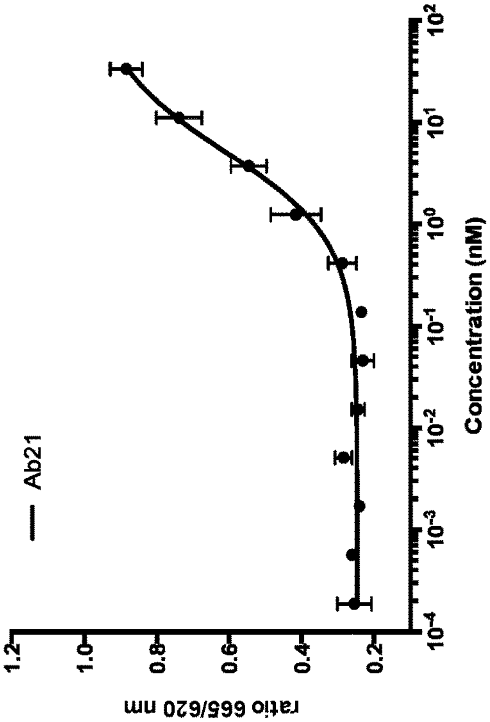
Figure 19D:
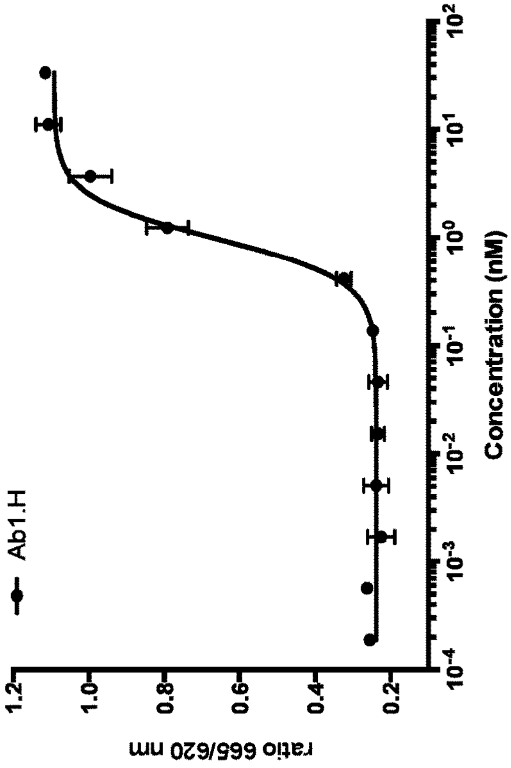
Figure 19E:
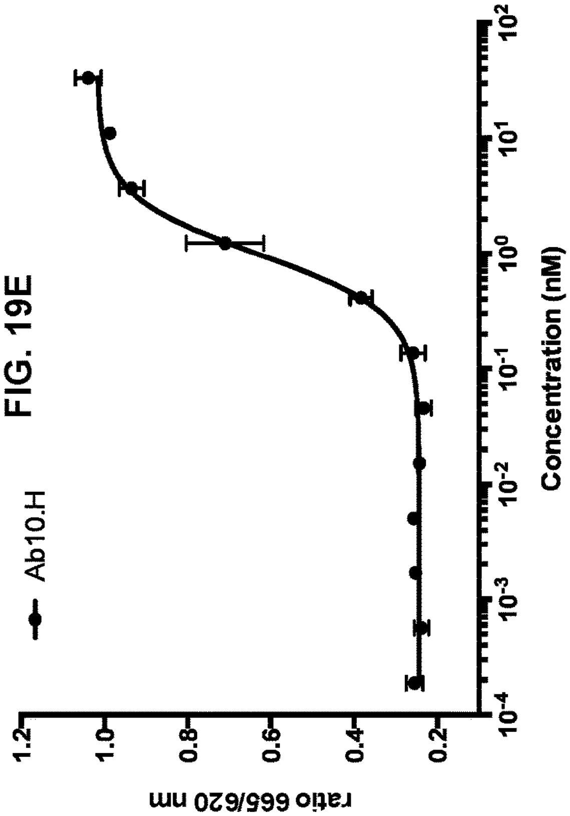
Figure 19F:
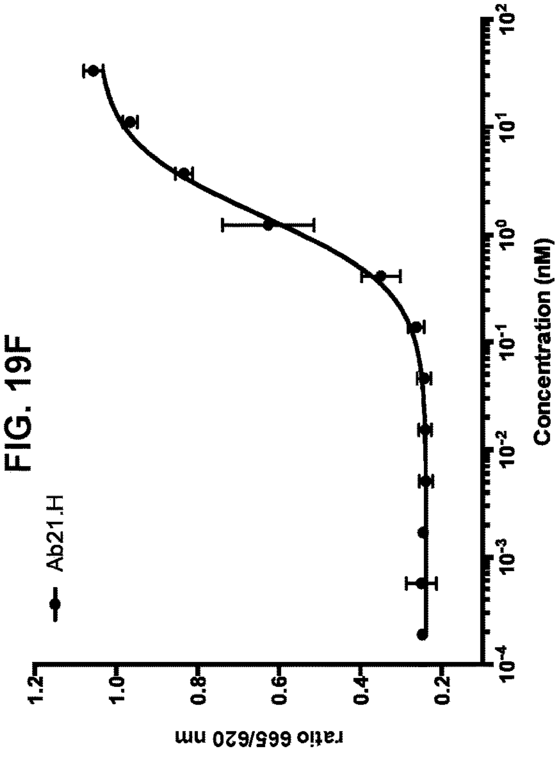
Figure 19G:
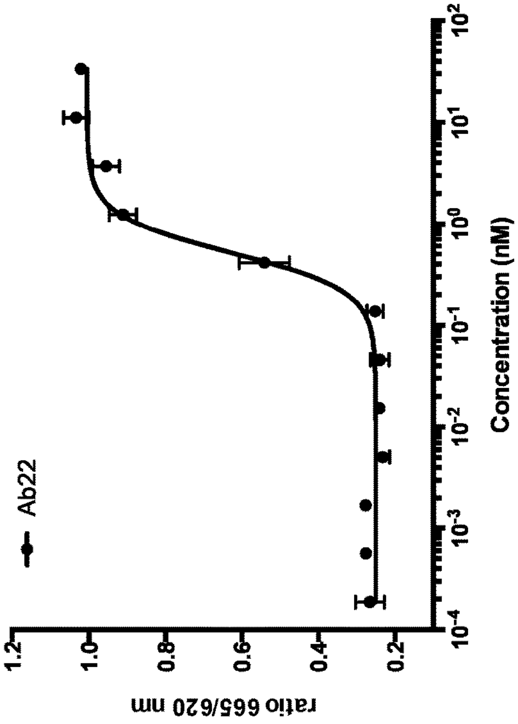
Figure 19H:
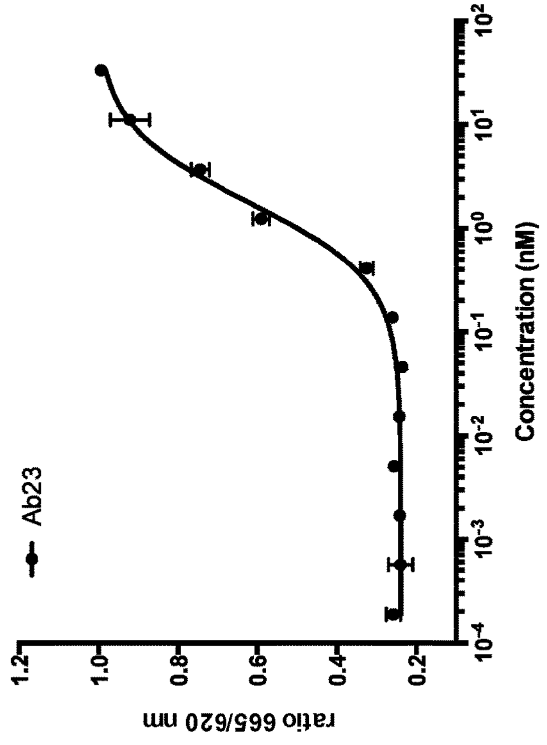
Figure 19I:
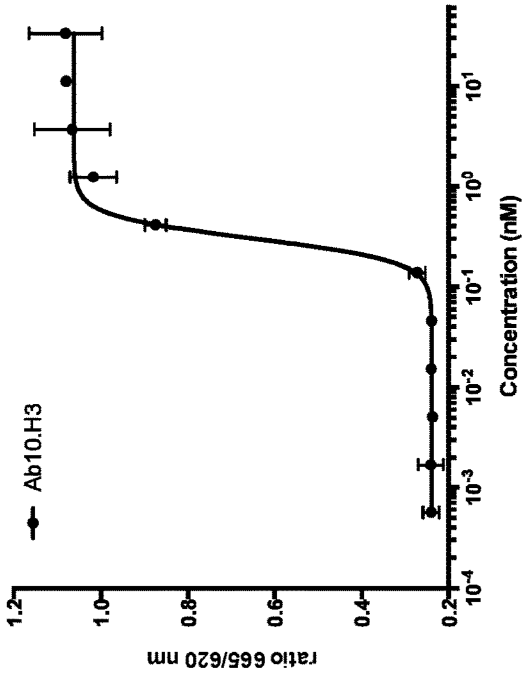
Figure 19J:
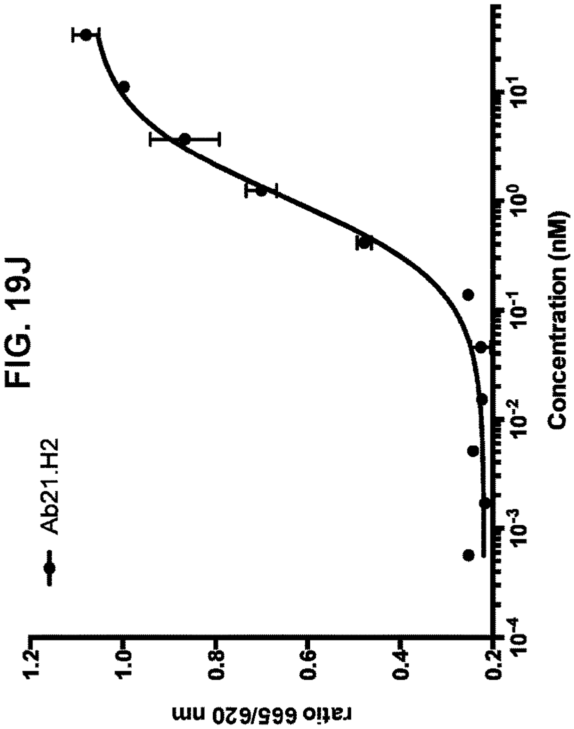
Figure 19K:
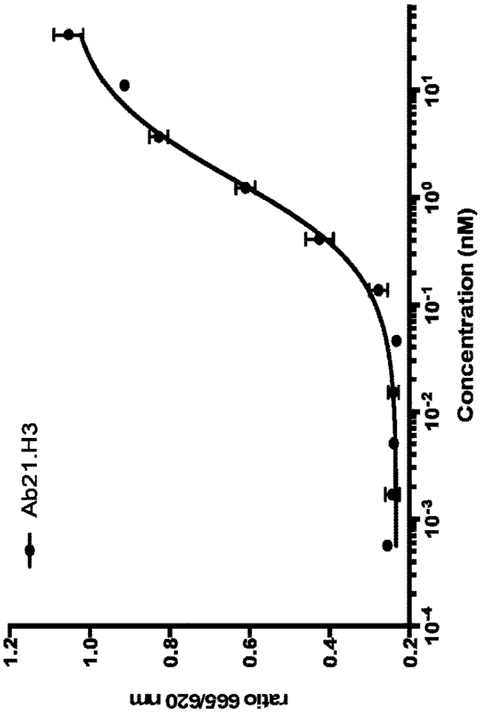
Figure 19L:
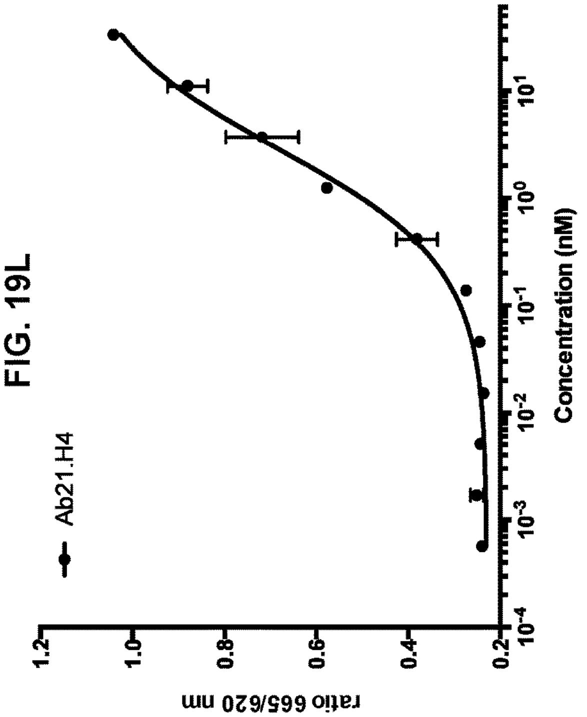

FIGS. 16A-16O (PACAP38) and FIGS. 17A-17O (PACAP27) show inhibition curves (for Ab10, Ab20, Ab21, Ab1.H, Ab10.H, Ab21.H, Ab22, Ab23, Ab10.H2, Ab10.H3, Ab10.H4, Ab10.H5, Ab21.H2, Ab21.H3, and Ab21.H4) that are representative of the inhibition curves obtained with the tested antibodies. The inhibition results were quantified for each antibody to yield an $IC_{50}$ value, which are summarized in Tables 2 and 3 below. These results demonstrated that anti-PACAP antibodies Ab10, Ab20, Ab21, Ab1.H, Ab10.H, Ab21.H, Ab22, Ab23, Ab10.H2, Ab10.H3, Ab10.H4, Ab10.H5, Ab21.H2, Ab21.H3, and Ab21.H4 inhibited PACAP38-induced CAMP increase in cells expressing PAC1-R (see FIGS. 16A-16O). Additionally, these results demonstrated that anti-PACAP antibodies Ab10, Ab20, Ab21, Ab1.H, Ab10.H, Ab21.H, Ab10.H2, Ab10.H3, Ab10.H4, Ab10.H5, Ab21.H2, Ab21.H3, and Ab21.H4, but not Ab22 or Ab23, inhibited PACAP27-induced cAMP increase in cells expressing PAC1-R (see FIGS. 17A-17O).

TABLE 2

Inhibition ($IC_{50}$) of PACAP38-induced and PACAP27-induced cAMP increase in cells expressing PAC1-R by anti-PACAP antibodies Ab10, Ab20, Ab21, Ab1.H, Ab10.H, Ab21.H, Ab22, and Ab23

| ANTIBODY | Inhibition of 0.1 nM PACAP38-induced PAC1-R mediated cAMP increase $IC_{50}$ (pM) | Inhibition of 0.1 nM PACAP27-induced PAC1-R mediated cAMP increase $IC_{50}$ (pM) |
|---|---|---|
| Ab10 | 180.3 | 227.0 |
| Ab20 | 368.2 | 187.8 |
| Ab21 | 239.1 | 140.2 |
| Ab1.H | 259.6 | 57.7 |
| Ab10.H | 163.4 | 84.0 |
| Ab21.H | 246.0 | 203.6 |
| Ab22 | 101.4 | n/a* |
| Ab23 | 114.9 | n/a* |

*n/a: not active because these Abs are PACAP38 specific

TABLE 3

Inhibition ($IC_{50}$) of PACAP38-induced and PACAP27-induced cAMP increase in cells expressing PAC1-R by anti-PACAP antibodies Ab10.H2, Ab10.H3, Ab10.H4, Ab10.H5, Ab21.H2, Ab21.H3, and Ab21.H4

| ANTIBODY | Inhibition of 0.1 nM PACAP38-induced PAC1-R mediated cAMP increase $IC_{50}$ (pM) | Inhibition of 1 nM PACAP27-induced PAC1-R mediated cAMP increase $IC_{50}$ (pM) |
|---|---|---|
| Ab10.H2 | 21.3 | 466 |
| Ab10.H3 | 30.7 | 321 |
| Ab10.H4 | 22.8 | 329 |
| Ab10.H5 | 22.7 | 733 |
| Ab21.H2 | 28.5 | 274 |
| Ab21.H3 | 65.3 | 318 |
| Ab21.H4 | 83.4 | 275 |

Example 2: Binding Affinities of Anti-PACAP Antibodies

Binding affinities of monoclonal antibodies for human PACAP were estimated using SPR on the PROTEON™ XPR36 (Bio-Rad, Hercules, CA). Antibody was immobilized to the surface of general amine coupling ("GLC" or "GLM") Chips (Bio-Rad, Hercules, CA). A dilution series of human PACAP38 (SEQ ID NO: 1241) prepared in 1×PBST Buffer (4.3 mM Na Phosphate, 1.4 mM K Phosphate, 135 mM NaCl, 2.7 mM KCl 0.05% Polysorbate-20) purchased from Teknova (Cat #P1192, Teknova, Hollister, CA) and supplemented with 0.25 M arginine (from J. T. BAKER®), 0.2 mg/ml BSA (Jackson Immuno Research Labs, West Grove, PA), and 0.005% sodium azide (VWR International, Radnor, PA) with the pH adjusted to 7 was used to query the antibodies. Antigen (ranging from 1.23 nM to 100 nM) was typically run sequentially with association times of 2-4 minutes and dissociation times of 3-120 minutes grouped with the PROTEON™ Manager Software (v3.1.0.6 (Bio-Rad, Hercules, CA)) and fitted using a 1:1 Langmuir binding model. Surfaces were regenerated between analyte queries using 0.85% Phosphoric Acid. A single $K_D$ was calculated for each antibody with association times limited near the rate of diffusion ($1.0\times10^6$) and dissociation times limited to $1.5\times10^{-5}$ where no discernible dissociation was observed.

The same procedure was used to determine binding affinities of antibodies for human VIP (SEQ ID NO: 1243) and PACAP27 (SEQ ID NO: 1242) though peptide concentrations ranged from 1.23 nM to 1000 nM with association times of 200 seconds and dissociation times of 3-120 minutes.

The measured antibody affinities for PACAP38 are listed in Table 4.

TABLE 4

Antibody affinity constants for PACAP38

| Antibody | ka (1/Ms) | kd (1/s) | $K_D$ (M) |
|---|---|---|---|
| Ab10 | 2.6E+05 | 2.0E−05 | 7.5E−11 |
| Ab20 | 1.2E+05 | 2.4E−05 | 2.1E−10 |
| Ab21 | 3.7E+05 | 1.0E−05 | 2.7E−11 |
| Ab22 | 3.7E+05 | 1.0E−05 | 2.7E−11 |
| Ab23 | 5.1E+05 | 3.6E−05 | 7.1E−11 |
| Ab1.H | 4.7E+05 | 1.0E−05 | 2.1E−11 |
| Ab10.H | 3.4E+05 | 1.0E−05 | 2.9E−11 |
| Ab21.H | 4.8E+05 | 1.0E−05 | 2.1E−11 |
| Ab10.H2 | 6.3E+05 | 1.4E−05 | 2.2E−11 |
| Ab10.H3 | 4.5E+05 | 1.0E−05 | 2.2E−11 |
| Ab10.H4 | 5.3E+05 | 1.0E−05 | 1.9E−11 |

Examples of antibody affinity constants for VIP are listed in Table 5.

TABLE 5

Antibody affinity constants for VIP

| Antibody | ka (1/Ms) | kd (1/s) | $K_D$ (M) |
|---|---|---|---|
| Ab10 | 3.7E+04 | 1.0E−02 | 2.8E−07 |
| Ab20 | 4.5E+05 | 4.8E−01 | 1.1E−06 |
| Ab21 | 1.7E+03 | 5.4E−04 | 3.1E−07 |
| Ab22 | 2.7E+05 | 1.8E−01 | 6.9E−07 |
| Ab23 | 4.3E+05 | 3.2E−01 | 7.3E−07 |
| Ab1.H | 3.8E+04 | 1.8E−01 | 4.8E−06 |
| Ab10.H | 3.8E+05 | 3.9E−02 | 1.0E−07 |
| Ab21.H | 1.4E+05 | 5.9E−02 | 4.4E−07 |
| Ab10.H2 | 2.0E+05 | 4.6E−02 | 2.3E−07 |
| Ab10.H3 | 1.4E+05 | 1.3E−02 | 9.1E−08 |
| Ab10.H4 | 1.5E+05 | 1.5E−02 | 9.8E−08 |

Examples of antibody affinity constants for PACAP27 are listed in Table 6.

TABLE 6

| Antibody affinity constants for PACAP27 | | | |
|---|---|---|---|
| Antibody | ka (1/Ms) | kd (1/s) | $K_D$ (M) |
| Ab10 | 1.0E+06 | 1.0E−05 | 1.0E−11 |
| Ab20 | 3.2E+05 | 2.2E−05 | 7.0E−11 |
| Ab21 | 7.9E+05 | 1.0E−05 | 1.3E−11 |
| Ab22 | 1.0E+00 | 1.0E−01 | 1.0E−01 |
| Ab23 | 8.9E+05 | 3.1E−02 | 3.5E−08 |
| Ab1.H | 7.6E+05 | 1.0E−05 | 1.3E−11 |
| Ab10.H | 5.3E+05 | 1.8E−05 | 3.3E−11 |
| Ab21.H | 6.3E+05 | 1.0E−05 | 1.6E−11 |
| Ab10.H2 | 2.1E+05 | 1.7E−05 | 7.8E−11 |
| Ab10.H3 | 1.7E+05 | 1.0E−05 | 5.9E−11 |
| Ab10.H4 | 1.9E+05 | 1.7E−05 | 9.3E−11 |

The binding affinity results of Tables 4 and 6 present data demonstrating that Ab23 weakly bound to PACAP27 as compared to its binding affinity for PACAP38. Tables 4 and 6 additionally present data demonstrating that Ab22 did not specifically recognize PACAP27, but that Ab22 specifically bound to PACAP38.

Example 3: Inhibition of PACAP38-Induced Signaling Via VPAC1-R

To identify antibodies that neutralize PACAP38-induced signaling via human VPAC1-R, CHO-K1 cells expressing human VPAC1-R were used in a cAMP HTRF cell-based assay. Antibody dilutions were incubated with PACAP38 at 4×the final concentration (5 nM) for 1 hour. While the antibody/antigen complexes were incubated for 1 hour, VPAC1-R expressing CHO-K1 cells (generated at Alder Biopharmaceuticals, by stable transfection of CHO-K1 cells (ATCC, catalog #CCL-61) with human VPAC1-R cDNA; selected clone 1 was used for in vitro cell based assays) were detached with 0.25% trypsin for 4 minutes. The cells were washed and re-suspended at $1\times10^6$ cells per ml culture media. 20 μl of Ab/antigen mixture was mixed with 20 μl of cells in HTRF plates and incubated with shaking for 30 minutes. 20 μl of $Eu^{3+}$ cryptate labeled anti-cAMP mAb (1:20 diluted) and 20 μl of (1:20 diluted) d2-labeled CAMP in lysis buffer were added to each well and incubated for 1 hour with shaking. The final concentration of PACAP38 in each well was 5 nM. Following incubation, plates were read (excitation 330 nm, emission 620/665 nm), and a ratio of 620:665 signal was determined.

FIGS. 18A-18L are representative of the inhibition curves obtained by this method (results are shown for Ab10, Ab20, Ab21, Ab1.H, Ab10.H, Ab21.H, Ab22, Ab23, Ab10.H3, Ab21.H2, Ab21.H3, and Ab21.H4, respectively). The computed $IC_{50}$ values for each antibody, which are shown below in Table 7, demonstrated that Ab10, Ab20, Ab21, Ab1.H, Ab10.H, Ab21.H, Ab22, Ab23, Ab10.H3, Ab21.H2, Ab21.H3, and Ab21.H4 inhibited PACAP38-induced CAMP increase in cells expressing human VPAC1-R.

TABLE 7

| Inhibition ($IC_{50}$) of PACAP38-induced cAMP increase in cells expressing human VPAC1-R by anti-PACAP antibodies | |
|---|---|
| ANTIBODY | Inhibition of 5 nM PACAP38-induced human VPAC1-R mediated cAMP increase $IC_{50}$ (pM) |
| Ab10 | 649.1 |
| Ab20 | 3889.0 |

TABLE 7-continued

| Inhibition ($IC_{50}$) of PACAP38-induced cAMP increase in cells expressing human VPAC1-R by anti-PACAP antibodies | |
|---|---|
| ANTIBODY | Inhibition of 5 nM PACAP38-induced human VPAC1-R mediated cAMP increase $IC_{50}$ (pM) |
| Ab21 | 2846.0 |
| Ab1.H | 1021.1 |
| Ab10.H | 1336.0 |
| Ab21.H | 2105.0 |
| Ab22 | 1300.0 |
| Ab23 | 2667.0 |
| Ab10.H3 | 1516.0 |
| Ab21.H2 | 2484.0 |
| Ab21.H3 | 2518.0 |
| Ab21.H4 | 2832.0 |

Example 4: Inhibition of PACAP38-Induced Signaling Via VPAC2-R

To identify antibodies that neutralize PACAP38-induced signaling via human VPAC2-R, CHO-K1 cells expressing human VPAC2-R were used in a CAMP HTRF cell based assay. Antibody dilutions were incubated with PACAP38 at 4×the final concentration (1 nM) for 1 hr. While the antibody/antigen complexes were incubated for 1 hour, VPAC2-R expressing CHO-K1 cells (generated at Alder Biopharmaceuticals, by stable transfection of CHO-K1 cells (ATCC, catalog #CCL-61) with human VPAC2-R cDNA; selected clone 8 was used for in vitro cell based assays) were detached with 0.25% trypsin for 4 minutes. The cells were washed and re-suspended at $1\times10^6$ cells per ml culture media. 20 μl of Ab/antigen mixture was mixed with 20 μl of cells in HTRF plates and incubated with shaking for 30 minutes. 20 μl of $Eu^{3+}$ cryptate labeled anti-cAMP mAb (1:20 diluted) and 20 μl of (1:20 diluted) d2-labeled CAMP in lysis buffer were added to each well and incubated for 1 hour with shaking. The final concentration of PACAP38 in the wells was 1 nM. Following incubation, plates were read (excitation 330 nm, emission 620/665 nm) and, a ratio of 620:665 signal was determined.

FIGS. 19A-19L are representative of the inhibition curves obtained by this method (results are shown for Ab10, Ab20, Ab21, Ab1.H, Ab10.H, Ab21.H, Ab22, Ab23, Ab10.H3, Ab21.H2, Ab21.H3, and Ab21.H4, respectively). The computed $IC_{50}$ values for each antibody, which are shown below in Table 8, demonstrated that Ab10, Ab20, Ab21, Ab1.H, Ab10.H, Ab21.H, Ab22, Ab23, Ab10.H3, Ab21.H2, Ab21.H3, and Ab21.H4 inhibited PACAP38-induced CAMP increase in cells expressing human VPAC2-R.

TABLE 8

| Inhibition ($IC_{50}$) of PACAP38-induced cAMP increase in cells expressing human VPAC2-R by anti-PACAP antibodies | |
|---|---|
| ANTIBODY | Inhibition of 1 nM PACAP38-induced human VPAC2-R mediated cAMP increase $IC_{50}$ (pM) |
| Ab10 | 188.5 |
| Ab20 | 14570.0 |
| Ab21 | 5215.0 |
| Ab1.H | 983.0 |
| Ab10.H | 988.0 |

TABLE 8-continued

Inhibition ($IC_{50}$) of PACAP38-induced cAMP increase in cells expressing human VPAC2-R by anti-PACAP antibodies

| ANTIBODY | Inhibition of 1 nM PACAP38-induced human VPAC2-R mediated cAMP increase $IC_{50}$ (pM) |
|---|---|
| Ab21.H | 1507.0 |
| Ab22 | 515.0 |
| Ab23 | 1789.0 |
| Ab10.H3 | 301.0 |
| Ab21.H2 | 1060.0 |
| Ab21.H3 | 1529.0 |
| Ab21.H4 | 2879.0 |

Example 5: Inhibition of PACAP38 Binding to PAC1-R-Expressing Cells

To identify antibodies that block PACAP38 binding to PAC1-R-expressing cells, adherent PC-12 cells (ATCC, Manassas, VA) expressing PAC1-R were used in a Europium-based PAC1-R-expressing cells binding assay. Antibody solutions were incubated with N-terminal biotinylated PACAP38 at 10× the final concentration (100 nM or 30 nM) for 1 hr, then added to PC-12 cells that were plated 24 hrs prior in black clear bottom 96 well plates (COSTAR™, Corning Incorporated, Corning, NY) and further incubated for 1 hr at room temperature. After three washes, the cells were incubated with 20 µl Europium-labeled streptavidin (PerkinElmer, Waltham, MA) for 1 hr at room temperature. Cells were washed three times, then 20 µl DELFIA® Enhancement solution (PerkinElmer, Waltham, MA) was added to each well and incubated for 15 minutes with gentle shaking. Plates were read (Time Resolved Fluorescence ("TRF")) on SPECTRAMAX® (Molecular Devices, Sunnyvale, CA) plate reader.

FIGS. 14A-14H are representative of the inhibition curves obtained by this method (results are shown for Ab10, Ab20, Ab21, Ab1.H, Ab10.H, Ab21.H, Ab22, and Ab23, respectively) wherein the PAC1-R expressing cells were PC-12 cells. The computed $IC_{50}$ values for each antibody, which are shown below in Table 9, demonstrated that Ab10, Ab20, Ab21, Ab1.H, Ab10.H, Ab21.H, Ab22, and Ab23 inhibited PACAP38 binding to PAC1-R expressing PC-12 cells.

TABLE 9

Inhibition ($IC_{50}$) of PACAP38 binding to PAC1-R-expressing PC-12 cells by anti-PACAP antibodies

| ANTIBODY | Inhibition of 100 nM biotinylated PACAP38 binding to PAC1R-expressing PC-12 cells $IC_{50}$ (nM) |
|---|---|
| Ab10 | 17.8 |
| Ab20 | 32.7 |
| **ANTIBODY** | **Inhibition of 30 nM Biotinylated PACAP38 binding to PAC1R-expressing PC-12 cells $IC_{50}$ (nM)** |
| Ab21 | 20.3 |
| Ab1.H | 56.3 |
| Ab10.H | 14.5 |

TABLE 9-continued

Inhibition ($IC_{50}$) of PACAP38 binding to PAC1-R-expressing PC-12 cells by anti-PACAP antibodies

| | |
|---|---|
| Ab21.H | 12.7 |
| Ab22 | 13.8 |
| Ab23 | 14.9 |

Example 6: PACAP38-Mediated Binding of Anti-PACAP Antibodies to the Cell Surface of PAC1-R-Expressing Cells To identify anti-PACAP antibodies that bind, via PACAP38, to the cell surface of PAC1-R expressing cells, adherent PC-12 cells (Japanese Collection of Research Bioresources Cell Bank) expressing PAC1-R were used in a cell surface binding-based assay. To perform the binding experiment, PAC1-R expressing PC-12 cells were first seeded into Corning 96 well white solid bottom plates (Corning, Corning, NY). Cells were initially seeded at $1\times10^5$ cells/well in a solution of complete RPMI ("cRPMI": RPMI medium supplemented with 10% sterile heat-inactivated FBS and 1% sterile antibiotic/antimycotic)+10% FBS, and the plates were allowed to incubate overnight at 37° C. On the day of the binding assay, antibodies at an initial concentration of 15 µg/ml were diluted at a 1:3 ratio in DELFIA® binding buffer (50 mM Tris, 150 mM NaCl, 0.1% azide, 2% horse serum) (Perkin-Elmer, Waltham, MA) to a total volume of 60 µL in a separate 96 well round bottom plate. PACAP38 was prepared for the binding assay by diluting it in DELFIA® binding buffer to a concentration of 200 nM, and then 60 µl of the diluted PACAP38 was added to each of the antibody-containing wells to form antibody: antigen complexes. Following addition of PACAP38, the antibody: antigen complexes were incubated at room temperature on a shaker for 1 hour. Separately, the PC-12 cells were prepared for addition of antibody: antigen complexes by washing the cells two times with DELFIA® wash buffer (50 mM Tris, 150 mM NaCl, 0.1% Azide) (Perkin-Elmer, Waltham, MA). After washing the cells two times and following the 1 hour room temperature incubation of the antibody: antigen complexes, 50 µl of the antibody: antigen complex was added to each well containing cells. The mixtures of cells and antibody: antigen complexes were then incubated for 30 minutes at room temperature. Following this 30 minute incubation, each mixture was washed two times with DELFIA® wash buffer (Perkin-Elmer, Waltham, MA).

DELFIA® Europium labeled anti-human IgG detection reagent (Cat #1244-330, Perkin-Elmer, Waltham, MA) was diluted to a concentration of 300 ng/ml in DELFIA® Binding Buffer. Following dilution, 50 µl of the anti-human IgG detection reagent was added to each well containing cells, and a 30 minute incubation at room temperature followed this addition of IgG detection reagent. After completion of the 30 minute room temperature incubation, the cells were then washed two times with DELFIA® wash buffer. Next, 50 µl of DELFIA® Enhancement Solution (Cat #1244-105, Perkin-Elmer, Waltham, MA) was added to each well containing cells for a final 15 minute room temperature incubation with shaking. The plates were then read (TRF, excitation 330 nm, emission 620 nm) on a SPECTRAMAX® (Molecular Devices, Sunnyvale, CA) plate reader.

Figure 15A:
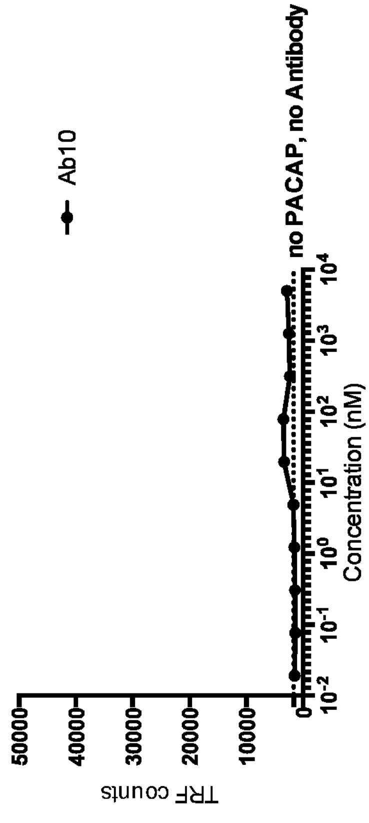
FIGS. 15A-15O provides representative data showing Ab10 (FIG. 15A), Ab20 (FIG. 15B), Ab21 (FIG. 15C), Ab1.H (FIG. 15D), Ab10.H (FIG. 15E), Ab21.H (FIG. 15F), Ab22 (FIG. 15G), Ab23 (FIG. 15H), Ab10.H2 (FIG. 15I), Ab10.H3 (FIG. 15J), Ab10.H4 (FIG. 15K), Ab10.H5 (FIG. 15L), Ab21.H2 (FIG. 15M), Ab21.H3 (FIG. 15N), and Ab21.H4 (FIG. 15O) binding to PAC1-R-expressing PC-12 cells in the presence of PACAP38 obtained following the protocol in Example 6 infra. The dashed line in FIG. 15A represents a no PACAP and no antibody control.
Figure 15B:
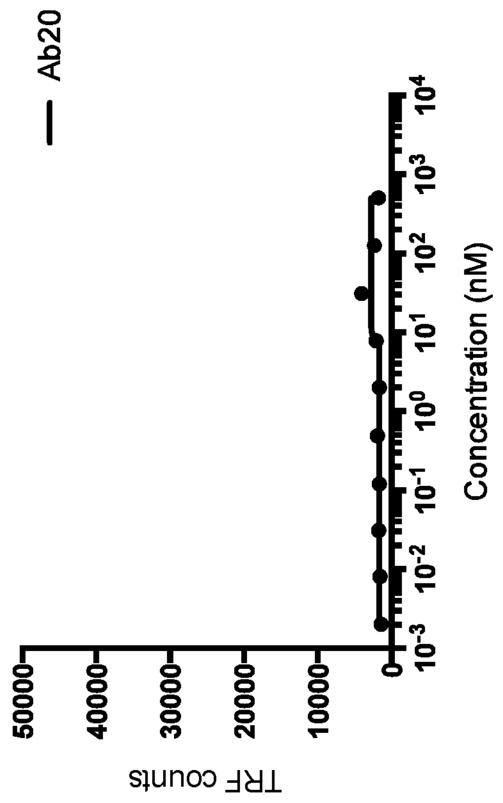
Figure 15C:
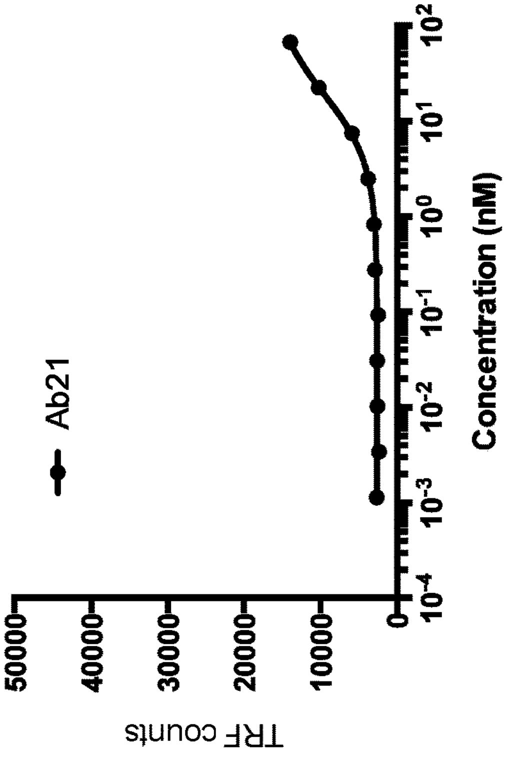
Figure 15D:
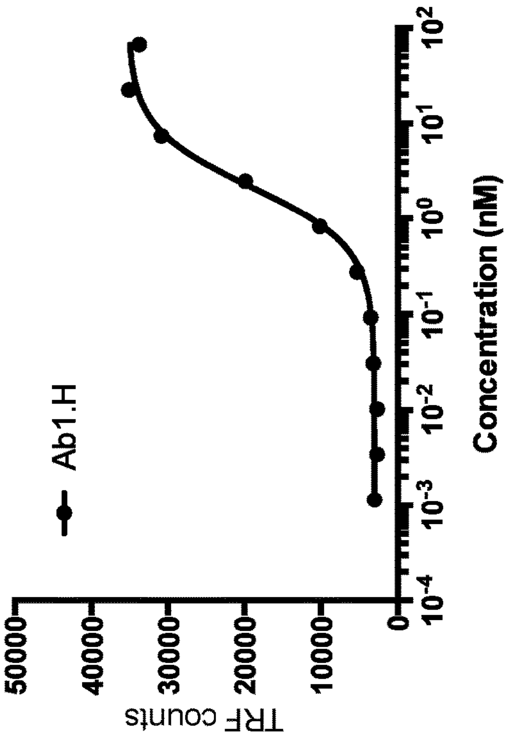
Figure 15E:
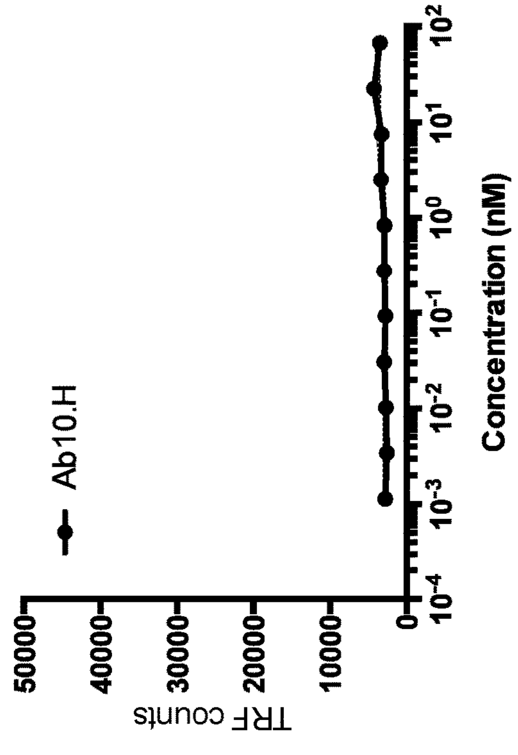
Figure 15F:
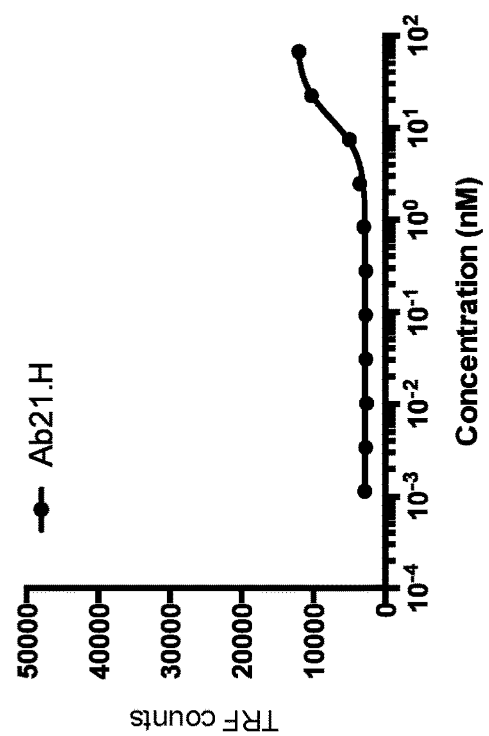
Figure 15G:
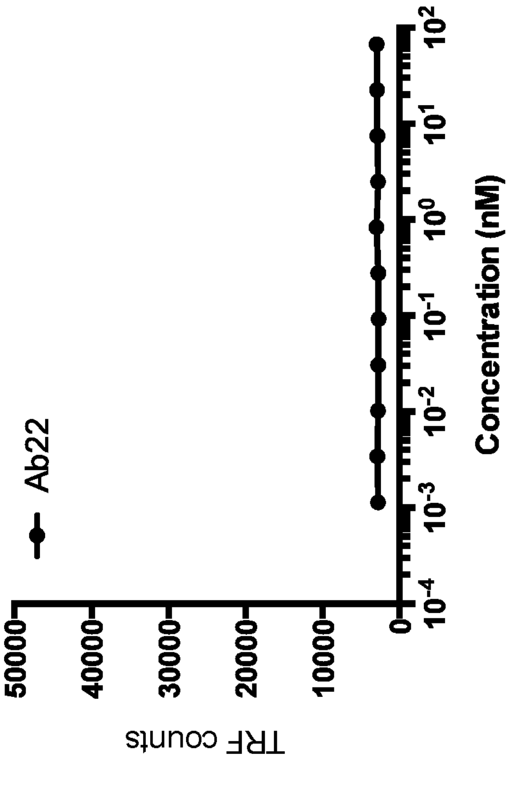
Figure 15H:
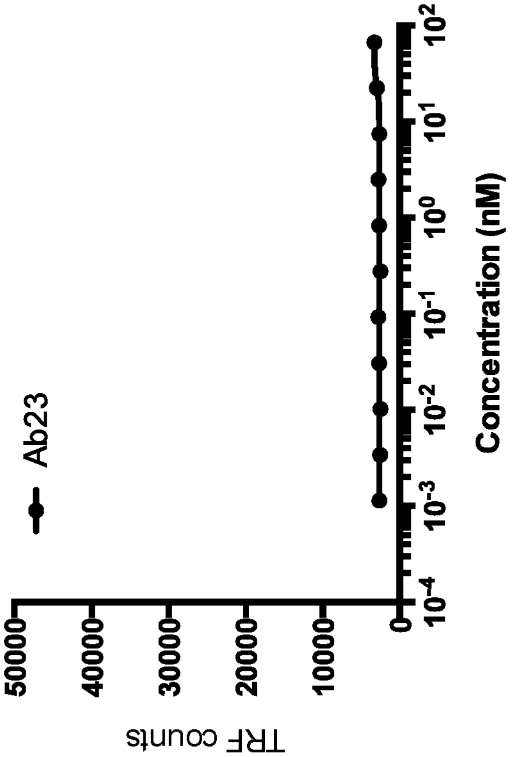
Figure 15I:
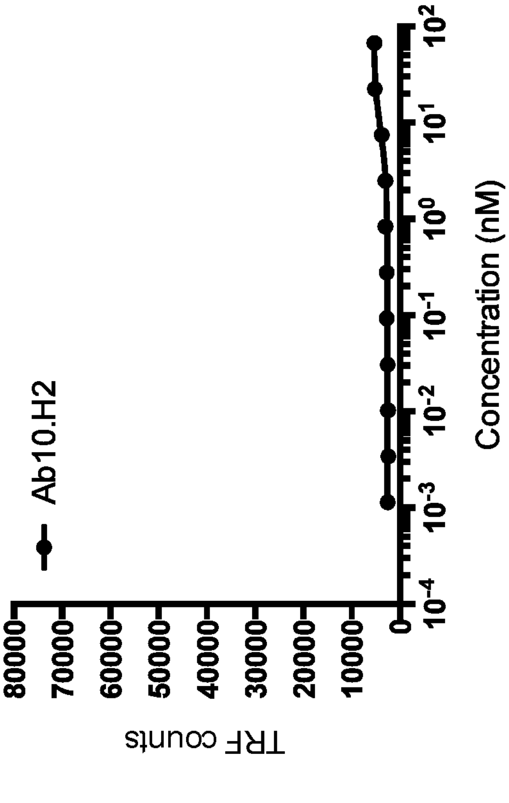
Figure 15J:
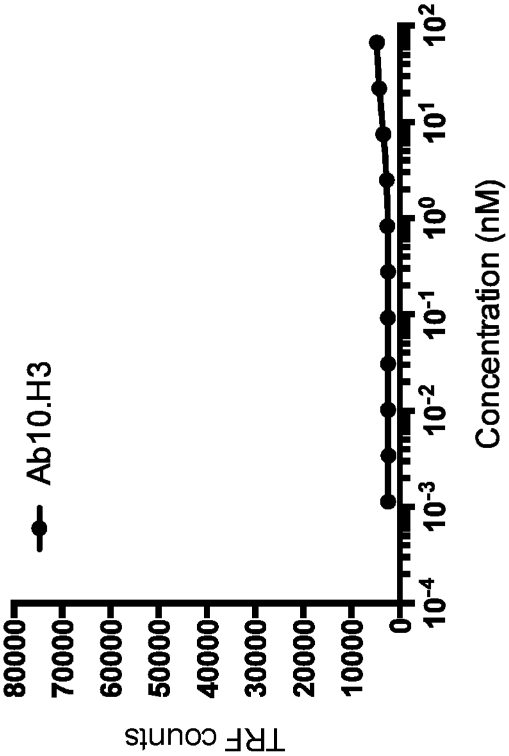
Figure 15K:
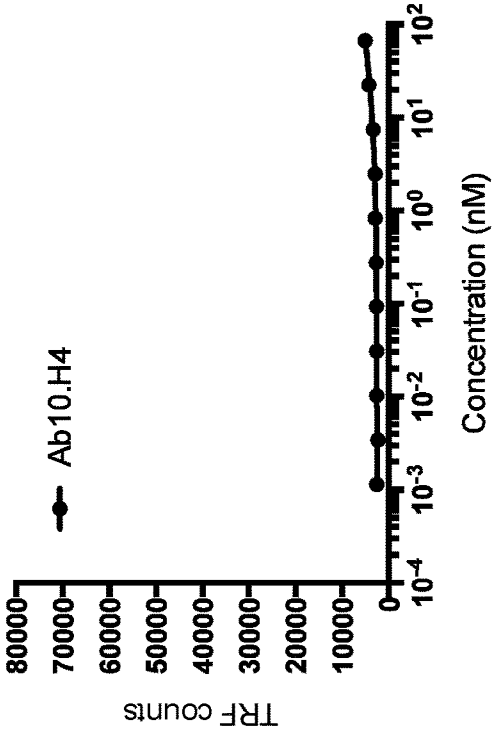
Figure 15L:
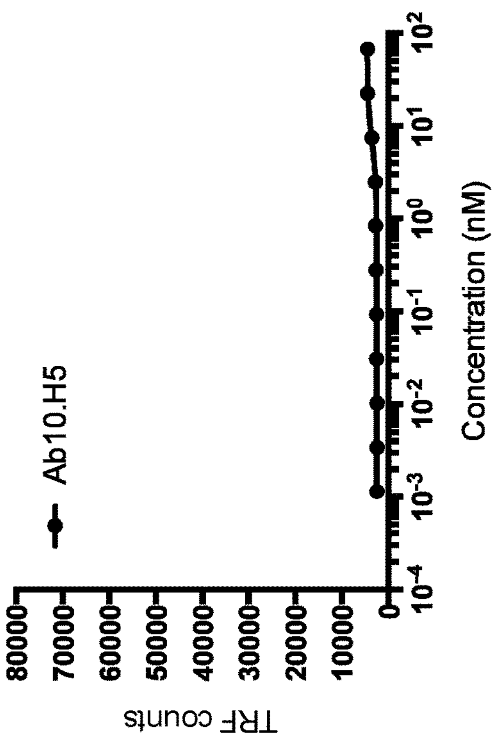
Figure 15M:
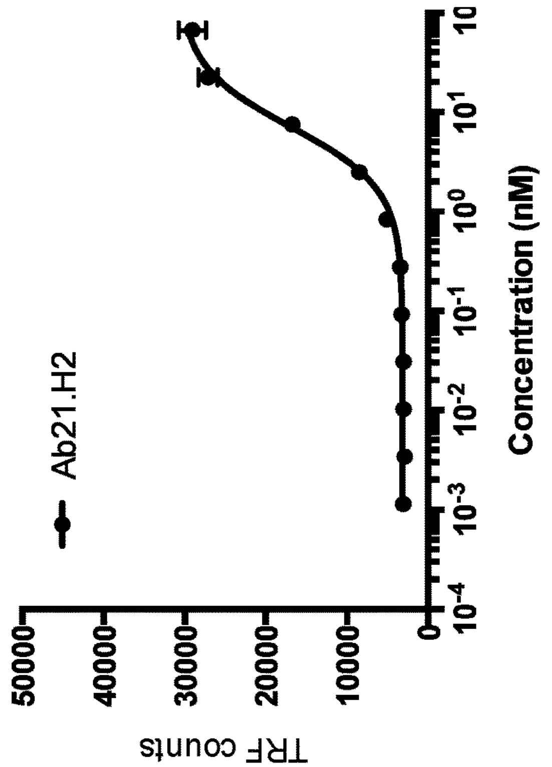
Figure 15N:
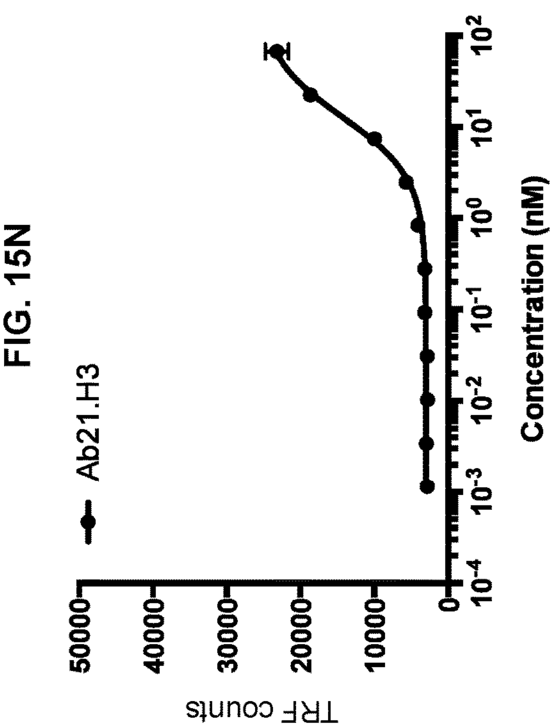
Figure 15O:
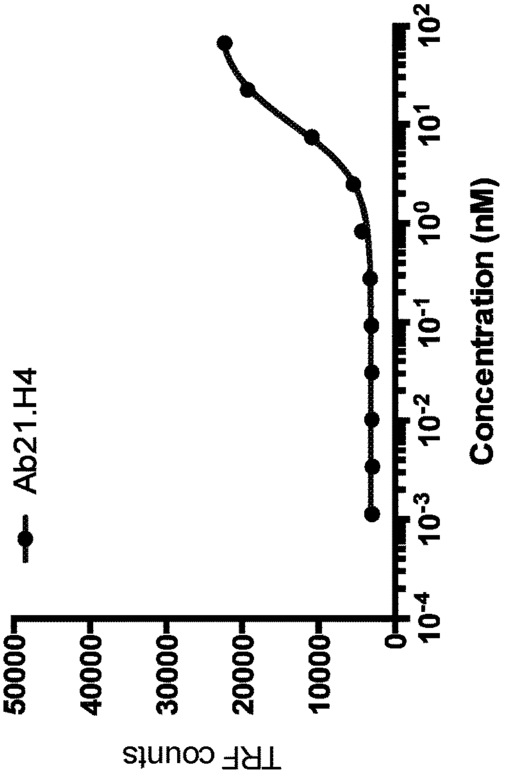

FIGS. 15A-15O are representative of the binding curves obtained by this method (results are shown for Ab10, Ab20, Ab21, Ab1.H, Ab10.H, Ab21.H, Ab22, Ab23, Ab10.H2, Ab10.H3, Ab10.H4, Ab10.H5, Ab21.H2, Ab21.H3, and Ab21.H4, respectively) wherein the PAC1-R expressing cells were PC-12 cells. Ab21.H2, Ab21.H3, and Ab21.H4 demonstrated limited binding to the surface of PAC1-R expressing cells in the presence of PACAP38. Ab1.H demonstrated strong binding to the surface of PAC1-R expressing cells in the presence of PACAP38, while Ab20, Ab21, Ab10.H, Ab21.H, Ab22, Ab23, Ab10.H2, Ab10.H3, Ab10.H4, and Ab10.H5 did not appear to appreciably bind to the surface of PAC1-R expressing cells using this assay. The strong binding of antibody Ab1.H and the limited binding of Ab21.H2, Ab21.H3, and Ab21.H4, to the cell surface of PAC1-R cells was only observed in the presence of PACAP38. Without intent to be bound by theory, it is hypothesized that the binding, either strong or limited, of the antibodies to the cell surface was mediated by binding of PACAP38 to GAGs that were present on the cell surface, since binding of PACAP38 by GAGs has been previously demonstrated as a PAC1-R receptor independent mechanism of PACAP38 binding and internalization by PC-12 cells (see Doan et al. (2012), Juhász et al. (2014), and Neree et al. (2015)).

Example 7: Inhibition of PACAP38-Induced Dermal Vasodilation in Rabbits by Anti-PACAP Antibody Ab1.H Intradermal injection of PACAP38 has been shown to elicit a localized vasodilation in rabbits and humans (Warren et al., *J. Cardio. Pharmacol.,* 29 (1): 83-87 (1992); and Seelinger et al., *Am. J. Path.,* 177 (5): 2563-2575, 2010). An in vivo efficacy study was conducted to determine the activity of Ab1.H to inhibit a localized dermal vasodilation induced by an intradermal injection of PACAP38 in male New Zealand White rabbits.

Groups of 4 rabbits were dosed with either 90 mg/kg of Ab1.H or with negative control vehicle (25 mM histidine, 250 mM sorbitol, pH 6.0). Injections were performed by IV (car vein) bolus administration on day 0. Prior to each rabbit PACAP38 challenge, the scapular region of each animal was clipped free of hair and wiped with 20% (v/v) alcohol in water. On day 2, the animals were pre-anesthetized with ketamine hydrochloride and maintained under deep anesthesia with isoflurane gas. Four sites (Region of Interest ("ROI")) for injection were identified on the back of each animal using a SHARPIE® permanent marker. Dermal vasodilation and blood perfusion were monitored using the PeriCam PSI NR system for Laser Speckle Contrast Analysis ("LASCA") imaging (Perimed, Järfälla, Sweden), before (baseline) and for 35 minutes after intradermal PACAP38 challenge. Intradermal PACAP38 challenge was performed as follows: each animal received single intradermal administrations (100 μl/site) of vehicle (one site or ROI) and PACAP38 at 30 pmoles/site (3 sites or 3 ROIs). The blood perfusion rates for each ROI were reported by the PeriCam PSI NR system in Perfusion units ("PU") and analyzed using PIMSoft (Ver. 1.5, Perimed, Järfälla, Sweden).

For each treatment group, the relative % PU change following Ab1.H or negative control administration compared to baseline was calculated for each ROI (% PU change for each PACAP38 challenge site-% PU change for the vehicle site). The relative % PU change in the Ab1.H group was compared to the relative % PU change in the Negative control group by performing a two-tailed unpaired t-test statistical evaluation using GraphPad Prism (version 5.0d, GraphPad Software, La Jolla, CA) software.

Figure 20:
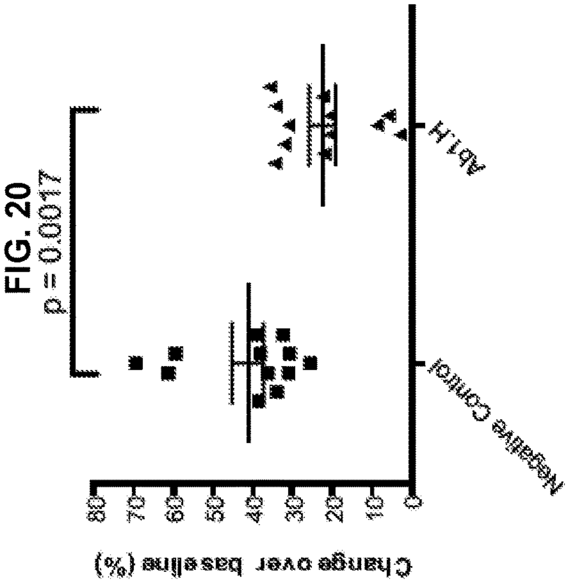
FIG. 20 provides representative data showing a reduction in vasodilation obtained by administering Ab1.H following PACAP38 administration in a rabbit model, relative to a vehicle control, obtained following the protocol in Example 7 infra.

FIG. 20 demonstrates that Ab1.H inhibited PACAP38-induced dermal vasodilation in rabbits, indicating effectiveness of the antibody at neutralizing PACAP38 activity in vivo.

Example 8: Inhibition of PACAP38-Induced Dermal Vasodilation in Rabbits by Anti-PACAP Antibody Ab10

Intradermal injection of PACAP38 has been shown to elicit a localized vasodilation in rabbits and humans (Warren et al., 1992; and Seelinger et al., 2010). An in vivo efficacy study was conducted to determine the activity of Ab10 to inhibit a localized dermal vasodilation induced by an intradermal injection of PACAP38 in male New Zealand White rabbits.

Groups of 4 rabbits were dosed with either 72 mg/kg of Ab10 or with isotype antibody control. Injections were by (car vein) bolus intravenous administration on day 0. Prior to each rabbit PACAP38 challenge, the scapular region of each animal was clipped free of hair and wiped with 20% (v/v) alcohol in water. On day 2, the animals were pre-anesthetized with ketamine hydrochloride and maintained under deep anesthesia with isoflurane gas. Four sites (ROIs) for injection were identified on the back of each animal using a SHARPIE® permanent marker. Dermal vasodilation and blood perfusion were monitored using the PeriCam PSI NR system for LASCA imaging (Perimed, Järfälla, Sweden), before (baseline) and for 35 minutes after intradermal PACAP38 challenge. Intradermal PACAP38 challenge was performed as follows: each animal received single intradermal administrations (100 μl/site) of vehicle (one site or ROI) and PACAP38 at 30 pmoles/site (3 sites or 3 ROIs). The blood perfusion rates for each ROI were reported by the PeriCam PSI NR system in PU and analyzed using PIMSoft (Ver. 1.5 (Perimed, Järfälla, Sweden)).

For each treatment group, the relative % PU change following Ab10 or Isotype Ab control administration compared to baseline was calculated for each ROI (% PU change for each PACAP38 challenge site-% PU change for the vehicle site). The relative % PU change in the Ab10 group was compared to the relative % PU change in the Isotype Ab control group by performing a two-tailed unpaired t-test statistical evaluation using GraphPad Prism (version 5.0d, GraphPad Software, La Jolla, CA) software.

Figure 21:
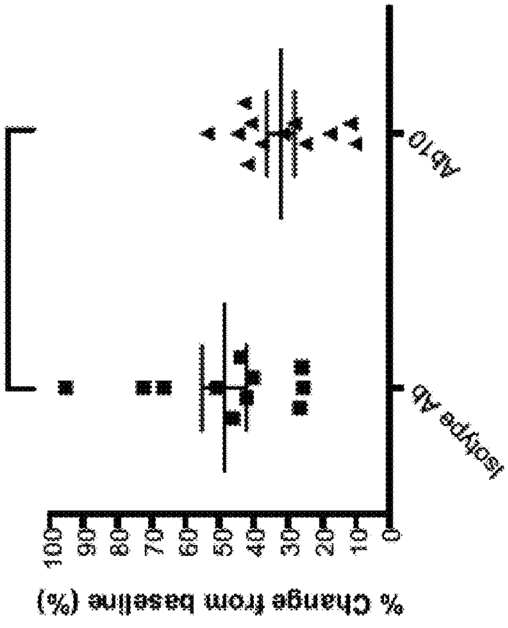
FIG. 21 provides representative data showing a reduction in vasodilation obtained by administering Ab10 following PACAP38 administration in a rabbit model, relative to an isotype antibody control, obtained following the protocol in Example 8 infra.

FIG. 21 demonstrates that Ab10 inhibited PACAP38-induced dermal vasodilation in rabbits, indicating effectiveness of the antibody at neutralizing PACAP38 activity in vivo.

Example 9: Epitope Binning of Anti-PACAP Antibodies, Ab1 and Ab10

Figure 22A:
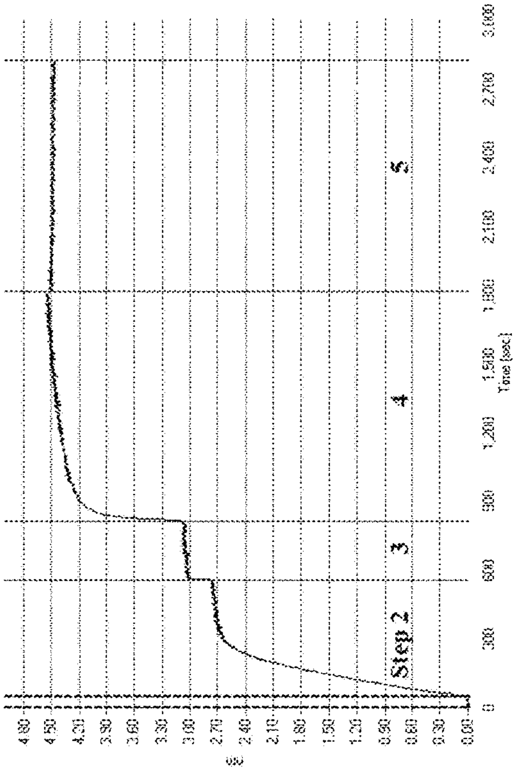
FIG. 22A provides epitope binning data for labeled Ab1 and unlabeled Ab10 obtained following the protocol in Example 9 infra.
Figure 22B:
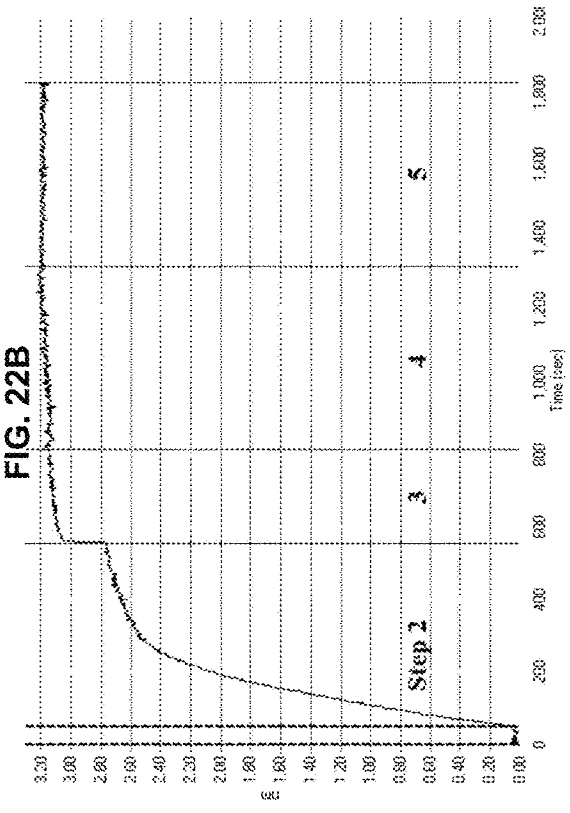
FIG. 22B provides epitope binning data for unlabeled Ab1 and labeled Ab10 obtained following the protocol in Example 9 infra.

Ab1 was biotinylated at a 10:1 molar ratio with biotin (Thermo Fisher Scientific, Waltham, MA) per manufacturer guidelines. A 5 step biolayer interferometry experiment was performed as follows: In step 1, streptavidin biosensors (Pall ForteBio LLC, Menlo Park, CA) were equilibrated for 50 seconds in 1× kinetics buffer (a 1:10 dilution in DBS of Pall ForteBio LLC, Menlo Park, CA, cat #18-5032). In step 2, a 2 μg/ml dilution of biotinylated antibody Ab1 in 1× kinetics buffer was immobilized for 500 seconds onto Streptavidin biosensors. In step 3, the antibody-functionalized biosensors were incubated in a solution of 2 μM unlabeled PACAP peptide (American Peptide Company, Sunnyvale, CA, catalog #34-0-20) in 1× kinetics buffer for 200 seconds. In step 4, the sensors were placed into 67 nM solutions of either unlabeled antibody Ab10 (FIG. 22A) or unlabeled antibody Ab1 as control (FIG. 22B) in 1× kinetics buffer for a 1000 second association step. Stability of binding was monitored during step 5 for a 1000 second dissociation in 1× kinetics buffer. In FIG. 22A, the "sandwich-style" capture of Ab10 via Ab1-captured PACAP indicates simultaneous and non-competitive binding of these two antibodies to PACAP. The control experiment in FIG. 22B shows minimal "sandwich-style" capture of Ab1 via Ab1-captured PACAP. The experiment was conducted on a ForteBio OCTET® QK instrument (Pall ForteBio LLC, Menlo Park, CA) at 30° C. and 1000 RPM.

Example 10: Inhibition of PACAP27 Binding to Human PAC1-R by Anti-PACAP Antibodies To identify antibodies that block PACAP27 binding to PAC1-R, antibodies at an initial concentration of 30 nM were diluted in incubation buffer (50 mM Hepes pH 7.4, 1 mM $CaCl_2$, 5 mM $MgCl_2$, 0.2% BSA) and serial 1:3 dilutions were performed. Antibody dilutions (30 nM, 10 nM, 3 nM, 1 nM, 0.3 nM, 0.1 nM, 0.03 nM, 0.01 nM, 0.003 nM and 0.001 nM) were then mixed and pre-incubated at 25° C. for 30 minutes with 0.1 nM of $^{125}$I-labelled PACAP27 in incubation buffer. The antibody: $^{125}$I-labelled PACAP27 mixture was then added to 0.5 μg aliquots of cell membranes derived from Chem-1 cells expressing human recombinant PAC1-R long isoform in incubation buffer. The mixture was then incubated for 1 hour at 25° C. Following incubation, the samples were filtered and washed. Afterward, the filters were counted to quantitate $^{125}$I-labelled PACAP27. As an experimental control, non-specific binding to the cell membranes was estimated using 0.1 μM of labeled PACAP27. The results indicated that Ab1.H, Ab10.H, Ab10.H3, and Ab21.H were capable of blocking PACAP27 binding to PAC1-R, thereby demonstrating inhibition of ligand-receptor binding by the tested antibodies presented in Table 10.

TABLE 10

Inhibition ($IC_{50}$) of 0.1 nM $^{125}$I-PACAP27 binding to PAC1-R by anti-PACAP antibodies

| ANTIBODY | $IC_{50}$ (nM) |
|---|---|
| Ab1.H | 0.70 |
| Ab10.H | 0.22 |
| Ab10.H3 | 0.21 |
| Ab21.H | 0.39 |

Example 11: Effect of Anti-PACAP Antibody on Light Aversion

To examine the effect of anti-PACAP antibodies on photophobia, a mouse model was employed in which mice were administered PACAP to trigger photophobia. Photophobia was detected using a light aversion assay using a light-dark box as described in Kaiser et al., *J. Neurosci.,* 32 (44): 15439-15449, 2012. Mice were then administered anti-PACAP antibodies Ab1.H, Ab10.H, or Ab10.H3 or an unrelated control antibody and their aversion to light quantitated. Results are reflected in FIGS. 23-25, FIG. 32, and FIGS. 33A-33B.

Light Aversion Assay

As described in Kaiser et al., the testing chambers were a plexiglas open field (27 cm wide×27 cm deep×20.3 cm high) containing three sets of 16 beam infrared arrays (two sets of perpendicular beams cross at a height of 1.0 cm to detect mouse location and locomotion, and the third beam crosses the width of the chamber at a height of 7.3 cm to detect vertical activity). The field was divided in two equal sized zones by a dark insert, which is a five-sided, black-colored plexiglas box with a top, but no floor. The use of infrared light beams allowed tracking in both zones. An opening (5.2 cm×6.8 cm) in the dark insert allowed free movement between zones. While the dark insert blocked direct light, some light could still enter through the opening. Each testing chamber was located inside a sound-attenuating cubicle (56 cm wide×38 cm deep×36 cm high) with a fan for ventilation (Med Associates, Inc.®, St. Albans, VT). A computer using Activity Monitor v6.02 (Med Associated Inc.) was used for recording data from the six chambers.

For each chamber, a LED panel was attached to the ceiling of the sound-attenuating cubicle. The LED panel contains 36 collimated 1 watt LEDs (5500 k Daylight White) (LEDwholesalers.com, Burlingame, CA). To control light intensity, each LED panel was connected to a dimmable LED driver (LINEARdrive®; eldoLED America Inc., San Jose, CA) leading to a potential range of light intensity from $3.0\times10^2$ to $2.7\times10^4$ 1×. Levels were further attenuated to $5.5\times10^1$ 1× using wax paper placed on a clear plexiglass tray below the LEDs. Light intensity was measured with Traceable Dual-Display Light Meter (Control Company, Friendswood, TX) placed on the floor of the testing chamber. At $2.7\times10^4$ 1×, LED lights generated some heat in the sound attenuating chamber with the dark zone at ~25° C. and light zone at ~27° C.

On the day of the experiment, mice were transported from animal housing and allowed to acclimate to the testing room (~22° C.) for at least 30 to 60 minutes with standard overhead fluorescent lighting (~200 lx inside the housing cage). Room lights remained on, unless noted otherwise. In addition, all sound-generating equipment were turned on during acclimation and remained on until testing was complete. There was minimal human presence in the room during acclimation. Behavioral testing was performed between 0800 CST and 1400 CST. Any abnormal physical conditions (e.g. missing eye) were noted.

Ten week old male and female CDI mice were used in the study (strain #022, Charles River, Wilmington, MA, US). Mice were allowed to recover from shipping for one to two weeks prior to testing.

Acclimation

All mice were acclimated in the testing room at least 30 to 60 minutes prior to being placed in the light/dark chamber. The light intensity in the chamber was initially set to $2.7\times10^3$ 1×. The mice were tested for thirty minutes in the chamber every day they were exposed to the light/dark chamber. Baseline time in light for each mouse was obtained by exposing the mice to the light/dark chamber twice, with a period of rest of three days between baseline measurements (FIGS. 23 and 25, "Baseline1" and "Baseline2," or "Baseline", respectively, and FIG. 32, "Baseline").

Treatment

Figure 25:
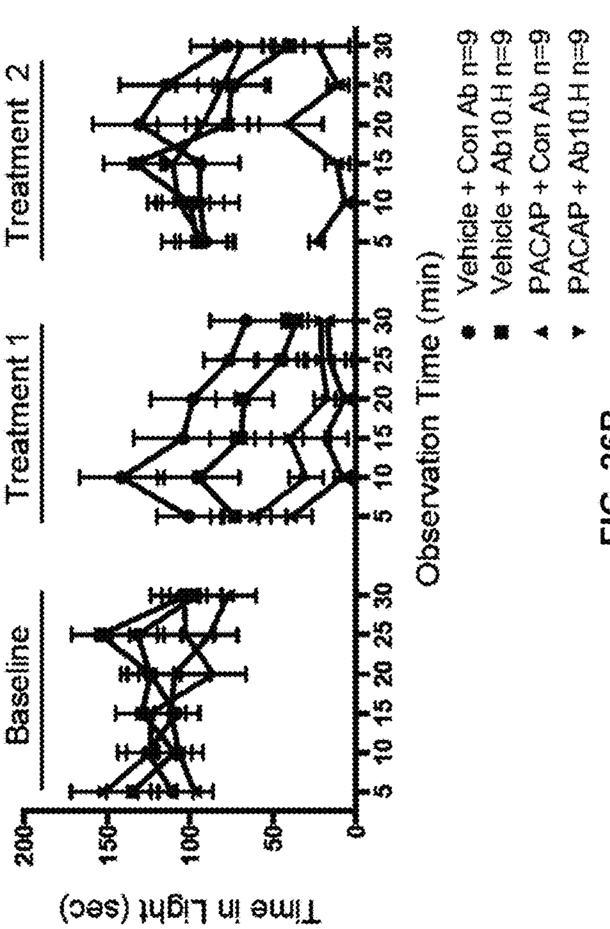
FIG. 25 provides representative data showing the in vivo effect of the administration of PACAP and an anti-PACAP antibody Ab10.H in a rodent photophobia model, which model detects the amount of time treated animals (mice) spend in the light per 5 min. interval compared to appropriate control animals obtained following the protocol in Example 11 infra.
Figure 26A:
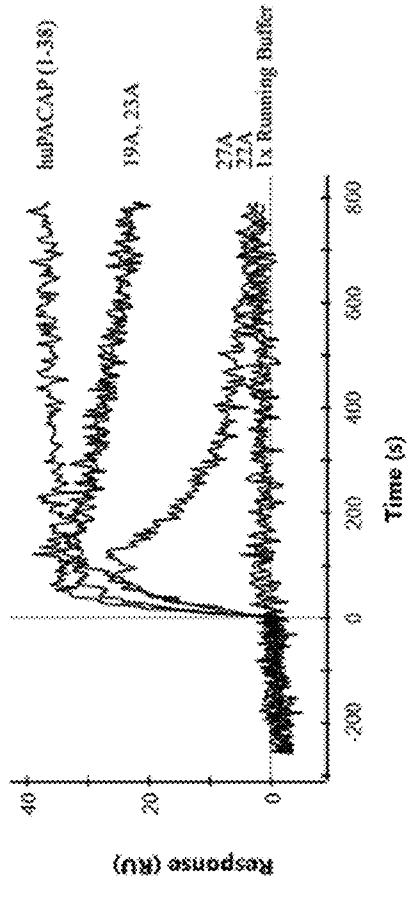
FIG. 26A presents results of surface plasmon resonance-based binding kinetics measurements for binding of anti-PACAP antibody Ab10 to PACAP alanine scanning mutants 19A, 22A, 23A, and 27A, along with controls including wild-type PACAP (labelled huPACAP (1-38)) (positive control) and 1× running buffer (negative control) obtained following the protocol in Example 12 infra.
Figure 26B:
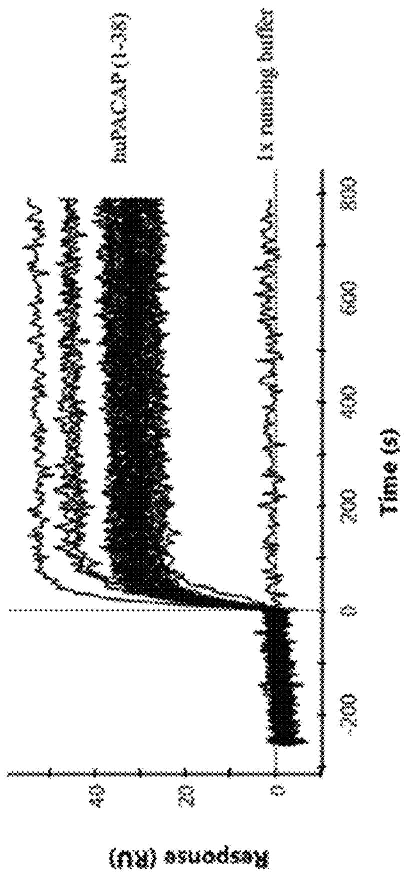
FIG. 26B presents results of surface plasmon resonance-based binding kinetics measurements for binding of anti-PACAP antibody Ab10 to PACAP alanine scanning mutants 1A-18A, 20A, 21A, 24V-26A, and 28A-38A, along with controls including wild-type PACAP (labelled huPACAP (1-38)) (positive control) and 1× running buffer (negative control) obtained following the protocol in Example 12 infra.
Figure 27A:
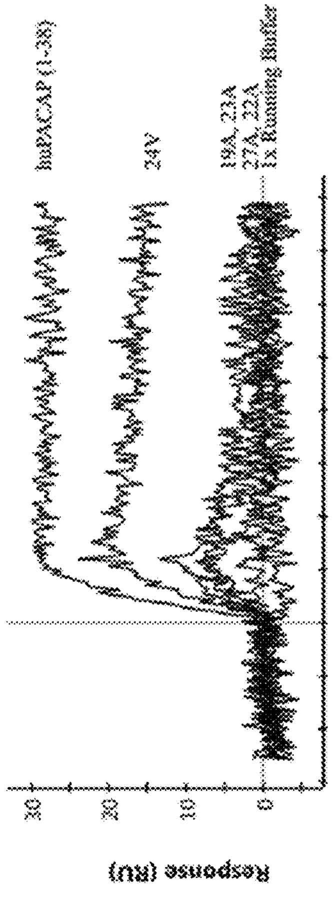
FIG. 27A presents results of surface plasmon resonance-based binding kinetics measurements for binding of anti-PACAP antibody Ab20 to PACAP alanine scanning mutants 19A, 22A, 23A, 24V, and 27A, along with controls including wild-type PACAP (labelled huPACAP (1-38)) (positive control) and 1× running buffer (negative control) obtained following the protocol in Example 12 infra.
Figure 27B:
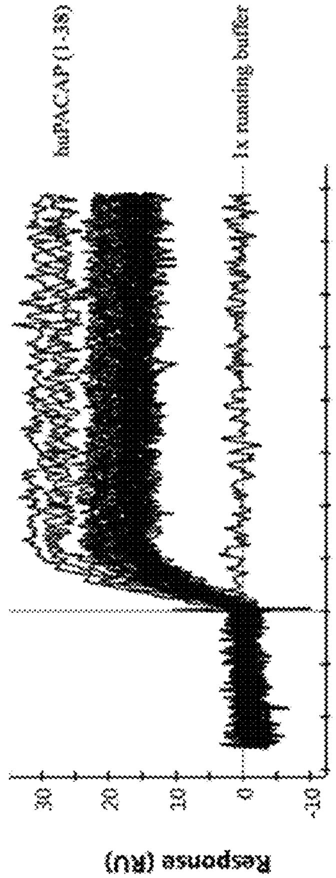
FIG. 27B presents results of surface plasmon resonance-based binding kinetics measurements for binding of anti-PACAP antibody Ab20 to PACAP alanine scanning mutants 1A-18A, 20A, 21A, 25A, 26A, and 28A-38A, along with controls including wild-type PACAP (labelled huPACAP (1-38)) (positive control) and 1× running buffer (negative control) obtained following the protocol in Example 12 infra.
Figure 28A:
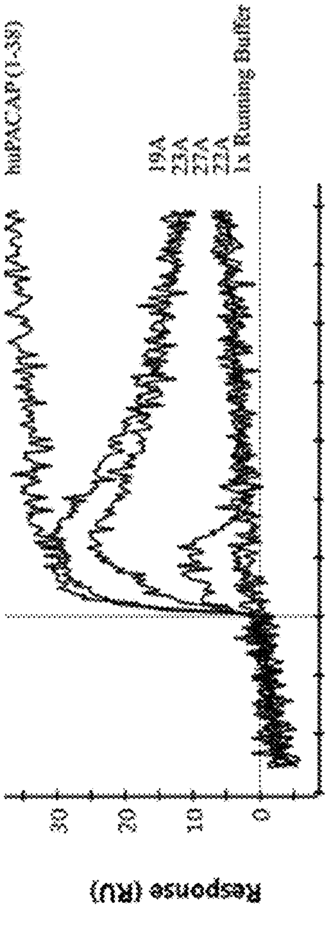
FIG. 28A presents results of surface plasmon resonance-based binding kinetics measurements for binding of anti-PACAP antibody Ab21 to PACAP alanine scanning mutants 19A, 22A, 23A, and 27A, along with controls including wild-type PACAP (labelled huPACAP (1-38)) (positive control) and 1× running buffer (negative control) obtained following the protocol in Example 12 infra.
Figure 28B:
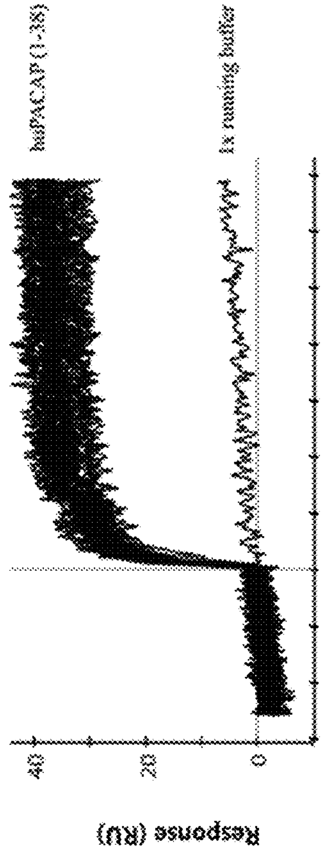
FIG. 28B presents results of binding kinetics measurements for binding of anti-PACAP antibody Ab21 to PACAP alanine scanning mutants 1A-18A, 20A, 21A, 24V-26A, and 28A-38A, along with controls including wild-type PACAP (labelled huPACAP (1-38)) (positive control) and 1× running buffer (negative control) obtained following the protocol in Example 12 infra.
Figure 29A:
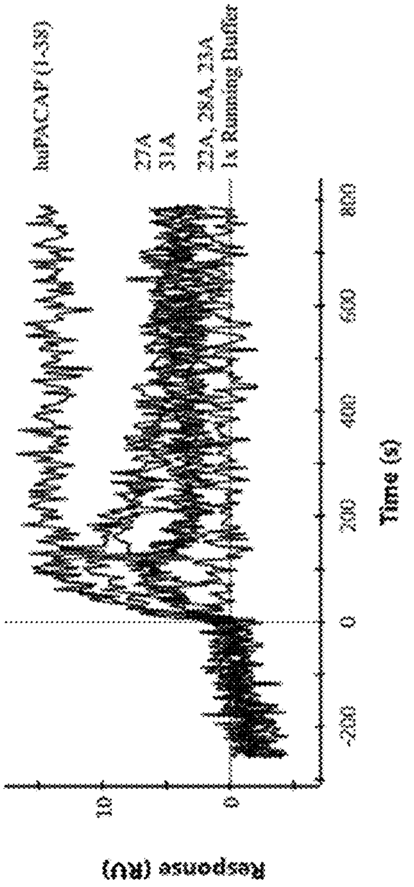
FIG. 29A presents results of surface plasmon resonance-based binding kinetics measurements for binding of anti-PACAP antibody Ab22 to PACAP alanine scanning mutants 22A, 23A, 27A, 28A, and 31A, along with controls including wild-type PACAP (labelled huPACAP (1-38)) (positive control) and 1× running buffer (negative control) obtained following the protocol in Example 12 infra.
Figure 29B:
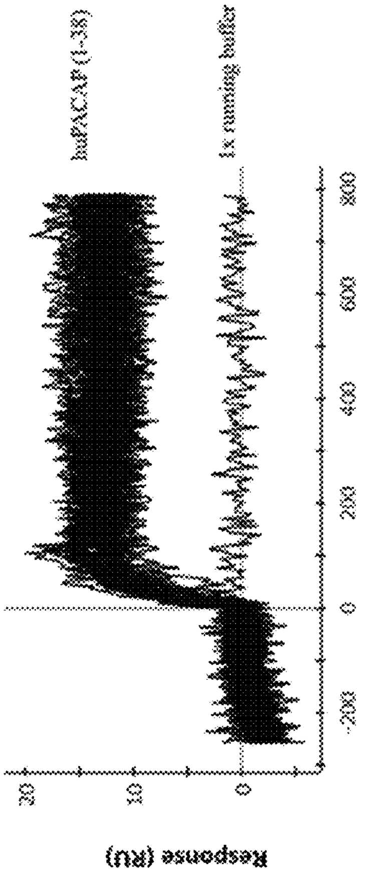
FIG. 29B presents results of surface plasmon resonance-based binding kinetics measurements for binding of anti-PACAP antibody Ab22 to PACAP alanine scanning mutants 1A-21A, 24V-26A, 29A, and 30A, along with controls including wild-type PACAP (labelled huPACAP (1-38)) (positive control) and 1× running buffer (negative control) obtained following the protocol in Example 12 infra.
Figure 30A:
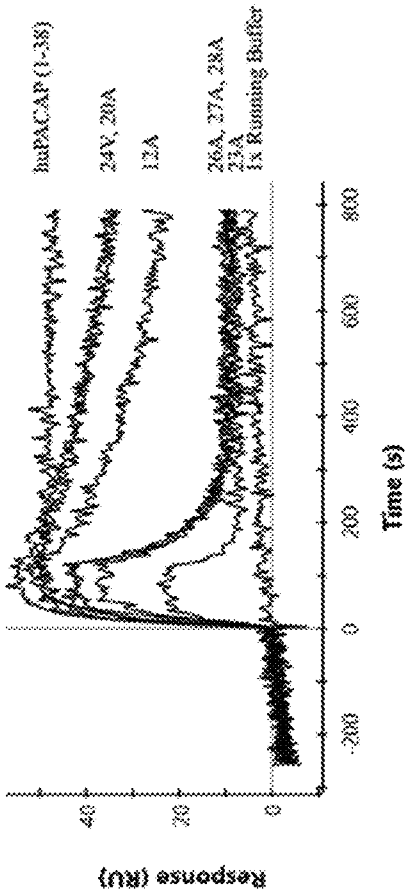
FIG. 30A presents results of surface plasmon resonance-based binding kinetics measurements for binding of anti-PACAP antibody Ab23 to PACAP alanine scanning mutants 12A, 20A, 23A, 24V, 26A, 27A, and 28A, along with controls including wild-type PACAP (labelled huPACAP (1-38)) (positive control) and 1× running buffer (negative control) obtained following the protocol in Example 12 infra.
Figure 30B:
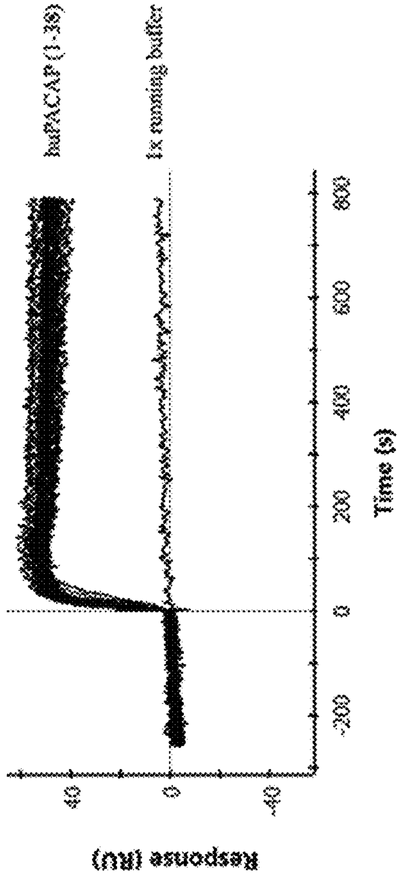
FIG. 30B presents results of surface plasmon resonance-based binding kinetics measurements for binding of anti-PACAP antibody Ab23 to PACAP alanine scanning mutants 1A-11A, 13A-19A, 21A, 22A, 25V, and 29A-31A, along with controls including wild-type PACAP (labelled huPACAP (1-38)) (positive control) and 1× running buffer (negative control) obtained following the protocol in Example 12 infra.
Figure 32:
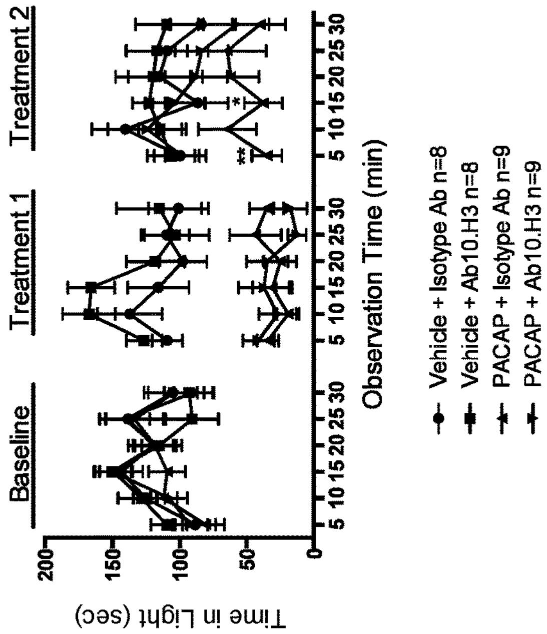
FIG. 32 provides representative data showing the in vivo effect of the administration of PACAP and an anti-PACAP antibody Ab10.H3 in a rodent photophobia model, which model detects the amount of time treated animals (mice) spend in the light per 5 min. interval compared to appropriate control animals obtained following the protocol in Example 11 infra.

In FIGS. 25 and 32, mice were administered 0.6 mg/kg PACAP by i.p. injection and rested for 30 minutes. The mice were then placed in the light/dark chamber for 30 minutes (FIGS. 25 and 32, "Treatment 1"). After a rest period of three days that followed either the Baseline 1 and Baseline 2 measurements of FIG. 23 or the Treatment 1 measurements of FIGS. 25 and 32, mice were administered 30 mg/kg of either anti-PACAP antibody or control IgG antibody (negative control antibody having the same framework as the tested antibodies and that recognizes digoxigenin) by i.p. injection. The mice were then returned to their home cage to rest for one day (24 hours) prior to testing. The mice were then administered 0.6 mg/kg PACAP or vehicle by i.p. injection and rested for 30 minutes. The mice were then placed in the light/dark chamber for 30 minutes (FIG. 23, "Treatment" FIGS. 25 and 32, "Treatment 2"). After each mouse was exposed to the light/dark chamber, the light/dark chamber and components were cleaned with germicidal wipes and dried. About 5 to 7 minutes after a mouse was placed in the light/dark chamber, the next mouse to be tested was injected with PACAP or vehicle, as described above. This interval was approximately the amount of time required to clean the light/dark chamber between experiments.

Motility Measurements

Motility was measured at 5 minute intervals over the 30 minute testing period as described in Kaiser et al., *J. Neurosci.,* 2012. Briefly, the number of vertical movements, such as rearing, ambulatory distance (cm, the total distance traveled during ambulatory movement status), transitions, and resting (percentage of time spent breaking no new beams), were measured by light beam. All motility parameters were normalized to the time spent in each zone to account for different amount of time spent in that zone; thus, the raw value for each parameter was divided by the time spent in that zone during the 5 min interval. Time spent in each chamber was analyzed using GraphPad Prism software (GraphPad Software, San Diego, CA), and reported as mean±standard error of the mean ("SEM"). Comparison was calculated by two-way repeated measure ANOVA, with Bonferroni's multiple-comparison test for post-hoc analysis.

Mice were excluded based on three criteria: (1) after the first two exposures to the box the baseline time in light was analyzed and any mouse that spent +/− one standard deviation of mean time in light at baseline was removed from the experiment and not given drug treatment, (2) mice were excluded from analysis if they were identified as statistical outliers (box plot, 10-90%), and (3) mice were excluded if they moved less than 10% of the time (combined light and dark).

Figure 23:
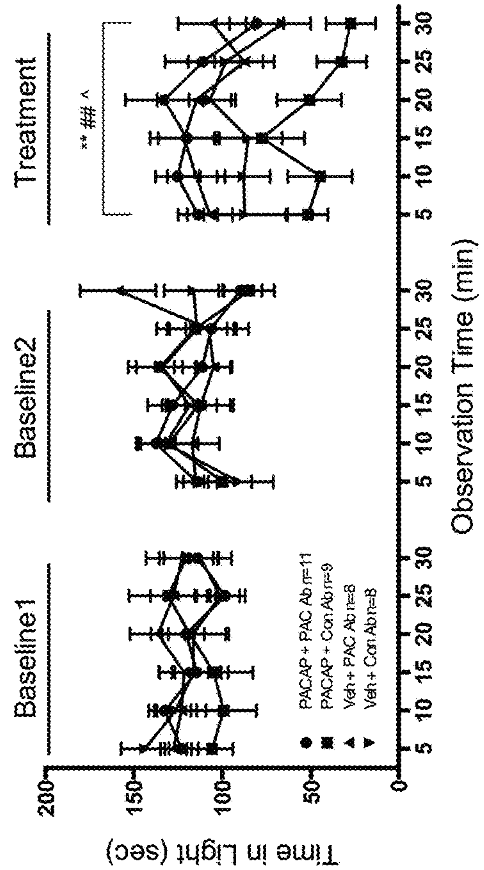
FIG. 23 provides representative data showing the in vivo effect of the administration of PACAP and an anti-PACAP antibody Ab1.H in a rodent photophobia model, which model detects the amount of time treated animals (mice) spend in the light per 5 min. interval compared to appropriate control animals obtained following the protocol in Example 11 infra.
Figure 24:
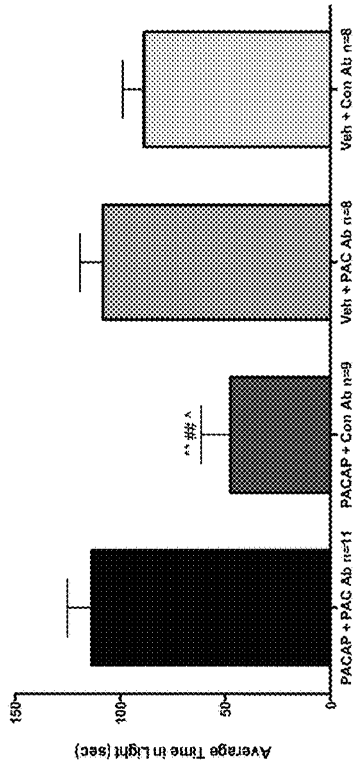
FIG. 24 provides representative data showing the in vivo effect of the administration of PACAP and anti-PACAP antibody Ab1.H in a rodent photophobia animal model, which detects the average amount of time treated animals (mice) spend in the light compared to appropriate control animals obtained following the protocol in Example 11 infra.

In three experiments comparing the response of mice administered antibody Ab1.H, Ab10.H, or Ab10.H3 to control IgG, the results indicate that mice administered anti-PACAP antibody Ab1.H, Ab10.H, or Ab10.H3 spent more time in light as compared to IgG control mice. FIG. 23 shows that mice behaved normally and similarly in both baseline measurements. On the other hand, the data provided in FIG. 23 show that mice treated with control IgG antibody and then PACAP spent statistically less time in light (squares) than mice administered anti-PACAP antibody Ab1.H and then PACAP (circles). (See, FIG. 23, "Treatment"). The data provided in FIG. 25 also show that mice behaved normally and similarly in baseline measurements. On the other hand, the data provided in FIG. 25 show that mice treated with control IgG antibody and then PACAP spent statistically less time in light (triangles) than mice administered anti-PACAP antibody Ab10.H and then PACAP (inverted triangles). (See, FIG. 25, "Treatment 2"). Time between each measurement, e.g., between Baseline and Treatment 1 (PACAP only), e.g., between Treatment 1 (PACAP only) and Treatment 2 (antibody followed by PACAP), was three days. The data provided in FIG. 32 also show that mice behaved normally and similarly in baseline measurements. On the other hand, the data provided in FIG. 32 show that mice treated with control IgG antibody and then PACAP spent statistically less time in light (triangles) than mice administered anti-PACAP antibody Ab10.H3 and then PACAP (inverted triangles). (See, FIG. 32, "Treatment 2"). Time between each measurement, e.g., Baseline and Treatment 1 (PACAP only), e.g., Treatment 1 (PACAP only) and Treatment 2 (antibody followed by PACAP), was three days. The mean±SEM is provided for each 5-minute interval. Mice administered vehicle only behaved as normal controls. Data provided in FIG. 24 shows that administration of either anti-PACAP antibody Ab1.H, or control IgG, and vehicle ("Veh+PAC Ab" and "Veh+Con Ab," respectively) did not markedly alter mouse behavior. FIG. 24 also shows that the average time of the mouse in light decreased when PACAP and control IgG were administered ("PACAP+Con Ab"), whereas mice administered anti-PACAP antibody Ab1.H and PACAP exhibited normal, non-light-sensitive behavior ("PACAP+PAC Ab").

Figure 33A:
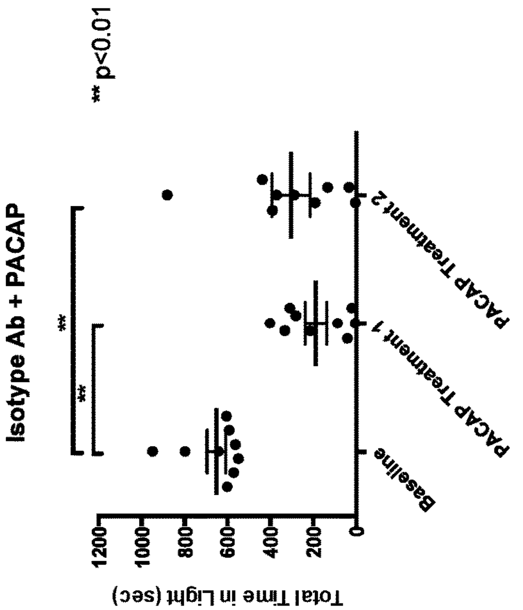
FIGS. 33A-33B provide data summarizing the data presented in FIG. 32, such that the total time in light over the entire 30 minute observation time period for each individual animal at Baseline, Treatment 1, and Treatment 2 are presented for animals in the isotype antibody groups (FIG. 33A) and animals in the Ab10.H3 groups (FIG. 33B).
Figure 33B:
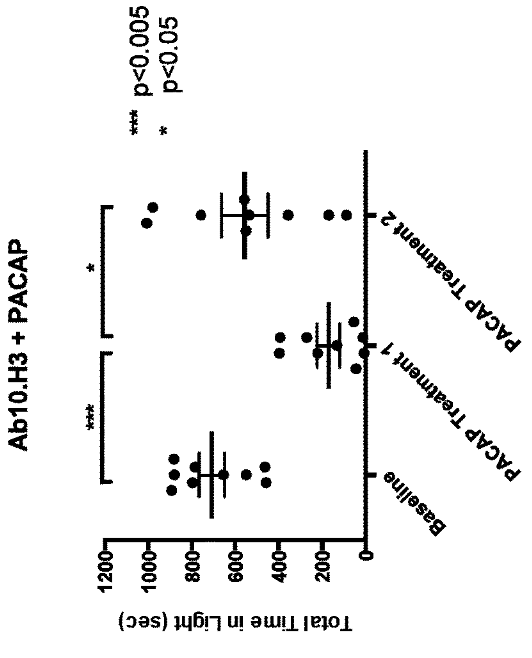

FIGS. 33A-33B summarize the data presented in FIG. 32, such that the total time in light over the entire 30 minute observation time period for each individual animal at Baseline, Treatment 1, and Treatment 2 are presented for animals in the isotype antibody groups (FIG. 33A) and animals in the Ab10.H3 groups (FIG. 33B).

Example 12: Epitope Mapping of Anti-PACAP Antibodies

In order to determine the epitopes contained within PACAP to which the anti-PACAP antibodies and antigen binding fragments thereof of the invention bind, alanine scanning experiments were used. To perform these experiments, PACAP peptides were synthesized with a single point mutation in each position replacing the native amino acid with an Alanine ("Ala"), and the consequences of a single point mutation as it relates to binding affinity of PACAP and an antibody were measured. Since an alanine residue already occupies positions 18, 24, and 25 of wild-type PACAP, according to convention, these Ala residues were replaced with Valine ("Val") to determine the possible effects of the removal of the alanine at these positions on the binding of the subject anti-PACAP antibodies to PACAP. Per the usual convention these Ala mutants were labeled according to the position in PACAP 1-38 followed by the letter code for the substituted amino acid, e.g., 10A indicates PACAP 1-38 substituted with alanine at amino acid position 10. Binding of monoclonal antibodies for human PACAP and each mutant peptide was detected using SPR on the PROTEON™ XRP36 (Bio-Rad Laboratories, Hercules, CA). Samples and sample controls were immobilized onto a PROTEON™ GLC sensor chip (Bio-Rad Laboratories, Hercules, CA) at a single density using standard amine coupling. The running buffer used for immobilization was DPBS/modified (HYCLONE™, GE Healthcare Life Sciences, Marlborough, MA) and immobilization was conducted at 25° C. The PROTEON™ GLC sensor chip (Bio-Rad Laboratories, Hercules, CA) was initialized and pre-conditioned per the manufacturer's protocol (bi-directional injections of 0.5% SDS, 50 mM NaOH, 100 mM HCl). The immobilization process was performed step-wise to ensure a unique antibody on the spots of the PROTEON™ Chip (Bio-Rad Laboratories, Hercules, CA). The surface of the chip was activated with a 1:1 mixture of 1-ethyl-3-(3-dimethylaminopropyl) carbodiimide/N-hydroxysuccinimide ("EDAC/NHS") and flow rate of 30 μL/min×5 minutes. Antibody samples were previously dialyzed or exchanged to 10 mM HEPES 150 mM NaCl pH 7.2, and the antibody concentration was quantified using a NANODROP™2000 spectrophotometer (Thermo Fisher Scientific, Waltham, MA). The immobilization targeted 2000-3000 response units ("RU").

Antibody samples (5 μg/ml) in 10 mM sodium acetate, pH 5.5, were flowed at 30 μL/min×4 minutes. Deactivation was achieved at a flow rate of 30 μL/min for 5 minutes using 0.3 M ethanolamine concomitantly with the next activation.

Following immobilization, the running buffer was changed to 1×PBST (4.3 mM sodium phosphate, 1.4 mM potassium phosphate, 135 mM NaCl, 2.7 mM KCl, 0.05% TWEEN®) with 0.2 M arginine HCl (to reduce non-specific binding), BSA (0.2 mg/ml, as a carrier) and PROCLIN300® (0.005% as a preservative, Sigma Aldrich, St. Louis, MO) and the chip surface was allowed to re-equilibrate with an injection of new running buffer. Stock solutions of human PACAP peptide (1-38) and alanine/valine mutant peptides (Molecular Weight(s): 4.5 kD) at a concentration of 1 mg/ml were added to the running buffer to final concentrations of 0.45 μg/ml (100 nM). These mixtures were then used to query individual spots on the chip surface with flow rates of 100 μL/min×2 minutes and allowed to dissociate for 600 seconds. Chip surfaces were regenerated between analytes by the addition of 0.85% phosphoric acid. Each of antibodies Ab10, Ab20, Ab21, Ab22, and Ab23 were examined under the same conditions as herein described.

Sensorgrams representing affinity data of mutant peptide binding to a panel of antibodies were assessed using multiple parameters. A visual inspection was first performed for each sensorgram to assess apparent maximal response ("$R_{max}$") relative to the wild-type PACAP peptide (1-38). Second, a visual inspection of the dissociation phase was performed with an emphasis on the curve shape relative to the wild-type PACAP peptide. Off-rates (dissociation rates) were calculated for wild-type PACAP peptide and the binding of each mutant peptide to the panel of antibodies. Finally, as a control experiment to confirm the integrity of each peptide variant (wild-type or mutant), the binding affinity of each member of the peptide library was individually determined for each member of a panel of antibodies that were known to bind wild-type PACAP, to ensure that each Ala mutant PACAP peptide exhibited binding affinity that was similar to the binding affinity of wild-type PACAP peptide. Collective assessment of all described parameters identified PACAP amino acid residues important for PACAP/antibody binding.

Binding and dissociation data are shown in FIGS. 26A-30B for binding of antibodies Ab10, Ab20, Ab21, Ab22, and Ab23 to wild-type PACAP and PACAP mutants. The upper panel in each figure contains the binding data for residues in PACAP that appeared to be important for antibody binding (labeled at the right end of the graph, e.g., "10A" indicates the binding data for the mutant containing alanine at position 10 of PACAP). The lower panel provides data points representing the degree of binding of the remaining PACAP alanine mutants, i.e., PACAP alanine mutants that bound to the tested antibody similar to wild-type PACAP. Based thereon, the residue was determined to likely not be important for antibody binding. As a positive control, both the upper and lower panels for each Figure also disclose the binding data obtained using wild-type PACAP (labeled huPACAP (1-38)).

FIGS. 31A-31B summarize the PACAP residue positions determined to contribute to antibody binding affinity based on data obtained in these alanine scanning studies. The positions listed in each column identify the PACAP alanine scanning mutants whose mutation led to a decrease in PACAP/antibody binding affinity. The residue positions are listed in column 3 of FIGS. 31A-31B according to the spatial arrangement of the residues along the PACAP primary sequence (from amino acid residue 1-38). The PACAP residue positions contributing most to antibody binding were interpreted to jointly comprise the epitopes bound by each antibody. Based on data obtained in these alanine scanning studies, the epitopes bound by each antibody were concluded to comprise the following residues:

(i) Ab10: residues 19, 22, 23, and 27 of human PACAP.

(ii) Ab20: residues 19, 22, 23, 24, and 27 of human PACAP.

(iii) Ab21: residues 19, 22, 23, and 27 of human PACAP.

(iv) Ab22: residues 22, 23, 27, 28, and 31 of human PACAP.

(v) Ab23: residues 12, 20, 23, 24, 26, 27, and 28 of human PACAP.

It was further noted based on the alanine scanning experimental results that the affinity of each of antibodies Ab10, Ab20, Ab21, Ab22, and Ab23 for PACAP involves or depends on residues 19, 22, 23, and/or 27 of human PACAP.

Additionally, it was observed that the affinity of each of antibodies Ab22 and Ab23 to PACAP involves or requires specific amino acid residues that are present in human wild-type PACAP38, but which are not present in human wild-type PACAP27, e.g., residues 28 and 31 of PACAP38.

With respect to the foregoing alanine scanning results humanized variants of the subject anti-PACAP antibodies should interact with the identical or substantially identical residues of human PACAP as humanization should not appreciably impact the specificity of the binding of the humanized anti-PACAP antibody to human PACAP compared to the parent (unhumanized) antibody. Particularly, Ab10.H, Ab10.H2, Ab10.H3, Ab10.H4, Ab10.H5, and Ab10.H6 should interact with the same residues on human PACAP as Ab10, and Ab21.H, Ab21.H2, Ab21.H3, and Ab21.H4 should interact with the same residues on human PACAP as Ab21.

Antibodies which bind to the same or overlapping epitopes on human PACAP as the subject antibodies may be produced and identified using method described herein. It is reasonable to anticipate that antibodies which bind to the same or overlapping epitope as any of the antibodies identified herein will likely possess similar biological activity absent a meaningful difference in binding kinetics. Particularly, such antibodies should antagonize one or more of the biological effects elicited by PACAP analogously to the exemplified anti-PACAP antibodies which bind these epitopes. Additionally, antibodies that bind to these same or overlapping epitopes, or a subset of residues thereof, are anticipated to mimic the binding characteristics of the subject antibodies. For example such antibodies are expected to selectively bind to PACAP and not bind or bind with much less affinity (weaker) to VIP or other peptides within this family of neuropeptides.

Example 13: Effect of Anti-PACAP Antibodies on Induction of Lacrimation and Increase of Facial Temperature Upon Intranasal Delivery of Umbellulone Noxious chemical stimulation of rat facial mucosa has been shown to increase facial and intracranial blood flow, as well as lacrimation, through activation of the trigemino-parasympathetic reflex, and can therefore serve as an experimental model for vascular dysfunctions in cluster headache, trigeminal neuralgia, and possibly migraine (Gottselig & Messlinger, Cephalalgia 2004, 24, 206-214; Nassini et al., Brain 2012, 135, 376-390; Khan et al., Cephalalgia 2014, 34 (5), 382-391). To examine the effect of anti-PACAP antibodies on intranasal irritant-induced lacrimation, an in vivo lacrimation assay was performed in a rat model. In said assay, lacrimation was triggered through intranasal administration of Umbellulone (Sigma Aldrich, St. Louis, MO), a noxious chemical agent. Lacrimation was determined by the distance of wetting on Schirmer's test strips, as described below, and the effect of anti-PACAP or anti-PAC1R antibodies on said lacrimation was measured. Additionally, intranasal administration of Umbellulone resulted in increased skin temperature on the nose of the animals as measured by an IR thermometer. No changes in temperature on the footpad were observed after the administration of Umbellulone. The effect of anti-PACAP or anti-PAC1R antibodies on changes in nose skin temperature was also monitored These measurements of Umbellulone effects on lacrimation and facial temperature represent, to the best of Applicants' knowledge, the first model showing antagonism of endogenously released PACAP through use of a chemical stimulant.

For the present assay, 60 male SPRAGUE DAWLEY® rats (Envigo, Huntingdon, Cambridgeshire, United Kingdom) plus 3 extra rats for randomization were used. The rats weighed between 250-275 grams at the time of their arrival, and they were acclimated for at least 7 days after their arrival in the testing room.

On study day −1, the rats were randomized into treatment groups by body weight. Following treatment group assignments, the rats were treated with anti-PACAP antibody Ab10.H3, an isotype-matched control antibody, or a proprietary anti-PAC1-R antibody administered intravenously at 20 mg/kg.

On study day 0, fresh Umbellulone was prepared by diluting Umbellulone oil to 0.2 μmol/kg in 0.5% DMSO in water in an amber glass vial. Schirmer's test strips, used to measure tear production, were modified by cutting 2 mm of width from the supplied 5 mm wide test strip, which resulted in a test strip ~3 mm wide ("modified Schirmer's test strips). Before dosing, the rats had their nose and right foot temperature taken with a Thermoworks (American Fork, UT) TW2 IR thermometer with emissivity that was set to 0.97. The thermometer was held within ~2.5 cm of the nose or footpad for the reading. Animals were anesthetized with inhaled isoflurane. Following anesthetization, 50 μl of 0.2 μmol of Umbellulone or 50 μl of 0.5% DMSO (vehicle control) were administered intranasally 2 mm into the right nostril over a 5 second period. 5 minutes post intranasal dosing the temperature of the rats was measured again using the process described above.

At 60 minutes post intranasal-dosing, the rats were anesthetized and had a modified Schirmer's test strip placed at the medial side of the right lower eye lid for a period of 5 minutes. After 5 minutes the test strip was read for tear production using the pre-printed hash marks (millimeter subdivisions) on the strip.

Figure 34A:
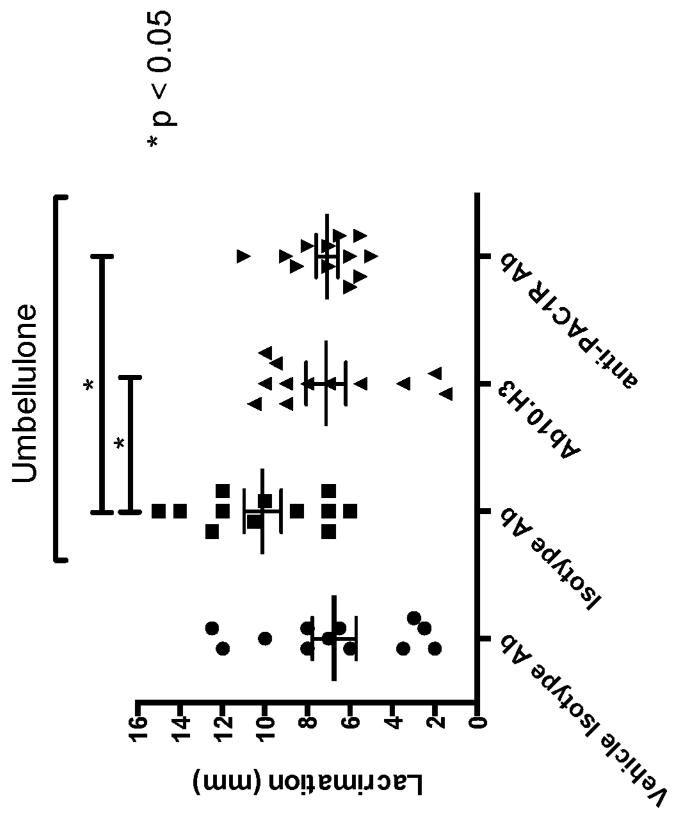
FIGS. 34A-34B provide representative data showing the in vivo effect of the administration of an anti-PACAP antibody Ab10.H3, an isotype antibody, or a proprietary anti-PAC1-R antibody, on lacrimation obtained following the protocol in Example 13 infra. The measurements were plotted for individual animals in each group in FIG. 34A, and the average measurement for animals in each group was plotted in FIG. 34B.
Figure 34B:
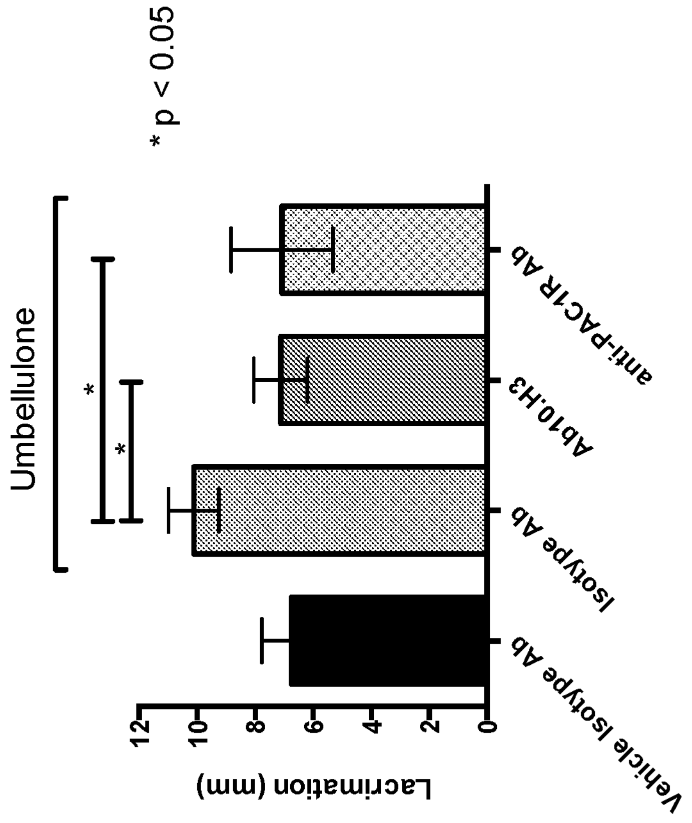
Figure 35B:
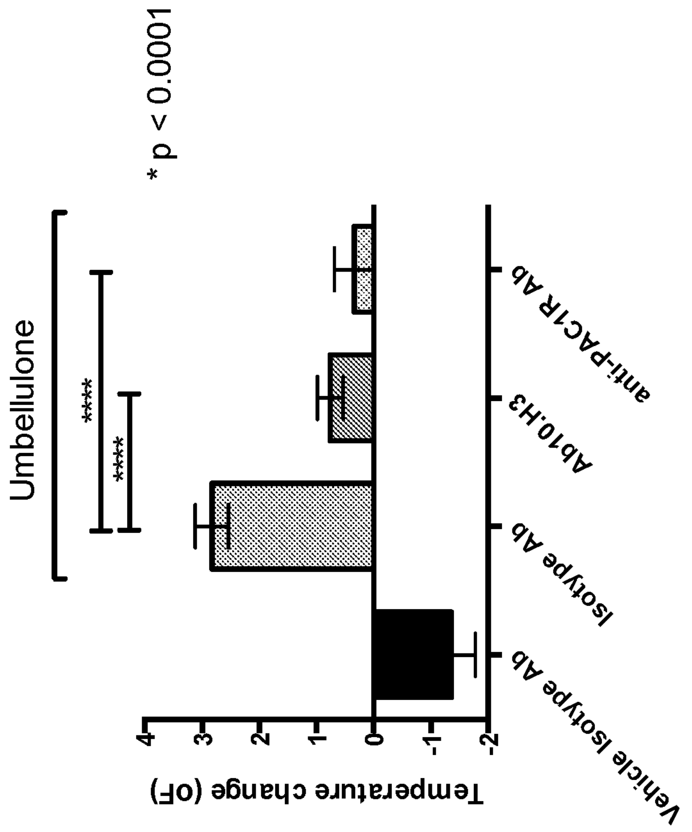
FIGS. 35A-35B provide representative data showing the in vivo effect of the administration of an anti-PACAP antibody Ab10.H3, an isotype antibody, or a proprietary anti-PAC1-R antibody, on the change in nose temperature obtained following the protocol in Example 13 infra. The measurements were plotted for individual animals in each group in FIG. 35A, and the average measurement for animals in each group was plotted in FIG. 35B.
Figure 35A:
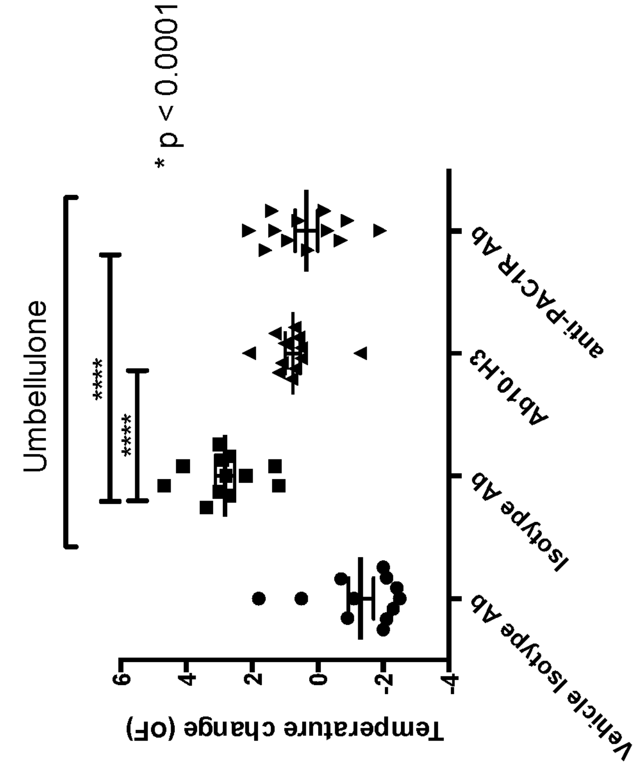

Anti-PACAP antibody Ab10.H3 and a proprietary anti-PAC1R antibody demonstrated a statistically significant decrease in the tear production that resulted from intranasal administration of Umbellulone as compared to animals treated with the isotype-matched control antibody (FIGS. 34A-34B). Additionally, animals treated with Ab10.H3 and anti-PAC1R antibody that were administered with Umbellulone demonstrated a statistically significant lower skin temperature on the nose as compared to animals treated with the isotype-matched control antibody and that were administered with Umbellulone (FIGS. 35A-35B). These results suggested that the anti-PACAP antibody Ab10.H3 or a proprietary anti-PAC1R antibody could successfully decrease the trigeminal parasympathetic reflex as measured by lacrimation and nose temperature upon intranasal administration of Umbellulone.

Example 14: Binding Affinities of Anti-PACAP Antibodies Ab21.H2, Ab21.H3, and Ab21.H4

Binding affinities of monoclonal antibodies for human PACAP were estimated using SPR on the PROTEON™ XPR36 (Bio-Rad, Hercules, CA). Antibody was immobilized to the surface of general amine coupling ("GLC" or "GLM") Chips (Bio-Rad, Hercules, CA). A dilution series of human PACAP38 (SEQ ID NO: 1241) prepared in 1×PBST Buffer (4.3 mM Na Phosphate, 1.4 mM K Phosphate, 135 mM NaCl, 2.7 mM KCl 0.05% Polysorbate-20) purchased from Teknova (Cat #P1192, Teknova, Hollister, CA) and supplemented with 0.25 M arginine (from J. T. BAKER®), 0.2 mg/ml BSA (Jackson Immuno Research Labs, West Grove, PA), and 0.005% sodium azide (VWR International, Radnor, PA) with the pH adjusted to 6.8-7.45 was used to query the antibodies. Antigen (ranging from 1.23 nM to 100 nM) was typically run sequentially with association times of 2-4 minutes and dissociation times of 3-120 minutes grouped with the PROTEON™ Manager Software (v3.1.0.6 (Bio-Rad, Hercules, CA)) and fitted using a 1:1 Langmuir binding model. Surfaces were regenerated between analyte queries using 0.85% Phosphoric Acid, 0.5% SDS, and 0.1N NaOH. A single $K_D$ was calculated for each antibody with association times limited near the rate of diffusion ($1.0\times10^6$) and dissociation times limited to $1.5\times10^{-5}$ where no discernible dissociation was observed.

The same procedure was used to determine binding affinities of antibodies for human VIP (SEQ ID NO: 1243) and PACAP27 (SEQ ID NO: 1242) though peptide concentrations ranged from 1.23 nM to 1000 nM with association times of 240 seconds and dissociation times of 3-120 minutes.

The measured antibody affinities for PACAP38 are listed in Table 11.

TABLE 11

Antibody affinity constants for PACAP38

| Antibody | ka (1/Ms) | kd (1/s) | $K_D$ (M) |
|---|---|---|---|
| Ab21.H2 | 5.86E+05 | 1.00E−05 | 1.71E−11 |
| Ab21.H3 | 4.49E+05 | 1.00E−05 | 2.23E−11 |
| Ab21.H4 | 4.20E+05 | 1.00E−05 | 2.38E−11 |

Examples of antibody affinity constants for VIP are listed in Table 12.

TABLE 12

Antibody affinity constants for VIP

| Antibody | ka (1/Ms) | kd (1/s) | $K_D$ (M) |
|---|---|---|---|
| Ab21.H2 | 4.88E+04 | 1.10E−02 | 2.25E−07 |
| Ab21.H3 | 5.87E+04 | 2.49E−02 | 4.24E−07 |
| Ab21.H4 | 5.53E+04 | 2.89E−02 | 5.23E−07 |

Examples of antibody affinity constants for PACAP27 are listed in Table 13.

TABLE 13

| Antibody affinity constants for PACAP27 | | | |
|---|---|---|---|
| Antibody | ka (1/Ms) | kd (1/s) | $K_D$ (M) |
| Ab21.H2 | 4.30E+05 | 1.00E−05 | 2.33E−11 |
| Ab21.H3 | 3.22E+05 | 1.00E−05 | 3.11E−11 |
| Ab21.H4 | 2.85E+05 | 1.00E−05 | 3.51E−11 |

Having fully described and enabled the invention, the invention is further described by the claims that follow.

What is claimed is:

1. An isolated nucleic acid or nucleic acids which encode an anti-pituitary adenylate cyclase-activating peptide (anti-PACAP) antibody or antigen binding fragment wherein the encoded antibody or antigen binding fragment comprises (i) a variable heavy chain comprising a CDR1 consisting of SEQ ID NO: 1284; a CDR2 consisting of SEQ ID NO: 1286; and a CDR3 consisting of SEQ ID NO: 1288; and (ii) a variable light chain comprising a CDR1 consisting of SEQ ID NO: 1304; a CDR2 consisting of SEQ ID NO: 1306; and a CDR3 consisting of SEQ ID NO: 1308.

2. An isolated nucleic acid or nucleic acids which encode an anti-pituitary adenylate cyclase-activating peptide (anti-PACAP) antibody or antigen binding fragment according to claim 1, which comprises a variable heavy chain comprising an amino acid sequence with at least 90% sequence identity to SEQ ID NO: 1282 and a variable light chain comprising an amino acid sequence with at least 90% sequence identity to SEQ ID NO: 1302.

3. An isolated nucleic acid or nucleic acids which encode an anti-pituitary adenylate cyclase-activating peptide (anti-PACAP) antibody or antigen binding fragment according to claim 1, which comprises a variable heavy chain comprising an amino acid sequence with at least 95% sequence identity to SEQ ID NO: 1282 and a variable light chain comprising an amino acid sequence with at least 95% sequence identity to SEQ ID NO: 1302.

4. An isolated nucleic acid or nucleic acids which encode an anti-pituitary adenylate cyclase-activating peptide (anti-PACAP) antibody or antigen binding fragment according to claim 1, which comprises a variable heavy chain comprising an amino acid sequence with at least 98% sequence identity to SEQ ID NO: 1282 and a variable light chain comprising an amino acid sequence with at least 98% sequence identity to SEQ ID NO: 1302.

5. An isolated nucleic acid or nucleic acids which encode an anti-pituitary adenylate cyclase-activating peptide (anti-PACAP) antibody or antigen binding fragment according to claim 1, which comprises a variable heavy chain comprising the amino acid of SEQ ID NO: 1282 and a variable light chain comprising the amino acid of SEQ ID NO: 1302.

6. An isolated nucleic acid or nucleic acids according to claim 1, wherein the encoded anti-PACAP antibody or antigen binding fragment:

a.) is chimeric, human or humanized;

b.) is selected from the group consisting of scFvs, nanobodies, Immunoglobulin Previously Presented Antigen Receptors ("IgNARs"), fragment antigen binding ("Fab") fragments, Fab' fragments, monovalent antigen binding fragments, and $F(ab')_2$ fragments;

c.) substantially or entirely lacks N-glycosylation and/or O-glycosylation;

d.) comprises a human constant domain;

e.) is an IgG1, IgG2, IgG3, or IgG4 antibody;

f.) comprises an Fc region that has been modified to alter at least one of effector function, half-life, proteolysis, or glycosylation, g.) comprises an Fc region that comprises the sequence of SEQ ID NO: 1244, 1245 or 1246; or h.) comprises a combination of one or more of a.) to g.).

7. An expression vector which comprises an isolated nucleic acid or nucleic acids according to claim 1.

8. An expression vector which comprises an isolated nucleic acid or nucleic acids according to claim 2.

9. An expression vector which comprises an isolated nucleic acid or nucleic acids according to claim 5.

10. An isolated recombinant cell which comprises an isolated nucleic acid or nucleic acid according to claim 1.

11. An isolated recombinant cell which comprises an isolated nucleic acid or nucleic acids according to claim 2.

12. An isolated recombinant cell which comprises an isolated nucleic acid or nucleic acids according to claim 5.

13. The isolated recombinant cell according to claim 10, which comprises a mammalian, bacterial, fungal, yeast, avian, amphibian, plant or insect cell.

14. The isolated recombinant cell according to claim 10, which comprises a Chinese Hamster Ovary (CHO) cell.

15. The isolated recombinant cell according to claim 10, which comprises a Chinese Hamster Ovary (CHO) cell selected from one of the following subclones or sub-cell lines: DP12 (CHO K1 dhfr-) cell line, NS0 cells, CHO-DXB11 (CHO-DUKX), CHO-pro3, CHO-DG44, CHO 1-15, CHO DP-12, Lec2, M1WT3, Lec8, or pgsA-745.

16. The isolated recombinant cell according to claim 13, which comprises a *Pichia pastoris, Pichia methanolica* or *Hansenula polymorpha* cell.

17. A method of expressing an anti-pituitary adenylate cyclase-activating peptide (anti-PACAP) antibody or antigen binding fragment thereof comprising culturing the isolated recombinant cell of claim 10 under conditions that provide for expression of the antibody or antigen binding fragment thereof encoded by said isolated nucleic acid or nucleic acids.

18. A method of expressing an anti-pituitary adenylate cyclase-activating peptide (anti-PACAP) antibody or antigen binding fragment thereof comprising culturing the isolated recombinant cell of claim 12 under conditions that provide for expression of the antibody or antigen binding fragment thereof encoded by said isolated nucleic acid or nucleic acids.

* * * * *

SEQUENCE LISTING

Sequence total quantity: 1600
SEQ ID NO: 1 moltype = length =
SEQUENCE: 1
000

SEQ ID NO: 2 moltype = length =
SEQUENCE: 2
000

SEQ ID NO: 3 moltype = length =
SEQUENCE: 3
000

SEQ ID NO: 4 moltype = length =
SEQUENCE: 4
000

SEQ ID NO: 5 moltype = length =
SEQUENCE: 5
000

SEQ ID NO: 6 moltype = length =
SEQUENCE: 6
000

SEQ ID NO: 7 moltype = length =
SEQUENCE: 7
000

SEQ ID NO: 8 moltype = length =
SEQUENCE: 8
000

SEQ ID NO: 9 moltype = length =
SEQUENCE: 9
000

SEQ ID NO: 10 moltype = length =
SEQUENCE: 10
000

SEQ ID NO: 11 moltype = length =
SEQUENCE: 11
000

SEQ ID NO: 12 moltype = length =
SEQUENCE: 12
000

SEQ ID NO: 13 moltype = length =
SEQUENCE: 13
000

SEQ ID NO: 14 moltype = length =
SEQUENCE: 14
000

SEQ ID NO: 15 moltype = length =
SEQUENCE: 15
000

SEQ ID NO: 16 moltype = length =
SEQUENCE: 16
000

SEQ ID NO: 17 moltype = length =
SEQUENCE: 17
000

SEQ ID NO: 18 moltype = length =
SEQUENCE: 18
000

SEQ ID NO: 19 moltype = length =
SEQUENCE: 19
000

SEQ ID NO: 20 moltype = length =
SEQUENCE: 20
000

SEQ ID NO: 21 moltype = length =
SEQUENCE: 21
000

SEQ ID NO: 22 moltype = length =
SEQUENCE: 22
000

SEQ ID NO: 23 moltype = length =
SEQUENCE: 23
000

SEQ ID NO: 24 moltype = length =
SEQUENCE: 24
000

SEQ ID NO: 25 moltype = length =
SEQUENCE: 25
000

SEQ ID NO: 26 moltype = length =
SEQUENCE: 26
000

SEQ ID NO: 27 moltype = length =
SEQUENCE: 27
000

SEQ ID NO: 28 moltype = length =
SEQUENCE: 28
000

SEQ ID NO: 29 moltype = length =
SEQUENCE: 29
000

SEQ ID NO: 30 moltype = length =
SEQUENCE: 30
000

SEQ ID NO: 31 moltype = length =
SEQUENCE: 31
000

SEQ ID NO: 32 moltype = length =
SEQUENCE: 32
000

SEQ ID NO: 33 moltype = length =
SEQUENCE: 33
000

SEQ ID NO: 34 moltype = length =
SEQUENCE: 34
000

SEQ ID NO: 35 moltype = length =
SEQUENCE: 35
000

SEQ ID NO: 36 moltype = length =
SEQUENCE: 36

000

SEQ ID NO: 37 moltype = length =
SEQUENCE: 37
000

SEQ ID NO: 38 moltype = length =
SEQUENCE: 38
000

SEQ ID NO: 39 moltype = length =
SEQUENCE: 39
000

SEQ ID NO: 40 moltype = length =
SEQUENCE: 40
000

SEQ ID NO: 41 moltype = length =
SEQUENCE: 41
000

SEQ ID NO: 42 moltype = length =
SEQUENCE: 42
000

SEQ ID NO: 43 moltype = length =
SEQUENCE: 43
000

SEQ ID NO: 44 moltype = length =
SEQUENCE: 44
000

SEQ ID NO: 45 moltype = length =
SEQUENCE: 45
000

SEQ ID NO: 46 moltype = length =
SEQUENCE: 46
000

SEQ ID NO: 47 moltype = length =
SEQUENCE: 47
000

SEQ ID NO: 48 moltype = length =
SEQUENCE: 48
000

SEQ ID NO: 49 moltype = length =
SEQUENCE: 49
000

SEQ ID NO: 50 moltype = length =
SEQUENCE: 50
000

SEQ ID NO: 51 moltype = length =
SEQUENCE: 51
000

SEQ ID NO: 52 moltype = length =
SEQUENCE: 52
000

SEQ ID NO: 53 moltype = length =
SEQUENCE: 53
000

SEQ ID NO: 54 moltype = length =
SEQUENCE: 54
000

SEQ ID NO: 55 moltype = length =
SEQUENCE: 55
000

SEQ ID NO: 56 moltype = length =

SEQUENCE: 56
000

SEQ ID NO: 57 moltype = length =
SEQUENCE: 57
000

SEQ ID NO: 58 moltype = length =
SEQUENCE: 58
000

SEQ ID NO: 59 moltype = length =
SEQUENCE: 59
000

SEQ ID NO: 60 moltype = length =
SEQUENCE: 60
000

SEQ ID NO: 61 moltype = length =
SEQUENCE: 61
000

SEQ ID NO: 62 moltype = length =
SEQUENCE: 62
000

SEQ ID NO: 63 moltype = length =
SEQUENCE: 63
000

SEQ ID NO: 64 moltype = length =
SEQUENCE: 64
000

SEQ ID NO: 65 moltype = length =
SEQUENCE: 65
000

SEQ ID NO: 66 moltype = length =
SEQUENCE: 66
000

SEQ ID NO: 67 moltype = length =
SEQUENCE: 67
000

SEQ ID NO: 68 moltype = length =
SEQUENCE: 68
000

SEQ ID NO: 69 moltype = length =
SEQUENCE: 69
000

SEQ ID NO: 70 moltype = length =
SEQUENCE: 70
000

SEQ ID NO: 71 moltype = length =
SEQUENCE: 71
000

SEQ ID NO: 72 moltype = length =
SEQUENCE: 72
000

SEQ ID NO: 73 moltype = length =
SEQUENCE: 73
000

SEQ ID NO: 74 moltype = length =
SEQUENCE: 74
000

SEQ ID NO: 75 moltype = length =
SEQUENCE: 75
000

SEQ ID NO: 76 moltype = length =
SEQUENCE: 76
000

SEQ ID NO: 77 moltype = length =
SEQUENCE: 77
000

SEQ ID NO: 78 moltype = length =
SEQUENCE: 78
000

SEQ ID NO: 79 moltype = length =
SEQUENCE: 79
000

SEQ ID NO: 80 moltype = length =
SEQUENCE: 80
000

SEQ ID NO: 81 moltype = length =
SEQUENCE: 81
000

SEQ ID NO: 82 moltype = length =
SEQUENCE: 82
000

SEQ ID NO: 83 moltype = length =
SEQUENCE: 83
000

SEQ ID NO: 84 moltype = length =
SEQUENCE: 84
000

SEQ ID NO: 85 moltype = length =
SEQUENCE: 85
000

SEQ ID NO: 86 moltype = length =
SEQUENCE: 86
000

SEQ ID NO: 87 moltype = length =
SEQUENCE: 87
000

SEQ ID NO: 88 moltype = length =
SEQUENCE: 88
000

SEQ ID NO: 89 moltype = length =
SEQUENCE: 89
000

SEQ ID NO: 90 moltype = length =
SEQUENCE: 90
000

SEQ ID NO: 91 moltype = length =
SEQUENCE: 91
000

SEQ ID NO: 92 moltype = length =
SEQUENCE: 92
000

SEQ ID NO: 93 moltype = length =
SEQUENCE: 93
000

SEQ ID NO: 94 moltype = length =
SEQUENCE: 94
000

SEQ ID NO: 95 moltype = length =
SEQUENCE: 95
000

SEQ ID NO: 96 moltype = length =
SEQUENCE: 96
000

SEQ ID NO: 97 moltype = length =
SEQUENCE: 97
000

SEQ ID NO: 98 moltype = length =
SEQUENCE: 98
000

SEQ ID NO: 99 moltype = length =
SEQUENCE: 99
000

SEQ ID NO: 100 moltype = length =
SEQUENCE: 100
000

SEQ ID NO: 101 moltype = length =
SEQUENCE: 101
000

SEQ ID NO: 102 moltype = length =
SEQUENCE: 102
000

SEQ ID NO: 103 moltype = length =
SEQUENCE: 103
000

SEQ ID NO: 104 moltype = length =
SEQUENCE: 104
000

SEQ ID NO: 105 moltype = length =
SEQUENCE: 105
000

SEQ ID NO: 106 moltype = length =
SEQUENCE: 106
000

SEQ ID NO: 107 moltype = length =
SEQUENCE: 107
000

SEQ ID NO: 108 moltype = length =
SEQUENCE: 108
000

SEQ ID NO: 109 moltype = length =
SEQUENCE: 109
000

SEQ ID NO: 110 moltype = length =
SEQUENCE: 110
000

SEQ ID NO: 111 moltype = length =
SEQUENCE: 111
000

SEQ ID NO: 112 moltype = length =
SEQUENCE: 112
000

SEQ ID NO: 113 moltype = length =
SEQUENCE: 113
000

SEQ ID NO: 114 moltype = length =
SEQUENCE: 114
000

SEQ ID NO: 115 moltype = length =
SEQUENCE: 115

000

SEQ ID NO: 116 moltype = length =
SEQUENCE: 116
000

SEQ ID NO: 117 moltype = length =
SEQUENCE: 117
000

SEQ ID NO: 118 moltype = length =
SEQUENCE: 118
000

SEQ ID NO: 119 moltype = length =
SEQUENCE: 119
000

SEQ ID NO: 120 moltype = length =
SEQUENCE: 120
000

SEQ ID NO: 121 moltype = length =
SEQUENCE: 121
000

SEQ ID NO: 122 moltype = length =
SEQUENCE: 122
000

SEQ ID NO: 123 moltype = length =
SEQUENCE: 123
000

SEQ ID NO: 124 moltype = length =
SEQUENCE: 124
000

SEQ ID NO: 125 moltype = length =
SEQUENCE: 125
000

SEQ ID NO: 126 moltype = length =
SEQUENCE: 126
000

SEQ ID NO: 127 moltype = length =
SEQUENCE: 127
000

SEQ ID NO: 128 moltype = length =
SEQUENCE: 128
000

SEQ ID NO: 129 moltype = length =
SEQUENCE: 129
000

SEQ ID NO: 130 moltype = length =
SEQUENCE: 130
000

SEQ ID NO: 131 moltype = length =
SEQUENCE: 131
000

SEQ ID NO: 132 moltype = length =
SEQUENCE: 132
000

SEQ ID NO: 133 moltype = length =
SEQUENCE: 133
000

SEQ ID NO: 134 moltype = length =
SEQUENCE: 134
000

SEQ ID NO: 135 moltype = length =

SEQUENCE: 135
000

SEQ ID NO: 136 moltype = length =
SEQUENCE: 136
000

SEQ ID NO: 137 moltype = length =
SEQUENCE: 137
000

SEQ ID NO: 138 moltype = length =
SEQUENCE: 138
000

SEQ ID NO: 139 moltype = length =
SEQUENCE: 139
000

SEQ ID NO: 140 moltype = length =
SEQUENCE: 140
000

SEQ ID NO: 141 moltype = length =
SEQUENCE: 141
000

SEQ ID NO: 142 moltype = length =
SEQUENCE: 142
000

SEQ ID NO: 143 moltype = length =
SEQUENCE: 143
000

SEQ ID NO: 144 moltype = length =
SEQUENCE: 144
000

SEQ ID NO: 145 moltype = length =
SEQUENCE: 145
000

SEQ ID NO: 146 moltype = length =
SEQUENCE: 146
000

SEQ ID NO: 147 moltype = length =
SEQUENCE: 147
000

SEQ ID NO: 148 moltype = length =
SEQUENCE: 148
000

SEQ ID NO: 149 moltype = length =
SEQUENCE: 149
000

SEQ ID NO: 150 moltype = length =
SEQUENCE: 150
000

SEQ ID NO: 151 moltype = length =
SEQUENCE: 151
000

SEQ ID NO: 152 moltype = length =
SEQUENCE: 152
000

SEQ ID NO: 153 moltype = length =
SEQUENCE: 153
000

SEQ ID NO: 154 moltype = length =
SEQUENCE: 154
000

SEQ ID NO: 155 moltype = length =
SEQUENCE: 155
000

SEQ ID NO: 156 moltype = length =
SEQUENCE: 156
000

SEQ ID NO: 157 moltype = length =
SEQUENCE: 157
000

SEQ ID NO: 158 moltype = length =
SEQUENCE: 158
000

SEQ ID NO: 159 moltype = length =
SEQUENCE: 159
000

SEQ ID NO: 160 moltype = length =
SEQUENCE: 160
000

SEQ ID NO: 161 moltype = length =
SEQUENCE: 161
000

SEQ ID NO: 162 moltype = length =
SEQUENCE: 162
000

SEQ ID NO: 163 moltype = length =
SEQUENCE: 163
000

SEQ ID NO: 164 moltype = length =
SEQUENCE: 164
000

SEQ ID NO: 165 moltype = length =
SEQUENCE: 165
000

SEQ ID NO: 166 moltype = length =
SEQUENCE: 166
000

SEQ ID NO: 167 moltype = length =
SEQUENCE: 167
000

SEQ ID NO: 168 moltype = length =
SEQUENCE: 168
000

SEQ ID NO: 169 moltype = length =
SEQUENCE: 169
000

SEQ ID NO: 170 moltype = length =
SEQUENCE: 170
000

SEQ ID NO: 171 moltype = length =
SEQUENCE: 171
000

SEQ ID NO: 172 moltype = length =
SEQUENCE: 172
000

SEQ ID NO: 173 moltype = length =
SEQUENCE: 173
000

SEQ ID NO: 174 moltype = length =
SEQUENCE: 174
000

SEQ ID NO: 175 moltype = length =
SEQUENCE: 175
000

SEQ ID NO: 176 moltype = length =
SEQUENCE: 176
000

SEQ ID NO: 177 moltype = length =
SEQUENCE: 177
000

SEQ ID NO: 178 moltype = length =
SEQUENCE: 178
000

SEQ ID NO: 179 moltype = length =
SEQUENCE: 179
000

SEQ ID NO: 180 moltype = length =
SEQUENCE: 180
000

SEQ ID NO: 181 moltype = length =
SEQUENCE: 181
000

SEQ ID NO: 182 moltype = length =
SEQUENCE: 182
000

SEQ ID NO: 183 moltype = length =
SEQUENCE: 183
000

SEQ ID NO: 184 moltype = length =
SEQUENCE: 184
000

SEQ ID NO: 185 moltype = length =
SEQUENCE: 185
000

SEQ ID NO: 186 moltype = length =
SEQUENCE: 186
000

SEQ ID NO: 187 moltype = length =
SEQUENCE: 187
000

SEQ ID NO: 188 moltype = length =
SEQUENCE: 188
000

SEQ ID NO: 189 moltype = length =
SEQUENCE: 189
000

SEQ ID NO: 190 moltype = length =
SEQUENCE: 190
000

SEQ ID NO: 191 moltype = length =
SEQUENCE: 191
000

SEQ ID NO: 192 moltype = length =
SEQUENCE: 192
000

SEQ ID NO: 193 moltype = length =
SEQUENCE: 193
000

SEQ ID NO: 194 moltype = length =
SEQUENCE: 194

000

SEQ ID NO: 195 moltype = length =
SEQUENCE: 195
000

SEQ ID NO: 196 moltype = length =
SEQUENCE: 196
000

SEQ ID NO: 197 moltype = length =
SEQUENCE: 197
000

SEQ ID NO: 198 moltype = length =
SEQUENCE: 198
000

SEQ ID NO: 199 moltype = length =
SEQUENCE: 199
000

SEQ ID NO: 200 moltype = length =
SEQUENCE: 200
000

SEQ ID NO: 201 moltype = length =
SEQUENCE: 201
000

SEQ ID NO: 202 moltype = length =
SEQUENCE: 202
000

SEQ ID NO: 203 moltype = length =
SEQUENCE: 203
000

SEQ ID NO: 204 moltype = length =
SEQUENCE: 204
000

SEQ ID NO: 205 moltype = length =
SEQUENCE: 205
000

SEQ ID NO: 206 moltype = length =
SEQUENCE: 206
000

SEQ ID NO: 207 moltype = length =
SEQUENCE: 207
000

SEQ ID NO: 208 moltype = length =
SEQUENCE: 208
000

SEQ ID NO: 209 moltype = length =
SEQUENCE: 209
000

SEQ ID NO: 210 moltype = length =
SEQUENCE: 210
000

SEQ ID NO: 211 moltype = length =
SEQUENCE: 211
000

SEQ ID NO: 212 moltype = length =
SEQUENCE: 212
000

SEQ ID NO: 213 moltype = length =
SEQUENCE: 213
000

SEQ ID NO: 214 moltype = length =

```
SEQUENCE: 214
000

SEQ ID NO: 215        moltype =   length =
SEQUENCE: 215
000

SEQ ID NO: 216        moltype =   length =
SEQUENCE: 216
000

SEQ ID NO: 217        moltype =   length =
SEQUENCE: 217
000

SEQ ID NO: 218        moltype =   length =
SEQUENCE: 218
000

SEQ ID NO: 219        moltype =   length =
SEQUENCE: 219
000

SEQ ID NO: 220        moltype =   length =
SEQUENCE: 220
000

SEQ ID NO: 221        moltype =   length =
SEQUENCE: 221
000

SEQ ID NO: 222        moltype =   length =
SEQUENCE: 222
000

SEQ ID NO: 223        moltype =   length =
SEQUENCE: 223
000

SEQ ID NO: 224        moltype =   length =
SEQUENCE: 224
000

SEQ ID NO: 225        moltype =   length =
SEQUENCE: 225
000

SEQ ID NO: 226        moltype =   length =
SEQUENCE: 226
000

SEQ ID NO: 227        moltype =   length =
SEQUENCE: 227
000

SEQ ID NO: 228        moltype =   length =
SEQUENCE: 228
000

SEQ ID NO: 229        moltype =   length =
SEQUENCE: 229
000

SEQ ID NO: 230        moltype =   length =
SEQUENCE: 230
000

SEQ ID NO: 231        moltype =   length =
SEQUENCE: 231
000

SEQ ID NO: 232        moltype =   length =
SEQUENCE: 232
000

SEQ ID NO: 233        moltype =   length =
SEQUENCE: 233
000
```

SEQ ID NO: 234 moltype = length =
SEQUENCE: 234
000

SEQ ID NO: 235 moltype = length =
SEQUENCE: 235
000

SEQ ID NO: 236 moltype = length =
SEQUENCE: 236
000

SEQ ID NO: 237 moltype = length =
SEQUENCE: 237
000

SEQ ID NO: 238 moltype = length =
SEQUENCE: 238
000

SEQ ID NO: 239 moltype = length =
SEQUENCE: 239
000

SEQ ID NO: 240 moltype = length =
SEQUENCE: 240
000

SEQ ID NO: 241 moltype = length =
SEQUENCE: 241
000

SEQ ID NO: 242 moltype = length =
SEQUENCE: 242
000

SEQ ID NO: 243 moltype = length =
SEQUENCE: 243
000

SEQ ID NO: 244 moltype = length =
SEQUENCE: 244
000

SEQ ID NO: 245 moltype = length =
SEQUENCE: 245
000

SEQ ID NO: 246 moltype = length =
SEQUENCE: 246
000

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252
000

SEQ ID NO: 253 moltype = length =
SEQUENCE: 253
000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266
000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =
SEQUENCE: 272
000

SEQ ID NO: 273 moltype = length =
SEQUENCE: 273

000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =
SEQUENCE: 286
000

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

SEQ ID NO: 293 moltype = length =

SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

SEQ ID NO: 298 moltype = length =
SEQUENCE: 298
000

SEQ ID NO: 299 moltype = length =
SEQUENCE: 299
000

SEQ ID NO: 300 moltype = length =
SEQUENCE: 300
000

SEQ ID NO: 301 moltype = length =
SEQUENCE: 301
000

SEQ ID NO: 302 moltype = length =
SEQUENCE: 302
000

SEQ ID NO: 303 moltype = length =
SEQUENCE: 303
000

SEQ ID NO: 304 moltype = length =
SEQUENCE: 304
000

SEQ ID NO: 305 moltype = length =
SEQUENCE: 305
000

SEQ ID NO: 306 moltype = length =
SEQUENCE: 306
000

SEQ ID NO: 307 moltype = length =
SEQUENCE: 307
000

SEQ ID NO: 308 moltype = length =
SEQUENCE: 308
000

SEQ ID NO: 309 moltype = length =
SEQUENCE: 309
000

SEQ ID NO: 310 moltype = length =
SEQUENCE: 310
000

SEQ ID NO: 311 moltype = length =
SEQUENCE: 311
000

SEQ ID NO: 312 moltype = length =
SEQUENCE: 312
000

SEQ ID NO: 313 moltype = length =
SEQUENCE: 313
000

SEQ ID NO: 314 moltype = length =
SEQUENCE: 314
000

SEQ ID NO: 315 moltype = length =
SEQUENCE: 315
000

SEQ ID NO: 316 moltype = length =
SEQUENCE: 316
000

SEQ ID NO: 317 moltype = length =
SEQUENCE: 317
000

SEQ ID NO: 318 moltype = length =
SEQUENCE: 318
000

SEQ ID NO: 319 moltype = length =
SEQUENCE: 319
000

SEQ ID NO: 320 moltype = length =
SEQUENCE: 320
000

SEQ ID NO: 321 moltype = length =
SEQUENCE: 321
000

SEQ ID NO: 322 moltype = length =
SEQUENCE: 322
000

SEQ ID NO: 323 moltype = length =
SEQUENCE: 323
000

SEQ ID NO: 324 moltype = length =
SEQUENCE: 324
000

SEQ ID NO: 325 moltype = length =
SEQUENCE: 325
000

SEQ ID NO: 326 moltype = length =
SEQUENCE: 326
000

SEQ ID NO: 327 moltype = length =
SEQUENCE: 327
000

SEQ ID NO: 328 moltype = length =
SEQUENCE: 328
000

SEQ ID NO: 329 moltype = length =
SEQUENCE: 329
000

SEQ ID NO: 330 moltype = length =
SEQUENCE: 330
000

SEQ ID NO: 331 moltype = length =
SEQUENCE: 331
000

SEQ ID NO: 332 moltype = length =
SEQUENCE: 332
000

SEQ ID NO: 333 moltype = length =
SEQUENCE: 333
000

SEQ ID NO: 334 moltype = length =
SEQUENCE: 334
000

SEQ ID NO: 335 moltype = length =
SEQUENCE: 335
000

SEQ ID NO: 336 moltype = length =
SEQUENCE: 336
000

SEQ ID NO: 337 moltype = length =
SEQUENCE: 337
000

SEQ ID NO: 338 moltype = length =
SEQUENCE: 338
000

SEQ ID NO: 339 moltype = length =
SEQUENCE: 339
000

SEQ ID NO: 340 moltype = length =
SEQUENCE: 340
000

SEQ ID NO: 341 moltype = length =
SEQUENCE: 341
000

SEQ ID NO: 342 moltype = length =
SEQUENCE: 342
000

SEQ ID NO: 343 moltype = length =
SEQUENCE: 343
000

SEQ ID NO: 344 moltype = length =
SEQUENCE: 344
000

SEQ ID NO: 345 moltype = length =
SEQUENCE: 345
000

SEQ ID NO: 346 moltype = length =
SEQUENCE: 346
000

SEQ ID NO: 347 moltype = length =
SEQUENCE: 347
000

SEQ ID NO: 348 moltype = length =
SEQUENCE: 348
000

SEQ ID NO: 349 moltype = length =
SEQUENCE: 349
000

SEQ ID NO: 350 moltype = length =
SEQUENCE: 350
000

SEQ ID NO: 351 moltype = length =
SEQUENCE: 351
000

SEQ ID NO: 352 moltype = length =
SEQUENCE: 352

000

SEQ ID NO: 353 moltype = length =
SEQUENCE: 353
000

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =
SEQUENCE: 365
000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

SEQ ID NO: 371 moltype = length =
SEQUENCE: 371
000

SEQ ID NO: 372 moltype = length =

SEQUENCE: 372
000

SEQ ID NO: 373 moltype = length =
SEQUENCE: 373
000

SEQ ID NO: 374 moltype = length =
SEQUENCE: 374
000

SEQ ID NO: 375 moltype = length =
SEQUENCE: 375
000

SEQ ID NO: 376 moltype = length =
SEQUENCE: 376
000

SEQ ID NO: 377 moltype = length =
SEQUENCE: 377
000

SEQ ID NO: 378 moltype = length =
SEQUENCE: 378
000

SEQ ID NO: 379 moltype = length =
SEQUENCE: 379
000

SEQ ID NO: 380 moltype = length =
SEQUENCE: 380
000

SEQ ID NO: 381 moltype = length =
SEQUENCE: 381
000

SEQ ID NO: 382 moltype = length =
SEQUENCE: 382
000

SEQ ID NO: 383 moltype = length =
SEQUENCE: 383
000

SEQ ID NO: 384 moltype = length =
SEQUENCE: 384
000

SEQ ID NO: 385 moltype = length =
SEQUENCE: 385
000

SEQ ID NO: 386 moltype = length =
SEQUENCE: 386
000

SEQ ID NO: 387 moltype = length =
SEQUENCE: 387
000

SEQ ID NO: 388 moltype = length =
SEQUENCE: 388
000

SEQ ID NO: 389 moltype = length =
SEQUENCE: 389
000

SEQ ID NO: 390 moltype = length =
SEQUENCE: 390
000

SEQ ID NO: 391 moltype = length =
SEQUENCE: 391
000

```
SEQ ID NO: 392         moltype =   length =
SEQUENCE: 392
000

SEQ ID NO: 393         moltype =   length =
SEQUENCE: 393
000

SEQ ID NO: 394         moltype =   length =
SEQUENCE: 394
000

SEQ ID NO: 395         moltype =   length =
SEQUENCE: 395
000

SEQ ID NO: 396         moltype =   length =
SEQUENCE: 396
000

SEQ ID NO: 397         moltype =   length =
SEQUENCE: 397
000

SEQ ID NO: 398         moltype =   length =
SEQUENCE: 398
000

SEQ ID NO: 399         moltype =   length =
SEQUENCE: 399
000

SEQ ID NO: 400         moltype =   length =
SEQUENCE: 400
000

SEQ ID NO: 401         moltype = AA  length = 439
FEATURE                Location/Qualifiers
REGION                 1..439
                       note = Humanized antibody sequence
source                 1..439
                       mol_type = protein
                       organism = synthetic construct
SEQUENCE: 401
QSVEESGGRL VTPGTPLTLT CTVSGIDLNS YYMTWVRQAP GKGLEWIGFI DAGGDAYYAS  60
WAKGRFTISK TSTTVDLKIT SPTTEDTATY FCARDLDLWG QGTLVTVSSA STKGPSVFPL  120
APSSKSTSGG TAALGCLVKD YFPEPVTVSW NSGALTSGVH TFPAVLQSSG LYSLSSVVTV  180
PSSSLGTQTY ICNVNHKPSN TKVDARVEPK SCDKTHTCPP CPAPELLGGP SVFLFPPKPK  240
DTLMISRTPE VTCVVVDVSH EDPEVKFNWY VDGVEVHNAK TKPREEQYAS TYRVVSVLTV  300
LHQDWLNGKE YKCKVSNKAL PAPIEKTISK AKGQPREPQV YTLPPSREEM TKNQVSLTCL  360
VKGFYPSDIA VEWESNGQPE NNYKTTPPVL DSDGSFFLYS KLTVDKSRWQ QGNVFSCSVM  420
HEALHNHYTQ KSLSLSPGK                                              439

SEQ ID NO: 402         moltype = AA  length = 109
FEATURE                Location/Qualifiers
REGION                 1..109
                       note = Humanized antibody sequence
source                 1..109
                       mol_type = protein
                       organism = synthetic construct
SEQUENCE: 402
QSVEESGGRL VTPGTPLTLT CTVSGIDLNS YYMTWVRQAP GKGLEWIGFI DAGGDAYYAS  60
WAKGRFTISK TSTTVDLKIT SPTTEDTATY FCARDLDLWG QGTLVTVSS             109

SEQ ID NO: 403         moltype = AA  length = 29
FEATURE                Location/Qualifiers
source                 1..29
                       mol_type = protein
                       organism = Oryctolagus cuniculus
SEQUENCE: 403
QSVEESGGRL VTPGTPLTLT CTVSGIDLN                                   29

SEQ ID NO: 404         moltype = AA  length = 5
FEATURE                Location/Qualifiers
source                 1..5
                       mol_type = protein
                       organism = Oryctolagus cuniculus
SEQUENCE: 404
SYYMT                                                             5
```

```
SEQ ID NO: 405          moltype = AA  length = 14
FEATURE                 Location/Qualifiers
source                  1..14
                        mol_type = protein
                        organism = Oryctolagus cuniculus
SEQUENCE: 405
WVRQAPGKGL EWIG                                                     14

SEQ ID NO: 406          moltype = AA  length = 16
FEATURE                 Location/Qualifiers
source                  1..16
                        mol_type = protein
                        organism = Oryctolagus cuniculus
SEQUENCE: 406
FIDAGGDAYY ASWAKG                                                   16

SEQ ID NO: 407          moltype = AA  length = 30
FEATURE                 Location/Qualifiers
source                  1..30
                        mol_type = protein
                        organism = Oryctolagus cuniculus
SEQUENCE: 407
RFTISKTSTT VDLKITSPTT EDTATYFCAR                                    30

SEQ ID NO: 408          moltype = AA  length = 4
FEATURE                 Location/Qualifiers
source                  1..4
                        mol_type = protein
                        organism = Oryctolagus cuniculus
SEQUENCE: 408
DLDL                                                                4

SEQ ID NO: 409          moltype = AA  length = 11
FEATURE                 Location/Qualifiers
REGION                  1..11
                        note = Humanized antibody sequence
source                  1..11
                        mol_type = protein
                        organism = synthetic construct
SEQUENCE: 409
WGQGTLVTVS S                                                        11

SEQ ID NO: 410          moltype = AA  length = 330
FEATURE                 Location/Qualifiers
REGION                  1..330
                        note = Humanized antibody sequence
source                  1..330
                        mol_type = protein
                        organism = synthetic construct
SEQUENCE: 410
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDARVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 411          moltype = DNA  length = 1317
FEATURE                 Location/Qualifiers
misc_feature            1..1317
                        note = Humanized antibody sequence
source                  1..1317
                        mol_type = other DNA
                        organism = synthetic construct
SEQUENCE: 411
cagtcggtgg aggagtccgg gggtcgcctg gtcacgcctg ggacacccct gacactcacc  60
tgcacagtct ctggaatcga cctcaatagc tactacatga cctgggtccg ccaggctcca  120
gggaaggggc tggaatggat cggattcatt gatgctggtg gtgacgcata ctacgcgagc  180
tgggcgaaag gccgattcac catctccaaa acctcgacca cggtggatct gaaaatcacc  240
agtccgacaa ccgaggacac ggccacctat ttctgtgcca gagatcttga cttgtggggc  300
cagggcaccc tggtcaccgt ctcgagcgcc tccaccaagg gcccatcggt cttccccctg  360
gcaccctcct ccaagagcac ctctgggggc acagcggccc tgggctgcct ggtcaaggac  420
tacttccccg aaccggtgac ggtgtcgtgg aactcaggcg ccctgaccag cggcgtgcac  480
accttcccgg ctgtcctaca gtcctcagga ctctactccc tcagcagcgt ggtgaccgtg  540
ccctccagca gcttgggcac ccagacctac atctgcaacg tgaatcacaa gcccagcaac  600
accaaggtgg acgcgagagt tgagcccaaa tcttgtgaca aaactcacac atgcccaccg  660
tgcccagcac ctgaactcct ggggggaccg tcagtcttcc tcttcccccc aaaacccaag  720
gacaccctca tgatctcccg gacccctgag gtcacatgcg tggtggtgga cgtgagccac  780
```

```
gaagaccctg aggtcaagtt caactggtac gtggacggcg tggaggtgca taatgccaag  840
acaaagccgc gggaggagca gtacgccagc acgtaccgtg tggtcagcgt cctcaccgtc  900
ctgcaccagg actggctgaa tggcaaggag tacaagtgca aggtctccaa caaagccctc  960
ccagccccca tcgagaaaac catctccaaa gccaaagggc agccccgaga accacaggtg  1020
tacaccctgc ccccatcccg ggaggagatg accaagaacc aggtcagcct gacctgcctg  1080
gtcaaaggct tctatcccag cgacatcgcc gtggagtggg agagcaatgg gcagccggag  1140
aacaactaca agaccacgcc tcccgtgctg gactccgacg gctccttctt cctctacagc  1200
aagctcaccg tggacaagag caggtggcag caggggaacg tcttctcatg ctccgtgatg  1260
catgaggctc tgcacaacca ctacacgcag aagagcctct ccctgtctcc gggtaaa     1317

SEQ ID NO: 412          moltype = DNA  length = 327
FEATURE                 Location/Qualifiers
misc_feature            1..327
                        note = Humanized antibody sequence
source                  1..327
                        mol_type = other DNA
                        organism = synthetic construct
SEQUENCE: 412
cagtcggtgg aggagtccgg gggtcgcctg gtcacgcctg ggacacccct gacactcacc  60
tgcacagtct ctggaatcga cctcaatagc tactacatga cctgggtccg ccaggctcca  120
gggaaggggc tggaatggat cggattcatt gatgctggtg gtgacgcata ctacgcgagc  180
tgggcgaaag gccgattcac catctccaaa acctcgacca cggtggatct gaaaatcacc  240
agtccgacaa ccgaggacac ggccacctat ttctgtgcca gagatcttga cttgtggggc  300
cagggcaccc tggtcaccgt ctcgagc                                      327

SEQ ID NO: 413          moltype = DNA  length = 87
FEATURE                 Location/Qualifiers
source                  1..87
                        mol_type = unassigned DNA
                        organism = Oryctolagus cuniculus
SEQUENCE: 413
cagtcggtgg aggagtccgg gggtcgcctg gtcacgcctg ggacacccct gacactcacc  60
tgcacagtct ctggaatcga cctcaat                                      87

SEQ ID NO: 414          moltype = DNA  length = 15
FEATURE                 Location/Qualifiers
source                  1..15
                        mol_type = unassigned DNA
                        organism = Oryctolagus cuniculus
SEQUENCE: 414
agctactaca tgacc                                                   15

SEQ ID NO: 415          moltype = DNA  length = 42
FEATURE                 Location/Qualifiers
source                  1..42
                        mol_type = unassigned DNA
                        organism = Oryctolagus cuniculus
SEQUENCE: 415
tgggtccgcc aggctccagg gaaggggctg gaatggatcg ga                     42

SEQ ID NO: 416          moltype = DNA  length = 48
FEATURE                 Location/Qualifiers
source                  1..48
                        mol_type = unassigned DNA
                        organism = Oryctolagus cuniculus
SEQUENCE: 416
ttcattgatg ctggtggtga cgcatactac gcgagctggg cgaaaggc               48

SEQ ID NO: 417          moltype = DNA  length = 90
FEATURE                 Location/Qualifiers
source                  1..90
                        mol_type = unassigned DNA
                        organism = Oryctolagus cuniculus
SEQUENCE: 417
cgattcacca tctccaaaac ctcgaccacg gtggatctga aaatcaccag tccgacaacc  60
gaggacacgg ccacctattt ctgtgccaga                                   90

SEQ ID NO: 418          moltype = DNA  length = 12
FEATURE                 Location/Qualifiers
source                  1..12
                        mol_type = unassigned DNA
                        organism = Oryctolagus cuniculus
SEQUENCE: 418
gatcttgact tg                                                      12

SEQ ID NO: 419          moltype = DNA  length = 33
FEATURE                 Location/Qualifiers
misc_feature            1..33
                        note = Humanized antibody sequence
```

```
source                  1..33
                        mol_type = other DNA
                        organism = synthetic construct
SEQUENCE: 419
tggggccagg gcaccctggt caccgtctcg agc                              33

SEQ ID NO: 420          moltype = DNA  length = 990
FEATURE                 Location/Qualifiers
misc_feature            1..990
                        note = Humanized antibody sequence
source                  1..990
                        mol_type = other DNA
                        organism = synthetic construct
SEQUENCE: 420
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacgcgag agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                  990

SEQ ID NO: 421          moltype = AA  length = 216
FEATURE                 Location/Qualifiers
REGION                  1..216
                        note = Humanized antibody sequence
source                  1..216
                        mol_type = protein
                        organism = synthetic construct
SEQUENCE: 421
AAVLTQTPSP VSAAVGGTVT INCQSSESVY GNYLAWFQQK PGQPPKLLIY EASKLESGVP  60
SRFSGSGSGT QFTLTISDLQ CDDAATYYCA GGDISEGVAF GGGTEVVVKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 422          moltype = AA  length = 110
FEATURE                 Location/Qualifiers
REGION                  1..110
                        note = Humanized antibody sequence
source                  1..110
                        mol_type = protein
                        organism = synthetic construct
SEQUENCE: 422
AAVLTQTPSP VSAAVGGTVT INCQSSESVY GNYLAWFQQK PGQPPKLLIY EASKLESGVP  60
SRFSGSGSGT QFTLTISDLQ CDDAATYYCA GGDISEGVAF GGGTEVVVKR            110

SEQ ID NO: 423          moltype = AA  length = 23
FEATURE                 Location/Qualifiers
source                  1..23
                        mol_type = protein
                        organism = Oryctolagus cuniculus
SEQUENCE: 423
AAVLTQTPSP VSAAVGGTVT INC                                         23

SEQ ID NO: 424          moltype = AA  length = 12
FEATURE                 Location/Qualifiers
source                  1..12
                        mol_type = protein
                        organism = Oryctolagus cuniculus
SEQUENCE: 424
QSSESVYGNY LA                                                     12

SEQ ID NO: 425          moltype = AA  length = 15
FEATURE                 Location/Qualifiers
source                  1..15
                        mol_type = protein
                        organism = Oryctolagus cuniculus
SEQUENCE: 425
WFQQKPGQPP KLLIY                                                  15
```

```
SEQ ID NO: 426         moltype = AA  length = 7
FEATURE                Location/Qualifiers
source                 1..7
                       mol_type = protein
                       organism = Oryctolagus cuniculus
SEQUENCE: 426
EASKLES                                                           7

SEQ ID NO: 427         moltype = AA  length = 32
FEATURE                Location/Qualifiers
source                 1..32
                       mol_type = protein
                       organism = Oryctolagus cuniculus
SEQUENCE: 427
GVPSRFSGSG SGTQFTLTIS DLQCDDAATY YC                               32

SEQ ID NO: 428         moltype = AA  length = 10
FEATURE                Location/Qualifiers
source                 1..10
                       mol_type = protein
                       organism = Oryctolagus cuniculus
SEQUENCE: 428
AGGDISEGVA                                                        10

SEQ ID NO: 429         moltype = AA  length = 11
FEATURE                Location/Qualifiers
REGION                 1..11
                       note = Humanized antibody sequence
source                 1..11
                       mol_type = protein
                       organism = synthetic construct
SEQUENCE: 429
FGGGTEVVVK R                                                      11

SEQ ID NO: 430         moltype = AA  length = 106
FEATURE                Location/Qualifiers
REGION                 1..106
                       note = Humanized antibody sequence
source                 1..106
                       mol_type = protein
                       organism = synthetic construct
SEQUENCE: 430
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 431         moltype = DNA  length = 648
FEATURE                Location/Qualifiers
misc_feature           1..648
                       note = Humanized antibody sequence
source                 1..648
                       mol_type = other DNA
                       organism = synthetic construct
SEQUENCE: 431
gccgccgtgc tgacccagac tccatctccc gtgtctgcag ctgtgggagg cacagtcacc  60
atcaattgcc agtccagtga gagtgtttac ggtaactact tagcctggtt tcagcagaaa  120
ccagggcagc ctcccaagct cctgatctac gaagcatcca aactggaatc tggggtccca  180
tcgcggttca gcggcagtgg atctgggaca cagttcactc tcaccatcag cgacttgcag  240
tgtgacgatg ctgccactta ctactgtgca ggcggtgata ttagtgaagg tgttgctttc  300
ggcggaggga ccgaggtggt ggtcaaacgt acggtagcgg ccccatctgt cttcatcttc  360
ccgccatctg atgagcagtt gaaatctgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt              648

SEQ ID NO: 432         moltype = DNA  length = 330
FEATURE                Location/Qualifiers
misc_feature           1..330
                       note = Humanized antibody sequence
source                 1..330
                       mol_type = other DNA
                       organism = synthetic construct
SEQUENCE: 432
gccgccgtgc tgacccagac tccatctccc gtgtctgcag ctgtgggagg cacagtcacc  60
atcaattgcc agtccagtga gagtgtttac ggtaactact tagcctggtt tcagcagaaa  120
ccagggcagc ctcccaagct cctgatctac gaagcatcca aactggaatc tggggtccca  180
tcgcggttca gcggcagtgg atctgggaca cagttcactc tcaccatcag cgacttgcag  240
tgtgacgatg ctgccactta ctactgtgca ggcggtgata ttagtgaagg tgttgctttc  300
```

```
ggcggaggga ccgaggtggt ggtcaaacgt                                  330

SEQ ID NO: 433          moltype = DNA  length = 69
FEATURE                 Location/Qualifiers
source                  1..69
                        mol_type = unassigned DNA
                        organism = Oryctolagus cuniculus
SEQUENCE: 433
gccgccgtgc tgacccagac tccatctccc gtgtctgcag ctgtgggagg cacagtcacc  60
atcaattgc                                                          69

SEQ ID NO: 434          moltype = DNA  length = 36
FEATURE                 Location/Qualifiers
source                  1..36
                        mol_type = unassigned DNA
                        organism = Oryctolagus cuniculus
SEQUENCE: 434
cagtccagtg agagtgttta cggtaactac ttagcc                            36

SEQ ID NO: 435          moltype = DNA  length = 45
FEATURE                 Location/Qualifiers
source                  1..45
                        mol_type = unassigned DNA
                        organism = Oryctolagus cuniculus
SEQUENCE: 435
tggtttcagc agaaaccagg gcagcctccc aagctcctga tctac                  45

SEQ ID NO: 436          moltype = DNA  length = 21
FEATURE                 Location/Qualifiers
source                  1..21
                        mol_type = unassigned DNA
                        organism = Oryctolagus cuniculus
SEQUENCE: 436
gaagcatcca aactggaatc t                                            21

SEQ ID NO: 437          moltype = DNA  length = 96
FEATURE                 Location/Qualifiers
source                  1..96
                        mol_type = unassigned DNA
                        organism = Oryctolagus cuniculus
SEQUENCE: 437
ggggtcccat cgcggttcag cggcagtgga tctgggacac agttcactct caccatcagc  60
gacttgcagt gtgacgatgc tgccacttac tactgt                            96

SEQ ID NO: 438          moltype = DNA  length = 30
FEATURE                 Location/Qualifiers
source                  1..30
                        mol_type = unassigned DNA
                        organism = Oryctolagus cuniculus
SEQUENCE: 438
gcaggcggtg atattagtga aggtgttgct                                   30

SEQ ID NO: 439          moltype = DNA  length = 33
FEATURE                 Location/Qualifiers
misc_feature            1..33
                        note = Humanized antibody sequence
source                  1..33
                        mol_type = other DNA
                        organism = synthetic construct
SEQUENCE: 439
ttcggcggag ggaccgaggt ggtggtcaaa cgt                               33

SEQ ID NO: 440          moltype = DNA  length = 318
FEATURE                 Location/Qualifiers
misc_feature            1..318
                        note = Humanized antibody sequence
source                  1..318
                        mol_type = other DNA
                        organism = synthetic construct
SEQUENCE: 440
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318

SEQ ID NO: 441          moltype = AA  length = 439
FEATURE                 Location/Qualifiers
```

```
REGION                 1..439
                       note = Humanized antibody sequence
source                 1..439
                       mol_type = protein
                       organism = synthetic construct
SEQUENCE: 441
QSVEESGGRL VTPGTPLTLT CTVSGIDLSS YYMSWVRQAP GKGLEWIGFI DTDGSAYYAT  60
WAKGRFTISK TSTTVDLKIT SPTTEDTATY FCARDLDLWG PGTLVTVSSA STKGPSVFPL  120
APSSKSTSGG TAALGCLVKD YFPEPVTVSW NSGALTSGVH TFPAVLQSSG LYSLSSVVTV  180
PSSSLGTQTY ICNVNHKPSN TKVDKKVEPK SCDKTHTCPP CPAPELLGGP SVFLFPPKPK  240
DTLMISRTPE VTCVVVDVSH EDPEVKFNWY VDGVEVHNAK TKPREEQYAS TYRVVSVLTV  300
LHQDWLNGKE YKCKVSNKAL PAPIEKTISK AKGQPREPQV YTLPPSREEM TKNQVSLTCL  360
VKGFYPSDIA VEWESNGQPE NNYKTTPPVL DSDGSFFLYS KLTVDKSRWQ QGNVFSCSVM  420
HEALHNHYTQ KSLSLSPGK                                               439

SEQ ID NO: 442         moltype = AA  length = 109
FEATURE                Location/Qualifiers
REGION                 1..109
                       note = Humanized antibody sequence
source                 1..109
                       mol_type = protein
                       organism = synthetic construct
SEQUENCE: 442
QSVEESGGRL VTPGTPLTLT CTVSGIDLSS YYMSWVRQAP GKGLEWIGFI DTDGSAYYAT  60
WAKGRFTISK TSTTVDLKIT SPTTEDTATY FCARDLDLWG PGTLVTVSS              109

SEQ ID NO: 443         moltype = AA  length = 29
FEATURE                Location/Qualifiers
source                 1..29
                       mol_type = protein
                       organism = Oryctolagus cuniculus
SEQUENCE: 443
QSVEESGGRL VTPGTPLTLT CTVSGIDLS                                    29

SEQ ID NO: 444         moltype = AA  length = 5
FEATURE                Location/Qualifiers
source                 1..5
                       mol_type = protein
                       organism = Oryctolagus cuniculus
SEQUENCE: 444
SYYMS                                                              5

SEQ ID NO: 445         moltype = AA  length = 14
FEATURE                Location/Qualifiers
source                 1..14
                       mol_type = protein
                       organism = Oryctolagus cuniculus
SEQUENCE: 445
WVRQAPGKGL EWIG                                                    14

SEQ ID NO: 446         moltype = AA  length = 16
FEATURE                Location/Qualifiers
source                 1..16
                       mol_type = protein
                       organism = Oryctolagus cuniculus
SEQUENCE: 446
FIDTDGSAYY ATWAKG                                                  16

SEQ ID NO: 447         moltype = AA  length = 30
FEATURE                Location/Qualifiers
source                 1..30
                       mol_type = protein
                       organism = Oryctolagus cuniculus
SEQUENCE: 447
RFTISKTSTT VDLKITSPTT EDTATYFCAR                                   30

SEQ ID NO: 448         moltype = AA  length = 4
FEATURE                Location/Qualifiers
source                 1..4
                       mol_type = protein
                       organism = Oryctolagus cuniculus
SEQUENCE: 448
DLDL                                                               4

SEQ ID NO: 449         moltype = AA  length = 11
FEATURE                Location/Qualifiers
REGION                 1..11
                       note = Humanized antibody sequence
source                 1..11
```

```
                         mol_type = protein
                         organism = synthetic construct
SEQUENCE: 449
WGPGTLVTVS S                                                        11

SEQ ID NO: 450           moltype = AA  length = 330
FEATURE                  Location/Qualifiers
REGION                   1..330
                         note = Humanized antibody sequence
source                   1..330
                         mol_type = protein
                         organism = synthetic construct
SEQUENCE: 450
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 451           moltype = DNA  length = 1317
FEATURE                  Location/Qualifiers
misc_feature             1..1317
                         note = Humanized antibody sequence
source                   1..1317
                         mol_type = other DNA
                         organism = synthetic construct
SEQUENCE: 451
cagtcggtgg aggagtccgg gggtcgcctg gtcacgcctg ggacacccct gacactcacc  60
tgcacagtct ctggaatcga cctcagtagc tactacatga gctgggtccg ccaggctcca  120
gggaaggggc tggaatggat cggattcatt gatactgatg gtagcgcata ctacgcgacc  180
tgggcgaaag gccgattcac catctccaaa acctcgacca cggtggatct gaaaatcacc  240
agtccgacaa ccgaggacac ggccacctat ttctgtgcca gagatcttga cttgtggggc  300
ccgggcaccc tcgtcaccgt ctcgagcgcc tccaccaagg gcccatcggt cttccccctg  360
gcaccctcct ccaagagcac ctctgggggc acagcggccc tgggctgcct ggtcaaggac  420
tacttccccg aaccggtgac ggtgtcgtgg aactcaggcg ccctgaccag cggcgtgcac  480
accttcccgg ctgtcctaca gtcctcagga ctctactccc tcagcagcgt ggtgaccgtg  540
ccctccagca gcttgggcac ccagacctac atctgcaacg tgaatcacaa gcccagcaac  600
accaaggtgg acaagaaagt tgagcccaaa tcttgtgaca aaactcacac atgcccaccg  660
tgcccagcac ctgaactcct ggggggaccg tcagtcttcc tcttcccccc aaaacccaag  720
gacaccctca tgatctcccg gacccctgag gtcacatgcg tggtggtgga cgtgagccac  780
gaagaccctg aggtcaagtt caactggtac gtggacggcg tggaggtgca taatgccaag  840
acaaagccgc gggaggagca gtacgccagc acgtaccgtg tggtcagcgt cctcaccgtc  900
ctgcaccagg actggctgaa tggcaaggag tacaagtgca aggtctccaa caaagccctc  960
ccagccccca tcgagaaaac catctccaaa gccaaagggc agccccgaga accacaggtg  1020
tacaccctgc ccccatcccg ggaggagatg accaagaacc aggtcagcct gacctgcctg  1080
gtcaaaggct tctatcccag cgacatcgcc gtggagtggg agagcaatgg gcagccggag  1140
aacaactaca agaccacgcc tcccgtgctg gactccgacg gctccttctt cctctacagc  1200
aagctcaccg tggacaagag caggtggcag caggggaacg tcttctcatg ctccgtgatg  1260
catgaggctc tgcacaacca ctacacgcag aagagcctct ccctgtctcc gggtaaa     1317

SEQ ID NO: 452           moltype = DNA  length = 327
FEATURE                  Location/Qualifiers
misc_feature             1..327
                         note = Humanized antibody sequence
source                   1..327
                         mol_type = other DNA
                         organism = synthetic construct
SEQUENCE: 452
cagtcggtgg aggagtccgg gggtcgcctg gtcacgcctg ggacacccct gacactcacc  60
tgcacagtct ctggaatcga cctcagtagc tactacatga gctgggtccg ccaggctcca  120
gggaaggggc tggaatggat cggattcatt gatactgatg gtagcgcata ctacgcgacc  180
tgggcgaaag gccgattcac catctccaaa acctcgacca cggtggatct gaaaatcacc  240
agtccgacaa ccgaggacac ggccacctat ttctgtgcca gagatcttga cttgtggggc  300
ccgggcaccc tcgtcaccgt ctcgagc                                       327

SEQ ID NO: 453           moltype = DNA  length = 87
FEATURE                  Location/Qualifiers
source                   1..87
                         mol_type = unassigned DNA
                         organism = Oryctolagus cuniculus
SEQUENCE: 453
cagtcggtgg aggagtccgg gggtcgcctg gtcacgcctg ggacacccct gacactcacc  60
tgcacagtct ctggaatcga cctcagt                                       87

SEQ ID NO: 454           moltype = DNA  length = 15
FEATURE                  Location/Qualifiers
source                   1..15
                         mol_type = unassigned DNA
```

```
                        organism = Oryctolagus cuniculus
SEQUENCE: 454
agctactaca tgagc                                                15

SEQ ID NO: 455          moltype = DNA  length = 42
FEATURE                 Location/Qualifiers
source                  1..42
                        mol_type = unassigned DNA
                        organism = Oryctolagus cuniculus
SEQUENCE: 455
tgggtccgcc aggctccagg gaaggggctg gaatggatcg ga                  42

SEQ ID NO: 456          moltype = DNA  length = 48
FEATURE                 Location/Qualifiers
source                  1..48
                        mol_type = unassigned DNA
                        organism = Oryctolagus cuniculus
SEQUENCE: 456
ttcattgata ctgatggtag cgcatactac gcgacctggg cgaaaggc            48

SEQ ID NO: 457          moltype = DNA  length = 90
FEATURE                 Location/Qualifiers
source                  1..90
                        mol_type = unassigned DNA
                        organism = Oryctolagus cuniculus
SEQUENCE: 457
cgattcacca tctccaaaac ctcgaccacg gtggatctga aaatcaccag tccgacaacc  60
gaggacacgg ccacctattt ctgtgccaga                                90

SEQ ID NO: 458          moltype = DNA  length = 12
FEATURE                 Location/Qualifiers
source                  1..12
                        mol_type = unassigned DNA
                        organism = Oryctolagus cuniculus
SEQUENCE: 458
gatcttgact tg                                                   12

SEQ ID NO: 459          moltype = DNA  length = 33
FEATURE                 Location/Qualifiers
misc_feature            1..33
                        note = Humanized antibody sequence
source                  1..33
                        mol_type = other DNA
                        organism = synthetic construct
SEQUENCE: 459
tggggcccgg gcaccctcgt caccgtctcg agc                            33

SEQ ID NO: 460          moltype = DNA  length = 990
FEATURE                 Location/Qualifiers
misc_feature            1..990
                        note = Humanized antibody sequence
source                  1..990
                        mol_type = other DNA
                        organism = synthetic construct
SEQUENCE: 460
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                990

SEQ ID NO: 461          moltype = AA  length = 216
FEATURE                 Location/Qualifiers
REGION                  1..216
                        note = Humanized antibody sequence
source                  1..216
                        mol_type = protein
```

```
                         organism = synthetic construct
SEQUENCE: 461
AAVLTQTPSP VSAAVGGTVS ISCQSSESVY SNYLAWFQQK PGQPPKFLIY EASKLASGVP  60
SRFKGSGSGT QFTLTISDVQ CDDAGTYYCA GGYSSEGVAF GGGTEVVVKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 462           moltype = AA  length = 110
FEATURE                  Location/Qualifiers
REGION                   1..110
                         note = Humanized antibody sequence
source                   1..110
                         mol_type = protein
                         organism = synthetic construct
SEQUENCE: 462
AAVLTQTPSP VSAAVGGTVS ISCQSSESVY SNYLAWFQQK PGQPPKFLIY EASKLASGVP  60
SRFKGSGSGT QFTLTISDVQ CDDAGTYYCA GGYSSEGVAF GGGTEVVVKR            110

SEQ ID NO: 463           moltype = AA  length = 23
FEATURE                  Location/Qualifiers
source                   1..23
                         mol_type = protein
                         organism = Oryctolagus cuniculus
SEQUENCE: 463
AAVLTQTPSP VSAAVGGTVS ISC                                         23

SEQ ID NO: 464           moltype = AA  length = 12
FEATURE                  Location/Qualifiers
source                   1..12
                         mol_type = protein
                         organism = Oryctolagus cuniculus
SEQUENCE: 464
QSSESVYSNY LA                                                     12

SEQ ID NO: 465           moltype = AA  length = 15
FEATURE                  Location/Qualifiers
source                   1..15
                         mol_type = protein
                         organism = Oryctolagus cuniculus
SEQUENCE: 465
WFQQKPGQPP KFLIY                                                  15

SEQ ID NO: 466           moltype = AA  length = 7
FEATURE                  Location/Qualifiers
source                   1..7
                         mol_type = protein
                         organism = Oryctolagus cuniculus
SEQUENCE: 466
EASKLAS                                                           7

SEQ ID NO: 467           moltype = AA  length = 32
FEATURE                  Location/Qualifiers
source                   1..32
                         mol_type = protein
                         organism = Oryctolagus cuniculus
SEQUENCE: 467
GVPSRFKGSG SGTQFTLTIS DVQCDDAGTY YC                               32

SEQ ID NO: 468           moltype = AA  length = 10
FEATURE                  Location/Qualifiers
source                   1..10
                         mol_type = protein
                         organism = Oryctolagus cuniculus
SEQUENCE: 468
AGGYSSEGVA                                                        10

SEQ ID NO: 469           moltype = AA  length = 11
FEATURE                  Location/Qualifiers
REGION                   1..11
                         note = Humanized antibody sequence
source                   1..11
                         mol_type = protein
                         organism = synthetic construct
SEQUENCE: 469
FGGGTEVVVK R                                                      11

SEQ ID NO: 470           moltype = AA  length = 106
FEATURE                  Location/Qualifiers
REGION                   1..106
```

```
                        note = Humanized antibody sequence
source                  1..106
                        mol_type = protein
                        organism = synthetic construct
SEQUENCE: 470
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 471          moltype = DNA  length = 648
FEATURE                 Location/Qualifiers
misc_feature            1..648
                        note = Humanized antibody sequence
source                  1..648
                        mol_type = other DNA
                        organism = synthetic construct
SEQUENCE: 471
gccgccgtgc tgacccagac tccatctccc gtgtctgcag ctgtgggagg cacagtcagc  60
atcagttgcc agtccagtga gagtgtttat agtaactact tagcctggtt tcagcagaaa  120
ccagggcagc ctcctaagtt cttgatctac gaagcatcca aactggcatc tggggtccca  180
tcgcggttca aaggcagtgg atctgggaca cagttcactc tcaccatcag cgacgtgcag  240
tgtgacgatg ctggcactta ctactgtgca ggcggctata gtagtgaagg tgttgctttc  300
ggcggaggga ccgaggtggt ggtcaaacgt acggtagcgg ccccatctgt cttcatcttc  360
ccgccatctg atgagcagtt gaaatctgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt              648

SEQ ID NO: 472          moltype = DNA  length = 330
FEATURE                 Location/Qualifiers
misc_feature            1..330
                        note = Humanized antibody sequence
source                  1..330
                        mol_type = other DNA
                        organism = synthetic construct
SEQUENCE: 472
gccgccgtgc tgacccagac tccatctccc gtgtctgcag ctgtgggagg cacagtcagc  60
atcagttgcc agtccagtga gagtgtttat agtaactact tagcctggtt tcagcagaaa  120
ccagggcagc ctcctaagtt cttgatctac gaagcatcca aactggcatc tggggtccca  180
tcgcggttca aaggcagtgg atctgggaca cagttcactc tcaccatcag cgacgtgcag  240
tgtgacgatg ctggcactta ctactgtgca ggcggctata gtagtgaagg tgttgctttc  300
ggcggaggga ccgaggtggt ggtcaaacgt                                  330

SEQ ID NO: 473          moltype = DNA  length = 69
FEATURE                 Location/Qualifiers
source                  1..69
                        mol_type = unassigned DNA
                        organism = Oryctolagus cuniculus
SEQUENCE: 473
gccgccgtgc tgacccagac tccatctccc gtgtctgcag ctgtgggagg cacagtcagc  60
atcagttgc                                                         69

SEQ ID NO: 474          moltype = DNA  length = 36
FEATURE                 Location/Qualifiers
source                  1..36
                        mol_type = unassigned DNA
                        organism = Oryctolagus cuniculus
SEQUENCE: 474
cagtccagtg agagtgttta tagtaactac ttagcc                           36

SEQ ID NO: 475          moltype = DNA  length = 45
FEATURE                 Location/Qualifiers
source                  1..45
                        mol_type = unassigned DNA
                        organism = Oryctolagus cuniculus
SEQUENCE: 475
tggtttcagc agaaaccagg gcagcctcct aagttcttga tctac                 45

SEQ ID NO: 476          moltype = DNA  length = 21
FEATURE                 Location/Qualifiers
source                  1..21
                        mol_type = unassigned DNA
                        organism = Oryctolagus cuniculus
SEQUENCE: 476
gaagcatcca aactggcatc t                                           21

SEQ ID NO: 477          moltype = DNA  length = 96
FEATURE                 Location/Qualifiers
source                  1..96
```

```
                        mol_type = unassigned DNA
                        organism = Oryctolagus cuniculus
SEQUENCE: 477
ggggtcccat cgcggttcaa aggcagtgga tctgggacac agttcactct caccatcagc  60
gacgtgcagt gtgacgatgc tggcacttac tactgt                            96

SEQ ID NO: 478          moltype = DNA  length = 30
FEATURE                 Location/Qualifiers
source                  1..30
                        mol_type = unassigned DNA
                        organism = Oryctolagus cuniculus
SEQUENCE: 478
gcaggcggct atagtagtga aggtgttgct                                   30

SEQ ID NO: 479          moltype = DNA  length = 33
FEATURE                 Location/Qualifiers
misc_feature            1..33
                        note = Humanized antibody sequence
source                  1..33
                        mol_type = other DNA
                        organism = synthetic construct
SEQUENCE: 479
ttcggcggag ggaccgaggt ggtggtcaaa cgt                               33

SEQ ID NO: 480          moltype = DNA  length = 318
FEATURE                 Location/Qualifiers
misc_feature            1..318
                        note = Humanized antibody sequence
source                  1..318
                        mol_type = other DNA
                        organism = synthetic construct
SEQUENCE: 480
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318

SEQ ID NO: 481          moltype =   length =
SEQUENCE: 481
000

SEQ ID NO: 482          moltype =   length =
SEQUENCE: 482
000

SEQ ID NO: 483          moltype =   length =
SEQUENCE: 483
000

SEQ ID NO: 484          moltype =   length =
SEQUENCE: 484
000

SEQ ID NO: 485          moltype =   length =
SEQUENCE: 485
000

SEQ ID NO: 486          moltype =   length =
SEQUENCE: 486
000

SEQ ID NO: 487          moltype =   length =
SEQUENCE: 487
000

SEQ ID NO: 488          moltype =   length =
SEQUENCE: 488
000

SEQ ID NO: 489          moltype =   length =
SEQUENCE: 489
000

SEQ ID NO: 490          moltype =   length =
SEQUENCE: 490
000
```

SEQ ID NO: 491 moltype = length =
SEQUENCE: 491
000

SEQ ID NO: 492 moltype = length =
SEQUENCE: 492
000

SEQ ID NO: 493 moltype = length =
SEQUENCE: 493
000

SEQ ID NO: 494 moltype = length =
SEQUENCE: 494
000

SEQ ID NO: 495 moltype = length =
SEQUENCE: 495
000

SEQ ID NO: 496 moltype = length =
SEQUENCE: 496
000

SEQ ID NO: 497 moltype = length =
SEQUENCE: 497
000

SEQ ID NO: 498 moltype = length =
SEQUENCE: 498
000

SEQ ID NO: 499 moltype = length =
SEQUENCE: 499
000

SEQ ID NO: 500 moltype = length =
SEQUENCE: 500
000

SEQ ID NO: 501 moltype = length =
SEQUENCE: 501
000

SEQ ID NO: 502 moltype = length =
SEQUENCE: 502
000

SEQ ID NO: 503 moltype = length =
SEQUENCE: 503
000

SEQ ID NO: 504 moltype = length =
SEQUENCE: 504
000

SEQ ID NO: 505 moltype = length =
SEQUENCE: 505
000

SEQ ID NO: 506 moltype = length =
SEQUENCE: 506
000

SEQ ID NO: 507 moltype = length =
SEQUENCE: 507
000

SEQ ID NO: 508 moltype = length =
SEQUENCE: 508
000

SEQ ID NO: 509 moltype = length =
SEQUENCE: 509
000

SEQ ID NO: 510 moltype = length =
SEQUENCE: 510
000

SEQ ID NO: 511 moltype = length =
SEQUENCE: 511
000

SEQ ID NO: 512 moltype = length =
SEQUENCE: 512
000

SEQ ID NO: 513 moltype = length =
SEQUENCE: 513
000

SEQ ID NO: 514 moltype = length =
SEQUENCE: 514
000

SEQ ID NO: 515 moltype = length =
SEQUENCE: 515
000

SEQ ID NO: 516 moltype = length =
SEQUENCE: 516
000

SEQ ID NO: 517 moltype = length =
SEQUENCE: 517
000

SEQ ID NO: 518 moltype = length =
SEQUENCE: 518
000

SEQ ID NO: 519 moltype = length =
SEQUENCE: 519
000

SEQ ID NO: 520 moltype = length =
SEQUENCE: 520
000

SEQ ID NO: 521 moltype = length =
SEQUENCE: 521
000

SEQ ID NO: 522 moltype = length =
SEQUENCE: 522
000

SEQ ID NO: 523 moltype = length =
SEQUENCE: 523
000

SEQ ID NO: 524 moltype = length =
SEQUENCE: 524
000

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530

000

SEQ ID NO: 531 moltype = length =
SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =
SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = length =
SEQUENCE: 542
000

SEQ ID NO: 543 moltype = length =
SEQUENCE: 543
000

SEQ ID NO: 544 moltype = length =
SEQUENCE: 544
000

SEQ ID NO: 545 moltype = length =
SEQUENCE: 545
000

SEQ ID NO: 546 moltype = length =
SEQUENCE: 546
000

SEQ ID NO: 547 moltype = length =
SEQUENCE: 547
000

SEQ ID NO: 548 moltype = length =
SEQUENCE: 548
000

SEQ ID NO: 549 moltype = length =
SEQUENCE: 549
000

SEQ ID NO: 550 moltype = length =

SEQUENCE: 550
000

SEQ ID NO: 551 moltype = length =
SEQUENCE: 551
000

SEQ ID NO: 552 moltype = length =
SEQUENCE: 552
000

SEQ ID NO: 553 moltype = length =
SEQUENCE: 553
000

SEQ ID NO: 554 moltype = length =
SEQUENCE: 554
000

SEQ ID NO: 555 moltype = length =
SEQUENCE: 555
000

SEQ ID NO: 556 moltype = length =
SEQUENCE: 556
000

SEQ ID NO: 557 moltype = length =
SEQUENCE: 557
000

SEQ ID NO: 558 moltype = length =
SEQUENCE: 558
000

SEQ ID NO: 559 moltype = length =
SEQUENCE: 559
000

SEQ ID NO: 560 moltype = length =
SEQUENCE: 560
000

SEQ ID NO: 561 moltype = length =
SEQUENCE: 561
000

SEQ ID NO: 562 moltype = length =
SEQUENCE: 562
000

SEQ ID NO: 563 moltype = length =
SEQUENCE: 563
000

SEQ ID NO: 564 moltype = length =
SEQUENCE: 564
000

SEQ ID NO: 565 moltype = length =
SEQUENCE: 565
000

SEQ ID NO: 566 moltype = length =
SEQUENCE: 566
000

SEQ ID NO: 567 moltype = length =
SEQUENCE: 567
000

SEQ ID NO: 568 moltype = length =
SEQUENCE: 568
000

SEQ ID NO: 569 moltype = length =
SEQUENCE: 569
000

SEQ ID NO: 570 moltype = length =
SEQUENCE: 570
000

SEQ ID NO: 571 moltype = length =
SEQUENCE: 571
000

SEQ ID NO: 572 moltype = length =
SEQUENCE: 572
000

SEQ ID NO: 573 moltype = length =
SEQUENCE: 573
000

SEQ ID NO: 574 moltype = length =
SEQUENCE: 574
000

SEQ ID NO: 575 moltype = length =
SEQUENCE: 575
000

SEQ ID NO: 576 moltype = length =
SEQUENCE: 576
000

SEQ ID NO: 577 moltype = length =
SEQUENCE: 577
000

SEQ ID NO: 578 moltype = length =
SEQUENCE: 578
000

SEQ ID NO: 579 moltype = length =
SEQUENCE: 579
000

SEQ ID NO: 580 moltype = length =
SEQUENCE: 580
000

SEQ ID NO: 581 moltype = length =
SEQUENCE: 581
000

SEQ ID NO: 582 moltype = length =
SEQUENCE: 582
000

SEQ ID NO: 583 moltype = length =
SEQUENCE: 583
000

SEQ ID NO: 584 moltype = length =
SEQUENCE: 584
000

SEQ ID NO: 585 moltype = length =
SEQUENCE: 585
000

SEQ ID NO: 586 moltype = length =
SEQUENCE: 586
000

SEQ ID NO: 587 moltype = length =
SEQUENCE: 587
000

SEQ ID NO: 588 moltype = length =
SEQUENCE: 588
000

SEQ ID NO: 589 moltype = length =
SEQUENCE: 589
000

SEQ ID NO: 590 moltype = length =
SEQUENCE: 590
000

SEQ ID NO: 591 moltype = length =
SEQUENCE: 591
000

SEQ ID NO: 592 moltype = length =
SEQUENCE: 592
000

SEQ ID NO: 593 moltype = length =
SEQUENCE: 593
000

SEQ ID NO: 594 moltype = length =
SEQUENCE: 594
000

SEQ ID NO: 595 moltype = length =
SEQUENCE: 595
000

SEQ ID NO: 596 moltype = length =
SEQUENCE: 596
000

SEQ ID NO: 597 moltype = length =
SEQUENCE: 597
000

SEQ ID NO: 598 moltype = length =
SEQUENCE: 598
000

SEQ ID NO: 599 moltype = length =
SEQUENCE: 599
000

SEQ ID NO: 600 moltype = length =
SEQUENCE: 600
000

SEQ ID NO: 601 moltype = length =
SEQUENCE: 601
000

SEQ ID NO: 602 moltype = length =
SEQUENCE: 602
000

SEQ ID NO: 603 moltype = length =
SEQUENCE: 603
000

SEQ ID NO: 604 moltype = length =
SEQUENCE: 604
000

SEQ ID NO: 605 moltype = length =
SEQUENCE: 605
000

SEQ ID NO: 606 moltype = length =
SEQUENCE: 606
000

SEQ ID NO: 607 moltype = length =
SEQUENCE: 607
000

SEQ ID NO: 608 moltype = length =
SEQUENCE: 608
000

SEQ ID NO: 609 moltype = length =
SEQUENCE: 609

000

SEQ ID NO: 610 moltype = length =
SEQUENCE: 610
000

SEQ ID NO: 611 moltype = length =
SEQUENCE: 611
000

SEQ ID NO: 612 moltype = length =
SEQUENCE: 612
000

SEQ ID NO: 613 moltype = length =
SEQUENCE: 613
000

SEQ ID NO: 614 moltype = length =
SEQUENCE: 614
000

SEQ ID NO: 615 moltype = length =
SEQUENCE: 615
000

SEQ ID NO: 616 moltype = length =
SEQUENCE: 616
000

SEQ ID NO: 617 moltype = length =
SEQUENCE: 617
000

SEQ ID NO: 618 moltype = length =
SEQUENCE: 618
000

SEQ ID NO: 619 moltype = length =
SEQUENCE: 619
000

SEQ ID NO: 620 moltype = length =
SEQUENCE: 620
000

SEQ ID NO: 621 moltype = length =
SEQUENCE: 621
000

SEQ ID NO: 622 moltype = length =
SEQUENCE: 622
000

SEQ ID NO: 623 moltype = length =
SEQUENCE: 623
000

SEQ ID NO: 624 moltype = length =
SEQUENCE: 624
000

SEQ ID NO: 625 moltype = length =
SEQUENCE: 625
000

SEQ ID NO: 626 moltype = length =
SEQUENCE: 626
000

SEQ ID NO: 627 moltype = length =
SEQUENCE: 627
000

SEQ ID NO: 628 moltype = length =
SEQUENCE: 628
000

SEQ ID NO: 629 moltype = length =

SEQUENCE: 629
000

SEQ ID NO: 630 moltype = length =
SEQUENCE: 630
000

SEQ ID NO: 631 moltype = length =
SEQUENCE: 631
000

SEQ ID NO: 632 moltype = length =
SEQUENCE: 632
000

SEQ ID NO: 633 moltype = length =
SEQUENCE: 633
000

SEQ ID NO: 634 moltype = length =
SEQUENCE: 634
000

SEQ ID NO: 635 moltype = length =
SEQUENCE: 635
000

SEQ ID NO: 636 moltype = length =
SEQUENCE: 636
000

SEQ ID NO: 637 moltype = length =
SEQUENCE: 637
000

SEQ ID NO: 638 moltype = length =
SEQUENCE: 638
000

SEQ ID NO: 639 moltype = length =
SEQUENCE: 639
000

SEQ ID NO: 640 moltype = length =
SEQUENCE: 640
000

SEQ ID NO: 641 moltype = length =
SEQUENCE: 641
000

SEQ ID NO: 642 moltype = length =
SEQUENCE: 642
000

SEQ ID NO: 643 moltype = length =
SEQUENCE: 643
000

SEQ ID NO: 644 moltype = length =
SEQUENCE: 644
000

SEQ ID NO: 645 moltype = length =
SEQUENCE: 645
000

SEQ ID NO: 646 moltype = length =
SEQUENCE: 646
000

SEQ ID NO: 647 moltype = length =
SEQUENCE: 647
000

SEQ ID NO: 648 moltype = length =
SEQUENCE: 648
000

SEQ ID NO: 649 moltype = length =
SEQUENCE: 649
000

SEQ ID NO: 650 moltype = length =
SEQUENCE: 650
000

SEQ ID NO: 651 moltype = length =
SEQUENCE: 651
000

SEQ ID NO: 652 moltype = length =
SEQUENCE: 652
000

SEQ ID NO: 653 moltype = length =
SEQUENCE: 653
000

SEQ ID NO: 654 moltype = length =
SEQUENCE: 654
000

SEQ ID NO: 655 moltype = length =
SEQUENCE: 655
000

SEQ ID NO: 656 moltype = length =
SEQUENCE: 656
000

SEQ ID NO: 657 moltype = length =
SEQUENCE: 657
000

SEQ ID NO: 658 moltype = length =
SEQUENCE: 658
000

SEQ ID NO: 659 moltype = length =
SEQUENCE: 659
000

SEQ ID NO: 660 moltype = length =
SEQUENCE: 660
000

SEQ ID NO: 661 moltype = length =
SEQUENCE: 661
000

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669
000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675
000

SEQ ID NO: 676 moltype = length =
SEQUENCE: 676
000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

SEQ ID NO: 680 moltype = length =
SEQUENCE: 680
000

SEQ ID NO: 681 moltype = length =
SEQUENCE: 681
000

SEQ ID NO: 682 moltype = length =
SEQUENCE: 682
000

SEQ ID NO: 683 moltype = length =
SEQUENCE: 683
000

SEQ ID NO: 684 moltype = length =
SEQUENCE: 684
000

SEQ ID NO: 685 moltype = length =
SEQUENCE: 685
000

SEQ ID NO: 686 moltype = length =
SEQUENCE: 686
000

SEQ ID NO: 687 moltype = length =
SEQUENCE: 687
000

SEQ ID NO: 688 moltype = length =
SEQUENCE: 688

000

SEQ ID NO: 689 moltype = length =
SEQUENCE: 689
000

SEQ ID NO: 690 moltype = length =
SEQUENCE: 690
000

SEQ ID NO: 691 moltype = length =
SEQUENCE: 691
000

SEQ ID NO: 692 moltype = length =
SEQUENCE: 692
000

SEQ ID NO: 693 moltype = length =
SEQUENCE: 693
000

SEQ ID NO: 694 moltype = length =
SEQUENCE: 694
000

SEQ ID NO: 695 moltype = length =
SEQUENCE: 695
000

SEQ ID NO: 696 moltype = length =
SEQUENCE: 696
000

SEQ ID NO: 697 moltype = length =
SEQUENCE: 697
000

SEQ ID NO: 698 moltype = length =
SEQUENCE: 698
000

SEQ ID NO: 699 moltype = length =
SEQUENCE: 699
000

SEQ ID NO: 700 moltype = length =
SEQUENCE: 700
000

SEQ ID NO: 701 moltype = length =
SEQUENCE: 701
000

SEQ ID NO: 702 moltype = length =
SEQUENCE: 702
000

SEQ ID NO: 703 moltype = length =
SEQUENCE: 703
000

SEQ ID NO: 704 moltype = length =
SEQUENCE: 704
000

SEQ ID NO: 705 moltype = length =
SEQUENCE: 705
000

SEQ ID NO: 706 moltype = length =
SEQUENCE: 706
000

SEQ ID NO: 707 moltype = length =
SEQUENCE: 707
000

SEQ ID NO: 708 moltype = length =

SEQUENCE: 708
000

SEQ ID NO: 709 moltype = length =
SEQUENCE: 709
000

SEQ ID NO: 710 moltype = length =
SEQUENCE: 710
000

SEQ ID NO: 711 moltype = length =
SEQUENCE: 711
000

SEQ ID NO: 712 moltype = length =
SEQUENCE: 712
000

SEQ ID NO: 713 moltype = length =
SEQUENCE: 713
000

SEQ ID NO: 714 moltype = length =
SEQUENCE: 714
000

SEQ ID NO: 715 moltype = length =
SEQUENCE: 715
000

SEQ ID NO: 716 moltype = length =
SEQUENCE: 716
000

SEQ ID NO: 717 moltype = length =
SEQUENCE: 717
000

SEQ ID NO: 718 moltype = length =
SEQUENCE: 718
000

SEQ ID NO: 719 moltype = length =
SEQUENCE: 719
000

SEQ ID NO: 720 moltype = length =
SEQUENCE: 720
000

SEQ ID NO: 721 moltype = length =
SEQUENCE: 721
000

SEQ ID NO: 722 moltype = length =
SEQUENCE: 722
000

SEQ ID NO: 723 moltype = length =
SEQUENCE: 723
000

SEQ ID NO: 724 moltype = length =
SEQUENCE: 724
000

SEQ ID NO: 725 moltype = length =
SEQUENCE: 725
000

SEQ ID NO: 726 moltype = length =
SEQUENCE: 726
000

SEQ ID NO: 727 moltype = length =
SEQUENCE: 727
000

SEQ ID NO: 728 moltype = length =
SEQUENCE: 728
000

SEQ ID NO: 729 moltype = length =
SEQUENCE: 729
000

SEQ ID NO: 730 moltype = length =
SEQUENCE: 730
000

SEQ ID NO: 731 moltype = length =
SEQUENCE: 731
000

SEQ ID NO: 732 moltype = length =
SEQUENCE: 732
000

SEQ ID NO: 733 moltype = length =
SEQUENCE: 733
000

SEQ ID NO: 734 moltype = length =
SEQUENCE: 734
000

SEQ ID NO: 735 moltype = length =
SEQUENCE: 735
000

SEQ ID NO: 736 moltype = length =
SEQUENCE: 736
000

SEQ ID NO: 737 moltype = length =
SEQUENCE: 737
000

SEQ ID NO: 738 moltype = length =
SEQUENCE: 738
000

SEQ ID NO: 739 moltype = length =
SEQUENCE: 739
000

SEQ ID NO: 740 moltype = length =
SEQUENCE: 740
000

SEQ ID NO: 741 moltype = length =
SEQUENCE: 741
000

SEQ ID NO: 742 moltype = length =
SEQUENCE: 742
000

SEQ ID NO: 743 moltype = length =
SEQUENCE: 743
000

SEQ ID NO: 744 moltype = length =
SEQUENCE: 744
000

SEQ ID NO: 745 moltype = length =
SEQUENCE: 745
000

SEQ ID NO: 746 moltype = length =
SEQUENCE: 746
000

SEQ ID NO: 747 moltype = length =
SEQUENCE: 747
000

SEQ ID NO: 748 moltype = length =
SEQUENCE: 748
000

SEQ ID NO: 749 moltype = length =
SEQUENCE: 749
000

SEQ ID NO: 750 moltype = length =
SEQUENCE: 750
000

SEQ ID NO: 751 moltype = length =
SEQUENCE: 751
000

SEQ ID NO: 752 moltype = length =
SEQUENCE: 752
000

SEQ ID NO: 753 moltype = length =
SEQUENCE: 753
000

SEQ ID NO: 754 moltype = length =
SEQUENCE: 754
000

SEQ ID NO: 755 moltype = length =
SEQUENCE: 755
000

SEQ ID NO: 756 moltype = length =
SEQUENCE: 756
000

SEQ ID NO: 757 moltype = length =
SEQUENCE: 757
000

SEQ ID NO: 758 moltype = length =
SEQUENCE: 758
000

SEQ ID NO: 759 moltype = length =
SEQUENCE: 759
000

SEQ ID NO: 760 moltype = length =
SEQUENCE: 760
000

SEQ ID NO: 761 moltype = length =
SEQUENCE: 761
000

SEQ ID NO: 762 moltype = length =
SEQUENCE: 762
000

SEQ ID NO: 763 moltype = length =
SEQUENCE: 763
000

SEQ ID NO: 764 moltype = length =
SEQUENCE: 764
000

SEQ ID NO: 765 moltype = length =
SEQUENCE: 765
000

SEQ ID NO: 766 moltype = length =
SEQUENCE: 766
000

SEQ ID NO: 767 moltype = length =
SEQUENCE: 767

000

SEQ ID NO: 768 moltype = length =
SEQUENCE: 768
000

SEQ ID NO: 769 moltype = length =
SEQUENCE: 769
000

SEQ ID NO: 770 moltype = length =
SEQUENCE: 770
000

SEQ ID NO: 771 moltype = length =
SEQUENCE: 771
000

SEQ ID NO: 772 moltype = length =
SEQUENCE: 772
000

SEQ ID NO: 773 moltype = length =
SEQUENCE: 773
000

SEQ ID NO: 774 moltype = length =
SEQUENCE: 774
000

SEQ ID NO: 775 moltype = length =
SEQUENCE: 775
000

SEQ ID NO: 776 moltype = length =
SEQUENCE: 776
000

SEQ ID NO: 777 moltype = length =
SEQUENCE: 777
000

SEQ ID NO: 778 moltype = length =
SEQUENCE: 778
000

SEQ ID NO: 779 moltype = length =
SEQUENCE: 779
000

SEQ ID NO: 780 moltype = length =
SEQUENCE: 780
000

SEQ ID NO: 781 moltype = length =
SEQUENCE: 781
000

SEQ ID NO: 782 moltype = length =
SEQUENCE: 782
000

SEQ ID NO: 783 moltype = length =
SEQUENCE: 783
000

SEQ ID NO: 784 moltype = length =
SEQUENCE: 784
000

SEQ ID NO: 785 moltype = length =
SEQUENCE: 785
000

SEQ ID NO: 786 moltype = length =
SEQUENCE: 786
000

SEQ ID NO: 787 moltype = length =

SEQUENCE: 787
000

SEQ ID NO: 788 moltype = length =
SEQUENCE: 788
000

SEQ ID NO: 789 moltype = length =
SEQUENCE: 789
000

SEQ ID NO: 790 moltype = length =
SEQUENCE: 790
000

SEQ ID NO: 791 moltype = length =
SEQUENCE: 791
000

SEQ ID NO: 792 moltype = length =
SEQUENCE: 792
000

SEQ ID NO: 793 moltype = length =
SEQUENCE: 793
000

SEQ ID NO: 794 moltype = length =
SEQUENCE: 794
000

SEQ ID NO: 795 moltype = length =
SEQUENCE: 795
000

SEQ ID NO: 796 moltype = length =
SEQUENCE: 796
000

SEQ ID NO: 797 moltype = length =
SEQUENCE: 797
000

SEQ ID NO: 798 moltype = length =
SEQUENCE: 798
000

SEQ ID NO: 799 moltype = length =
SEQUENCE: 799
000

SEQ ID NO: 800 moltype = length =
SEQUENCE: 800
000

SEQ ID NO: 801 moltype = length =
SEQUENCE: 801
000

SEQ ID NO: 802 moltype = length =
SEQUENCE: 802
000

SEQ ID NO: 803 moltype = length =
SEQUENCE: 803
000

SEQ ID NO: 804 moltype = length =
SEQUENCE: 804
000

SEQ ID NO: 805 moltype = length =
SEQUENCE: 805
000

SEQ ID NO: 806 moltype = length =
SEQUENCE: 806
000

SEQ ID NO: 807 moltype = length =
SEQUENCE: 807
000

SEQ ID NO: 808 moltype = length =
SEQUENCE: 808
000

SEQ ID NO: 809 moltype = length =
SEQUENCE: 809
000

SEQ ID NO: 810 moltype = length =
SEQUENCE: 810
000

SEQ ID NO: 811 moltype = length =
SEQUENCE: 811
000

SEQ ID NO: 812 moltype = length =
SEQUENCE: 812
000

SEQ ID NO: 813 moltype = length =
SEQUENCE: 813
000

SEQ ID NO: 814 moltype = length =
SEQUENCE: 814
000

SEQ ID NO: 815 moltype = length =
SEQUENCE: 815
000

SEQ ID NO: 816 moltype = length =
SEQUENCE: 816
000

SEQ ID NO: 817 moltype = length =
SEQUENCE: 817
000

SEQ ID NO: 818 moltype = length =
SEQUENCE: 818
000

SEQ ID NO: 819 moltype = length =
SEQUENCE: 819
000

SEQ ID NO: 820 moltype = length =
SEQUENCE: 820
000

SEQ ID NO: 821 moltype = length =
SEQUENCE: 821
000

SEQ ID NO: 822 moltype = length =
SEQUENCE: 822
000

SEQ ID NO: 823 moltype = length =
SEQUENCE: 823
000

SEQ ID NO: 824 moltype = length =
SEQUENCE: 824
000

SEQ ID NO: 825 moltype = length =
SEQUENCE: 825
000

SEQ ID NO: 826 moltype = length =
SEQUENCE: 826
000

```
SEQ ID NO: 827         moltype =   length =
SEQUENCE: 827
000

SEQ ID NO: 828         moltype =   length =
SEQUENCE: 828
000

SEQ ID NO: 829         moltype =   length =
SEQUENCE: 829
000

SEQ ID NO: 830         moltype =   length =
SEQUENCE: 830
000

SEQ ID NO: 831         moltype =   length =
SEQUENCE: 831
000

SEQ ID NO: 832         moltype =   length =
SEQUENCE: 832
000

SEQ ID NO: 833         moltype =   length =
SEQUENCE: 833
000

SEQ ID NO: 834         moltype =   length =
SEQUENCE: 834
000

SEQ ID NO: 835         moltype =   length =
SEQUENCE: 835
000

SEQ ID NO: 836         moltype =   length =
SEQUENCE: 836
000

SEQ ID NO: 837         moltype =   length =
SEQUENCE: 837
000

SEQ ID NO: 838         moltype =   length =
SEQUENCE: 838
000

SEQ ID NO: 839         moltype =   length =
SEQUENCE: 839
000

SEQ ID NO: 840         moltype =   length =
SEQUENCE: 840
000

SEQ ID NO: 841         moltype = AA  length = 439
FEATURE                Location/Qualifiers
REGION                 1..439
                       note = Humanized antibody sequence
source                 1..439
                       mol_type = protein
                       organism = synthetic construct
SEQUENCE: 841
QSVEESGGRL VTPGTPLTLT CTVSGIDLSS YYMTWVRQAP GKGLEWVGFI DAGGSAYYAT  60
WAKGRFTISK ASTTVDLKIT SPTTEDTATY FCARDLDLWG PGTLVTVSSA STKGPSVFPL  120
APSSKSTSGG TAALGCLVKD YFPEPVTVSW NSGALTSGVH TFPAVLQSSG LYSLSSVVTV  180
PSSSLGTQTY ICNVNHKPSN TKVDKKVEPK SCDKTHTCPP CPAPELLGGP SVFLFPPKPK  240
DTLMISRTPE VTCVVVDVSH EDPEVKFNWY VDGVEVHNAK TKPREEQYAS TYRVVSVLTV  300
LHQDWLNGKE YKCKVSNKAL PAPIEKTISK AKGQPREPQV YTLPPSREEM TKNQVSLTCL  360
VKGFYPSDIA VEWESNGQPE NNYKTTPPVL DSDGSFFLYS KLTVDKSRWQ QGNVFSCSVM  420
HEALHNHYTQ KSLSLSPGK                                             439

SEQ ID NO: 842         moltype = AA  length = 109
FEATURE                Location/Qualifiers
REGION                 1..109
                       note = Humanized antibody sequence
source                 1..109
```

```
                         mol_type = protein
                         organism = synthetic construct
SEQUENCE: 842
QSVEESGGRL VTPGTPLTLT CTVSGIDLSS YYMTWVRQAP GKGLEWVGFI DAGGSAYYAT  60
WAKGRFTISK ASTTVDLKIT SPTTEDTATY FCARDLDLWG PGTLVTVSS            109

SEQ ID NO: 843          moltype = AA  length = 29
FEATURE                 Location/Qualifiers
source                  1..29
                        mol_type = protein
                        organism = Oryctolagus cuniculus
SEQUENCE: 843
QSVEESGGRL VTPGTPLTLT CTVSGIDLS                                   29

SEQ ID NO: 844          moltype = AA  length = 5
FEATURE                 Location/Qualifiers
source                  1..5
                        mol_type = protein
                        organism = Oryctolagus cuniculus
SEQUENCE: 844
SYYMT                                                             5

SEQ ID NO: 845          moltype = AA  length = 14
FEATURE                 Location/Qualifiers
source                  1..14
                        mol_type = protein
                        organism = Oryctolagus cuniculus
SEQUENCE: 845
WVRQAPGKGL EWVG                                                   14

SEQ ID NO: 846          moltype = AA  length = 16
FEATURE                 Location/Qualifiers
source                  1..16
                        mol_type = protein
                        organism = Oryctolagus cuniculus
SEQUENCE: 846
FIDAGGSAYY ATWAKG                                                 16

SEQ ID NO: 847          moltype = AA  length = 30
FEATURE                 Location/Qualifiers
source                  1..30
                        mol_type = protein
                        organism = Oryctolagus cuniculus
SEQUENCE: 847
RFTISKASTT VDLKITSPTT EDTATYFCAR                                  30

SEQ ID NO: 848          moltype = AA  length = 4
FEATURE                 Location/Qualifiers
source                  1..4
                        mol_type = protein
                        organism = Oryctolagus cuniculus
SEQUENCE: 848
DLDL                                                              4

SEQ ID NO: 849          moltype = AA  length = 11
FEATURE                 Location/Qualifiers
REGION                  1..11
                        note = Humanized antibody sequence
source                  1..11
                        mol_type = protein
                        organism = synthetic construct
SEQUENCE: 849
WGPGTLVTVS S                                                      11

SEQ ID NO: 850          moltype = AA  length = 330
FEATURE                 Location/Qualifiers
REGION                  1..330
                        note = Humanized antibody sequence
source                  1..330
                        mol_type = protein
                        organism = synthetic construct
SEQUENCE: 850
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330
```

```
SEQ ID NO: 851          moltype = DNA  length = 1317
FEATURE                 Location/Qualifiers
misc_feature            1..1317
                        note = Humanized antibody sequence
source                  1..1317
                        mol_type = other DNA
                        organism = synthetic construct
SEQUENCE: 851
cagtcggtgg aggagtccgg gggtcgcctg gtcacgcctg ggacacccct gacactcacc  60
tgcacagtct ctggaatcga cctcagtagc tactacatga cctgggtccg ccaggctcca  120
gggaaggggc tggaatgggt cggattcatt gatgctggtg gtagcgcata ctacgcgacc  180
tgggcaaaag gccgattcac catctccaaa gcctcgacca cggtggatct gaaaatcacc  240
agtccgacaa ccgaggacac ggccacctat ttctgtgcca gagatcttga cttgtggggc  300
ccgggcaccc tggtcaccgt ctcgagcgcc tccaccaagg gcccatcggt cttccccctg  360
gcaccctcct ccaagagcac ctctgggggc acagcggccc tgggctgcct ggtcaaggac  420
tacttccccg aaccggtgac ggtgtcgtgg aactcaggcg ccctgaccag cggcgtgcac  480
accttcccgg ctgtcctaca gtcctcagga ctctactccc tcagcagcgt ggtgaccgtg  540
ccctccagca gcttgggcac ccagacctac atctgcaacg tgaatcacaa gcccagcaac  600
accaaggtgg acaagaaagt tgagcccaaa tcttgtgaca aaactcacac atgcccaccg  660
tgcccagcac ctgaactcct ggggggaccg tcagtcttcc tcttcccccc aaaacccaag  720
gacaccctca tgatctcccg gacccctgag gtcacatgcg tggtggtgga cgtgagccac  780
gaagaccctg aggtcaagtt caactggtac gtggacggcg tggaggtgca taatgccaag  840
acaaagccgc gggaggagca gtacgccagc acgtaccgtg tggtcagcgt cctcaccgtc  900
ctgcaccagg actggctgaa tggcaaggag tacaagtgca aggtctccaa caaagccctc  960
ccagccccca tcgagaaaac catctccaaa gccaaagggc agccccgaga accacaggtg  1020
tacaccctgc ccccatcccg ggaggagatg accaagaacc aggtcagcct gacctgcctg  1080
gtcaaaggct tctatcccag cgacatcgcc gtggagtggg agagcaatgg gcagccggag  1140
aacaactaca agaccacgcc tcccgtgctg gactccgacg gctccttctt cctctacagc  1200
aagctcaccg tggacaagag caggtggcag caggggaacg tcttctcatg ctccgtgatg  1260
catgaggctc tgcacaacca ctacacgcag aagagcctct ccctgtctcc gggtaaa     1317

SEQ ID NO: 852          moltype = DNA  length = 327
FEATURE                 Location/Qualifiers
misc_feature            1..327
                        note = Humanized antibody sequence
source                  1..327
                        mol_type = other DNA
                        organism = synthetic construct
SEQUENCE: 852
cagtcggtgg aggagtccgg gggtcgcctg gtcacgcctg ggacacccct gacactcacc  60
tgcacagtct ctggaatcga cctcagtagc tactacatga cctgggtccg ccaggctcca  120
gggaaggggc tggaatgggt cggattcatt gatgctggtg gtagcgcata ctacgcgacc  180
tgggcaaaag gccgattcac catctccaaa gcctcgacca cggtggatct gaaaatcacc  240
agtccgacaa ccgaggacac ggccacctat ttctgtgcca gagatcttga cttgtggggc  300
ccgggcaccc tggtcaccgt ctcgagc                                      327

SEQ ID NO: 853          moltype = DNA  length = 87
FEATURE                 Location/Qualifiers
source                  1..87
                        mol_type = unassigned DNA
                        organism = Oryctolagus cuniculus
SEQUENCE: 853
cagtcggtgg aggagtccgg gggtcgcctg gtcacgcctg ggacacccct gacactcacc  60
tgcacagtct ctggaatcga cctcagt                                      87

SEQ ID NO: 854          moltype = DNA  length = 15
FEATURE                 Location/Qualifiers
source                  1..15
                        mol_type = unassigned DNA
                        organism = Oryctolagus cuniculus
SEQUENCE: 854
agctactaca tgacc                                                   15

SEQ ID NO: 855          moltype = DNA  length = 42
FEATURE                 Location/Qualifiers
source                  1..42
                        mol_type = unassigned DNA
                        organism = Oryctolagus cuniculus
SEQUENCE: 855
tgggtccgcc aggctccagg gaaggggctg gaatgggtcg ga                     42

SEQ ID NO: 856          moltype = DNA  length = 48
FEATURE                 Location/Qualifiers
source                  1..48
                        mol_type = unassigned DNA
                        organism = Oryctolagus cuniculus
SEQUENCE: 856
ttcattgatg ctggtggtag cgcatactac gcgacctggg caaaaggc               48
```

```
SEQ ID NO: 857          moltype = DNA  length = 90
FEATURE                 Location/Qualifiers
source                  1..90
                        mol_type = unassigned DNA
                        organism = Oryctolagus cuniculus
SEQUENCE: 857
cgattcacca tctccaaagc ctcgaccacg gtggatctga aaatcaccag tccgacaacc  60
gaggacacgg ccacctattt ctgtgccaga                                   90

SEQ ID NO: 858          moltype = DNA  length = 12
FEATURE                 Location/Qualifiers
source                  1..12
                        mol_type = unassigned DNA
                        organism = Oryctolagus cuniculus
SEQUENCE: 858
gatcttgact tg                                                      12

SEQ ID NO: 859          moltype = DNA  length = 33
FEATURE                 Location/Qualifiers
misc_feature            1..33
                        note = Humanized antibody sequence
source                  1..33
                        mol_type = other DNA
                        organism = synthetic construct
SEQUENCE: 859
tggggcccgg gcaccctggt caccgtctcg agc                               33

SEQ ID NO: 860          moltype = DNA  length = 990
FEATURE                 Location/Qualifiers
misc_feature            1..990
                        note = Humanized antibody sequence
source                  1..990
                        mol_type = other DNA
                        organism = synthetic construct
SEQUENCE: 860
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 861          moltype = AA  length = 216
FEATURE                 Location/Qualifiers
REGION                  1..216
                        note = Humanized antibody sequence
source                  1..216
                        mol_type = protein
                        organism = synthetic construct
SEQUENCE: 861
AAVLTQTPSP VSAAVGGTVS ISCKSSESVY GDYLAWFQQK PGQPPKQLIY DASTLASGVP  60
SRFKGSGSGT QFTLTISGVQ CDDAATYYCA GGYVSAGVAF GGGTEVVVKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 862          moltype = AA  length = 110
FEATURE                 Location/Qualifiers
REGION                  1..110
                        note = Humanized antibody sequence
source                  1..110
                        mol_type = protein
                        organism = synthetic construct
SEQUENCE: 862
AAVLTQTPSP VSAAVGGTVS ISCKSSESVY GDYLAWFQQK PGQPPKQLIY DASTLASGVP  60
SRFKGSGSGT QFTLTISGVQ CDDAATYYCA GGYVSAGVAF GGGTEVVVKR             110

SEQ ID NO: 863          moltype = AA  length = 23
FEATURE                 Location/Qualifiers
```

```
source                  1..23
                        mol_type = protein
                        organism = Oryctolagus cuniculus
SEQUENCE: 863
AAVLTQTPSP VSAAVGGTVS ISC                                          23

SEQ ID NO: 864          moltype = AA  length = 12
FEATURE                 Location/Qualifiers
source                  1..12
                        mol_type = protein
                        organism = Oryctolagus cuniculus
SEQUENCE: 864
KSSESVYGDY LA                                                      12

SEQ ID NO: 865          moltype = AA  length = 15
FEATURE                 Location/Qualifiers
source                  1..15
                        mol_type = protein
                        organism = Oryctolagus cuniculus
SEQUENCE: 865
WFQQKPGQPP KQLIY                                                   15

SEQ ID NO: 866          moltype = AA  length = 7
FEATURE                 Location/Qualifiers
source                  1..7
                        mol_type = protein
                        organism = Oryctolagus cuniculus
SEQUENCE: 866
DASTLAS                                                            7

SEQ ID NO: 867          moltype = AA  length = 32
FEATURE                 Location/Qualifiers
source                  1..32
                        mol_type = protein
                        organism = Oryctolagus cuniculus
SEQUENCE: 867
GVPSRFKGSG SGTQFTLTIS GVQCDDAATY YC                                32

SEQ ID NO: 868          moltype = AA  length = 10
FEATURE                 Location/Qualifiers
source                  1..10
                        mol_type = protein
                        organism = Oryctolagus cuniculus
SEQUENCE: 868
AGGYVSAGVA                                                         10

SEQ ID NO: 869          moltype = AA  length = 11
FEATURE                 Location/Qualifiers
REGION                  1..11
                        note = Humanized antibody sequence
source                  1..11
                        mol_type = protein
                        organism = synthetic construct
SEQUENCE: 869
FGGGTEVVVK R                                                       11

SEQ ID NO: 870          moltype = AA  length = 106
FEATURE                 Location/Qualifiers
REGION                  1..106
                        note = Humanized antibody sequence
source                  1..106
                        mol_type = protein
                        organism = synthetic construct
SEQUENCE: 870
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 871          moltype = DNA  length = 648
FEATURE                 Location/Qualifiers
misc_feature            1..648
                        note = Humanized antibody sequence
source                  1..648
                        mol_type = other DNA
                        organism = synthetic construct
SEQUENCE: 871
gccgccgtgc tgacccagac tccatctccc gtgtctgcag ctgtgggagg cacagtcagc  60
atcagttgca agtccagtga gagcgtttat ggtgactact tagcctggtt tcagcagaaa  120
ccagggcagc ctcccaagca actgatctat gatgcatcca ctctggcatc tggggtccca  180
tcgcggttca aaggcagtgg atctgggaca cagttcactc tcaccatcag cggcgtgcag  240
```

```
tgtgacgatg ctgccactta ctactgtgca ggcggttatg ttagtgcagg tgttgctttc  300
ggcggaggga ccgaggtggt ggtcaaacgt acggtagcgg ccccatctgt cttcatcttc  360
ccgccatctg atgagcagtt gaaatctgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt              648

SEQ ID NO: 872         moltype = DNA  length = 330
FEATURE                Location/Qualifiers
misc_feature           1..330
                       note = Humanized antibody sequence
source                 1..330
                       mol_type = other DNA
                       organism = synthetic construct
SEQUENCE: 872
gccgccgtgc tgacccagac tccatctccc gtgtctgcag ctgtgggagg cacagtcagc  60
atcagttgca agtccagtga gagcgtttat ggtgactact tagcctggtt tcagcagaaa  120
ccagggcagc ctcccaagca actgatctat gatgcatcca ctctggcatc tggggtccca  180
tcgcggttca aaggcagtgg atctgggaca cagttcactc tcaccatcag cggcgtgcag  240
tgtgacgatg ctgccactta ctactgtgca ggcggttatg ttagtgcagg tgttgctttc  300
ggcggaggga ccgaggtggt ggtcaaacgt                                  330

SEQ ID NO: 873         moltype = DNA  length = 69
FEATURE                Location/Qualifiers
source                 1..69
                       mol_type = unassigned DNA
                       organism = Oryctolagus cuniculus
SEQUENCE: 873
gccgccgtgc tgacccagac tccatctccc gtgtctgcag ctgtgggagg cacagtcagc  60
atcagttgc                                                         69

SEQ ID NO: 874         moltype = DNA  length = 36
FEATURE                Location/Qualifiers
source                 1..36
                       mol_type = unassigned DNA
                       organism = Oryctolagus cuniculus
SEQUENCE: 874
aagtccagtg agagcgttta tggtgactac ttagcc                           36

SEQ ID NO: 875         moltype = DNA  length = 45
FEATURE                Location/Qualifiers
source                 1..45
                       mol_type = unassigned DNA
                       organism = Oryctolagus cuniculus
SEQUENCE: 875
tggtttcagc agaaaccagg gcagcctccc aagcaactga tctat                 45

SEQ ID NO: 876         moltype = DNA  length = 21
FEATURE                Location/Qualifiers
source                 1..21
                       mol_type = unassigned DNA
                       organism = Oryctolagus cuniculus
SEQUENCE: 876
gatgcatcca ctctggcatc t                                           21

SEQ ID NO: 877         moltype = DNA  length = 96
FEATURE                Location/Qualifiers
source                 1..96
                       mol_type = unassigned DNA
                       organism = Oryctolagus cuniculus
SEQUENCE: 877
ggggtcccat cgcggttcaa aggcagtgga tctgggacac agttcactct caccatcagc  60
ggcgtgcagt gtgacgatgc tgccacttac tactgt                           96

SEQ ID NO: 878         moltype = DNA  length = 30
FEATURE                Location/Qualifiers
source                 1..30
                       mol_type = unassigned DNA
                       organism = Oryctolagus cuniculus
SEQUENCE: 878
gcaggcggtt atgttagtgc aggtgttgct                                  30

SEQ ID NO: 879         moltype = DNA  length = 33
FEATURE                Location/Qualifiers
misc_feature           1..33
                       note = Humanized antibody sequence
source                 1..33
                       mol_type = other DNA
```

```
                        organism = synthetic construct
SEQUENCE: 879
ttcggcggag ggaccgaggt ggtggtcaaa cgt                             33

SEQ ID NO: 880          moltype = DNA  length = 318
FEATURE                 Location/Qualifiers
misc_feature            1..318
                        note = Humanized antibody sequence
source                  1..318
                        mol_type = other DNA
                        organism = synthetic construct
SEQUENCE: 880
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                              318

SEQ ID NO: 881          moltype = AA  length = 442
FEATURE                 Location/Qualifiers
REGION                  1..442
                        note = Humanized antibody sequence
source                  1..442
                        mol_type = protein
                        organism = synthetic construct
SEQUENCE: 881
QEQLVESGGG LVQPEGSLTL TCTASGFDFS SNAMCWVRQA PGKGLEWIGS IYNADGKNYY  60
AIWAKGRFTI SRTSSTTVTL QMTSLTAADT ATYFCARDFD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDARV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                         442

SEQ ID NO: 882          moltype = AA  length = 112
FEATURE                 Location/Qualifiers
REGION                  1..112
                        note = Humanized antibody sequence
source                  1..112
                        mol_type = protein
                        organism = synthetic construct
SEQUENCE: 882
QEQLVESGGG LVQPEGSLTL TCTASGFDFS SNAMCWVRQA PGKGLEWIGS IYNADGKNYY  60
AIWAKGRFTI SRTSSTTVTL QMTSLTAADT ATYFCARDFD LWGQGTLVTV SS          112

SEQ ID NO: 883          moltype = AA  length = 30
FEATURE                 Location/Qualifiers
source                  1..30
                        mol_type = protein
                        organism = Oryctolagus cuniculus
SEQUENCE: 883
QEQLVESGGG LVQPEGSLTL TCTASGFDFS                                 30

SEQ ID NO: 884          moltype = AA  length = 5
FEATURE                 Location/Qualifiers
source                  1..5
                        mol_type = protein
                        organism = Oryctolagus cuniculus
SEQUENCE: 884
SNAMC                                                            5

SEQ ID NO: 885          moltype = AA  length = 14
FEATURE                 Location/Qualifiers
source                  1..14
                        mol_type = protein
                        organism = Oryctolagus cuniculus
SEQUENCE: 885
WVRQAPGKGL EWIG                                                  14

SEQ ID NO: 886          moltype = AA  length = 17
FEATURE                 Location/Qualifiers
source                  1..17
                        mol_type = protein
                        organism = Oryctolagus cuniculus
SEQUENCE: 886
SIYNADGKNY YAIWAKG                                               17
```

```
SEQ ID NO: 887          moltype = AA  length = 31
FEATURE                 Location/Qualifiers
source                  1..31
                        mol_type = protein
                        organism = Oryctolagus cuniculus
SEQUENCE: 887
RFTISRTSST TVTLQMTSLT AADTATYFCA R                                31

SEQ ID NO: 888          moltype = AA  length = 4
FEATURE                 Location/Qualifiers
source                  1..4
                        mol_type = protein
                        organism = Oryctolagus cuniculus
SEQUENCE: 888
DFDL                                                              4

SEQ ID NO: 889          moltype = AA  length = 11
FEATURE                 Location/Qualifiers
REGION                  1..11
                        note = Humanized antibody sequence
source                  1..11
                        mol_type = protein
                        organism = synthetic construct
SEQUENCE: 889
WGQGTLVTVS S                                                      11

SEQ ID NO: 890          moltype = AA  length = 330
FEATURE                 Location/Qualifiers
REGION                  1..330
                        note = Humanized antibody sequence
source                  1..330
                        mol_type = protein
                        organism = synthetic construct
SEQUENCE: 890
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDARVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 891          moltype = DNA  length = 1326
FEATURE                 Location/Qualifiers
misc_feature            1..1326
                        note = Humanized antibody sequence
source                  1..1326
                        mol_type = other DNA
                        organism = synthetic construct
SEQUENCE: 891
caggagcagc tggtggagtc cgggggaggc ctggtccagc ctgagggatc cctgacactc  60
acctgcacag cctctggatt cgacttcagt agcaatgcaa tgtgctgggt ccgccaggct  120
ccagggaagg gcctggagtg gatcggatcc atttataatg ctgatggtaa gaattattac  180
gcgatttggg cgaaaggccg attcaccatc tccagaacct cgtcgaccac ggtgactctg  240
caaatgacca gtctgacagc cgcggacacg gccacctatt tctgtgcgag agactttgac  300
ttgtggggcc agggcaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga cgcgagagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                            1326

SEQ ID NO: 892          moltype = DNA  length = 336
FEATURE                 Location/Qualifiers
misc_feature            1..336
                        note = Humanized antibody sequence
source                  1..336
                        mol_type = other DNA
```

```
                         organism = synthetic construct
SEQUENCE: 892
caggagcagc tggtggagtc cgggggaggc ctggtccagc ctgagggatc cctgacactc  60
acctgcacag cctctggatt cgacttcagt agcaatgcaa tgtgctgggt ccgccaggct  120
ccagggaagg gcctggagtg gatcggatcc atttataatg ctgatggtaa gaattattac  180
gcgatttggg cgaaaggccg attcaccatc tccagaacct cgtcgaccac ggtgactctg  240
caaatgacca gtctgacagc cgcggacacg gccacctatt tctgtgcgag agactttgac  300
ttgtggggcc agggcaccct cgtcaccgtc tcgagc                           336

SEQ ID NO: 893           moltype = DNA  length = 90
FEATURE                  Location/Qualifiers
source                   1..90
                         mol_type = unassigned DNA
                         organism = Oryctolagus cuniculus
SEQUENCE: 893
caggagcagc tggtggagtc cgggggaggc ctggtccagc ctgagggatc cctgacactc  60
acctgcacag cctctggatt cgacttcagt                                  90

SEQ ID NO: 894           moltype = DNA  length = 15
FEATURE                  Location/Qualifiers
source                   1..15
                         mol_type = unassigned DNA
                         organism = Oryctolagus cuniculus
SEQUENCE: 894
agcaatgcaa tgtgc                                                  15

SEQ ID NO: 895           moltype = DNA  length = 42
FEATURE                  Location/Qualifiers
source                   1..42
                         mol_type = unassigned DNA
                         organism = Oryctolagus cuniculus
SEQUENCE: 895
tgggtccgcc aggctccagg gaagggcctg gagtggatcg ga                    42

SEQ ID NO: 896           moltype = DNA  length = 51
FEATURE                  Location/Qualifiers
source                   1..51
                         mol_type = unassigned DNA
                         organism = Oryctolagus cuniculus
SEQUENCE: 896
tccatttata atgctgatgg taagaattat tacgcgattt gggcgaaagg c          51

SEQ ID NO: 897           moltype = DNA  length = 93
FEATURE                  Location/Qualifiers
source                   1..93
                         mol_type = unassigned DNA
                         organism = Oryctolagus cuniculus
SEQUENCE: 897
cgattcacca tctccagaac ctcgtcgacc acggtgactc tgcaaatgac cagtctgaca  60
gccgcggaca cggccaccta tttctgtgcg aga                              93

SEQ ID NO: 898           moltype = DNA  length = 12
FEATURE                  Location/Qualifiers
source                   1..12
                         mol_type = unassigned DNA
                         organism = Oryctolagus cuniculus
SEQUENCE: 898
gactttgact tg                                                     12

SEQ ID NO: 899           moltype = DNA  length = 33
FEATURE                  Location/Qualifiers
misc_feature             1..33
                         note = Humanized antibody sequence
source                   1..33
                         mol_type = other DNA
                         organism = synthetic construct
SEQUENCE: 899
tggggccagg gcaccctcgt caccgtctcg agc                              33

SEQ ID NO: 900           moltype = DNA  length = 990
FEATURE                  Location/Qualifiers
misc_feature             1..990
                         note = Humanized antibody sequence
source                   1..990
                         mol_type = other DNA
                         organism = synthetic construct
SEQUENCE: 900
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
```

```
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacgcgag agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 901          moltype = AA  length = 219
FEATURE                 Location/Qualifiers
REGION                  1..219
                        note = Humanized antibody sequence
source                  1..219
                        mol_type = protein
                        organism = synthetic construct
SEQUENCE: 901
AAVLTQTPSP VSAAVGGTVT INCQSSQSVY DNDWLAWFQQ KPGQPPKLLI YLTSTLASGV  60
PSRFSGSGSG TQFTLTISGV QCDDAATYYC LGGYDEDGDT HVFGGGTEVV VKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 902          moltype = AA  length = 113
FEATURE                 Location/Qualifiers
REGION                  1..113
                        note = Humanized antibody sequence
source                  1..113
                        mol_type = protein
                        organism = synthetic construct
SEQUENCE: 902
AAVLTQTPSP VSAAVGGTVT INCQSSQSVY DNDWLAWFQQ KPGQPPKLLI YLTSTLASGV  60
PSRFSGSGSG TQFTLTISGV QCDDAATYYC LGGYDEDGDT HVFGGGTEVV VKR         113

SEQ ID NO: 903          moltype = AA  length = 23
FEATURE                 Location/Qualifiers
source                  1..23
                        mol_type = protein
                        organism = Oryctolagus cuniculus
SEQUENCE: 903
AAVLTQTPSP VSAAVGGTVT INC                                          23

SEQ ID NO: 904          moltype = AA  length = 13
FEATURE                 Location/Qualifiers
source                  1..13
                        mol_type = protein
                        organism = Oryctolagus cuniculus
SEQUENCE: 904
QSSQSVYDND WLA                                                     13

SEQ ID NO: 905          moltype = AA  length = 15
FEATURE                 Location/Qualifiers
source                  1..15
                        mol_type = protein
                        organism = Oryctolagus cuniculus
SEQUENCE: 905
WFQQKPGQPP KLLIY                                                   15

SEQ ID NO: 906          moltype = AA  length = 7
FEATURE                 Location/Qualifiers
source                  1..7
                        mol_type = protein
                        organism = Oryctolagus cuniculus
SEQUENCE: 906
LTSTLAS                                                            7

SEQ ID NO: 907          moltype = AA  length = 32
FEATURE                 Location/Qualifiers
source                  1..32
                        mol_type = protein
                        organism = Oryctolagus cuniculus
SEQUENCE: 907
GVPSRFSGSG SGTQFTLTIS GVQCDDAATY YC                                32
```

```
SEQ ID NO: 908         moltype = AA  length = 12
FEATURE                Location/Qualifiers
source                 1..12
                       mol_type = protein
                       organism = Oryctolagus cuniculus
SEQUENCE: 908
LGGYDEDGDT HV                                                      12

SEQ ID NO: 909         moltype = AA  length = 11
FEATURE                Location/Qualifiers
REGION                 1..11
                       note = Humanized antibody sequence
source                 1..11
                       mol_type = protein
                       organism = synthetic construct
SEQUENCE: 909
FGGGTEVVVK R                                                       11

SEQ ID NO: 910         moltype = AA  length = 106
FEATURE                Location/Qualifiers
REGION                 1..106
                       note = Humanized antibody sequence
source                 1..106
                       mol_type = protein
                       organism = synthetic construct
SEQUENCE: 910
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 911         moltype = DNA  length = 657
FEATURE                Location/Qualifiers
misc_feature           1..657
                       note = Humanized antibody sequence
source                 1..657
                       mol_type = other DNA
                       organism = synthetic construct
SEQUENCE: 911
gcagccgtgc tgacccagac accatcgccc gtgtctgcag ctgtgggagg cacagtcacc  60
atcaattgcc agtccagtca gagtgtttat gataacgact ggttagcctg gttccagcag  120
aaaccagggc agcctcccaa gctcctgatc tatctgacat ccactctggc atctggagtc  180
ccatcgcggt tcagcggcag tggatctggg acacagttca ctctcaccat cagtggtgtg  240
cagtgtgacg atgctgccac ttactactgt ctaggcggct atgatgaaga tggtgatacg  300
catgttttcg gcggagggac cgaggtggtg gtcaaacgta cggtagcggc cccatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 912         moltype = DNA  length = 339
FEATURE                Location/Qualifiers
misc_feature           1..339
                       note = Humanized antibody sequence
source                 1..339
                       mol_type = other DNA
                       organism = synthetic construct
SEQUENCE: 912
gcagccgtgc tgacccagac accatcgccc gtgtctgcag ctgtgggagg cacagtcacc  60
atcaattgcc agtccagtca gagtgtttat gataacgact ggttagcctg gttccagcag  120
aaaccagggc agcctcccaa gctcctgatc tatctgacat ccactctggc atctggagtc  180
ccatcgcggt tcagcggcag tggatctggg acacagttca ctctcaccat cagtggtgtg  240
cagtgtgacg atgctgccac ttactactgt ctaggcggct atgatgaaga tggtgatacg  300
catgttttcg gcggagggac cgaggtggtg gtcaaacgt                         339

SEQ ID NO: 913         moltype = DNA  length = 69
FEATURE                Location/Qualifiers
source                 1..69
                       mol_type = unassigned DNA
                       organism = Oryctolagus cuniculus
SEQUENCE: 913
gcagccgtgc tgacccagac accatcgccc gtgtctgcag ctgtgggagg cacagtcacc  60
atcaattgc                                                          69

SEQ ID NO: 914         moltype = DNA  length = 39
FEATURE                Location/Qualifiers
source                 1..39
                       mol_type = unassigned DNA
                       organism = Oryctolagus cuniculus
```

```
SEQUENCE: 914
cagtccagtc agagtgttta tgataacgac tggttagcc                      39

SEQ ID NO: 915          moltype = DNA  length = 45
FEATURE                 Location/Qualifiers
source                  1..45
                        mol_type = unassigned DNA
                        organism = Oryctolagus cuniculus
SEQUENCE: 915
tggttccagc agaaaccagg gcagcctccc aagctcctga tctat               45

SEQ ID NO: 916          moltype = DNA  length = 21
FEATURE                 Location/Qualifiers
source                  1..21
                        mol_type = unassigned DNA
                        organism = Oryctolagus cuniculus
SEQUENCE: 916
ctgacatcca ctctggcatc t                                         21

SEQ ID NO: 917          moltype = DNA  length = 96
FEATURE                 Location/Qualifiers
source                  1..96
                        mol_type = unassigned DNA
                        organism = Oryctolagus cuniculus
SEQUENCE: 917
ggagtcccat cgcggttcag cggcagtgga tctgggacac agttcactct caccatcagt  60
ggtgtgcagt gtgacgatgc tgccacttac tactgt                         96

SEQ ID NO: 918          moltype = DNA  length = 36
FEATURE                 Location/Qualifiers
source                  1..36
                        mol_type = unassigned DNA
                        organism = Oryctolagus cuniculus
SEQUENCE: 918
ctaggcggct atgatgaaga tggtgatacg catgtt                         36

SEQ ID NO: 919          moltype = DNA  length = 33
FEATURE                 Location/Qualifiers
misc_feature            1..33
                        note = Humanized antibody sequence
source                  1..33
                        mol_type = other DNA
                        organism = synthetic construct
SEQUENCE: 919
ttcggcggag ggaccgaggt ggtggtcaaa cgt                            33

SEQ ID NO: 920          moltype = DNA  length = 318
FEATURE                 Location/Qualifiers
misc_feature            1..318
                        note = Humanized antibody sequence
source                  1..318
                        mol_type = other DNA
                        organism = synthetic construct
SEQUENCE: 920
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                             318

SEQ ID NO: 921          moltype = AA  length = 447
FEATURE                 Location/Qualifiers
REGION                  1..447
                        note = Humanized antibody sequence
source                  1..447
                        mol_type = protein
                        organism = synthetic construct
SEQUENCE: 921
QSVEESGGRL VTPGTPLTLT CTVSGFSLNN YAMSWVRQAP GKGLEWIGIM GVNDITYYAS  60
WAKGRFTISK TSTTVDLKMT SLTTEDTATY FCTREIRDDG DSSDKLWGPG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDARVEPKSC DKTHTCPPCP APELLGGPSV  240
FLFPPKPKDT LMISRTPEVT CVVVDVSHED PEVKFNWYVD GVEVHNAKTK PREEQYASTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                   447

SEQ ID NO: 922          moltype = AA  length = 117
```

```
FEATURE                 Location/Qualifiers
REGION                  1..117
                        note = Humanized antibody sequence
source                  1..117
                        mol_type = protein
                        organism = synthetic construct
SEQUENCE: 922
QSVEESGGRL VTPGTPLTLT CTVSGFSLNN YAMSWVRQAP GKGLEWIGIM GVNDITYYAS  60
WAKGRFTISK TSTTVDLKMT SLTTEDTATY FCTREIRDDG DSSDKLWGPG TLVTVSS     117

SEQ ID NO: 923          moltype = AA  length = 29
FEATURE                 Location/Qualifiers
source                  1..29
                        mol_type = protein
                        organism = Oryctolagus cuniculus
SEQUENCE: 923
QSVEESGGRL VTPGTPLTLT CTVSGFSLN                                    29

SEQ ID NO: 924          moltype = AA  length = 5
FEATURE                 Location/Qualifiers
source                  1..5
                        mol_type = protein
                        organism = Oryctolagus cuniculus
SEQUENCE: 924
NYAMS                                                              5

SEQ ID NO: 925          moltype = AA  length = 14
FEATURE                 Location/Qualifiers
source                  1..14
                        mol_type = protein
                        organism = Oryctolagus cuniculus
SEQUENCE: 925
WVRQAPGKGL EWIG                                                    14

SEQ ID NO: 926          moltype = AA  length = 16
FEATURE                 Location/Qualifiers
source                  1..16
                        mol_type = protein
                        organism = Oryctolagus cuniculus
SEQUENCE: 926
IMGVNDITYY ASWAKG                                                  16

SEQ ID NO: 927          moltype = AA  length = 30
FEATURE                 Location/Qualifiers
source                  1..30
                        mol_type = protein
                        organism = Oryctolagus cuniculus
SEQUENCE: 927
RFTISKTSTT VDLKMTSLTT EDTATYFCTR                                   30

SEQ ID NO: 928          moltype = AA  length = 12
FEATURE                 Location/Qualifiers
source                  1..12
                        mol_type = protein
                        organism = Oryctolagus cuniculus
SEQUENCE: 928
EIRDDGDSSD KL                                                      12

SEQ ID NO: 929          moltype = AA  length = 11
FEATURE                 Location/Qualifiers
REGION                  1..11
                        note = Humanized antibody sequence
source                  1..11
                        mol_type = protein
                        organism = synthetic construct
SEQUENCE: 929
WGPGTLVTVS S                                                       11

SEQ ID NO: 930          moltype = AA  length = 330
FEATURE                 Location/Qualifiers
REGION                  1..330
                        note = Humanized antibody sequence
source                  1..330
                        mol_type = protein
                        organism = synthetic construct
SEQUENCE: 930
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDARVEP KSCDKTHTCP PCPAPELLGG  120
PSVFLFPPKP KDTLMISRTP EVTCVVVDVS HEDPEVKFNW YVDGVEVHNA KTKPREEQYA  180
```

```
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 931         moltype = DNA  length = 1341
FEATURE                Location/Qualifiers
misc_feature           1..1341
                       note = Humanized antibody sequence
source                 1..1341
                       mol_type = other DNA
                       organism = synthetic construct
SEQUENCE: 931
cagtcggtgg aggagtccgg gggtcgcctg gtcacgcctg ggacacccct gacactcacc  60
tgcaccgtct ctggattctc cctcaataac tatgcaatga gctgggtccg ccaggctcca  120
gggaaggggc tggaatggat cggaatcatg ggtgttaatg atatcacata ctacgcgagc  180
tgggcgaaag gccgattcac catctccaaa acctcgacca cggtggatct gaaaatgacc  240
agtctgacaa ccgaggacac ggccacctat ttctgtacta gagagatccg tgatgatggt  300
gatagttctg ataagttgtg gggcccgggc accctcgtca ccgtctcgag cgcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacgcga gagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacgc cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggagga gatgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagagc  1320
ctctccctgt ctccgggtaa a                                           1341

SEQ ID NO: 932         moltype = DNA  length = 351
FEATURE                Location/Qualifiers
misc_feature           1..351
                       note = Humanized antibody sequence
source                 1..351
                       mol_type = other DNA
                       organism = synthetic construct
SEQUENCE: 932
cagtcggtgg aggagtccgg gggtcgcctg gtcacgcctg ggacacccct gacactcacc  60
tgcaccgtct ctggattctc cctcaataac tatgcaatga gctgggtccg ccaggctcca  120
gggaaggggc tggaatggat cggaatcatg ggtgttaatg atatcacata ctacgcgagc  180
tgggcgaaag gccgattcac catctccaaa acctcgacca cggtggatct gaaaatgacc  240
agtctgacaa ccgaggacac ggccacctat ttctgtacta gagagatccg tgatgatggt  300
gatagttctg ataagttgtg gggcccgggc accctcgtca ccgtctcgag c          351

SEQ ID NO: 933         moltype = DNA  length = 87
FEATURE                Location/Qualifiers
source                 1..87
                       mol_type = unassigned DNA
                       organism = Oryctolagus cuniculus
SEQUENCE: 933
cagtcggtgg aggagtccgg gggtcgcctg gtcacgcctg ggacacccct gacactcacc  60
tgcaccgtct ctggattctc cctcaat                                     87

SEQ ID NO: 934         moltype = DNA  length = 15
FEATURE                Location/Qualifiers
source                 1..15
                       mol_type = unassigned DNA
                       organism = Oryctolagus cuniculus
SEQUENCE: 934
aactatgcaa tgagc                                                  15

SEQ ID NO: 935         moltype = DNA  length = 42
FEATURE                Location/Qualifiers
source                 1..42
                       mol_type = unassigned DNA
                       organism = Oryctolagus cuniculus
SEQUENCE: 935
tgggtccgcc aggctccagg gaaggggctg gaatggatcg ga                    42

SEQ ID NO: 936         moltype = DNA  length = 48
FEATURE                Location/Qualifiers
source                 1..48
```

```
                         mol_type = unassigned DNA
                         organism = Oryctolagus cuniculus
SEQUENCE: 936
atcatgggtg ttaatgatat cacatactac gcgagctggg cgaaaggc             48

SEQ ID NO: 937           moltype = DNA  length = 90
FEATURE                  Location/Qualifiers
source                   1..90
                         mol_type = unassigned DNA
                         organism = Oryctolagus cuniculus
SEQUENCE: 937
cgattcacca tctccaaaac ctcgaccacg gtggatctga aaatgaccag tctgacaacc  60
gaggacacgg ccacctattt ctgtactaga                                 90

SEQ ID NO: 938           moltype = DNA  length = 36
FEATURE                  Location/Qualifiers
source                   1..36
                         mol_type = unassigned DNA
                         organism = Oryctolagus cuniculus
SEQUENCE: 938
gagatccgtg atgatggtga tagttctgat aagttg                          36

SEQ ID NO: 939           moltype = DNA  length = 33
FEATURE                  Location/Qualifiers
misc_feature             1..33
                         note = Humanized antibody sequence
source                   1..33
                         mol_type = other DNA
                         organism = synthetic construct
SEQUENCE: 939
tggggcccgg gcaccctcgt caccgtctcg agc                             33

SEQ ID NO: 940           moltype = DNA  length = 990
FEATURE                  Location/Qualifiers
misc_feature             1..990
                         note = Humanized antibody sequence
source                   1..990
                         mol_type = other DNA
                         organism = synthetic construct
SEQUENCE: 940
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacgcgag agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                 990

SEQ ID NO: 941           moltype = AA  length = 219
FEATURE                  Location/Qualifiers
REGION                   1..219
                         note = Humanized antibody sequence
source                   1..219
                         mol_type = protein
                         organism = synthetic construct
SEQUENCE: 941
AIKMTQTPSS VSAAVGGTVT INCQASEDIY TNLAWYQQKP GQPPNLLIYD ASDLASGVPS  60
RFSGSGDGTQ FTLTISAVQC EDAATYYCQG VAWSSNTGYG SAFGGGTEVV VKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                       219

SEQ ID NO: 942           moltype = AA  length = 113
FEATURE                  Location/Qualifiers
REGION                   1..113
                         note = Humanized antibody sequence
source                   1..113
                         mol_type = protein
                         organism = synthetic construct
SEQUENCE: 942
```

```
AIKMTQTPSS VSAAVGGTVT INCQASEDIY TNLAWYQQKP GQPPNLLIYD ASDLASGVPS  60
RFSGSGDGTQ FTLTISAVQC EDAATYYCQG VAWSSNTGYG SAFGGGTEVV VKR         113

SEQ ID NO: 943         moltype = AA  length = 23
FEATURE                Location/Qualifiers
source                 1..23
                       mol_type = protein
                       organism = Oryctolagus cuniculus
SEQUENCE: 943
AIKMTQTPSS VSAAVGGTVT INC                                          23

SEQ ID NO: 944         moltype = AA  length = 11
FEATURE                Location/Qualifiers
source                 1..11
                       mol_type = protein
                       organism = Oryctolagus cuniculus
SEQUENCE: 944
QASEDIYTNL A                                                       11

SEQ ID NO: 945         moltype = AA  length = 15
FEATURE                Location/Qualifiers
source                 1..15
                       mol_type = protein
                       organism = Oryctolagus cuniculus
SEQUENCE: 945
WYQQKPGQPP NLLIY                                                   15

SEQ ID NO: 946         moltype = AA  length = 7
FEATURE                Location/Qualifiers
source                 1..7
                       mol_type = protein
                       organism = Oryctolagus cuniculus
SEQUENCE: 946
DASDLAS                                                            7

SEQ ID NO: 947         moltype = AA  length = 32
FEATURE                Location/Qualifiers
source                 1..32
                       mol_type = protein
                       organism = Oryctolagus cuniculus
SEQUENCE: 947
GVPSRFSGSG DGTQFTLTIS AVQCEDAATY YC                                32

SEQ ID NO: 948         moltype = AA  length = 14
FEATURE                Location/Qualifiers
source                 1..14
                       mol_type = protein
                       organism = Oryctolagus cuniculus
SEQUENCE: 948
QGVAWSSNTG YGSA                                                    14

SEQ ID NO: 949         moltype = AA  length = 11
FEATURE                Location/Qualifiers
REGION                 1..11
                       note = Humanized antibody sequence
source                 1..11
                       mol_type = protein
                       organism = synthetic construct
SEQUENCE: 949
FGGGTEVVVK R                                                       11

SEQ ID NO: 950         moltype = AA  length = 106
FEATURE                Location/Qualifiers
REGION                 1..106
                       note = Humanized antibody sequence
source                 1..106
                       mol_type = protein
                       organism = synthetic construct
SEQUENCE: 950
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 951         moltype = DNA  length = 657
FEATURE                Location/Qualifiers
misc_feature           1..657
                       note = Humanized antibody sequence
source                 1..657
                       mol_type = other DNA
                       organism = synthetic construct
```

```
SEQUENCE: 951
gccatcaaaa tgacccagac tccatcctcc gtgtctgcag ctgtgggagg cacagtcacc  60
atcaattgcc aggccagtga ggacatttac accaatttag cctggtatca gcagaaacca  120
gggcagcctc ccaacctcct gatctatgat gcatccgatc tggcatctgg ggtcccgtcg  180
cggttcagcg gcagtggaga tgggacacag ttcactctca ccatcagcgc cgtgcagtgt  240
gaagatgctg ccacttacta ctgtcaaggt gttgcttgga gtagtaatac tggttatggt  300
tccgctttcg gcggagggac cgaggtggtg gtcaaacgta cggtagcggc cccatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 952         moltype = DNA  length = 339
FEATURE                Location/Qualifiers
misc_feature           1..339
                       note = Humanized antibody sequence
source                 1..339
                       mol_type = other DNA
                       organism = synthetic construct
SEQUENCE: 952
gccatcaaaa tgacccagac tccatcctcc gtgtctgcag ctgtgggagg cacagtcacc  60
atcaattgcc aggccagtga ggacatttac accaatttag cctggtatca gcagaaacca  120
gggcagcctc ccaacctcct gatctatgat gcatccgatc tggcatctgg ggtcccgtcg  180
cggttcagcg gcagtggaga tgggacacag ttcactctca ccatcagcgc cgtgcagtgt  240
gaagatgctg ccacttacta ctgtcaaggt gttgcttgga gtagtaatac tggttatggt  300
tccgctttcg gcggagggac cgaggtggtg gtcaaacgt                         339

SEQ ID NO: 953         moltype = DNA  length = 69
FEATURE                Location/Qualifiers
source                 1..69
                       mol_type = unassigned DNA
                       organism = Oryctolagus cuniculus
SEQUENCE: 953
gccatcaaaa tgacccagac tccatcctcc gtgtctgcag ctgtgggagg cacagtcacc  60
atcaattgc                                                          69

SEQ ID NO: 954         moltype = DNA  length = 33
FEATURE                Location/Qualifiers
source                 1..33
                       mol_type = unassigned DNA
                       organism = Oryctolagus cuniculus
SEQUENCE: 954
caggccagtg aggacattta caccaattta gcc                               33

SEQ ID NO: 955         moltype = DNA  length = 45
FEATURE                Location/Qualifiers
source                 1..45
                       mol_type = unassigned DNA
                       organism = Oryctolagus cuniculus
SEQUENCE: 955
tggtatcagc agaaaccagg gcagcctccc aacctcctga tctat                  45

SEQ ID NO: 956         moltype = DNA  length = 21
FEATURE                Location/Qualifiers
source                 1..21
                       mol_type = unassigned DNA
                       organism = Oryctolagus cuniculus
SEQUENCE: 956
gatgcatccg atctggcatc t                                            21

SEQ ID NO: 957         moltype = DNA  length = 96
FEATURE                Location/Qualifiers
source                 1..96
                       mol_type = unassigned DNA
                       organism = Oryctolagus cuniculus
SEQUENCE: 957
ggggtcccgt cgcggttcag cggcagtgga gatgggacac agttcactct caccatcagc  60
gccgtgcagt gtgaagatgc tgccacttac tactgt                            96

SEQ ID NO: 958         moltype = DNA  length = 42
FEATURE                Location/Qualifiers
source                 1..42
                       mol_type = unassigned DNA
                       organism = Oryctolagus cuniculus
SEQUENCE: 958
caaggtgttg cttggagtag taatactggt tatggttccg ct                     42

SEQ ID NO: 959         moltype = DNA  length = 33
```

```
FEATURE               Location/Qualifiers
misc_feature          1..33
                      note = Humanized antibody sequence
source                1..33
                      mol_type = other DNA
                      organism = synthetic construct
SEQUENCE: 959
ttcggcggag ggaccgaggt ggtggtcaaa cgt                              33

SEQ ID NO: 960        moltype = DNA  length = 318
FEATURE               Location/Qualifiers
misc_feature          1..318
                      note = Humanized antibody sequence
source                1..318
                      mol_type = other DNA
                      organism = synthetic construct
SEQUENCE: 960
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318

SEQ ID NO: 961        moltype = AA  length = 442
FEATURE               Location/Qualifiers
REGION                1..442
                      note = Humanized antibody sequence
source                1..442
                      mol_type = protein
                      organism = synthetic construct
SEQUENCE: 961
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                           442

SEQ ID NO: 962        moltype = AA  length = 112
FEATURE               Location/Qualifiers
REGION                1..112
                      note = Humanized antibody sequence
source                1..112
                      mol_type = protein
                      organism = synthetic construct
SEQUENCE: 962
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SS          112

SEQ ID NO: 963        moltype = AA  length = 30
FEATURE               Location/Qualifiers
REGION                1..30
                      note = Humanized antibody sequence
source                1..30
                      mol_type = protein
                      organism = synthetic construct
SEQUENCE: 963
EVQLVESGGG LVQPGGSLRL SCAASGIDLN                                   30

SEQ ID NO: 964        moltype = AA  length = 5
FEATURE               Location/Qualifiers
source                1..5
                      mol_type = protein
                      organism = Oryctolagus cuniculus
SEQUENCE: 964
SYYMT                                                              5

SEQ ID NO: 965        moltype = AA  length = 14
FEATURE               Location/Qualifiers
REGION                1..14
                      note = Humanized antibody sequence
source                1..14
                      mol_type = protein
                      organism = synthetic construct
SEQUENCE: 965
WVRQAPGKGL EWIG                                                    14
```

```
SEQ ID NO: 966          moltype = AA  length = 16
FEATURE                 Location/Qualifiers
source                  1..16
                        mol_type = protein
                        organism = Oryctolagus cuniculus
SEQUENCE: 966
FIDAGGDAYY ASWAKG                                                  16

SEQ ID NO: 967          moltype = AA  length = 32
FEATURE                 Location/Qualifiers
REGION                  1..32
                        note = Humanized antibody sequence
source                  1..32
                        mol_type = protein
                        organism = synthetic construct
SEQUENCE: 967
RFTISRDNSK NTVYLQMNSL RAEDTAVYFC AR                                32

SEQ ID NO: 968          moltype = AA  length = 4
FEATURE                 Location/Qualifiers
source                  1..4
                        mol_type = protein
                        organism = Oryctolagus cuniculus
SEQUENCE: 968
DLDL                                                               4

SEQ ID NO: 969          moltype = AA  length = 11
FEATURE                 Location/Qualifiers
REGION                  1..11
                        note = Humanized antibody sequence
source                  1..11
                        mol_type = protein
                        organism = synthetic construct
SEQUENCE: 969
WGQGTLVTVS S                                                       11

SEQ ID NO: 970          moltype = AA  length = 330
FEATURE                 Location/Qualifiers
REGION                  1..330
                        note = Humanized antibody sequence
source                  1..330
                        mol_type = protein
                        organism = synthetic construct
SEQUENCE: 970
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 971          moltype = DNA  length = 1326
FEATURE                 Location/Qualifiers
misc_feature            1..1326
                        note = Humanized antibody sequence
source                  1..1326
                        mol_type = other DNA
                        organism = synthetic construct
SEQUENCE: 971
gaggtgcagc ttgtggagtc tgggggaggc ttggtccagc ctgggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
```

```
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                             1326

SEQ ID NO: 972          moltype = DNA  length = 336
FEATURE                 Location/Qualifiers
misc_feature            1..336
                        note = Humanized antibody sequence
source                  1..336
                        mol_type = other DNA
                        organism = synthetic construct
SEQUENCE: 972
gaggtgcagc ttgtggagtc tgggggaggc ttggtccagc ctgggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                            336

SEQ ID NO: 973          moltype = DNA  length = 90
FEATURE                 Location/Qualifiers
misc_feature            1..90
                        note = Humanized antibody sequence
source                  1..90
                        mol_type = other DNA
                        organism = synthetic construct
SEQUENCE: 973
gaggtgcagc ttgtggagtc tgggggaggc ttggtccagc ctgggggtc cctgagactc  60
tcctgtgcag cctctggaat cgacctcaat                                   90

SEQ ID NO: 974          moltype = DNA  length = 15
FEATURE                 Location/Qualifiers
source                  1..15
                        mol_type = unassigned DNA
                        organism = Oryctolagus cuniculus
SEQUENCE: 974
agctactaca tgacc                                                   15

SEQ ID NO: 975          moltype = DNA  length = 42
FEATURE                 Location/Qualifiers
misc_feature            1..42
                        note = Humanized antibody sequence
source                  1..42
                        mol_type = other DNA
                        organism = synthetic construct
SEQUENCE: 975
tgggtccgtc aggctccagg gaaggggctg gagtggatcg ga                     42

SEQ ID NO: 976          moltype = DNA  length = 48
FEATURE                 Location/Qualifiers
source                  1..48
                        mol_type = unassigned DNA
                        organism = Oryctolagus cuniculus
SEQUENCE: 976
ttcattgatg ctggtggtga cgcatactac gcgagctggg cgaaaggc               48

SEQ ID NO: 977          moltype = DNA  length = 96
FEATURE                 Location/Qualifiers
misc_feature            1..96
                        note = Humanized antibody sequence
source                  1..96
                        mol_type = other DNA
                        organism = synthetic construct
SEQUENCE: 977
cgattcacca tctccagaga caattccaag aacaccgtgt atcttcaaat gaacagcctg  60
agagctgagg acactgctgt gtatttctgt gctaga                            96

SEQ ID NO: 978          moltype = DNA  length = 12
FEATURE                 Location/Qualifiers
source                  1..12
                        mol_type = unassigned DNA
                        organism = Oryctolagus cuniculus
SEQUENCE: 978
gatcttgact tg                                                      12

SEQ ID NO: 979          moltype = DNA  length = 33
FEATURE                 Location/Qualifiers
misc_feature            1..33
```

```
                          note = Humanized antibody sequence
source                    1..33
                          mol_type = other DNA
                          organism = synthetic construct
SEQUENCE: 979
tggggccaag ggaccctcgt caccgtctcg agc                              33

SEQ ID NO: 980            moltype = DNA  length = 990
FEATURE                   Location/Qualifiers
misc_feature              1..990
                          note = Humanized antibody sequence
source                    1..990
                          mol_type = other DNA
                          organism = synthetic construct
SEQUENCE: 980
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                  990

SEQ ID NO: 981            moltype = AA  length = 216
FEATURE                   Location/Qualifiers
REGION                    1..216
                          note = Humanized antibody sequence
source                    1..216
                          mol_type = protein
                          organism = synthetic construct
SEQUENCE: 981
DAQLTQSPST LSASVGDRVT ITCQSSESVY GNYLAWFQQK PGKAPKFLIY EASKLESGVP  60
SRFSGSGSGT EFTLTISSLQ PDDFATYYCA GGDISEGVAF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 982            moltype = AA  length = 110
FEATURE                   Location/Qualifiers
REGION                    1..110
                          note = Humanized antibody sequence
source                    1..110
                          mol_type = protein
                          organism = synthetic construct
SEQUENCE: 982
DAQLTQSPST LSASVGDRVT ITCQSSESVY GNYLAWFQQK PGKAPKFLIY EASKLESGVP  60
SRFSGSGSGT EFTLTISSLQ PDDFATYYCA GGDISEGVAF GGGTKVEIKR             110

SEQ ID NO: 983            moltype = AA  length = 23
FEATURE                   Location/Qualifiers
REGION                    1..23
                          note = Humanized antibody sequence
source                    1..23
                          mol_type = protein
                          organism = synthetic construct
SEQUENCE: 983
DAQLTQSPST LSASVGDRVT ITC                                         23

SEQ ID NO: 984            moltype = AA  length = 12
FEATURE                   Location/Qualifiers
source                    1..12
                          mol_type = protein
                          organism = Oryctolagus cuniculus
SEQUENCE: 984
QSSESVYGNY LA                                                     12

SEQ ID NO: 985            moltype = AA  length = 15
FEATURE                   Location/Qualifiers
REGION                    1..15
                          note = Humanized antibody sequence
```

```
source                  1..15
                        mol_type = protein
                        organism = synthetic construct
SEQUENCE: 985
WFQQKPGKAP KFLIY                                                15

SEQ ID NO: 986          moltype = AA  length = 7
FEATURE                 Location/Qualifiers
source                  1..7
                        mol_type = protein
                        organism = Oryctolagus cuniculus
SEQUENCE: 986
EASKLES                                                         7

SEQ ID NO: 987          moltype = AA  length = 32
FEATURE                 Location/Qualifiers
REGION                  1..32
                        note = Humanized antibody sequence
source                  1..32
                        mol_type = protein
                        organism = synthetic construct
SEQUENCE: 987
GVPSRFSGSG SGTEFTLTIS SLQPDDFATY YC                             32

SEQ ID NO: 988          moltype = AA  length = 10
FEATURE                 Location/Qualifiers
source                  1..10
                        mol_type = protein
                        organism = Oryctolagus cuniculus
SEQUENCE: 988
AGGDISEGVA                                                      10

SEQ ID NO: 989          moltype = AA  length = 11
FEATURE                 Location/Qualifiers
REGION                  1..11
                        note = Humanized antibody sequence
source                  1..11
                        mol_type = protein
                        organism = synthetic construct
SEQUENCE: 989
FGGGTKVEIK R                                                    11

SEQ ID NO: 990          moltype = AA  length = 106
FEATURE                 Location/Qualifiers
REGION                  1..106
                        note = Humanized antibody sequence
source                  1..106
                        mol_type = protein
                        organism = synthetic construct
SEQUENCE: 990
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 991          moltype = DNA  length = 648
FEATURE                 Location/Qualifiers
misc_feature            1..648
                        note = Humanized antibody sequence
source                  1..648
                        mol_type = other DNA
                        organism = synthetic construct
SEQUENCE: 991
gacgcccagc tgacccagtc tccttccacc ctgtctgcat ctgtaggaga cagagtcacc  60
atcacttgtc agtccagtga gagtgtttac ggtaactact tagcctggtt tcagcagaaa  120
ccaggaaaag cccctaagtt cctgatctat gaagcatcca aactggaatc tggagtccca  180
tcaaggttca gcggcagtgg atctggaaca gaattcactc tcaccatcag cagcctgcag  240
cctgatgatt ttgcaactta ctactgtgca ggcggtgata ttagtgaagg tgttgctttc  300
ggcggaggaa ccaaggtgga aatcaaacgt acggtagcgg ccccatctgt cttcatcttc  360
ccgccatctg atgagcagtt gaaatctgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt              648

SEQ ID NO: 992          moltype = DNA  length = 330
FEATURE                 Location/Qualifiers
misc_feature            1..330
                        note = Humanized antibody sequence
source                  1..330
                        mol_type = other DNA
```

```
                         organism = synthetic construct
SEQUENCE: 992
gacgcccagc tgacccagtc tccttccacc ctgtctgcat ctgtaggaga cagagtcacc  60
atcacttgtc agtccagtga gagtgtttac ggtaactact tagcctggtt tcagcagaaa  120
ccaggaaaag cccctaagtt cctgatctat gaagcatcca aactggaatc tggagtccca  180
tcaaggttca gcggcagtgg atctggaaca gaattcactc tcaccatcag cagcctgcag  240
cctgatgatt ttgcaactta ctactgtgca ggcggtgata ttagtgaagg tgttgctttc  300
ggcggaggaa ccaaggtgga aatcaaacgt                                    330

SEQ ID NO: 993           moltype = DNA  length = 69
FEATURE                  Location/Qualifiers
misc_feature             1..69
                         note = Humanized antibody sequence
source                   1..69
                         mol_type = other DNA
                         organism = synthetic construct
SEQUENCE: 993
gacgcccagc tgacccagtc tccttccacc ctgtctgcat ctgtaggaga cagagtcacc  60
atcacttgt                                                           69

SEQ ID NO: 994           moltype = DNA  length = 36
FEATURE                  Location/Qualifiers
source                   1..36
                         mol_type = unassigned DNA
                         organism = Oryctolagus cuniculus
SEQUENCE: 994
cagtccagtg agagtgttta cggtaactac ttagcc                             36

SEQ ID NO: 995           moltype = DNA  length = 45
FEATURE                  Location/Qualifiers
misc_feature             1..45
                         note = Humanized antibody sequence
source                   1..45
                         mol_type = other DNA
                         organism = synthetic construct
SEQUENCE: 995
tggtttcagc agaaaccagg aaaagcccct aagttcctga tctat                   45

SEQ ID NO: 996           moltype = DNA  length = 21
FEATURE                  Location/Qualifiers
source                   1..21
                         mol_type = unassigned DNA
                         organism = Oryctolagus cuniculus
SEQUENCE: 996
gaagcatcca aactggaatc t                                             21

SEQ ID NO: 997           moltype = DNA  length = 96
FEATURE                  Location/Qualifiers
misc_feature             1..96
                         note = Humanized antibody sequence
source                   1..96
                         mol_type = other DNA
                         organism = synthetic construct
SEQUENCE: 997
ggagtcccat caaggttcag cggcagtgga tctggaacag aattcactct caccatcagc  60
agcctgcagc ctgatgattt tgcaacttac tactgt                             96

SEQ ID NO: 998           moltype = DNA  length = 30
FEATURE                  Location/Qualifiers
source                   1..30
                         mol_type = unassigned DNA
                         organism = Oryctolagus cuniculus
SEQUENCE: 998
gcaggcggtg atattagtga aggtgttgct                                    30

SEQ ID NO: 999           moltype = DNA  length = 33
FEATURE                  Location/Qualifiers
misc_feature             1..33
                         note = Humanized antibody sequence
source                   1..33
                         mol_type = other DNA
                         organism = synthetic construct
SEQUENCE: 999
ttcggcggag gaaccaaggt ggaaatcaaa cgt                                33

SEQ ID NO: 1000          moltype = DNA  length = 318
FEATURE                  Location/Qualifiers
misc_feature             1..318
                         note = Humanized antibody sequence
```

```
source                  1..318
                        mol_type = other DNA
                        organism = synthetic construct
SEQUENCE: 1000
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318

SEQ ID NO: 1001        moltype =   length =
SEQUENCE: 1001
000

SEQ ID NO: 1002        moltype =   length =
SEQUENCE: 1002
000

SEQ ID NO: 1003        moltype =   length =
SEQUENCE: 1003
000

SEQ ID NO: 1004        moltype =   length =
SEQUENCE: 1004
000

SEQ ID NO: 1005        moltype =   length =
SEQUENCE: 1005
000

SEQ ID NO: 1006        moltype =   length =
SEQUENCE: 1006
000

SEQ ID NO: 1007        moltype =   length =
SEQUENCE: 1007
000

SEQ ID NO: 1008        moltype =   length =
SEQUENCE: 1008
000

SEQ ID NO: 1009        moltype =   length =
SEQUENCE: 1009
000

SEQ ID NO: 1010        moltype =   length =
SEQUENCE: 1010
000

SEQ ID NO: 1011        moltype =   length =
SEQUENCE: 1011
000

SEQ ID NO: 1012        moltype =   length =
SEQUENCE: 1012
000

SEQ ID NO: 1013        moltype =   length =
SEQUENCE: 1013
000

SEQ ID NO: 1014        moltype =   length =
SEQUENCE: 1014
000

SEQ ID NO: 1015        moltype =   length =
SEQUENCE: 1015
000

SEQ ID NO: 1016        moltype =   length =
SEQUENCE: 1016
000

SEQ ID NO: 1017        moltype =   length =
SEQUENCE: 1017
000
```

SEQ ID NO: 1018 moltype = length =
SEQUENCE: 1018
000

SEQ ID NO: 1019 moltype = length =
SEQUENCE: 1019
000

SEQ ID NO: 1020 moltype = length =
SEQUENCE: 1020
000

SEQ ID NO: 1021 moltype = length =
SEQUENCE: 1021
000

SEQ ID NO: 1022 moltype = length =
SEQUENCE: 1022
000

SEQ ID NO: 1023 moltype = length =
SEQUENCE: 1023
000

SEQ ID NO: 1024 moltype = length =
SEQUENCE: 1024
000

SEQ ID NO: 1025 moltype = length =
SEQUENCE: 1025
000

SEQ ID NO: 1026 moltype = length =
SEQUENCE: 1026
000

SEQ ID NO: 1027 moltype = length =
SEQUENCE: 1027
000

SEQ ID NO: 1028 moltype = length =
SEQUENCE: 1028
000

SEQ ID NO: 1029 moltype = length =
SEQUENCE: 1029
000

SEQ ID NO: 1030 moltype = length =
SEQUENCE: 1030
000

SEQ ID NO: 1031 moltype = length =
SEQUENCE: 1031
000

SEQ ID NO: 1032 moltype = length =
SEQUENCE: 1032
000

SEQ ID NO: 1033 moltype = length =
SEQUENCE: 1033
000

SEQ ID NO: 1034 moltype = length =
SEQUENCE: 1034
000

SEQ ID NO: 1035 moltype = length =
SEQUENCE: 1035
000

SEQ ID NO: 1036 moltype = length =
SEQUENCE: 1036
000

SEQ ID NO: 1037 moltype = length =
SEQUENCE: 1037
000

SEQ ID NO: 1038 moltype = length =
SEQUENCE: 1038
000

SEQ ID NO: 1039 moltype = length =
SEQUENCE: 1039
000

SEQ ID NO: 1040 moltype = length =
SEQUENCE: 1040
000

SEQ ID NO: 1041 moltype = length =
SEQUENCE: 1041
000

SEQ ID NO: 1042 moltype = length =
SEQUENCE: 1042
000

SEQ ID NO: 1043 moltype = length =
SEQUENCE: 1043
000

SEQ ID NO: 1044 moltype = length =
SEQUENCE: 1044
000

SEQ ID NO: 1045 moltype = length =
SEQUENCE: 1045
000

SEQ ID NO: 1046 moltype = length =
SEQUENCE: 1046
000

SEQ ID NO: 1047 moltype = length =
SEQUENCE: 1047
000

SEQ ID NO: 1048 moltype = length =
SEQUENCE: 1048
000

SEQ ID NO: 1049 moltype = length =
SEQUENCE: 1049
000

SEQ ID NO: 1050 moltype = length =
SEQUENCE: 1050
000

SEQ ID NO: 1051 moltype = length =
SEQUENCE: 1051
000

SEQ ID NO: 1052 moltype = length =
SEQUENCE: 1052
000

SEQ ID NO: 1053 moltype = length =
SEQUENCE: 1053
000

SEQ ID NO: 1054 moltype = length =
SEQUENCE: 1054
000

SEQ ID NO: 1055 moltype = length =
SEQUENCE: 1055
000

SEQ ID NO: 1056 moltype = length =
SEQUENCE: 1056
000

SEQ ID NO: 1057 moltype = length =
SEQUENCE: 1057

000

SEQ ID NO: 1058 moltype = length =
SEQUENCE: 1058
000

SEQ ID NO: 1059 moltype = length =
SEQUENCE: 1059
000

SEQ ID NO: 1060 moltype = length =
SEQUENCE: 1060
000

SEQ ID NO: 1061 moltype = length =
SEQUENCE: 1061
000

SEQ ID NO: 1062 moltype = length =
SEQUENCE: 1062
000

SEQ ID NO: 1063 moltype = length =
SEQUENCE: 1063
000

SEQ ID NO: 1064 moltype = length =
SEQUENCE: 1064
000

SEQ ID NO: 1065 moltype = length =
SEQUENCE: 1065
000

SEQ ID NO: 1066 moltype = length =
SEQUENCE: 1066
000

SEQ ID NO: 1067 moltype = length =
SEQUENCE: 1067
000

SEQ ID NO: 1068 moltype = length =
SEQUENCE: 1068
000

SEQ ID NO: 1069 moltype = length =
SEQUENCE: 1069
000

SEQ ID NO: 1070 moltype = length =
SEQUENCE: 1070
000

SEQ ID NO: 1071 moltype = length =
SEQUENCE: 1071
000

SEQ ID NO: 1072 moltype = length =
SEQUENCE: 1072
000

SEQ ID NO: 1073 moltype = length =
SEQUENCE: 1073
000

SEQ ID NO: 1074 moltype = length =
SEQUENCE: 1074
000

SEQ ID NO: 1075 moltype = length =
SEQUENCE: 1075
000

SEQ ID NO: 1076 moltype = length =
SEQUENCE: 1076
000

SEQ ID NO: 1077 moltype = length =

SEQUENCE: 1077
000

SEQ ID NO: 1078 moltype = length =
SEQUENCE: 1078
000

SEQ ID NO: 1079 moltype = length =
SEQUENCE: 1079
000

SEQ ID NO: 1080 moltype = length =
SEQUENCE: 1080
000

SEQ ID NO: 1081 moltype = length =
SEQUENCE: 1081
000

SEQ ID NO: 1082 moltype = length =
SEQUENCE: 1082
000

SEQ ID NO: 1083 moltype = length =
SEQUENCE: 1083
000

SEQ ID NO: 1084 moltype = length =
SEQUENCE: 1084
000

SEQ ID NO: 1085 moltype = length =
SEQUENCE: 1085
000

SEQ ID NO: 1086 moltype = length =
SEQUENCE: 1086
000

SEQ ID NO: 1087 moltype = length =
SEQUENCE: 1087
000

SEQ ID NO: 1088 moltype = length =
SEQUENCE: 1088
000

SEQ ID NO: 1089 moltype = length =
SEQUENCE: 1089
000

SEQ ID NO: 1090 moltype = length =
SEQUENCE: 1090
000

SEQ ID NO: 1091 moltype = length =
SEQUENCE: 1091
000

SEQ ID NO: 1092 moltype = length =
SEQUENCE: 1092
000

SEQ ID NO: 1093 moltype = length =
SEQUENCE: 1093
000

SEQ ID NO: 1094 moltype = length =
SEQUENCE: 1094
000

SEQ ID NO: 1095 moltype = length =
SEQUENCE: 1095
000

SEQ ID NO: 1096 moltype = length =
SEQUENCE: 1096
000

SEQ ID NO: 1097 moltype = length =
SEQUENCE: 1097
000

SEQ ID NO: 1098 moltype = length =
SEQUENCE: 1098
000

SEQ ID NO: 1099 moltype = length =
SEQUENCE: 1099
000

SEQ ID NO: 1100 moltype = length =
SEQUENCE: 1100
000

SEQ ID NO: 1101 moltype = length =
SEQUENCE: 1101
000

SEQ ID NO: 1102 moltype = length =
SEQUENCE: 1102
000

SEQ ID NO: 1103 moltype = length =
SEQUENCE: 1103
000

SEQ ID NO: 1104 moltype = length =
SEQUENCE: 1104
000

SEQ ID NO: 1105 moltype = length =
SEQUENCE: 1105
000

SEQ ID NO: 1106 moltype = length =
SEQUENCE: 1106
000

SEQ ID NO: 1107 moltype = length =
SEQUENCE: 1107
000

SEQ ID NO: 1108 moltype = length =
SEQUENCE: 1108
000

SEQ ID NO: 1109 moltype = length =
SEQUENCE: 1109
000

SEQ ID NO: 1110 moltype = length =
SEQUENCE: 1110
000

SEQ ID NO: 1111 moltype = length =
SEQUENCE: 1111
000

SEQ ID NO: 1112 moltype = length =
SEQUENCE: 1112
000

SEQ ID NO: 1113 moltype = length =
SEQUENCE: 1113
000

SEQ ID NO: 1114 moltype = length =
SEQUENCE: 1114
000

SEQ ID NO: 1115 moltype = length =
SEQUENCE: 1115
000

SEQ ID NO: 1116 moltype = length =
SEQUENCE: 1116
000

SEQ ID NO: 1117 moltype = length =
SEQUENCE: 1117
000

SEQ ID NO: 1118 moltype = length =
SEQUENCE: 1118
000

SEQ ID NO: 1119 moltype = length =
SEQUENCE: 1119
000

SEQ ID NO: 1120 moltype = length =
SEQUENCE: 1120
000

SEQ ID NO: 1121 moltype = length =
SEQUENCE: 1121
000

SEQ ID NO: 1122 moltype = length =
SEQUENCE: 1122
000

SEQ ID NO: 1123 moltype = length =
SEQUENCE: 1123
000

SEQ ID NO: 1124 moltype = length =
SEQUENCE: 1124
000

SEQ ID NO: 1125 moltype = length =
SEQUENCE: 1125
000

SEQ ID NO: 1126 moltype = length =
SEQUENCE: 1126
000

SEQ ID NO: 1127 moltype = length =
SEQUENCE: 1127
000

SEQ ID NO: 1128 moltype = length =
SEQUENCE: 1128
000

SEQ ID NO: 1129 moltype = length =
SEQUENCE: 1129
000

SEQ ID NO: 1130 moltype = length =
SEQUENCE: 1130
000

SEQ ID NO: 1131 moltype = length =
SEQUENCE: 1131
000

SEQ ID NO: 1132 moltype = length =
SEQUENCE: 1132
000

SEQ ID NO: 1133 moltype = length =
SEQUENCE: 1133
000

SEQ ID NO: 1134 moltype = length =
SEQUENCE: 1134
000

SEQ ID NO: 1135 moltype = length =
SEQUENCE: 1135
000

SEQ ID NO: 1136 moltype = length =
SEQUENCE: 1136

000

SEQ ID NO: 1137 moltype = length =
SEQUENCE: 1137
000

SEQ ID NO: 1138 moltype = length =
SEQUENCE: 1138
000

SEQ ID NO: 1139 moltype = length =
SEQUENCE: 1139
000

SEQ ID NO: 1140 moltype = length =
SEQUENCE: 1140
000

SEQ ID NO: 1141 moltype = length =
SEQUENCE: 1141
000

SEQ ID NO: 1142 moltype = length =
SEQUENCE: 1142
000

SEQ ID NO: 1143 moltype = length =
SEQUENCE: 1143
000

SEQ ID NO: 1144 moltype = length =
SEQUENCE: 1144
000

SEQ ID NO: 1145 moltype = length =
SEQUENCE: 1145
000

SEQ ID NO: 1146 moltype = length =
SEQUENCE: 1146
000

SEQ ID NO: 1147 moltype = length =
SEQUENCE: 1147
000

SEQ ID NO: 1148 moltype = length =
SEQUENCE: 1148
000

SEQ ID NO: 1149 moltype = length =
SEQUENCE: 1149
000

SEQ ID NO: 1150 moltype = length =
SEQUENCE: 1150
000

SEQ ID NO: 1151 moltype = length =
SEQUENCE: 1151
000

SEQ ID NO: 1152 moltype = length =
SEQUENCE: 1152
000

SEQ ID NO: 1153 moltype = length =
SEQUENCE: 1153
000

SEQ ID NO: 1154 moltype = length =
SEQUENCE: 1154
000

SEQ ID NO: 1155 moltype = length =
SEQUENCE: 1155
000

SEQ ID NO: 1156 moltype = length =

SEQUENCE: 1156
000

SEQ ID NO: 1157 moltype = length =
SEQUENCE: 1157
000

SEQ ID NO: 1158 moltype = length =
SEQUENCE: 1158
000

SEQ ID NO: 1159 moltype = length =
SEQUENCE: 1159
000

SEQ ID NO: 1160 moltype = length =
SEQUENCE: 1160
000

SEQ ID NO: 1161 moltype = length =
SEQUENCE: 1161
000

SEQ ID NO: 1162 moltype = length =
SEQUENCE: 1162
000

SEQ ID NO: 1163 moltype = length =
SEQUENCE: 1163
000

SEQ ID NO: 1164 moltype = length =
SEQUENCE: 1164
000

SEQ ID NO: 1165 moltype = length =
SEQUENCE: 1165
000

SEQ ID NO: 1166 moltype = length =
SEQUENCE: 1166
000

SEQ ID NO: 1167 moltype = length =
SEQUENCE: 1167
000

SEQ ID NO: 1168 moltype = length =
SEQUENCE: 1168
000

SEQ ID NO: 1169 moltype = length =
SEQUENCE: 1169
000

SEQ ID NO: 1170 moltype = length =
SEQUENCE: 1170
000

SEQ ID NO: 1171 moltype = length =
SEQUENCE: 1171
000

SEQ ID NO: 1172 moltype = length =
SEQUENCE: 1172
000

SEQ ID NO: 1173 moltype = length =
SEQUENCE: 1173
000

SEQ ID NO: 1174 moltype = length =
SEQUENCE: 1174
000

SEQ ID NO: 1175 moltype = length =
SEQUENCE: 1175
000

SEQ ID NO: 1176 moltype = length =
SEQUENCE: 1176
000

SEQ ID NO: 1177 moltype = length =
SEQUENCE: 1177
000

SEQ ID NO: 1178 moltype = length =
SEQUENCE: 1178
000

SEQ ID NO: 1179 moltype = length =
SEQUENCE: 1179
000

SEQ ID NO: 1180 moltype = length =
SEQUENCE: 1180
000

SEQ ID NO: 1181 moltype = length =
SEQUENCE: 1181
000

SEQ ID NO: 1182 moltype = length =
SEQUENCE: 1182
000

SEQ ID NO: 1183 moltype = length =
SEQUENCE: 1183
000

SEQ ID NO: 1184 moltype = length =
SEQUENCE: 1184
000

SEQ ID NO: 1185 moltype = length =
SEQUENCE: 1185
000

SEQ ID NO: 1186 moltype = length =
SEQUENCE: 1186
000

SEQ ID NO: 1187 moltype = length =
SEQUENCE: 1187
000

SEQ ID NO: 1188 moltype = length =
SEQUENCE: 1188
000

SEQ ID NO: 1189 moltype = length =
SEQUENCE: 1189
000

SEQ ID NO: 1190 moltype = length =
SEQUENCE: 1190
000

SEQ ID NO: 1191 moltype = length =
SEQUENCE: 1191
000

SEQ ID NO: 1192 moltype = length =
SEQUENCE: 1192
000

SEQ ID NO: 1193 moltype = length =
SEQUENCE: 1193
000

SEQ ID NO: 1194 moltype = length =
SEQUENCE: 1194
000

SEQ ID NO: 1195 moltype = length =
SEQUENCE: 1195
000

```
SEQ ID NO: 1196        moltype =   length =
SEQUENCE: 1196
000

SEQ ID NO: 1197        moltype =   length =
SEQUENCE: 1197
000

SEQ ID NO: 1198        moltype =   length =
SEQUENCE: 1198
000

SEQ ID NO: 1199        moltype =   length =
SEQUENCE: 1199
000

SEQ ID NO: 1200        moltype =   length =
SEQUENCE: 1200
000

SEQ ID NO: 1201        moltype = AA  length = 442
FEATURE                Location/Qualifiers
REGION                 1..442
                       note = Humanized antibody sequence
source                 1..442
                       mol_type = protein
                       organism = synthetic construct
SEQUENCE: 1201
EVQLVESGGG LVQPGGSLRL SCAASGIDLS SYYMTWVRQA PGKGLEWIGF IDAGGSAYYA  60
TWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                          442

SEQ ID NO: 1202        moltype = AA  length = 112
FEATURE                Location/Qualifiers
REGION                 1..112
                       note = Humanized antibody sequence
source                 1..112
                       mol_type = protein
                       organism = synthetic construct
SEQUENCE: 1202
EVQLVESGGG LVQPGGSLRL SCAASGIDLS SYYMTWVRQA PGKGLEWIGF IDAGGSAYYA  60
TWAKGRFTIS RDNSKNTVYL QMNSLRAEDT AVYFCARDLD LWGQGTLVTV SS          112

SEQ ID NO: 1203        moltype = AA  length = 30
FEATURE                Location/Qualifiers
REGION                 1..30
                       note = Humanized antibody sequence
source                 1..30
                       mol_type = protein
                       organism = synthetic construct
SEQUENCE: 1203
EVQLVESGGG LVQPGGSLRL SCAASGIDLS                                  30

SEQ ID NO: 1204        moltype = AA  length = 5
FEATURE                Location/Qualifiers
source                 1..5
                       mol_type = protein
                       organism = Oryctolagus cuniculus
SEQUENCE: 1204
SYYMT                                                             5

SEQ ID NO: 1205        moltype = AA  length = 14
FEATURE                Location/Qualifiers
REGION                 1..14
                       note = Humanized antibody sequence
source                 1..14
                       mol_type = protein
                       organism = synthetic construct
SEQUENCE: 1205
WVRQAPGKGL EWIG                                                   14

SEQ ID NO: 1206        moltype = AA  length = 16
FEATURE                Location/Qualifiers
```

```
source                  1..16
                        mol_type = protein
                        organism = Oryctolagus cuniculus
SEQUENCE: 1206
FIDAGGSAYY ATWAKG                                            16

SEQ ID NO: 1207         moltype = AA  length = 32
FEATURE                 Location/Qualifiers
REGION                  1..32
                        note = Humanized antibody sequence
source                  1..32
                        mol_type = protein
                        organism = synthetic construct
SEQUENCE: 1207
RFTISRDNSK NTVYLQMNSL RAEDTAVYFC AR                          32

SEQ ID NO: 1208         moltype = AA  length = 4
FEATURE                 Location/Qualifiers
source                  1..4
                        mol_type = protein
                        organism = Oryctolagus cuniculus
SEQUENCE: 1208
DLDL                                                         4

SEQ ID NO: 1209         moltype = AA  length = 11
FEATURE                 Location/Qualifiers
REGION                  1..11
                        note = Humanized antibody sequence
source                  1..11
                        mol_type = protein
                        organism = synthetic construct
SEQUENCE: 1209
WGQGTLVTVS S                                                 11

SEQ ID NO: 1210         moltype = AA  length = 330
FEATURE                 Location/Qualifiers
REGION                  1..330
                        note = Humanized antibody sequence
source                  1..330
                        mol_type = protein
                        organism = synthetic construct
SEQUENCE: 1210
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                             330

SEQ ID NO: 1211         moltype = DNA  length = 1326
FEATURE                 Location/Qualifiers
misc_feature            1..1326
                        note = Humanized antibody sequence
source                  1..1326
                        mol_type = other DNA
                        organism = synthetic construct
SEQUENCE: 1211
gaggtgcagc ttgtggagtc tgggggaggc ttggtccagc ctggggggtc cctgagactc  60
tcctgtgcag cctctggaat cgacctcagt agctactaca tgacctgggt ccgtcaggct  120
ccagggaagg ggctggagtg gatcggattc attgatgctg gtggtagcgc atactacgcg  180
acctgggcaa aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
```

```
ggtaaa                                                          1326

SEQ ID NO: 1212        moltype = DNA  length = 336
FEATURE                Location/Qualifiers
misc_feature           1..336
                       note = Humanized antibody sequence
source                 1..336
                       mol_type = other DNA
                       organism = synthetic construct
SEQUENCE: 1212
gaggtgcagc ttgtggagtc tgggggaggc ttggtccagc ctgggggtc cctgagactc  60
tcctgtgcag cctctggaat cgacctcagt agctactaca tgacctgggt ccgtcaggct  120
ccagggaagg ggctggagtg gatcggattc attgatgctg gtggtagcgc atactacgcg  180
acctgggcaa aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                         336

SEQ ID NO: 1213        moltype = DNA  length = 90
FEATURE                Location/Qualifiers
misc_feature           1..90
                       note = Humanized antibody sequence
source                 1..90
                       mol_type = other DNA
                       organism = synthetic construct
SEQUENCE: 1213
gaggtgcagc ttgtggagtc tgggggaggc ttggtccagc ctgggggtc cctgagactc  60
tcctgtgcag cctctggaat cgacctcagt                                 90

SEQ ID NO: 1214        moltype = DNA  length = 15
FEATURE                Location/Qualifiers
source                 1..15
                       mol_type = unassigned DNA
                       organism = Oryctolagus cuniculus
SEQUENCE: 1214
agctactaca tgacc                                                 15

SEQ ID NO: 1215        moltype = DNA  length = 42
FEATURE                Location/Qualifiers
misc_feature           1..42
                       note = Humanized antibody sequence
source                 1..42
                       mol_type = other DNA
                       organism = synthetic construct
SEQUENCE: 1215
tgggtccgtc aggctccagg gaaggggctg gagtggatcg ga                   42

SEQ ID NO: 1216        moltype = DNA  length = 48
FEATURE                Location/Qualifiers
source                 1..48
                       mol_type = unassigned DNA
                       organism = Oryctolagus cuniculus
SEQUENCE: 1216
ttcattgatg ctggtggtag cgcatactac gcgacctggg caaaaggc             48

SEQ ID NO: 1217        moltype = DNA  length = 96
FEATURE                Location/Qualifiers
misc_feature           1..96
                       note = Humanized antibody sequence
source                 1..96
                       mol_type = other DNA
                       organism = synthetic construct
SEQUENCE: 1217
cgattcacca tctccagaga caattccaag aacaccgtgt atcttcaaat gaacagcctg  60
agagctgagg acactgctgt gtatttctgt gctaga                          96

SEQ ID NO: 1218        moltype = DNA  length = 12
FEATURE                Location/Qualifiers
source                 1..12
                       mol_type = unassigned DNA
                       organism = Oryctolagus cuniculus
SEQUENCE: 1218
gatcttgact tg                                                    12

SEQ ID NO: 1219        moltype = DNA  length = 33
FEATURE                Location/Qualifiers
misc_feature           1..33
                       note = Humanized antibody sequence
source                 1..33
                       mol_type = other DNA
```

```
                         organism = synthetic construct
SEQUENCE: 1219
tggggccaag ggaccctcgt caccgtctcg agc                            33

SEQ ID NO: 1220          moltype = DNA  length = 990
FEATURE                  Location/Qualifiers
misc_feature             1..990
                         note = Humanized antibody sequence
source                   1..990
                         mol_type = other DNA
                         organism = synthetic construct
SEQUENCE: 1220
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                 990

SEQ ID NO: 1221          moltype = AA  length = 216
FEATURE                  Location/Qualifiers
REGION                   1..216
                         note = Humanized antibody sequence
source                   1..216
                         mol_type = protein
                         organism = synthetic construct
SEQUENCE: 1221
DAQLTQSPST LSASVGDRVT ITCKSSESVY GDYLAWFQQK PGKAPKQLIY DASTLASGVP  60
SRFSGSGSGT EFTLTISSLQ PDDFATYYCA GGYVSAGVAF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                          216

SEQ ID NO: 1222          moltype = AA  length = 110
FEATURE                  Location/Qualifiers
REGION                   1..110
                         note = Humanized antibody sequence
source                   1..110
                         mol_type = protein
                         organism = synthetic construct
SEQUENCE: 1222
DAQLTQSPST LSASVGDRVT ITCKSSESVY GDYLAWFQQK PGKAPKQLIY DASTLASGVP  60
SRFSGSGSGT EFTLTISSLQ PDDFATYYCA GGYVSAGVAF GGGTKVEIKR            110

SEQ ID NO: 1223          moltype = AA  length = 23
FEATURE                  Location/Qualifiers
REGION                   1..23
                         note = Humanized antibody sequence
source                   1..23
                         mol_type = protein
                         organism = synthetic construct
SEQUENCE: 1223
DAQLTQSPST LSASVGDRVT ITC                                       23

SEQ ID NO: 1224          moltype = AA  length = 12
FEATURE                  Location/Qualifiers
source                   1..12
                         mol_type = protein
                         organism = Oryctolagus cuniculus
SEQUENCE: 1224
KSSESVYGDY LA                                                   12

SEQ ID NO: 1225          moltype = AA  length = 15
FEATURE                  Location/Qualifiers
REGION                   1..15
                         note = Humanized antibody sequence
source                   1..15
                         mol_type = protein
                         organism = synthetic construct
```

```
SEQUENCE: 1225
WFQQKPGKAP KQLIY                                                   15

SEQ ID NO: 1226        moltype = AA  length = 7
FEATURE                Location/Qualifiers
source                 1..7
                       mol_type = protein
                       organism = Oryctolagus cuniculus
SEQUENCE: 1226
DASTLAS                                                            7

SEQ ID NO: 1227        moltype = AA  length = 32
FEATURE                Location/Qualifiers
REGION                 1..32
                       note = Humanized antibody sequence
source                 1..32
                       mol_type = protein
                       organism = synthetic construct
SEQUENCE: 1227
GVPSRFSGSG SGTEFTLTIS SLQPDDFATY YC                                32

SEQ ID NO: 1228        moltype = AA  length = 10
FEATURE                Location/Qualifiers
source                 1..10
                       mol_type = protein
                       organism = Oryctolagus cuniculus
SEQUENCE: 1228
AGGYVSAGVA                                                         10

SEQ ID NO: 1229        moltype = AA  length = 11
FEATURE                Location/Qualifiers
REGION                 1..11
                       note = Humanized antibody sequence
source                 1..11
                       mol_type = protein
                       organism = synthetic construct
SEQUENCE: 1229
FGGGTKVEIK R                                                       11

SEQ ID NO: 1230        moltype = AA  length = 106
FEATURE                Location/Qualifiers
REGION                 1..106
                       note = Humanized antibody sequence
source                 1..106
                       mol_type = protein
                       organism = synthetic construct
SEQUENCE: 1230
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 1231        moltype = DNA  length = 648
FEATURE                Location/Qualifiers
misc_feature           1..648
                       note = Humanized antibody sequence
source                 1..648
                       mol_type = other DNA
                       organism = synthetic construct
SEQUENCE: 1231
gacgcccagc tgacccagtc tccttccacc ctgtctgcat ctgtaggaga cagagtcacc  60
atcacttgta agtccagtga gagcgtttat ggtgactact tagcctggtt tcagcagaaa  120
ccaggaaaag cccctaagca actgatctat gatgcatcca ctctggcatc tggagtccca  180
tcaaggttca gcggcagtgg atctggaaca gaattcactc tcaccatcag cagcctgcag  240
cctgatgatt ttgcaactta ctactgtgca ggcggttatg ttagtgcagg tgttgctttc  300
ggcggaggaa ccaaggtgga aatcaaacgt acggtagcgg ccccatctgt cttcatcttc  360
ccgccatctg atgagcagtt gaaatctgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt               648

SEQ ID NO: 1232        moltype = DNA  length = 330
FEATURE                Location/Qualifiers
misc_feature           1..330
                       note = Humanized antibody sequence
source                 1..330
                       mol_type = other DNA
                       organism = synthetic construct
SEQUENCE: 1232
gacgcccagc tgacccagtc tccttccacc ctgtctgcat ctgtaggaga cagagtcacc  60
```

```
atcacttgta agtccagtga gagcgtttat ggtgactact tagcctggtt tcagcagaaa  120
ccaggaaaag cccctaagca actgatctat gatgcatcca ctctggcatc tggagtccca  180
tcaaggttca gcggcagtgg atctggaaca gaattcactc tcaccatcag cagcctgcag  240
cctgatgatt ttgcaactta ctactgtgca ggcggttatg ttagtgcagg tgttgctttc  300
ggcggaggaa ccaaggtgga aatcaaacgt                                  330

SEQ ID NO: 1233        moltype = DNA  length = 69
FEATURE                Location/Qualifiers
misc_feature           1..69
                       note = Humanized antibody sequence
source                 1..69
                       mol_type = other DNA
                       organism = synthetic construct
SEQUENCE: 1233
gacgcccagc tgacccagtc tccttccacc ctgtctgcat ctgtaggaga cagagtcacc  60
atcacttgt                                                         69

SEQ ID NO: 1234        moltype = DNA  length = 36
FEATURE                Location/Qualifiers
source                 1..36
                       mol_type = unassigned DNA
                       organism = Oryctolagus cuniculus
SEQUENCE: 1234
aagtccagtg agagcgttta tggtgactac ttagcc                           36

SEQ ID NO: 1235        moltype = DNA  length = 45
FEATURE                Location/Qualifiers
misc_feature           1..45
                       note = Humanized antibody sequence
source                 1..45
                       mol_type = other DNA
                       organism = synthetic construct
SEQUENCE: 1235
tggtttcagc agaaaccagg aaaagcccct aagcaactga tctat                 45

SEQ ID NO: 1236        moltype = DNA  length = 21
FEATURE                Location/Qualifiers
source                 1..21
                       mol_type = unassigned DNA
                       organism = Oryctolagus cuniculus
SEQUENCE: 1236
gatgcatcca ctctggcatc t                                           21

SEQ ID NO: 1237        moltype = DNA  length = 96
FEATURE                Location/Qualifiers
misc_feature           1..96
                       note = Humanized antibody sequence
source                 1..96
                       mol_type = other DNA
                       organism = synthetic construct
SEQUENCE: 1237
ggagtcccat caaggttcag cggcagtgga tctggaacag aattcactct caccatcagc  60
agcctgcagc ctgatgattt tgcaacttac tactgt                           96

SEQ ID NO: 1238        moltype = DNA  length = 30
FEATURE                Location/Qualifiers
source                 1..30
                       mol_type = unassigned DNA
                       organism = Oryctolagus cuniculus
SEQUENCE: 1238
gcaggcggtt atgttagtgc aggtgttgct                                  30

SEQ ID NO: 1239        moltype = DNA  length = 33
FEATURE                Location/Qualifiers
misc_feature           1..33
                       note = Humanized antibody sequence
source                 1..33
                       mol_type = other DNA
                       organism = synthetic construct
SEQUENCE: 1239
ttcggcggag gaaccaaggt ggaaatcaaa cgt                              33

SEQ ID NO: 1240        moltype = DNA  length = 318
FEATURE                Location/Qualifiers
misc_feature           1..318
                       note = Humanized antibody sequence
source                 1..318
                       mol_type = other DNA
                       organism = synthetic construct
```

```
SEQUENCE: 1240
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318

SEQ ID NO: 1241        moltype = AA  length = 38
FEATURE                Location/Qualifiers
MOD_RES                38
                       note = AMIDATION
source                 1..38
                       mol_type = protein
                       organism = Homo sapiens
SEQUENCE: 1241
HSDGIFTDSY SRYRKQMAVK KYLAAVLGKR YKQRVKNK                          38

SEQ ID NO: 1242        moltype = AA  length = 27
FEATURE                Location/Qualifiers
MOD_RES                27
                       note = AMIDATION
source                 1..27
                       mol_type = protein
                       organism = Homo sapiens
SEQUENCE: 1242
HSDGIFTDSY SRYRKQMAVK KYLAAVL                                      27

SEQ ID NO: 1243        moltype = AA  length = 28
FEATURE                Location/Qualifiers
MOD_RES                28
                       note = AMIDATION
source                 1..28
                       mol_type = protein
                       organism = Homo sapiens
SEQUENCE: 1243
HSDAVFTDNY TRLRKQMAVK KYLNSILN                                     28

SEQ ID NO: 1244        moltype = AA  length = 330
FEATURE                Location/Qualifiers
REGION                 1..330
                       note = Humanized antibody sequence
source                 1..330
                       mol_type = protein
                       organism = synthetic construct
SEQUENCE: 1244
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 1245        moltype = AA  length = 330
FEATURE                Location/Qualifiers
REGION                 1..330
                       note = Humanized antibody sequence
source                 1..330
                       mol_type = protein
                       organism = synthetic construct
SEQUENCE: 1245
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDARVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 1246        moltype = AA  length = 330
FEATURE                Location/Qualifiers
REGION                 1..330
                       note = Humanized antibody sequence
source                 1..330
                       mol_type = protein
                       organism = synthetic construct
SEQUENCE: 1246
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
```

```
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 1247        moltype =   length =
SEQUENCE: 1247
000

SEQ ID NO: 1248        moltype =   length =
SEQUENCE: 1248
000

SEQ ID NO: 1249        moltype =   length =
SEQUENCE: 1249
000

SEQ ID NO: 1250        moltype =   length =
SEQUENCE: 1250
000

SEQ ID NO: 1251        moltype =   length =
SEQUENCE: 1251
000

SEQ ID NO: 1252        moltype =   length =
SEQUENCE: 1252
000

SEQ ID NO: 1253        moltype =   length =
SEQUENCE: 1253
000

SEQ ID NO: 1254        moltype =   length =
SEQUENCE: 1254
000

SEQ ID NO: 1255        moltype =   length =
SEQUENCE: 1255
000

SEQ ID NO: 1256        moltype =   length =
SEQUENCE: 1256
000

SEQ ID NO: 1257        moltype =   length =
SEQUENCE: 1257
000

SEQ ID NO: 1258        moltype =   length =
SEQUENCE: 1258
000

SEQ ID NO: 1259        moltype =   length =
SEQUENCE: 1259
000

SEQ ID NO: 1260        moltype =   length =
SEQUENCE: 1260
000

SEQ ID NO: 1261        moltype =   length =
SEQUENCE: 1261
000

SEQ ID NO: 1262        moltype =   length =
SEQUENCE: 1262
000

SEQ ID NO: 1263        moltype =   length =
SEQUENCE: 1263
000

SEQ ID NO: 1264        moltype =   length =
SEQUENCE: 1264
000

SEQ ID NO: 1265        moltype =   length =
SEQUENCE: 1265
000
```

SEQ ID NO: 1266 moltype = length =
SEQUENCE: 1266
000

SEQ ID NO: 1267 moltype = length =
SEQUENCE: 1267
000

SEQ ID NO: 1268 moltype = length =
SEQUENCE: 1268
000

SEQ ID NO: 1269 moltype = length =
SEQUENCE: 1269
000

SEQ ID NO: 1270 moltype = length =
SEQUENCE: 1270
000

SEQ ID NO: 1271 moltype = length =
SEQUENCE: 1271
000

SEQ ID NO: 1272 moltype = length =
SEQUENCE: 1272
000

SEQ ID NO: 1273 moltype = length =
SEQUENCE: 1273
000

SEQ ID NO: 1274 moltype = length =
SEQUENCE: 1274
000

SEQ ID NO: 1275 moltype = length =
SEQUENCE: 1275
000

SEQ ID NO: 1276 moltype = length =
SEQUENCE: 1276
000

SEQ ID NO: 1277 moltype = length =
SEQUENCE: 1277
000

SEQ ID NO: 1278 moltype = length =
SEQUENCE: 1278
000

SEQ ID NO: 1279 moltype = length =
SEQUENCE: 1279
000

SEQ ID NO: 1280 moltype = length =
SEQUENCE: 1280
000

```
SEQ ID NO: 1281        moltype = AA  length = 442
FEATURE                Location/Qualifiers
REGION                 1..442
                       note = Humanized Antibody
source                 1..442
                       mol_type = protein
                       organism = synthetic construct
SEQUENCE: 1281
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                         442
```

SEQ ID NO: 1282 moltype = AA length = 112

```
FEATURE                Location/Qualifiers
REGION                 1..112
                       note = Humanized Antibody
source                 1..112
                       mol_type = protein
                       organism = synthetic construct
SEQUENCE: 1282
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SS          112

SEQ ID NO: 1283        moltype = AA  length = 30
FEATURE                Location/Qualifiers
REGION                 1..30
                       note = Humanized Antibody
source                 1..30
                       mol_type = protein
                       organism = synthetic construct
SEQUENCE: 1283
EVQLVESGGG LVQPGGSLRL SCAASGIDLN                                   30

SEQ ID NO: 1284        moltype = AA  length = 5
FEATURE                Location/Qualifiers
source                 1..5
                       mol_type = protein
                       organism = Oryctolagus cuniculus
SEQUENCE: 1284
SYYMT                                                              5

SEQ ID NO: 1285        moltype = AA  length = 14
FEATURE                Location/Qualifiers
REGION                 1..14
                       note = Humanized Antibody
source                 1..14
                       mol_type = protein
                       organism = synthetic construct
SEQUENCE: 1285
WVRQAPGKGL EWIG                                                    14

SEQ ID NO: 1286        moltype = AA  length = 16
FEATURE                Location/Qualifiers
source                 1..16
                       mol_type = protein
                       organism = Oryctolagus cuniculus
SEQUENCE: 1286
FIDAGGDAYY ASWAKG                                                  16

SEQ ID NO: 1287        moltype = AA  length = 32
FEATURE                Location/Qualifiers
REGION                 1..32
                       note = Humanized Antibody
source                 1..32
                       mol_type = protein
                       organism = synthetic construct
SEQUENCE: 1287
RFTISRDNSK NTVYLQMNSL RAEDTAVYFC AR                                32

SEQ ID NO: 1288        moltype = AA  length = 4
FEATURE                Location/Qualifiers
source                 1..4
                       mol_type = protein
                       organism = Oryctolagus cuniculus
SEQUENCE: 1288
DLDL                                                               4

SEQ ID NO: 1289        moltype = AA  length = 11
FEATURE                Location/Qualifiers
REGION                 1..11
                       note = Humanized Antibody
source                 1..11
                       mol_type = protein
                       organism = synthetic construct
SEQUENCE: 1289
WGQGTLVTVS S                                                       11

SEQ ID NO: 1290        moltype = AA  length = 330
FEATURE                Location/Qualifiers
REGION                 1..330
                       note = Humanized Antibody
source                 1..330
```

```
                        mol_type = protein
                        organism = synthetic construct
SEQUENCE: 1290
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 1291         moltype = DNA  length = 1326
FEATURE                 Location/Qualifiers
misc_feature            1..1326
                        note = Humanized Antibody
source                  1..1326
                        mol_type = other DNA
                        organism = synthetic construct
SEQUENCE: 1291
gaggtgcagc ttgtggagtc tgggggaggc ttggtccagc ctggggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                            1326

SEQ ID NO: 1292         moltype = DNA  length = 336
FEATURE                 Location/Qualifiers
misc_feature            1..336
                        note = Humanized Antibody
source                  1..336
                        mol_type = other DNA
                        organism = synthetic construct
SEQUENCE: 1292
gaggtgcagc ttgtggagtc tgggggaggc ttggtccagc ctggggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                           336

SEQ ID NO: 1293         moltype = DNA  length = 90
FEATURE                 Location/Qualifiers
misc_feature            1..90
                        note = Humanized Antibody
source                  1..90
                        mol_type = other DNA
                        organism = synthetic construct
SEQUENCE: 1293
gaggtgcagc ttgtggagtc tgggggaggc ttggtccagc ctggggggtc cctgagactc  60
tcctgtgcag cctctggaat cgacctcaat                                  90

SEQ ID NO: 1294         moltype = DNA  length = 15
FEATURE                 Location/Qualifiers
source                  1..15
                        mol_type = unassigned DNA
                        organism = Oryctolagus cuniculus
SEQUENCE: 1294
agctactaca tgacc                                                  15

SEQ ID NO: 1295         moltype = DNA  length = 42
FEATURE                 Location/Qualifiers
misc_feature            1..42
```

```
                        note = Humanized Antibody
source                  1..42
                        mol_type = other DNA
                        organism = synthetic construct
SEQUENCE: 1295
tgggtccgtc aggctccagg gaaggggctg gagtggatcg ga                    42

SEQ ID NO: 1296         moltype = DNA  length = 48
FEATURE                 Location/Qualifiers
source                  1..48
                        mol_type = unassigned DNA
                        organism = Oryctolagus cuniculus
SEQUENCE: 1296
ttcattgatg ctggtggtga cgcatactac gcgagctggg cgaaaggc              48

SEQ ID NO: 1297         moltype = DNA  length = 96
FEATURE                 Location/Qualifiers
misc_feature            1..96
                        note = Humanized Antibody
source                  1..96
                        mol_type = other DNA
                        organism = synthetic construct
SEQUENCE: 1297
cgattcacca tctccagaga caattccaag aacaccgtgt atcttcaaat gaacagcctg  60
agagctgagg acactgctgt gtatttctgt gctaga                           96

SEQ ID NO: 1298         moltype = DNA  length = 12
FEATURE                 Location/Qualifiers
source                  1..12
                        mol_type = unassigned DNA
                        organism = Oryctolagus cuniculus
SEQUENCE: 1298
gatcttgact tg                                                     12

SEQ ID NO: 1299         moltype = DNA  length = 33
FEATURE                 Location/Qualifiers
misc_feature            1..33
                        note = Humanized Antibody
source                  1..33
                        mol_type = other DNA
                        organism = synthetic construct
SEQUENCE: 1299
tggggccaag ggaccctcgt caccgtctcg agc                              33

SEQ ID NO: 1300         moltype = DNA  length = 990
FEATURE                 Location/Qualifiers
misc_feature            1..990
                        note = Humanized Antibody
source                  1..990
                        mol_type = other DNA
                        organism = synthetic construct
SEQUENCE: 1300
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                  990

SEQ ID NO: 1301         moltype = AA  length = 215
FEATURE                 Location/Qualifiers
REGION                  1..215
                        note = Humanized Antibody
source                  1..215
                        mol_type = protein
                        organism = synthetic construct
SEQUENCE: 1301
AVLTQSPSTL SASVGDRVTI TCQSSESVYG NYLAWFQQKP GKAPKFLIYE ASKLESGVPS  60
```

```
RFSGSGSGTE FTLTISSLQP DDFATYYCAG GDISEGVAFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 1302        moltype = AA  length = 109
FEATURE                Location/Qualifiers
REGION                 1..109
                       note = Humanized Antibody
source                 1..109
                       mol_type = protein
                       organism = synthetic construct
SEQUENCE: 1302
AVLTQSPSTL SASVGDRVTI TCQSSESVYG NYLAWFQQKP GKAPKFLIYE ASKLESGVPS  60
RFSGSGSGTE FTLTISSLQP DDFATYYCAG GDISEGVAFG GGTKVEIKR              109

SEQ ID NO: 1303        moltype = AA  length = 22
FEATURE                Location/Qualifiers
REGION                 1..22
                       note = Humanized Antibody
source                 1..22
                       mol_type = protein
                       organism = synthetic construct
SEQUENCE: 1303
AVLTQSPSTL SASVGDRVTI TC                                           22

SEQ ID NO: 1304        moltype = AA  length = 12
FEATURE                Location/Qualifiers
source                 1..12
                       mol_type = protein
                       organism = Oryctolagus cuniculus
SEQUENCE: 1304
QSSESVYGNY LA                                                      12

SEQ ID NO: 1305        moltype = AA  length = 15
FEATURE                Location/Qualifiers
REGION                 1..15
                       note = Humanized Antibody
source                 1..15
                       mol_type = protein
                       organism = synthetic construct
SEQUENCE: 1305
WFQQKPGKAP KFLIY                                                   15

SEQ ID NO: 1306        moltype = AA  length = 7
FEATURE                Location/Qualifiers
source                 1..7
                       mol_type = protein
                       organism = Oryctolagus cuniculus
SEQUENCE: 1306
EASKLES                                                            7

SEQ ID NO: 1307        moltype = AA  length = 32
FEATURE                Location/Qualifiers
REGION                 1..32
                       note = Humanized Antibody
source                 1..32
                       mol_type = protein
                       organism = synthetic construct
SEQUENCE: 1307
GVPSRFSGSG SGTEFTLTIS SLQPDDFATY YC                                32

SEQ ID NO: 1308        moltype = AA  length = 10
FEATURE                Location/Qualifiers
source                 1..10
                       mol_type = protein
                       organism = Oryctolagus cuniculus
SEQUENCE: 1308
AGGDISEGVA                                                         10

SEQ ID NO: 1309        moltype = AA  length = 11
FEATURE                Location/Qualifiers
REGION                 1..11
                       note = Humanized Antibody
source                 1..11
                       mol_type = protein
                       organism = synthetic construct
SEQUENCE: 1309
FGGGTKVEIK R                                                       11
```

```
SEQ ID NO: 1310        moltype = AA  length = 106
FEATURE                Location/Qualifiers
REGION                 1..106
                       note = Humanized Antibody
source                 1..106
                       mol_type = protein
                       organism = synthetic construct
SEQUENCE: 1310
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 1311        moltype = DNA  length = 645
FEATURE                Location/Qualifiers
misc_feature           1..645
                       note = Humanized Antibody
source                 1..645
                       mol_type = other DNA
                       organism = synthetic construct
SEQUENCE: 1311
gccgtgctga cccagtctcc ttccaccctg tctgcatctg taggagacag agtcaccatc  60
acttgtcagt ccagtgagag tgtttacggt aactacttag cctggtttca gcagaaacca  120
ggaaaagccc ctaagttcct gatctatgaa gcatccaaac tggaatctgg agtcccatca  180
aggttcagcg gcagtggatc tggaacagaa ttcactctca ccatcagcag cctgcagcct  240
gatgattttg caacttacta ctgtgcaggc ggtgatatta gtgaaggtgt tgctttcggc  300
ggaggaacca aggtggaaat caaacgtacg gtagcggccc catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                 645

SEQ ID NO: 1312        moltype = DNA  length = 327
FEATURE                Location/Qualifiers
misc_feature           1..327
                       note = Humanized Antibody
source                 1..327
                       mol_type = other DNA
                       organism = synthetic construct
SEQUENCE: 1312
gccgtgctga cccagtctcc ttccaccctg tctgcatctg taggagacag agtcaccatc  60
acttgtcagt ccagtgagag tgtttacggt aactacttag cctggtttca gcagaaacca  120
ggaaaagccc ctaagttcct gatctatgaa gcatccaaac tggaatctgg agtcccatca  180
aggttcagcg gcagtggatc tggaacagaa ttcactctca ccatcagcag cctgcagcct  240
gatgattttg caacttacta ctgtgcaggc ggtgatatta gtgaaggtgt tgctttcggc  300
ggaggaacca aggtggaaat caaacgt                                     327

SEQ ID NO: 1313        moltype = DNA  length = 66
FEATURE                Location/Qualifiers
misc_feature           1..66
                       note = Humanized Antibody
source                 1..66
                       mol_type = other DNA
                       organism = synthetic construct
SEQUENCE: 1313
gccgtgctga cccagtctcc ttccaccctg tctgcatctg taggagacag agtcaccatc  60
acttgt                                                            66

SEQ ID NO: 1314        moltype = DNA  length = 36
FEATURE                Location/Qualifiers
source                 1..36
                       mol_type = unassigned DNA
                       organism = Oryctolagus cuniculus
SEQUENCE: 1314
cagtccagtg agagtgttta cggtaactac ttagcc                           36

SEQ ID NO: 1315        moltype = DNA  length = 45
FEATURE                Location/Qualifiers
misc_feature           1..45
                       note = Humanized Antibody
source                 1..45
                       mol_type = other DNA
                       organism = synthetic construct
SEQUENCE: 1315
tggtttcagc agaaaccagg aaaagcccct aagttcctga tctat                 45

SEQ ID NO: 1316        moltype = DNA  length = 21
FEATURE                Location/Qualifiers
source                 1..21
                       mol_type = unassigned DNA
```

```
                         organism = Oryctolagus cuniculus
SEQUENCE: 1316
gaagcatcca aactggaatc t                                            21

SEQ ID NO: 1317          moltype = DNA  length = 96
FEATURE                  Location/Qualifiers
misc_feature             1..96
                         note = Humanized Antibody
source                   1..96
                         mol_type = other DNA
                         organism = synthetic construct
SEQUENCE: 1317
ggagtcccat caaggttcag cggcagtgga tctggaacag aattcactct caccatcagc  60
agcctgcagc ctgatgattt tgcaacttac tactgt                            96

SEQ ID NO: 1318          moltype = DNA  length = 30
FEATURE                  Location/Qualifiers
source                   1..30
                         mol_type = unassigned DNA
                         organism = Oryctolagus cuniculus
SEQUENCE: 1318
gcaggcggtg atattagtga aggtgttgct                                   30

SEQ ID NO: 1319          moltype = DNA  length = 33
FEATURE                  Location/Qualifiers
misc_feature             1..33
                         note = Humanized Antibody
source                   1..33
                         mol_type = other DNA
                         organism = synthetic construct
SEQUENCE: 1319
ttcggcggag gaaccaaggt ggaaatcaaa cgt                               33

SEQ ID NO: 1320          moltype = DNA  length = 318
FEATURE                  Location/Qualifiers
misc_feature             1..318
                         note = Humanized Antibody
source                   1..318
                         mol_type = other DNA
                         organism = synthetic construct
SEQUENCE: 1320
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318

SEQ ID NO: 1321          moltype = AA  length = 442
FEATURE                  Location/Qualifiers
REGION                   1..442
                         note = Humanized Antibody
source                   1..442
                         mol_type = protein
                         organism = synthetic construct
SEQUENCE: 1321
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                           442

SEQ ID NO: 1322          moltype = AA  length = 112
FEATURE                  Location/Qualifiers
REGION                   1..112
                         note = Humanized Antibody
source                   1..112
                         mol_type = protein
                         organism = synthetic construct
SEQUENCE: 1322
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SS          112

SEQ ID NO: 1323          moltype = AA  length = 30
FEATURE                  Location/Qualifiers
REGION                   1..30
```

```
                        note = Humanized Antibody
source                  1..30
                        mol_type = protein
                        organism = synthetic construct
SEQUENCE: 1323
EVQLVESGGG LVQPGGSLRL SCAASGIDLN                                    30

SEQ ID NO: 1324         moltype = AA  length = 5
FEATURE                 Location/Qualifiers
source                  1..5
                        mol_type = protein
                        organism = Oryctolagus cuniculus
SEQUENCE: 1324
SYYMT                                                               5

SEQ ID NO: 1325         moltype = AA  length = 14
FEATURE                 Location/Qualifiers
REGION                  1..14
                        note = Humanized Antibody
source                  1..14
                        mol_type = protein
                        organism = synthetic construct
SEQUENCE: 1325
WVRQAPGKGL EWIG                                                     14

SEQ ID NO: 1326         moltype = AA  length = 16
FEATURE                 Location/Qualifiers
source                  1..16
                        mol_type = protein
                        organism = Oryctolagus cuniculus
SEQUENCE: 1326
FIDAGGDAYY ASWAKG                                                   16

SEQ ID NO: 1327         moltype = AA  length = 32
FEATURE                 Location/Qualifiers
REGION                  1..32
                        note = Humanized Antibody
source                  1..32
                        mol_type = protein
                        organism = synthetic construct
SEQUENCE: 1327
RFTISRDNSK NTVYLQMNSL RAEDTAVYFC AR                                 32

SEQ ID NO: 1328         moltype = AA  length = 4
FEATURE                 Location/Qualifiers
source                  1..4
                        mol_type = protein
                        organism = Oryctolagus cuniculus
SEQUENCE: 1328
DLDL                                                                4

SEQ ID NO: 1329         moltype = AA  length = 11
FEATURE                 Location/Qualifiers
REGION                  1..11
                        note = Humanized Antibody
source                  1..11
                        mol_type = protein
                        organism = synthetic construct
SEQUENCE: 1329
WGQGTLVTVS S                                                        11

SEQ ID NO: 1330         moltype = AA  length = 330
FEATURE                 Location/Qualifiers
REGION                  1..330
                        note = Humanized Antibody
source                  1..330
                        mol_type = protein
                        organism = synthetic construct
SEQUENCE: 1330
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 1331         moltype = DNA  length = 1326
FEATURE                 Location/Qualifiers
misc_feature            1..1326
```

```
                        note = Humanized Antibody
source                  1..1326
                        mol_type = other DNA
                        organism = synthetic construct
SEQUENCE: 1331
gaggtgcagc ttgtggagtc tgggggaggc ttggtccagc ctgggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                            1326

SEQ ID NO: 1332         moltype = DNA  length = 336
FEATURE                 Location/Qualifiers
misc_feature            1..336
                        note = Humanized Antibody
source                  1..336
                        mol_type = other DNA
                        organism = synthetic construct
SEQUENCE: 1332
gaggtgcagc ttgtggagtc tgggggaggc ttggtccagc ctgggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                           336

SEQ ID NO: 1333         moltype = DNA  length = 90
FEATURE                 Location/Qualifiers
misc_feature            1..90
                        note = Humanized Antibody
source                  1..90
                        mol_type = other DNA
                        organism = synthetic construct
SEQUENCE: 1333
gaggtgcagc ttgtggagtc tgggggaggc ttggtccagc ctgggggtc cctgagactc  60
tcctgtgcag cctctggaat cgacctcaat                                  90

SEQ ID NO: 1334         moltype = DNA  length = 15
FEATURE                 Location/Qualifiers
source                  1..15
                        mol_type = unassigned DNA
                        organism = Oryctolagus cuniculus
SEQUENCE: 1334
agctactaca tgacc                                                  15

SEQ ID NO: 1335         moltype = DNA  length = 42
FEATURE                 Location/Qualifiers
misc_feature            1..42
                        note = Humanized Antibody
source                  1..42
                        mol_type = other DNA
                        organism = synthetic construct
SEQUENCE: 1335
tgggtccgtc aggctccagg gaaggggctg gagtggatcg ga                    42

SEQ ID NO: 1336         moltype = DNA  length = 48
FEATURE                 Location/Qualifiers
source                  1..48
                        mol_type = unassigned DNA
                        organism = Oryctolagus cuniculus
SEQUENCE: 1336
```

```
ttcattgatg ctggtggtga cgcatactac gcgagctggg cgaaaggc              48

SEQ ID NO: 1337        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1337
cgattcacca tctccagaga caattccaag aacaccgtgt atcttcaaat gaacagcctg  60
agagctgagg acactgctgt gtatttctgt gctaga                            96

SEQ ID NO: 1338        moltype = DNA  length = 12
FEATURE                Location/Qualifiers
source                 1..12
                       mol_type = unassigned DNA
                       organism = Oryctolagus cuniculus
SEQUENCE: 1338
gatcttgact tg                                                      12

SEQ ID NO: 1339        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1339
tggggccaag ggaccctcgt caccgtctcg agc                               33

SEQ ID NO: 1340        moltype = DNA  length = 990
FEATURE                Location/Qualifiers
misc_feature           1..990
                       note = Humanized Antibody
source                 1..990
                       mol_type = other DNA
                       organism = synthetic construct
SEQUENCE: 1340
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 1341        moltype = AA  length = 216
FEATURE                Location/Qualifiers
REGION                 1..216
                       note = Humanized Antibody
source                 1..216
                       mol_type = protein
                       organism = synthetic construct
SEQUENCE: 1341
DIQLTQSPST LSASVGDRVT ITCQSSESVY GNYLAWFQQK PGKAPKFLIY EASKLESGVP  60
SRFSGSGSGT EFTLTISSLQ PDDFATYYCA GGDISEGVAF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 1342        moltype = AA  length = 110
FEATURE                Location/Qualifiers
REGION                 1..110
                       note = Humanized Antibody
source                 1..110
                       mol_type = protein
                       organism = synthetic construct
SEQUENCE: 1342
DIQLTQSPST LSASVGDRVT ITCQSSESVY GNYLAWFQQK PGKAPKFLIY EASKLESGVP  60
```

```
SRFSGSGSGT EFTLTISSLQ PDDFATYYCA GGDISEGVAF GGGTKVEIKR           110

SEQ ID NO: 1343        moltype = AA  length = 23
FEATURE                Location/Qualifiers
REGION                 1..23
                       note = Humanized Antibody
source                 1..23
                       mol_type = protein
                       organism = synthetic construct
SEQUENCE: 1343
DIQLTQSPST LSASVGDRVT ITC                                        23

SEQ ID NO: 1344        moltype = AA  length = 12
FEATURE                Location/Qualifiers
source                 1..12
                       mol_type = protein
                       organism = Oryctolagus cuniculus
SEQUENCE: 1344
QSSESVYGNY LA                                                    12

SEQ ID NO: 1345        moltype = AA  length = 15
FEATURE                Location/Qualifiers
REGION                 1..15
                       note = Humanized Antibody
source                 1..15
                       mol_type = protein
                       organism = synthetic construct
SEQUENCE: 1345
WFQQKPGKAP KFLIY                                                 15

SEQ ID NO: 1346        moltype = AA  length = 7
FEATURE                Location/Qualifiers
source                 1..7
                       mol_type = protein
                       organism = Oryctolagus cuniculus
SEQUENCE: 1346
EASKLES                                                          7

SEQ ID NO: 1347        moltype = AA  length = 32
FEATURE                Location/Qualifiers
REGION                 1..32
                       note = Humanized Antibody
source                 1..32
                       mol_type = protein
                       organism = synthetic construct
SEQUENCE: 1347
GVPSRFSGSG SGTEFTLTIS SLQPDDFATY YC                              32

SEQ ID NO: 1348        moltype = AA  length = 10
FEATURE                Location/Qualifiers
source                 1..10
                       mol_type = protein
                       organism = Oryctolagus cuniculus
SEQUENCE: 1348
AGGDISEGVA                                                       10

SEQ ID NO: 1349        moltype = AA  length = 11
FEATURE                Location/Qualifiers
REGION                 1..11
                       note = Humanized Antibody
source                 1..11
                       mol_type = protein
                       organism = synthetic construct
SEQUENCE: 1349
FGGGTKVEIK R                                                     11

SEQ ID NO: 1350        moltype = AA  length = 106
FEATURE                Location/Qualifiers
REGION                 1..106
                       note = Humanized Antibody
source                 1..106
                       mol_type = protein
                       organism = synthetic construct
SEQUENCE: 1350
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 1351        moltype = DNA  length = 648
FEATURE                Location/Qualifiers
```

```
misc_feature           1..648
                       note = Humanized Antibody
source                 1..648
                       mol_type = other DNA
                       organism = synthetic construct
SEQUENCE: 1351
gacatccagc tgacccagtc tccttccacc ctgtctgcat ctgtaggaga cagagtcacc  60
atcacttgtc agtccagtga gagtgtttac ggtaactact tagcctggtt tcagcagaaa  120
ccaggaaaag cccctaagtt cctgatctat gaagcatcca aactggaatc tggagtccca  180
tcaaggttca gcggcagtgg atctggaaca gaattcactc tcaccatcag cagcctgcag  240
cctgatgatt ttgcaactta ctactgtgca ggcggtgata ttagtgaagg tgttgctttc  300
ggcggaggaa ccaaggtgga aatcaaacgt acggtagcgg ccccatctgt cttcatcttc  360
ccgccatctg atgagcagtt gaaatctgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt              648

SEQ ID NO: 1352        moltype = DNA  length = 330
FEATURE                Location/Qualifiers
misc_feature           1..330
                       note = Humanized Antibody
source                 1..330
                       mol_type = other DNA
                       organism = synthetic construct
SEQUENCE: 1352
gacatccagc tgacccagtc tccttccacc ctgtctgcat ctgtaggaga cagagtcacc  60
atcacttgtc agtccagtga gagtgtttac ggtaactact tagcctggtt tcagcagaaa  120
ccaggaaaag cccctaagtt cctgatctat gaagcatcca aactggaatc tggagtccca  180
tcaaggttca gcggcagtgg atctggaaca gaattcactc tcaccatcag cagcctgcag  240
cctgatgatt ttgcaactta ctactgtgca ggcggtgata ttagtgaagg tgttgctttc  300
ggcggaggaa ccaaggtgga aatcaaacgt                                  330

SEQ ID NO: 1353        moltype = DNA  length = 69
FEATURE                Location/Qualifiers
misc_feature           1..69
                       note = Humanized Antibody
source                 1..69
                       mol_type = other DNA
                       organism = synthetic construct
SEQUENCE: 1353
gacatccagc tgacccagtc tccttccacc ctgtctgcat ctgtaggaga cagagtcacc  60
atcacttgt                                                         69

SEQ ID NO: 1354        moltype = DNA  length = 36
FEATURE                Location/Qualifiers
source                 1..36
                       mol_type = unassigned DNA
                       organism = Oryctolagus cuniculus
SEQUENCE: 1354
cagtccagtg agagtgttta cggtaactac ttagcc                           36

SEQ ID NO: 1355        moltype = DNA  length = 45
FEATURE                Location/Qualifiers
misc_feature           1..45
                       note = Humanized Antibody
source                 1..45
                       mol_type = other DNA
                       organism = synthetic construct
SEQUENCE: 1355
tggtttcagc agaaaccagg aaaagcccct aagttcctga tctat                 45

SEQ ID NO: 1356        moltype = DNA  length = 21
FEATURE                Location/Qualifiers
source                 1..21
                       mol_type = unassigned DNA
                       organism = Oryctolagus cuniculus
SEQUENCE: 1356
gaagcatcca aactggaatc t                                           21

SEQ ID NO: 1357        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1357
ggagtcccat caaggttcag cggcagtgga tctggaacag aattcactct caccatcagc  60
```

```
agcctgcagc ctgatgattt tgcaacttac tactgt                          96

SEQ ID NO: 1358        moltype = DNA  length = 30
FEATURE                Location/Qualifiers
source                 1..30
                       mol_type = unassigned DNA
                       organism = Oryctolagus cuniculus
SEQUENCE: 1358
gcaggcggtg atattagtga aggtgttgct                                 30

SEQ ID NO: 1359        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1359
ttcggcggag gaaccaaggt ggaaatcaaa cgt                             33

SEQ ID NO: 1360        moltype = DNA  length = 318
FEATURE                Location/Qualifiers
misc_feature           1..318
                       note = Humanized Antibody
source                 1..318
                       mol_type = other DNA
                       organism = synthetic construct
SEQUENCE: 1360
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                              318

SEQ ID NO: 1361        moltype = AA  length = 442
FEATURE                Location/Qualifiers
REGION                 1..442
                       note = Humanized Antibody
source                 1..442
                       mol_type = protein
                       organism = synthetic construct
SEQUENCE: 1361
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                         442

SEQ ID NO: 1362        moltype = AA  length = 112
FEATURE                Location/Qualifiers
REGION                 1..112
                       note = Humanized Antibody
source                 1..112
                       mol_type = protein
                       organism = synthetic construct
SEQUENCE: 1362
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SS          112

SEQ ID NO: 1363        moltype = AA  length = 30
FEATURE                Location/Qualifiers
REGION                 1..30
                       note = Humanized Antibody
source                 1..30
                       mol_type = protein
                       organism = synthetic construct
SEQUENCE: 1363
EVQLVESGGG LVQPGGSLRL SCAASGIDLN                                 30

SEQ ID NO: 1364        moltype = AA  length = 5
FEATURE                Location/Qualifiers
source                 1..5
                       mol_type = protein
                       organism = Oryctolagus cuniculus
SEQUENCE: 1364
```

```
SYYMT                                                              5

SEQ ID NO: 1365        moltype = AA  length = 14
FEATURE                Location/Qualifiers
REGION                 1..14
                       note = Humanized Antibody
source                 1..14
                       mol_type = protein
                       organism = synthetic construct
SEQUENCE: 1365
WVRQAPGKGL EWIG                                                    14

SEQ ID NO: 1366        moltype = AA  length = 16
FEATURE                Location/Qualifiers
source                 1..16
                       mol_type = protein
                       organism = Oryctolagus cuniculus
SEQUENCE: 1366
FIDAGGDAYY ASWAKG                                                  16

SEQ ID NO: 1367        moltype = AA  length = 32
FEATURE                Location/Qualifiers
REGION                 1..32
                       note = Humanized Antibody
source                 1..32
                       mol_type = protein
                       organism = synthetic construct
SEQUENCE: 1367
RFTISRDNSK NTVYLQMNSL RAEDTAVYFC AR                                32

SEQ ID NO: 1368        moltype = AA  length = 4
FEATURE                Location/Qualifiers
source                 1..4
                       mol_type = protein
                       organism = Oryctolagus cuniculus
SEQUENCE: 1368
DLDL                                                               4

SEQ ID NO: 1369        moltype = AA  length = 11
FEATURE                Location/Qualifiers
REGION                 1..11
                       note = Humanized Antibody
source                 1..11
                       mol_type = protein
                       organism = synthetic construct
SEQUENCE: 1369
WGQGTLVTVS S                                                       11

SEQ ID NO: 1370        moltype = AA  length = 330
FEATURE                Location/Qualifiers
REGION                 1..330
                       note = Humanized Antibody
source                 1..330
                       mol_type = protein
                       organism = synthetic construct
SEQUENCE: 1370
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 1371        moltype = DNA  length = 1326
FEATURE                Location/Qualifiers
misc_feature           1..1326
                       note = Humanized Antibody
source                 1..1326
                       mol_type = other DNA
                       organism = synthetic construct
SEQUENCE: 1371
gaggtgcagc ttgtggagtc tgggggaggc ttggtccagc ctgggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
```

```
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                             1326

SEQ ID NO: 1372        moltype = DNA  length = 336
FEATURE                Location/Qualifiers
misc_feature           1..336
                       note = Humanized Antibody
source                 1..336
                       mol_type = other DNA
                       organism = synthetic construct
SEQUENCE: 1372
gaggtgcagc ttgtggagtc tgggggaggc ttggtccagc ctgggggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                            336

SEQ ID NO: 1373        moltype = DNA  length = 90
FEATURE                Location/Qualifiers
misc_feature           1..90
                       note = Humanized Antibody
source                 1..90
                       mol_type = other DNA
                       organism = synthetic construct
SEQUENCE: 1373
gaggtgcagc ttgtggagtc tgggggaggc ttggtccagc ctgggggggtc cctgagactc  60
tcctgtgcag cctctggaat cgacctcaat                                   90

SEQ ID NO: 1374        moltype = DNA  length = 15
FEATURE                Location/Qualifiers
source                 1..15
                       mol_type = unassigned DNA
                       organism = Oryctolagus cuniculus
SEQUENCE: 1374
agctactaca tgacc                                                   15

SEQ ID NO: 1375        moltype = DNA  length = 42
FEATURE                Location/Qualifiers
misc_feature           1..42
                       note = Humanized Antibody
source                 1..42
                       mol_type = other DNA
                       organism = synthetic construct
SEQUENCE: 1375
tgggtccgtc aggctccagg gaaggggctg gagtggatcg ga                     42

SEQ ID NO: 1376        moltype = DNA  length = 48
FEATURE                Location/Qualifiers
source                 1..48
                       mol_type = unassigned DNA
                       organism = Oryctolagus cuniculus
SEQUENCE: 1376
ttcattgatg ctggtggtga cgcatactac gcgagctggg cgaaaggc               48

SEQ ID NO: 1377        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1377
cgattcacca tctccagaga caattccaag aacaccgtgt atcttcaaat gaacagcctg  60
agagctgagg acactgctgt gtatttctgt gctaga                            96
```

```
SEQ ID NO: 1378        moltype = DNA  length = 12
FEATURE                Location/Qualifiers
source                 1..12
                       mol_type = unassigned DNA
                       organism = Oryctolagus cuniculus
SEQUENCE: 1378
gatcttgact tg                                                      12

SEQ ID NO: 1379        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1379
tggggccaag ggaccctcgt caccgtctcg agc                               33

SEQ ID NO: 1380        moltype = DNA  length = 990
FEATURE                Location/Qualifiers
misc_feature           1..990
                       note = Humanized Antibody
source                 1..990
                       mol_type = other DNA
                       organism = synthetic construct
SEQUENCE: 1380
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 1381        moltype = AA  length = 216
FEATURE                Location/Qualifiers
REGION                 1..216
                       note = Humanized Antibody
source                 1..216
                       mol_type = protein
                       organism = synthetic construct
SEQUENCE: 1381
DIVLTQSPST LSASVGDRVT ITCQSSESVY GNYLAWFQQK PGKAPKFLIY EASKLESGVP  60
SRFSGSGSGT EFTLTISSLQ PDDFATYYCA GGDISEGVAF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 1382        moltype = AA  length = 110
FEATURE                Location/Qualifiers
REGION                 1..110
                       note = Humanized Antibody
source                 1..110
                       mol_type = protein
                       organism = synthetic construct
SEQUENCE: 1382
DIVLTQSPST LSASVGDRVT ITCQSSESVY GNYLAWFQQK PGKAPKFLIY EASKLESGVP  60
SRFSGSGSGT EFTLTISSLQ PDDFATYYCA GGDISEGVAF GGGTKVEIKR             110

SEQ ID NO: 1383        moltype = AA  length = 23
FEATURE                Location/Qualifiers
REGION                 1..23
                       note = Humanized Antibody
source                 1..23
                       mol_type = protein
                       organism = synthetic construct
SEQUENCE: 1383
DIVLTQSPST LSASVGDRVT ITC                                          23

SEQ ID NO: 1384        moltype = AA  length = 12
```

```
FEATURE                 Location/Qualifiers
source                  1..12
                        mol_type = protein
                        organism = Oryctolagus cuniculus
SEQUENCE: 1384
QSSESVYGNY LA                                                   12

SEQ ID NO: 1385         moltype = AA  length = 15
FEATURE                 Location/Qualifiers
REGION                  1..15
                        note = Humanized Antibody
source                  1..15
                        mol_type = protein
                        organism = synthetic construct
SEQUENCE: 1385
WFQQKPGKAP KFLIY                                                15

SEQ ID NO: 1386         moltype = AA  length = 7
FEATURE                 Location/Qualifiers
source                  1..7
                        mol_type = protein
                        organism = Oryctolagus cuniculus
SEQUENCE: 1386
EASKLES                                                         7

SEQ ID NO: 1387         moltype = AA  length = 32
FEATURE                 Location/Qualifiers
REGION                  1..32
                        note = Humanized Antibody
source                  1..32
                        mol_type = protein
                        organism = synthetic construct
SEQUENCE: 1387
GVPSRFSGSG SGTEFTLTIS SLQPDDFATY YC                             32

SEQ ID NO: 1388         moltype = AA  length = 10
FEATURE                 Location/Qualifiers
source                  1..10
                        mol_type = protein
                        organism = Oryctolagus cuniculus
SEQUENCE: 1388
AGGDISEGVA                                                      10

SEQ ID NO: 1389         moltype = AA  length = 11
FEATURE                 Location/Qualifiers
REGION                  1..11
                        note = Humanized Antibody
source                  1..11
                        mol_type = protein
                        organism = synthetic construct
SEQUENCE: 1389
FGGGTKVEIK R                                                    11

SEQ ID NO: 1390         moltype = AA  length = 106
FEATURE                 Location/Qualifiers
REGION                  1..106
                        note = Humanized Antibody
source                  1..106
                        mol_type = protein
                        organism = synthetic construct
SEQUENCE: 1390
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 1391         moltype = DNA  length = 648
FEATURE                 Location/Qualifiers
misc_feature            1..648
                        note = Humanized Antibody
source                  1..648
                        mol_type = other DNA
                        organism = synthetic construct
SEQUENCE: 1391
gacatcgtgc tgacccagtc tccttccacc ctgtctgcat ctgtaggaga cagagtcacc  60
atcacttgtc agtccagtga gagtgtttac ggtaactact tagcctggtt tcagcagaaa  120
ccaggaaaag cccctaagtt cctgatctat gaagcatcca aactggaatc tggagtccca  180
tcaaggttca gcggcagtgg atctggaaca gaattcactc tcaccatcag cagcctgcag  240
cctgatgatt ttgcaactta ctactgtgca ggcggtgata ttagtgaagg tgttgctttc  300
ggcggaggaa ccaaggtgga aatcaaacgt acggtagcgg ccccatctgt cttcatcttc  360
ccgccatctg atgagcagtt gaaatctgga actgcctctg ttgtgtgcct gctgaataac  420
```

```
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt             648

SEQ ID NO: 1392        moltype = DNA  length = 330
FEATURE                Location/Qualifiers
misc_feature           1..330
                       note = Humanized Antibody
source                 1..330
                       mol_type = other DNA
                       organism = synthetic construct
SEQUENCE: 1392
gacatcgtgc tgacccagtc tccttccacc ctgtctgcat ctgtaggaga cagagtcacc  60
atcacttgtc agtccagtga gagtgtttac ggtaactact tagcctggtt tcagcagaaa  120
ccaggaaaag cccctaagtt cctgatctat gaagcatcca aactggaatc tggagtccca  180
tcaaggttca gcggcagtgg atctggaaca gaattcactc tcaccatcag cagcctgcag  240
cctgatgatt ttgcaactta ctactgtgca ggcggtgata ttagtgaagg tgttgctttc  300
ggcggaggaa ccaaggtgga aatcaaacgt                                  330

SEQ ID NO: 1393        moltype = DNA  length = 69
FEATURE                Location/Qualifiers
misc_feature           1..69
                       note = Humanized Antibody
source                 1..69
                       mol_type = other DNA
                       organism = synthetic construct
SEQUENCE: 1393
gacatcgtgc tgacccagtc tccttccacc ctgtctgcat ctgtaggaga cagagtcacc  60
atcacttgt                                                         69

SEQ ID NO: 1394        moltype = DNA  length = 36
FEATURE                Location/Qualifiers
source                 1..36
                       mol_type = unassigned DNA
                       organism = Oryctolagus cuniculus
SEQUENCE: 1394
cagtccagtg agagtgttta cggtaactac ttagcc                           36

SEQ ID NO: 1395        moltype = DNA  length = 45
FEATURE                Location/Qualifiers
misc_feature           1..45
                       note = Humanized Antibody
source                 1..45
                       mol_type = other DNA
                       organism = synthetic construct
SEQUENCE: 1395
tggtttcagc agaaaccagg aaaagcccct aagttcctga tctat                45

SEQ ID NO: 1396        moltype = DNA  length = 21
FEATURE                Location/Qualifiers
source                 1..21
                       mol_type = unassigned DNA
                       organism = Oryctolagus cuniculus
SEQUENCE: 1396
gaagcatcca aactggaatc t                                           21

SEQ ID NO: 1397        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1397
ggagtcccat caaggttcag cggcagtgga tctggaacag aattcactct caccatcagc  60
agcctgcagc ctgatgattt tgcaacttac tactgt                           96

SEQ ID NO: 1398        moltype = DNA  length = 30
FEATURE                Location/Qualifiers
source                 1..30
                       mol_type = unassigned DNA
                       organism = Oryctolagus cuniculus
SEQUENCE: 1398
gcaggcggtg atattagtga aggtgttgct                                  30

SEQ ID NO: 1399        moltype = DNA  length = 33
FEATURE                Location/Qualifiers
misc_feature           1..33
```

```
                        note = Humanized Antibody
source                  1..33
                        mol_type = other DNA
                        organism = synthetic construct
SEQUENCE: 1399
ttcggcggag gaaccaaggt ggaaatcaaa cgt                              33

SEQ ID NO: 1400         moltype = DNA  length = 318
FEATURE                 Location/Qualifiers
misc_feature            1..318
                        note = Humanized Antibody
source                  1..318
                        mol_type = other DNA
                        organism = synthetic construct
SEQUENCE: 1400
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                               318

SEQ ID NO: 1401         moltype = AA  length = 442
FEATURE                 Location/Qualifiers
REGION                  1..442
                        note = Humanized Antibody
source                  1..442
                        mol_type = protein
                        organism = synthetic construct
SEQUENCE: 1401
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                          442

SEQ ID NO: 1402         moltype = AA  length = 112
FEATURE                 Location/Qualifiers
REGION                  1..112
                        note = Humanized Antibody
source                  1..112
                        mol_type = protein
                        organism = synthetic construct
SEQUENCE: 1402
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SS          112

SEQ ID NO: 1403         moltype = AA  length = 30
FEATURE                 Location/Qualifiers
REGION                  1..30
                        note = Humanized Antibody
source                  1..30
                        mol_type = protein
                        organism = synthetic construct
SEQUENCE: 1403
EVQLVESGGG LVQPGGSLRL SCAASGIDLN                                  30

SEQ ID NO: 1404         moltype = AA  length = 5
FEATURE                 Location/Qualifiers
source                  1..5
                        mol_type = protein
                        organism = Oryctolagus cuniculus
SEQUENCE: 1404
SYYMT                                                             5

SEQ ID NO: 1405         moltype = AA  length = 14
FEATURE                 Location/Qualifiers
REGION                  1..14
                        note = Humanized Antibody
source                  1..14
                        mol_type = protein
                        organism = synthetic construct
SEQUENCE: 1405
WVRQAPGKGL EWIG                                                   14

SEQ ID NO: 1406         moltype = AA  length = 16
```

```
FEATURE                 Location/Qualifiers
source                  1..16
                        mol_type = protein
                        organism = Oryctolagus cuniculus
SEQUENCE: 1406
FIDAGGDAYY ASWAKG                                                   16

SEQ ID NO: 1407         moltype = AA  length = 32
FEATURE                 Location/Qualifiers
REGION                  1..32
                        note = Humanized Antibody
source                  1..32
                        mol_type = protein
                        organism = synthetic construct
SEQUENCE: 1407
RFTISRDNSK NTVYLQMNSL RAEDTAVYFC AR                                 32

SEQ ID NO: 1408         moltype = AA  length = 4
FEATURE                 Location/Qualifiers
source                  1..4
                        mol_type = protein
                        organism = Oryctolagus cuniculus
SEQUENCE: 1408
DLDL                                                                4

SEQ ID NO: 1409         moltype = AA  length = 11
FEATURE                 Location/Qualifiers
REGION                  1..11
                        note = Humanized Antibody
source                  1..11
                        mol_type = protein
                        organism = synthetic construct
SEQUENCE: 1409
WGQGTLVTVS S                                                        11

SEQ ID NO: 1410         moltype = AA  length = 330
FEATURE                 Location/Qualifiers
REGION                  1..330
                        note = Humanized Antibody
source                  1..330
                        mol_type = protein
                        organism = synthetic construct
SEQUENCE: 1410
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 1411         moltype = DNA  length = 1326
FEATURE                 Location/Qualifiers
misc_feature            1..1326
                        note = Humanized Antibody
source                  1..1326
                        mol_type = other DNA
                        organism = synthetic construct
SEQUENCE: 1411
gaggtgcagc ttgtggagtc tgggggaggc ttggtccagc ctggggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
```

```
tccgtgatgc atgaggctct gcacaaccac tacacgcaga agagcctctc cctgtctccg  1320
ggtaaa                                                             1326

SEQ ID NO: 1412        moltype = DNA  length = 336
FEATURE                Location/Qualifiers
misc_feature           1..336
                       note = Humanized Antibody
source                 1..336
                       mol_type = other DNA
                       organism = synthetic construct
SEQUENCE: 1412
gaggtgcagc ttgtggagtc tgggggaggc ttggtccagc ctggggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                            336

SEQ ID NO: 1413        moltype = DNA  length = 90
FEATURE                Location/Qualifiers
misc_feature           1..90
                       note = Humanized Antibody
source                 1..90
                       mol_type = other DNA
                       organism = synthetic construct
SEQUENCE: 1413
gaggtgcagc ttgtggagtc tgggggaggc ttggtccagc ctggggggtc cctgagactc  60
tcctgtgcag cctctggaat cgacctcaat                                   90

SEQ ID NO: 1414        moltype = DNA  length = 15
FEATURE                Location/Qualifiers
source                 1..15
                       mol_type = unassigned DNA
                       organism = Oryctolagus cuniculus
SEQUENCE: 1414
agctactaca tgacc                                                   15

SEQ ID NO: 1415        moltype = DNA  length = 42
FEATURE                Location/Qualifiers
misc_feature           1..42
                       note = Humanized Antibody
source                 1..42
                       mol_type = other DNA
                       organism = synthetic construct
SEQUENCE: 1415
tgggtccgtc aggctccagg gaaggggctg gagtggatcg ga                     42

SEQ ID NO: 1416        moltype = DNA  length = 48
FEATURE                Location/Qualifiers
source                 1..48
                       mol_type = unassigned DNA
                       organism = Oryctolagus cuniculus
SEQUENCE: 1416
ttcattgatg ctggtggtga cgcatactac gcgagctggg cgaaaggc               48

SEQ ID NO: 1417        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1417
cgattcacca tctccagaga caattccaag aacaccgtgt atcttcaaat gaacagcctg  60
agagctgagg acactgctgt gtatttctgt gctaga                            96

SEQ ID NO: 1418        moltype = DNA  length = 12
FEATURE                Location/Qualifiers
source                 1..12
                       mol_type = unassigned DNA
                       organism = Oryctolagus cuniculus
SEQUENCE: 1418
gatcttgact tg                                                      12

SEQ ID NO: 1419        moltype = DNA  length = 33
FEATURE                Location/Qualifiers
misc_feature           1..33
                       note = Humanized Antibody
source                 1..33
```

```
                         mol_type = other DNA
                         organism = synthetic construct
SEQUENCE: 1419
tggggccaag ggaccctcgt caccgtctcg agc                              33

SEQ ID NO: 1420          moltype = DNA  length = 990
FEATURE                  Location/Qualifiers
misc_feature             1..990
                         note = Humanized Antibody
source                   1..990
                         mol_type = other DNA
                         organism = synthetic construct
SEQUENCE: 1420
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                  990

SEQ ID NO: 1421          moltype = AA  length = 214
FEATURE                  Location/Qualifiers
REGION                   1..214
                         note = Humanized Antibody
source                   1..214
                         mol_type = protein
                         organism = synthetic construct
SEQUENCE: 1421
QLTQSPSTLS ASVGDRVTIT CQSSESVYGN YLAWFQQKPG KAPKFLIYEA SKLESGVPSR  60
FSGSGSGTEF TLTISSLQPD DFATYYCAGG DISEGVAFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 1422          moltype = AA  length = 108
FEATURE                  Location/Qualifiers
REGION                   1..108
                         note = Humanized Antibody
source                   1..108
                         mol_type = protein
                         organism = synthetic construct
SEQUENCE: 1422
QLTQSPSTLS ASVGDRVTIT CQSSESVYGN YLAWFQQKPG KAPKFLIYEA SKLESGVPSR  60
FSGSGSGTEF TLTISSLQPD DFATYYCAGG DISEGVAFGG GTKVEIKR               108

SEQ ID NO: 1423          moltype = AA  length = 21
FEATURE                  Location/Qualifiers
REGION                   1..21
                         note = Humanized Antibody
source                   1..21
                         mol_type = protein
                         organism = synthetic construct
SEQUENCE: 1423
QLTQSPSTLS ASVGDRVTIT C                                           21

SEQ ID NO: 1424          moltype = AA  length = 12
FEATURE                  Location/Qualifiers
source                   1..12
                         mol_type = protein
                         organism = Oryctolagus cuniculus
SEQUENCE: 1424
QSSESVYGNY LA                                                     12

SEQ ID NO: 1425          moltype = AA  length = 15
FEATURE                  Location/Qualifiers
REGION                   1..15
                         note = Humanized Antibody
source                   1..15
                         mol_type = protein
```

```
                      organism = synthetic construct
SEQUENCE: 1425
WFQQKPGKAP KFLIY                                          15

SEQ ID NO: 1426       moltype = AA  length = 7
FEATURE               Location/Qualifiers
source                1..7
                      mol_type = protein
                      organism = Oryctolagus cuniculus
SEQUENCE: 1426
EASKLES                                                   7

SEQ ID NO: 1427       moltype = AA  length = 32
FEATURE               Location/Qualifiers
REGION                1..32
                      note = Humanized Antibody
source                1..32
                      mol_type = protein
                      organism = synthetic construct
SEQUENCE: 1427
GVPSRFSGSG SGTEFTLTIS SLQPDDFATY YC                       32

SEQ ID NO: 1428       moltype = AA  length = 10
FEATURE               Location/Qualifiers
source                1..10
                      mol_type = protein
                      organism = Oryctolagus cuniculus
SEQUENCE: 1428
AGGDISEGVA                                                10

SEQ ID NO: 1429       moltype = AA  length = 11
FEATURE               Location/Qualifiers
REGION                1..11
                      note = Humanized Antibody
source                1..11
                      mol_type = protein
                      organism = synthetic construct
SEQUENCE: 1429
FGGGTKVEIK R                                              11

SEQ ID NO: 1430       moltype = AA  length = 106
FEATURE               Location/Qualifiers
REGION                1..106
                      note = Humanized Antibody
source                1..106
                      mol_type = protein
                      organism = synthetic construct
SEQUENCE: 1430
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC        106

SEQ ID NO: 1431       moltype = DNA  length = 642
FEATURE               Location/Qualifiers
misc_feature          1..642
                      note = Humanized Antibody
source                1..642
                      mol_type = other DNA
                      organism = synthetic construct
SEQUENCE: 1431
cagctgaccc agtctccttc caccctgtct gcatctgtag gagacagagt caccatcact  60
tgtcagtcca gtgagagtgt ttacggtaac tacttagcct ggtttcagca gaaaccagga  120
aaagccccta agttcctgat ctatgaagca tccaaactgg aatctggagt cccatcaagg  180
ttcagcggca gtggatctgg aacagaattc actctcacca tcagcagcct gcagcctgat  240
gattttgcaa cttactactg tgcaggcggt gatattagtg aaggtgttgc tttcggcgga  300
ggaaccaagg tggaaatcaa acgtacggta gcggccccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt            642

SEQ ID NO: 1432       moltype = DNA  length = 324
FEATURE               Location/Qualifiers
misc_feature          1..324
                      note = Humanized Antibody
source                1..324
                      mol_type = other DNA
                      organism = synthetic construct
SEQUENCE: 1432
```

```
cagctgaccc agtctccttc caccctgtct gcatctgtag gagacagagt caccatcact  60
tgtcagtcca gtgagagtgt ttacggtaac tacttagcct ggtttcagca gaaaccagga  120
aaagccccta agttcctgat ctatgaagca tccaaactgg aatctggagt cccatcaagg  180
ttcagcggca gtggatctgg aacagaattc actctcacca tcagcagcct gcagcctgat  240
gattttgcaa cttactactg tgcaggcggt gatattagtg aaggtgttgc tttcggcgga  300
ggaaccaagg tggaaatcaa acgt                                         324

SEQ ID NO: 1433        moltype = DNA  length = 63
FEATURE                Location/Qualifiers
misc_feature           1..63
                       note = Humanized Antibody
source                 1..63
                       mol_type = other DNA
                       organism = synthetic construct
SEQUENCE: 1433
cagctgaccc agtctccttc caccctgtct gcatctgtag gagacagagt caccatcact  60
tgt                                                                63

SEQ ID NO: 1434        moltype = DNA  length = 36
FEATURE                Location/Qualifiers
source                 1..36
                       mol_type = unassigned DNA
                       organism = Oryctolagus cuniculus
SEQUENCE: 1434
cagtccagtg agagtgttta cggtaactac ttagcc                            36

SEQ ID NO: 1435        moltype = DNA  length = 45
FEATURE                Location/Qualifiers
misc_feature           1..45
                       note = Humanized Antibody
source                 1..45
                       mol_type = other DNA
                       organism = synthetic construct
SEQUENCE: 1435
tggtttcagc agaaaccagg aaaagcccct aagttcctga tctat                  45

SEQ ID NO: 1436        moltype = DNA  length = 21
FEATURE                Location/Qualifiers
source                 1..21
                       mol_type = unassigned DNA
                       organism = Oryctolagus cuniculus
SEQUENCE: 1436
gaagcatcca aactggaatc t                                            21

SEQ ID NO: 1437        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1437
ggagtcccat caaggttcag cggcagtgga tctggaacag aattcactct caccatcagc  60
agcctgcagc ctgatgattt tgcaacttac tactgt                            96

SEQ ID NO: 1438        moltype = DNA  length = 30
FEATURE                Location/Qualifiers
source                 1..30
                       mol_type = unassigned DNA
                       organism = Oryctolagus cuniculus
SEQUENCE: 1438
gcaggcggtg atattagtga aggtgttgct                                   30

SEQ ID NO: 1439        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1439
ttcggcggag gaaccaaggt ggaaatcaaa cgt                               33

SEQ ID NO: 1440        moltype = DNA  length = 318
FEATURE                Location/Qualifiers
misc_feature           1..318
                       note = Humanized Antibody
source                 1..318
                       mol_type = other DNA
```

```
                        organism = synthetic construct
SEQUENCE: 1440
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                               318

SEQ ID NO: 1441         moltype = AA  length = 442
FEATURE                 Location/Qualifiers
REGION                  1..442
                        note = Humanized Antibody
source                  1..442
                        mol_type = protein
                        organism = synthetic construct
SEQUENCE: 1441
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                          442

SEQ ID NO: 1442         moltype = AA  length = 112
FEATURE                 Location/Qualifiers
REGION                  1..112
                        note = Humanized Antibody
source                  1..112
                        mol_type = protein
                        organism = synthetic construct
SEQUENCE: 1442
EVQLVESGGG LVQPGGSLRL SCAASGIDLN SYYMTWVRQA PGKGLEWIGF IDAGGDAYYA  60
SWAKGRFTIS RDNSKNTVYL QMNSLRAEDT AVYFCARDLD LWGQGTLVTV SS          112

SEQ ID NO: 1443         moltype = AA  length = 30
FEATURE                 Location/Qualifiers
REGION                  1..30
                        note = Humanized Antibody
source                  1..30
                        mol_type = protein
                        organism = synthetic construct
SEQUENCE: 1443
EVQLVESGGG LVQPGGSLRL SCAASGIDLN                                  30

SEQ ID NO: 1444         moltype = AA  length = 5
FEATURE                 Location/Qualifiers
source                  1..5
                        mol_type = protein
                        organism = Oryctolagus cuniculus
SEQUENCE: 1444
SYYMT                                                             5

SEQ ID NO: 1445         moltype = AA  length = 14
FEATURE                 Location/Qualifiers
REGION                  1..14
                        note = Humanized Antibody
source                  1..14
                        mol_type = protein
                        organism = synthetic construct
SEQUENCE: 1445
WVRQAPGKGL EWIG                                                   14

SEQ ID NO: 1446         moltype = AA  length = 16
FEATURE                 Location/Qualifiers
source                  1..16
                        mol_type = protein
                        organism = Oryctolagus cuniculus
SEQUENCE: 1446
FIDAGGDAYY ASWAKG                                                 16

SEQ ID NO: 1447         moltype = AA  length = 32
FEATURE                 Location/Qualifiers
REGION                  1..32
                        note = Humanized Antibody
source                  1..32
                        mol_type = protein
```

```
                          organism = synthetic construct
SEQUENCE: 1447
RFTISRDNSK NTVYLQMNSL RAEDTAVYFC AR                              32

SEQ ID NO: 1448           moltype = AA  length = 4
FEATURE                   Location/Qualifiers
source                    1..4
                          mol_type = protein
                          organism = Oryctolagus cuniculus
SEQUENCE: 1448
DLDL                                                             4

SEQ ID NO: 1449           moltype = AA  length = 11
FEATURE                   Location/Qualifiers
REGION                    1..11
                          note = Humanized Antibody
source                    1..11
                          mol_type = protein
                          organism = synthetic construct
SEQUENCE: 1449
WGQGTLVTVS S                                                     11

SEQ ID NO: 1450           moltype = AA  length = 330
FEATURE                   Location/Qualifiers
REGION                    1..330
                          note = Humanized Antibody
source                    1..330
                          mol_type = protein
                          organism = synthetic construct
SEQUENCE: 1450
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 1451           moltype = DNA  length = 1326
FEATURE                   Location/Qualifiers
misc_feature              1..1326
                          note = Humanized Antibody
source                    1..1326
                          mol_type = other DNA
                          organism = synthetic construct
SEQUENCE: 1451
gaggtgcagc ttgtggagtc tgggggaggc ttggtccagc ctgggggtc cctgagactc  60
tcctgtgcag cctctggaat cgacctcaat agctactaca tgacctgggt ccgtcaggct  120
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                           1326

SEQ ID NO: 1452           moltype = DNA  length = 336
FEATURE                   Location/Qualifiers
misc_feature              1..336
                          note = Humanized Antibody
source                    1..336
                          mol_type = other DNA
                          organism = synthetic construct
SEQUENCE: 1452
gaggtgcagc ttgtggagtc tgggggaggc ttggtccagc ctgggggtc cctgagactc  60
tcctgtgcag cctctggaat cgacctcaat agctactaca tgacctgggt ccgtcaggct  120
```

```
ccagggaagg ggctggagtg gatcggattc attgatgctg gtggtgacgc atactacgcg  180
agctgggcga aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                            336

SEQ ID NO: 1453        moltype = DNA  length = 90
FEATURE                Location/Qualifiers
misc_feature           1..90
                       note = Humanized Antibody
source                 1..90
                       mol_type = other DNA
                       organism = synthetic construct
SEQUENCE: 1453
gaggtgcagc ttgtggagtc tggggggaggc ttggtccagc ctggggggtc cctgagactc  60
tcctgtgcag cctctggaat cgacctcaat                                   90

SEQ ID NO: 1454        moltype = DNA  length = 15
FEATURE                Location/Qualifiers
source                 1..15
                       mol_type = unassigned DNA
                       organism = Oryctolagus cuniculus
SEQUENCE: 1454
agctactaca tgacc                                                   15

SEQ ID NO: 1455        moltype = DNA  length = 42
FEATURE                Location/Qualifiers
misc_feature           1..42
                       note = Humanized Antibody
source                 1..42
                       mol_type = other DNA
                       organism = synthetic construct
SEQUENCE: 1455
tgggtccgtc aggctccagg gaaggggctg gagtggatcg ga                     42

SEQ ID NO: 1456        moltype = DNA  length = 48
FEATURE                Location/Qualifiers
source                 1..48
                       mol_type = unassigned DNA
                       organism = Oryctolagus cuniculus
SEQUENCE: 1456
ttcattgatg ctggtggtga cgcatactac gcgagctggg cgaaaggc               48

SEQ ID NO: 1457        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1457
cgattcacca tctccagaga caattccaag aacaccgtgt atcttcaaat gaacagcctg  60
agagctgagg acactgctgt gtatttctgt gctaga                            96

SEQ ID NO: 1458        moltype = DNA  length = 12
FEATURE                Location/Qualifiers
source                 1..12
                       mol_type = unassigned DNA
                       organism = Oryctolagus cuniculus
SEQUENCE: 1458
gatcttgact tg                                                      12

SEQ ID NO: 1459        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1459
tggggccaag ggaccctcgt caccgtctcg agc                               33

SEQ ID NO: 1460        moltype = DNA  length = 990
FEATURE                Location/Qualifiers
misc_feature           1..990
                       note = Humanized Antibody
source                 1..990
                       mol_type = other DNA
                       organism = synthetic construct
SEQUENCE: 1460
```

```
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                  990

SEQ ID NO: 1461        moltype = AA  length = 215
FEATURE                Location/Qualifiers
REGION                 1..215
                       note = Humanized Antibody
source                 1..215
                       mol_type = protein
                       organism = synthetic construct
SEQUENCE: 1461
QVLTQSPSTL SASVGDRVTI TCQSSESVYG NYLAWFQQKP GKAPKFLIYE ASKLESGVPS  60
RFSGSGSGTE FTLTISSLQP DDFATYYCAG GDISEGVAFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 1462        moltype = AA  length = 109
FEATURE                Location/Qualifiers
REGION                 1..109
                       note = Humanized Antibody
source                 1..109
                       mol_type = protein
                       organism = synthetic construct
SEQUENCE: 1462
QVLTQSPSTL SASVGDRVTI TCQSSESVYG NYLAWFQQKP GKAPKFLIYE ASKLESGVPS  60
RFSGSGSGTE FTLTISSLQP DDFATYYCAG GDISEGVAFG GGTKVEIKR             109

SEQ ID NO: 1463        moltype = AA  length = 22
FEATURE                Location/Qualifiers
REGION                 1..22
                       note = Humanized Antibody
source                 1..22
                       mol_type = protein
                       organism = synthetic construct
SEQUENCE: 1463
QVLTQSPSTL SASVGDRVTI TC                                          22

SEQ ID NO: 1464        moltype = AA  length = 12
FEATURE                Location/Qualifiers
source                 1..12
                       mol_type = protein
                       organism = Oryctolagus cuniculus
SEQUENCE: 1464
QSSESVYGNY LA                                                     12

SEQ ID NO: 1465        moltype = AA  length = 15
FEATURE                Location/Qualifiers
REGION                 1..15
                       note = Humanized Antibody
source                 1..15
                       mol_type = protein
                       organism = synthetic construct
SEQUENCE: 1465
WFQQKPGKAP KFLIY                                                  15

SEQ ID NO: 1466        moltype = AA  length = 7
FEATURE                Location/Qualifiers
source                 1..7
                       mol_type = protein
                       organism = Oryctolagus cuniculus
SEQUENCE: 1466
EASKLES                                                           7

SEQ ID NO: 1467        moltype = AA  length = 32
```

```
FEATURE                Location/Qualifiers
REGION                 1..32
                       note = Humanized Antibody
source                 1..32
                       mol_type = protein
                       organism = synthetic construct
SEQUENCE: 1467
GVPSRFSGSG SGTEFTLTIS SLQPDDFATY YC                               32

SEQ ID NO: 1468        moltype = AA  length = 10
FEATURE                Location/Qualifiers
source                 1..10
                       mol_type = protein
                       organism = Oryctolagus cuniculus
SEQUENCE: 1468
AGGDISEGVA                                                        10

SEQ ID NO: 1469        moltype = AA  length = 11
FEATURE                Location/Qualifiers
REGION                 1..11
                       note = Humanized Antibody
source                 1..11
                       mol_type = protein
                       organism = synthetic construct
SEQUENCE: 1469
FGGGTKVEIK R                                                      11

SEQ ID NO: 1470        moltype = AA  length = 106
FEATURE                Location/Qualifiers
REGION                 1..106
                       note = Humanized Antibody
source                 1..106
                       mol_type = protein
                       organism = synthetic construct
SEQUENCE: 1470
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 1471        moltype = DNA  length = 645
FEATURE                Location/Qualifiers
misc_feature           1..645
                       note = Humanized Antibody
source                 1..645
                       mol_type = other DNA
                       organism = synthetic construct
SEQUENCE: 1471
caggtgctga cccagtctcc ttccaccctg tctgcatctg taggagacag agtcaccatc  60
acttgtcagt ccagtgagag tgtttacggt aactacttag cctggtttca gcagaaacca  120
ggaaaagccc ctaagttcct gatctatgaa gcatccaaac tggaatctgg agtcccatca  180
aggttcagcg gcagtggatc tggaacagaa ttcactctca ccatcagcag cctgcagcct  240
gatgattttg caacttacta ctgtgcaggc ggtgatatta gtgaaggtgt tgctttcggc  300
ggaggaacca aggtggaaat caaacgtacg gtagcggccc catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                 645

SEQ ID NO: 1472        moltype = DNA  length = 327
FEATURE                Location/Qualifiers
misc_feature           1..327
                       note = Humanized Antibody
source                 1..327
                       mol_type = other DNA
                       organism = synthetic construct
SEQUENCE: 1472
caggtgctga cccagtctcc ttccaccctg tctgcatctg taggagacag agtcaccatc  60
acttgtcagt ccagtgagag tgtttacggt aactacttag cctggtttca gcagaaacca  120
ggaaaagccc ctaagttcct gatctatgaa gcatccaaac tggaatctgg agtcccatca  180
aggttcagcg gcagtggatc tggaacagaa ttcactctca ccatcagcag cctgcagcct  240
gatgattttg caacttacta ctgtgcaggc ggtgatatta gtgaaggtgt tgctttcggc  300
ggaggaacca aggtggaaat caaacgt                                     327

SEQ ID NO: 1473        moltype = DNA  length = 66
FEATURE                Location/Qualifiers
misc_feature           1..66
                       note = Humanized Antibody
source                 1..66
                       mol_type = other DNA
```

```
                         organism = synthetic construct
SEQUENCE: 1473
caggtgctga cccagtctcc ttccaccctg tctgcatctg taggagacag agtcaccatc  60
acttgt                                                             66

SEQ ID NO: 1474          moltype = DNA  length = 36
FEATURE                  Location/Qualifiers
source                   1..36
                         mol_type = unassigned DNA
                         organism = Oryctolagus cuniculus
SEQUENCE: 1474
cagtccagtg agagtgttta cggtaactac ttagcc                            36

SEQ ID NO: 1475          moltype = DNA  length = 45
FEATURE                  Location/Qualifiers
misc_feature             1..45
                         note = Humanized Antibody
source                   1..45
                         mol_type = other DNA
                         organism = synthetic construct
SEQUENCE: 1475
tggtttcagc agaaaccagg aaaagcccct aagttcctga tctat                  45

SEQ ID NO: 1476          moltype = DNA  length = 21
FEATURE                  Location/Qualifiers
source                   1..21
                         mol_type = unassigned DNA
                         organism = Oryctolagus cuniculus
SEQUENCE: 1476
gaagcatcca aactggaatc t                                            21

SEQ ID NO: 1477          moltype = DNA  length = 96
FEATURE                  Location/Qualifiers
misc_feature             1..96
                         note = Humanized Antibody
source                   1..96
                         mol_type = other DNA
                         organism = synthetic construct
SEQUENCE: 1477
ggagtcccat caaggttcag cggcagtgga tctggaacag aattcactct caccatcagc  60
agcctgcagc ctgatgattt tgcaacttac tactgt                            96

SEQ ID NO: 1478          moltype = DNA  length = 30
FEATURE                  Location/Qualifiers
source                   1..30
                         mol_type = unassigned DNA
                         organism = Oryctolagus cuniculus
SEQUENCE: 1478
gcaggcggtg atattagtga aggtgttgct                                   30

SEQ ID NO: 1479          moltype = DNA  length = 33
FEATURE                  Location/Qualifiers
misc_feature             1..33
                         note = Humanized Antibody
source                   1..33
                         mol_type = other DNA
                         organism = synthetic construct
SEQUENCE: 1479
ttcggcggag gaaccaaggt ggaaatcaaa cgt                               33

SEQ ID NO: 1480          moltype = DNA  length = 318
FEATURE                  Location/Qualifiers
misc_feature             1..318
                         note = Humanized Antibody
source                   1..318
                         mol_type = other DNA
                         organism = synthetic construct
SEQUENCE: 1480
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318

SEQ ID NO: 1481          moltype = AA  length = 442
FEATURE                  Location/Qualifiers
REGION                   1..442
                         note = Humanized Antibody
```

```
source                  1..442
                        mol_type = protein
                        organism = synthetic construct
SEQUENCE: 1481
EVQLVESGGG LVQPGGSLRL SCAASGIDLS SYYMTWVRQA PGKGLEWIGF IDAGGSAYYA  60
TWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                          442

SEQ ID NO: 1482         moltype = AA  length = 112
FEATURE                 Location/Qualifiers
REGION                  1..112
                        note = Humanized Antibody
source                  1..112
                        mol_type = protein
                        organism = synthetic construct
SEQUENCE: 1482
EVQLVESGGG LVQPGGSLRL SCAASGIDLS SYYMTWVRQA PGKGLEWIGF IDAGGSAYYA  60
TWAKGRFTIS RDNSKNTVYL QMNSLRAEDT AVYFCARDLD LWGQGTLVTV SS          112

SEQ ID NO: 1483         moltype = AA  length = 30
FEATURE                 Location/Qualifiers
REGION                  1..30
                        note = Humanized Antibody
source                  1..30
                        mol_type = protein
                        organism = synthetic construct
SEQUENCE: 1483
EVQLVESGGG LVQPGGSLRL SCAASGIDLS                                  30

SEQ ID NO: 1484         moltype = AA  length = 5
FEATURE                 Location/Qualifiers
source                  1..5
                        mol_type = protein
                        organism = Oryctolagus cuniculus
SEQUENCE: 1484
SYYMT                                                             5

SEQ ID NO: 1485         moltype = AA  length = 14
FEATURE                 Location/Qualifiers
REGION                  1..14
                        note = Humanized Antibody
source                  1..14
                        mol_type = protein
                        organism = synthetic construct
SEQUENCE: 1485
WVRQAPGKGL EWIG                                                   14

SEQ ID NO: 1486         moltype = AA  length = 16
FEATURE                 Location/Qualifiers
source                  1..16
                        mol_type = protein
                        organism = Oryctolagus cuniculus
SEQUENCE: 1486
FIDAGGSAYY ATWAKG                                                 16

SEQ ID NO: 1487         moltype = AA  length = 32
FEATURE                 Location/Qualifiers
REGION                  1..32
                        note = Humanized Antibody
source                  1..32
                        mol_type = protein
                        organism = synthetic construct
SEQUENCE: 1487
RFTISRDNSK NTVYLQMNSL RAEDTAVYFC AR                               32

SEQ ID NO: 1488         moltype = AA  length = 4
FEATURE                 Location/Qualifiers
source                  1..4
                        mol_type = protein
                        organism = Oryctolagus cuniculus
SEQUENCE: 1488
DLDL                                                              4

SEQ ID NO: 1489         moltype = AA  length = 11
```

```
FEATURE                Location/Qualifiers
REGION                 1..11
                       note = Humanized Antibody
source                 1..11
                       mol_type = protein
                       organism = synthetic construct
SEQUENCE: 1489
WGQGTLVTVS S                                                     11

SEQ ID NO: 1490        moltype = AA  length = 330
FEATURE                Location/Qualifiers
REGION                 1..330
                       note = Humanized Antibody
source                 1..330
                       mol_type = protein
                       organism = synthetic construct
SEQUENCE: 1490
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 1491        moltype = DNA  length = 1326
FEATURE                Location/Qualifiers
misc_feature           1..1326
                       note = Humanized Antibody
source                 1..1326
                       mol_type = other DNA
                       organism = synthetic construct
SEQUENCE: 1491
gaggtgcagc ttgtggagtc tgggggaggc ttggtccagc ctggggggtc cctgagactc  60
tcctgtgcag cctctggaat cgacctcagt agctactaca tgacctgggt ccgtcaggct  120
ccagggaagg ggctggagtg gatcggattc attgatgctg gtggtagcgc atactacgcg  180
acctgggcaa aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                           1326

SEQ ID NO: 1492        moltype = DNA  length = 336
FEATURE                Location/Qualifiers
misc_feature           1..336
                       note = Humanized Antibody
source                 1..336
                       mol_type = other DNA
                       organism = synthetic construct
SEQUENCE: 1492
gaggtgcagc ttgtggagtc tgggggaggc ttggtccagc ctggggggtc cctgagactc  60
tcctgtgcag cctctggaat cgacctcagt agctactaca tgacctgggt ccgtcaggct  120
ccagggaagg ggctggagtg gatcggattc attgatgctg gtggtagcgc atactacgcg  180
acctgggcaa aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                          336

SEQ ID NO: 1493        moltype = DNA  length = 90
FEATURE                Location/Qualifiers
misc_feature           1..90
                       note = Humanized Antibody
source                 1..90
                       mol_type = other DNA
                       organism = synthetic construct
SEQUENCE: 1493
```

```
gaggtgcagc ttgtggagtc tgggggaggc ttggtccagc ctgggggggtc cctgagactc  60
tcctgtgcag cctctggaat cgacctcagt                                    90

SEQ ID NO: 1494        moltype = DNA  length = 15
FEATURE                Location/Qualifiers
source                 1..15
                       mol_type = unassigned DNA
                       organism = Oryctolagus cuniculus
SEQUENCE: 1494
agctactaca tgacc                                                    15

SEQ ID NO: 1495        moltype = DNA  length = 42
FEATURE                Location/Qualifiers
misc_feature           1..42
                       note = Humanized Antibody
source                 1..42
                       mol_type = other DNA
                       organism = synthetic construct
SEQUENCE: 1495
tgggtccgtc aggctccagg gaaggggctg gagtggatcg ga                      42

SEQ ID NO: 1496        moltype = DNA  length = 48
FEATURE                Location/Qualifiers
source                 1..48
                       mol_type = unassigned DNA
                       organism = Oryctolagus cuniculus
SEQUENCE: 1496
ttcattgatg ctggtggtag cgcatactac gcgacctggg caaaaggc                48

SEQ ID NO: 1497        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1497
cgattcacca tctccagaga caattccaag aacaccgtgt atcttcaaat gaacagcctg  60
agagctgagg acactgctgt gtatttctgt gctaga                             96

SEQ ID NO: 1498        moltype = DNA  length = 12
FEATURE                Location/Qualifiers
source                 1..12
                       mol_type = unassigned DNA
                       organism = Oryctolagus cuniculus
SEQUENCE: 1498
gatcttgact tg                                                       12

SEQ ID NO: 1499        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1499
tggggccaag ggaccctcgt caccgtctcg agc                                33

SEQ ID NO: 1500        moltype = DNA  length = 990
FEATURE                Location/Qualifiers
misc_feature           1..990
                       note = Humanized Antibody
source                 1..990
                       mol_type = other DNA
                       organism = synthetic construct
SEQUENCE: 1500
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
```

```
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 1501        moltype = AA  length = 215
FEATURE                Location/Qualifiers
REGION                 1..215
                       note = Humanized Antibody
source                 1..215
                       mol_type = protein
                       organism = synthetic construct
SEQUENCE: 1501
AVLTQSPSTL SASVGDRVTI TCKSSESVYG DYLAWFQQKP GKAPKQLIYD ASTLASGVPS  60
RFSGSGSGTE FTLTISSLQP DDFATYYCAG GYVSAGVAFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                              215

SEQ ID NO: 1502        moltype = AA  length = 109
FEATURE                Location/Qualifiers
REGION                 1..109
                       note = Humanized Antibody
source                 1..109
                       mol_type = protein
                       organism = synthetic construct
SEQUENCE: 1502
AVLTQSPSTL SASVGDRVTI TCKSSESVYG DYLAWFQQKP GKAPKQLIYD ASTLASGVPS  60
RFSGSGSGTE FTLTISSLQP DDFATYYCAG GYVSAGVAFG GGTKVEIKR             109

SEQ ID NO: 1503        moltype = AA  length = 22
FEATURE                Location/Qualifiers
REGION                 1..22
                       note = Humanized Antibody
source                 1..22
                       mol_type = protein
                       organism = synthetic construct
SEQUENCE: 1503
AVLTQSPSTL SASVGDRVTI TC                                           22

SEQ ID NO: 1504        moltype = AA  length = 12
FEATURE                Location/Qualifiers
source                 1..12
                       mol_type = protein
                       organism = Oryctolagus cuniculus
SEQUENCE: 1504
KSSESVYGDY LA                                                      12

SEQ ID NO: 1505        moltype = AA  length = 15
FEATURE                Location/Qualifiers
REGION                 1..15
                       note = Humanized Antibody
source                 1..15
                       mol_type = protein
                       organism = synthetic construct
SEQUENCE: 1505
WFQQKPGKAP KQLIY                                                   15

SEQ ID NO: 1506        moltype = AA  length = 7
FEATURE                Location/Qualifiers
source                 1..7
                       mol_type = protein
                       organism = Oryctolagus cuniculus
SEQUENCE: 1506
DASTLAS                                                            7

SEQ ID NO: 1507        moltype = AA  length = 32
FEATURE                Location/Qualifiers
REGION                 1..32
                       note = Humanized Antibody
source                 1..32
                       mol_type = protein
                       organism = synthetic construct
SEQUENCE: 1507
GVPSRFSGSG SGTEFTLTIS SLQPDDFATY YC                                32

SEQ ID NO: 1508        moltype = AA  length = 10
FEATURE                Location/Qualifiers
source                 1..10
                       mol_type = protein
```

```
                        organism = Oryctolagus cuniculus
SEQUENCE: 1508
AGGYVSAGVA                                                        10

SEQ ID NO: 1509         moltype = AA  length = 11
FEATURE                 Location/Qualifiers
REGION                  1..11
                        note = Humanized Antibody
source                  1..11
                        mol_type = protein
                        organism = synthetic construct
SEQUENCE: 1509
FGGGTKVEIK R                                                      11

SEQ ID NO: 1510         moltype = AA  length = 106
FEATURE                 Location/Qualifiers
REGION                  1..106
                        note = Humanized Antibody
source                  1..106
                        mol_type = protein
                        organism = synthetic construct
SEQUENCE: 1510
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 1511         moltype = DNA  length = 645
FEATURE                 Location/Qualifiers
misc_feature            1..645
                        note = Humanized Antibody
source                  1..645
                        mol_type = other DNA
                        organism = synthetic construct
SEQUENCE: 1511
gccgtgctga cccagtctcc ttccaccctg tctgcatctg taggagacag agtcaccatc  60
acttgtaagt ccagtgagag cgtttatggt gactacttag cctggtttca gcagaaacca  120
ggaaaagccc ctaagcaact gatctatgat gcatccactc tggcatctgg agtcccatca  180
aggttcagcg gcagtggatc tggaacagaa ttcactctca ccatcagcag cctgcagcct  240
gatgattttg caacttacta ctgtgcaggc ggttatgtta gtgcaggtgt tgctttcggc  300
ggaggaacca aggtggaaat caaacgtacg gtagcggccc catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgt                 645

SEQ ID NO: 1512         moltype = DNA  length = 327
FEATURE                 Location/Qualifiers
misc_feature            1..327
                        note = Humanized Antibody
source                  1..327
                        mol_type = other DNA
                        organism = synthetic construct
SEQUENCE: 1512
gccgtgctga cccagtctcc ttccaccctg tctgcatctg taggagacag agtcaccatc  60
acttgtaagt ccagtgagag cgtttatggt gactacttag cctggtttca gcagaaacca  120
ggaaaagccc ctaagcaact gatctatgat gcatccactc tggcatctgg agtcccatca  180
aggttcagcg gcagtggatc tggaacagaa ttcactctca ccatcagcag cctgcagcct  240
gatgattttg caacttacta ctgtgcaggc ggttatgtta gtgcaggtgt tgctttcggc  300
ggaggaacca aggtggaaat caaacgt                                     327

SEQ ID NO: 1513         moltype = DNA  length = 66
FEATURE                 Location/Qualifiers
misc_feature            1..66
                        note = Humanized Antibody
source                  1..66
                        mol_type = other DNA
                        organism = synthetic construct
SEQUENCE: 1513
gccgtgctga cccagtctcc ttccaccctg tctgcatctg taggagacag agtcaccatc  60
acttgt                                                            66

SEQ ID NO: 1514         moltype = DNA  length = 36
FEATURE                 Location/Qualifiers
source                  1..36
                        mol_type = unassigned DNA
                        organism = Oryctolagus cuniculus
SEQUENCE: 1514
aagtccagtg agagcgttta tggtgactac ttagcc                           36
```

```
SEQ ID NO: 1515        moltype = DNA  length = 45
FEATURE                Location/Qualifiers
misc_feature           1..45
                       note = Humanized Antibody
source                 1..45
                       mol_type = other DNA
                       organism = synthetic construct
SEQUENCE: 1515
tggtttcagc agaaaccagg aaaagcccct aagcaactga tctat                 45

SEQ ID NO: 1516        moltype = DNA  length = 21
FEATURE                Location/Qualifiers
source                 1..21
                       mol_type = unassigned DNA
                       organism = Oryctolagus cuniculus
SEQUENCE: 1516
gatgcatcca ctctggcatc t                                           21

SEQ ID NO: 1517        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1517
ggagtcccat caaggttcag cggcagtgga tctggaacag aattcactct caccatcagc  60
agcctgcagc ctgatgattt tgcaacttac tactgt                           96

SEQ ID NO: 1518        moltype = DNA  length = 30
FEATURE                Location/Qualifiers
source                 1..30
                       mol_type = unassigned DNA
                       organism = Oryctolagus cuniculus
SEQUENCE: 1518
gcaggcggtt atgttagtgc aggtgttgct                                  30

SEQ ID NO: 1519        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1519
ttcggcggag gaaccaaggt ggaaatcaaa cgt                              33

SEQ ID NO: 1520        moltype = DNA  length = 318
FEATURE                Location/Qualifiers
misc_feature           1..318
                       note = Humanized Antibody
source                 1..318
                       mol_type = other DNA
                       organism = synthetic construct
SEQUENCE: 1520
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                               318

SEQ ID NO: 1521        moltype = AA  length = 442
FEATURE                Location/Qualifiers
REGION                 1..442
                       note = Humanized Antibody
source                 1..442
                       mol_type = protein
                       organism = synthetic construct
SEQUENCE: 1521
EVQLVESGGG LVQPGGSLRL SCAASGIDLS SYYMTWVRQA PGKGLEWIGF IDAGGSAYYA  60
TWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                          442
```

```
SEQ ID NO: 1522        moltype = AA  length = 112
FEATURE                Location/Qualifiers
REGION                 1..112
                       note = Humanized Antibody
source                 1..112
                       mol_type = protein
                       organism = synthetic construct
SEQUENCE: 1522
EVQLVESGGG LVQPGGSLRL SCAASGIDLS SYYMTWVRQA PGKGLEWIGF IDAGGSAYYA  60
TWAKGRFTIS RDNSKNTVYL QMNSLRAEDT AVYFCARDLD LWGQGTLVTV SS          112

SEQ ID NO: 1523        moltype = AA  length = 30
FEATURE                Location/Qualifiers
REGION                 1..30
                       note = Humanized Antibody
source                 1..30
                       mol_type = protein
                       organism = synthetic construct
SEQUENCE: 1523
EVQLVESGGG LVQPGGSLRL SCAASGIDLS                                   30

SEQ ID NO: 1524        moltype = AA  length = 5
FEATURE                Location/Qualifiers
source                 1..5
                       mol_type = protein
                       organism = Oryctolagus cuniculus
SEQUENCE: 1524
SYYMT                                                              5

SEQ ID NO: 1525        moltype = AA  length = 14
FEATURE                Location/Qualifiers
REGION                 1..14
                       note = Humanized Antibody
source                 1..14
                       mol_type = protein
                       organism = synthetic construct
SEQUENCE: 1525
WVRQAPGKGL EWIG                                                    14

SEQ ID NO: 1526        moltype = AA  length = 16
FEATURE                Location/Qualifiers
source                 1..16
                       mol_type = protein
                       organism = Oryctolagus cuniculus
SEQUENCE: 1526
FIDAGGSAYY ATWAKG                                                  16

SEQ ID NO: 1527        moltype = AA  length = 32
FEATURE                Location/Qualifiers
REGION                 1..32
                       note = Humanized Antibody
source                 1..32
                       mol_type = protein
                       organism = synthetic construct
SEQUENCE: 1527
RFTISRDNSK NTVYLQMNSL RAEDTAVYFC AR                                32

SEQ ID NO: 1528        moltype = AA  length = 4
FEATURE                Location/Qualifiers
source                 1..4
                       mol_type = protein
                       organism = Oryctolagus cuniculus
SEQUENCE: 1528
DLDL                                                               4

SEQ ID NO: 1529        moltype = AA  length = 11
FEATURE                Location/Qualifiers
REGION                 1..11
                       note = Humanized Antibody
source                 1..11
                       mol_type = protein
                       organism = synthetic construct
SEQUENCE: 1529
WGQGTLVTVS S                                                       11

SEQ ID NO: 1530        moltype = AA  length = 330
FEATURE                Location/Qualifiers
REGION                 1..330
                       note = Humanized Antibody
```

```
source                1..330
                      mol_type = protein
                      organism = synthetic construct
SEQUENCE: 1530
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 1531       moltype = DNA  length = 1326
FEATURE               Location/Qualifiers
misc_feature          1..1326
                      note = Humanized Antibody
source                1..1326
                      mol_type = other DNA
                      organism = synthetic construct
SEQUENCE: 1531
gaggtgcagc ttgtggagtc tgggggaggc ttggtccagc ctgggggtc cctgagactc  60
tcctgtgcag cctctggaat cgacctcagt agctactaca tgacctgggt ccgtcaggct  120
ccagggaagg ggctggagtg gatcggattc attgatgctg gtggtagcgc atactacgcg  180
acctgggcaa aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                            1326

SEQ ID NO: 1532       moltype = DNA  length = 336
FEATURE               Location/Qualifiers
misc_feature          1..336
                      note = Humanized Antibody
source                1..336
                      mol_type = other DNA
                      organism = synthetic construct
SEQUENCE: 1532
gaggtgcagc ttgtggagtc tgggggaggc ttggtccagc ctgggggtc cctgagactc  60
tcctgtgcag cctctggaat cgacctcagt agctactaca tgacctgggt ccgtcaggct  120
ccagggaagg ggctggagtg gatcggattc attgatgctg gtggtagcgc atactacgcg  180
acctgggcaa aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                            336

SEQ ID NO: 1533       moltype = DNA  length = 90
FEATURE               Location/Qualifiers
misc_feature          1..90
                      note = Humanized Antibody
source                1..90
                      mol_type = other DNA
                      organism = synthetic construct
SEQUENCE: 1533
gaggtgcagc ttgtggagtc tgggggaggc ttggtccagc ctgggggtc cctgagactc  60
tcctgtgcag cctctggaat cgacctcagt                                  90

SEQ ID NO: 1534       moltype = DNA  length = 15
FEATURE               Location/Qualifiers
source                1..15
                      mol_type = unassigned DNA
                      organism = Oryctolagus cuniculus
SEQUENCE: 1534
agctactaca tgacc                                                  15

SEQ ID NO: 1535       moltype = DNA  length = 42
FEATURE               Location/Qualifiers
```

```
misc_feature          1..42
                      note = Humanized Antibody
source                1..42
                      mol_type = other DNA
                      organism = synthetic construct
SEQUENCE: 1535
tgggtccgtc aggctccagg gaaggggctg gagtggatcg ga                    42

SEQ ID NO: 1536       moltype = DNA  length = 48
FEATURE               Location/Qualifiers
source                1..48
                      mol_type = unassigned DNA
                      organism = Oryctolagus cuniculus
SEQUENCE: 1536
ttcattgatg ctggtggtag cgcatactac gcgacctggg caaaaggc              48

SEQ ID NO: 1537       moltype = DNA  length = 96
FEATURE               Location/Qualifiers
misc_feature          1..96
                      note = Humanized Antibody
source                1..96
                      mol_type = other DNA
                      organism = synthetic construct
SEQUENCE: 1537
cgattcacca tctccagaga caattccaag aacaccgtgt atcttcaaat gaacagcctg  60
agagctgagg acactgctgt gtatttctgt gctaga                            96

SEQ ID NO: 1538       moltype = DNA  length = 12
FEATURE               Location/Qualifiers
source                1..12
                      mol_type = unassigned DNA
                      organism = Oryctolagus cuniculus
SEQUENCE: 1538
gatcttgact tg                                                      12

SEQ ID NO: 1539       moltype = DNA  length = 33
FEATURE               Location/Qualifiers
misc_feature          1..33
                      note = Humanized Antibody
source                1..33
                      mol_type = other DNA
                      organism = synthetic construct
SEQUENCE: 1539
tggggccaag ggaccctcgt caccgtctcg agc                               33

SEQ ID NO: 1540       moltype = DNA  length = 990
FEATURE               Location/Qualifiers
misc_feature          1..990
                      note = Humanized Antibody
source                1..990
                      mol_type = other DNA
                      organism = synthetic construct
SEQUENCE: 1540
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 1541       moltype = AA  length = 216
FEATURE               Location/Qualifiers
REGION                1..216
                      note = Humanized Antibody
source                1..216
                      mol_type = protein
                      organism = synthetic construct
SEQUENCE: 1541
```

```
DIQLTQSPST LSASVGDRVT ITCKSSESVY GDYLAWFQQK PGKAPKQLIY DASTLASGVP  60
SRFSGSGSGT EFTLTISSLQ PDDFATYYCA GGYVSAGVAF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 1542        moltype = AA  length = 110
FEATURE                Location/Qualifiers
REGION                 1..110
                       note = Humanized Antibody
source                 1..110
                       mol_type = protein
                       organism = synthetic construct
SEQUENCE: 1542
DIQLTQSPST LSASVGDRVT ITCKSSESVY GDYLAWFQQK PGKAPKQLIY DASTLASGVP  60
SRFSGSGSGT EFTLTISSLQ PDDFATYYCA GGYVSAGVAF GGGTKVEIKR             110

SEQ ID NO: 1543        moltype = AA  length = 23
FEATURE                Location/Qualifiers
REGION                 1..23
                       note = Humanized Antibody
source                 1..23
                       mol_type = protein
                       organism = synthetic construct
SEQUENCE: 1543
DIQLTQSPST LSASVGDRVT ITC                                          23

SEQ ID NO: 1544        moltype = AA  length = 12
FEATURE                Location/Qualifiers
source                 1..12
                       mol_type = protein
                       organism = Oryctolagus cuniculus
SEQUENCE: 1544
KSSESVYGDY LA                                                      12

SEQ ID NO: 1545        moltype = AA  length = 15
FEATURE                Location/Qualifiers
REGION                 1..15
                       note = Humanized Antibody
source                 1..15
                       mol_type = protein
                       organism = synthetic construct
SEQUENCE: 1545
WFQQKPGKAP KQLIY                                                   15

SEQ ID NO: 1546        moltype = AA  length = 7
FEATURE                Location/Qualifiers
source                 1..7
                       mol_type = protein
                       organism = Oryctolagus cuniculus
SEQUENCE: 1546
DASTLAS                                                            7

SEQ ID NO: 1547        moltype = AA  length = 32
FEATURE                Location/Qualifiers
REGION                 1..32
                       note = Humanized Antibody
source                 1..32
                       mol_type = protein
                       organism = synthetic construct
SEQUENCE: 1547
GVPSRFSGSG SGTEFTLTIS SLQPDDFATY YC                                32

SEQ ID NO: 1548        moltype = AA  length = 10
FEATURE                Location/Qualifiers
source                 1..10
                       mol_type = protein
                       organism = Oryctolagus cuniculus
SEQUENCE: 1548
AGGYVSAGVA                                                         10

SEQ ID NO: 1549        moltype = AA  length = 11
FEATURE                Location/Qualifiers
REGION                 1..11
                       note = Humanized Antibody
source                 1..11
                       mol_type = protein
                       organism = synthetic construct
SEQUENCE: 1549
FGGGTKVEIK R                                                       11
```

```
SEQ ID NO: 1550        moltype = AA  length = 106
FEATURE                Location/Qualifiers
REGION                 1..106
                       note = Humanized Antibody
source                 1..106
                       mol_type = protein
                       organism = synthetic construct
SEQUENCE: 1550
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 1551        moltype = DNA  length = 648
FEATURE                Location/Qualifiers
misc_feature           1..648
                       note = Humanized Antibody
source                 1..648
                       mol_type = other DNA
                       organism = synthetic construct
SEQUENCE: 1551
gacatccagc tgacccagtc tccttccacc ctgtctgcat ctgtaggaga cagagtcacc  60
atcacttgta agtccagtga gagcgtttat ggtgactact tagcctggtt tcagcagaaa  120
ccaggaaaag cccctaagca actgatctat gatgcatcca ctctggcatc tggagtccca  180
tcaaggttca gcggcagtgg atctggaaca gaattcactc tcaccatcag cagcctgcag  240
cctgatgatt ttgcaactta ctactgtgca ggcggttatg ttagtgcagg tgttgctttc  300
ggcggaggaa ccaaggtgga aatcaaacgt acggtagcgg ccccatctgt cttcatcttc  360
ccgccatctg atgagcagtt gaaatctgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt              648

SEQ ID NO: 1552        moltype = DNA  length = 330
FEATURE                Location/Qualifiers
misc_feature           1..330
                       note = Humanized Antibody
source                 1..330
                       mol_type = other DNA
                       organism = synthetic construct
SEQUENCE: 1552
gacatccagc tgacccagtc tccttccacc ctgtctgcat ctgtaggaga cagagtcacc  60
atcacttgta agtccagtga gagcgtttat ggtgactact tagcctggtt tcagcagaaa  120
ccaggaaaag cccctaagca actgatctat gatgcatcca ctctggcatc tggagtccca  180
tcaaggttca gcggcagtgg atctggaaca gaattcactc tcaccatcag cagcctgcag  240
cctgatgatt ttgcaactta ctactgtgca ggcggttatg ttagtgcagg tgttgctttc  300
ggcggaggaa ccaaggtgga aatcaaacgt                                  330

SEQ ID NO: 1553        moltype = DNA  length = 69
FEATURE                Location/Qualifiers
misc_feature           1..69
                       note = Humanized Antibody
source                 1..69
                       mol_type = other DNA
                       organism = synthetic construct
SEQUENCE: 1553
gacatccagc tgacccagtc tccttccacc ctgtctgcat ctgtaggaga cagagtcacc  60
atcacttgt                                                         69

SEQ ID NO: 1554        moltype = DNA  length = 36
FEATURE                Location/Qualifiers
source                 1..36
                       mol_type = unassigned DNA
                       organism = Oryctolagus cuniculus
SEQUENCE: 1554
aagtccagtg agagcgttta tggtgactac ttagcc                           36

SEQ ID NO: 1555        moltype = DNA  length = 45
FEATURE                Location/Qualifiers
misc_feature           1..45
                       note = Humanized Antibody
source                 1..45
                       mol_type = other DNA
                       organism = synthetic construct
SEQUENCE: 1555
tggtttcagc agaaaccagg aaaagcccct aagcaactga tctat                 45

SEQ ID NO: 1556        moltype = DNA  length = 21
FEATURE                Location/Qualifiers
source                 1..21
```

```
                        mol_type = unassigned DNA
                        organism = Oryctolagus cuniculus
SEQUENCE: 1556
gatgcatcca ctctggcatc t                                           21

SEQ ID NO: 1557         moltype = DNA  length = 96
FEATURE                 Location/Qualifiers
misc_feature            1..96
                        note = Humanized Antibody
source                  1..96
                        mol_type = other DNA
                        organism = synthetic construct
SEQUENCE: 1557
ggagtcccat caaggttcag cggcagtgga tctggaacag aattcactct caccatcagc  60
agcctgcagc ctgatgattt tgcaacttac tactgt                           96

SEQ ID NO: 1558         moltype = DNA  length = 30
FEATURE                 Location/Qualifiers
source                  1..30
                        mol_type = unassigned DNA
                        organism = Oryctolagus cuniculus
SEQUENCE: 1558
gcaggcggtt atgttagtgc aggtgttgct                                  30

SEQ ID NO: 1559         moltype = DNA  length = 33
FEATURE                 Location/Qualifiers
misc_feature            1..33
                        note = Humanized Antibody
source                  1..33
                        mol_type = other DNA
                        organism = synthetic construct
SEQUENCE: 1559
ttcggcggag gaaccaaggt ggaaatcaaa cgt                              33

SEQ ID NO: 1560         moltype = DNA  length = 318
FEATURE                 Location/Qualifiers
misc_feature            1..318
                        note = Humanized Antibody
source                  1..318
                        mol_type = other DNA
                        organism = synthetic construct
SEQUENCE: 1560
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                               318

SEQ ID NO: 1561         moltype = AA  length = 442
FEATURE                 Location/Qualifiers
REGION                  1..442
                        note = Humanized Antibody
source                  1..442
                        mol_type = protein
                        organism = synthetic construct
SEQUENCE: 1561
EVQLVESGGG LVQPGGSLRL SCAASGIDLS SYYMTWVRQA PGKGLEWIGF IDAGGSAYYA  60
TWAKGRFTIS RDNSKNTVYL QMNSLRAEDT AVYFCARDLD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YASTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                          442

SEQ ID NO: 1562         moltype = AA  length = 112
FEATURE                 Location/Qualifiers
REGION                  1..112
                        note = Humanized Antibody
source                  1..112
                        mol_type = protein
                        organism = synthetic construct
SEQUENCE: 1562
EVQLVESGGG LVQPGGSLRL SCAASGIDLS SYYMTWVRQA PGKGLEWIGF IDAGGSAYYA  60
TWAKGRFTIS RDNSKNTVYL QMNSLRAEDT AVYFCARDLD LWGQGTLVTV SS          112

SEQ ID NO: 1563         moltype = AA  length = 30
FEATURE                 Location/Qualifiers
```

```
REGION                  1..30
                        note = Humanized Antibody
source                  1..30
                        mol_type = protein
                        organism = synthetic construct
SEQUENCE: 1563
EVQLVESGGG LVQPGGSLRL SCAASGIDLS                                  30

SEQ ID NO: 1564         moltype = AA  length = 5
FEATURE                 Location/Qualifiers
source                  1..5
                        mol_type = protein
                        organism = Oryctolagus cuniculus
SEQUENCE: 1564
SYYMT                                                             5

SEQ ID NO: 1565         moltype = AA  length = 14
FEATURE                 Location/Qualifiers
REGION                  1..14
                        note = Humanized Antibody
source                  1..14
                        mol_type = protein
                        organism = synthetic construct
SEQUENCE: 1565
WVRQAPGKGL EWIG                                                   14

SEQ ID NO: 1566         moltype = AA  length = 16
FEATURE                 Location/Qualifiers
source                  1..16
                        mol_type = protein
                        organism = Oryctolagus cuniculus
SEQUENCE: 1566
FIDAGGSAYY ATWAKG                                                 16

SEQ ID NO: 1567         moltype = AA  length = 32
FEATURE                 Location/Qualifiers
REGION                  1..32
                        note = Humanized Antibody
source                  1..32
                        mol_type = protein
                        organism = synthetic construct
SEQUENCE: 1567
RFTISRDNSK NTVYLQMNSL RAEDTAVYFC AR                               32

SEQ ID NO: 1568         moltype = AA  length = 4
FEATURE                 Location/Qualifiers
source                  1..4
                        mol_type = protein
                        organism = Oryctolagus cuniculus
SEQUENCE: 1568
DLDL                                                              4

SEQ ID NO: 1569         moltype = AA  length = 11
FEATURE                 Location/Qualifiers
REGION                  1..11
                        note = Humanized Antibody
source                  1..11
                        mol_type = protein
                        organism = synthetic construct
SEQUENCE: 1569
WGQGTLVTVS S                                                      11

SEQ ID NO: 1570         moltype = AA  length = 330
FEATURE                 Location/Qualifiers
REGION                  1..330
                        note = Humanized Antibody
source                  1..330
                        mol_type = protein
                        organism = synthetic construct
SEQUENCE: 1570
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 1571         moltype = DNA  length = 1326
FEATURE                 Location/Qualifiers
```

```
misc_feature           1..1326
                       note = Humanized Antibody
source                 1..1326
                       mol_type = other DNA
                       organism = synthetic construct
SEQUENCE: 1571
gaggtgcagc ttgtggagtc tgggggaggc ttggtccagc ctgggggtc cctgagactc  60
tcctgtgcag cctctggaat cgacctcagt agctactaca tgacctgggt ccgtcaggct  120
ccagggaagg ggctggagtg gatcggattc attgatgctg gtggtagcgc atactacgcg  180
acctgggcaa aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagcgcct ccaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagaaagtt gagcccaaat cttgtgacaa aactcacaca  660
tgcccaccgt gcccagcacc tgaactcctg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacgccagca cgtaccgtgt ggtcagcgtc  900
ctcaccgtcc tgcaccagga ctggctgaat ggcaaggagt acaagtgcaa ggtctccaac  960
aaagccctcc cagcccccat cgagaaaacc atctccaaag ccaaagggca gccccgagaa  1020
ccacaggtgt acaccctgcc cccatcccgg gaggagatga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaa                                                             1326

SEQ ID NO: 1572        moltype = DNA  length = 336
FEATURE                Location/Qualifiers
misc_feature           1..336
                       note = Humanized Antibody
source                 1..336
                       mol_type = other DNA
                       organism = synthetic construct
SEQUENCE: 1572
gaggtgcagc ttgtggagtc tgggggaggc ttggtccagc ctgggggtc cctgagactc  60
tcctgtgcag cctctggaat cgacctcagt agctactaca tgacctgggt ccgtcaggct  120
ccagggaagg ggctggagtg gatcggattc attgatgctg gtggtagcgc atactacgcg  180
acctgggcaa aaggccgatt caccatctcc agagacaatt ccaagaacac cgtgtatctt  240
caaatgaaca gcctgagagc tgaggacact gctgtgtatt tctgtgctag agatcttgac  300
ttgtggggcc aagggaccct cgtcaccgtc tcgagc                            336

SEQ ID NO: 1573        moltype = DNA  length = 90
FEATURE                Location/Qualifiers
misc_feature           1..90
                       note = Humanized Antibody
source                 1..90
                       mol_type = other DNA
                       organism = synthetic construct
SEQUENCE: 1573
gaggtgcagc ttgtggagtc tgggggaggc ttggtccagc ctgggggtc cctgagactc  60
tcctgtgcag cctctggaat cgacctcagt                                   90

SEQ ID NO: 1574        moltype = DNA  length = 15
FEATURE                Location/Qualifiers
source                 1..15
                       mol_type = unassigned DNA
                       organism = Oryctolagus cuniculus
SEQUENCE: 1574
agctactaca tgacc                                                   15

SEQ ID NO: 1575        moltype = DNA  length = 42
FEATURE                Location/Qualifiers
misc_feature           1..42
                       note = Humanized Antibody
source                 1..42
                       mol_type = other DNA
                       organism = synthetic construct
SEQUENCE: 1575
tgggtccgtc aggctccagg gaaggggctg gagtggatcg ga                     42

SEQ ID NO: 1576        moltype = DNA  length = 48
FEATURE                Location/Qualifiers
source                 1..48
                       mol_type = unassigned DNA
                       organism = Oryctolagus cuniculus
```

```
SEQUENCE: 1576
ttcattgatg ctggtggtag cgcatactac gcgacctggg caaaaggc              48

SEQ ID NO: 1577        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1577
cgattcacca tctccagaga caattccaag aacaccgtgt atcttcaaat gaacagcctg  60
agagctgagg acactgctgt gtatttctgt gctaga                            96

SEQ ID NO: 1578        moltype = DNA  length = 12
FEATURE                Location/Qualifiers
source                 1..12
                       mol_type = unassigned DNA
                       organism = Oryctolagus cuniculus
SEQUENCE: 1578
gatcttgact tg                                                      12

SEQ ID NO: 1579        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1579
tggggccaag ggaccctcgt caccgtctcg agc                               33

SEQ ID NO: 1580        moltype = DNA  length = 990
FEATURE                Location/Qualifiers
misc_feature           1..990
                       note = Humanized Antibody
source                 1..990
                       mol_type = other DNA
                       organism = synthetic construct
SEQUENCE: 1580
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacgcc  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggaggag  720
atgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagagcc tctccctgtc tccgggtaaa                                   990

SEQ ID NO: 1581        moltype = AA  length = 216
FEATURE                Location/Qualifiers
REGION                 1..216
                       note = Humanized Antibody
source                 1..216
                       mol_type = protein
                       organism = synthetic construct
SEQUENCE: 1581
DIVLTQSPST LSASVGDRVT ITCKSSESVY GDYLAWFQQK PGKAPKQLIY DASTLASGVP  60
SRFSGSGSGT EFTLTISSLQ PDDFATYYCA GGYVSAGVAF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 1582        moltype = AA  length = 110
FEATURE                Location/Qualifiers
REGION                 1..110
                       note = Humanized Antibody
source                 1..110
                       mol_type = protein
                       organism = synthetic construct
SEQUENCE: 1582
```

```
DIVLTQSPST LSASVGDRVT ITCKSSESVY GDYLAWFQQK PGKAPKQLIY DASTLASGVP  60
SRFSGSGSGT EFTLTISSLQ PDDFATYYCA GGYVSAGVAF GGGTKVEIKR             110

SEQ ID NO: 1583        moltype = AA  length = 23
FEATURE                Location/Qualifiers
REGION                 1..23
                       note = Humanized Antibody
source                 1..23
                       mol_type = protein
                       organism = synthetic construct
SEQUENCE: 1583
DIVLTQSPST LSASVGDRVT ITC                                          23

SEQ ID NO: 1584        moltype = AA  length = 12
FEATURE                Location/Qualifiers
source                 1..12
                       mol_type = protein
                       organism = Oryctolagus cuniculus
SEQUENCE: 1584
KSSESVYGDY LA                                                      12

SEQ ID NO: 1585        moltype = AA  length = 15
FEATURE                Location/Qualifiers
REGION                 1..15
                       note = Humanized Antibody
source                 1..15
                       mol_type = protein
                       organism = synthetic construct
SEQUENCE: 1585
WFQQKPGKAP KQLIY                                                   15

SEQ ID NO: 1586        moltype = AA  length = 7
FEATURE                Location/Qualifiers
source                 1..7
                       mol_type = protein
                       organism = Oryctolagus cuniculus
SEQUENCE: 1586
DASTLAS                                                            7

SEQ ID NO: 1587        moltype = AA  length = 32
FEATURE                Location/Qualifiers
REGION                 1..32
                       note = Humanized Antibody
source                 1..32
                       mol_type = protein
                       organism = synthetic construct
SEQUENCE: 1587
GVPSRFSGSG SGTEFTLTIS SLQPDDFATY YC                                32

SEQ ID NO: 1588        moltype = AA  length = 10
FEATURE                Location/Qualifiers
source                 1..10
                       mol_type = protein
                       organism = Oryctolagus cuniculus
SEQUENCE: 1588
AGGYVSAGVA                                                         10

SEQ ID NO: 1589        moltype = AA  length = 11
FEATURE                Location/Qualifiers
REGION                 1..11
                       note = Humanized Antibody
source                 1..11
                       mol_type = protein
                       organism = synthetic construct
SEQUENCE: 1589
FGGGTKVEIK R                                                       11

SEQ ID NO: 1590        moltype = AA  length = 106
FEATURE                Location/Qualifiers
REGION                 1..106
                       note = Humanized Antibody
source                 1..106
                       mol_type = protein
                       organism = synthetic construct
SEQUENCE: 1590
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 1591        moltype = DNA  length = 648
```

```
FEATURE                Location/Qualifiers
misc_feature           1..648
                       note = Humanized Antibody
source                 1..648
                       mol_type = other DNA
                       organism = synthetic construct
SEQUENCE: 1591
gacatcgtgc tgacccagtc tccttccacc ctgtctgcat ctgtaggaga cagagtcacc  60
atcacttgta agtccagtga gagcgtttat ggtgactact tagcctggtt tcagcagaaa  120
ccaggaaaag cccctaagca actgatctat gatgcatcca ctctggcatc tggagtccca  180
tcaaggttca gcggcagtgg atctggaaca gaattcactc tcaccatcag cagcctgcag  240
cctgatgatt ttgcaactta ctactgtgca ggcggttatg ttagtgcagg tgttgctttc  300
ggcggaggaa ccaaggtgga aatcaaacgt acggtagcgg ccccatctgt cttcatcttc  360
ccgccatctg atgagcagtt gaaatctgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagca cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgt              648

SEQ ID NO: 1592        moltype = DNA  length = 330
FEATURE                Location/Qualifiers
misc_feature           1..330
                       note = Humanized Antibody
source                 1..330
                       mol_type = other DNA
                       organism = synthetic construct
SEQUENCE: 1592
gacatcgtgc tgacccagtc tccttccacc ctgtctgcat ctgtaggaga cagagtcacc  60
atcacttgta agtccagtga gagcgtttat ggtgactact tagcctggtt tcagcagaaa  120
ccaggaaaag cccctaagca actgatctat gatgcatcca ctctggcatc tggagtccca  180
tcaaggttca gcggcagtgg atctggaaca gaattcactc tcaccatcag cagcctgcag  240
cctgatgatt ttgcaactta ctactgtgca ggcggttatg ttagtgcagg tgttgctttc  300
ggcggaggaa ccaaggtgga aatcaaacgt                                  330

SEQ ID NO: 1593        moltype = DNA  length = 69
FEATURE                Location/Qualifiers
misc_feature           1..69
                       note = Humanized Antibody
source                 1..69
                       mol_type = other DNA
                       organism = synthetic construct
SEQUENCE: 1593
gacatcgtgc tgacccagtc tccttccacc ctgtctgcat ctgtaggaga cagagtcacc  60
atcacttgt                                                          69

SEQ ID NO: 1594        moltype = DNA  length = 36
FEATURE                Location/Qualifiers
source                 1..36
                       mol_type = unassigned DNA
                       organism = Oryctolagus cuniculus
SEQUENCE: 1594
aagtccagtg agagcgttta tggtgactac ttagcc                            36

SEQ ID NO: 1595        moltype = DNA  length = 45
FEATURE                Location/Qualifiers
misc_feature           1..45
                       note = Humanized Antibody
source                 1..45
                       mol_type = other DNA
                       organism = synthetic construct
SEQUENCE: 1595
tggtttcagc agaaaccagg aaaagcccct aagcaactga tctat                  45

SEQ ID NO: 1596        moltype = DNA  length = 21
FEATURE                Location/Qualifiers
source                 1..21
                       mol_type = unassigned DNA
                       organism = Oryctolagus cuniculus
SEQUENCE: 1596
gatgcatcca ctctggcatc t                                            21

SEQ ID NO: 1597        moltype = DNA  length = 96
FEATURE                Location/Qualifiers
misc_feature           1..96
                       note = Humanized Antibody
source                 1..96
                       mol_type = other DNA
                       organism = synthetic construct
SEQUENCE: 1597
```

-continued

```
ggagtcccat caaggttcag cggcagtgga tctggaacag aattcactct caccatcagc  60
agcctgcagc ctgatgattt tgcaacttac tactgt                            96

SEQ ID NO: 1598        moltype = DNA  length = 30
FEATURE                Location/Qualifiers
source                 1..30
                       mol_type = unassigned DNA
                       organism = Oryctolagus cuniculus
SEQUENCE: 1598
gcaggcggtt atgttagtgc aggtgttgct                                   30

SEQ ID NO: 1599        moltype = DNA  length = 33
FEATURE                Location/Qualifiers
misc_feature           1..33
                       note = Humanized Antibody
source                 1..33
                       mol_type = other DNA
                       organism = synthetic construct
SEQUENCE: 1599
ttcggcggag gaaccaaggt ggaaatcaaa cgt                               33

SEQ ID NO: 1600        moltype = DNA  length = 318
FEATURE                Location/Qualifiers
misc_feature           1..318
                       note = Humanized Antibody
source                 1..318
                       mol_type = other DNA
                       organism = synthetic construct
SEQUENCE: 1600
acggtagcgg ccccatctgt cttcatcttc ccgccatctg atgagcagtt gaaatctgga  60
actgcctctg ttgtgtgcct gctgaataac ttctatccca gagaggccaa agtacagtgg  120
aaggtggata acgccctcca atcgggtaac tcccaggaga gtgtcacaga gcaggacagc  180
aaggacagca cctacagcct cagcagcacc ctgacgctga gcaaagcaga ctacgagaaa  240
cacaaagtct acgcctgcga agtcacccat cagggcctga gctcgcccgt cacaaagagc  300
ttcaacaggg gagagtgt                                                318
```